US012385072B2

(12) United States Patent
Buck

(10) Patent No.: US 12,385,072 B2
(45) **Date of Patent: *Aug. 12, 2025**

(54) BIDIRECTIONAL MULTI-ENZYMATIC SCAFFOLDS FOR BIOSYNTHESIZING CANNABINOIDS

(71) Applicant: Khona Scientific Holdings, Inc., Lone Tree, CO (US)

(72) Inventor: Jordan Buck, Boulder, CO (US)

(73) Assignee: Khona Scientific Holdings, Inc., Lone Tree, CO (US)

( * ) Notice: Subject to any disclaimer, the term of this patent is extended or adjusted under 35 U.S.C. 154(b) by 349 days.

This patent is subject to a terminal disclaimer.

(21) Appl. No.: 17/962,229

(22) Filed: Oct. 7, 2022

(65) Prior Publication Data

US 2023/0265465 A1 Aug. 24, 2023

Related U.S. Application Data

(63) Continuation of application No. 16/694,417, filed on Nov. 25, 2019, now Pat. No. 11,525,148.

(60) Provisional application No. 62/836,265, filed on Apr. 19, 2019, provisional application No. 62/771,839, filed on Nov. 27, 2018.

(51) Int. Cl.

| | |
|---|---|
| ***C12P 7/42*** | (2006.01) |
| ***C12N 15/70*** | (2006.01) |
| ***C12N 15/74*** | (2006.01) |
| ***C12N 15/81*** | (2006.01) |
| ***C12N 15/82*** | (2006.01) |

(52) U.S. Cl.

CPC ................ *C12P 7/42* (2013.01); *C12N 15/70* (2013.01); *C12N 15/74* (2013.01); *C12N 15/81* (2013.01); *C12N 15/8222* (2013.01); *C12N 2330/51* (2013.01); *C12N 2800/40* (2013.01); *C12Y 101/01034* (2013.01); *C12Y 101/01157* (2013.01); *C12Y 103/01038* (2013.01); *C12Y 103/03* (2013.01); *C12Y 121/03007* (2015.07); *C12Y 121/03008* (2015.07); *C12Y 203/01009* (2013.01); *C12Y 203/01016* (2013.01); *C12Y 203/01206* (2015.07); *C12Y 203/03008* (2013.01); *C12Y 203/0301* (2013.01); *C12Y 205/01001* (2013.01); *C12Y 207/01036* (2013.01); *C12Y 207/04002* (2013.01); *C12Y 401/01033* (2013.01); *C12Y 402/01017* (2013.01); *C12Y 404/01026* (2015.07); *C12Y 503/03002* (2013.01); *C12Y 604/01002* (2013.01)

(58) Field of Classification Search

None

See application file for complete search history.

(56) References Cited

U.S. PATENT DOCUMENTS

| | | | | |
|---|---|---|---|---|
| 8,697,654 | B2 | 4/2014 | Cheng et al. | |
| 8,884,100 | B2 | 11/2014 | Page et al. | |
| 9,822,384 | B2 | 11/2017 | Poulos et al. | |
| 9,856,460 | B2 | 1/2018 | Dueber et al. | |
| 11,525,148 | B2 * | 12/2022 | Buck ...................... | C12N 15/74 |
| 2003/0143562 | A1 | 7/2003 | Anderson et al. | |
| 2005/0204419 | A1 | 9/2005 | Helgeson et al. | |
| 2011/0008829 | A1 | 1/2011 | Dueber et al. | |
| 2011/0145940 | A1 | 6/2011 | Voytas et al. | |
| 2012/0144523 | A1 | 6/2012 | Page et al. | |
| 2013/0130347 | A1 | 5/2013 | Delisa et al. | |
| 2013/0164808 | A1 | 6/2013 | McAuliffe et al. | |
| 2014/0370595 | A1 | 12/2014 | Dueber et al. | |
| 2016/0010126 | A1 | 1/2016 | Poulos et al. | |
| 2017/0139496 | A1 | 5/2017 | Kang et al. | |
| 2017/0166950 | A1 | 6/2017 | Wolkowicz | |
| 2019/0055314 | A1 | 2/2019 | Luo et al. | |

FOREIGN PATENT DOCUMENTS

| | | |
|---|---|---|
| CA | 2644548 | 9/2007 |
| CN | 103360471 | 10/2013 |
| CN | 106414747 | 2/2017 |
| WO | WO 2014113738 | 7/2014 |
| WO | WO 2015196275 | 12/2015 |
| WO | WO 2016010827 | 1/2016 |
| WO | WO 2017139496 | 8/2017 |
| WO | WO 2018200888 | 11/2018 |

OTHER PUBLICATIONS

Chichili et al., "Linkers in the structural biology of protein-protein interactions," Protein Sci., Feb. 2013, 22(2):153-167.

Andre et al. (2016) Cannabissativa: The Plant of the Thousand and One Molecules, Frontiers Plant Sci., vol. 7, article 19, pp. 1-15.

Becker et al., "High-Efficiency Transformation of Yeast by Electroporation," Meth. Enzymology, 1991, 194:182-187.

Carvalho et al., "Designing microorganisms for heterologous biosynthesis of cannabinoids," FEMS Yeast Research, Jun. 2017, 17(4):fox037, 11 pages.

Chen et al., "Fusion protein linkers: Property, design and functionality," Adv. Drug Deliv. Reviews, Oct. 2013, 65(10):1357-1369.

Cho et al., "Targeted genome engineering in human cells with the Cas9 RNA-guided endonuclease," Nat. Biotechnology, Mar. 2013, 31(3):230-232.

Christian et al., "Targeting DNA Double-Strand Breaks with TAL Effector Nucleases," Genetics, Oct. 1, 2010, 186(2):757-761.

Cong et al., "Multiplex Genome Engineering Using CRISPR/Cas Systems," Science, Feb. 15, 2013, 339(6121):819-823.

Dicarlo et al., "Genome engineering in *Saccharomyces cerevisiae* using CRISPR-Cas systems," Nucleic Acids Research, Apr. 2013, 41(7):4336-4343.

(Continued)

*Primary Examiner* — Christian L Fronda

(74) *Attorney, Agent, or Firm* — Fish & Richardson P.C.

(57) ABSTRACT

This document relates to using bidirectional, multi-enzymatic scaffolds to biosynthesize cannabinoids in recombinant hosts.

21 Claims, 55 Drawing Sheets

Specification includes a Sequence Listing.

(56) References Cited

OTHER PUBLICATIONS

Dinkel et al., "The eukaryotic linear motif resource ELM: 10 years and counting," Nucleic Acids Research, Jan. 2014, 42(Database issue):D259-D266.

Dueber et al., "Synthetic protein scaffolds provide modular control over metabolic flux," Nat. Biotechnology, Aug. 2009, 27(8):753-759.

Durrens et al., "Expression of the avian gag-myc oncogene in *Saccharomyces cerevisiae*," Curr. Genetics, Jul. 1990, 18(1):7-12.

EP Extended Search Report in European Appln. No. 19888674.9, dated Jul. 22, 2022, 6 pages.

Gagne, et al., "Identification of olivetolic acid cyclase from Cannabis sativa reveals a unique catalytic route to plant polyketides," Proc. Natl. Acad. Sci. USA, Jul. 31, 2012, 109(31):12811-12816.

GenBank Accession No. AAA52679.1, "3-hydroxy-3-methylglutaryl coenzyme A reductase [*Homo sapiens*]," dated Nov. 8, 1994, 2 pages.

GenBank Accession No. AAA62411.1, "3-hydroxy-3-methylglutaryl coenzyme A synthase [*Homo sapiens*]," dated Feb. 24, 1995, 1 page.

GenBank Accession No. AAA74463.1, "ATP citrate-lyase [Rattus norvegicus]," dated Aug. 18, 1995, 1 page.

GenBank Accession No. AAC49920.1, "isopentenyl diphosphate:dimethylallyl diphosphate isomerase [*Arabidopsis thaliana*]," dated Feb. 24, 1998, 1 page.

GenBank Accession No. AAC50440.1, "mevalonate pyrophosphate decarboxylase [*Homo sapiens*]," dated Apr. 16, 1996, 1 page.

GenBank Accession No. AAC67348.1, "mevalonate diphosphate decarboxylase [*Arabidopsis thaliana*]," dated Mar. 11, 2002, 1 page.

GenBank Accession No. AAD31719.1, "mevalonate kinase [*Arabidopsis thaliana*]," dated May 10, 2000, 1 page.

GenBank Accession No. AAF82407.1, "mevalonate kinase [*Homo sapiens*]," dated Jun. 10, 2016, 1 page.

GenBank Accession No. AAH06089.1, "Phosphomevalonate kinase [*Homo sapiens*]," dated Oct. 19, 2016, 2 pages.

GenBank Accession No. AAH10004.1, "Farnesyl diphosphate synthase (farnesyl pyrophosphate synthetase, dimethylallyltranstransferase, geranyltranstransferase) [*Homo sapiens*]," dated Jul. 15, 2006, 2 pages.

GenBank Accession No. AAH30985.1, "Malonyl CoA:ACP acyltransferase (mitochondrial) [*Homo sapiens*]," dated Sep. 8, 2006, 2 pages.

GenBank Accession No. AAH31149.1, "Crk protein [Mus musculus]," dated Oct. 7, 2003, 2 pages.

GenBank Accession No. AAK56081.1, "ATP citrate lyase [Mus musculus]," dated Feb. 21, 2002, 1 page.

GenBank Accession No. AAK79760.1, "1-deoxy-D-xylulose 5-phosphate reductoisomerase [Clostridium acetobutylicum ATCC 824]," dated Jan. 30, 2014, 1 page.

GenBank Accession No. AAK80036.1, "Deoxyxylulose-5-phosphate synthase [Clostridium acetobutylicum ATCC 824]," dated Jan. 30, 2014, 1 page.

GenBank Accession No. AAK80816.1, "Acetyl-CoA acetyltransferase [Clostridium acetobutylicum ATCC 824]," dated Jan. 30, 2014, 1 page.

GenBank Accession No. AAK80844.1, "Isopentenyl monophosphate kinase, IPK [Clostridium acetobutylicum ATCC 824]," dated Jan. 30, 2014, 1 page.

GenBank Accession No. AAK81121.1, "4-diphosphocytidyl-2-methylerithritol synthase (Sugar Nucleotide Phosphorylase family) [Clostridium acetobutylicum ATCC 824]," dated Jan. 30, 2014, 1 page.

GenBank Accession No. AAM61343.1, "1-deoxy-D-xylulose 5-phosphate reductoisomerase DXR [*Arabidopsis thaliana*]," dated Jan. 27, 2006, 1 page.

GenBank Accession No. AAM67058.1, "acetoacyl-CoA-thiolase [*Arabidopsis thaliana*]," dated Jan. 27, 2006, 1 page.

GenBank Accession No. AAN17431.1, "putative 3-hydroxybutyryl-CoA dehydrogenase [*Arabidopsis thaliana*], " dated Sep. 24, 2002, 2 pages.

GenBank Accession No. AAN81487.1, "1-hydroxy-2-methyl-2-(E)-butenyl 4-diphosphate synthase [*Escherichia coli* CFT073]," dated Jan. 31, 2014, 1 page.

GenBank Accession No. AAP35407.1, "isopentenyl-diphosphate delta isomerase [*Homo sapiens*]," dated May 13, 2003, 1 page.

GenBank Accession No. AAP86010.1, "putative enoyl-(ACP) reductase (plasmid) [Cupriavidus necator H16]," dated Jul. 25, 2016, 1 page.

GenBank Accession No. AAP94122.1, "acetyl-CoA carboxylase 1 [*Homo sapiens*]," dated Jul. 27, 2003, 2 pages.

GenBank Accession No. AAS11086.1, "acetyl-CoA carboxylase, biotin carboxylase [Treponema denticola ATCC 35405]," dated Jan. 31, 2014, 2 pages.

GenBank Accession No. AAS11105.1, "3-hydroxyacyl-CoA dehydrogenase, putative [Treponema denticola ATCC 35405]," dated Jan. 31, 2014, 2 pages.

GenBank Accession No. AAS11855.1, "4-diphosphocytidyl-2C-methyl-D-erythritol kinase [Treponema denticola ATCC 35405]," dated Jan. 31, 2014, 2 pages.

GenBank Accession No. AAS12424.1, "1-deoxy-D-xylulose-5-phosphate synthase [Treponema denticola ATCC 35405]," dated Jan. 31, 2014, 2 pages.

GenBank Accession No. AAS12810.1, "2-C-methyl-D-erythritol 4-phosphate cytidylyltransferase [Treponema denticola ATCC 35405]," dated Jan. 31, 2014, 2 pages.

GenBank Accession No. AAS12811.1, "2C-methyl-D-erythritol 2,4-cyclodiphosphate synthase [Treponema denticola ATCC 35405]," dated Jan. 31, 2014, 2 pages.

GenBank Accession No. AAS12860.1, "1-deoxy-D-xylulose 5-phosphate reductoisomerase [Treponema denticola ATCC 35405]," dated Jan. 31, 2014, 2 pages.

GenBank Accession No. AC157384.3, "Bos taurus clone CH240-61D19, Working Draft Sequence, 6 unordered pieces," dated Jul. 11, 2008, 46 pages.

GenBank Accession No. ACJ56139.1, "Geranyltranstransferase(Farnesyl-diphosphate synthase) [Acinetobacter baumannii AB307-0294]," dated Jan. 31, 2014, 1 page.

GenBank Accession No. ACJ57023.1, "Enoyl-CoA hydratase [Acinetobacter baumannii AB307-0294]," dated Jan. 31, 2014, 1 page.

GenBank Accession No. ACJ58210.1, "4-hydroxy-3-methylbut-2-en-1-yl diphosphate synthase [Acinetobacter baumannii AB307-0294]," dated Jan. 31, 2014, 2 pages.

GenBank Accession No. ACJ59227.1, "2C-methyl-D-erythritol 2,4-cyclodiphosphate synthase [Acinetobacter baumannii AB307-0294]," dated Jan. 31, 2014, 1 page.

GenBank Accession No. ACS85236.1, "malonyl CoA-acyl carrier protein transacylase [Dickeya paradisiaca Ech703]," dated Oct. 25, 2017, 1 page.

GenBank Accession No. ADI91469.1, "enoyl-CoA hydratase [Acinetobacter oleivorans DR1]," dated Jan. 30, 2014, 1 page.

GenBank Accession No. AEC07908.1, "4-(cytidine 5'-phospho)-2-C-methyl-D-erithritol kinase [*Arabidopsis thaliana*]," dated Jul. 20, 2017, 2 pages.

GenBank Accession No. AED97354.1, "4-hydroxy-3-methylbut-2-enyl diphosphate synthase [*Arabidopsis thaliana*]," dated Jul. 20, 2017, 3 pages.

GenBank Accession No. AEE35849.1, "hydroxy methylglutaryl CoA reductase 1 [*Arabidopsis thaliana*]," dated Jul. 20, 2017, 4 pages.

GenBank Accession No. AEE83052.1, "hydroxymethylglutaryl-CoA synthase / HMG-CoA synthase / 3-hydroxy-3-methylglutaryl coenzyme A synthase [*Arabidopsis thaliana*]," dated Jul. 20, 2017, 3 pages.

GenBank Accession No. AEE86362.1, "4-hydroxy-3-methylbut-2-enyl diphosphate reductase [*Arabidopsis thaliana*]," dated Jul. 20, 2017, 4 pages.

GenBank Accession No. AFD33345.1, "acyl-activating enzyme 1 [Cannabis sativa]," dated Aug. 1, 2012, 1 page.

GenBank Accession No. AFD33347.1, "acyl-activating enzyme 3 [Cannabis sativa]," dated Aug. 1, 2012, 1 page.

GenBank Accession No. AFN42527.1, "olivetolic acid cyclase [Cannabis sativa]," dated Aug. 2, 2012, 1 page.

(56) References Cited

OTHER PUBLICATIONS

GenBank Accession No. AGO55277.1, "polyketide biosynthesis malonyl CoA-acyl carrier protein transacylase BaeC [Serratia plymuthica 4Rx13]," dated Jan. 30, 2014, 2 pages.
GenBank Accession No. AHM22925.1, "2-C-methyl-D-erythritol 2,4-cyclodiphosphate synthase [Nicotiana tabacum]," dated Mar. 22, 2014, 1 page.
GenBank Accession No. AIE72439.1, "trans-2-enoyl-CoA reductase (plasmid) [Klebsiella michiganensis]," dated Jul. 8, 2016, 2 pages.
GenBank Accession No. AIZ91493.1, "3-hydroxyacyl-CoA dehydrogenase [*Escherichia coli* str. K-12 substr. MG1655]," dated Dec. 15, 2014, 2 pages.
GenBank Accession No. ALI39443.1, "acetyl-CoA acetyltransferase [*Escherichia coli* str. K-12 substr. MG1655]," dated Dec. 16, 2015, 2 pages.
GenBank Accession No. AMC97367.1, "pyruvate dehydrogenase [*Escherichia coli* str. K-12 substr. MG1655]," dated Feb. 2, 2016, 2 pages.
GenBank Accession No. ANM65835.1, "1-deoxy-D-xylulose 5-phosphate synthase 1 [*Arabidopsis thaliana*]," dated Jul. 20, 2017, 2 pages.
GenBank Accession No. AUG14916.1, "dihydrolipoyllysine-residue acetyltransferase component of pyruvate dehydrogenase complex [*Escherichia coli* str. K-12 substr. MG1655]," dated Dec. 17, 2017, 2 pages.
GenBank Accession No. BAA21534.1, "N-WASP [Rattus rattus]," dated Dec. 27, 2006, 1 page.
GenBank Accession No. BAB00624.1, "ATP citrate-lyase [Ciona intestinalis]," dated Jul. 15, 2000, 1 page.
GenBank Accession No. BAB21592.1, "2-C-methyl-D-erythritol 4-phosphate cytidyltransferase [*Arabidopsis thaliana*]," dated Feb. 14, 2004, 1 page.
GenBank Accession No. BAC41356.1, "tetrahydrocannabinolic acid synthase precursor [Cannabis sativa]," dated Sep. 15, 2004, 1 page.
GenBank Accession No. BAF65033.1, "cannabidiolic acid synthase [Cannabis sativa]," dated Jun. 29, 2007, 1 page.
GenBank Accession No. BAG14339.1, "olivetol synthase [Cannabis sativa]," dated Jun. 20, 2009, 1 page.
GenBank Accession No. CAJ91294.1, "Enoyl-CoA hydratase [Cupriavidus necator H16]," dated Mar. 7, 2015, 2 pages.
GenBank Accession No. CAJ92510.1, "pyruvate dehydrogenase complex, dehydrogenase (E1) component [Cupriavidus necator H16]," dated Mar. 7, 2015, 2 pages.
GenBank Accession No. CAJ92511.1, "dihydrolipoamide acetyltransferase (E2) component of pyruvate dehydrogenase complex [Cupriavidus necator H16]," dated Mar. 7, 2015, 2 pgs.
GenBank Accession No. CAJ92573.1, "Acetyl-CoA acetyltransferase [Cupriavidus necator H16]," dated Mar. 7, 2015, 2 pages.
GenBank Accession No. CAQ66339.1, "Phosphomevalonate kinase [Lactobacillus casei BL23]," dated Feb. 27, 2015, 2 pages.
GenBank Accession No. CAQ66619.1, "Pyruvate dehydrogenase complex, E2 component, dihydrolipoamide acetyltransferase [Lactobacillus casei BL23]," dated Feb. 27, 2015, 2 pages.
GenBank Accession No. CAQ66794.1, "Mevalonate kinase [Lactobacillus casei BL23]," dated Feb. 27, 2015, 2 pages.
GenBank Accession No. CAQ66795.1, "Diphosphomevalonate decarboxylase [Lactobacillus casei BL23]," dated Feb. 27, 2015, 2 pages.
GenBank Accession No. CAQ66796.1, "Isopentenyl-diphosphate delta-isomerase (IPP isomerase) (Isopentenyl pyrophosphate isomerase) [Lactobacillus casei BL23]," dated Feb. 27, 2015, 2 pages.
GenBank Accession No. CAQ66932.1, "Farnesyl-diphosphate synthase [Lactobacillus casei BL23]," dated Feb. 27, 2015, 2 pages.
GenBank Accession No. CAQ67081.1, "Hydroxymethylglutaryl-CoA synthase [Lactobacillus casei BL23]," dated Feb. 27, 2015, 2 pages.
GenBank Accession No. CAQ67082.1, "Hydroxymethylglutaryl-CoA reductase [Lactobacillus casei BL23]," dated Feb. 27, 2015, 2 pages.
GenBank Accession No. CAQ67083.1, "Acetyl-CoA acetyltransferase (Acetoacetyl-CoA thiolase) [Lactobacillus casei BL23]," dated Feb. 27, 2015, 2 pages.
GenBank Accession No. CAQ67359.1, "Biotin carboxylase [Lactobacillus casei BL23]," dated Feb. 27, 2015, 2 pages.
GenBank Accession No. CDH63564.1, "4-hydroxy-3-methylbut-2-enyl diphosphate reductase [*Escherichia coli* PMV-1]," dated Sep. 18, 2013, 2 pages.
GenBank Accession No. CDH63708.1, "1-deoxy-D-xylulose 5-phosphate reductoisomerase [*Escherichia coli* PMV-1]," dated Sep. 18, 2013, 1 page.
GenBank Accession No. CDH63925.1, "1-deoxy-D-xylulose-5-phosphate synthase [*Escherichia coli* PMV-1]," dated Sep. 18, 2013, 1 page.
GenBank Accession No. CDH64802.1, "4-diphosphocytidyl-2-C-methyl-D-erythritol kinase [*Escherichia coli* PMV-1]," dated Sep. 18, 2013, 1 page.
GenBank Accession No. CDH66379.1, "2-C-methyl-D-erythritol 2,4-cyclodiphosphate synthase [*Escherichia coli* PMV-1]," dated Sep. 18, 2013, 2 pages.
GenBank Accession No. CDH66380.1, "2-C-methyl-D-erythritol 4-phosphate cytidylyltransferase [*Escherichia coli* PMV-1]," dated Sep. 18, 2013, 1 page.
GenBank Accession No. DAA07148.1, "TPA: Etr1p [*Saccharomyces cerevisiae* S288C]," dated Mar. 27, 2017, 2 pages.
GenBank Accession No. DAA07337.1, "TPA: pyruvate dehydrogenase (acetyl-transferring) subunit E1 beta [*Saccharomyces cerevisiae* S288C]," dated Mar. 27, 2017, 2 pages.
GenBank Accession No. DAA10474.1, "TPA: dihydrolipoyllysine-residue acetyltransferase [*Saccharomyces cerevisiae* S288C]," dated Mar. 27, 2017, 2 pages.
GenBank Accession No. DAA10992.1, "TPA: [acyl-carrier-protein] S-malonyltransferase [*Saccharomyces cerevisiae* S288C]," dated Mar. 27, 2017, 2 pages.
GenBank Accession No. EAZ63544.2, "Phosphomevalonate kinase [Scheffersomyces stipitis CBS 6054]," dated Jul. 11, 2011, 2 pages.
GenBank Accession No. EDL06069.1, "syntrophin, acidic 1, isoform CRA_b [Mus musculus]," dated Jul. 26, 2016, 2 pages.
GenBank Accession No. J04537.1, "*Arabidopsis thaliana* HMG-CoA reductase (HMG1) mRNA, complete cds," dated Sep. 29, 2015, 2 pages.
GenBank Accession No. JN717233.1, "Cannabis sativa acyl-activating enzyme 1 mRNA, complete cds," dated Aug. 1, 2012, 2 pages.
Havranek et al., "Automated design of specificity in molecular recognition," Nat. Struct. Biology, Jan. 2003, 10(1):45-52.
Horn et al., "Synthetic Protein Scaffolds Based on Peptide Motifs and Cognate Adaptor Domains for Improving Metabolic Productivity," Front. Bioeng. Biotechnology, Nov. 2015, 3:191, 7 pages.
Hwang et al., "Efficient genome editing in zebrafish using a CRISPR-Cas system," Nat. Biotechnology, Mar. 2013, 31(3):227-229.
Ito et al., "Transformation of Intact Yeast Cells Treated with Alkali Cations," J. Bacteriology, Jan. 1983, 153(1):163-168.
Jiang et al., "Manipulation of GES and ERG20 for geraniol overproduction in *Saccharomyces cerevisiae,*" Metab. Engineering, May 2017, 41:57-66.
Jiang et al., "RNA-guided editing of bacterial genomes using CRISPR-Cas systems," Nat. Biotechnology, Jan. 29, 2013, 31(3):233-239.
Jinek et al., "A Programmable Dual-RNA-Guided DNA Endonuclease in Adaptive Bacterial Immunity," Science, Aug. 17, 2012, 337(6096):816-821.
Kim et al., "Optimization of hexanoic acid production in recombinant *Escherichia coli* by precise flux rebalancing," Bioresour. Technology, Jan. 2018, 247:1253-1257.
Klein et al. (2014) Design and characterization of structured protein linkers with differing flexibilities, Prot. Eng. Design Select., vol. 27, No. 10, pp. 325-330.
Makarova et al., "Evolution and classification of the CRISPR-Cas systems," Nat. Rev. Microbiology, Jun. 2011, 9(6):467-477.
Mali et al, "RNA-Guided Human Genome Engineering via Cas9," Science, Feb. 15, 2013, 339(6121):823-826.

(56) References Cited

OTHER PUBLICATIONS

PCT International Search Report and Written Opinion in International Appln. No. PCT/US2019/063029, dated Feb. 6, 2020, 9 pages.
Proschel et al., "Engineering of metabolic pathways by artificial enzyme channels," Front. Bioeng. Biotechnology, Oct. 2015, 3:168, 13 pages.
Quintero et al. (2007) An improved system for estradiol-dependent regulation of gene expression in yeast, Microb. Cell Factor., vol. 6, No. 10, pp. 1-9.
Redden et al, (2015) The synthetic biology toolbox for tuning gene expression in yeast, FEMS Yest Res., vol. 15, pp. 1-10.
Reinke et al., "A Synthetic Coiled-Coil Interactome Provides Heterospecific Modules for Molecular Engineering," J. Am. Chem. Society, Apr. 13, 2010, 132(17):6025-6031.
Rodriguez et al., "ATP citrate lyase mediated cytosolic acetyl-CoA biosynthesis increases mevalonate production in *Saccharomyces cerevisiae,*" Microb. Cell Factories, Mar. 2016, 15:48, 12 pages.
Sirikantaramas et al., "The Gene Controlling Marijuana Psychoactivity," J. Biol. Chemistry, Jun. 9, 2004, 279(38):39767-39774.
Song et al., "Engineering *Saccharomyces cerevisiae* for geranylgeraniol overproduction by combinatorial design," Sci. Reports, Nov. 8, 2017, 7:14991, 11 pages.
Stout et al., "The hexanoyl-CoA precursor for cannabinoid biosynthesis is formed by an acyl-activating enzyme in Cannabis sativa trichomes," Plant Journal, Aug. 2012, 71(3):353-365.
Taura et al., "Cannabidiolic-acid synthase, the chemotype-determining enzyme in the fiber-type Cannabis sativa," FEBS Letters, Jun. 2007, 581(16):2929-2934.
Taura et al., "Characterization of olivetol synthase, a polyketide synthase putatively involved in cannabinoid biosynthetic pathway," FEBS Letters, Jun. 2009, 583(12):2061-2066.
Teyra et al., "Elucidation of the binding preferences of peptide recognition modules: SH3 and PDZ domains," FEBS Letters, Jun. 2012, 586(17):2631-2637.
Whitaker et al., "Metabolic Pathway Flux Enhancement by Synthetic Protein Scaffolding," Meth. Enzymology, 2011, 497(Part A):447-468.
Zakeri et al., "Peptide tag forming a rapid covalent bond to a protein, through engineering a bacterial adhesin," Proc. Natl. Acad. Sci. USA, Mar. 20, 2012, 109(12):E690-E697.
GenBank Accession No. AAS11585.1, "hydroxymethylbutenyl pyrophosphate reductase [Treponema denticola ATCC 35405]," dated Jan. 31, 2014, 2 pages.
GenBank Accession No. AAS11783.1, "1-hydroxy-2-methyl-2-(E)-butenyl 4-diphosphate synthase [Treponema denticola ATCC 35405]," dated Jan. 31, 2014, 2 pages.
GenBank Accession No. CAQ66617.1, "Pyruvate dehydrogenase complex, E1 component, alpha subunit [Lactobacillus casei BL23]," dated Feb. 27, 2015, 2 pages.

* cited by examiner

Figure 6A

ATP Citrate Lyase

MSAKAISEQTGKELLYKFICTTSAIQNRFKYARVTPDTDWARLLQDHPWLLSQNLVVKPDQLIKRRGKLGLVGVNLTL
DGVKSWLKPRLGQEATVGKATGFLKNFLIEPFVPHSQAEEFYVCIYATREGDYVLFHHEGGVDVGDVDAKAQKLLV
GVDEKLNPEDIKKHLLVHAPEDKKEILASFISGLFNFYEDLYFTYLEINPLVVTKDGVYVLDLAAKVDATADYICKVKWG
DIEFPPPFGREAYPEEAYIADLDAKSGASLKLTLLNPKGRIWTMVAGGGASVVYSDTICDLGGVNELANYGEYSGAP
SEQQTYDYAKTILSLMTREKHPDGKILIIGGSIANFTNVAATFKGIVRAIRDYQGPLKEHEVTIFVRRGGPNYQEGLRV
MGEVGKTTGIPIHVFGTETHMTAIVGMALGHRPIPNQPPTAAHTANFLLNASGSTSTPAPSRTASFSESRADEVAPAK
KAKPAMPQDSVPSPRSLQGKSTTLFSRHTKAIVWGMQTRAVQGMLDFDYVCSRDEPSVAAMVYPFTGDHKQKFY
WGHKEILIPVFKNMADAMRKHPEVDVLINFASLRSAYDSTMETMNYAQIRTIAIIAEGIPEALTRKLIKKADQKGVTIIGP
ATVGGIKPGCFKIGNTGGMLDNILASKLYRPGSVAYVSRSGGMSNELNNIISRTTDGVYEGVAIGGDRYPGSTFMDH
VLRYQDTPGVKMIVVLGEIGGTEEYKICRGIKEGRLTKPIVCWCIGTCATMFSSEVQFGHAGACANQASETAVAKNQ
ALKEAGVFVPRSFDELGEIIQSVYEDLVANGVIVPAQEVPPPTVPMDYSWARELGLIRKPASFMTSICDERGQELIYA
GMPITEVFKEEMGIGGVLGLLWFQKRLPKYSCQFIEMCLMVTADHGPAVSGAHNTIICARAGKDLVSSLTSGLLTIGD
RFGGALDAAAKMFSKAFDSGIIPMEFVNKMKKEGKLIMGIGHRVKSINNPDMRVQILKDYVRQHFPATPLLDYALEVE
KITTSKKPNLILNVDGLIGVAFVDMLRNCGSFTREEADEYIDIGALNGIFVLGRSMGFIGHYLDQKRLKQGLYRHPWD
DISYVLPEHMSM

Acetyl-CoA Acetyltransferase (atoB)

MKNCVIVSAVRTAIGSFNGSLASTSAIDLGATVIKAAIERAKIDSQHVDEVIMGNVLQAGLGQNPARQALLKSGLAETV
CGFTVNKVCGSGLKSVALAAQAIQAGQAQSIVAGGMENMSLAPYLLDAKARSGYRLGDGQVYDVILRDGLMCATH
GYHMGITAENVAKEYGITREMQDELALHSQRKAAAAIESGAFTAEIVPVNVVTRKKTFVFSQDEFPKANSTAEALGAL
RPAFDKAGTVTAGNASGINDGAAALVIMEESAALAAGLTPLARIKSYASGGVPPALMGMGPVPATQKALQLAGLQLA
DIDLIEANEAFAAQFLAVGKNLGFDSEKVNVNGGAIALGHPIGASGARILVTLLHAMQARDKTLGLATLCIGGGQGIAM
VIERLN

3-Hydroxybutyryl-CoA Dehydrogenase

MKKVCVIGAGTMGSGIAQAFAAKGFEVVLRDIKDEFVDRGLDFINKNLSKLVKKGKIEEATKVEILTRISGTVDLNMAA
DCDLVIEAAVERMDIKKQIFADLDNICKPETILASNTSSLSITEVASATKRPDKVIGMHFFNPAPVMKLVEVIRGIATSQE
TFDAVKETSIAIGKDPVEVAEAPGFVVNRILIPMINEAVGILAEGIASVEDIDKAMKLGANHPMGPLELGDFIGLDICLAI
MDVLYSETGDSKYRPHTLLKKYVRAGWLGRKSGKGFYDYSK

Enoyl-CoA Hydratase

MELNNVILEKEGKVAVVTINRPKALNALNSDTLKEMDYVIGEIENDSEVLAVILTGAGEKSFVAGADISEMKEMNTIEG
RKFGILGNKVFRRLELLEKPVIAAVNGFALGGGCEIAMSCDIRIASSNARFGQPEVGLGITPGFGGTQRLSRLVGMGM
AKQLIFTAQNIKADEALRIGLVNKVVEPSELMNTAKEIANKIVSNAPVAVKLSKQAINRGMQCDIDTALAFESEAFGECF
STEDQKDAMTAFIEKRKIEGFKNR

Trans-Enoyl-CoA Reductase

MIVKPMVRNNICLNAHPQGCKKGVEDQIEYTKKRITAEVKAGAKAPKNVLVLGCSNGYGLASRITAAFGYGAATIGVS
FEKAGSETKYGTPGWYNNLAFDEAAKREGLYSVTIDGDAFSDEIKAQVIEEAKKKGIKFDLIVYSLASPVRTDPDTGIM
HKSVLKPFGKTFTGKTVDPFTGELKEISAEPANDEEAAATVKVMGGEDWERWIKQLSKEGLLEEGCITLAYSYIGPEA
TQALYRKGTIGKAKEHLEATAHRLNKENPSIRAFVSVNKGLVTRASAVIPVIPLYLASLFKVMKEKGNHEGCIEQITRLY
AERLYRKDGTIPVDEENRIRIDDWELEEDVQKAVSALMEKVTGENAESLTDLAGYRHDFLASNGFDVEGINYEAEVE
RFDRI

Figure 6A (continued)

Beta-Ketothiolase (bktB)

MTREVVVVSGVRTAIGTFGGSLKDVAPAELGALVVREALARAQVSGDDVGHVVFGNVIQTEPRDMYLGRVAAVNG
GVTINAPALTVNRLCGSGLQAIVSAAQTILLGDTDVAIGGGAESMSRAPYLAPAARWGARMGDAGLVDMMLGALHD
PFHRIHMGVTAENVAKEYDISRAQQDEAALESHRRASAAIKAGYFKDQIVPVVSKGRKGDVTFDTDEHVRHDATIDD
MTKLRPVFVKENGTVTAGNASGLNDAAAAVVMMERAEAERRGLKPLARLVSYGHAGVDPKAMGIGPVPATKIALER
AGLQVSDLDVIEANEAFAAQACAVTKALGLDPAKVNPNGSGISLGHPIGATGALITVKALHELNRVQGRYALVTMCIG
GGQGIAAIFERI

HMG-CoA Synthase

MKLSTKLCWCGIKGRLRPQKQQQLHNTNLQMTELKKQKTAEQKTRPQNVGIKGIQIYIPTQCVNQSELEKFDGVSQ
GKYTIGLGQTNMSFVNDREDIYSMSLTVLSKLIKSYNIDTNKIGRLEVGTETLIDKSKSVKSVLMQLFGENTDVEGIDTL
NACYGGTNALFNSLNWIESNAWDGRDAIVVCGDIAIYDKGAARPTGGAGTVAMWIGPDAPIVFDSVRASYMEHAYD
FYKPDFTSEYPYVDGHFSLTCYVKALDQVYKSYSKKAISKGLVSDPAGSDALNVLKYFDYNVFHVPTCKLVTKSYGR
LLYNDFRANPQLFPEVDAELATRDYDESLTDKNIEKTFVNVAKPFHKERVAQSLIVPTNTGNMYTASVYAAFASLLNY
VGSDDLQGKRVGLFSYGSGLAASLYSCKIVGDVQHIIKELDITNKLAKRITETPKDYEAAIELRENAHLKKNFKPQGSIE
HLQSGVYYLTNIDDKFRRSYDVKK

Truncated HMG-CoA Reductase

MVAVRRKALSILAEAPVLASDRLPYKNYDYDRVFGACCENVIGYMPLPVGVIGPLVIDGTSYHIPMATTEGCLVASAM
RGCKAINAGGGATTVLTKDGMTRGPVVRFPTLKRSGACKIWLDSEEGQNAIKKAFNSTSRFARLQHIQTCLAGDLLF
MRFRTTTGDAMGMNMISKGVEYSLKQMVEEYGWEDMEVVSVSGNYCTDKKPAAINWIEGRGKSVVAEATIPGDVV
RKVLKSDVSALVELNIAKNLVGSAMAGSVGGFNAHAANLVTAVFLALGQDPAQNVESSNCITLMKEVDGDLRISVSM
PSIEVGTIGGGTVLEPQGAMLDLLGVRGPHATAPGTNARQLARIVACAVLAGELSLCAALAAGHLVQSHMTHNR

Mevalonate Kinase

MSLPFLTSAPGKVIIFGEHSAVYNKPAVAASVSALRTYLLISESSAPDTIELDFPDISFNHKWSINDFNAITEDQVNSQK
LAKAQQATDGLSQELVSLLDPLLAQLSESFHYHAAFCFLYMFVCLCPHAKNIKFSLKSTLPIGAGLGSSASISVSLALA
MAYLGGLIGSNDLEKLSENDKHIVNQWAFIGEKCIHGTPSGIDNAVATYGNALLFEKDSHNGTINTNNFKFLDDFPAIP
MILTYTRIPRSTKDLVARVRVLVTEKFPEVMKPILDAMGECALQGLEIMTKLSKCKGTDDEAVETNNELYEQLLELIRIN
HGLLVSIGVSHPGLELIKNLSDDLRIGSTKLTGAGGGGCSLTLLRRDITQEQIDSFKKKLQDDFSYETFETDLGGTGCC
LLSAKNLNKDLKIKSLVFQLFENKTTTKQQIDDLLLPGNTNLPWTS

Phosphomevalonate Kinase

MSELRAFSAPGKALLAGGYLVLDTKYEAFVVGLSARMHAVAHPYGSLQGSDKFEVRVKSKQFKDGEWLYHISPKSG
FIPVSIGGSKNPFIEKVIANVFSYFKPNMDDYCNRNLFVIDIFSDDAYHSQEDSVTEHRGNRRLSFHSHRIEEVPKTGL
GSSAGG[J1]LVTVLTTALASFFVSDLENNVDKYREVIHNLAQVAHCQAQGKIGSGFDVAAAAYGSIRYRRFPPALISNL
PDIGSATYGSKLAHLVDEEDWNITIKSNHLPSGLTLWMGDIKNGSETVKLVQKVKNWYDSHMPESLKIYTELDHANS
RFMDGLSKLDRLHETHDDYSDQIFESLERNDCTCQKYPEITEVRDAVATIRRSFRKITKESGADIEPPVQTSLLDDCQ
TLKGVLTCLIPGAGGYDAIAVITKQDVDLRAQTANDKRFSKVQWLDVTQADWGVRKEKDPETYLDK

Figure 6A (continued)

Diphosphomevalonate Decarboxylase

MTVYTASVTAPVNIATLKYWGKRDTKLNLPTNSSISVTLSQDDLRTLTSAATAPEFERDTLWLNGEPHSIDNERTQNC
LRDLRQLRKEMESKDASLPTLSQWKLHIVSENNFPTAAGLASSAAGFAALVSAIAKLYQLPQSTSEISRIARKGSGSA
CRSLFGGYVAWEMGKAEDGHDSMAVQIADSSDWPQMKACVLVVSDIKKDVSSTQGMQLTVATSELFKERIEHVVP
KRFEVMRKAIVEKDFATFAKETMMDSNSFHATCLDSFPPIFYMNDTSKRIISWCHTINQFYGETIVAYTFDAGPNAVL
YYLAENESKLFAFIYKLFGSVPGWDKKFTTEQLEAFNHQFESSNFTARELDLELQKDVARVILTQVGSGPQETNESLI
DAKTGLPKE

Isopentenyl-Diphosphate Delta-Isomerase

MTADNNSMPHGAVSSYAKLVQNQTPEDILEEFPEIIPLQQRPNTRSSETSNDESGETCFSGHDEEQIKLMNENCIVL
DWDDNAIGAGTKKVCHLMENIEKGLLHRAFSVFIFNEQGELLLQQRATEKITFPDLWTNTCCSHPLCIDDELGLKGKL
DDKIKGAITAAVRKLDHELGIPEDETKTRGKFHFLNRIHYMAPSNEPWGEHEIDYILFYKINAKENLTVNPNVNEVRDF
KWVSPNDLKTMFADPSYKFTPWFKIICENYLFNWWEQLDDLSEVENDRQIHRML

Geranyl-Diphosphate Synthase (ERG20$^{WW}$)

MEAKIDELINNDPVWSSQNESLISKPYNHILLKPGKNFRLNLIVQINRVMNLPKDQLAIVSQIVELLHNSSLLIDDIEDNA
PLRRGQTTSHLIWGVPSTINTANYMYFRAMQLVSQLTTKEPLYHWLITIFNEELINLHRGQGLDIYWRDFLPEIIPTQE
MYLNMVMNKTGGLFRLTLRLMEALSPSSHHGHSLVPFINLLGIIYQIRDDYLNLKDFQMSSEKGFAEDITEGKLSFPIV
HALNFTKTKGQTEQHNEILRILLLRTSDKDIKLKLIQILEFDTNSLAYTKNFINQLVNMIKNDNENKYLPDLASHSDTATN
LHDELLYIIDHLSEL

Olivetol Synthase

MNHLRAEGPASVLAIGTANPENILLQDEFPDYYFRVTKSEHMTQLKEKFRKICDKSMIRKRNCFLNEEHLKQNPRLVE
HEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSESDLELLVGQAIFGDGAAAVIVGAEPDESVGERPIFE
LVSTGQTILPNSEGTIGGHIREAGLIFDLHKDVPMLISNNIEKCLIEAFTPIGISDWNSIFWITHPGGKAILDKVEEKLHLK
SDKFVDSRHVLSEHGNMSSSTVLFVMDELRKRSLEEGKSTTGDGFEWGVLFGFGPGLTVERVVVRSVPIKY

Olivetolic Acid Cyclase

MAVKHLIVLKFKDEITEAQKEEFFKTYVNLVNIIPAMKDVYWGKDVTQKNKEEGYTHIVEVTFESVETIQDYIIHPAHVG
FGDVYRSFWEKLLIFDYTPRK

CBGA Synthase

MGLSSVCTFSFQTNYHTLLNPHNNNPKTSLLCYRHPKTPIKYSYNNFPSKHCSTKSFHLQNKCSESLSIAKNSIRAAT
TNQTEPPESDNHSVATKILNFGKACWKLQRPYTIIAFTSCACGLFGKELLHNTNLISWSLMFKAFFFLVAILCIASFTTTI
NQIYDLHIDRINKPDLPLASGEISVNTAWIMSIIVALFGLIITIKMKGGPLYIFGYCFGIFGGIVYSVPPFRWKQNPSTAFL
LNFLAHIITNFTFYYASRAALGLPFELRPSFTFLLAFMKSMGSALALIKDASDVEGDTKFGISTLASKYGSRNLTLFCSG
IVLLSYVAAILAGIIWPQAFNSNVMLLSHAILAFWLILQTRDFALTNYDPEAGRRFYEFMWKLYYAEYLVYVFI

Figure 6A (continued)

Acetyl-CoA Carboxylase

MSEESLFESSPQKMEYEITNYSERHTELPGHFIGLNTVDKLEESPLRDFVKSHGGHTVISKILIANNGIAAVKEIRSVRK
WAYETFGDDRTVQFVAMATPEDLEANAEYIRMADQYIEVPGGTNNNNYANVDLIVDIAERADVDAVWAGWGHASE
NPLLPEKLSQSKRKVIFIGPPGNAMRSLGDKISSTIVAQSAKVPCIPWSGTGVDTVHVDEKTGLVSVDDDIYQKGCCT
SPEDGLQKAKRIGFPVMIKASEGGGGKGIRQVEREEDFIALYHQAANEIPGSPIFIMKLAGRARHLEVQLLADQYGTNI
SLFGRDCSVQRRHQKIIEEAPVTIAKAETFHEMEKAAVRLGKLVGYVSAGTVEYLYSHDDGKFYFLELNPRLQVEHP
TTEMVSGVNLPAAQLQIAMGIPMHRISDIRTLYGMNPHSASEIDFEFKTQDATKKQRRPIPKGHCTACRITSEDPNDG
FKPSGGTLHELNFRSSSNVWGYFSVGNNGNIHSFSDSQFGHIFAFGENRQASRKHMVVALKELSIRGDFRTTVEYLI
KLLETEDFEDNTITTGWLDDLITHKMTAEKPDPTLAVICGAATKAFLASEEARHKYIESLQKGQVLSKDLLQTMFPVDF
IHEGKRYKFTVAKSGNDRYTLFINGSKCDIILRQLSDGGLLIAIGGKSHTIYWKEEVAATRLSVDSMTTLLEVENDPTQL
RTPSPGKLVKFLVENGEHIIKGQPYAEIEVMKMQMPLVSQENGIVQLLKQPGSTIVAGDIMAIMTLDDPSKVKHALPFE
GMLPDFGSPVIEGTKPAYKFKSLVSTLENILKGYDNQVIMNASLQQLIEVLRNPKLPYSEWKLHISALHSRLPAKLDEQ
MEELVARSLRRGAVFPARQLSKLIDMAVKNPEYNPDKLLGAVVEPLADIAHKYSNGLEAHEHSIFVHFLEEYYEVEKL
FNGPNVREENIILKLRDENPKDLDKVALTVLSHSKVSAKNNLILAILKHYQPLCKLSSKVSAIFSTPLQHIVELESKATAK
VALQAREILIQGALPSVKERTEQIEHILKSSVVKVAYGSSNPKRSEPDLNILKDLIDSNYVVFDVLLQFLTHQDPVVTAA
AAQVYIRRAYRAYTIGDIRVHEGVTVPIVEWKFQLPSAAFSTFPTVKSKMGMNRAVSVSDLSYVANSQSSPLREGILM
AVDHLDDVDEILSQSLEVIPRHQSSSNGPAPDRSGSSASLSNVANVCVASTEGFESEEEILVRLREILDLNKQELINAS
IRRITFMFGFKDGSYPKYYTFNGPNYNENETIRHIEPALAFQLELGRLSNFNIKPIFTDNRNIHVYEAVSKTSPLDKRFF
TRGIIRTGHIRDDISIQEYLTSEANRLMSDILDNLEVTDTSNSDLNHIFINFIAVFDISPEDVEAAFGGFLERFGKRLLRLR
VSSAEIRIIIKDPQTGAPVPLRALINNVSGYVIKTEMYTEVKNAKGEWVFKSLGKPGSMHLRPIATPYPVKEWLQPKRY
KAHLMGTTYVYDFPELFRQASSSQWKNFSADVKLTDDFFISNELIEDENGELTEVEREPGANAIGMVAFKITVKTPEY
PRGRQFVVVANDITFKIGSFGPQEDEFFNKVTEYARKRGIPRIYLAANSGARIGMAEEIVPLFQVAWNDAANPDKGF
QYLYLTSEGMETLKKFDKENSVLTERTVINGEERFVIKTIIGSEDGLGVECLRGSGLIAGATSRAYHDIFTITLVTCRSV
GIGAYLVRLGQRAIQVEGQPIILTGAPAINKMLGREVYTSNLQLGGTQIMYNNGVSHLTAVDDLAGVEKIVEWMSYVP
AKRNMPVPILETKDTWDRPVDFTPTNDETYDVRWMIEGRETESGFEYGLFDKGSFFETLSGWAKGVVVGRARLGGI
PLGVIGVETRTVENLIPADPANPNSAETLIQEPGQVWHPNSAFKTAQAINDFNNGEQLPMMILANWRGFSGGQRDM
FNEVLKYGSFIVDALVDYKQPIIIYIPPTGELRGGSWVVVDPTINADQMEMYADVNARAGVLEPQGMVGIKFRREKLL
DTMNRLDDKYRELRSQLSNKSLAPEVHQQISKQLADRERELLPIYGQISLQFADLHDRSSRMVAKGVISKELEWTEA
RRFFFWRLRRRLNEEYLIKRLSHQVGEASRLEKIARIRSWYPASVDHEDDRQVATWIEENYKTLDDKLKGLKLESFA
QDLAKKIRSDHDNAIDGLSEVIKMLSTDDKEKLLKTLK

CBDA Synthase

MKCSTFSFWFVCKIIFFFFSFNIQTSIANPRENFLKCFSQYIPNNATNLKLVYTQNNPLYMSVLNSTIHNLRFTSDTTPK
PLVIVTPSHVSHIQGTILCSKKVGLQIRTRSGGHDSEGMSYISQVPFVIVDLRNMRSIKIDVHSQTAWVEAGATLGEVY
YWVNEKNENLSLAAGYCPTVCAGGHFGGGGYGPLMRNYGLAADNIIDAHLVNVHGKVLDRKSMGEDLFWALRGG
GAESFGIIVAWKIRLVAVPKSTMFSVKKIMEIHELVKLVNKWQNIAYKYDKDLLLMTHFITRNITDNQGKNKTAIHTYFS
SVFLGGVDSLVDLMNKSFPELGIKKTDCRQLSWIDTIIFYSGVVNYDTDNFNKEILLDRSAGQNGAFKIKLDYVKKPIP
ESVFVQILEKLYEEDIGAGMYALYPYGGIMDEISESAIPFPHRAGILYELWYICSWEKQEDNEKHLNWIRNIYNFMTPY
VSKNPRLAYLNYRDLDIGINDPKNPNNYTQARIWGEKYFGKNFDRLVKVKTLVDPNNFFRNEQSIPPLPRHRH

CBCA Synthase

MNCSTFSFWFVCKIIFFFLSFNIQISIANPQENFLKCFSEYIPNNPANPKFIYTQHDQLYMSVLNSTIQNLRFTSDTTPK
PLVIVTPSNVSHIQASILCSKKVGLQIRTRSGGHDAEGLSYISQVPFAIVDLRNMHTVKVDIHSQTAWVEAGATLGEVY
YWINEMNENFSFPGGYCPTVGVGGHFSGGGYGALMRNYGLAADNIIDAHLVNVDGKVLDRKSMGEDLFWAIRGGG
GENFGIIAACKIKLVVVPSKATIFSVKKNMEIHGLVKLFNKWQNIAYKYDKDLMLTTHFRTRNITDNHGKNKTTVHGYF
SSIFLGGVDSLVDLMNKSFPELGIKKTDCKELSWIDTTIFYSGVVNYNTANFKKEILLDRSAGKKTAFSIKLDYVKKLIPE
TAMVKILEKLYEEEVGVGMYVLYPYGGIMDEISESAIPFPHRAGIMYELWYTATWEKQEDNEKHINWVRSVYNFTTP
YVSQNPRLAYLNYRDLDLGKTNPESPNNYTQARIWGEKYFGKNFNRLVKVKTKADPNNFFRNEQSIPPLPPRHH

Figure 6A (continued)

Hexanoyl-CoA Synthetase

MGKNYKSLDSVVASDFIALGITSEVAETLHGRLAEIVCNYGAATPQTWINIANHILSPDLPFSLHQMLFYGCYKDFGPA
PPAWIPDPEKVKSTNLGALLEKRGKEFLGVKYKDPISSFSHFQEFSVRNPEVYWRTVLMDEMKISFSKDPECILRRD
DINNPGGSEWLPGGYLNSAKNCLNVNSNKKLNDTMIVWRDEGNDDLPLNKLTLDQLRKRVWLVGYALEEMGLEKG
CAIAIDMPMHVDAVVIYLAIVLAGYVVVSIADSFSAPEISTRLRLSKAKAIFTQDHIIRGKKRIPLYSRVVEAKSPMAIVIP
CSGSNIGAELRDGDISWDYFLERAKEFKNCEFTAREQPVDAYTNILFSSGTTGEPKAIPWTQATPLKAAADGWSHLD
IRKGDVIVWPTNLGWMMGPWLVYASLLNGASIALYNGSPLVSGFAKFVQDAKVTMLGVVPSIVRSWKSTNCVSGYD
WSTIRCFSSSGEASNVDEYLWLMGRANYKPVIEMCGGTEIGGAFSAGSFLQAQSLSSFSSQCMGCTLYILDKNGYP
MPKNKPGIGELALGPVMFGASKTLLNGNHHDVYFKGMPTLNGEVLRRHGDIFELTSNGYYHAHGRADDTMNIGGIKI
SSIEIERVCNEVDDRVFETTAIGVPPLGGGPEQLVIFFVLKDSNDTTIDLNQLRLSFNLGLQKKLNPLFKVTRVVPLSSL
PRTATNKIMRRVLRQQFSHFE

Figure 6B

ATP Citrate Lyase – Enzyme Linker – cTPR6 Spacer – ID Linker – ID1

MSAKAISEQTGKELLYKFICTTSAIQNRFKYARVTPDTDWARLLQDHPWLLSQNLVVKPDQLIKRRGKLGLVGVNLTL
DGVKSWLKPRLGQEATVGKATGFLKNFLIEPFVPHSQAEEFYVCIYATREGDYVLFHHEGGVDVGDVDAKAQKLLV
GVDEKLNPEDIKKHLLVHAPEDKKEILASFISGLFNFYEDLYFTYLEINPLVVTKDGVYVLDLAAKVDATADYICKVKWG
DIEFPPPFGREAYPEEAYIADLDAKSGASLKLTLLNPKGRIWTMVAGGGASVVYSDTICDLGGVNELANYGEYSGAP
SEQQTYDYAKTILSLMTREKHPDGKILIIGGSIANFTNVAATFKGIVRAIRDYQGPLKEHEVTIFVRRGGPNYQEGLRV
MGEVGKTTGIPIHVFGTETHMTAIVGMALGHRPIPNQPPTAAHTANFLLNASGSTSTPAPSRTASFSESRADEVAPAK
KAKPAMPQDSVPSPRSLQGKSTTLFSRHTKAIVWGMQTRAVQGMLDFDYVCSRDEPSVAAMVYPFTGDHKQKFY
WGHKEILIPVFKNMADAMRKHPEVDVLINFASLRSAYDSTMETMNYAQIRTIAIIAEGIPEALTRKLIKKADQKGVTIIGP
ATVGGIKPGCFKIGNTGGMLDNILASKLYRPGSVAYVSRSGGMSNELNNIISRTTDGVYEGVAIGGDRYPGSTFMDH
VLRYQDTPGVKMIVVLGEIGGTEEYKICRGIKEGRLTKPIVCWCIGTCATMFSSEVQFGHAGACANQASETAVAKNQ
ALKEAGVFVPRSFDELGEIIQSVYEDLVANGVIVPAQEVPPPTVPMDYSWARELGLIRKPASFMTSICDERGQELIYA
GMPITEVFKEEMGIGGVLGLLWFQKRLPKYSCQFIEMCLMVTADHGPAVSGAHNTIICARAGKDLVSSLTSGLLTIGD
RFGGALDAAAKMFSKAFDSGIIPMEFVNKMKKEGKLIMGIGHRVKSINNPDMRVQILKDYVRQHFPATPLLDYALEVE
KITTSKKPNLILNVDGLIGVAFVDMLRNCGSFTREEADEYIDIGALNGIFVLGRSMGFIGHYLDQKRLKQGLYRHPWD
DISYVLPEHMSMKLSGGGGSGGGGSGGGGSAEAWYNLGNAYYKQGDYQKAIEYYQKALELDPNNAEAWYNLGNA
YYKQGDYQKAIEYYQKALELDPNNAEAWYNLGNAYYKQGDYQKAIEDYQKALELDPNNLQAEAWKNLGNAYYKQG
DYQKAIEYYQKALELDPNNASAWYNLGNAYYKQGDYQKAIEYYQKALELDPNNAKAWYRRGNAYYKQGDYQKAIE
DYQKALELDPNNRSRSAGGGGSGGGGSGGGGASSYYHHHHHHLESTSLYKKAGSGSNLVAQLENEVASLENENE
TLKKKNLHKKDLIAYLEKEIANLRKKIEEGSAGSAAGSGEFGSAEAAAKEAAAKAGSAGSAAGSGEFGSSYYHHHHH
HLESTSLYKKAGSGSARNAYLRKKIARLKKDNLQLERDEQNLEKIIANLRDEIARLENEVASHEQ

Acetyl-CoA Acetyltransferase (atoB) – Enzyme Linker – cTPR6 Spacer – ID Linker – ID2

MKNCVIVSAVRTAIGSFNGSLASTSAIDLGATVIKAAIERAKIDSQHVDEVIMGNVLQAGLGQNPARQALLKSGLAETV
CGFTVNKVCGSGLKSVALAAQAIQAGQAQSIVAGGMENMSLAPYLLDAKARSGYRLGDGQVYDVILRDGLMCATH
GYHMGITAENVAKEYGITREMQDELALHSQRKAAAAIESGAFTAEIVPVNVVTRKKTFVFSQDEFPKANSTAEALGAL
RPAFDKAGTVTAGNASGINDGAAALVIMEESAALAAGLTPLARIKSYASGGVPPALMGMGPVPATQKALQLAGLQLA
DIDLIEANEAFAAQFLAVGKNLGFDSEKVNVNGGAIALGHPIGASGARILVTLLHAMQARDKTLGLATLCIGGGQGIAM
VIERLNKLSGGGGSGGGGSGGGGSAEAWYNLGNAYYKQGDYQKAIEYYQKALELDPNNAEAWYNLGNAYYKQGD
YQKAIEYYQKALELDPNNAEAWYNLGNAYYKQGDYQKAIEDYQKALELDPNNLQAEAWKNLGNAYYKQGDYQKAIE
YYQKALELDPNNASAWYNLGNAYYKQGDYQKAIEYYQKALELDPNNAKAWYRRGNAYYKQGDYQKAIEDYQKALE
LDPNNRSRSAGGGGSGGGGSGGGGASSYYHHHHHHLESTSLYKKAGSGSNEVTTLENDAAFIENENAYLEKEIAR
LRKEKAALRNRLAHKKGSAGSAAGSGEFGSAEAAAKEAAAKAGSAGSAAGSGEFGSSYYHHHHHHLESTSLYKKA
GSGSQKVAELKNRVAVKLNRNEQLKNKVEELKNRNAYLKNELATLENEVARLENDVAE

3-Hydroxybutyryl-CoA Dehydrogenase – Enzyme Linker – cTPR6 Spacer – ID Linker – ID3

MKKVCVIGAGTMGSGIAQAFAAKGFEVVLRDIKDEFVDRGLDFINKNLSKLVKKGKIEEATKVEILTRISGTVDLNMAADCDL
VIEAAVERMDIKKQIFADLDNICKPETILASNTSSLSITEVASATKRPDKVIGMHFFNPAPVMKLVEVIRGIATSQETFDAVKET
SIAIGKDPVEVAEAPGFVVNRILIPMINEAVGILAEGIASVEDIDKAMKLGANHPMGPLELGDFIGLDICLAIMDVLYSETGDSK
YRPHTLLKKYVRAGWLGRKSGKGFYDYSKKLSGGGGSGGGGSGGGGSAEAWYNLGNAYYKQGDYQKAIEYYQKALEL
DPNNAEAWYNLGNAYYKQGDYQKAIEYYQKALELDPNNAEAWYNLGNAYYKQGDYQKAIEDYQKALELDPNNLQAEAW
KNLGNAYYKQGDYQKAIEYYQKALELDPNNASAWYNLGNAYYKQGDYQKAIEYYQKALELDPNNAKAWYRRGNAYYKQ
GDYQKAIEDYQKALELDPNNRSRSAGGGGSGGGGSGGGGASENLYFQGENLYFQGDSSESCWNCGRKASETCSGCNT
ARYCGSFCQHKDWEKHHHICGQTLQAQQGSAGSAAGSGEFGSAEAAAKEAAAKAGSAGSAAGSGEFGSMAVSESQLK
KMVSKYKYRDLTVRETVNVITLYKDLKPVLDSYVFNDGSSRELMNLTGTIPVPYRGNTYNIPICLWLLDTYPYNPPICFVKPT
SSMTIKTGKHVDANGKIYLPYLHEWKHPQSDLLGLIQVMIVVFGDEPPVFSRP

Figure 6B (continued)

Enoyl-CoA Hydratase – Enzyme Linker – cTPR6 Spacer – ID Linker – ID4

MELNNVILEKEGKVAVVTINRPKALNALNSDTLKEMDYVIGEIENDSEVLAVILTGAGEKSFVAGADISEMKEMNTIEG
RKFGILGNKVFRRLELLEKPVIAAVNGFALGGGCEIAMSCDIRIASSNARFGQPEVGLGITPGFGGTQRLSRLVGMGM
AKQLIFTAQNIKADEALRIGLVNKVVEPSELMNTAKEIANKIVSNAPVAVKLSKQAINRGMQCDIDTALAFESEAFGECF
STEDQKDAMTAFIEKRKIEGFKNRKLSGGGGSGGGGSGGGGSAEAWYNLGNAYYKQGDYQKAIEYYQKALELDPN
NAEAWYNLGNAYYKQGDYQKAIEYYQKALELDPNNAEAWYNLGNAYYKQGDYQKAIEDYQKALELDPNNLQAEAW
KNLGNAYYKQGDYQKAIEYYQKALELDPNNASAWYNLGNAYYKQGDYQKAIEYYQKALELDPNNAKAWYRRGNAY
YKQGDYQKAIEDYQKALELDPNNRSRSAGGGGSGGGGSGGGGASGPLGSPLTASMLASAPPQEQKQMLGERLFP
LIQAMHPTLAGKITGMLLEIDNSELLHMLESPESLRSKVDEAVAVLQAHQAKEAAQKAGSAGSAAGSGEFGSAEAAA
KEAAAKAGSAGSAAGSGEFGSNTNMSVPTDGAVTTSQIPASEQETLVRPKPLLLKLLKSVGAQKDTYTMKEVLFYLG
QYIMTKRLYDEKQQHIVYCSNDLLGDLFGVPSFSVKEHRKIYTMIYRNLVV

Trans-Enoyl-CoA Reductase – Enzyme Linker – cTPR6 Spacer – ID Linker – ID5

MIVKPMVRNNICLNAHPQGCKKGVEDQIEYTKKRITAEVKAGAKAPKNVLVLGCSNGYGLASRITAAFGYGAATIGVS
FEKAGSETKYGTPGWYNNLAFDEAAKREGLYSVTIDGDAFSDEIKAQVIEEAKKKGIKFDLIVYSLASPVRTDPDTGIM
HKSVLKPFGKTFTGKTVDPFTGELKEISAEPANDEEAAATVKVMGGEDWERWIKQLSKEGLLEEGCITLAYSYIGPEA
TQALYRKGTIGKAKEHLEATAHRLNKENPSIRAFVSVNKGLVTRASAVIPVIPLYLASLFKVMKEKGNHEGCIEQITRLY
AERLYRKDGTIPVDEENRIRIDDWELEEDVQKAVSALMEKVTGENAESLTDLAGYRHDFLASNGFDVEGINYEAEVE
RFDRIKLSGGGGSGGGGSGGGGSAEAWYNLGNAYYKQGDYQKAIEYYQKALELDPNNAEAWYNLGNAYYKQGDY
QKAIEYYQKALELDPNNAEAWYNLGNAYYKQGDYQKAIEDYQKALELDPNNLQAEAWKNLGNAYYKQGDYQKAIEY
YQKALELDPNNASAWYNLGNAYYKQGDYQKAIEYYQKALELDPNNAKAWYRRGNAYYKQGDYQKAIEDYQKALEL
DPNNRSRSAGGGGSGGGGSGGGGASSYYHHHHHHLESTSLYKKAGSGSNLLATLRSTAAVLENENHVLEKEKEKL
RKEKEQLLNKLEAYKGSAGSAAGSGEFGSAEAAAKEAAAKAGSAGSAAGSGEFGSSYYHHHHHHLESTSLYKKAG
SGSKRIAYLRKKIAALKKDNANLEKDIANLENEIERLIKEIKTLENEVASHEQ

Beta-Ketothiolase (bktB) – Enzyme Linker – cTPR6 Spacer – ID Linker – ID6

MTREVVVVSGVRTAIGTFGGSLKDVAPAELGALVVREALARAQVSGDDVGHVVFGNVIQTEPRDMYLGRVAAVNG
GVTINAPALTVNRLCGSGLQAIVSAAQTILLGDTDVAIGGGAESMSRAPYLAPAARWGARMGDAGLVDMMLGALHD
PFHRIHMGVTAENVAKEYDISRAQQDEAALESHRRASAAIKAGYFKDQIVPVVSKGRKGDVTFDTDEHVRHDATIDD
MTKLRPVFVKENGTVTAGNASGLNDAAAAVVMMERAEAERRGLKPLARLVSYGHAGVDPKAMGIGPVPATKIALER
AGLQVSDLDVIEANEAFAAQACAVTKALGLDPAKVNPNGSGISLGHPIGATGALITVKALHELNRVQGRYALVTMCIG
GGQGIAAIFERIKLSGGGGSGGGGSGGGGSAEAWYNLGNAYYKQGDYQKAIEYYQKALELDPNNAEAWYNLGNAY
YKQGDYQKAIEYYQKALELDPNNAEAWYNLGNAYYKQGDYQKAIEDYQKALELDPNNLQAEAWKNLGNAYYKQGD
YQKAIEYYQKALELDPNNASAWYNLGNAYYKQGDYQKAIEYYQKALELDPNNAKAWYRRGNAYYKQGDYQKAIED
YQKALELDPNNRSRSAGGGGSGGGGSGGGGASDVMWEYKWENTGDAELYGPFTSAQMQTWVSEGYFPDGVYC
RKLDPPGGQFYNSKRIDFDLYTGSAGSAAGSGEFGSAEAAAKEAAAKAGSAGSAAGSGEFGSESDSVEFNNAISYV
NKIKTRFLDHPEIYRSFLEILHTYQKEQLHTKGRPFRGMSEEEVFTEVANLFRGQEDLLSEFGQFLPEAKR

Figure 6B (continued)

HMG-CoA Synthase – Enzyme Linker – cTPR6 Spacer – ID Linker – ID7

MKLSTKLCWCGIKGRLRPQKQQQLHNTNLQMTELKKQKTAEQKTRPQNVGIKGIQIYIPTQCVNQSELEKFDGVSQ
GKYTIGLGQTNMSFVNDREDIYSMSLTVLSKLIKSYNIDTNKIGRLEVGTETLIDKSKSVKSVLMQLFGENTDVEGIDTL
NACYGGTNALFNSLNWIESNAWDGRDAIVVCGDIAIYDKGAARPTGGAGTVAMWIGPDAPIVFDSVRASYMEHAYD
FYKPDFTSEYPYVDGHFSLTCYVKALDQVYKSYSKKAISKGLVSDPAGSDALNVLKYFDYNVFHVPTCKLVTKSYGR
LLYNDFRANPQLFPEVDAELATRDYDESLTDKNIEKTFVNVAKPFHKERVAQSLIVPTNTGNMYTASVYAAFASLLNY
VGSDDLQGKRVGLFSYGSGLAASLYSCKIVGDVQHIIKELDITNKLAKRITETPKDYEAAIELRENAHLKKNFKPQGSIE
HLQSGVYYLTNIDDKFRRSYDVKKKLSGGGGSGGGGSGGGGSAEAWYNLGNAYYKQGDYQKAIEYYQKALELDP
NNAEAWYNLGNAYYKQGDYQKAIEYYQKALELDPNNAEAWYNLGNAYYKQGDYQKAIEDYQKALELDPNNLQAEA
WKNLGNAYYKQGDYQKAIEYYQKALELDPNNASAWYNLGNAYYKQGDYQKAIEYYQKALELDPNNAKAWYRRGN
AYYKQGDYQKAIEDYQKALELDPNNRSRSAGGGGSGGGGSGGGGASLGPLPPGWEVRSTVSGRIYFVDHNNRTT
QFTDPRLHGSAGSAAGSGEFGSAEAAAKEAAAKAGSAGSAAGSGEFGSGAMGPLPPGWEKRTDSNGRVYFVNH
NTRITQWEDPRS

Truncated HMG-CoA Reductase – Enzyme Linker – cTPR6 Spacer – ID Linker – ID8

MVAVRRKALSILAEAPVLASDRLPYKNYDYDRVFGACCENVIGYMPLPVGVIGPLVIDGTSYHIPMATTEGCLVASAM
RGCKAINAGGGATTVLTKDGMTRGPVVRFPTLKRSGACKIWLDSEEGQNAIKKAFNSTSRFARLQHIQTCLAGDLLF
MRFRTTTGDAMGMNMISKGVEYSLKQMVEEYGWEDMEVVSVSGNYCTDKKPAAINWIEGRGKSVVAEATIPGDVV
RKVLKSDVSALVELNIAKNLVGSAMAGSVGGFNAHAANLVTAVFLALGQDPAQNVESSNCITLMKEVDGDLRISVSM
PSIEVGTIGGGTVLEPQGAMLDLLGVRGPHATAPGTNARQLARIVACAVLAGELSLCAALAAGHLVQSHMTHNRKLS
GGGGSGGGGSGGGGSAEAWYNLGNAYYKQGDYQKAIEYYQKALELDPNNAEAWYNLGNAYYKQGDYQKAIEYY
QKALELDPNNAEAWYNLGNAYYKQGDYQKAIEDYQKALELDPNNLQAEAWKNLGNAYYKQGDYQKAIEYYQKALE
LDPNNASAWYNLGNAYYKQGDYQKAIEYYQKALELDPNNAKAWYRRGNAYYKQGDYQKAIEDYQKALELDPNNRS
RSAGGGGSGGGGSGGGGASSYYHHHHHHLESTSLYKKAGSEFFRRERNKMAAAKCRNRRRELTDTLQAETDQLE
DEKSALQTEIANLLKEKEKLEFILAAHRPACKIPDDLGFPEEMSLEGSAGSAAGSGEFGSAEAAAKEAAAKAGSAGSA
AGSGEFGSSYYHHHHHHLESTSLYKKAGSGSQKVESLKQKIEELKQRKAQLKNDIANLEKEIAYAET

Mevalonate Kinase – Enzyme Linker – cTPR6 Spacer – ID Linker – ID9

MSLPFLTSAPGKVIIFGEHSAVYNKPAVAASVSALRTYLLISESSAPDTIELDFPDISFNHKWSINDFNAITEDQVNSQK
LAKAQQATDGLSQELVSLLDPLLAQLSESFHYHAAFCFLYMFVCLCPHAKNIKFSLKSTLPIGAGLGSSASISVSLALA
MAYLGGLIGSNDLEKLSENDKHIVNQWAFIGEKCIHGTPSGIDNAVATYGNALLFEKDSHNGTINTNNFKFLDDFPAIP
MILTYTRIPRSTKDLVARVRVLVTEKFPEVMKPILDAMGECALQGLEIMTKLSKCKGTDDEAVETNNELYEQLLELIRIN
HGLLVSIGVSHPGLELIKNLSDDLRIGSTKLTGAGGGGCSLTLLRRDITQEQIDSFKKKLQDDFSYETFETDLGGTGCC
LLSAKNLNKDLKIKSLVFQLFENKTTTKQQIDDLLLPGNTNLPWTSKLSGGGGSGGGGSGGGGSAEAWYNLGNAYY
KQGDYQKAIEYYQKALELDPNNAEAWYNLGNAYYKQGDYQKAIEYYQKALELDPNNAEAWYNLGNAYYKQGDYQK
AIEDYQKALELDPNNLQAEAWKNLGNAYYKQGDYQKAIEYYQKALELDPNNASAWYNLGNAYYKQGDYQKAIEYYQ
KALELDPNNAKAWYRRGNAYYKQGDYQKAIEDYQKALELDPNNRSRSAGGGGSGGGGSGGGGASMEPAMEPET
LEARINRATNPLNKELDWASINGFCEQLNEDFEGPPLATRLLAHKIQSPQEWEAIQALTVLETCMKSCGKRFHDEVG
KFRFLNELIKVVSPKYLGSRTSEKVKNKILELLYSWTVGLPEEVKIAEAYQMLKKQGIVKSGSAGSAAGSGEFGSAEA
AAKEAAAKAGSAGSAAGSGEFGSGAMGSMAEAEGESLESWLNKATNPSNRQEDWEYIIGFCDQINKELEGPQIAV
RLLAHKIQSPQEWEALQALTVLEACMKNCGRRFHNEVGKFRFLNELIKVVSPKYLGDRVSEKVKTKVIELLYSWTMA
LPEEAKIKDAYHMLKRQGIVQSDPPIPVDRTLIPSPPPRPKN

Figure 6B (continued)

Phosphomevalonate Kinase – Enzyme Linker – cTPR6 Spacer – ID Linker – ID10

MSELRAFSAPGKALLAGGYLVLDTKYEAFVVGLSARMHAVAHPYGSLQGSDKFEVRVKSKQFKDGEWLYHISPKSG
FIPVSIGGSKNPFIEKVIANVFSYFKPNMDDYCNRNLFVIDIFSDDAYHSQEDSVTEHRGNRRLSFHSHRIEEVPKTGL
GSSAGG[J2]LVTVLTTALASFFVSDLENNVDKYREVIHNLAQVAHCQAQGKIGSGFDVAAAAYGSIRYRRFPPALISNL
PDIGSATYGSKLAHLVDEEDWNITIKSNHLPSGLTLWMGDIKNGSETVKLVQKVKNWYDSHMPESLKIYTELDHANS
RFMDGLSKLDRLHETHDDYSDQIFESLERNDCTCQKYPEITEVRDAVATIRRSFRKITKESGADIEPPVQTSLLDDCQ
TLKGVLTCLIPGAGGYDAIAVITKQDVDLRAQTANDKRFSKVQWLDVTQADWGVRKEKDPETYLDKKLSGGGGSGG
GGSGGGGSAEAWYNLGNAYYKQGDYQKAIEYYQKALELDPNNAEAWYNLGNAYYKQGDYQKAIEYYQKALELDP
NNAEAWYNLGNAYYKQGDYQKAIEDYQKALELDPNNLQAEAWKNLGNAYYKQGDYQKAIEYYQKALELDPNNASA
WYNLGNAYYKQGDYQKAIEYYQKALELDPNNAKAWYRRGNAYYKQGDYQKAIEDYQKALELDPNNRSRSAGGGG
SGGGGSGGGGASSYYHHHHHHLESTSLYKKAGSGSQKVEELKNKIAELENRNAVKKNRVAHLKQEIAYLKDELAAH
EFEGSAGSAAGSGEFGSAEAAAKEAAAKAGSAGSAAGSGEFGSSYYHHHHHHLESTSLYKKAGSGSFENVTHEFIL
ATLENENAKLRRLEAKLERELARLRNEVAWL

Diphosphomevalonate Decarboxylase – Enzyme Linker – cTPR6 Spacer – ID Linker – ID11

MTVYTASVTAPVNIATLKYWGKRDTKLNLPTNSSISVTLSQDDLRTLTSAATAPEFERDTLWLNGEPHSIDNERTQNC
LRDLRQLRKEMESKDASLPTLSQWKLHIVSENNFPTAAGLASSAAGFAALVSAIAKLYQLPQSTSEISRIARKGSGSA
CRSLFGGYVAWEMGKAEDGHDSMAVQIADSSDWPQMKACVLVVSDIKKDVSSTQGMQLTVATSELFKERIEHVVP
KRFEVMRKAIVEKDFATFAKETMMDSNSFHATCLDSFPPIFYMNDTSKRIISWCHTINQFYGETIVAYTFDAGPNAVL
YYLAENESKLFAFIYKLFGSVPGWDKKFTTEQLEAFNHQFESSNFTARELDLELQKDVARVILTQVGSGPQETNESLI
DAKTGLPKEKLSGGGGSGGGGSGGGGSAEAWYNLGNAYYKQGDYQKAIEYYQKALELDPNNAEAWYNLGNAYYK
QGDYQKAIEYYQKALELDPNNAEAWYNLGNAYYKQGDYQKAIEDYQKALELDPNNLQAEAWKNLGNAYYKQGDYQ
KAIEYYQKALELDPNNASAWYNLGNAYYKQGDYQKAIEYYQKALELDPNNAKAWYRRGNAYYKQGDYQKAIEDYQ
KALELDPNNRSRSAGGGGSGGGGSGGGGASAMADLEQKVLEMEASTYDGVFIWKISDFPRKRQEAVAGRIPAIFS
PAFYTSRYGYKMCLRIYLNGDGTGRGTHLSLFFVVMKGPNDALLRWPFNQKVTLMLLDQNNREHVIDAFRPDVTSS
SFQRPVNDMNIASGCPLFCPVSKMEAKNSYVRDDAIFIKAIVDLTGLGSAGSAAGSGEFGSAEAAAKEAAAKAGSAG
SAAGSGEFGSASIKLQSSDGEIFEVDVEIAKQSVTIKTMLEDLGMDDEGDDDPVPLPNVNAAILKKVIQWCTHHKDDP
PPPEDDENKEKRTDDIPVWDQEFLKVDQGTLFELILAANYLDIKGLLDVTCKTVANMIKGKTPEEIRKTFNIKNDFTEE
EEAQVRKENQWC

Isopentenyl-Diphosphate Delta-Isomerase – Enzyme Linker – cTPR6 Spacer – ID Linker – ID12

MTADNNSMPHGAVSSYAKLVQNQTPEDILEEFPEIIPLQQRPNTRSSETSNDESGETCFSGHDEEQIKLMNENCIVL
DWDDNAIGAGTKKVCHLMENIEKGLLHRAFSVFIFNEQGELLLQQRATEKITFPDLWTNTCCSHPLCIDDELGLKGKL
DDKIKGAITAAVRKLDHELGIPEDETKTRGKFHFLNRIHYMAPSNEPWGEHEIDYILFYKINAKENLTVNPNVNEVRDF
KWVSPNDLKTMFADPSYKFTPWFKIICENYLFNWWEQLDDLSEVENDRQIHRMLKLSGGGGSGGGGSGGGGSAE
AWYNLGNAYYKQGDYQKAIEYYQKALELDPNNAEAWYNLGNAYYKQGDYQKAIEYYQKALELDPNNAEAWYNLGN
AYYKQGDYQKAIEDYQKALELDPNNLQAEAWKNLGNAYYKQGDYQKAIEYYQKALELDPNNASAWYNLGNAYYKQ
GDYQKAIEYYQKALELDPNNAKAWYRRGNAYYKQGDYQKAIEDYQKALELDPNNRSRSAGGGGSGGGGSGGGGA
SSYYHHHHHHLESTSLYKKAGSGSNTVKELKNYIQELEERNAELKNLKEHLKFAKAELEFELAAHKFEGSAGSAAGS
GEFGSAEAAAKEAAAKAGSAGSAAGSGEFGSSYYHHHHHHLESTSLYKKAGSGSQKVAQLKNRVAYKLKENAKLE
NIVARLENDNANLEKDIANLEKDIANLERDVAR

Figure 6B (continued)

Geranyl-Diphosphate Synthase (ERG20$^{WW}$) – Enzyme Linker – cTPR6 Spacer – ID Linker – ID13

MEAKIDELINNDPVWSSQNESLISKPYNHILLKPGKNFRLNLIVQINRVMNLPKDQLAIVSQIVELLHNSSLLIDDIEDNA
PLRRGQTTSHLIWGVPSTINTANYMYFRAMQLVSQLTTKEPLYHWLITIFNEELINLHRGQGLDIYWRDFLPEIIPTQE
MYLNMVMNKTGGLFRLTLRLMEALSPSSHHGHSLVPFINLLGIIYQIRDDYLNLKDFQMSSEKGFAEDITEGKLSFPIV
HALNFTKTKGQTEQHNEILRILLLRTSDKDIKLKLIQILEFDTNSLAYTKNFINQLVNMIKNDNENKYLPDLASHSDTATN
LHDELLYIIDHLSELKLSGGGGSGGGGSGGGGSAEAWYNLGNAYYKQGDYQKAIEYYQKALELDPNNAEAWYNLG
NAYYKQGDYQKAIEYYQKALELDPNNAEAWYNLGNAYYKQGDYQKAIEDYQKALELDPNNLQAEAWKNLGNAYYK
QGDYQKAIEYYQKALELDPNNASAWYNLGNAYYKQGDYQKAIEYYQKALELDPNNAKAWYRRGNAYYKQGDYQK
AIEDYQKALELDPNNRSRSAGGGGSGGGGSGGGGASLCTMKKGPSGYGFNLHSDKSKPGQFIRSVDPDSPAEAS
GLRAQDRIVEVNGVCMEGKQHGDVVSAIRAGGDETKLLVVDREGSAGSAAGSGEFGSAEAAAKEAAAKAGSAGSA
AGSGEFGSSSGAIIYTVELKRYGGPLGITISGTEEPFDPIIISSLTKGGLAERTGAIHIGDRILAINSSSLKGKPLSEAIHLL
QMAGETVTLKIKKQTDAQPASS

Olivetol Synthase – Enzyme Linker – cTPR6 Spacer – ID Linker – ID14

MNHLRAEGPASVLAIGTANPENILLQDEFPDYYFRVTKSEHMTQLKEKFRKICDKSMIRKRNCFLNEEHLKQNPRLVE
HEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSESDLELLVGQAIFGDGAAAVIVGAEPDESVGERPIFE
LVSTGQTILPNSEGTIGGHIREAGLIFDLHKDVPMLISNNIEKCLIEAFTPIGISDWNSIFWITHPGGKAILDKVEEKLHLK
SDKFVDSRHVLSEHGNMSSSTVLFVMDELRKRSLEEGKSTTGDGFEWGVLFGFGPGLTVERVVVRSVPIKYKLSGG
GGSGGGGSGGGGSAEAWYNLGNAYYKQGDYQKAIEYYQKALELDPNNAEAWYNLGNAYYKQGDYQKAIEYYQKA
LELDPNNAEAWYNLGNAYYKQGDYQKAIEDYQKALELDPNNLQAEAWKNLGNAYYKQGDYQKAIEYYQKALELDP
NNASAWYNLGNAYYKQGDYQKAIEYYQKALELDPNNAKAWYRRGNAYYKQGDYQKAIEDYQKALELDPNNRSRSA
GGGGSGGGGSGGGGASGNNLETYEWYNKSISRDKAEKLLLDTGKEGAFMVRDSRTPGTYTVSVFTKAIISENPCIK
HYHIKETNDSPKRYYVAEKYVFDSIPLLIQYHQYNGGGLVTRLRYPVCGGSAGSAAGSGEFGSAEAAAKEAAAKAG
SAGSAAGSGEFGSGSHPWFFGKIPRAKAEEMLSKQRHDGAFLIRESESAPGDFSLSVKFGNDVQHFKVLRDGAGK
YFLWVVKFNSLNELVDYHRSTSVSRNQQIFLRDIEQVPQQPT

Olivetolic Acid Cyclase – Enzyme Linker – cTPR6 Spacer – ID Linker – ID15

MAVKHLIVLKFKDEITEAQKEEFFKTYVNLVNIIPAMKDVYWGKDVTQKNKEEGYTHIVEVTFESVETIQDYIIHPAHVG
FGDVYRSFWEKLLIFDYTPRKKLSGGGGSGGGGSGGGGSAEAWYNLGNAYYKQGDYQKAIEYYQKALELDPNNA
EAWYNLGNAYYKQGDYQKAIEYYQKALELDPNNAEAWYNLGNAYYKQGDYQKAIEDYQKALELDPNNLQAEAWKN
LGNAYYKQGDYQKAIEYYQKALELDPNNASAWYNLGNAYYKQGDYQKAIEYYQKALELDPNNAKAWYRRGNAYYK
QGDYQKAIEDYQKALELDPNNRSRSAGGGGSGGGGSGGGGASGQDRSEATLIKRFKGEGVRYKAKLIGIDEVSAA
RGDKLCQDSMMKLKGVVAGARSKGEHKQKIFLTISFGGIKIFDEKTGALQHHHAVHEISYIAKDITDHRAFGYVCGKE
GNHRFVAIKTAQAAEPVILDLRDLFQLIYELKQREELEKKAGSAGSAAGSGEFGSAEAAAKEAAAKAGSAGSAAGSG
EFGSGSHMGSQFWVTSQKTEASERCGLQGSYILRVEAEKLTLLTLGAQSQILEPLLFWPYTLLRRYGRDKVMFSFE
AGRRCPSGPGTFTFQTSQGNDIFQAVEAAIQQQKAQGKVGQAQDILRLEHHHHHH

Figure 6B (continued)

CBGA Synthase – Enzyme Linker – cTPR6 Spacer – ID Linker – ID16

MGLSSVCTFSFQTNYHTLLNPHNNNPKTSLLCYRHPKTPIKYSYNNFPSKHCSTKSFHLQNKCSESLSIAKNSIRAAT
TNQTEPPESDNHSVATKILNFGKACWKLQRPYTIIAFTSCACGLFGKELLHNTNLISWSLMFKAFFFLVAILCIASFTTTI
NQIYDLHIDRINKPDLPLASGEISVNTAWIMSIIVALFGLIITIKMKGGPLYIFGYCFGIFGGIVYSVPPFRWKQNPSTAFL
LNFLAHIITNFTFYYASRAALGLPFELRPSFTFLLAFMKSMGSALALIKDASDVEGDTKFGISTLASKYGSRNLTLFCSG
IVLLSYVAAILAGIIWPQAFNSNVMLLSHAILAFWLILQTRDFALTNYDPEAGRRFYEFMWKLYYAEYLVYVFIKLSGGG
GSGGGGSGGGGSAEAWYNLGNAYYKQGDYQKAIEYYQKALELDPNNAEAWYNLGNAYYKQGDYQKAIEYYQKAL
ELDPNNAEAWYNLGNAYYKQGDYQKAIEDYQKALELDPNNLQAEAWKNLGNAYYKQGDYQKAIEYYQKALELDPN
NASAWYNLGNAYYKQGDYQKAIEYYQKALELDPNNAKAWYRRGNAYYKQGDYQKAIEDYQKALELDPNNRSRSAG
GGGSGGGGSGGGGASAEYVRALFDFNGNDEEDLPFKKGDILRIRDKPEEQWWNAEDSEGKRGMIPVPYVEKYGS
AGSAAGSGEFGSAEAAAKEAAAKAGSAGSAAGSGEFGSLIKHMRAEALFDFTGNSKLELNFKAGDVIFLLSRINKDW
LEGTVRGATGIFPLSFVKILK

Acetyl-CoA Carboxylase – Enzyme Linker – cTPR6 Spacer – ID Linker – ID17

MSEESLFESSPQKMEYEITNYSERHTELPGHFIGLNTVDKLEESPLRDFVKSHGGHTVISKILIANNGIAAVKEIRSVRK
WAYETFGDDRTVQFVAMATPEDLEANAEYIRMADQYIEVPGGTNNNNYANVDLIVDIAERADVDAVWAGWGHASE
NPLLPEKLSQSKRKVIFIGPPGNAMRSLGDKISSTIVAQSAKVPCIPWSGTGVDTVHVDEKTGLVSVDDDIYQKGCCT
SPEDGLQKAKRIGFPVMIKASEGGGGKGIRQVEREEDFIALYHQAANEIPGSPIFIMKLAGRARHLEVQLLADQYGTNI
SLFGRDCSVQRRHQKIIEEAPVTIAKAETFHEMEKAAVRLGKLVGYVSAGTVEYLYSHDDGKFYFLELNPRLQVEHP
TTEMVSGVNLPAAQLQIAMGIPMHRISDIRTLYGMNPHSASEIDFEFKTQDATKKQRRPIPKGHCTACRITSEDPNDG
FKPSGGTLHELNFRSSSNVWGYFSVGNNGNIHSFSDSQFGHIFAFGENRQASRKHMVVALKELSIRGDFRTTVEYLI
KLLETEDFEDNTITTGWLDDLITHKMTAEKPDPTLAVICGAATKAFLASEEARHKYIESLQKGQVLSKDLLQTMFPVDF
IHEGKRYKFTVAKSGNDRYTLFINGSKCDIILRQLSDGGLLIAIGGKSHTIYWKEEVAATRLSVDSMTTLLEVENDPTQL
RTPSPGKLVKFLVENGEHIIKGQPYAEIEVMKMQMPLVSQENGIVQLLKQPGSTIVAGDIMAIMTLDDPSKVKHALPFE
GMLPDFGSPVIEGTKPAYKFKSLVSTLENILKGYDNQVIMNASLQQLIEVLRNPKLPYSEWKLHISALHSRLPAKLDEQ
MEELVARSLRRGAVFPARQLSKLIDMAVKNPEYNPDKLLGAVVEPLADIAHKYSNGLEAHEHSIFVHFLEEYYEVEKL
FNGPNVREENIILKLRDENPKDLDKVALTVLSHSKVSAKNNLILAILKHYQPLCKLSSKVSAIFSTPLQHIVELESKATAK
VALQAREILIQGALPSVKERTEQIEHILKSSVVKVAYGSSNPKRSEPDLNILKDLIDSNYVVFDVLLQFLTHQDPVVTAA
AAQVYIRRAYRAYTIGDIRVHEGVTVPIVEWKFQLPSAAFSTFPTVKSKMGMNRAVSVSDLSYVANSQSSPLREGILM
AVDHLDDVDEILSQSLEVIPRHQSSSNGPAPDRSGSSASLSNVANVCVASTEGFESEEEILVRLREILDLNKQELINAS
IRRITFMFGFKDGSYPKYYTFNGPNYNENETIRHIEPALAFQLELGRLSNFNIKPIFTDNRNIHVYEAVSKTSPLDKRFF
TRGIIRTGHIRDDISIQEYLTSEANRLMSDILDNLEVTDTSNSDLNHIFINFIAVFDISPEDVEAAFGGFLERFGKRLLRLR
VSSAEIRIIIKDPQTGAPVPLRALINNVSGYVIKTEMYTEVKNAKGEWVFKSLGKPGSMHLRPIATPYPVKEWLQPKRY
KAHLMGTTYVYDFPELFRQASSSQWKNFSADVKLTDDFFISNELIEDENGELTEVEREPGANAIGMVAFKITVKTPEY
PRGRQFVVVANDITFKIGSFGPQEDEFFNKVTEYARKRGIPRIYLAANSGARIGMAEEIVPLFQVAWNDAANPDKGF
QYLYLTSEGMETLKKFDKENSVLTERTVINGEERFVIKTIIGSEDGLGVECLRGSGLIAGATSRAYHDIFTITLVTCRSV
GIGAYLVRLGQRAIQVEGQPIILTGAPAINKMLGREVYTSNLQLGGTQIMYNNGVSHLTAVDDLAGVEKIVEWMSYVP
AKRNMPVPILETKDTWDRPVDFTPTNDETYDVRWMIEGRETESGFEYGLFDKGSFFETLSGWAKGVVVGRARLGGI
PLGVIGVETRTVENLIPADPANPNSAETLIQEPGQVWHPNSAFKTAQAINDFNNGEQLPMMILANWRGFSGGQRDM
FNEVLKYGSFIVDALVDYKQPIIIYIPPTGELRGGSWVVVDPTINADQMEMYADVNARAGVLEPQGMVGIKFRREKLL
DTMNRLDDKYRELRSQLSNKSLAPEVHQQISKQLADRERELLPIYGQISLQFADLHDRSSRMVAKGVISKELEWTEA
RRFFFWRLRRRLNEEYLIKRLSHQVGEASRLEKIARIRSWYPASVDHEDDRQVATWIEENYKTLDDKLKGLKLESFA
QDLAKKIRSDHDNAIDGLSEVIKMLSTDDKEKLLKTLKKLSGGGGSGGGGSGGGGSAEAWYNLGNAYYKQGDYQK
AIEYYQKALELDPNNAEAWYNLGNAYYKQGDYQKAIEYYQKALELDPNNAEAWYNLGNAYYKQGDYQKAIEDYQKA
LELDPNNLQAEAWKNLGNAYYKQGDYQKAIEYYQKALELDPNNASAWYNLGNAYYKQGDYQKAIEYYQKALELDP
NNAKAWYRRGNAYYKQGDYQKAIEDYQKALELDPNNRSRSAGGGGSGGGGSGGGGASGSHMRLGAQSIQPTAN
LDRTDDLVYLNVMELVRAVLELKNELAQLPPEGYVVVVKNVGLTLRKLIGSVDDLLPSLPSSSRTEIEGTQKLLNKDLA
ELINKMRLAQQNAVTSLSEECKRQMLTASHTLAVDAKNLLDAVDQAKVLANLAHPPAEGSAGSAAGSGEFGSAEAA
AKEAAAKAGSAGSAAGSGEFGSGAMATPGSENVLPREPLIATAVKFLQNSRVRQSPLATRRAFLKKKGLTDEEIDM
AFQQSGTAADEPSSLW

Figure 6C

Cannabinoidergic Metabolon Scaffold – (Myc)$_3$

MGSAGSAAGSGEFGSAGSAAGSGEFGSAGSAAGSGEFSYYHHHHHHLESTSLYKKAGSGSARNAYLRKKIA
RLKKDNLQLERDEQNLEKIIANLRDEIARLENEVASHEQGSAGSAAGSGEFAEAAAKEAAAKAGSAGSAAGSG
EFSYYHHHHHHLESTSLYKKAGSGSNLVAQLENEVASLENENETLKKKNLHKKDLIAYLEKEIANLRKKIEEGSA
GSAAGSGEFGSAEAAAKEAAAKEAAAKEAAAKAGSAGSAAGSGEFGSSYYHHHHHHLESTSLYKKAGSGSQ
KVAELKNRVAVKLNRNEQLKNKVEELKNRNAYLKNELATLENEVARLENDVAEGSAGSAAGSGEFAEAAAKEA
AAKAGSAGSAAGSGEFSYYHHHHHHLESTSLYKKAGSGSNEVTTLENDAAFIENENAYLEKEIARLRKEKAALR
NRLAHKKGSAGSAAGSGEFGSAEAAAKEAAAKEAAAKEAAAKAGSAGSAAGSGEFGSRPPTISNPPPLISSAK
HPSVGSAGSAAGSGEFAEAAAKEAAAKAGSAGSAAGSGEFNFLQSRPEPTAPPEESFRSGGSAGSAAGSGE
FGSAEAAAKEAAAKEAAAKEAAAKAGSAGSAAGSGEFGSSKGTGLNPNAKVWQEIAPGNGSAGSAAGSGEF
AEAAAKEAAAKAGSAGSAAGSGEFPDGGTTFEHLWSSLEPDSTYGSAGSAAGSGEFGSAEAAAKEAAAKEA
AAKEAAAKAGSAGSAAGSGEFGSSYYHHHHHHLESTSLYKKAGSGSKRIAYLRKKIAALKKDNANLEKDIANLE
NEIERLIKEIKTLENEVASHEQGSAGSAAGSGEFAEAAAKEAAAKAGSAGSAAGSGEFSYYHHHHHHLESTSLY
KKAGSGSNLLATLRSTAAVLENENHVLEKEKEKLRKEKEQLLNKLEAYKGSAGSAAGSGEFGSAEAAAKEAAA
KEAAAKEAAAKAGSAGSAAGSGEFGSPATSQHPPPPPGHRSQAPSHGSAGSAAGSGEFAEAAAKEAAAKAG
SAGSAAGSGEFELNSLLILLEAAEYLERRDRGSAGSAAGSGEFGSAEAAAKEAAAKEAAAKEAAAKAGSAGSA
AGSGEFGSRPPTISNPPPLISSAKHPSVGSAGSAAGSGEFAEAAAKEAAAKAGSAGSAAGSGEFNFLQSRPEP
TAPPEESFRSGGSAGSAAGSGEFGSAEAAAKEAAAKEAAAKEAAAKAGSAGSAAGSGEFGSSKGTGLNPNA
KVWQEIAPGNGSAGSAAGSGEFAEAAAKEAAAKAGSAGSAAGSGEFPDGGTTFEHLWSSLEPDSTYGSAGS
AAGSGEFGSAEAAAKEAAAKEAAAKEAAAKAGSAGSAAGSGEFGSSYYHHHHHHLESTSLYKKAGSGSKRIA
YLRKKIAALKKDNANLEKDIANLENEIERLIKEIKTLENEVASHEQGSAGSAAGSGEFAEAAAKEAAAKAGSAGS
AAGSGEFSYYHHHHHHLESTSLYKKAGSGSNLLATLRSTAAVLENENHVLEKEKEKLRKEKEQLLNKLEAYKG
SAGSAAGSGEFGSAEAAAKEAAAKEAAAKEAAAKAGSAGSAAGSGEFGSALVDDAADYEPPPSNNEEALGSA
GSAAGSGEFAEAAAKEAAAKAGSAGSAAGSGEFRELFDDPSYVNVQNLDKARQGSAGSAAGSGEFGSAEAA
AKEAAAKEAAAKEAAAKAGSAGSAAGSGEFGSKNTKSMNFDNPVYRKTTEEEGSAGSAAGSGEFAEAAAKE
AAAKAGSAGSAAGSGEFRSLPSTWIENKLYGMSDPNWGSAGSAAGSGEFGSAEAAAKEAAAKEAAAKEAAA
KAGSAGSAAGSGEFGSVVDNSPPPALPPKKRQSAPSGSAGSAAGSGEFAEAAAKEAAAKAGSAGSAAGSGE
FTQRSKPQPAVPPRPSADLILGSAGSAAGSGEFGSAEAAAKEAAAKEAAAKEAAAKAGSAGSAAGSGEFGST
DEEREETEEEVYLLNSTTLGSAGSAAGSGEFAEAAAKEAAAKAGSAGSAAGSGEFDGNVSGTQRLDSATVRT
YSCGSAGSAAGSGEFGSAEAAAKEAAAKEAAAKEAAAKAGSAGSAAGSGEFGSSYYHHHHHHLESTSLYKK
AGSGSQKVAQLKNRVAYKLKENAKLENIVARLENDNANLEKDIANLEKDIANLERDVARGSAGSAAGSGEFAE
AAAKEAAAKAGSAGSAAGSGEFSYYHHHHHHLESTSLYKKAGSGSNTVKELKNYIQELEERNAELKNLKEHLK
FAKAELEFELAAHKFEGSAGSAAGSGEFGSAEAAAKEAAAKEAAAKEAAAKAGSAGSAAGSGEFGSHDDSLP
HPQQATDDSGHESDGSAGSAAGSGEFAEAAAKEAAAKAGSAGSAAGSGEFGSPNAGSVEQTPKKPGLRRR
GSAGSAAGSGEFGSAEAAAKEAAAKEAAAKEAAAKAGSAGSAAGSGEFGSSYYHHHHHHLESTSLYKKAGS
GSFENVTHEFILATLENENAKLRRLEAKLERELARLRNEVAWLGSAGSAAGSGEFAEAAAKEAAAKAGSAGSA
AGSGEFSYYHHHHHHLESTSLYKKAGSGSQKVEELKNKIAELENRNAVKKNRVAHLKQEIAYLKDELAAHEFE
GSAGSAAGSGEFGSAEAAAKEAAAKEAAAKEAAAKAGSAGSAAGSGEFGSVSSTKLVSFHDDSDEDLLHIGS
AGSAAGSGEFAEAAAKEAAAKAGSAGSAAGSGEFAAATPISTFHDDSDEDLLHVGSAGSAAGSGEFGSAEAA
AKEAAAKEAAAKEAAAKAGSAGSAAGSGEFGSSYYHHHHHHLESTSLYKKAGSGSQKVESLKQKIEELKQRK
AQLKNDIANLEKEIAYAETGSAGSAAGSGEFAEAAAKEAAAKAGSAGSAAGSGEFSYYHHHHHHLESTSLYKK
AGSEFFRRERNKMAAAKCRNRRRELTDTLQAETDQLEDEKSALQTEIANLLKEKEKLEFILAAHRPACKIPDDL
GFPEEMSLEGSAGSAAGSGEFGSAEAAAKEAAAKEAAAKEAAAKAGSAGSAAGSGEFGSFQMPADTPPPAY
LPPEDPMTGSAGSAAGSGEFAEAAAKEAAAKAGSAGSAAGSGEFERESNEEPPPPYEDPYWGNGGSAGSA
AGSGEFGSAEAAAKEAAAKEAAAKEAAAKAGSAGSAAGSGEFGSSYYHHHHHHLESTSLYKKAGSGSQKVA
ELKNRVAVKLNRNEQLKNKVEELKNRNAYLKNELATLENEVARLENDVAEGSAGSAAGSGEFAEAAAKEAAAK

Figure 6C (continued)

AGSAGSAAGSGEFSYYHHHHHHLESTSLYKKAGSGSNEVTTLENDAAFIENENAYLEKEIARLRKEKAALRNRL
AHKKSYYHHHHHHLESTSLYKKAGSGSARNAYLRKKIARLKKDNLQLERDEQNLEKIIANLRDEIARLENEVASH
EQGSAGSAAGSGEFAEAAAKEAAAKAGSAGSAAGSGEFSYYHHHHHHLESTSLYKKAGSGSNLVAQLENEV
ASLENENETLKKKNLHKKDLIAYLEKEIANLRKKIEEGSAGSAAGSGEFGSAEAAAKEAAAKEAAAKEAAAKAG
SAGSAAGSGEFGSEQKLISEEDLEQKLISEEDLEQKLISEEDLGSAGSAAGSGEFGSAGSAAGSGEFGSAGSA
AGSGEF

Figure 6D

Malonyl-CoA Metabolon Scaffold – $(FLAG)_3$

MGSAGSAAGSGEFGSAGSAAGSGEFGSAGSAAGSGEFSYYHHHHHHLESTSLYKKAGSGSARNAYLRKKIA
RLKKDNLQLERDEQNLEKIIANLRDEIARLENEVASHEQGSAGSAAGSGEFAEAAAKEAAAKAGSAGSAAGSG
EFSYYHHHHHHLESTSLYKKAGSGSNLVAQLENEVASLENENETLKKKNLHKKDLIAYLEKEIANLRKKIEEGSA
GSAAGSGEFGSAEAAAKEAAAKEAAAKEAAAKAGSAGSAAGSGEFGSSATRELDELMASLSDFKIQGGSAGS
AAGSGEFAEAAAKEAAAKAGSAGSAAGSGEFDLALSENWAQEFLAAGDAVDGSAGSAAGSGEFGSAEAAAK
EAAAKEAAAKEAAAKAGSAGSAAGSGEFGSDYKDDDDKDYKDDDDKDYKDDDDKGSAGSAAGSGEFGSAG
SAAGSGEFGSAGSAAGSGEF

SEQUENCE LISTING

```
Sequence total quantity: 212
SEQ ID NO: 1            moltype = AA  length = 11
FEATURE                 Location/Qualifiers
source                  1..11
                        mol_type = protein
                        organism = synthetic construct
SEQUENCE: 1
PPPALPPKRR R                                                       11

SEQ ID NO: 2            moltype = AA  length = 32
FEATURE                 Location/Qualifiers
source                  1..32
                        mol_type = protein
                        organism = synthetic construct
SEQUENCE: 2
LVGALMHVMQ KRSRAIHSSD EGEDQAGDED ED                                32

SEQ ID NO: 3            moltype = AA  length = 43
FEATURE                 Location/Qualifiers
source                  1..43
```

```
                      mol_type = protein
                      organism = synthetic construct
SEQUENCE: 3
ITIRAAFLEK ENTALRTEIA ELEKEVGRCE NIVSKYETRY GPL                     43

SEQ ID NO: 4          moltype = AA  length = 43
FEATURE               Location/Qualifiers
source                1..43
                      mol_type = protein
                      organism = synthetic construct
SEQUENCE: 4
LEIRAAFLEK ENTALRTRAA ELRKRVGRCR NIVSKYETRY GPL                     43

SEQ ID NO: 5          moltype = AA  length = 70
FEATURE               Location/Qualifiers
source                1..70
                      mol_type = protein
                      organism = synthetic construct
SEQUENCE: 5
SYYHHHHHHL ESTSLYKKAG SGSNLVAQLE NEVASLENEN ETLKKKNLHK KDLIAYLEKE  60
IANLRKKIEE                                                          70

SEQ ID NO: 6          moltype = AA  length = 73
FEATURE               Location/Qualifiers
source                1..73
                      mol_type = protein
                      organism = synthetic construct
SEQUENCE: 6
SYYHHHHHHL ESTSLYKKAG SGSARNAYLR KKIARLKKDN LQLERDEQNL EKIIANLRDE  60
IARLENEVAS HEQ                                                      73

SEQ ID NO: 7          moltype = AA  length = 65
FEATURE               Location/Qualifiers
source                1..65
                      mol_type = protein
                      organism = synthetic construct
SEQUENCE: 7
SYYHHHHHHL ESTSLYKKAG SGSNEVTTLE NDAAFIENEN AYLEKEIARL RKEKAALRNR  60
LAHKK                                                               65

SEQ ID NO: 8          moltype = AA  length = 77
FEATURE               Location/Qualifiers
source                1..77
                      mol_type = protein
                      organism = synthetic construct
SEQUENCE: 8
SYYHHHHHHL ESTSLYKKAG SGSQKVAELK NRVAVKLNRN EQLKNKVEEL KNRNAYLKNE  60
LATLENEVAR LENDVAE                                                  77

SEQ ID NO: 9          moltype = AA  length = 64
FEATURE               Location/Qualifiers
source                1..64
                      mol_type = protein
                      organism = synthetic construct
SEQUENCE: 9
ENLYFQGENL YFQGDSSESC WNCGRKASET CSGCNTARYC GSFCQHKDWE KHHHICGQTL  60
QAQQ                                                                64

SEQ ID NO: 10         moltype = AA  length = 145
FEATURE               Location/Qualifiers
source                1..145
                      mol_type = protein
                      organism = synthetic construct
SEQUENCE: 10
MAVSESQLKK MVSKYKYRDL TVRETVNVIT LYKDLKPVLD SYVFNDGSSR ELMNLTGTIP  60
VPYRGNTYNI PICLWLLDTY PYNPPICFVK PTSSMTIKTG KHVDANGKIY LPYLHEWKHP  120
QSDLLGLIQV MIVVFGDEPP VFSRP                                         145

SEQ ID NO: 11         moltype = AA  length = 88
FEATURE               Location/Qualifiers
source                1..88
                      mol_type = protein
                      organism = synthetic construct
SEQUENCE: 11
GPLGSPLTAS MLASAPPQEQ KQMLGERLFP LIQAMHPTLA GKITGMLLEI DNSELLHMLE  60
SPESLRSKVD EAVAVLQAHQ AKEAAQKA                                      88

SEQ ID NO: 12         moltype = AA  length = 107
FEATURE               Location/Qualifiers
```

-continued

```
source                  1..107
                        mol_type = protein
                        organism = synthetic construct
SEQUENCE: 12
NTNMSVPTDG AVTTSQIPAS EQETLVRPKP LLLKLLKSVG AQKDTYTMKE VLFYLGQYIM  60
TKRLYDEKQQ HIVYCSNDLL GDLFGVPSFS VKEHRKIYTM IYRNLVV                107

SEQ ID NO: 13           moltype = AA  length = 65
FEATURE                 Location/Qualifiers
source                  1..65
                        mol_type = protein
                        organism = synthetic construct
SEQUENCE: 13
SYYHHHHHHL ESTSLYKKAG SGSNLLATLR STAAVLENEN HVLEKEKEKL RKEKEQLLNK  60
LEAYK                                                              65

SEQ ID NO: 14           moltype = AA  length = 73
FEATURE                 Location/Qualifiers
source                  1..73
                        mol_type = protein
                        organism = synthetic construct
SEQUENCE: 14
SYYHHHHHHL ESTSLYKKAG SGSKRIAYLR KKIAALKKDN ANLEKDIANL ENEIERLIKE  60
IKTLENEVAS HEQ                                                     73

SEQ ID NO: 15           moltype = AA  length = 62
FEATURE                 Location/Qualifiers
source                  1..62
                        mol_type = protein
                        organism = synthetic construct
SEQUENCE: 15
DVMWEYKWEN TGDAELYGPF TSAQMQTWVS EGYFPDGVYC RKLDPPGGQF YNSKRIDFDL  60
YT                                                                 62

SEQ ID NO: 16           moltype = AA  length = 85
FEATURE                 Location/Qualifiers
source                  1..85
                        mol_type = protein
                        organism = synthetic construct
SEQUENCE: 16
ESDSVEFNNA ISYVNKIKTR FLDHPEIYRS FLEILHTYQK EQLHTKGRPF RGMSEEEVFT  60
EVANLFRGQE DLLSEFGQFL PEAKR                                        85

SEQ ID NO: 17           moltype = AA  length = 36
FEATURE                 Location/Qualifiers
source                  1..36
                        mol_type = protein
                        organism = synthetic construct
SEQUENCE: 17
LGPLPPGWEV RSTVSGRIYF VDHNNRTTQF TDPRLH                            36

SEQ ID NO: 18           moltype = AA  length = 37
FEATURE                 Location/Qualifiers
source                  1..37
                        mol_type = protein
                        organism = synthetic construct
SEQUENCE: 18
GAMGPLPPGW EKRTDSNGRV YFVNHNTRIT QWEDPRS                           37

SEQ ID NO: 19           moltype = AA  length = 101
FEATURE                 Location/Qualifiers
source                  1..101
                        mol_type = protein
                        organism = synthetic construct
SEQUENCE: 19
SYYHHHHHHL ESTSLYKKAG SEFFRRERNK MAAAKCRNRR RELTDTLQAE TDQLEDEKSA  60
LQTEIANLLK EKEKLEFILA AHRPACKIPD DLGFPEEMSL E                      101

SEQ ID NO: 20           moltype = AA  length = 59
FEATURE                 Location/Qualifiers
source                  1..59
                        mol_type = protein
                        organism = synthetic construct
SEQUENCE: 20
SYYHHHHHHL ESTSLYKKAG SGSQKVESLK QKIEELKQRK AQLKNDIANL EKEIAYAET   59

SEQ ID NO: 21           moltype = AA  length = 147
FEATURE                 Location/Qualifiers
source                  1..147
```

```
                        mol_type = protein
                        organism = synthetic construct
SEQUENCE: 21
MEPAMEPETL EARINRATNP LNKELDWASI NGFCEQLNED FEGPPLATRL LAHKIQSPQE  60
WEAIQALTVL ETCMKSCGKR FHDEVGKFRF LNELIKVVSP KYLGSRTSEK VKNKILELLY  120
SWTVGLPEEV KIAEAYQMLK KQGIVKS                                      147

SEQ ID NO: 22           moltype = AA  length = 171
FEATURE                 Location/Qualifiers
source                  1..171
                        mol_type = protein
                        organism = synthetic construct
SEQUENCE: 22
GAMGSMAEAE GESLESWLNK ATNPSNRQED WEYIIGFCDQ INKELEGPQI AVRLLAHKIQ  60
SPQEWEALQA LTVLEACMKN CGRRFHNEVG KFRFLNELIK VVSPKYLGDR VSEKVKTKVI  120
ELLYSWTMAL PEEAKIKDAY HMLKRQGIVQ SDPPIPVDRT LIPSPPPRPK N            171

SEQ ID NO: 23           moltype = AA  length = 67
FEATURE                 Location/Qualifiers
source                  1..67
                        mol_type = protein
                        organism = synthetic construct
SEQUENCE: 23
SYYHHHHHHL ESTSLYKKAG SGSQKVEELK NKIAELENRN AVKKNRVAHL KQEIAYLKDE  60
LAAHEFE                                                            67

SEQ ID NO: 24           moltype = AA  length = 64
FEATURE                 Location/Qualifiers
source                  1..64
                        mol_type = protein
                        organism = synthetic construct
SEQUENCE: 24
SYYHHHHHHL ESTSLYKKAG SGSFENVTHE FILATLENEN AKLRRLEAKL ERELARLRNE  60
VAWL                                                               64

SEQ ID NO: 25           moltype = AA  length = 168
FEATURE                 Location/Qualifiers
source                  1..168
                        mol_type = protein
                        organism = synthetic construct
SEQUENCE: 25
AMADLEQKVL EMEASTYDGV FIWKISDFPR KRQEAVAGRI PAIFSPAFYT SRYGYKMCLR  60
IYLNGDGTGR GTHLSLFFVV MKGPNDALLR WPFNQKVTLM LLDQNNREHV IDAFRPDVTS  120
SSFQRPVNDM NIASGCPLFC PVSKMEAKNS YVRDDAIFIK AIVDLTGL               168

SEQ ID NO: 26           moltype = AA  length = 159
FEATURE                 Location/Qualifiers
source                  1..159
                        mol_type = protein
                        organism = synthetic construct
SEQUENCE: 26
ASIKLQSSDG EIFEVDVEIA KQSVTIKTML EDLGMDDEGD DDPVPLPNVN AAILKKVIQW  60
CTHHKDDPPP PEDDENKEKR TDDIPVWDQE FLKVDQGTLF ELILAANYLD IKGLLDVTCK  120
TVANMIKGKT PEEIRKTFNI KNDFTEEEEA QVRKENQWC                          159

SEQ ID NO: 27           moltype = AA  length = 67
FEATURE                 Location/Qualifiers
source                  1..67
                        mol_type = protein
                        organism = synthetic construct
SEQUENCE: 27
SYYHHHHHHL ESTSLYKKAG SGSNTVKELK NYIQELEERN AELKNLKEHL KFAKAELEFE  60
LAAHKFE                                                            67

SEQ ID NO: 28           moltype = AA  length = 77
FEATURE                 Location/Qualifiers
source                  1..77
                        mol_type = protein
                        organism = synthetic construct
SEQUENCE: 28
SYYHHHHHHL ESTSLYKKAG SGSQKVAQLK NRVAYKLKEN AKLENIVARL ENDNANLEKD  60
IANLEKDIAN LERDVAR                                                 77

SEQ ID NO: 29           moltype = AA  length = 81
FEATURE                 Location/Qualifiers
source                  1..81
                        mol_type = protein
                        organism = synthetic construct
SEQUENCE: 29
```

```
LCTMKKGPSG YGFNLHSDKS KPGQFIRSVD PDSPAEASGL RAQDRIVEVN GVCMEGKQHG  60
DVVSAIRAGG DETKLLVVDR E                                            81

SEQ ID NO: 30          moltype = AA  length = 97
FEATURE                Location/Qualifiers
source                 1..97
                       mol_type = protein
                       organism = synthetic construct
SEQUENCE: 30
SSGAIIYTVE LKRYGGPLGI TISGTEEPFD PIIISSLTKG GLAERTGAIH IGDRILAINS  60
SSLKGKPLSE AIHLLQMAGE TVTLKIKKQT DAQPASS                           97

SEQ ID NO: 31          moltype = AA  length = 109
FEATURE                Location/Qualifiers
source                 1..109
                       mol_type = protein
                       organism = synthetic construct
SEQUENCE: 31
GNNLETYEWY NKSISRDKAE KLLLDTGKEG AFMVRDSRTP GTYTVSVFTK AIISENPCIK  60
HYHIKETNDS PKRYYVAEKY VFDSIPLLIQ YHQYNGGGLV TRLRYPVCG              109

SEQ ID NO: 32          moltype = AA  length = 104
FEATURE                Location/Qualifiers
source                 1..104
                       mol_type = protein
                       organism = synthetic construct
SEQUENCE: 32
GSHPWFFGKI PRAKAEEMLS KQRHDGAFLI RESESAPGDF SLSVKFGNDV QHFKVLRDGA  60
GKYFLWVVKF NSLNELVDYH RSTSVSRNQQ IFLRDIEQVP QQPT                   104

SEQ ID NO: 33          moltype = AA  length = 152
FEATURE                Location/Qualifiers
source                 1..152
                       mol_type = protein
                       organism = synthetic construct
SEQUENCE: 33
GQDRSEATLI KRFKGEGVRY KAKLIGIDEV SAARGDKLCQ DSMMKLKGVV AGARSKGEHK  60
QKIFLTISFG GIKIFDEKTG ALQHHHAVHE ISYIAKDITD HRAFGYVCGK EGNHRFVAIK  120
TAQAAEPVIL DLRDLFQLIY ELKQREELEK KA                                152

SEQ ID NO: 34          moltype = AA  length = 57
FEATURE                Location/Qualifiers
source                 1..57
                       mol_type = protein
                       organism = synthetic construct
SEQUENCE: 34
AEYVRALFDF NGNDEEDLPF KKGDILRIRD KPEEQWWNAE DSEGKRGMIP VPYVEKY     57

SEQ ID NO: 35          moltype = AA  length = 60
FEATURE                Location/Qualifiers
source                 1..60
                       mol_type = protein
                       organism = synthetic construct
SEQUENCE: 35
LIKHMRAEAL FDFTGNSKLE LNFKAGDVIF LLSRINKDWL EGTVRGATGI FPLSFVKILK  60

SEQ ID NO: 36          moltype = AA  length = 153
FEATURE                Location/Qualifiers
source                 1..153
                       mol_type = protein
                       organism = synthetic construct
SEQUENCE: 36
GSHMRLGAQS IQPTANLDRT DDLVYLNVME LVRAVLELKN ELAQLPPEGY VVVVKNVGLT  60
LRKLIGSVDD LLPSLPSSSR TEIEGTQKLL NKDLAELINK MRLAQQNAVT SLSEECKRQM  120
LTASHTLAVD AKNLLDAVDQ AKVLANLAHP PAE                               153

SEQ ID NO: 37          moltype = AA  length = 70
FEATURE                Location/Qualifiers
source                 1..70
                       mol_type = protein
                       organism = synthetic construct
SEQUENCE: 37
GAMATPGSEN VLPREPLIAT AVKFLQNSRV RQSPLATRRA FLKKKGLTDE EIDMAFQQSG  60
TAADEPSSLW                                                         70

SEQ ID NO: 38          moltype = AA  length = 20
FEATURE                Location/Qualifiers
source                 1..20
                       mol_type = protein
```

-continued

```
                        organism = synthetic construct
SEQUENCE: 38
RPPTISNPPP LISSAKHPSV                                              20

SEQ ID NO: 39           moltype = AA  length = 20
FEATURE                 Location/Qualifiers
source                  1..20
                        mol_type = protein
                        organism = synthetic construct
SEQUENCE: 39
NFLQSRPEPT APPEESFRSG                                              20

SEQ ID NO: 40           moltype = AA  length = 20
FEATURE                 Location/Qualifiers
source                  1..20
                        mol_type = protein
                        organism = synthetic construct
SEQUENCE: 40
SKGTGLNPNA KVWQEIAPGN                                              20

SEQ ID NO: 41           moltype = AA  length = 20
FEATURE                 Location/Qualifiers
source                  1..20
                        mol_type = protein
                        organism = synthetic construct
SEQUENCE: 41
PDGGTTFEHL WSSLEPDSTY                                              20

SEQ ID NO: 42           moltype = AA  length = 20
FEATURE                 Location/Qualifiers
source                  1..20
                        mol_type = protein
                        organism = synthetic construct
SEQUENCE: 42
PATSQHPPPP PGHRSQAPSH                                              20

SEQ ID NO: 43           moltype = AA  length = 20
FEATURE                 Location/Qualifiers
source                  1..20
                        mol_type = protein
                        organism = synthetic construct
SEQUENCE: 43
ELNSLLILLE AAEYLERRDR                                              20

SEQ ID NO: 44           moltype = AA  length = 20
FEATURE                 Location/Qualifiers
source                  1..20
                        mol_type = protein
                        organism = synthetic construct
SEQUENCE: 44
FQMPADTPPP AYLPPEDPMT                                              20

SEQ ID NO: 45           moltype = AA  length = 20
FEATURE                 Location/Qualifiers
source                  1..20
                        mol_type = protein
                        organism = synthetic construct
SEQUENCE: 45
ERESNEEPPP PYEDPYWGNG                                              20

SEQ ID NO: 46           moltype = AA  length = 20
FEATURE                 Location/Qualifiers
source                  1..20
                        mol_type = protein
                        organism = synthetic construct
SEQUENCE: 46
VSSTKLVSFH DDSDEDLLHI                                              20

SEQ ID NO: 47           moltype = AA  length = 20
FEATURE                 Location/Qualifiers
source                  1..20
                        mol_type = protein
                        organism = synthetic construct
SEQUENCE: 47
AAATPISTFH DDSDEDLLHV                                              20

SEQ ID NO: 48           moltype = AA  length = 20
FEATURE                 Location/Qualifiers
source                  1..20
```

```
                        mol_type = protein
                        organism = synthetic construct
SEQUENCE: 48
HDDSLPHPQQ ATDDSGHESD                                                20

SEQ ID NO: 49           moltype = AA  length = 20
FEATURE                 Location/Qualifiers
source                  1..20
                        mol_type = protein
                        organism = synthetic construct
SEQUENCE: 49
GSPNAGSVEQ TPKKPGLRRR                                                20

SEQ ID NO: 50           moltype = AA  length = 20
FEATURE                 Location/Qualifiers
source                  1..20
                        mol_type = protein
                        organism = synthetic construct
SEQUENCE: 50
TDEEREETEE EVYLLNSTTL                                                20

SEQ ID NO: 51           moltype = AA  length = 20
FEATURE                 Location/Qualifiers
source                  1..20
                        mol_type = protein
                        organism = synthetic construct
SEQUENCE: 51
DGNVSGTQRL DSATVRTYSC                                                20

SEQ ID NO: 52           moltype = AA  length = 20
FEATURE                 Location/Qualifiers
source                  1..20
                        mol_type = protein
                        organism = synthetic construct
SEQUENCE: 52
ALVDDAADYE PPPSNNEEAL                                                20

SEQ ID NO: 53           moltype = AA  length = 20
FEATURE                 Location/Qualifiers
source                  1..20
                        mol_type = protein
                        organism = synthetic construct
SEQUENCE: 53
RELFDDPSYV NVQNLDKARQ                                                20

SEQ ID NO: 54           moltype = AA  length = 20
FEATURE                 Location/Qualifiers
source                  1..20
                        mol_type = protein
                        organism = synthetic construct
SEQUENCE: 54
KNTKSMNFDN PVYRKTTEEE                                                20

SEQ ID NO: 55           moltype = AA  length = 20
FEATURE                 Location/Qualifiers
source                  1..20
                        mol_type = protein
                        organism = synthetic construct
SEQUENCE: 55
RSLPSTWIEN KLYGMSDPNW                                                20

SEQ ID NO: 56           moltype = AA  length = 20
FEATURE                 Location/Qualifiers
source                  1..20
                        mol_type = protein
                        organism = synthetic construct
SEQUENCE: 56
VVDNSPPPAL PPKKRQSAPS                                                20

SEQ ID NO: 57           moltype = AA  length = 20
FEATURE                 Location/Qualifiers
source                  1..20
                        mol_type = protein
                        organism = synthetic construct
SEQUENCE: 57
TQRSKPQPAV PPRPSADLIL                                                20

SEQ ID NO: 58           moltype = AA  length = 20
FEATURE                 Location/Qualifiers
```

```
source                  1..20
                        mol_type = protein
                        organism = synthetic construct
SEQUENCE: 58
SATRELDELM ASLSDFKIQG                                                20

SEQ ID NO: 59           moltype = AA  length = 20
FEATURE                 Location/Qualifiers
source                  1..20
                        mol_type = protein
                        organism = synthetic construct
SEQUENCE: 59
DLALSENWAQ EFLAAGDAVD                                                20

SEQ ID NO: 60           moltype = AA  length = 16
FEATURE                 Location/Qualifiers
source                  1..16
                        mol_type = protein
                        organism = synthetic construct
SEQUENCE: 60
GSGSGSGSGS GSGSGS                                                    16

SEQ ID NO: 61           moltype = AA  length = 20
FEATURE                 Location/Qualifiers
source                  1..20
                        mol_type = protein
                        organism = synthetic construct
SEQUENCE: 61
GSGSGSGSGS GSGSGSGSGS                                                20

SEQ ID NO: 62           moltype = AA  length = 30
FEATURE                 Location/Qualifiers
source                  1..30
                        mol_type = protein
                        organism = synthetic construct
SEQUENCE: 62
GSGSGSGSGS GSGSGSGSGS GSGSGSGSGS                                     30

SEQ ID NO: 63           moltype = AA  length = 15
FEATURE                 Location/Qualifiers
source                  1..15
                        mol_type = protein
                        organism = synthetic construct
SEQUENCE: 63
GGGGSGGGGS GGGGS                                                     15

SEQ ID NO: 64           moltype = AA  length = 20
FEATURE                 Location/Qualifiers
source                  1..20
                        mol_type = protein
                        organism = synthetic construct
SEQUENCE: 64
GGGGSGGGGS GGGGSGGGGS                                                20

SEQ ID NO: 65           moltype = AA  length = 10
FEATURE                 Location/Qualifiers
source                  1..10
                        mol_type = protein
                        organism = synthetic construct
SEQUENCE: 65
EAAAKEAAAK                                                           10

SEQ ID NO: 66           moltype = AA  length = 15
FEATURE                 Location/Qualifiers
source                  1..15
                        mol_type = protein
                        organism = synthetic construct
SEQUENCE: 66
EAAAKEAAAK EAAAK                                                     15

SEQ ID NO: 67           moltype = AA  length = 20
FEATURE                 Location/Qualifiers
source                  1..20
                        mol_type = protein
                        organism = synthetic construct
SEQUENCE: 67
EAAAKEAAAK EAAAKEAAAK                                                20

SEQ ID NO: 68           moltype = AA  length = 6
```

-continued

```
FEATURE              Location/Qualifiers
source               1..6
                     mol_type = protein
                     organism = synthetic construct
SEQUENCE: 68
AAAGGM                                                    6

SEQ ID NO: 69        moltype = AA  length = 14
FEATURE              Location/Qualifiers
source               1..14
                     mol_type = protein
                     organism = synthetic construct
SEQUENCE: 69
AAAGGMPPAA AGGM                                           14

SEQ ID NO: 70        moltype = AA  length = 6
FEATURE              Location/Qualifiers
source               1..6
                     mol_type = protein
                     organism = synthetic construct
SEQUENCE: 70
AAAGGM                                                    6

SEQ ID NO: 71        moltype = AA  length = 9
FEATURE              Location/Qualifiers
source               1..9
                     mol_type = protein
                     organism = synthetic construct
SEQUENCE: 71
PPAAAGGMM                                                 9

SEQ ID NO: 72        moltype = AA  length = 12
FEATURE              Location/Qualifiers
source               1..12
                     mol_type = protein
                     organism = synthetic construct
SEQUENCE: 72
GSAGSAAGSG EF                                             12

SEQ ID NO: 73        moltype = AA  length = 18
FEATURE              Location/Qualifiers
source               1..18
                     mol_type = protein
                     organism = synthetic construct
SEQUENCE: 73
KLSGGGGSGG GGSGGGGS                                       18

SEQ ID NO: 74        moltype = AA  length = 40
FEATURE              Location/Qualifiers
source               1..40
                     mol_type = protein
                     organism = synthetic construct
SEQUENCE: 74
GSAGSAAGSG EFGSAEAAAK EAAAKAGSAG SAAGSGEFGS               40

SEQ ID NO: 75        moltype = AA  length = 36
FEATURE              Location/Qualifiers
source               1..36
                     mol_type = protein
                     organism = synthetic construct
SEQUENCE: 75
GSAGSAAGSG EFAEAAAKEA AAKAGSAGSA AGSGEF                   36

SEQ ID NO: 76        moltype = AA  length = 50
FEATURE              Location/Qualifiers
source               1..50
                     mol_type = protein
                     organism = synthetic construct
SEQUENCE: 76
GSAGSAAGSG EFGSAEAAAK EAAAKEAAAK EAAAKAGSAG SAAGSGEFGS    50

SEQ ID NO: 77        moltype = AA  length = 211
FEATURE              Location/Qualifiers
source               1..211
                     mol_type = protein
                     organism = synthetic construct
SEQUENCE: 77
AEAWYNLGNA YYKQGDYQKA IEYYQKALEL DPNNAEAWYN LGNAYYKQGD YQKAIEYYQK  60
ALELDPNNAE AWYNLGNAYY KQGDYQKAIE DYQKALELDP NNLQAEAWKN LGNAYYKQGD  120
```

-continued

```
YQKAIEYYQK ALELDPNNAS AWYNLGNAYY KQGDYQKAIE YYQKALELDP NNAKAWYRRG  180
NAYYKQGDYQ KAIEDYQKAL ELDPNNRSRS A                                 211

SEQ ID NO: 78          moltype = AA  length = 16
FEATURE                Location/Qualifiers
source                 1..16
                       mol_type = protein
                       organism = synthetic construct
SEQUENCE: 78
GGGGSGGGGS GGGGAS                                                  16

SEQ ID NO: 79          moltype = AA  length = 36
FEATURE                Location/Qualifiers
source                 1..36
                       mol_type = protein
                       organism = synthetic construct
SEQUENCE: 79
GSAGSAAGSG EFGSAGSAAG SGEFGSAGSA AGSGEF                            36

SEQ ID NO: 80          moltype = AA  length = 116
FEATURE                Location/Qualifiers
source                 1..116
                       mol_type = protein
                       organism = synthetic construct
SEQUENCE: 80
GSAGSAAGSG EFGSAEAAAK EAAAKEAAAK EAAAKAGSAG SAAGSGEFGS EQKLISEEDL  60
EQKLISEEDL EQKLISEEDL GSAGSAAGSG EFGSAGSAAG SGEFGSAGSA AGSGEF      116

SEQ ID NO: 81          moltype = AA  length = 110
FEATURE                Location/Qualifiers
source                 1..110
                       mol_type = protein
                       organism = synthetic construct
SEQUENCE: 81
GSAGSAAGSG EFGSAEAAAK EAAAKEAAAK EAAAKAGSAG SAAGSGEFGS DYKDDDDKDY  60
KDDDDKDYKD DDDKGSAGSA AGSGEFGSAG SAAGSGEFGS AGSAAGSGEF             110

SEQ ID NO: 82          moltype = DNA  length = 30
FEATURE                Location/Qualifiers
source                 1..30
                       mol_type = other DNA
                       organism = synthetic construct
SEQUENCE: 82
cggcacccct acaaacagaa ggaatataaa                                   30

SEQ ID NO: 83          moltype = AA  length = 1101
FEATURE                Location/Qualifiers
source                 1..1101
                       mol_type = protein
                       organism = Homo sapiens
SEQUENCE: 83
MSAKAISEQT GKELLYKFIC TTSAIQNRFK YARVTPDTDW ARLLQDHPWL LSQNLVVKPD  60
QLIKRRGKLG LVGVNLTLDG VKSWLKPRLG QEATVGKATG FLKNFLIEPF VPHSQAEEFY  120
VCIYATREGD YVLFHHEGGV DVGDVDAKAQ KLLVGVDEKL NPEDIKKHLL VHAPEDKKEI  180
LASFISGLFN FYEDLYFTYL EINPLVVTKD GVYVLDLAAK VDATADYICK VKWGDIEFPP  240
PFGREAYPEE AYIADLDAKS GASLKLTLLN PKGRIWTMVA GGGASVVYSD TICDLGGVNE  300
LANYGEYSGA PSEQQTYDYA KTILSLMTRE KHPDGKILII GGSIANFTNV AATFKGIVRA  360
IRDYQGPLKE HEVTIFVRRG GPNYQEGLRV MGEVGKTTGI PIHVFGTETH MTAIVGMALG  420
HRPIPNQPPT AAHTANFLLN ASGSTSTPAP SRTASFSESR ADEVAPAKKA KPAMPQDSVP  480
SPRSLQGKST TLFSRHTKAI VWGMQTRAVQ GMLDFDYVCS RDEPSVAAMV YPFTGDHKQK  540
FYWGHKEILI PVFKNMADAM RKHPEVDVLI NFASLRSAYD STMETMNYAQ IRTIAIIAEG  600
IPEALTRKLI KKADQKGVTI IGPATVGGIK PGCFKIGNTG GMLDNILASK LYRPGSVAYV  660
SRSGGMSNEL NNIISRTTDG VYEGVAIGGD RYPGSTFMDH VLRYQDTPGV KMIVVLGEIG  720
GTEEYKICRG IKEGRLTKPI VCWCIGTCAT MFSSEVQFGH AGACANQASE TAVAKNQALK  780
EAGVFVPRSF DELGEIIQSV YEDLVANGVI VPAQEVPPPT VPMDYSWARE LGLIRKPASF  840
MTSICDERGQ ELIYAGMPIT EVFKEEMGIG GVLGLLWFQK RLPKYSCQFI EMCLMVTADH  900
GPAVSGAHNT IICARAGKDL VSSLTSGLLT IGDRFGGALD AAAKMFSKAF DSGIIPMEFV  960
NKMKKEGKLI MGIGHRVKSI NNPDMRVQIL KDYVRQHFPA TPLLDYALEV EKITTSKKPN  1020
LILNVDGLIG VAFVDMLRNC GSFTREEADE YIDIGALNGI FVLGRSMGFI GHYLDQKRLK  1080
QGLYRHPWDD ISYVLPEHMS M                                            1101

SEQ ID NO: 84          moltype = AA  length = 394
FEATURE                Location/Qualifiers
source                 1..394
                       mol_type = protein
                       organism = Escherichia coli
SEQUENCE: 84
MKNCVIVSAV RTAIGSFNGS LASTSAIDLG ATVIKAAIER AKIDSQHVDE VIMGNVLQAG  60
LGQNPARQAL LKSGLAETVC GFTVNKVCGS GLKSVALAAQ AIQAGQAQSI VAGGMENMSL  120
```

-continued

```
APYLLDAKAR SGYRLGDGQV YDVILRDGLM CATHGYHMGI TAENVAKEYG ITREMQDELA  180
LHSQRKAAAA IESGAFTAEI VPVNVVTRKK TFVFSQDEFP KANSTAEALG ALRPAFDKAG  240
TVTAGNASGI NDGAAALVIM EESAALAAGL TPLARIKSYA SGGVPPALMG MGPVPATQKA  300
LQLAGLQLAD IDLIEANEAF AAQFLAVGKN LGFDSEKVNV NGGAIALGHP IGASGARILV  360
TLLHAMQARD KTLGLATLCI GGGQGIAMVI ERLN                              394

SEQ ID NO: 85          moltype = AA  length = 282
FEATURE                Location/Qualifiers
source                 1..282
                       mol_type = protein
                       organism = Clostridium acetobutylicum
SEQUENCE: 85
MKKVCVIGAG TMGSGIAQAF AAKGFEVVLR DIKDEFVDRG LDFINKNLSK LVKKGKIEEA  60
TKVEILTRIS GTVDLNMAAD CDLVIEAAVE RMDIKKQIFA DLDNICKPET ILASNTSSLS  120
ITEVASATKR PDKVIGMHFF NPAPVMKLVE VIRGIATSQE TFDAVKETSI AIGKDPVEVA  180
EAPGFVVNRI LIPMINEAVG ILAEGIASVE DIDKAMKLGA NHPMGPLELG DFIGLDICLA  240
IMDVLYSETG DSKYRPHTLL KKYVRAGWLG RKSGKGFYDY SK                     282

SEQ ID NO: 86          moltype = AA  length = 261
FEATURE                Location/Qualifiers
source                 1..261
                       mol_type = protein
                       organism = Clostridium acetobutylicum
SEQUENCE: 86
MELNNVILEK EGKVAVVTIN RPKALNALNS DTLKEMDYVI GEIENDSEVL AVILTGAGEK  60
SFVAGADISE MKEMNTIEGR KFGILGNKVF RRLELLEKPV IAAVNGFALG GGCEIAMSCD  120
IRIASSNARF GQPEVGLGIT PGFGGTQRLS RLVGMGMAKQ LIFTAQNIKA DEALRIGLVN  180
KVVEPSELMN TAKEIANKIV SNAPVAVKLS KQAINRGMQC DIDTALAFES EAFGECFSTE  240
DQKDAMTAFI EKRKIEGFKN R                                            261

SEQ ID NO: 87          moltype = AA  length = 394
FEATURE                Location/Qualifiers
source                 1..394
                       mol_type = protein
                       organism = Cupriavidus necator
SEQUENCE: 87
MTREVVVVSG VRTAIGTFGG SLKDVAPAEL GALVVREALA RAQVSGDDVG HVVFGNVIQT  60
EPRDMYLGRV AAVNGGVTIN APALTVNRLC GSGLQAIVSA AQTILLGDTD VAIGGGAESM  120
SRAPYLAPAA RWGARMGDAG LVDMMLGALH DPFHRIHMGV TAENVAKEYD ISRAQQDEAA  180
LESHRRASAA IKAGYFKDQI VPVVSKGRKG DVTFDTDEHV RHDATIDDMT KLRPVFVKEN  240
GTVTAGNASG LNDAAAAVVM MERAEAERRG LKPLARLVSY GHAGVDPKAM GIGPVPATKI  300
ALERAGLQVS DLDVIEANEA FAAQACAVTK ALGLDPAKVN PNGSGISLGH PIGATGALIT  360
VKALHELNRV QGRYALVTMC IGGGQGIAAI FERI                              394

SEQ ID NO: 88          moltype = AA  length = 397
FEATURE                Location/Qualifiers
source                 1..397
                       mol_type = protein
                       organism = Treponema denticola
SEQUENCE: 88
MIVKPMVRNN ICLNAHPQGC KKGVEDQIEY TKKRITAEVK AGAKAPKNVL VLGCSNGYGL  60
ASRITAAFGY GAATIGVSFE KAGSETKYGT PGWYNNLAFD EAAKREGLYS VTIDGDAFSD  120
EIKAQVIEEA KKKGIKFDLI VYSLASPVRT DPDTGIMHKS VLKPFGKTFT GKTVDPFTGE  180
LKEISAEPAN DEEAAATVKV MGGEDWERWI KQLSKEGLLE EGCITLAYSY IGPEATQALY  240
RKGTIGKAKE HLEATAHRLN KENPSIRAFV SVNKGLVTRA SAVIPVIPLY LASLFKVMKE  300
KGNHEGCIEQ ITRLYAERLY RKDGTIPVDE ENRIRIDDWE LEEDVQKAVS ALMEKVTGEN  360
AESLTDLAGY RHDFLASNGF DVEGINYEAE VERFDRI                           397

SEQ ID NO: 89          moltype = AA  length = 720
FEATURE                Location/Qualifiers
source                 1..720
                       mol_type = protein
                       organism = Cannabis sativa
SEQUENCE: 89
MGKNYKSLDS VVASDFIALG ITSEVAETLH GRLAEIVCNY GAATPQTWIN IANHILSPDL  60
PFSLHQMLFY GCYKDFGPAP PAWIPDPEKV KSTNLGALLE KRGKEFLGVK YKDPISSFSH  120
FQEFSVRNPE VYWRTVLMDE MKISFSKDPE CILRRDDINN PGGSEWLPGG YLNSAKNCLN  180
VNSNKKLNDT MIVWRDEGND DLPLNKLTLD QLRKRVWLVG YALEEMGLEK GCAIAIDMPM  240
HVDAVVIYLA IVLAGYVVVS IADSFSAPEI STRLRLSKAK AIFTQDHIIR GKKRIPLYSR  300
VVEAKSPMAI VIPCSGSNIG AELRDGDISW DYFLERAKEF KNCEFTAREQ PVDAYTNILF  360
SSGTTGEPKA IPWTQATPLK AAADGWSHLD IRKGDVIVWP TNLGWMMGPW LVYASLLNGA  420
SIALYNGSPL VSGFAKFVQD AKVTMLGVVP SIVRSWKSTN CVSGYDWSTI RCFSSSGEAS  480
NVDEYLWLMG RANYKPVIEM CGGTEIGGAF SAGSFLQAQS LSSFSSQCMG CTLYILDKNG  540
YPMPKNKPGI GELALGPVMF GASKTLLNGN HHDVYFKGMP TLNGEVLRRH GDIFELTSNG  600
YYHAHGRADD TMNIGGIKIS SIEIERVCNE VDDRVFETTA IGVPPLGGGP EQLVIFFVLK  660
DSNDTTIDLN QLRLSFNLGL QKKLNPLFKV TRVVPLSSLP RTATNKIMRR VLRQQFSHFE  720

SEQ ID NO: 90          moltype = AA  length = 491
FEATURE                Location/Qualifiers
```

```
source                 1..491
                       mol_type = protein
                       organism = Saccharomyces cerevisiae
SEQUENCE: 90
MKLSTKLCWC GIKGRLRPQK QQQLHNTNLQ MTELKKQKTA EQKTRPQNVG IKGIQIYIPT  60
QCVNQSELEK FDGVSQGKYT IGLGQTNMSF VNDREDIYSM SLTVLSKLIK SYNIDTNKIG  120
RLEVGTETLI DKSKSVKSVL MQLFGENTDV EGIDTLNACY GGTNALFNSL NWIESNAWDG  180
RDAIVVCGDI AIYDKGAARP TGGAGTVAMW IGPDAPIVFD SVRASYMEHA YDFYKPDFTS  240
EYPYVDGHFS LTCYVKALDQ VYKSYSKKAI SKGLVSDPAG SDALNVLKYF DYNVFHVPTC  300
KLVTKSYGRL LYNDFRANPQ LFPEVDAELA TRDYDESLTD KNIEKTFVNV AKPFHKERVA  360
QSLIVPTNTG NMYTASVYAA FASLLNYVGS DDLQGKRVGL FSYGSGLAAS LYSCKIVGDV  420
QHIIKELDIT NKLAKRITET PKDYEAAIEL RENAHLKKNF KPQGSIEHLQ SGVYYLTNID  480
DKFRRSYDVK K                                                      491

SEQ ID NO: 91          moltype = AA  length = 381
FEATURE                Location/Qualifiers
source                 1..381
                       mol_type = protein
                       organism = Saccharomyces cerevisiae
SEQUENCE: 91
MVAVRRKALS ILAEAPVLAS DRLPYKNYDY DRVFGACCEN VIGYMPLPVG VIGPLVIDGT  60
SYHIPMATTE GCLVASAMRG CKAINAGGGA TTVLTKDGMT RGPVVRFPTL KRSGACKIWL  120
DSEEGQNAIK KAFNSTSRFA RLQHIQTCLA GDLLFMRFRT TTGDAMGMNM ISKGVEYSLK  180
QMVEEYGWED MEVVSVSGNY CTDKKPAAIN WIEGRGKSVV AEATIPGDVV RKVLKSDVSA  240
LVELNIAKNL VGSAMAGSVG GFNAHAANLV TAVFLALGQD PAQNVESSNC ITLMKEVDGD  300
LRISVSMPSI EVGTIGGGTV LEPQGAMLDL LGVRGPHATA PGTNARQLAR IVACAVLAGE  360
LSLCAALAAG HLVQSHMTHN R                                           381

SEQ ID NO: 92          moltype = AA  length = 443
FEATURE                Location/Qualifiers
source                 1..443
                       mol_type = protein
                       organism = Saccharomyces cerevisiae
SEQUENCE: 92
MSLPFLTSAP GKVIIFGEHS AVYNKPAVAA SVSALRTYLL ISESSAPDTI ELDFPDISFN  60
HKWSINDFNA ITEDQVNSQK LAKAQQATDG LSQELVSLLD PLLAQLSESF HYHAAFCFLY  120
MFVCLCPHAK NIKFSLKSTL PIGAGLGSSA SISVSLALAM AYLGGLIGSN DLEKLSENDK  180
HIVNQWAFIG EKCIHGTPSG IDNAVATYGN ALLFEKDSHN GTINTNNFKF LDDFPAIPMI  240
LTYTRIPRST KDLVARVRVL VTEKFPEVMK PILDAMGECA LQGLEIMTKL SKCKGTDDEA  300
VETNNELYEQ LLELIRINHG LLVSIGVSHP GLELIKNLSD DLRIGSTKLT GAGGGGCSLT  360
LLRRDITQEQ IDSFKKKLQD DFSYETFETD LGGTGCCLLS AKNLNKDLKI KSLVFQLFEN  420
KTTTKQQIDD LLLPGNTNLP WTS                                         443

SEQ ID NO: 93          moltype = AA  length = 452
FEATURE                Location/Qualifiers
source                 1..452
                       mol_type = protein
                       organism = Saccharomyces cerevisiae
SEQUENCE: 93
MSELRAFSAP GKALLAGGYL VLDTKYEAFV VGLSARMHAV AHPYGSLQGS DKFEVRVKSK  60
QFKDGEWLYH ISPKSGFIPV SIGGSKNPFI EKVIANVFSY FKPNMDDYCN RNLFVIDIFS  120
DDAYHSQEDS VTEHRGNRRL SFHSHRIEEV PKTGLGSSAG GLVTVLTTAL ASFFVSDLEN  180
NVDKYREVIH NLAQVAHCQA QGKIGSGFDV AAAAYGSIRY RRFPPALISN LPDIGSATYG  240
SKLAHLVDEE DWNITIKSNH LPSGLTLWMG DIKNGSETVK LVQKVKNWYD SHMPESLKIY  300
TELDHANSRF MDGLSKLDRL HETHDDYSDQ IFESLERNDC TCQKYPEITE VRDAVATIRR  360
SFRKITKESG ADIEPPVQTS LLDDCQTLKG VLTCLIPGAG GYDAIAVITK QDVDLRAQTA  420
NDKRFSKVQW LDVTQADWGV RKEKDPETYL DK                                452

SEQ ID NO: 94          moltype = AA  length = 396
FEATURE                Location/Qualifiers
source                 1..396
                       mol_type = protein
                       organism = Saccharomyces cerevisiae
SEQUENCE: 94
MTVYTASVTA PVNIATLKYW GKRDTKLNLP TNSSISVTLS QDDLRTLTSA ATAPEFERDT  60
LWLNGEPHSI DNERTQNCLR DLRQLRKEME SKDASLPTLS QWKLHIVSEN NFPTAAGLAS  120
SAAGFAALVS AIAKLYQLPQ STSEISRIAR KGSGSACRSL FGGYVAWEMG KAEDGHDSMA  180
VQIADSSDWP QMKACVLVVS DIKKDVSSTQ GMQLTVATSE LFKERIEHVV PKRFEVMRKA  240
IVEKDFATFA KETMMDSNSF HATCLDSFPP IFYMNDTSKR IISWCHTINQ FYGETIVAYT  300
FDAGPNAVLY YLAENESKLF AFIYKLFGSV PGWDKKFTTE QLEAFNHQFE SSNFTARELD  360
LELQKDVARV ILTQVGSGPQ ETNESLIDAK TGLPKE                            396

SEQ ID NO: 95          moltype = AA  length = 288
FEATURE                Location/Qualifiers
source                 1..288
                       mol_type = protein
                       organism = Saccharomyces cerevisiae
SEQUENCE: 95
MTADNNSMPH GAVSSYAKLV QNQTPEDILE EFPEIIPLQQ RPNTRSSETS NDESGETCFS  60
```

-continued

```
GHDEEQIKLM NENCIVLDWD DNAIGAGTKK VCHLMENIEK GLLHRAFSVF IFNEQGELLL  120
QQRATEKITF PDLWTNTCCS HPLCIDDELG LKGKLDDKIK GAITAAVRKL DHELGIPEDE  180
TKTRGKFHFL NRIHYMAPSN EPWGEHEIDY ILFYKINAKE NLTVNPNVNE VRDFKWVSPN  240
DLKTMFADPS YKFTPWFKII CENYLFNWWE QLDDLSEVEN DRQIHRML               288

SEQ ID NO: 96          moltype = AA  length = 335
FEATURE                Location/Qualifiers
source                 1..335
                       mol_type = protein
                       organism = Saccharomyces cerevisiae
SEQUENCE: 96
MEAKIDELIN NDPVWSSQNE SLISKPYNHI LLKPGKNFRL NLIVQINRVM NLPKDQLAIV  60
SQIVELLHNS SLLIDDIEDN APLRRGQTTS HLIWGVPSTI NTANYMYFRA MQLVSQLTTK  120
EPLYHWLITI FNEELINLHR GQGLDIYWRD FLPEIIPTQE MYLNMVMNKT GGLFRLTLRL  180
MEALSPSSHH GHSLVPFINL LGIIYQIRDD YLNLKDFQMS SEKGFAEDIT EGKLSFPIVH  240
ALNFTKTKGQ TEQHNEILRI LLLRTSDKDI KLKLIQILEF DTNSLAYTKN FINQLVNMIK  300
NDNENKYLPD LASHSDTATN LHDELLYIID HLSEL                             335

SEQ ID NO: 97          moltype = AA  length = 2233
FEATURE                Location/Qualifiers
source                 1..2233
                       mol_type = protein
                       organism = Saccharomyces cerevisiae
SEQUENCE: 97
MSEESLFESS PQKMEYEITN YSERHTELPG HFIGLNTVDK LEESPLRDFV KSHGGHTVIS  60
KILIANNGIA AVKEIRSVRK WAYETFGDDR TVQFVAMATP EDLEANAEYI RMADQYIEVP  120
GGTNNNNYAN VDLIVDIAER ADVDAVWAGW GHASENPLLP EKLSQSKRKV IFIGPPGNAM  180
RSLGDKISST IVAQSAKVPC IPWSGTGVDT VHVDEKTGLV SVDDDIYQKG CCTSPEDGLQ  240
KAKRIGFPVM IKASEGGGGK GIRQVEREED FIALYHQAAN EIPGSPIFIM KLAGRARHLE  300
VQLLADQYGT NISLFGRDCS VQRRHQKIIE EAPVTIAKAE TFHEMEKAAV RLGKLVGYVS  360
AGTVEYLYSH DDGKFYFLEL NPRLQVEHPT TEMVSGVNLP AAQLQIAMGI PMHRISDIRT  420
LYGMNPHSAS EIDFEFKTQD ATKKQRRPIP KGHCTACRIT SEDPNDGFKP SGGTLHELNF  480
RSSSNVWGYF SVGNNGNIHS FSDSQFGHIF AFGENRQASR KHMVVALKEL SIRGDFRTTV  540
EYLIKLLETE DFEDNTITTG WLDDLITHKM TAEKPDPTLA VICGAATKAF LASEEARHKY  600
IESLQKGQVL SKDLLQTMFP VDFIHEGKRY KFTVAKSGND RYTLFINGSK CDIILRQLSD  660
GGLLIAIGGK SHTIYWKEEV AATRLSVDSM TTLLEVENDP TQLRTPSPGK LVKFLVENGE  720
HIIKGQPYAE IEVMKMQMPL VSQENGIVQL LKQPGSTIVA GDIMAIMTLD DPSKVKHALP  780
FEGMLPDFGS PVIEGTKPAY KFKSLVSTLE NILKGYDNQV IMNASLQQLI EVLRNPKLPY  840
SEWKLHISAL HSRLPAKLDE QMEELVARSL RRGAVFPARQ LSKLIDMAVK NPEYNPDKLL  900
GAVVEPLADI AHKYSNGLEA HEHSIFVHFL EEYYEVEKLF NGPNVREENI ILKLRDENPK  960
DLDKVALTVL SHSKVSAKNN LILAILKHYQ PLCKLSSKVS AIFSTPLQHI VELESKATAK  1020
VALQAREILI QGALPSVKER TEQIEHILKS SVVKVAYGSS NPKRSEPDLN ILKDLIDSNY  1080
VVFDVLLQFL THQDPVVTAA AAQVYIRRAY RAYTIGDIRV HEGVTVPIVE WKFQLPSAAF  1140
STFPTVKSKM GMNRAVSVSD LSYVANSQSS PLREGILMAV DHLDDVDEIL SQSLEVIPRH  1200
QSSSNGPAPD RSGSSASLSN VANVCVASTE GFESEEEILV RLREILDLNK QELINASIRR  1260
ITFMFGFKDG SYPKYYTFNG PNYNENETIR HIEPALAFQL ELGRLSNFNI KPIFTDNRNI  1320
HVYEAVSKTS PLDKRFFTRG IIRTGHIRDD ISIQEYLTSE ANRLMSDILD NLEVTDTSNS  1380
DLNHIFINFI AVFDISPEDV EAAFGGFLER FGKRLLRLRV SSAEIRIIIK DPQTGAPVPL  1440
RALINNVSGY VIKTEMYTEV KNAKGEWVFK SLGKPGSMHL RPIATPYPVK EWLQPKRYKA  1500
HLMGTTYVYD FPELFRQASS SQWKNFSADV KLTDDFFISN ELIEDENGEL TEVEREPGAN  1560
AIGMVAFKIT VKTPEYPRGR QFVVVANDIT FKIGSFGPQE DEFFNKVTEY ARKRGIPRIY  1620
LAANSGARIG MAEEIVPLFQ VAWNDAANPD KGFQYLYLTS EGMETLKKFD KENSVLTERT  1680
VINGEERFVI KTIIGSEDGL GVECLRGSGL IAGATSRAYH DIFTITLVTC RSVGIGAYLV  1740
RLGQRAIQVE GQPIILTGAP AINKMLGREV YTSNLQLGGT QIMYNNGVSH LTAVDDLAGV  1800
EKIVEWMSYV PAKRNMPVPI LETKDTWDRP VDFTPTNDET YDVRWMIEGR ETESGFEYGL  1860
FDKGSFFETL SGWAKGVVVG RARLGGIPLG VIGVETRTVE NLIPADPANP NSAETLIQEP  1920
GQVWHPNSAF KTAQAINDFN NGEQLPMMIL ANWRGFSGGQ RDMFNEVLKY GSFIVDALVD  1980
YKQPIIIYIP PTGELRGGSW VVVDPTINAD QMEMYADVNA RAGVLEPQGM VGIKFRREKL  2040
LDTMNRLDDK YRELRSQLSN KSLAPEVHQQ ISKQLADRER ELLPIYGQIS LQFADLHDRS  2100
SRMVAKGVIS KELEWTEARR FFFWRLRRRL NEEYLIKRLS HQVGEASRLE KIARIRSWYP  2160
ASVDHEDDRQ VATWIEENYK TLDDKLKGLK LESFAQDLAK KIRSDHDNAI DGLSEVIKML  2220
STDDKEKLLK TLK                                                     2233

SEQ ID NO: 98          moltype = AA  length = 385
FEATURE                Location/Qualifiers
source                 1..385
                       mol_type = protein
                       organism = Cannabis sativa
SEQUENCE: 98
MNHLRAEGPA SVLAIGTANP ENILLQDEFP DYYFRVTKSE HMTQLKEKFR KICDKSMIRK  60
RNCFLNEEHL KQNPRLVEHE MQTLDARQDM LVVEVPKLGK DACAKAIKEW GQPKSKITHL  120
IFTSASTTDM PGADYHCAKL LGLSPSVKRV MMYQLGCYGG GTVLRIAKDI AENNKGARVL  180
AVCCDIMACL FRGPSESDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LHLKSDKFVD SRHVLSEHGN MSSSTVLFVM DELRKRSLEE GKSTTGDGFE  360
WGVLFGFGPG LTVERVVVRS VPIKY                                        385

SEQ ID NO: 99          moltype = AA  length = 101
FEATURE                Location/Qualifiers
```

```
source                1..101
                      mol_type = protein
                      organism = Cannabis sativa
SEQUENCE: 99
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                     101

SEQ ID NO: 100        moltype = AA  length = 395
FEATURE               Location/Qualifiers
source                1..395
                      mol_type = protein
                      organism = Cannabis sativa
SEQUENCE: 100
MGLSSVCTFS FQTNYHTLLN PHNNNPKTSL LCYRHPKTPI KYSYNNFPSK HCSTKSFHLQ  60
NKCSESLSIA KNSIRAATTN QTEPPESDNH SVATKILNFG KACWKLQRPY TIIAFTSCAC  120
GLFGKELLHN TNLISWSLMF KAFFFLVAIL CIASFTTTIN QIYDLHIDRI NKPDLPLASG  180
EISVNTAWIM SIIVALFGLI ITIKMKGGPL YIFGYCFGIF GGIVYSVPPF RWKQNPSTAF  240
LLNFLAHIIT NFTFYYASRA ALGLPFELRP SFTFLLAFMK SMGSALALIK DASDVEGDTK  300
FGISTLASKY GSRNLTLFCS GIVLLSYVAA ILAGIIWPQA FNSNVMLLSH AILAFWLILQ  360
TRDFALTNYD PEAGRRFYEF MWKLYYAEYL VYVFI                           395

SEQ ID NO: 101        moltype = AA  length = 544
FEATURE               Location/Qualifiers
source                1..544
                      mol_type = protein
                      organism = Cannabis sativa
SEQUENCE: 101
MKCSTFSFWF VCKIIFFFFS FNIQTSIANP RENFLKCFSQ YIPNNATNLK LVYTQNNPLY  60
MSVLNSTIHN LRFTSDTTPK PLVIVTPSHV SHIQGTILCS KKVGLQIRTR SGGHDSEGMS  120
YISQVPFVIV DLRNMRSIKI DVHSQTAWVE AGATLGEVYY WVNEKNENLS LAAGYCPTVC  180
AGGHFGGGGY GPLMRNYGLA ADNIIDAHLV NVHGKVLDRK SMGEDLFWAL RGGGAESFGI  240
IVAWKIRLVA VPKSTMFSVK KIMEIHELVK LVNKWQNIAY KYDKDLLLMT HFITRNITDN  300
QGKNKTAIHT YFSSVFLGGV DSLVDLMNKS FPELGIKKTD CRQLSWIDTI IFYSGVVNYD  360
TDNFNKEILL DRSAGQNGAF KIKLDYVKKP IPESVFVQIL EKLYEEDIGA GMYALYPYGG  420
IMDEISESAI PFPHRAGILY ELWYICSWEK QEDNEKHLNW IRNIYNFMTP YVSKNPRLAY  480
LNYRDLDIGI NDPKNPNNYT QARIWGEKYF GKNFDRLVKV KTLVDPNNFF RNEQSIPPLP  540
RHRH                                                             544

SEQ ID NO: 102        moltype = AA  length = 545
FEATURE               Location/Qualifiers
source                1..545
                      mol_type = protein
                      organism = Cannabis sativa
SEQUENCE: 102
MNCSTFSFWF VCKIIFFFLS FNIQISIANP QENFLKCFSE YIPNNPANPK FIYTQHDQLY  60
MSVLNSTIQN LRFTSDTTPK PLVIVTPSNV SHIQASILCS KKVGLQIRTR SGGHDAEGLS  120
YISQVPFAIV DLRNMHTVKV DIHSQTAWVE AGATLGEVYY WINEMNENFS FPGGYCPTVG  180
VGGHFSGGGY GALMRNYGLA ADNIIDAHLV NVDGKVLDRK SMGEDLFWAI RGGGGENFGI  240
IAACKIKLVV VPSKATIFSV KKNMEIHGLV KLFNKWQNIA YKYDKDLMLT THFRTRNITD  300
NHGKNKTTVH GYFSSIFLGG VDSLVDLMNK SFPELGIKKT DCKELSWIDT TIFYSGVVNY  360
NTANFKKEIL LDRSAGKKTA FSIKLDYVKK LIPETAMVKI LEKLYEEEVG VGMYVLYPYG  420
GIMDEISESA IPFPHRAGIM YELWYTATWE KQEDNEKHIN WVRSVYNFTT PYVSQNPRLA  480
YLNYRDLDLG KTNPESPNNY TQARIWGEKY FGKNFNRLVK VKTKADPNNF FRNEQSIPPL  540
PPRHH                                                            545

SEQ ID NO: 103        moltype = AA  length = 1529
FEATURE               Location/Qualifiers
source                1..1529
                      mol_type = protein
                      organism = synthetic construct
SEQUENCE: 103
MSAKAISEQT GKELLYKFIC TTSAIQNRFK YARVTPDTDW ARLLQDHPWL LSQNLVVKPD  60
QLIKRRGKLG LVGVNLTLDG VKSWLKPRLG QEATVGKATG FLKNFLIEPF VPHSQAEEFY  120
VCIYATREGD YVLFHHEGGV DVGDVDAKAQ KLLVGVDEKL NPEDIKKHLL VHAPEDKKEI  180
LASFISGLFN FYEDLYFTYL EINPLVVTKD GVYVLDLAAK VDATADYICK VKWGDIEFPP  240
PFGREAYPEE AYIADLDAKS GASLKLTLLN PKGRIWTMVA GGGASVVYSD TICDLGGVNE  300
LANYGEYSGA PSEQQTYDYA KTILSLMTRE KHPDGKILII GGSIANFTNV AATFKGIVRA  360
IRDYQGPLKE HEVTIFVRRG GPNYQEGLRV MGEVGKTTGI PIHVFGTETH MTAIVGMALG  420
HRPIPNQPPT AAHTANFLLN ASGSTSTPAP SRTASFSESR ADEVAPAKKA KPAMPQDSVP  480
SPRSLQGKST TLFSRHTKAI VWGMQTRAVQ GMLDFDYVCS RDEPSVAAMV YPFTGDHKQK  540
FYWGHKEILI PVFKNMADAM RKHPEVDVLI NFASLRSAYD STMETMNYAQ IRTIAIIAEG  600
IPEALTRKLI KKADQKGVTI IGPATVGGIK PGCFKIGNTG GMLDNILASK LYRPGSVAYV  660
SRSGGMSNEL NNIISRTTDG VYEGVAIGGD RYPGSTFMDH VLRYQDTPGV KMIVVLGEIG  720
GTEEYKICRG IKEGRLTKPI VCWCIGTCAT MFSSEVQFGH AGACANQASE TAVAKNQALK  780
EAGVFVPRSF DELGEIIQSV YEDLVANGVI VPAQEVPPPT VPMDYSWARE LGLIRKPASF  840
MTSICDERGQ ELIYAGMPIT EVFKEEMGIG GVLGLLWFQK RLPKYSCQFI EMCLMVTADH  900
GPAVSGAHNT IICARAGKDL VSSLTSGLLT IGDRFGGALD AAAKMFSKAF DSGIIPMEFV  960
NKMKKEGKLI MGIGHRVKSI NNPDMRVQIL KDYVRQHFPA TPLLDYALEV EKITTSKKPN  1020
LILNVDGLIG VAFVDMLRNC GSFTREEADE YIDIGALNGI FVLGRSMGFI GHYLDQKRLK  1080
```

-continued

```
QGLYRHPWDD ISYVLPEHMS MKLSGGGGSG GGGSGGGGSA EAWYNLGNAY YKQGDYQKAI  1140
EYYQKALELD PNNAEAWYNL GNAYYKQGDY QKAIEYYQKA LELDPNNAEA WYNLGNAYYK  1200
QGDYQKAIED YQKALELDPN NLQAEAWKNL GNAYYKQGDY QKAIEYYQKA LELDPNNASA  1260
WYNLGNAYYK QGDYQKAIEY YQKALELDPN NAKAWYRRGN AYYKQGDYQK AIEDYQKALE  1320
LDPNNRSRSA GGGGSGGGGS GGGGASSYYH HHHHHLESTS LYKKAGSGSN LVAQLENEVA  1380
SLENENETLK KKNLHKKDLI AYLEKEIANL RKKIEEGSAG SAAGSGEFGS AEAAAKEAAA  1440
KAGSAGSAAG SGEFGSSYYH HHHHHLESTS LYKKAGSGSA RNAYLRKKIA RLKKDNLQLE  1500
RDEQNLEKII ANLRDEIARL ENEVASHEQ                                    1529

SEQ ID NO: 104         moltype = AA  length = 821
FEATURE                Location/Qualifiers
source                 1..821
                       mol_type = protein
                       organism = synthetic construct
SEQUENCE: 104
MKNCVIVSAV RTAIGSFNGS LASTSAIDLG ATVIKAAIER AKIDSQHVDE VIMGNVLQAG  60
LGQNPARQAL LKSGLAETVC GFTVNKVCGS GLKSVALAAQ AIQAGQAQSI VAGGMENMSL  120
APYLLDAKAR SGYRLGDGQV YDVILRDGLM CATHGYHMGI TAENVAKEYG ITREMQDELA  180
LHSQRKAAAA IESGAFTAEI VPVNVVTRKK TFVFSQDEFP KANSTAEALG ALRPAFDKAG  240
TVTAGNASGI NDGAAALVIM EESAALAAGL TPLARIKSYA SGGVPPALMG MGPVPATQKA  300
LQLAGLQLAD IDLIEANEAF AAQFLAVGKN LGFDSEKVNV NGGAIALGHP IGASGARILV  360
TLLHAMQARD KTLGLATLCI GGGQGIAMVI ERLNKLSGGG GSGGGGSGGG GSAEAWYNLG  420
NAYYKQGDYQ KAIEYYQKAL ELDPNNAEAW YNLGNAYYKQ GDYQKAIEYY QKALELDPNN  480
AEAWYNLGNA YYKQGDYQKA IEDYQKALEL DPNNLQAEAW KNLGNAYYKQ GDYQKAIEYY  540
QKALELDPNN ASAWYNLGNA YYKQGDYQKA IEYYQKALEL DPNNAKAWYR RGNAYYKQGD  600
YQKAIEDYQK ALELDPNNRS RSAGGGGSGG GGSGGGGASS YYHHHHHHLE STSLYKKAGS  660
GSNEVTTLEN DAAFIENENA YLEKEIARLR KEKAALRNRL AHKKGSAGSA AGSGEFGSAE  720
AAAKEAAAKA GSAGSAAGSG EFGSSYYHHH HHHLESTSLY KKAGSGSQKV AELKNRVAVK  780
LNRNEQLKNK VEELKNRNAY LKNELATLEN EVARLENDVA E                      821

SEQ ID NO: 105         moltype = AA  length = 776
FEATURE                Location/Qualifiers
source                 1..776
                       mol_type = protein
                       organism = synthetic construct
SEQUENCE: 105
MKKVCVIGAG TMGSGIAQAF AAKGFEVVLR DIKDEFVDRG LDFINKNLSK LVKKGKIEEA  60
TKVEILTRIS GTVDLNMAAD CDLVIEAAVE RMDIKKQIFA DLDNICKPET ILASNTSSLS  120
ITEVASATKR PDKVIGMHFF NPAPVMKLVE VIRGIATSQE TFDAVKETSI AIGKDPVEVA  180
EAPGFVVNRI LIPMINEAVG ILAEGIASVE DIDKAMKLGA NHPMGPLELG DFIGLDICLA  240
IMDVLYSETG DSKYRPHTLL KKYVRAGWLG RKSGKGFYDY SKKLSGGGGS GGGGSGGGGS  300
AEAWYNLGNA YYKQGDYQKA IEYYQKALEL DPNNAEAWYN LGNAYYKQGD YQKAIEYYQK  360
ALELDPNNAE AWYNLGNAYY KQGDYQKAIE DYQKALELDP NNLQAEAWKN LGNAYYKQGD  420
YQKAIEYYQK ALELDPNNAS AWYNLGNAYY KQGDYQKAIE YYQKALELDP NNAKAWYRRG  480
NAYYKQGDYQ KAIEDYQKAL ELDPNNRSRS AGGGGSGGGG SGGGGASENL YFQGENLYFQ  540
GDSSESCWNC GRKASETCSG CNTARYCGSF CQHKDWEKHH HICGQTLQAQ QGSAGSAAGS  600
GEFGSAEAAA KEAAAKAGSA GSAAGSGEFG SMAVSESQLK KMVSKYKYRD LTVRETVNVI  660
TLYKDLKPVL DSYVFNDGSS RELMNLTGTI PVPYRGNTYN IPICLWLLDT YPYNPPICFV  720
KPTSSMTIKT GKHVDANGKI YLPYLHEWKH PQSDLLGLIQ VMIVVFGDEP PVFSRP      776

SEQ ID NO: 106         moltype = AA  length = 741
FEATURE                Location/Qualifiers
source                 1..741
                       mol_type = protein
                       organism = synthetic construct
SEQUENCE: 106
MELNNVILEK EGKVAVVTIN RPKALNALNS DTLKEMDYVI GEIENDSEVL AVILTGAGEK  60
SFVAGADISE MKEMNTIEGR KFGILGNKVF RRLELLEKPV IAAVNGFALG GGCEIAMSCD  120
IRIASSNARF GQPEVGLGIT PGFGGTQRLS RLVGMGMAKQ LIFTAQNIKA DEALRIGLVN  180
KVVEPSELMN TAKEIANKIV SNAPVAVKLS KQAINRGMQC DIDTALAFES EAFGECFSTE  240
DQKDAMTAFI EKRKIEGFKN RKLSGGGGSG GGGSGGGGSA EAWYNLGNAY YKQGDYQKAI  300
EYYQKALELD PNNAEAWYNL GNAYYKQGDY QKAIEYYQKA LELDPNNAEA WYNLGNAYYK  360
QGDYQKAIED YQKALELDPN NLQAEAWKNL GNAYYKQGDY QKAIEYYQKA LELDPNNASA  420
WYNLGNAYYK QGDYQKAIEY YQKALELDPN NAKAWYRRGN AYYKQGDYQK AIEDYQKALE  480
LDPNNRSRSA GGGGSGGGGS GGGGASGPLG SPLTASMLAS APPQEQKQML GERLFPLIQA  540
MHPTLAGKIT GMLLEIDNSE LLHMLESPES LRSKVDEAVA VLQAHQAKEA AQKAGSAGSA  600
AGSGEFGSAE AAAKEAAAKA GSAGSAAGSG EFGSNTNMSV PTDGAVTTSQ IPASEQETLV  660
RPKPLLLKLL KSVGAQKDTY TMKEVLFYLG QYIMTKRLYD EKQQHIVYCS NDLLGDLFGV  720
PSFSVKEHRK IYTMIYRNLV V                                            741

SEQ ID NO: 107         moltype = AA  length = 820
FEATURE                Location/Qualifiers
source                 1..820
                       mol_type = protein
                       organism = synthetic construct
SEQUENCE: 107
MIVKPMVRNN ICLNAHPQGC KKGVEDQIEY TKKRITAEVK AGAKAPKNVL VLGCSNGYGL  60
ASRITAAFGY GAATIGVSFE KAGSETKYGT PGWYNNLAFD EAAKREGLYS VTIDGDAFSD  120
EIKAQVIEEA KKKGIKFDLI VYSLASPVRT DPDTGIMHKS VLKPFGKTFT GKTVDPFTGE  180
```

-continued

```
LKEISAEPAN DEEAAATVKV MGGEDWERWI KQLSKEGLLE EGCITLAYSY IGPEATQALY  240
RKGTIGKAKE HLEATAHRLN KENPSIRAFV SVNKGLVTRA SAVIPVIPLY LASLFKVMKE  300
KGNHEGCIEQ ITRLYAERLY RKDGTIPVDE ENRIRIDDWE LEEDVQKAVS ALMEKVTGEN  360
AESLTDLAGY RHDFLASNGF DVEGINYEAE VERFDRIKLS GGGGSGGGGS GGGGSAEAWY  420
NLGNAYYKQG DYQKAIEYYQ KALELDPNNA EAWYNLGNAY YKQGDYQKAI EYYQKALELD  480
PNNAEAWYNL GNAYYKQGDY QKAIEDYQKA LELDPNNLQA EAWKNLGNAY YKQGDYQKAI  540
EYYQKALELD PNNASAWYNL GNAYYKQGDY QKAIEYYQKA LELDPNNAKA WYRRGNAYYK  600
QGDYQKAIED YQKALELDPN NRSRSAGGGG SGGGGSGGGG ASSYYHHHHH HLESTSLYKK  660
AGSGSNLLAT LRSTAAVLEN ENHVLEKEKE KLRKEKEQLL NKLEAYKGSA GSAAGSGEFG  720
SAEAAAKEAA AKAGSAGSAA GSGEFGSSYY HHHHHHLEST SLYKKAGSGS KRIAYLRKKI  780
AALKKDNANL EKDIANLENE IERLIKEIKT LENEVASHEQ                        820

SEQ ID NO: 108          moltype = AA  length = 826
FEATURE                 Location/Qualifiers
source                  1..826
                        mol_type = protein
                        organism = synthetic construct
SEQUENCE: 108
MTREVVVVSG VRTAIGTFGG SLKDVAPAEL GALVVREALA RAQVSGDDVG HVVFGNVIQT  60
EPRDMYLGRV AAVNGGVTIN APALTVNRLC GSGLQAIVSA AQTILLGDTD VAIGGGAESM  120
SRAPYLAPAA RWGARMGDAG LVDMMLGALH DPFHRIHMGV TAENVAKEYD ISRAQQDEAA  180
LESHRRASAA IKAGYFKDQI VPVVSKGRKG DVTFDTDEHV RHDATIDDMT KLRPVFVKEN  240
GTVTAGNASG LNDAAAAVVM MERAEAERRG LKPLARLVSY GHAGVDPKAM GIGPVPATKI  300
ALERAGLQVS DLDVIEANEA FAAQACAVTK ALGLDPAKVN PNGSGISLGH PIGATGALIT  360
VKALHELNRV QGRYALVTMC IGGGQGIAAI FERIKLSGGG GSGGGGSGGG GSAEAWYNLG  420
NAYYKQGDYQ KAIEYYQKAL ELDPNNAEAW YNLGNAYYKQ GDYQKAIEYY QKALELDPNN  480
AEAWYNLGNA YYKQGDYQKA IEDYQKALEL DPNNLQAEAW KNLGNAYYKQ GDYQKAIEYY  540
QKALELDPNN ASAWYNLGNA YYKQGDYQKA IEYYQKALEL DPNNAKAWYR RGNAYYKQGD  600
YQKAIEDYQK ALELDPNNRS RSAGGGGSGG GGSGGGGASD VMWEYKWENT GDAELYGPFT  660
SAQMQTWVSE GYFPDGVYCR KLDPPGGQFY NSKRIDFDLY TGSAGSAAGS GEFGSAEAAA  720
KEAAAKAGSA GSAAGSGEFG SESDSVEFNN AISYVNKIKT RFLDHPEIYR SFLEILHTYQ  780
KEQLHTKGRP FRGMSEEEVF TEVANLFRGQ EDLLSEFGQF LPEAKR                 826

SEQ ID NO: 109          moltype = AA  length = 849
FEATURE                 Location/Qualifiers
source                  1..849
                        mol_type = protein
                        organism = synthetic construct
SEQUENCE: 109
MKLSTKLCWC GIKGRLRPQK QQQLHNTNLQ MTELKKQKTA EQKTRPQNVG IKGIQIYIPT  60
QCVNQSELEK FDGVSQGKYT IGLGQTNMSF VNDREDIYSM SLTVLSKLIK SYNIDTNKIG  120
RLEVGTETLI DKSKSVKSVL MQLFGENTDV EGIDTLNACY GGTNALFNSL NWIESNAWDG  180
RDAIVVCGDI AIYDKGAARP TGGAGTVAMW IGPDAPIVFD SVRASYMEHA YDFYKPDFTS  240
EYPYVDGHFS LTCYVKALDQ VYKSYSKKAI SKGLVSDPAG SDALNVLKYF DYNVFHVPTC  300
KLVTKSYGRL LYNDFRANPQ LFPEVDAELA TRDYDESLTD KNIEKTFVNV AKPFHKERVA  360
QSLIVPTNTG NMYTASVYAA FASLLNYVGS DDLQGKRVGL FSYGSGLAAS LYSCKIVGDV  420
QHIIKELDIT NKLAKRITET PKDYEAAIEL RENAHLKKNF KPQGSIEHLQ SGVYYLTNID  480
DKFRRSYDVK KKLSGGGGSG GGGSGGGGSA EAWYNLGNAY YKQGDYQKAI EYYQKALELD  540
PNNAEAWYNL GNAYYKQGDY QKAIEYYQKA LELDPNNAEA WYNLGNAYYK QGDYQKAIED  600
YQKALELDPN NLQAEAWKNL GNAYYKQGDY QKAIEYYQKA LELDPNNASA WYNLGNAYYK  660
QGDYQKAIEY YQKALELDPN NAKAWYRRGN AYYKQGDYQK AIEDYQKALE LDPNNRSRSA  720
GGGGSGGGGS GGGGASLGPL PPGWEVRSTV SGRIYFVDHN NRTTQFTDPR LHGSAGSAAG  780
SGEFGSAEAA AKEAAAKAGS AGSAAGSGEF GSGAMGPLPP GWEKRTDSNG RVYFVNHNTR  840
ITQWEDPRS                                                          849

SEQ ID NO: 110          moltype = AA  length = 826
FEATURE                 Location/Qualifiers
source                  1..826
                        mol_type = protein
                        organism = synthetic construct
SEQUENCE: 110
MVAVRRKALS ILAEAPVLAS DRLPYKNYDY DRVFGACCEN VIGYMPLPVG VIGPLVIDGT  60
SYHIPMATTE GCLVASAMRG CKAINAGGGA TTVLTKDGMT RGPVVRFPTL KRSGACKIWL  120
DSEEGQNAIK KAFNSTSRFA RLQHIQTCLA GDLLFMRFRT TTGDAMGMNM ISKGVEYSLK  180
QMVEEYGWED MEVVSVSGNY CTDKKPAAIN WIEGRGKSVV AEATIPGDVV RKVLKSDVSA  240
LVELNIAKNL VGSAMAGSVG GFNAHAANLV TAVFLALGQD PAQNVESSNC ITLMKEVDGD  300
LRISVSMPSI EVGTIGGGTV LEPQGAMLDL LGVRGPHATA PGTNARQLAR IVACAVLAGE  360
LSLCAALAAG HLVQSHMTHN RKLSGGGGSG GGGSGGGGSA EAWYNLGNAY YKQGDYQKAI  420
EYYQKALELD PNNAEAWYNL GNAYYKQGDY QKAIEYYQKA LELDPNNAEA WYNLGNAYYK  480
QGDYQKAIED YQKALELDPN NLQAEAWKNL GNAYYKQGDY QKAIEYYQKA LELDPNNASA  540
WYNLGNAYYK QGDYQKAIEY YQKALELDPN NAKAWYRRGN AYYKQGDYQK AIEDYQKALE  600
LDPNNRSRSA GGGGSGGGGS GGGGASSYYH HHHHHLESTS LYKKAGSEFF RRERNKMAAA  660
KCRNRRRELT DTLQAETDQL EDEKSALQTE IANLLKEKEK LEFILAAHRP ACKIPDDLGF  720
PEEMSLEGSA GSAAGSGEFG SAEAAAKEAA AKAGSAGSAA GSGEFGSSYY HHHHHHLEST  780
SLYKKAGSGS QKVESLKQKI EELKQRKAQL KNDIANLEKE IAYAET                 826

SEQ ID NO: 111          moltype = AA  length = 1046
FEATURE                 Location/Qualifiers
source                  1..1046
```

```
                        mol_type = protein
                        organism = synthetic construct
SEQUENCE: 111
MSLPFLTSAP GKVIIFGEHS AVYNKPAVAA SVSALRTYLL ISESSAPDTI ELDFPDISFN  60
HKWSINDFNA ITEDQVNSQK LAKAQQATDG LSQELVSLLD PLLAQLSESF HYHAAFCFLY  120
MFVCLCPHAK NIKFSLKSTL PIGAGLGSSA SISVSLALAM AYLGGLIGSN DLEKLSENDK  180
HIVNQWAFIG EKCIHGTPSG IDNAVATYGN ALLFEKDSHN GTINTNNFKF LDDFPAIPMI  240
LTYTRIPRST KDLVARVRVL VTEKFPEVMK PILDAMGECA LQGLEIMTKL SKCKGTDDEA  300
VETNNELYEQ LLELIRINHG LLVSIGVSHP GLELIKNLSD DLRIGSTKLT GAGGGGCSLT  360
LLRRDITQEQ IDSFKKKLQD DFSYETFETD LGGTGCCLLS AKNLNKDLKI KSLVFQLFEN  420
KTTTKQQIDD LLLPGNTNLP WTSKLSGGGG SGGGGSGGGG SAEAWYNLGN AYYKQGDYQK  480
AIEYYQKALE LDPNNAEAWY NLGNAYYKQG DYQKAIEYYQ KALELDPNNA EAWYNLGNAY  540
YKQGDYQKAI EDYQKALELD PNNLQAEAWK NLGNAYYKQG DYQKAIEYYQ KALELDPNNA  600
SAWYNLGNAY YKQGDYQKAI EYYQKALELD PNNAKAWYRR GNAYYKQGDY QKAIEDYQKA  660
LELDPNNRSR SAGGGGSGGG GSGGGGASME PAMEPETLEA RINRATNPLN KELDWASING  720
FCEQLNEDFE GPPLATRLLA HKIQSPQEWE AIQALTVLET CMKSCGKRFH DEVGKFRFLN  780
ELIKVVSPKY LGSRTSEKVK NKILELLYSW TVGLPEEVKI AEAYQMLKKQ GIVKSGSAGS  840
AAGSGEFGSA EAAAKEAAAK AGSAGSAAGS GEFGSGAMGS MAEAEGESLE SWLNKATNPS  900
NRQEDWEYII GFCDQINKEL EGPQIAVRLL AHKIQSPQEW EALQALTVLE ACMKNCGRRF  960
HNEVGKFRFL NELIKVVSPK YLGDRVSEKV KTKVIELLYS WTMALPEEAK IKDAYHMLKR  1020
QGIVQSDPPI PVDRTLIPSP PPRPKN                                     1046

SEQ ID NO: 112          moltype = AA  length = 868
FEATURE                 Location/Qualifiers
source                  1..868
                        mol_type = protein
                        organism = synthetic construct
SEQUENCE: 112
MSELRAFSAP GKALLAGGYL VLDTKYEAFV VGLSARMHAV AHPYGSLQGS DKFEVRVKSK  60
QFKDGEWLYH ISPKSGFIPV SIGGSKNPFI EKVIANVFSY FKPNMDDYCN RNLFVIDIFS  120
DDAYHSQEDS VTEHRGNRRL SFHSHRIEEV PKTGLGSSAG GLVTVLTTAL ASFFVSDLEN  180
NVDKYREVIH NLAQVAHCQA QGKIGSGFDV AAAAYGSIRY RRFPPALISN LPDIGSATYG  240
SKLAHLVDEE DWNITIKSNH LPSGLTLWMG DIKNGSETVK LVQKVKNWYD SHMPESLKIY  300
TELDHANSRF MDGLSKLDRL HETHDDYSDQ IFESLERNDC TCQKYPEITE VRDAVATIRR  360
SFRKITKESG ADIEPPVQTS LLDDCQTLKG VLTCLIPGAG GYDAIAVITK QDVDLRAQTA  420
NDKRFSKVQW LDVTQADWGV RKEKDPETYL DKKLSGGGGS GGGGSGGGGS AEAWYNLGNA  480
YYKQGDYQKA IEYYQKALEL DPNNAEAWYN LGNAYYKQGD YQKAIEYYQK ALELDPNNAE  540
AWYNLGNAYY KQGDYQKAIE DYQKALELDP NNLQAEAWKN LGNAYYKQGD YQKAIEYYQK  600
ALELDPNNAS AWYNLGNAYY KQGDYQKAIE YYQKALELDP NNAKAWYRRG NAYYKQGDYQ  660
KAIEDYQKAL ELDPNNRSRS AGGGGSGGGG SGGGGASSYY HHHHHHLEST SLYKKAGSGS  720
QKVEELKNKI AELENRNAVK KNRVAHLKQE IAYLKDELAA HEFEGSAGSA AGSGEFGSAE  780
AAAKEAAAKA GSAGSAAGSG EFGSSYYHHH HHHLESTSLY KKAGSGSFEN VTHEFILATL  840
ENENAKLRRL EAKLERELAR LRNEVAWL                                   868

SEQ ID NO: 113          moltype = AA  length = 1008
FEATURE                 Location/Qualifiers
source                  1..1008
                        mol_type = protein
                        organism = synthetic construct
SEQUENCE: 113
MTVYTASVTA PVNIATLKYW GKRDTKLNLP TNSSISVTLS QDDLRTLTSA ATAPEFERDT  60
LWLNGEPHSI DNERTQNCLR DLRQLRKEME SKDASLPTLS QWKLHIVSEN NFPTAAGLAS  120
SAAGFAALVS AIAKLYQLPQ STSEISRIAR KGSGSACRSL FGGYVAWEMG KAEDGHDSMA  180
VQIADSSDWP QMKACVLVVS DIKKDVSSTQ GMQLTVATSE LFKERIEHVV PKRFEVMRKA  240
IVEKDFATFA KETMMDSNSF HATCLDSFPP IFYMNDTSKR IISWCHTINQ FYGETIVAYT  300
FDAGPNAVLY YLAENESKLF AFIYKLFGSV PGWDKKFTTE QLEAFNHQFE SSNFTARELD  360
LELQKDVARV ILTQVGSGPQ ETNESLIDAK TGLPKEKLSG GGGSGGGGSG GGGSAEAWYN  420
LGNAYYKQGD YQKAIEYYQK ALELDPNNAE AWYNLGNAYY KQGDYQKAIE YYQKALELDP  480
NNAEAWYNLG NAYYKQGDYQ KAIEDYQKAL ELDPNNLQAE AWKNLGNAYY KQGDYQKAIE  540
YYQKALELDP NNASAWYNLG NAYYKQGDYQ KAIEYYQKAL ELDPNNAKAW YRRGNAYYKQ  600
GDYQKAIEDY QKALELDPNN RSRSAGGGGS GGGGSGGGGA SAMADLEQKV LEMEASTYDG  660
VFIWKISDFP RKRQEAVAGR IPAIFSPAFY TSRYGYKMCL RIYLNGDGTG RGTHLSLFFV  720
VMKGPNDALL RWPFNQKVTL MLLDQNNREH VIDAFRPDVT SSSFQRPVND MNIASGCPLF  780
CPVSKMEAKN SYVRDDAIFI KAIVDLTGLG SAGSAAGSGE FGSAEAAAKE AAAKAGSAGS  840
AAGSGEFGSA SIKLQSSDGE IFEVDVEIAK QSVTIKTMLE DLGMDDEGDD DPVPLPNVNA  900
AILKKVIQWC THHKDDPPPP EDDENKEKRT DDIPVWDQEF LKVDQGTLFE LILAANYLDI  960
KGLLDVTCKT VANMIKGKTP EEIRKTFNIK NDFTEEEEAQ VRKENQWC              1008

SEQ ID NO: 114          moltype = AA  length = 717
FEATURE                 Location/Qualifiers
source                  1..717
                        mol_type = protein
                        organism = synthetic construct
SEQUENCE: 114
MTADNNSMPH GAVSSYAKLV QNQTPEDILE EFPEIIPLQQ RPNTRSSETS NDESGETCFS  60
GHDEEQIKLM NENCIVLDWD DNAIGAGTKK VCHLMENIEK GLLHRAFSVF IFNEQGELLL  120
QQRATEKITF PDLWTNTCCS HPLCIDDELG LKGKLDDKIK GAITAAVRKL DHELGIPEDE  180
TKTRGKFHFL NRIHYMAPSN EPWGEHEIDY ILFYKINAKE NLTVNPNVNE VRDFKWVSPN  240
DLKTMFADPS YKFTPWFKII CENYLFNWWE QLDDLSEVEN DRQIHRMLKL SGGGGSGGGG  300
```

```
SGGGGSAEAW YNLGNAYYKQ GDYQKAIEYY QKALELDPNN AEAWYNLGNA YYKQGDYQKA  360
IEYYQKALEL DPNNAEAWYN LGNAYYKQGD YQKAIEDYQK ALELDPNNLQ AEAWKNLGNA  420
YYKQGDYQKA IEYYQKALEL DPNNASAWYN LGNAYYKQGD YQKAIEYYQK ALELDPNNAK  480
AWYRRGNAYY KQGDYQKAIE DYQKALELDP NNRSRSAGGG GSGGGGSGGG GASSYYHHHH  540
HHLESTSLYK KAGSGSNTVK ELKNYIQELE ERNAELKNLK EHLKFAKAEL EFELAAHKFE  600
GSAGSAAGSG EFGSAEAAAK EAAAKAGSAG SAAGSGEFGS SYYHHHHHHL ESTSLYKKAG  660
SGSQKVAQLK NRVAYKLKEN AKLENIVARL ENDNANLEKD IANLEKDIAN LERDVAR     717

SEQ ID NO: 115          moltype = AA  length = 798
FEATURE                 Location/Qualifiers
source                  1..798
                        mol_type = protein
                        organism = synthetic construct
SEQUENCE: 115
MEAKIDELIN NDPVWSSQNE SLISKPYNHI LLKPGKNFRL NLIVQINRVM NLPKDQLAIV  60
SQIVELLHNS SLLIDDIEDN APLRRGQTTS HLIWGVPSTI NTANYMYFRA MQLVSQLTTK  120
EPLYHWLITI FNEELINLHR GQGLDIYWRD FLPEIIPTQE MYLNMVMNKT GGLFRLTLRL  180
MEALSPSSHH GHSLVPFINL LGIIYQIRDD YLNLKDFQMS SEKGFAEDIT EGKLSFPIVH  240
ALNFTKTKGQ TEQHNEILRI LLLRTSDKDI KLKLIQILEF DTNSLAYTKN FINQLVNMIK  300
NDNENKYLPD LASHSDTATN LHDELLYIID HLSELKLSGG GGSGGGGSGG GGSAEAWYNL  360
GNAYYKQGDY QKAIEYYQKA LELDPNNAEA WYNLGNAYYK QGDYQKAIEY YQKALELDPN  420
NAEAWYNLGN AYYKQGDYQK AIEDYQKALE LDPNNLQAEA WKNLGNAYYK QGDYQKAIEY  480
YQKALELDPN NASAWYNLGN AYYKQGDYQK AIEYYQKALE LDPNNAKAWY RRGNAYYKQG  540
DYQKAIEDYQ KALELDPNNR SRSAGGGGSG GGGSGGGGAS LCTMKKGPSG YGFNLHSDKS  600
KPGQFIRSVD PDSPAEASGL RAQDRIVEVN GVCMEGKQHG DVVSAIRAGG DETKLLVVDR  660
EGSAGSAAGS GEFGSAEAAA KEAAAKAGSA GSAAGSGEFG SSSGAIIYTV ELKRYGGPLG  720
ITISGTEEPF DPIIISSLTK GGLAERTGAI HIGDRILAIN SSSLKGKPLS EAIHLLQMAG  780
ETVTLKIKKQ TDAQPASS                                                798

SEQ ID NO: 116          moltype = AA  length = 883
FEATURE                 Location/Qualifiers
source                  1..883
                        mol_type = protein
                        organism = synthetic construct
SEQUENCE: 116
MNHLRAEGPA SVLAIGTANP ENILLQDEFP DYYFRVTKSE HMTQLKEKFR KICDKSMIRK  60
RNCFLNEEHL KQNPRLVEHE MQTLDARQDM LVVEVPKLGK DACAKAIKEW GQPKSKITHL  120
IFTSASTTDM PGADYHCAKL LGLSPSVKRV MMYQLGCYGG GTVLRIAKDI AENNKGARVL  180
AVCCDIMACL FRGPSESDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LHLKSDKFVD SRHVLSEHGN MSSSTVLFVM DELRKRSLEE GKSTTGDGFE  360
WGVLFGFGPG LTVERVVVRS VPIKYKLSGG GGSGGGGSGG GGSAEAWYNL GNAYYKQGDY  420
QKAIEYYQKA LELDPNNAEA WYNLGNAYYK QGDYQKAIEY YQKALELDPN NAEAWYNLGN  480
AYYKQGDYQK AIEDYQKALE LDPNNLQAEA WKNLGNAYYK QGDYQKAIEY YQKALELDPN  540
NASAWYNLGN AYYKQGDYQK AIEYYQKALE LDPNNAKAWY RRGNAYYKQG DYQKAIEDYQ  600
KALELDPNNR SRSAGGGGSG GGGSGGGGAS GNNLETYEWY NKSISRDKAE KLLLDTGKEG  660
AFMVRDSRTP GTYTVSVFTK AIISENPCIK HYHIKETNDS PKRYYVAEKY VFDSIPLLIQ  720
YHQYNGGGLV TRLRYPVCGG SAGSAAGSGE FGSAEAAAKE AAAKAGSAGS AAGSGEFGSG  780
SHPWFFGKIP RAKAEEMLSK QRHDGAFLIR ESESAPGDFS LSVKFGNDVQ HFKVLRDGAG  840
KYFLWVVKFN SLNELVDYHR STSVSRNQQI FLRDIEQVPQ QPT                    883

SEQ ID NO: 117          moltype = AA  length = 665
FEATURE                 Location/Qualifiers
source                  1..665
                        mol_type = protein
                        organism = synthetic construct
SEQUENCE: 117
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR KKLSGGGGSG GGGSGGGGSA  120
EAWYNLGNAY YKQGDYQKAI EYYQKALELD PNNAEAWYNL GNAYYKQGDY QKAIEYYQKA  180
LELDPNNAEA WYNLGNAYYK QGDYQKAIED YQKALELDPN NLQAEAWKNL GNAYYKQGDY  240
QKAIEYYQKA LELDPNNASA WYNLGNAYYK QGDYQKAIEY YQKALELDPN NAKAWYRRGN  300
AYYKQGDYQK AIEDYQKALE LDPNNRSRSA GGGGSGGGGS GGGGASGQDR SEATLIKRFK  360
GEGVRYKAKL IGIDEVSAAR GDKLCQDSMM KLKGVVAGAR SKGEHKQKIF LTISFGGIKI  420
FDEKTGALQH HHAVHEISYI AKDITDHRAF GYVCGKEGNH RFVAIKTAQA AEPVILDLRD  480
LFQLIYELKQ REELEKKAGS AGSAAGSGEF GSAEAAAKEA AAKAGSAGSA AGSGEFGSGS  540
HMGSQFWVTS QKTEASERCG LQGSYILRVE AEKLTLLTLG AQSQILEPLL FWPYTLLRRY  600
GRDKVMFSFE AGRRCPSGPG TFTFQTSQGN DIFQAVEAAI QQQKAQGKVG QAQDILRLEH  660
HHHHH                                                              665

SEQ ID NO: 118          moltype = AA  length = 797
FEATURE                 Location/Qualifiers
source                  1..797
                        mol_type = protein
                        organism = synthetic construct
SEQUENCE: 118
MGLSSVCTFS FQTNYHTLLN PHNNNPKTSL LCYRHPKTPI KYSYNNFPSK HCSTKSFHLQ  60
NKCSESLSIA KNSIRAATTN QTEPPESDNH SVATKILNFG KACWKLQRPY TIIAFTSCAC  120
GLFGKELLHN TNLISWSLMF KAFFFLVAIL CIASFTTTIN QIYDLHIDRI NKPDLPLASG  180
```

-continued

EISVNTAWIM SIIVALFGLI ITIKMKGGPL YIFGYCFGIF GGIVYSVPPF RWKQNPSTAF 240
LLNFLAHIIT NFTFYYASRA ALGLPFELRP SFTFLLAFMK SMGSALALIK DASDVEGDTK 300
FGISTLASKY GSRNLTLFCS GIVLLSYVAA ILAGIIWPQA FNSNVMLLSH AILAFWLILQ 360
TRDFALTNYD PEAGRRFYEF MWKLYYAEYL VYVFIKLSGG GGSGGGGSGG GGSAEAWYNL 420
GNAYYKQGDY QKAIEYYQKA LELDPNNAEA WYNLGNAYYK QGDYQKAIEY YQKALELDPN 480
NAEAWYNLGN AYYKQGDYQK AIEDYQKALE LDPNNLQAEA WKNLGNAYYK QGDYQKAIEY 540
YQKALELDPN NASAWYNLGN AYYKQGDYQK AIEYYQKALE LDPNNAKAWY RRGNAYYKQG 600
DYQKAIEDYQ KALELDPNNR SRSAGGGGSG GGGSGGGGAS AEYVRALFDF NGNDEEDLPF 660
KKGDILRIRD KPEEQWWNAE DSEGKRGMIP VPYVEKYGSA GSAAGSGEFG SAEAAAKEAA 720
AKAGSAGSAA GSGEFGSLIK HMRAEALFDF TGNSKLELNF KAGDVIFLLS RINKDWLEGT 780
VRGATGIFPL SFVKILK 797

SEQ ID NO: 119 moltype = AA length = 3620
FEATURE Location/Qualifiers
source 1..3620
mol_type = protein
organism = synthetic construct
SEQUENCE: 119
MGSAGSAAGS GEFGSAGSAA GSGEFGSAGS AAGSGEFSYY HHHHHHLEST SLYKKAGSGS 60
ARNAYLRKKI ARLKKDNLQL ERDEQNLEKI IANLRDEIAR LENEVASHEQ GSAGSAAGSG 120
EFAEAAAKEA AAKAGSAGSA AGSGEFSYYH HHHHHLESTS LYKKAGSGSN LVAQLENEVA 180
SLENENETLK KKNLHKKDLI AYLEKEIANL RKKIEEGSAG SAAGSGEFGS AEAAAKEAAA 240
KEAAAKEAAA KAGSAGSAAG SGEFGSSYYH HHHHHLESTS LYKKAGSGSQ KVAELKNRVA 300
VKLNRNEQLK NKVEELKNRN AYLKNELATL ENEVARLEND VAEGSAGSAA GSGEFAEAAA 360
KEAAAKAGSA GSAAGSGEFS YYHHHHHHLE STSLYKKAGS GSNEVTTLEN DAAFIENENA 420
YLEKEIARLR KEKAALRNRL AHKKGSAGSA AGSGEFGSAE AAAKEAAAKE AAAKEAAAKA 480
GSAGSAAGSG EFGSRPPTIS NPPPLISSAK HPSVGSAGSA AGSGEFAEAA AKEAAAKAGS 540
AGSAAGSGEF NFLQSRPEPT APPEESFRSG GSAGSAAGSG EFGSAEAAAK EAAAKEAAAK 600
EAAAKAGSAG SAAGSGEFGS SKGTGLNPNA KVWQEIAPGN GSAGSAAGSG EFAEAAAKEA 660
AAKAGSAGSA AGSGEFPDGG TTFEHLWSSL EPDSTYGSAG SAAGSGEFGS AEAAAKEAAA 720
KEAAAKEAAA KAGSAGSAAG SGEFGSSYYH HHHHHLESTS LYKKAGSGSK RIAYLRKKIA 780
ALKKDNANLE KDIANLENEI ERLIKEIKTL ENEVASHEQG SAGSAAGSGE FAEAAAKEAA 840
AKAGSAGSAA GSGEFSYYHH HHHHLESTSL YKKAGSGSNL LATLRSTAAV LENENHVLEK 900
EKEKLRKEKE QLLNKLEAYK GSAGSAAGSG EFGSAEAAAK EAAAKEAAAK EAAAKAGSAG 960
SAAGSGEFGS PATSQHPPPP PGHRSQAPSH GSAGSAAGSG EFAEAAAKEA AAKAGSAGSA 1020
AGSGEFELNS LLILLEAAEY LERRDRGSAG SAAGSGEFGS AEAAAKEAAA KEAAAKEAAA 1080
KAGSAGSAAG SGEFGSRPPT ISNPPPLISS AKHPSVGSAG SAAGSGEFAE AAAKEAAAKA 1140
GSAGSAAGSG EFNFLQSRPE PTAPPEESFR SGGSAGSAAG SGEFGSAEAA AKEAAAKEAA 1200
AKEAAAKAGS AGSAAGSGEF GSSKGTGLNP NAKVWQEIAP GNGSAGSAAG SGEFAEAAAK 1260
EAAAKAGSAG SAAGSGEFPD GGTTFEHLWS SLEPDSTYGS AGSAAGSGEF GSAEAAAKEA 1320
AAKEAAAKEA AAKAGSAGSA AGSGEFGSSY YHHHHHHLES TSLYKKAGSG SKRIAYLRKK 1380
IAALKKDNAN LEKDIANLEN EIERLIKEIK TLENEVASHE QGSAGSAAGS GEFAEAAAKE 1440
AAAKAGSAGS AAGSGEFSYY HHHHHHLEST SLYKKAGSGS NLLATLRSTA AVLENENHVL 1500
EKEKEKLRKE KEQLLNKLEA YKGSAGSAAG SGEFGSAEAA AKEAAAKEAA AKEAAAKAGS 1560
AGSAAGSGEF GSALVDDAAD YEPPPSNNEE ALGSAGSAAG SGEFAEAAAK EAAAKAGSAG 1620
SAAGSGEFRE LFDDPSYVNV QNLDKARQGS AGSAAGSGEF GSAEAAAKEA AAKEAAAKEA 1680
AAKAGSAGSA AGSGEFGSKN TKSMNFDNPV YRKTTEEEGS AGSAAGSGEF AEAAAKEAAA 1740
KAGSAGSAAG SGEFRSLPST WIENKLYGMS DPNWGSAGSA AGSGEFGSAE AAAKEAAAKE 1800
AAAKEAAAKA GSAGSAAGSG EFGSVVDNSP PPALPPKKRQ SAPSGSAGSA AGSGEFAEAA 1860
AKEAAAKAGS AGSAAGSGEF TQRSKPQPAV PPRPSADLIL GSAGSAAGSG EFGSAEAAAK 1920
EAAAKEAAAK EAAAKAGSAG SAAGSGEFGS TDEEREETEE EVYLLNSTTL GSAGSAAGSG 1980
EFAEAAAKEA AAKAGSAGSA AGSGEFDGNV SGTQRLDSAT VRTYSCGSAG SAAGSGEFGS 2040
AEAAAKEAAA KEAAAKEAAA KAGSAGSAAG SGEFGSSYYH HHHHHLESTS LYKKAGSGSQ 2100
KVAQLKNRVA YKLKENAKLE NIVARLENDN ANLEKDIANL EKDIANLERD VARGSAGSAA 2160
GSGEFAEAAA KEAAAKAGSA GSAAGSGEFS YYHHHHHHLE STSLYKKAGS GSNTVKELKN 2220
YIQELEERNA ELKNLKEHLK FAKAELEFEL AAHKFEGSAG SAAGSGEFGS AEAAAKEAAA 2280
KEAAAKEAAA KAGSAGSAAG SGEFGSHDDS LPHPQQATDD SGHESDGSAG SAAGSGEFAE 2340
AAAKEAAAKA GSAGSAAGSG EFGSPNAGSV EQTPKKPGLR RRGSAGSAAG SGEFGSAEAA 2400
AKEAAAKEAA AKEAAAKAGS AGSAAGSGEF GSSYYHHHHH HLESTSLYKK AGSGSFENVT 2460
HEFILATLEN ENAKLRRLEA KLERELARLR NEVAWLGSAG SAAGSGEFAE AAAKEAAAKA 2520
GSAGSAAGSG EFSYYHHHHH HLESTSLYKK AGSGSQKVEE LKNKIAELEN RNAVKKNRVA 2580
HLKQEIAYLK DELAAHEFEG SAGSAAGSGE FGSAEAAAKE AAAKEAAAKE AAAKAGSAGS 2640
AAGSGEFGSV SSTKLVSFHD DSDEDLLHIG SAGSAAGSGE FAEAAAKEAA AKAGSAGSAA 2700
GSGEFAAATP ISTFHDDSDE DLLHVGSAGS AAGSGEFGSA EAAAKEAAAK EAAAKEAAAK 2760
AGSAGSAAGS GEFGSSYYHH HHHHLESTSL YKKAGSGSQK VESLKQKIEE LKQRKAQLKN 2820
DIANLEKEIA YAETGSAGSA AGSGEFAEAA AKEAAAKAGS AGSAAGSGEF SYYHHHHHHL 2880
ESTSLYKKAG SEFFRRERNK MAAAKCRNRR RELTDTLQAE TDQLEDEKSA LQTEIANLLK 2940
EKEKLEFILA AHRPACKIPD DLGFPEEMSL EGSAGSAAGS GEFGSAEAAA KEAAAKEAAA 3000
KEAAAKAGSA GSAAGSGEFG SFQMPADTPP PAYLPPEDPM TGSAGSAAGS GEFAEAAAKE 3060
AAAKAGSAGS AAGSGEFERE SNEEPPPPYE DPYWGNGGSA GSAAGSGEFG SAEAAAKEAA 3120
AKEAAAKEAA AKAGSAGSAA GSGEFGSSYY HHHHHHLEST SLYKKAGSGS QKVAELKNRV 3180
AVKLNRNEQL KNKVEELKNR NAYLKNELAT LENEVARLEN DVAEGSAGSA AGSGEFAEAA 3240
AKEAAAKAGS AGSAAGSGEF SYYHHHHHHL ESTSLYKKAG SGSNEVTTLE NDAAFIENEN 3300
AYLEKEIARL RKEKAALRNR LAHKKSYYHH HHHHLESTSL YKKAGSGSAR NAYLRKKIAR 3360
LKKDNLQLER DEQNLEKIIA NLRDEIARLE NEVASHEQGS AGSAAGSGEF AEAAAKEAAA 3420
KAGSAGSAAG SGEFSYYHHH HHHLESTSLY KKAGSGSNLV AQLENEVASL ENENETLKKK 3480
NLHKKDLIAY LEKEIANLRK KIEEGSAGSA AGSGEFGSAE AAAKEAAAKE AAAKEAAAKA 3540
GSAGSAAGSG EFGSEQKLIS EEDLEQKLIS EEDLEQKLIS EEDLGSAGSA AGSGEFGSAG 3600
SAAGSGEFGS AGSAAGSGEF 3620

```
SEQ ID NO: 120         moltype = AA  length = 452
FEATURE                Location/Qualifiers
source                 1..452
                       mol_type = protein
                       organism = synthetic construct
SEQUENCE: 120
MGSAGSAAGS GEFGSAGSAA GSGEFGSAGS AAGSGEFSYY HHHHHHLEST SLYKKAGSGS  60
ARNAYLRKKI ARLKKDNLQL ERDEQNLEKI IANLRDEIAR LENEVASHEQ GSAGSAAGSG  120
EFAEAAAKEA AAKAGSAGSA AGSGEFSYYH HHHHHLESTS LYKKAGSGSN LVAQLENEVA  180
SLENENETLK KKNLHKKDLI AYLEKEIANL RKKIEEGSAG SAAGSGEFGS AEAAAKEAAA  240
KEAAAKEAAA KAGSAGSAAG SGEFGSSATR ELDELMASLS DFKIQGGSAG SAAGSGEFAE  300
AAAKEAAAKA GSAGSAAGSG EFDLALSENW AQEFLAAGDA VDGSAGSAAG SGEFGSAEAA  360
AKEAAAKEAA AKEAAAKAGS AGSAAGSGEF GSDYKDDDDK DYKDDDDKDY KDDDDKGSAG  420
SAAGSGEFGS AGSAAGSGEF GSAGSAAGSG EF                               452

SEQ ID NO: 121         moltype = DNA  length = 3303
FEATURE                Location/Qualifiers
source                 1..3303
                       mol_type = other DNA
                       organism = synthetic construct
SEQUENCE: 121
atgtctgcta aagctatttc tgaacaaact ggtaaagaat tgttgtataa atttatttgt  60
actacttctg ctattcaaaa tagatttaaa tatgctagag ttactccaga tactgattgg  120
gctagattgt tgcaagatca tccatggttg ttgtctcaaa atttggttgt taaaccagat  180
caattgatta aaagaagagg taaattgggt ttggttggtg ttaatttgac tttggatggt  240
gttaaatctt ggttgaaacc aagattgggt caagaagcta ctgttggtaa agctactggt  300
tttttgaaaa atttttgat tgaaccattt gttccacatt ctcaagctga agaattttat  360
gtttgtattt atgctactag agaaggtgat tatgttttgt ttcatcatga aggtggtgtt  420
gatgttggtg atgttgatgc taaagctcaa aaattgttgg ttggtgttga tgaaaaattg  480
aatccagaag atattaaaaa acatttgttg gttcatgctc cagaagataa aaaagaaatt  540
ttggcttctt ttatttctgg tttgtttaat ttttatgaag atttgtattt tacttatttg  600
gaaattaatc cattggttgt tactaaagat ggtgtttatg ttttggattt ggctgctaaa  660
gttgatgcta ctgctgatta tatttgtaaa gttaaatggg gtgatattga atttccacca  720
ccatttggta gagaagctta tccagaagaa gcttatattg ctgatttgga tgctaaatct  780
ggtgcttctt tgaaattgac tttgttgaat ccaaaaggta gaatttggac tatggttgct  840
ggtggtggtg cttctgttgt ttattctgat actatttgtg atttgggtgg tgttaatgaa  900
ttggctaatt atggtgaata ttctggtgct ccatctgaac aacaaactta tgattatgct  960
aaaactattt tgtctttgat gactagagaa aaacatccag atggtaaaat tttgattatt  1020
ggtggttcta ttgctaattt tactaatgtt gctgctactt ttaaaggtat tgttagagct  1080
attagagatt atcaaggtcc attgaaagaa catgaagtta ctatttttgt tagaagaggt  1140
ggtccaaatt atcaagaagg tttgagagtt atgggtgaag ttggtaaaac tactggtatt  1200
ccaattcatg tttttggtac tgaaactcat atgactgcta ttgttggtat ggctttgggt  1260
catagaccaa ttccaaatca accaccaact gctgctcata ctgctaattt tttgttgaat  1320
gcttctggtt ctacttctac tccagctcca tctagaactg cttcttttc tgaatctaga  1380
gctgatgaag ttgctccagc taaaaaagct aaaccagcta tgccacaaga ttctgttcca  1440
tctccaagat ctttgcaagg taaatctact actttgtttt ctagacatac taaagctatt  1500
gtttggggta tgcaaactag agctgttcaa ggtatgttgg attttgatta tgtttgttct  1560
agagatgaac catctgttgc tgctatggtt tatccattta ctggtgatca taaacaaaaa  1620
ttttattggg gtcataaaga aattttgatt ccagttttta aaaatatggc tgatgctatg  1680
agaaaacatc cagaagttga tgttttgatt aattttgctt ctttgagatc tgcttatgat  1740
tctactatgg aaactatgaa ttatgctcaa attagaacta ttgctattat tgctgaaggt  1800
attccagaag ctttgactag aaaattgatt aaaaaagctg atcaaaaagg tgttactatt  1860
attggtccag ctactgttgg tggtattaaa ccaggttgtt ttaaaattgg taatactggt  1920
ggtatgttgg ataatatttt ggcttctaaa ttgtatagac caggttctgt tgcttatgtt  1980
tctagatctg gtggtatgtc taatgaattg aataatatta tttctagaac tactgatggt  2040
gtttatgaag gtgttgctat tggtggtgat agatatccag gttctacttt tatggatcat  2100
gttttgagat atcaagatac tccaggtgtt aaaatgattg ttgttttggg tgaaattggt  2160
ggtactgaag aatataaaat ttgtagaggt attaaagaag gtagattgac taaaccaatt  2220
gtttgttggt gtattggtac ttgtgctact atgttttctt ctgaagttca atttggtcat  2280
gctggtgctt gtgctaatca agcttctgaa actgctgttg ctaaaaatca agctttgaaa  2340
gaagctggtg tttttgttcc aagatctttt gatgaattgg gtgaaattat tcaatctgtt  2400
tatgaagatt tggttgctaa tggtgttatt gttccagctc aagaagttcc accaccaact  2460
gttccaatgg attattcttg ggctagagaa ttgggtttga ttagaaaacc agcttctttt  2520
atgacttcta tttgtgatga aagaggtcaa gaattgattt atgctggtat gccaattact  2580
gaagttttta aagaagaaat gggtattggt ggtgttttgg gtttgttgtg gtttcaaaaa  2640
agattgccaa aatattcttg tcaatttatt gaaatgtgtt tgatggttac tgctgatcat  2700
ggtccagctg tttctggtgc tcataatact attatttgtg ctagagctgg taaagatttg  2760
gtttcttctt tgacttctgg tttgttgact attggtgata gatttggtgg tgctttggat  2820
gctgctgcta aaatgttttc taaagctttt gattctggta ttattccaat ggaatttgtt  2880
aataaaatga aaaaagaagg taaattgatt atgggtattg gtcatagagt taaatctatt  2940
aataatccag atatgagagt tcaaattttg aaagattatg ttagacaaca ttttccagct  3000
actccattgt tggattatgc tttggaagtt gaaaaaatta ctacttctaa aaaaccaaat  3060
ttgattttga atgttgatgg tttgattggt gttgcttttg ttgatatgtt gagaaattgt  3120
ggttctttta ctagagaaga agctgatgaa tatattgata ttggtgcttt gaatggtatt  3180
tttgttttgg gtagatctat gggttttatt ggtcattatt tggatcaaaa aagattgaaa  3240
caaggtttgt atagacatcc atgggatgat atttcttatg ttttgccaga acatatgtct  3300
atg                                                               3303
```

-continued

```
SEQ ID NO: 122          moltype = DNA  length = 1182
FEATURE                 Location/Qualifiers
source                  1..1182
                        mol_type = other DNA
                        organism = synthetic construct
SEQUENCE: 122
atgaaaaatt gtgttattgt ttctgctgtt agaactgcta ttggttcttt taatggttct  60
ttggcttcta cttctgctat tgatttgggt gctactgtta ttaaagctgc tattgaaaga  120
gctaaaattg attctcaaca tgttgatgaa gttattatgg gtaatgtttt gcaagctggt  180
ttgggtcaaa atccagctag acaagctttg ttgaaatctg gtttggctga aactgtttgt  240
ggttttactg ttaataaagt ttgtggttct ggtttgaaat ctgttgcttt ggctgctcaa  300
gctattcaag ctggtcaagc tcaatctatt gttgctggtg gtatggaaaa tatgtctttg  360
gctccatatt tgttggatgc taaagctaga tctggttata gattgggtga tggtcaagtt  420
tatgatgtta ttttgagaga tggtttgatg tgtgctactc atggttatca tatgggtatt  480
actgctgaaa atgttgctaa agaatatggt attactagag aaatgcaaga tgaattggct  540
ttgcattctc aaagaaaagc tgctgctgct attgaatctg gtgcttttac tgctgaaatt  600
gttccagtta atgttgttac tagaaaaaaa actttttgttt tttctcaaga tgaatttcca  660
aaagctaatt ctactgctga agctttgggt gctttgagac cagcttttga taaagctggt  720
actgttactg ctggtaatgc ttctggtatt aatgatggtg ctgctgcttt ggttattatg  780
gaagaatctg ctgctttggc tgctggtttg actccattgg ctagaattaa atcttatgct  840
tctggtggtg ttccaccagc tttgatgggt atgggtccag ttccagctac tcaaaaagct  900
ttgcaattgg ctggtttgca attggctgat attgatttga ttgaagctaa tgaagctttt  960
gctgctcaat ttttggctgt tggtaaaaat ttgggttttg attctgaaaa agttaatgtt  1020
aatggtggtg ctattgcttt gggtcatcca attggtgctt ctggtgctag aattttggtt  1080
actttgttgc atgctatgca agctagagat aaaactttgg gtttggctac tttgtgtatt  1140
ggtggtggtc aaggtattgc tatggttatt gaaagattga at                     1182

SEQ ID NO: 123          moltype = DNA  length = 846
FEATURE                 Location/Qualifiers
source                  1..846
                        mol_type = other DNA
                        organism = synthetic construct
SEQUENCE: 123
atgaaaaaag tttgtgttat tggtgctggt actatgggtt ctggtattgc tcaagctttt  60
gctgctaaag gttttgaagt tgttttgaga gatattaaag atgaatttgt tgatagaggt  120
ttggatttta ttaataaaaa tttgtctaaa ttggttaaaa aaggtaaaat tgaagaagct  180
actaaagttg aaattttgac tagaatttct ggtactgttg atttgaatat ggctgctgat  240
tgtgatttgg ttattgaagc tgctgttgaa agaatggata ttaaaaaaca aatttttgct  300
gatttggata atatttgtaa accagaaact attttggctt ctaatacttc ttctttgtct  360
attactgaag ttgcttctgc tactaaaaga ccagataaag ttattggtat gcattttttt  420
aatccagctc cagttatgaa attggttgaa gttattagag gtattgctac ttctcaagaa  480
acttttgatg ctgttaaaga aacttctatt gctattggta aagatccagt tgaagttgct  540
gaagctccag gttttgttgt taatagaatt ttgattccaa tgattaatga agctgttggt  600
attttggctg aaggtattgc ttctgttgaa gatattgata aagctatgaa attgggtgct  660
aatcatccaa tgggtccatt ggaattgggt gattttattg gtttggatat ttgtttggct  720
attatggatg ttttgtattc tgaaactggt gattctaaat atagaccaca tactttgttg  780
aaaaaatatg ttagagctgg ttggttgggt agaaaatctg gtaaaggttt ttatgattat  840
tctaaa                                                             846

SEQ ID NO: 124          moltype = DNA  length = 783
FEATURE                 Location/Qualifiers
source                  1..783
                        mol_type = other DNA
                        organism = synthetic construct
SEQUENCE: 124
atggaattga ataatgttat tttggaaaaa gaaggtaaag ttgctgttgt tactattaat  60
agaccaaaag ctttgaatgc tttgaattct gatactttga aagaaatgga ttatgttatt  120
ggtgaaattg aaaatgattc tgaagttttg gctgttattt tgactggtgc tggtgaaaaa  180
tcttttgttg ctggtgctga tatttctgaa atgaaagaaa tgaatactat tgaaggtaga  240
aaatttggta ttttgggtaa taaagttttt agaagattgg aattgttgga aaaaccagtt  300
attgctgctg ttaatggttt tgctttgggt ggtggttgtg aaattgctat gtcttgtgat  360
attagaattg cttcttctaa tgctagattt ggtcaaccag aagttggttt gggtattact  420
ccaggttttg gtggtactca aagattgtct agattggttg gtatgggtat ggctaaacaa  480
ttgattttta ctgctcaaaa tattaaagct gatgaagctt tgagaattgg tttggttaat  540
aaagttgttg aaccatctga attgatgaat actgctaaag aaattgctaa taaaattgtt  600
tctaatgctc cagttgctgt taaattgtct aaacaagcta ttaatagagg tatgcaatgt  660
gatattgata ctgctttggc ttttgaatct gaagcttttg gtgaatgttt ttctactgaa  720
gatcaaaaag atgctatgac tgcttttatt gaaaaaagaa aaattgaagg ttttaaaaat  780
aga                                                                783

SEQ ID NO: 125          moltype = DNA  length = 1191
FEATURE                 Location/Qualifiers
source                  1..1191
                        mol_type = other DNA
                        organism = synthetic construct
SEQUENCE: 125
atgattgtta aaccaatggt tagaaataat atttgtttga atgctcatcc acaaggttgt  60
aaaaaaggtg ttgaagatca aattgaatat actaaaaaaa gaattactgc tgaagttaaa  120
gctggtgcta aagctccaaa aaatgttttg gttttgggtt gttctaatgg ttatggtttg  180
```

```
gcttctagaa ttactgctgc ttttggttat ggtgctgcta ctattggtgt ttcttttgaa  240
aaagctggtt ctgaaactaa atatggtact ccaggttggt ataataattt ggcttttgat  300
gaagctgcta aaagagaagg tttgtattct gttactattg atggtgatgc tttttctgat  360
gaaattaaag ctcaagttat tgaagaagct aaaaaaaaag gtattaaatt tgatttgatt  420
gtttattctt tggcttctcc agttagaact gatccagata ctggtattat gcataaatct  480
gttttgaaac catttggtaa aactttttact ggtaaaactg ttgatccatt tactggtgaa  540
ttgaaagaaa tttctgctga accagctaat gatgaagaag ctgctgctac tgttaaagtt  600
atgggtggtg aagattggga aagatggatt aaacaattgt ctaaagaagg tttgttggaa  660
gaaggttgta ttactttggc ttattcttat attggtccag aagctactca agctttgtat  720
agaaaaggta ctattggtaa agctaaagaa catttggaag ctactgctca tagattgaat  780
aaagaaaatc catctattag agcttttgtt tctgttaata aaggtttggt tactagagct  840
tctgctgtta ttccagttat tccattgtat ttggcttctt tgtttaaagt tatgaaagaa  900
aaaggtaatc atgaaggttg tattgaacaa attactagat tgtatgctga aagattgtat  960
agaaaagatg gtactattcc agttgatgaa gaaaatagaa ttagaattga tgattgggaa  1020
ttggaagaag atgttcaaaa agctgtttct gctttgatgg aaaaagttac tggtgaaaat  1080
gctgaatctt tgactgattt ggctggttat agacatgatt ttttggcttc taatggtttt  1140
gatgttgaag gtattaatta tgaagctgaa gttgaaagat ttgatagaat t           1191

SEQ ID NO: 126         moltype = DNA  length = 1182
FEATURE                Location/Qualifiers
source                 1..1182
                       mol_type = other DNA
                       organism = synthetic construct
SEQUENCE: 126
atgactagag aagttgttgt tgtttctggt gttagaactg ctattggtac ttttggtggt  60
tctttgaaag atgttgctcc agctgaattg ggtgctttgg ttgttagaga agctttggct  120
agagctcaag tttctggtga tgatgttggt catgttgttt ttggtaatgt tattcaaact  180
gaaccaagag atatgtattt gggtagagtt gctgctgtta atggtggtgt tactattaat  240
gctccagctt tgactgttaa tagattgtgt ggttctggtt tgcaagctat tgtttctgct  300
gctcaaacta ttttgttggg tgatactgat gttgctattg gtggtggtgc tgaatctatg  360
tctagagctc catatttggc tccagctgct agatggggtg ctagaatggg tgatgctggt  420
ttggttgata tgatgttggg tgctttgcat gatccatttc atagaattca tatgggtgtt  480
actgctgaaa atgttgctaa agaatatgat atttctagag ctcaacaaga tgaagctgct  540
ttggaatctc atagaagagc ttctgctgct attaaagctg gttattttaa agatcaaatt  600
gttccagttg tttctaaagg tagaaaaggt gatgttactt ttgatactga tgaacatgtt  660
agacatgatg ctactattga tgatatgact aaattgagac cagtttttgt taaagaaaat  720
ggtactgtta ctgctggtaa tgcttctggt ttgaatgatg ctgctgctgc tgttgttatg  780
atggaaagag ctgaagctga aagaagaggt ttgaaaccat tggctagatt ggtttcttat  840
ggtcatgctg gtgttgatcc aaaagctatg ggtattggtc cagttccagc tactaaaatt  900
gctttggaaa gagctggttt gcaagtttct gatttggatg ttattgaagc taatgaagct  960
tttgctgctc aagcttgtgc tgttactaaa gctttgggtt tggatccagc taaagttaat  1020
ccaaatggtt ctggtatttc tttgggtcat ccaattggtg ctactggtgc tttgattact  1080
gttaaagctt tgcatgaatt gaatagagtt caaggtagat atgctttggt tactatgtgt  1140
attggtggtg gtcaaggtat tgctgctatt tttgaaagaa tt                     1182

SEQ ID NO: 127         moltype = DNA  length = 1476
FEATURE                Location/Qualifiers
source                 1..1476
                       mol_type = other DNA
                       organism = synthetic construct
SEQUENCE: 127
atgaaactct caactaaact ttgttggtgt ggtattaaag gaagacttag gccgcaaaag  60
caacaacaat tacacaatac aaacttgcaa atgactgaac taaaaaaaca aaagaccgct  120
gaacaaaaaa ccagacctca aaatgtcggt attaaaggta tccaaattta catcccaact  180
caatgtgtca accaatctga gctagagaaa tttgatggcg tttctcaagg taaatacaca  240
attggtctgg gccaaaccaa catgtctttt gtcaatgaca gagaagatat ctactcgatg  300
tccctaactg ttttgtctaa gttgatcaag agttacaaca tcgacaccaa caaaattggt  360
agattagaag tcggtactga aactctgatt gacaagtcca agtctgtcaa gtctgtcttg  420
atgcaattgt ttggtgaaaa cactgacgtc gaaggtattg acacgcttaa tgcctgttac  480
ggtggtacca acgcgttgtt caactctttg aactggattg aatctaacgc atgggatggt  540
agagacgcca ttgtagtttg cggtgatatt gccatctacg ataagggtgc cgcaagacca  600
accggtggtg ccggtactgt tgctatgtgg atcggtcctg atgctccaat tgtatttgac  660
tctgtaagag cttcttacat ggaacacgcc tacgattttt acaagccaga tttcaccagc  720
gaatatcctt acgtcgatgg tcatttttca ttaacttgtt acgtcaaggc tcttgatcaa  780
gtttacaaga gttattccaa gaaggctatt tctaaagggt tggttagcga tcccgctggt  840
tcggatgctt tgaacgtttt gaaatatttc gactacaacg ttttccatgt tccaacctgt  900
aaattggtca caaaatcata cggtagatta ctatataacg atttcagagc caatcctcaa  960
ttgttcccag aagttgacgc cgaattagct actcgcgatt atgacgaatc tttaaccgat  1020
aagaacattg aaaaaacttt tgttaatgtt gctaagccat tccacaaaga gagagttgcc  1080
caatctttga ttgttccaac aaacacaggt aacatgtaca ccgcatctgt ttatgccgcc  1140
tttgcatctc tattaaacta tgttggatct gacgacttac aaggcaagcg tgttggttta  1200
ttttcttacg gttccggttt agctgcatct ctatattctt gcaaaattgt tggtgacgtc  1260
caacatatta tcaaggaatt agatattact aacaaattag ccaagagaat caccgaaact  1320
ccaaaggatt acgaagctgc catcgaattg agagaaaatg cccatttgaa gaagaacttc  1380
aaacctcaag gttccattga gcatttgcaa agtggtgttt actacttgac caacatcgat  1440
gacaaattta gaagatctta cgatgttaaa aaataa                            1476

SEQ ID NO: 128         moltype = DNA  length = 1143
FEATURE                Location/Qualifiers
```

```
source                  1..1143
                        mol_type = other DNA
                        organism = synthetic construct
SEQUENCE: 128
atggttgcgg tacgtaggaa ggctctttca attttggcag aagctcctgt attagcatct  60
gatcgtttac catataaaaa ttatgactac gaccgcgtat ttggcgcttg ttgtgaaaat  120
gttataggtt acatgccttt gcccgttggt gttataggcc ccttggttat cgatggtaca  180
tcttatcata taccaatggc aactacagag ggttgtttgg tagcttctgc catgcgtggc  240
tgtaaggcaa tcaatgctgg cggtggtgca acaactgttt taactaagga tggtatgaca  300
agaggcccag tagtccgttt cccaactttg aaaagatctg gtgcctgtaa gatatggtta  360
gactcagaag agggacaaaa cgcaattaaa aaagctttta actctacatc aagatttgca  420
cgtctgcaac atattcaaac ttgtctagca ggagatttac tcttcatgag atttagaaca  480
actactggtg acgcaatggg tatgaatatg atttctaaag gtgtcgaata ctcattaaag  540
caaatggtag aagagtatgg ctgggaagat atggaggttg tctccgtttc tggtaactac  600
tgtaccgaca aaaaaccagc tgccatcaac tggatcgaag gtcgtggtaa gagtgtcgtc  660
gcagaagcta ctattcctgg tgatgttgtc agaaaagtgt taaaaagtga tgtttccgca  720
ttggttgagt tgaacattgc taagaatttg gttggatctg caatggctgg gtctgttggt  780
ggatttaacg cacatgcagc taatttagtg acagctgttt tcttggcatt aggacaagat  840
cctgcacaaa atgttgaaag ttccaactgt ataacattga tgaaagaagt ggacggtgat  900
ttgagaattt ccgtatccat gccatccatc gaagtaggta ccatcggtgg tggtactgtt  960
ctagaaccac aaggtgccat gttggactta ttaggtgtaa gaggcccgca tgctaccgct  1020
cctggtacca acgcacgtca attagcaaga atagttgcct gtgccgtctt ggcaggtgaa  1080
ttatccttat gtgctgccct agcagccggc catttggttc aaagtcatat gacccacaac  1140
agg                                                                1143

SEQ ID NO: 129          moltype = DNA  length = 1332
FEATURE                 Location/Qualifiers
source                  1..1332
                        mol_type = other DNA
                        organism = synthetic construct
SEQUENCE: 129
atgtcattac cgttcttaac ttctgcaccg ggaaaggtta ttatttttgg tgaacactct  60
gctgtgtaca acaagcctgc cgtcgctgct agtgtgtctg cgttgagaac ctacctgcta  120
ataagcgagt catctgcacc agatactatt gaattggact tcccggacat tagctttaat  180
cataagtggt ccatcaatga tttcaatgcc atcaccgagg atcaagtaaa ctcccaaaaa  240
ttggccaagg ctcaacaagc caccgatggc ttgtctcagg aactcgttag tcttttggat  300
ccgttgttag ctcaactatc cgaatccttc cactaccatg cagcgttttg tttcctgtat  360
atgtttgttt gcctatgccc ccatgccaag aatattaagt tttctttaaa gtctacttta  420
cccatcggtg ctgggttggg ctcaagcgcc tctatttctg tatcactggc cttagctatg  480
gcctacttgg gggggttaat aggatctaat gacttggaaa agctgtcaga aaacgataag  540
catatagtga atcaatgggc cttcataggt gaaaagtgta ttcacggtac cccttcagga  600
atagataacg ctgtggccac ttatggtaat gccctgctat ttgaaaaaga ctcacataat  660
ggaacaataa acacaaacaa ttttaagttc ttagatgatt tcccagccat tccaatgatc  720
ctaacctata ctagaattcc aaggtctaca aaagatcttg ttgctcgcgt tcgtgtgttg  780
gtcaccgaga aatttcctga agttatgaag ccaattctag atgccatggg tgaatgtgcc  840
ctacaaggct tagagatcat gactaagtta agtaaatgta aaggcaccga tgacgaggct  900
gtagaaacta ataatgaact gtatgaacaa ctattggaat tgataagaat aaatcatgga  960
ctgcttgtct caatcggtgt ttctcatcct ggattagaac ttattaaaaa tctgagcgat  1020
gatttgagaa ttggctccac aaaacttacc ggtgctggtg gcggcggttg ctctttgact  1080
ttgttacgaa gagacattac tcaagagcaa attgacagct tcaaaaagaa attgcaagat  1140
gattttagtt acgagacatt tgaaacagac ttgggtggga ctggctgctg tttgttaagc  1200
gcaaaaaatt tgaataaaga tcttaaaatc aaatccctag tattccaatt atttgaaaat  1260
aaaactacca caaagcaaca aattgacgat ctattattgc caggaaacac gaatttacca  1320
tggacttcat aa                                                      1332

SEQ ID NO: 130          moltype = DNA  length = 1356
FEATURE                 Location/Qualifiers
source                  1..1356
                        mol_type = other DNA
                        organism = synthetic construct
SEQUENCE: 130
atgtcagagt tgagagcctt cagtgcccca gggaaagcgt tactagctgg tggatattta  60
gttttagata caaaatatga agcatttgta gtcggattat cggcaagaat gcatgctgta  120
gcccatcctt acggttcatt gcaagggtct gataagtttg aagtgcgtgt gaaaagtaaa  180
caatttaaag atggggagtg gctgtaccat ataagtccta aaagtggctt cattcctgtt  240
tcgataggcg gatctaagaa ccctttcatt gaaaaagtta tcgctaacgt atttagctac  300
tttaaaccta acatggacga ctactgcaat agaaacttgt tcgttattga tattttctct  360
gatgatgcct accattctca ggaggatagc gttaccgaac atcgtggcaa cagaagattg  420
agttttcatt cgcacagaat tgaagaagtt cccaaaacag ggctgggctc ctcggcaggt  480
ttagtcacag ttttaactac agctttggcc tcctttttttg tatcggacct ggaaaataat  540
gtagacaaat atagagaagt tattcataat ttagcacaag ttgctcattg tcaagctcag  600
ggtaaaattg gaagcgggtt tgatgtagcg gcggcagcat atggatctat cagatataga  660
agattcccac ccgcattaat ctctaatttg ccagatattg gaagtgctac ttacggcagt  720
aaactggcgc atttggttga tgaagaagac tggaatatta cgattaaaag taaccattta  780
ccttcgggat taactttatg gatgggcgat attaagaatg gttcagaaac agtaaaactg  840
gtccagaagg taaaaaattg gtatgattcg catatgccag aaagcttgaa aatatataca  900
gaactcgatc atgcaaattc tagatttatg gatggactat ctaaactaga tcgcttacac  960
gagactcatg acgattacag cgatcagata tttgagtctc ttgagaggaa tgactgtacc  1020
tgtcaaaagt atcctgaaat cacagaagtt agagatgcag ttgccacaat tagacgttcc  1080
```

```
tttagaaaaa taactaaaga atctggtgcc gatatcgaac ctcccgtaca aactagctta  1140
ttggatgatt gccagacctt aaaaggagtt cttacttgct taatacctgg tgctggtggt  1200
tatgacgcca ttgcagtgat tactaagcaa gatgttgatc ttagggctca aaccgctaat  1260
gacaaaagat tttctaaggt tcaatggctg gatgtaactc aggctgactg ggtgttagg   1320
aaagaaaaag atccggaaac ttatcttgat aaataa                             1356

SEQ ID NO: 131          moltype = DNA  length = 1191
FEATURE                 Location/Qualifiers
source                  1..1191
                        mol_type = other DNA
                        organism = synthetic construct
SEQUENCE: 131
atgaccgttt acacagcatc cgttaccgca cccgtcaaca tcgcaaccct taagtattgg  60
gggaaaaggg acacgaagtt gaatctgccc accaattcgt ccatatcagt gactttatcg  120
caagatgacc tcagaacgtt gacctctgcg gctactgcac ctgagtttga acgcgacact  180
ttgtggttaa atggagaacc acacagcatc gacaatgaaa gaactcaaaa ttgtctgcgc  240
gacctacgcc aattaagaaa ggaaatggaa tcgaaggacg cctcattgcc cacattatct  300
caatggaaac tccacattgt ctccgaaaat aactttccta cagcagctgg tttagcttcc  360
tccgctgctg gctttgctgc attggtctct gcaattgcta agttatacca attaccacag  420
tcaacttcag aaatatctag aatagcaaga aaggggtctg gttcagcttg tagatcgttg  480
tttggcggat acgtggcctg ggaaatggga aaagctgaag atggtcatga ttccatggca  540
gtacaaatcg cagacagctc tgactggcct cagatgaaag cttgtgtcct agttgtcagc  600
gatattaaaa aggatgtgag ttccactcag ggtatgcaat tgaccgtggc aacctccgaa  660
ctatttaaag aaagaattga acatgtcgta ccaaagagat ttgaagtcat gcgtaaagcc  720
attgttgaaa aagatttcgc cacctttgca aaggaaacaa tgatggattc caactctttc  780
catgccacat gtttggactc tttccctcca atattctaca tgaatgacac ttccaagcgt  840
atcatcagtt ggtgccacac cattaatcag ttttacggag aaacaatcgt tgcatacacg  900
tttgatgcag gtccaaatgc tgtgttgtac tacttagctg aaaatgagtc gaaactcttt  960
gcatttatct ataaattgtt tggctctgtt cctggatggg acaagaaatt tactactgag  1020
cagcttgagg ctttcaacca tcaatttgaa tcatctaact ttactgcacg tgaattggat  1080
cttgagttgc aaaaggatgt tgccagagtg attttaactc aagtcggttc aggcccacaa  1140
gaaacaaacg aatctttgat tgacgcaaag actggtctac caaaggaata a           1191

SEQ ID NO: 132          moltype = DNA  length = 867
FEATURE                 Location/Qualifiers
source                  1..867
                        mol_type = other DNA
                        organism = synthetic construct
SEQUENCE: 132
atgactgccg acaacaatag tatgccccat ggtgcagtat ctagttacgc caaattagtg  60
caaaaccaaa cacctgaaga cattttggaa gagtttcctg aaattattcc attacaacaa  120
agacctaata cccgatctag tgagacgtca aatgacgaaa gcggagaaac atgtttttct  180
ggtcatgatg aggagcaaat taagttaatg aatgaaaatt gtattgtttt ggattgggac  240
gataatgcta ttggtgccgg taccaagaaa gtttgtcatt taatggaaaa tattgaaaag  300
ggtttactac atcgtgcatt ctccgtcttt attttcaatg aacaaggtga attactttta  360
caacaaagag ccactgaaaa aataactttc cctgatcttt ggactaacac atgctgctct  420
catccactat gtattgatga cgaattaggt ttgaagggta agctagacga taagattaag  480
ggcgctatta ctgcggcggt gagaaaacta gatcatgaat taggtattcc agaagatgaa  540
actaagacaa ggggtaagtt tcacttttta aacagaatcc attacatggc accaagcaat  600
gaaccatggg gtgaacatga aattgattac atcctatttt ataagatcaa cgctaaagaa  660
aacttgactg tcaacccaaa cgtcaatgaa gttagagact tcaaatgggt ttcaccaaat  720
gatttgaaaa ctatgtttgc tgacccaagt tacaagttta cgccttggtt taagattatt  780
tgcgagaatt acttattcaa ctggtgggag caattagatg acctttctga agtggaaaat  840
gacaggcaaa ttcatagaat gctataa                                       867

SEQ ID NO: 133          moltype = DNA  length = 1059
FEATURE                 Location/Qualifiers
source                  1..1059
                        mol_type = other DNA
                        organism = synthetic construct
SEQUENCE: 133
atggcttcag aaaaggaaat aagaagagaa agattcttga acgtattccc aaagttagtt  60
gaagaattga acgctagttt gttagcttat ggtatgccta aagaagcctg cgattggtat  120
gctcactctt taaactacaa tactccaggt ggtaaattga atagaggttt gagtgtagtt  180
gatacttatg ctatcttgtc taacaaaacc gttgaacaat taggtcaaga agaatacgaa  240
aaggtcgcta tcttgggttg gtgtattgaa ttgttgcaag catacttttt ggttgccgat  300
gacatgatgg ataagtctat aacaagaaga ggtcaaccat gctggtacaa agttccagaa  360
gttggtgaaa tagccataaa tgatgctttt atgttggaag ccgctatcta taaattgttg  420
aagtcacatt tcagaaacga aaagtactac atcgatatta ccgaattatt ccacgaagtt  480
actttccaaa cagaattggg tcaattgatg gatttgataa ctgcacctga agataaagtt  540
gacttgtcaa agttttcctt gaagaaacat tcattcatcg tcacctttga aactgcttat  600
tactccttct atttgccagt cgccttggct atgtacgtag ctggtattac tgatgaaaaa  660
gacttgaagc aagcaagaga tgttttgata cctttgggtg aatacttcca aatccaagat  720
gactacttag actgtttcgg tactccagaa caaataggta aaatcggtac agatattcaa  780
gacaataagt gcagttgggt tattaacaag gctttggaat tagcatctgc cgaacaaaga  840
aagactttgg atgaaaacta cggtaaaaag gactcagttg ctgaagcaaa gtgtaagaaa  900
atttttaatg atttgaagat tgaacaattg taccatgaat acgaagaatc catcgctaaa  960
gacttaaagg caaagattag tcaagttgat gaatcaagag gttttaaagc cgacgttttg  1020
acagctttct tgaataaggt ctacaagaga tcaaagtag                          1059
```

```
SEQ ID NO: 134          moltype = DNA  length = 1155
FEATURE                 Location/Qualifiers
source                  1..1155
                        mol_type = other DNA
                        organism = synthetic construct
SEQUENCE: 134
atgaatcatt tgagagctga aggtccagct tctgttttgg ctattggtac tgctaatcca  60
gaaaatattt tgttgcaaga tgaatttcca gattattatt ttagagttac taaatctgaa  120
catatgactc aattgaaaga aaaatttaga aaaatttgtg ataaatctat gattagaaaa  180
agaaattgtt ttttgaatga agaacatttg aaacaaaatc caagattggt tgaacatgaa  240
atgcaaactt tggatgctag acaagatatg ttggttgttg aagttccaaa attgggtaaa  300
gatgcttgtg ctaaagctat taaagaatgg ggtcaaccaa aatctaaaat tactcatttg  360
atttttactt ctgcttctac tactgatatg ccaggtgctg attatcattg tgctaaattg  420
ttgggtttgt ctccatctgt taaaagagtt atgatgtatc aattgggttg ttatggtggt  480
ggtactgttt tgagaattgc taaagatatt gctgaaaata ataaaggtgc tagagttttg  540
gctgtttgtt gtgatattat ggcttgtttg tttagaggtc catctgaatc tgatttggaa  600
ttgttggttg gtcaagctat ttttggtgat ggtgctgctg ctgttattgt tggtgctgaa  660
ccagatgaat ctgttggtga aagaccaatt tttgaattgg tttctactgg tcaaactatt  720
ttgccaaatt ctgaaggtac tattggtggt catattagag aagctggttt gatttttgat  780
ttgcataaag atgttccaat gttgatttct aataatattg aaaaatgttt gattgaagct  840
tttactccaa ttggtatttc tgattggaat tctatttttt ggattactca tccaggtggt  900
aaagctattt tggataaagt tgaagaaaaa ttgcatttga aatctgataa atttgttgat  960
tctagacatg ttttgtctga acatggtaat atgtcttctt ctactgtttt gtttgttatg  1020
gatgaattga gaaaaagatc tttggaagaa ggtaaatcta ctactggtga tggttttgaa  1080
tggggtgttt tgtttggttt tggtccaggt ttgactgttg aaagagttgt tgttagatct  1140
gttccaatta aatat                                                   1155

SEQ ID NO: 135          moltype = DNA  length = 303
FEATURE                 Location/Qualifiers
source                  1..303
                        mol_type = other DNA
                        organism = synthetic construct
SEQUENCE: 135
atggctgtta aacatttgat tgttttgaaa tttaaagatg aaattactga agctcaaaaa  60
gaagaatttt ttaaaactta tgttaatttg gttaatatta ttccagctat gaaagatgtt  120
tattggggta aagatgttac tcaaaaaaat aaagaagaag gttatactca tattgttgaa  180
gttactttg aatctgttga aactattcaa gattatatta ttcatccagc tcatgttggt  240
tttggtgatg tttatagatc tttttgggaa aaattgttga tttttgatta tactccaaga  300
aaa                                                                303

SEQ ID NO: 136          moltype = DNA  length = 1185
FEATURE                 Location/Qualifiers
source                  1..1185
                        mol_type = other DNA
                        organism = synthetic construct
SEQUENCE: 136
atgggtttgt cttctgtttg tacttttttct tttcaaacta attatcatac tttgttgaat  60
ccacataata ataatccaaa aacttctttg ttgtgttata gacatccaaa aactccaatt  120
aaatattctt ataataattt tccatctaaa cattgttcta ctaaatcttt tcatttgcaa  180
aataaatgtt ctgaatcttt gtctattgct aaaaattcta ttagagctgc tactactaat  240
caaactgaac caccagaatc tgataatcat tctgttgcta ctaaaatttt gaattttggt  300
aaagcttgtt ggaaattgca aagaccatat actattattg cttttacttc ttgtgcttgt  360
ggtttgtttg gtaaagaatt gttgcataat actaatttga tttcttggtc tttgatgttt  420
aaagcttttt ttttttggt tgctattttg tgtattgctt cttttactac tactattaat  480
caaatttatg atttgcatat tgatagaatt aataaaccag atttgccatt ggcttctggt  540
gaaatttctg ttaatactgc ttggattatg tctattattg ttgctttgtt tggtttgatt  600
attactatta aatgaaaggg tggtccattg tatatttttg gttattgttt tggtattttt  660
ggtggtattg tttattctgt tccaccattt agatggaaac aaaatccatc tactgctttt  720
ttgttgaatt ttttggctca tattattact aattttactt tttattatgc ttctagagct  780
gctttgggtt tgccatttga attgagacca tcttttactt ttttgttggc ttttatgaaa  840
tctatgggtt ctgctttggc tttgattaaa gatgcttctg atgttgaagg tgatactaaa  900
tttggtattt ctactttggc ttctaaatat ggttctagaa atttgacttt gttttgttct  960
ggtattgttt tgttgtctta tgttgctgct attttggctg gtattatttg gccacaagct  1020
tttaattcta atgttatgtt gttgtctcat gctattttgg ctttttggtt gattttgcaa  1080
actagagatt ttgctttgac taattatgat ccagaagctg gtagaagatt ttatgaattt  1140
atgtggaaat tgtattatgc tgaatatttg gtttatgttt ttatt                  1185

SEQ ID NO: 137          moltype = DNA  length = 6702
FEATURE                 Location/Qualifiers
source                  1..6702
                        mol_type = other DNA
                        organism = synthetic construct
SEQUENCE: 137
atgagcgaag aaagcttatt cgagtcttct ccacagaaga tggagtacga aattacaaac  60
tactcagaaa gacatacaga acttccaggt catttcattg gcctcaatac agtagataaa  120
ctagaggagt ccccgttaag ggactttgtt aagagtcacg gtggtcacac ggtcatatcc  180
aagatcctga tagcaaataa tggtattgcc gccgtgaaag aaattagatc cgtcagaaaa  240
tgggcatacg agacgttcgg cgatgacaga accgtccaat tcgtcgccat ggccacccca  300
```

-continued gaagatctgg aggccaacgc agaatatatc cgtatggccg atcaatacat tgaagtgcca 360
ggtggtacta ataataacaa ctacgctaac gtagacttga tcgtagacat cgccgaaaga 420
gcagacgtag acgccgtatg ggctggctgg ggtcacgcct ccgagaatcc actattgcct 480
gaaaaattgt cccagtctaa gaggaaagtc atctttattg ggcctccagg taacgccatg 540
aggtctttag gtgataaaat ctcctctacc attgtcgctc aaagtgctaa agtcccatgt 600
attccatggt ctggtaccgg tgttgacacc gttcacgtgg acgagaaaac cggtctggtc 660
tctgtcgacg atgacatcta tcaaaagggt tgttgtacct ctcctgaaga tggtttacaa 720
aaggccaagc gtattggttt tcctgtcatg attaaggcat ccgaaggtgg tggtggtaaa 780
ggtatcagac aagttgaacg tgaagaagat ttcatcgctt tataccacca ggcagccaac 840
gaaattccag gctcccccat tttcatcatg aagttggccg gtagagcgcg tcacttggaa 900
gttcaactgc tagcagatca gtacggtaca aatatttcct tgttcggtag agactgttcc 960
gttcagagac gtcatcaaaa aattatcgaa gaagcaccag ttacaattgc caaggctgaa 1020
acatttcacg agatggaaaa ggctgccgtc agactgggga aactagtcgg ttatgtctct 1080
gccggtaccg tggagtatct atattctcat gatgatggaa aattctactt tttagaattg 1140
aacccaagat tacaagtcga gcatccaaca acggaaatgg tctccggtgt taacttacct 1200
gcagctcaat tacaaatcgc tatgggtatc cctatgcata gaataagtga cattagaact 1260
ttatatggta tgaatcctca ttctgcctca gaaatcgatt tcgaattcaa aactcaagat 1320
gccaccaaga aacaaagaag acctattcca aagggtcatt gtaccgcttg tcgtatcaca 1380
tcagaagatc caaacgatgg attcaagcca tcgggtggta ctttgcatga actaaacttc 1440
cgttcttcct ctaatgtttg ggttacttc tccgtgggta acaatggtaa tattcactcc 1500
ttttcggact ctcagttcgg ccatattttt gcttttggtg aaaatagaca agcttccagg 1560
aaacacatgg ttgttgccct gaaggaattg tccattaggg gtgatttcag aactactgtg 1620
gaatacttga tcaaactttt ggaaactgaa gatttcgagg ataacactat taccaccggt 1680
tggttggacg atttgattac tcataaaatg accgctgaaa agcctgatcc aactcttgcc 1740
gtcatttgcg gtgccgctac aaaggctttc ttagcatctg aagaagcccg ccacaagtat 1800
atcgaatcct tacaaaaggg acaagttcta tctaaagacc tactgcaaac tatgttccct 1860
gtagatttta tccatgaggg taaaagatac aagttcaccg tagctaaatc cggtaatgac 1920
cgttacacat tatttatcaa tggttctaaa tgtgatatca tactgcgtca actatctgat 1980
ggtggtcttt tgattgccat aggcggtaaa tcgcatacca tctattggaa agaagaagtt 2040
gctgctacaa gattatccgt tgactctatg actactttgt tggaagttga aaacgatcca 2100
acccagttgc gtactccatc ccctggtaaa ttggttaaat tcttggtgga aaatggtgaa 2160
cacattatca agggccaacc atatgcagaa attgaagtta tgaaaatgca aatgcctttg 2220
gtttctcaag aaaatggtat cgtccagtta ttaaagcaac ctggttctac cattgttgca 2280
ggtgatatca tggctattat gactcttgac gatccatcca aggtcaagca cgctctacca 2340
tttgaaggta tgctgccaga ttttggttct ccagttatcg aaggaaccaa acctgcctat 2400
aaattcaagt cattagtgtc tactttggaa aacattttga agggttatga caaccaagtt 2460
attatgaacg cttccttgca acaattgata gaggttttga gaaatccaaa actgccttac 2520
tcagaatgga aactacacat ctctgcttta cattcaagat tgcctgctaa gctagatgaa 2580
caaatggaag agttagttgc acgttctttg agacgtggtg ctgttttccc agctagacaa 2640
ttaagtaaat tgattgatat ggccgtgaag aatcctgaat acaaccccga caaattgctg 2700
ggcgccgtcg tggaaccatt ggcggatatt gctcataagt actctaacgg gttagaagcc 2760
catgaacatt ctatatttgt ccatttcttg gaagaatatt acgaagttga aaagttattc 2820
aatggtccaa atgttcgtga ggaaaatatc attctgaaat tgcgtgatga aaaccctaaa 2880
gatctagata aagttgcgct aactgttttg tctcattcga aagtttcagc gaagaataac 2940
ctgatcctag ctatcttgaa acattatcaa ccattgtgca agttatcttc taaagtttct 3000
gccattttct ctactcctct acaacatatt gttgaactag aatctaaggc taccgctaag 3060
gtcgctctac aagcaagaga aattttgatt caaggcgctt taccttcggt caaggaaaga 3120
actgaacaaa ttgaacatat cttaaaatcc tctgttgtga aggttgccta tggctcatcc 3180
aatccaaagc gctctgaacc agatttgaat atcttgaagg acttgatcga ttctaattac 3240
gttgtgttcg atgttttact tcaattccta acccatcaag acccagttgt gactgctgca 3300
gctgctcaag tctatattcg tcgtgcttat cgtgcttaca ccataggaga tattagagtt 3360
cacgaaggtg tcacagttcc aattgttgaa tggaaattcc aactaccttc agctgcgttc 3420
tccacctttc caactgttaa atctaaaatg ggtatgaaca gggctgtttc tgtttcagat 3480
ttgtcatatg ttgcaaacag tcagtcatct ccgttaagag aaggtatttt gatggctgtg 3540
gatcatttag atgatgttga tgaaattttg tcacaaagtt tggaagttat tcctcgtcac 3600
caatcttctt ctaacggacc tgctcctgat cgttctggta gctccgcatc gttgagtaat 3660
gttgctaatg tttgtgttgc ttctacagaa ggtttcgaat ctgaagagga aattttggta 3720
aggttgagag aaattttgga tttgaataag caggaattaa tcaatgcttc tatccgtcgt 3780
atcacattta tgttcggttt taaagatggg tcttatccaa agtattatac ttttaacggt 3840
ccaaattata acgaaaatga aacaattcgt cacattgagc cggctttggc cttccaactg 3900
gaattaggaa gattgtccaa cttcaacatt aaaccaattt tcactgataa tagaaacatc 3960
catgtctacg aagctgttag taagacttct ccattggata agagattctt tacaagaggt 4020
attattagaa cgggtcatat ccgtgatgac atttctattc aagaatatct gacttctgaa 4080
gctaacagat tgatgagtga tatattggat aatttagaag tcaccgacac ttcaaattct 4140
gatttgaatc atatcttcat caacttcatt gcggtgtttg atatctctcc agaagatgtc 4200
gaagccgcct tcggtggttt cttagaaaga tttggtaaga gattgttgag attgcgtgtt 4260
tcttctgccg aaattagaat catcatcaaa gatcctcaaa caggtgcccc agtaccattg 4320
cgtgccttga tcaataacgt ttctggttat gttatcaaaa cagaaatgta caccgaagtc 4380
aagaacgcaa aaggtgaatg ggtatttaag tctttgggta aacctggatc catgcattta 4440
agacctattg ctactcctta ccctgttaag gaatggttgc aaccaaaacg ttataaggca 4500
cacttgatgg gtaccacata tgtctatgac ttcccagaat tattccgcca agcatcgtca 4560
tcccaatgga aaaatttctc tgcagatgtt aagttaacag atgatttctt tatttccaac 4620
gagttgattg aagatgaaaa cggcgaatta actgaggtgg aaagagaacc tggtgccaac 4680
gctattggta tggttgcctt taagattact gtaaagactc ctgaatatcc aagaggccgt 4740
caatttgttg ttgttgctaa cgatatcaca ttcaagatcg gttcctttgg tccacaagaa 4800
gacgaattct tcaataaggt tactgaatat gctagaaagc gtggtatccc aagaatttac 4860
ttggctgcaa actcaggtgc cagaattggt atggctgaag agattgttcc actatttcaa 4920
gttgcatgga atgatgctgc caatccggac aagggcttcc aatacttata cttaacaagt 4980
gaaggtatgg aaactttaaa gaaatttgac aaagaaaatt ctgttctcac tgaacgtact 5040

-continued

```
gttataaacg gtgaagaaag atttgtcatc aagacaatta ttggttctga agatgggtta  5100
ggtgtcgaat gtctacgtgg atctggttta attgctggtg caacgtcaag ggcttaccac  5160
gatatcttca ctatcacctt agtcacttgt agatccgtcg gtatcggtgc ttatttggtt  5220
cgtttgggtc aaagagctat tcaggtcgaa ggccagccaa ttattttaac tggtgctcct  5280
gcaatcaaca aaatgctggg tagagaagtt tatacttcta acttacaatt gggtggtact  5340
caaatcatgt ataacaacgg tgtttcacat ttgactgctg ttgacgattt agctggtgta  5400
gagaagattg ttgaatggat gtcttatgtt ccagccaagc gtaatatgcc agttcctatc  5460
ttggaaacta aagacacatg ggatagacca gttgatttca ctccaactaa tgatgaaact  5520
tacgatgtaa gatggatgat tgaaggtcgt gagactgaaa gtggatttga atatggtttg  5580
tttgataaag ggtctttctt tgaaactttg tcaggatggg ccaaaggtgt tgtcgttggt  5640
agagcccgtc ttggtggtat tccactgggt gttattggtg ttgaaacaag aactgtcgag  5700
aacttgattc ctgctgatcc agctaatcca aatagtgctg aaacattaat tcaagaacct  5760
ggtcaagttt ggcatccaaa ctccgccttc aagactgctc aagctatcaa tgactttaac  5820
aacggtgaac aattgccaat gatgattttg gccaactgga gaggtttctc tggtggtcaa  5880
cgtgatatgt tcaacgaagt cttgaagtat ggttcgttta ttgttgacgc attggtggat  5940
tacaaacaac caattattat ctatatccca cctaccggtg aactaagagg tggttcatgg  6000
gttgttgtcg atccaactat caacgctgac caaatggaaa tgtatgccga cgtcaacgct  6060
agagctggtg ttttggaacc acaaggtatg gttggtatca agttccgtag agaaaaattg  6120
ctggacacca tgaacagatt ggatgacaag tacagagaat tgagatctca attatccaac  6180
aagagtttgg ctccagaagt acatcagcaa atatccaagc aattagctga tcgtgagaga  6240
gaactattgc caatttacgg acaaatcagt cttcaatttg ctgatttgca cgataggtct  6300
tcacgtatgg tggccaaggg tgttatttct aaggaactgg aatggaccga ggcacgtcgt  6360
ttcttcttct ggagattgag aagaagattg aacgaagaat atttgattaa aaggttgagc  6420
catcaggtag gcgaagcatc aagattagaa aagatcgcaa gaattagatc gtggtaccct  6480
gcttcagtgg accatgaaga tgataggcaa gtcgcaacat ggattgaaga aaactacaaa  6540
actttggacg ataaactaaa gggtttgaaa ttagagtcat tcgctcaaga cttagctaaa  6600
aagatcagaa gcgaccatga caatgctatt gatggattat ctgaagttat caagatgtta  6660
tctaccgatg ataaagaaaa attgttgaag actttgaaat aa                    6702
```

```
SEQ ID NO: 138          moltype = DNA  length = 1632
FEATURE                 Location/Qualifiers
source                  1..1632
                        mol_type = other DNA
                        organism = synthetic construct
SEQUENCE: 138
atgaaatgtt ctactttttc tttttggttt gtttgtaaaa ttattttttt ttttttttct  60
tttaatattc aaacttctat tgctaatcca agagaaaatt ttttgaaatg tttttctcaa  120
tatattccaa ataatgctac taatttgaaa ttggtttata ctcaaaataa tccattgtat  180
atgtctgttt tgaattctac tattcataat ttgagattta cttctgatac tactccaaaa  240
ccattggtta ttgttactcc atctcatgtt tctcatattc aaggtactat tttgtgttct  300
aaaaaagttg gtttgcaaat tagaactaga tctggtggtc atgattctga aggtatgtct  360
tatatttctc aagttccatt tgttattgtt gatttgagaa atatgagatc tattaaaatt  420
gatgttcatt ctcaaactgc ttgggttgaa gctggtgcta ctttgggtga agtttattat  480
tgggttaatg aaaaaaatga aaatttgtct ttggctgctg gttattgtcc aactgtttgt  540
gctggtggtc attttggtgg tggtggttat ggtccattga tgagaaatta tggtttggct  600
gctgataata ttattgatgc tcatttggtt aatgttcatg gtaaagtttt ggatagaaaa  660
tctatgggtg aagatttgtt ttgggctttg agaggtggtg gtgctgaatc ttttggtatt  720
attgttgctt ggaaaattag attggttgct gttccaaaat ctactatgtt ttctgttaaa  780
aaaattatgg aaattcatga attggttaaa ttggttaata aatggcaaaa tattgcttat  840
aaatatgata aagatttgtt gttgatgact cattttatta ctagaaatat tactgataat  900
caaggtaaaa ataaaactgc tattcatact tatttttctt ctgttttttt gggtggtgtt  960
gattctttgg ttgatttgat gaataaatct tttccagaat tgggtattaa aaaaactgat  1020
tgtagacaat tgtcttggat tgatactatt atttttttatt ctggtgttgt taattatgat  1080
actgataatt ttaataaaga aattttgttg gatagatctg ctggtcaaaa tggtgctttt  1140
aaaattaaat tggattatgt taaaaaacca attccagaat ctgtttttgt tcaaattttg  1200
gaaaaattgt atgaagaaga tattggtgct ggtatgtatg ctttgtatcc atatggtggt  1260
attatggatg aaatttctga atctgctatt ccatttccac atagagctgg tattttgtat  1320
gaattgtggt atatttgttc ttgggaaaaa caagaagata atgaaaaaca tttgaattgg  1380
attagaaata tttataattt tatgactcca tatgttteta aaaatccaag attggcttat  1440
ttgaattata gagatttgga tattggtatt aatgatccaa aaaatccaaa taattatact  1500
caagctagaa tttggggtga aaaatatttt ggtaaaaatt ttgatagatt ggttaaagtt  1560
aaaactttgg ttgatccaaa taattttttt agaaatgaac aatctattcc accattgcca  1620
agacatagac at                                                     1632
```

```
SEQ ID NO: 139          moltype = DNA  length = 1635
FEATURE                 Location/Qualifiers
source                  1..1635
                        mol_type = other DNA
                        organism = synthetic construct
SEQUENCE: 139
atgaattgta gtactttctc tttctggttt gtttgtaaga ttatattttt ttttcttagt  60
ttcaatatac aaatttcaat tgcaaaccct caagaaaatt tccttaagtg cttttcagaa  120
tatatcccta ataatcctgc aaaccctaaa ttcatttata cacaacatga tcagttatat  180
atgtctgtct taaactctac cattcaaaat ttgaggttca cgtctgatac aaccccaaag  240
cctttagtta tcgtgacacc ctctaacgtt agtcatattc aggctagtat cttatgttca  300
aaaaaagtgg gtttacaaat cagaactagg tctggtggtc atgacgcgga aggtctgtct  360
tacatatctc aggtgccgtt tgcaatcgtt gatctacgta atatgcatac agttaaagtc  420
gatattcact ctcaaactgc atgggtcgag gctggtgcca ctctaggtga agtttattac  480
tggatcaatg aaatgaacga gaatttttcc ttcccaggtg gttattgtcc tactgtgggt  540
```

```
gtaggcggac actttctgg cggggggtat ggtgctttga tgaggaacta tggtttggcc  600
gccgataata taattgacgc ccatcttgta aacgtcgacg ggaaggttct ggaccgtaaa  660
tctatgggtg aagatttatt ctgggcgata agaggtggcg ggggagagaa ctttggtatt  720
atcgcagctt gtaagattaa gttagttgtt gtcccctcaa aagcaacaat tttttcagtg  780
aagaagaaca tggaaatcca cggtttggta aaactgttta ataaatggca gaatattgcc  840
tacaaatacg ataaggattt gatgttgaca acacatttca gaactagaaa tattactgac  900
aaccacggaa agaacaagac aaccgtccat ggatatttta gttctatttt cttaggcgga  960
gttgattcac tagtagactt aatgaacaag tctttccccg aattgggaat aaaaaaaacc  1020
gattgcaagg aattatcctg gatagataca acaatattct actctggagt cgttaattat  1080
aatacggcca actttaagaa ggaaatatta ttagatcgtt ccgcaggtaa aaagacagct  1140
ttttccataa aattggacta cgtcaaaaaa ttaattcctg agacagccat ggtaaaaata  1200
ttggaaaaat tgtacgaaga ggaggtaggc gtgggtatgt atgtgttata cccatacggt  1260
ggtattatgg atgaaatttc tgagagcgct attcccttcc cccatcgtgc aggtataatg  1320
tatgaattat ggtacacagc aacatgggaa aaacaagagg ataacgaaaa gcatattaat  1380
tgggtacgta gtgtgtacaa ctttacgaca ccttacgtgt cccaaaatcc aagattagcg  1440
tatttgaact atagagactt agatttaggt aaaacaaacc ctgagtctcc aaataattac  1500
acccaagcca ggatttgggg tgaaaaatac ttcggcaaaa atttcaatag attggttaag  1560
gtaaaaacta aggcggatcc aaacaatttt tttagaaatg agcagagtat tccgcccctg  1620
cctccaagac accat                                                   1635

SEQ ID NO: 140          moltype = DNA  length = 2160
FEATURE                 Location/Qualifiers
source                  1..2160
                        mol_type = other DNA
                        organism = synthetic construct
SEQUENCE: 140
atgggtaaaa attataaatc tttggattct gttgttgctt ctgattttat tgctttgggt  60
attacttctg aagttgctga aactttgcat ggtagattgg ctgaaattgt ttgtaattat  120
ggtgctgcta ctccacaaac ttggattaat attgctaatc atattttgtc tccagatttg  180
ccattttctt tgcatcaaat gttgttttat ggttgttata aagattttgg tccagctcca  240
ccagcttgga ttccagatcc agaaaaagtt aaatctacta atttgggtgc tttgttggaa  300
aaaagaggta aagaattttt gggtgttaaa tataaagatc caatttcttc tttttctcat  360
tttcaagaat tttctgttag aaatccagaa gtttattgga gaactgtttt gatggatgaa  420
atgaaaattt ctttttctaa agatccagaa tgtattttga gaagagatga tattaataat  480
ccaggtggtt ctgaatggtt gccaggtggt tatttgaatt ctgctaaaaa ttgtttgaat  540
gttaattcta ataaaaaatt gaatgatact atgattgttt ggagagatga aggtaatgat  600
gatttgccat tgaataaatt gactttggat caattgagaa aaagagtttg gttggttggt  660
tatgctttgg aagaaatggg tttggaaaaa ggttgtgcta ttgctattga tatgccaatg  720
catgttgatg ctgttgttat ttatttggct attgttttgg ctggttatgt tgttgtttct  780
attgctgatt ctttttctgc tccagaaatt tctactagat tgagattgtc taaagctaaa  840
gctattttta ctcaagatca tattattaga ggtaaaaaaa gaattccatt gtattctaga  900
gttgttgaag ctaaatctcc aatggctatt gttattccat gttctggttc taatattggt  960
gctgaattga gagatggtga tatttcttgg gattattttt tggaaagagc taaagaattt  1020
aaaaattgtg aatttactgc tagagaacaa ccagttgatg cttatactaa tattttgttt  1080
tcttctggta ctactggtga accaaaagct attccatgga ctcaagctac tccattgaaa  1140
gctgctgctg atggttggtc tcatttggat attagaaaag gtgatgttat tgtttggcca  1200
actaatttgg gttggatgat gggtccatgg ttggtttatg cttctttgtt gaatggtgct  1260
tctattgctt tgtataatgg ttctccattg gtttctggtt ttgctaaatt tgttcaagat  1320
gctaaagtta ctatgttggg tgttgttcca tctattgtta gatcttggaa atctactaat  1380
tgtgtttctg gttatgattg gtctactatt agatgttttt cttcttctgg tgaagcttct  1440
aatgttgatg aatatttgtg gttgatgggt agagctaatt ataaaccagt tattgaaatg  1500
tgtggtggta ctgaaattgg tggtgctttt tctgctggtt cttttttgca agctcaatct  1560
ttgtcttctt tttcttctca atgtatgggt tgtactttgt atattttgga taaaaatggt  1620
tatccaatgc caaaaaataa accaggtatt ggtgaattgg ctttgggtcc agttatgttt  1680
ggtgcttcta aaactttgtt gaatggtaat catcatgatg tttattttaa aggtatgcca  1740
actttgaatg gtgaagtttt gagaagacat ggtgatattt ttgaattgac ttctaatggt  1800
tattatcatg ctcatggtag agctgatgat actatgaata ttggtggtat taaaatttct  1860
tctattgaaa ttgaaagagt ttgtaatgaa gttgatgata gagtttttga aactactgct  1920
attggtgttc caccattggg tggtggtcca gaacaattgg ttattttttt tgttttgaaa  1980
gattctaatg atactactat tgatttgaat caattgagat tgtcttttaa tttgggtttg  2040
caaaaaaaat tgaatccatt gtttaaagtt actagagttg ttccattgtc ttctttgcca  2100
agaactgcta ctaataaaat tatgagaaga gttttgagac aacaattttc tcattttgaa  2160

SEQ ID NO: 141          moltype = DNA  length = 4587
FEATURE                 Location/Qualifiers
source                  1..4587
                        mol_type = other DNA
                        organism = synthetic construct
SEQUENCE: 141
atgtctgcta aagctatttc tgaacaaact ggtaaagaat tgttgtataa atttatttgt  60
actacttctg ctattcaaaa tagatttaaa tatgctagag ttactccaga tactgattgg  120
gctagattgt tgcaagatca tccatggttg ttgtctcaaa atttggttgt taaaccagat  180
caattgatta aaagaagagg taaattgggt ttggttggtg ttaatttgac tttggatggt  240
gttaaatctt ggttgaaacc aagattgggt caagaagcta ctgttggtaa agctactggt  300
tttttgaaaa atttttgat tgaaccattt gttccacatt ctcaagctga agaattttat  360
gtttgtattt atgctactag agaaggtgat tatgttttgt ttcatcatga aggtggtgtt  420
gatgttggtg atgttgatgc taaagctcaa aaattgttgg ttggtgttga tgaaaaattg  480
aatccagaag atattaaaaa acatttgttg gttcatgctc cagaagataa aaaagaaatt  540
ttggcttctt ttatttctgg tttgtttaat ttttatgaag atttgtattt tacttatttg  600
```

```
gaaattaatc cattggttgt tactaaagat ggtgtttatg ttttggattt ggctgctaaa  660
gttgatgcta ctgctgatta tatttgtaaa gttaaatggg gtgatattga atttccacca  720
ccatttggta gagaagctta tccagaagaa gcttatattg ctgatttgga tgctaaatct  780
ggtgcttctt tgaaattgac tttgttgaat ccaaaaggta gaatttggac tatggttgct  840
ggtggtggtg cttctgttgt ttattctgat actatttgtg atttgggtgg tgttaatgaa  900
ttggctaatt atggtgaata ttctggtgct ccatctgaac aacaaactta tgattatgct  960
aaaactattt tgtctttgat gactagagaa aaacatccag atggtaaaat tttgattatt  1020
ggtggttcta ttgctaattt tactaatgtt gctgctactt ttaaaggtat tgttagagct  1080
attagagatt atcaaggtcc attgaaagaa catgaagtta ctatttttgt tagaagaggt  1140
ggtccaaatt atcaagaagg tttgagagtt atgggtgaag ttggtaaaac tactggtatt  1200
ccaattcatg tttttggtac tgaaactcat atgactgcta ttgttggtat ggctttgggt  1260
catagaccaa ttccaaatca accaccaact gctgctcata ctgctaattt tttgttgaat  1320
gcttctggtt ctacttctac tccagctcca tctagaactg cttctttttc tgaatctaga  1380
gctgatgaag ttgctccagc taaaaaagct aaaccagcta tgccacaaga ttctgttcca  1440
tctccaagat ctttgcaagg taaatctact actttgtttt ctagacatac taaagctatt  1500
gtttggggta tgcaaactag agctgttcaa ggtatgttgg attttgatta tgtttgttct  1560
agagatgaac catctgttgc tgctatggtt tatccattta ctggtgatca taaacaaaaa  1620
ttttattggg gtcataaaga aattttgatt ccagttttta aaaatatggc tgatgctatg  1680
agaaaacatc cagaagttga tgttttgatt aattttgctt ctttgagatc tgcttatgat  1740
tctactatgg aaactatgaa ttatgctcaa attagaacta ttgctattat tgctgaaggt  1800
attccagaag ctttgactag aaaattgatt aaaaaagctg atcaaaaagg tgttactatt  1860
attggtccag ctactgttgg tggtattaaa ccaggttgtt ttaaaattgg taatactggt  1920
ggtatgttgg ataatatttt ggcttctaaa ttgtatagac caggttctgt tgcttatgtt  1980
tctagatctg gtggtatgtc taatgaattg aataatatta tttctagaac tactgatggt  2040
gtttatgaag gtgttgctat tggtggtgat agatatccag gttctacttt tatggatcat  2100
gttttgagat atcaagatac tccaggtgtt aaaatgattg ttgttttggg tgaaattggt  2160
ggtactgaag aatataaaat ttgtagaggt attaaagaag gtagattgac taaaccaatt  2220
gtttgttggt gtattggtac ttgtgctact atgttttctt ctgaagttca atttggtcat  2280
gctggtgctt gtgctaatca agcttctgaa actgctgttg ctaaaaatca agctttgaaa  2340
gaagctggtg tttttgttcc aagatctttt gatgaattgg gtgaaattat tcaatctgtt  2400
tatgaagatt tggttgctaa tggtgttatt gttccagctc aagaagttcc accaccaact  2460
gttccaatgg attattcttg ggctagagaa ttgggtttga ttagaaaacc agcttctttt  2520
atgacttcta tttgtgatga aagaggtcaa gaattgattt atgctggtat gccaattact  2580
gaagttttta aagaagaaat gggtattggt ggtgttttgg gtttgttgtg gtttcaaaaa  2640
agattgccaa aatattcttg tcaatttatt gaaatgtgtt tgatggttac tgctgatcat  2700
ggtccagctg tttctggtgc tcataatact attatttgtg ctagagctgg taaagatttg  2760
gtttcttctt tgacttctgg tttgttgact attggtgata gatttggtgg tgctttggat  2820
gctgctgcta aaatgttttc taaagctttt gattctggta ttattccaat ggaatttgtt  2880
aataaaatga aaaaagaagg taaattgatt atgggtattg gtcatagagt taaatctatt  2940
aataatccag atatgagagt tcaaattttg aaagattatg ttagacaaca ttttccagct  3000
actccattgt tggattatgc tttggaagtt gaaaaaatta ctacttctaa aaaaccaaat  3060
ttgattttga atgttgatgg tttgattggt gttgcttttg ttgatatgtt gagaaattgt  3120
ggttctttta ctagagaaga agctgatgaa tatattgata ttggtgcttt gaatggtatt  3180
tttgttttgg gtagatctat gggttttatt ggtcattatt tggatcaaaa aagattgaaa  3240
caaggtttgt atagacatcc atgggatgat atttcttatg ttttgccaga acatatgtct  3300
atgaaattgt ctggtggtgg tggttctggt ggtggtggtt ctggtggtgg tggttctgct  3360
gaagcttggt ataatttggg taatgcttat tataaacaag gtgattatca aaaagctatt  3420
gaatattatc aaaaagcttt ggaattggat ccaaataatg ctgaagcttg gtataatttg  3480
ggtaatgctt attataaaca aggtgattat caaaaagcta ttgaatatta tcaaaaagct  3540
ttggaattgg atccaaataa tgctgaagct tggtataatt tgggtaatgc ttattataaa  3600
caaggtgatt atcaaaaagc tattgaagat tatcaaaaag ctttggaatt ggatccaaat  3660
aatttgcaag ctgaagcttg gaaaaatttg ggtaatgctt attataaaca aggtgattat  3720
caaaaagcta ttgaatatta tcaaaaagct ttggaattgg atccaaataa tgcttctgct  3780
tggtataatt tgggtaatgc ttattataaa caaggtgatt atcaaaaagc tattgaatat  3840
tatcaaaaag ctttggaatt ggatccaaat aatgctaaag cttggtatag aagaggtaat  3900
gcttattata aacaaggtga ttatcaaaaa gctattgaag attatcaaaa agctttggaa  3960
ttggatccaa ataatagatc tagatctgct ggtggtggtg gttctggtgg tggtggttct  4020
ggtggtggtg gtgcttcttc ttattatcat catcatcatc atcatttgga atctacttct  4080
ttgtataaaa aagctggttc tggttctaat ttggttgctc aattggaaaa tgaagttgct  4140
tctttggaaa atgaaaatga aactttgaaa aaaaaaaatt tgcataaaaa agatttgatt  4200
gcttatttgg aaaaagaaat tgctaatttg agaaaaaaaa ttgaagaagg ttctgctggt  4260
tctgctgctg gttctggtga atttggttct gctgaagctg ctgctaaaga agctgctgct  4320
aaagctggtt ctgctggttc tgctgctggt tctggtgaat ttggttcttc ttattatcat  4380
catcatcatc atcatttgga atctacttct ttgtataaaa aagctggttc tggttctgct  4440
agaaatgctt atttgagaaa aaaaattgct agattgaaaa aagataattt gcaattggaa  4500
agagatgaac aaaatttgga aaaaattatt gctaatttga gagatgaaat tgctagattg  4560
gaaaatgaag ttgcttctca tgaacaa                                      4587
```

```
SEQ ID NO: 142          moltype = DNA  length = 2463
FEATURE                 Location/Qualifiers
source                  1..2463
                        mol_type = other DNA
                        organism = synthetic construct
SEQUENCE: 142
atgaaaaatt gtgttattgt ttctgctgtt agaactgcta ttggttcttt taatggttct  60
ttggcttcta cttctgctat tgatttgggt gctactgtta ttaaagctgc tattgaaaga  120
gctaaaattg attctcaaca tgttgatgaa gttattatgg gtaatgtttt gcaagctggt  180
ttgggtcaaa atccagctag acaagctttg ttgaaatctg gtttggctga aactgtttgt  240
ggttttactg ttaataaagt ttgtggttct ggtttgaaat ctgttgcttt ggctgctcaa  300
```

```
gctattcaag ctggtcaagc tcaatctatt gttgctggtg gtatggaaaa tatgtctttg  360
gctccatatt tgttggatgc taaagctaga tctggttata gattgggtga tggtcaagtt  420
tatgatgtta ttttgagaga tggtttgatg tgtgctactc atggttatca tatgggtatt  480
actgctgaaa atgttgctaa agaatatggt attactagag aaatgcaaga tgaattggct  540
ttgcattctc aaagaaaagc tgctgctgct attgaatctg gtgcttttac tgctgaaatt  600
gttccagtta atgttgttac tagaaaaaaa actttttgttt tttctcaaga tgaatttcca  660
aaagctaatt ctactgctga agctttgggt gctttgagac cagcttttga taaagctggt  720
actgttactg ctggtaatgc ttctggtatt aatgatggtg ctgctgcttt ggttattatg  780
gaagaatctg ctgctttggc tgctggtttg actccattgg ctagaattaa atcttatgct  840
tctggtggtg ttccaccagc tttgatgggt atgggtccag ttccagctac tcaaaaagct  900
ttgcaattgg ctggtttgca attggctgat attgatttga ttgaagctaa tgaagctttt  960
gctgctcaat ttttggctgt tggtaaaaat ttgggttttg attctgaaaa agttaatgtt  1020
aatggtggtg ctattgcttt gggtcatcca attggtgctt ctggtgctag aattttggtt  1080
actttgttgc atgctatgca agctagagat aaaactttgg gtttggctac tttgtgtatt  1140
ggtggtggtc aaggtattgc tatggttatt gaaagattga ataaattgtc tggtggtggt  1200
ggttctggtg gtggtggttc tggtggtggt ggttctgctg aagcttggta taatttgggt  1260
aatgcttatt ataaacaagg tgattatcaa aaagctattg aatattatca aaaagctttg  1320
gaattggatc caaataatgc tgaagcttgg tataatttgg gtaatgctta ttataaacaa  1380
ggtgattatc aaaaagctat tgaatattat caaaaagctt tggaattgga tccaaataat  1440
gctgaagctt ggtataattt gggtaatgct tattataaac aaggtgatta tcaaaaagct  1500
attgaagatt atcaaaaagc tttggaattg gatccaaata atttgcaagc tgaagcttgg  1560
aaaaatttgg gtaatgctta ttataaacaa ggtgattatc aaaaagctat tgaatattat  1620
caaaaagctt tggaattgga tccaaataat gcttctgctt ggtataattt gggtaatgct  1680
tattataaac aaggtgatta tcaaaaagct attgaatatt atcaaaaagc tttggaattg  1740
gatccaaata atgctaaagc ttggtataga agaggtaatg cttattataa acaaggtgat  1800
tatcaaaaag ctattgaaga ttatcaaaaa gctttggaat tggatccaaa taatagatct  1860
agatctgctg gtggtggtgg ttctggtggt ggtggttctg gtggtggtgg tgcttcttct  1920
tattatcatc atcatcatca tcatttggaa tctacttctt tgtataaaaa agctggttct  1980
ggttctaatg aagttactac tttggaaaat gatgctgctt ttattgaaaa tgaaaatgct  2040
tatttggaaa aagaaattgc tagattgaga aaagaaaaag ctgctttgag aaatagattg  2100
gctcataaaa aaggttctgc tggttctgct gctggttctg gtgaatttgg ttctgctgaa  2160
gctgctgcta aagaagctgc tgctaaagct ggttctgctg gttctgctgc tggttctggt  2220
gaatttggtt cttcttatta tcatcatcat catcatcatt tggaatctac ttctttgtat  2280
aaaaaagctg gttctggttc tcaaaaagtt gctgaattga aaaatagagt tgctgttaaa  2340
ttgaatagaa atgaacaatt gaaaaataaa gttgaagaat tgaaaaatag aaatgcttat  2400
ttgaaaaatg aattggctac tttggaaaat gaagttgcta gattggaaaa tgatgttgct  2460
gaa                                                                2463
```

```
SEQ ID NO: 143          moltype = DNA  length = 2328
FEATURE                 Location/Qualifiers
source                  1..2328
                        mol_type = other DNA
                        organism = synthetic construct
SEQUENCE: 143
atgaaaaaag tttgtgttat tggtgctggt actatgggtt ctggtattgc tcaagctttt  60
gctgctaaag gttttgaagt tgttttgaga gatattaaag atgaatttgt tgatagaggt  120
ttggatttta ttaataaaaa tttgtctaaa ttggttaaaa aaggtaaaat tgaagaagct  180
actaaagttg aaattttgac tagaatttct ggtactgttg atttgaatat ggctgctgat  240
tgtgatttgg ttattgaagc tgctgttgaa agaatggata ttaaaaaaca aattttttgct  300
gatttggata atatttgtaa accagaaact attttggctt ctaatacttc ttctttgtct  360
attactgaag ttgcttctgc tactaaaaga ccagataaag ttattggtat gcattttttt  420
aatccagctc cagttatgaa attggttgaa gttattagag gtattgctac ttctcaagaa  480
acttttgatg ctgttaaaga aacttctatt gctattggta aagatccagt tgaagttgct  540
gaagctccag gttttgttgt taatagaatt ttgattccaa tgattaatga agctgttggt  600
attttggctg aaggtattgc ttctgttgaa gatattgata aagctatgaa attgggtgct  660
aatcatccaa tgggtccatt ggaattgggt gattttattg gtttggatat ttgtttggct  720
attatggatg ttttgtattc tgaaactggt gattctaaat atagaccaca tactttgttg  780
aaaaaatatg ttagagctgg ttggttgggt agaaaatctg gtaaaggttt ttatgattat  840
tctaaaaaat tgtctggtgg tggtggttct ggtggtggtg gttctggtgg tggtggttct  900
gctgaagctt ggtataattt gggtaatgct tattataaac aaggtgatta tcaaaaagct  960
attgaatatt atcaaaaagc tttggaattg gatccaaata atgctgaagc ttggtataat  1020
ttgggtaatg cttattataa acaaggtgat tatcaaaaag ctattgaata ttatcaaaaa  1080
gctttggaat tggatccaaa taatgctgaa gcttggtata atttgggtaa tgcttattat  1140
aaacaaggtg attatcaaaa agctattgaa gattatcaaa aagctttgga attggatcca  1200
aataatttgc aagctgaagc ttggaaaaat ttgggtaatg cttattataa acaaggtgat  1260
tatcaaaaag ctattgaata ttatcaaaaa gctttggaat tggatccaaa taatgcttct  1320
gcttggtata atttgggtaa tgcttattat aaacaaggtg attatcaaaa agctattgaa  1380
tattatcaaa aagctttgga attggatcca aataatgcta aagcttggta tagaagaggt  1440
aatgcttatt ataaacaagg tgattatcaa aaagctattg aagattatca aaaagctttg  1500
gaattggatc caaataatag atctagatct gctggtggtg gtggttctgg tggtggtggt  1560
tctggtggtg gtggtgcttc tgaaaatttg tattttcaag gtgaaaattt gtattttcaa  1620
ggtgattctt ctgaatcttg ttggaattgt ggtagaaaag cttctgaaac ttgttctggt  1680
tgtaatactg ctagatattg tggttctttt tgtcaacata aagattggga aaaacatcat  1740
catatttgtg gtcaaacttt gcaagctcaa caaggttctg ctggttctgc tgctggttct  1800
ggtgaatttg gttctgctga agctgctgct aaagaagctg ctgctaaagc tggttctgct  1860
ggttctgctg ctggttctgg tgaatttggt tctatggctg tttctgaatc tcaattgaaa  1920
aaaatggttt ctaaatataa atatagagat ttgactgtta gagaaactgt taatgttatt  1980
actttgtata aagatttgaa accagttttg gattcttatg tttttaatga tggttcttct  2040
agagaattga tgaatttgac tggtactatt ccagttccat atagaggtaa tacttataat  2100
```

-continued

```
attccaattt gtttgtggtt gttggatact tatccatata atccaccaat ttgttttgtt  2160
aaaccaactt cttctatgac tattaaaact ggtaaacatg ttgatgctaa tggtaaaatt  2220
tatttgccat atttgcatga atggaaacat ccacaatctg atttgttggg tttgattcaa  2280
gttatgattg ttgtttttgg tgatgaacca ccagtttttt ctagacca               2328

SEQ ID NO: 144         moltype = DNA  length = 2223
FEATURE                Location/Qualifiers
source                 1..2223
                       mol_type = other DNA
                       organism = synthetic construct
SEQUENCE: 144
atggaattga ataatgttat tttggaaaaa gaaggtaaag ttgctgttgt tactattaat  60
agaccaaaag ctttgaatgc tttgaattct gatactttga aagaaatgga ttatgttatt  120
ggtgaaattg aaaatgattc tgaagttttg gctgttattt tgactggtgc tggtgaaaaa  180
tcttttgttg ctggtgctga tatttctgaa atgaaagaaa tgaatactat tgaaggtaga  240
aaatttggta ttttgggtaa taaagttttt agaagattgg aattgttgga aaaaccagtt  300
attgctgctg ttaatggttt tgctttgggt ggtggttgtg aaattgctat gtcttgtgat  360
attagaattg cttcttctaa tgctagattt ggtcaaccag aagttggttt gggtattact  420
ccaggttttg gtggtactca aagattgtct agattggttg gtatgggtat ggctaaacaa  480
ttgatttta ctgctcaaaa tattaaagct gatgaagctt tgagaattgg tttggttaat  540
aaagttgttg aaccatctga attgatgaat actgctaaag aaattgctaa taaaattgtt  600
tctaatgctc cagttgctgt taaattgtct aaacaagcta ttaatagagg tatgcaatgt  660
gatattgata ctgctttggc ttttgaatct gaagcttttg gtgaatgttt ttctactgaa  720
gatcaaaaag atgctatgac tgcttttatt gaaaaaagaa aaattgaagg ttttaaaaat  780
agaaaattgt ctggtggtgg tggttctggt ggtggtggtt ctggtggtgg tggttctgct  840
gaagcttggt ataatttggg taatgcttat tataaacaag gtgattatca aaaagctatt  900
gaatattatc aaaaagcttt ggaattggat ccaaataatg ctgaagcttg gtataatttg  960
ggtaatgctt attataaaca aggtgattat caaaaagcta ttgaatatta tcaaaaagct  1020
ttggaattgg atccaaataa tgctgaagct tggtataatt tgggtaatgc ttattataaa  1080
caaggtgatt atcaaaaagc tattgaagat tatcaaaaag ctttggaatt ggatccaaat  1140
aatttgcaag ctgaagcttg gaaaaatttg ggtaatgctt attataaaca aggtgattat  1200
caaaaagcta ttgaatatta tcaaaaagct ttggaattgg atccaaataa tgcttctgct  1260
tggtataatt tgggtaatgc ttattataaa caaggtgatt atcaaaaagc tattgaatat  1320
tatcaaaaag ctttggaatt ggatccaaat aatgctaaag cttggtatag aagaggtaat  1380
gcttattata aacaaggtga ttatcaaaaa gctattgaag attatcaaaa agctttggaa  1440
ttggatccaa ataatagatc tagatctgct ggtggtggtg gttctggtgg tggtggttct  1500
ggtggtggtg gtgcttctgg tccattgggt tctccattga ctgcttctat gttggcttct  1560
gctccaccac aagaacaaaa acaaatgttg ggtgaaagat tgtttccatt gattcaagct  1620
atgcatccaa ctttggctgg taaaattact ggtatgttgt tggaaattga taattctgaa  1680
ttgttgcata tgttggaatc tccagaatct ttgagatcta aagttgatga agctgttgct  1740
gttttgcaag ctcatcaagc taaagaagct gctcaaaaag ctggttctgc tggttctgct  1800
gctggttctg gtgaatttgg ttctgctgaa gctgctgcta aagaagctgc tgctaaagct  1860
ggttctgctg gttctgctgc tggttctggt gaatttggtt ctaatactaa tatgtctgtt  1920
ccaactgatg gtgctgttac tacttctcaa attccagctt ctgaacaaga aactttggtt  1980
agaccaaaac cattgttgtt gaaattgttg aaatctgttg gtgctcaaaa agatacttat  2040
actatgaaag aagttttgtt ttatttgggt caatatatta tgactaaaag attgtatgat  2100
gaaaaacaac aacatattgt ttattgttct aatgatttgt tgggtgattt gtttggtgtt  2160
ccatcttttt ctgttaaaga acatagaaaa atttatacta tgatttatag aaatttggtt  2220
gtt                                                                2223

SEQ ID NO: 145         moltype = DNA  length = 2460
FEATURE                Location/Qualifiers
source                 1..2460
                       mol_type = other DNA
                       organism = synthetic construct
SEQUENCE: 145
atgattgtta aaccaatggt tagaaataat atttgtttga atgctcatcc acaaggttgt  60
aaaaaaggtg ttgaagatca aattgaatat actaaaaaaa gaattactgc tgaagttaaa  120
gctggtgcta aagctccaaa aaatgttttg gttttgggtt gttctaatgg ttatggtttg  180
gcttctagaa ttactgctgc ttttggttat ggtgctgcta ctattggtgt ttcttttgaa  240
aaagctggtt ctgaaactaa atatggtact ccaggttggt ataataattt ggcttttgat  300
gaagctgcta aaagagaagg tttgtattct gttactattg atggtgatgc tttttctgat  360
gaaattaaag ctcaagttat tgaagaagct aaaaaaaaag gtattaaatt tgatttgatt  420
gtttattctt tggcttctcc agttagaact gatccagata ctggtattat gcataaatct  480
gttttgaaac catttggtaa aacttttact ggtaaaactg ttgatccatt tactggtgaa  540
ttgaaagaaa tttctgctga accagctaat gatgaagaag ctgctgctac tgttaaagtt  600
atgggtggtg aagattggga aagatggatt aaacaattgt ctaaagaagg tttgttggaa  660
gaaggttgta ttactttggc ttattcttat attggtccag aagctactca agctttgtat  720
agaaaaggta ctattggtaa agctaaagaa catttggaag ctactgctca tagattgaat  780
aaagaaaatc catctattag agcttttgtt tctgttaata aaggtttggt tactagagct  840
tctgctgtta ttccagttat tccattgtat ttggcttctt tgtttaaagt tatgaaagaa  900
aaaggtaatc atgaaggttg tattgaacaa attactagat tgtatgctga aagattgtat  960
agaaaagatg gtactattcc agttgatgaa gaaaatagaa ttagaattga tgattgggaa  1020
ttggaagaag atgttcaaaa agctgtttct gctttgatgg aaaaagttac tggtgaaaat  1080
gctgaatctt tgactgattt ggctggttat agacatgatt ttttggcttc taatggtttt  1140
gatgttgaag gtattaatta tgaagctgaa gttgaaagat ttgatagaat taaattgtct  1200
ggtggtggtg gttctggtgg tggtggttct ggtggtggtg gttctgctga agcttggtat  1260
aatttgggta atgcttatta taaacaaggt gattatcaaa aagctattga atattatcaa  1320
aaagctttgg aattggatcc aaataatgct gaagcttggt ataatttggg taatgcttat  1380
```

-continued

```
tataaacaag gtgattatca aaaagctatt gaatattatc aaaaagcttt ggaattggat  1440
ccaaataatg ctgaagcttg gtataatttg ggtaatgctt attataaaca aggtgattat  1500
caaaaagcta ttgaagatta tcaaaaagct ttggaattgg atccaaataa tttgcaagct  1560
gaagcttgga aaaatttggg taatgcttat tataaacaag gtgattatca aaaagctatt  1620
gaatattatc aaaaagcttt ggaattggat ccaaataatg cttctgcttg gtataatttg  1680
ggtaatgctt attataaaca aggtgattat caaaaagcta ttgaatatta tcaaaaagct  1740
ttggaattgg atccaaataa tgctaaagct tggtatagaa gaggtaatgc ttattataaa  1800
caaggtgatt atcaaaaagc tattgaagat tatcaaaaag ctttggaatt ggatccaaat  1860
aatagatcta gatctgctgg tggtggtggt tctggtggtg gtggttctgg tggtggtggt  1920
gcttcttctt attatcatca tcatcatcat catttggaat ctacttcttt gtataaaaaa  1980
gctggttctg gttctaattt gttggctact ttgagatcta ctgctgctgt tttggaaaat  2040
gaaaatcatg ttttggaaaa agaaaaagaa aaattgagaa aagaaaaaga acaattgttg  2100
aataaattgg aagcttataa aggttctgct ggttctgctg ctggttctgg tgaatttggt  2160
tctgctgaag ctgctgctaa agaagctgct gctaaagctg gttctgctgg ttctgctgct  2220
ggttctggtg aatttggttc ttcttattat catcatcatc atcatcattt ggaatctact  2280
tctttgtata aaaaagctgg ttctggttct aaaagaattg cttatttgag aaaaaaaatt  2340
gctgctttga aaaaagataa tgctaatttg gaaaaagata ttgctaattt ggaaaatgaa  2400
attgaaagat tgattaaaga aattaaaact ttggaaaatg aagttgcttc tcatgaacaa  2460

SEQ ID NO: 146         moltype = DNA  length = 2478
FEATURE                Location/Qualifiers
source                 1..2478
                       mol_type = other DNA
                       organism = synthetic construct
SEQUENCE: 146
atgactagag aagttgttgt tgtttctggt gttagaactg ctattggtac ttttggtggt  60
tctttgaaag atgttgctcc agctgaattg ggtgctttgg ttgttagaga agctttggct  120
agagctcaag tttctggtga tgatgttggt catgttgttt ttggtaatgt tattcaaact  180
gaaccaagag atatgtattt gggtagagtt gctgctgtta atggtggtgt tactattaat  240
gctccagctt tgactgttaa tagattgtgt ggttctggtt tgcaagctat tgtttctgct  300
gctcaaacta ttttgttggg tgatactgat gttgctattg gtggtggtgc tgaatctatg  360
tctagagctc catatttggc tccagctgct agatggggtg ctagaatggg tgatgctggt  420
ttggttgata tgatgttggg tgctttgcat gatccatttc atagaattca tatgggtgtt  480
actgctgaaa atgttgctaa agaatatgat atttctagag ctcaacaaga tgaagctgct  540
ttggaatctc atagaagagc ttctgctgct attaaagctg gttattttaa agatcaaatt  600
gttccagttg tttctaaagg tagaaaaggt gatgttactt ttgatactga tgaacatgtt  660
agacatgatg ctactattga tgatatgact aaattgagac cagtttttgt taaagaaaat  720
ggtactgtta ctgctggtaa tgcttctggt ttgaatgatg ctgctgctgc tgttgttatg  780
atggaaagag ctgaagctga aagaagaggt ttgaaaccat tggctagatt ggtttcttat  840
ggtcatgctg gtgttgatcc aaaagctatg ggtattggtc cagttccagc tactaaaatt  900
gctttggaaa gagctggttt gcaagtttct gatttggatg ttattgaagc taatgaagct  960
tttgctgctc aagcttgtgc tgttactaaa gctttgggtt tggatccagc taaagttaat  1020
ccaaatggtt ctggtatttc tttgggtcat ccaattggtg ctactggtgc tttgattact  1080
gttaaagctt tgcatgaatt gaatagagtt caaggtagat atgctttggt tactatgtgt  1140
attggtggtg gtcaaggtat tgctgctatt tttgaaagaa ttaaattgtc tggtggtggt  1200
ggttctggtg gtggtggttc tggtggtggt ggttctgctg aagcttggta taatttgggt  1260
aatgcttatt ataaacaagg tgattatcaa aaagctattg aatattatca aaaagctttg  1320
gaattggatc caaataatgc tgaagcttgg tataatttgg gtaatgctta ttataaacaa  1380
ggtgattatc aaaaagctat tgaatattat caaaaagctt tggaattgga tccaaataat  1440
gctgaagctt ggtataattt gggtaatgct tattataaac aaggtgatta tcaaaaagct  1500
attgaagatt atcaaaaagc tttggaattg gatccaaata atttgcaagc tgaagcttgg  1560
aaaaatttgg gtaatgctta ttataaacaa ggtgattatc aaaaagctat tgaatattat  1620
caaaaagctt tggaattgga tccaaataat gcttctgctt ggtataattt gggtaatgct  1680
tattataaac aaggtgatta tcaaaaagct attgaatatt atcaaaaagc tttggaattg  1740
gatccaaata atgctaaagc ttggtataga agaggtaatg cttattataa acaaggtgat  1800
tatcaaaaag ctattgaaga ttatcaaaaa gctttggaat tggatccaaa taatagatct  1860
agatctgctg gtggtggtgg ttctggtggt ggtggttctg gtggtggtgg tgcttctgat  1920
gttatgtggg aatataaatg ggaaaatact ggtgatgctg aattgtatgg tccatttact  1980
tctgctcaaa tgcaaacttg ggtttctgaa ggttattttc cagatggtgt ttattgtaga  2040
aaattggatc caccaggtgg tcaattttat aattctaaaa gaattgattt tgatttgtat  2100
actggttctg ctggttctgc tgctggttct ggtgaatttg gttctgctga agctgctgct  2160
aaagaagctg ctgctaaagc tggttctgct ggttctgctg ctggttctgg tgaatttggt  2220
tctgaatctg attctgttga atttaataat gctatttctt atgttaataa aattaaaact  2280
agatttttgg atcatccaga aatttataga tctttttttgg aaattttgca tacttatcaa  2340
aaagaacaat tgcatactaa aggtagacca tttagaggta tgtctgaaga agaagttttt  2400
actgaagttg ctaatttgtt tagaggtcaa gaagatttgt tgtctgaatt tggtcaattt  2460
ttgccagaag ctaaaaga                                                2478

SEQ ID NO: 147         moltype = DNA  length = 2550
FEATURE                Location/Qualifiers
source                 1..2550
                       mol_type = other DNA
                       organism = synthetic construct
SEQUENCE: 147
atgaaactct caactaaact ttgttggtgt ggtattaaag gaagacttag gccgcaaaag  60
caacaacaat tacacaatac aaacttgcaa atgactgaac taaaaaaaca aaagaccgct  120
gaacaaaaaa ccagacctca aaatgtcggt attaaaggta tccaaattta catcccaact  180
caatgtgtca accaatctga gctagagaaa tttgatggcg tttctcaagg taaatacaca  240
attggtctgg gccaaaccaa catgtctttt gtcaatgaca gagaagatat ctactcgatg  300
```

-continued

```
tccctaactg ttttgtctaa gttgatcaag agttacaaca tcgacaccaa caaaattggt  360
agattagaag tcggtactga aactctgatt gacaagtcca agtctgtcaa gtctgtcttg  420
atgcaattgt ttggtgaaaa cactgacgtc gaaggtattg acacgcttaa tgcctgttac  480
ggtggtacca acgcgttgtt caactctttg aactggattg aatctaacgc atgggatggt  540
agagacgcca ttgtagtttg cggtgatatt gccatctacg ataagggtgc cgcaagacca  600
accggtggtg ccggtactgt tgctatgtgg atcggtcctg atgctccaat tgtatttgac  660
tctgtaagag cttcttacat ggaacacgcc tacgattttt acaagccaga tttcaccagc  720
gaatatcctt acgtcgatgg tcatttttca ttaacttgtt acgtcaaggc tcttgatcaa  780
gtttacaaga gttattccaa gaaggctatt tctaaagggt tggttagcga tcccgctggt  840
tcggatgctt tgaacgtttt gaaatatttc gactacaacg ttttccatgt tccaacctgt  900
aaattggtca caaaatcata cggtagatta ctatataacg atttcagagc caatcctcaa  960
ttgttcccag aagttgacgc cgaattagct actcgcgatt atgacgaatc tttaaccgat  1020
aagaacattg aaaaaacttt tgttaatgtt gctaagccat tccacaaaga gagagttgcc  1080
caatctttga ttgttccaac aaacacaggt aacatgtaca ccgcatctgt ttatgccgcc  1140
tttgcatctc tattaaacta tgttggatct gacgacttac aaggcaagcg tgttggttta  1200
ttttcttacg gttccggttt agctgcatct ctatattctt gcaaaattgt tggtgacgtc  1260
caacatatta tcaaggaatt agatattact aacaaattag ccaagagaat caccgaaact  1320
ccaaaggatt acgaagctgc catcgaattg agagaaaatg cccatttgaa gaagaacttc  1380
aaacctcaag gttccattga gcatttgcaa agtggtgttt actacttgac caacatcgat  1440
gacaaattta gaagatctta cgatgttaaa aaataaaaat tgtctggtgg tggtggttct  1500
ggtggtggtg gttctggtgg tggtggttct gctgaagctt ggtataattt gggtaatgct  1560
tattataaac aaggtgatta tcaaaaagct attgaatatt atcaaaaagc tttggaattg  1620
gatccaaata atgctgaagc ttggtataat ttgggtaatg cttattataa acaaggtgat  1680
tatcaaaaag ctattgaata ttatcaaaaa gctttggaat tggatccaaa taatgctgaa  1740
gcttggtata atttgggtaa tgcttattat aaacaaggtg attatcaaaa agctattgaa  1800
gattatcaaa aagctttgga attggatcca aataatttgc aagctgaagc ttggaaaaat  1860
ttgggtaatg cttattataa acaaggtgat tatcaaaaag ctattgaata ttatcaaaaa  1920
gctttggaat tggatccaaa taatgcttct gcttggtata atttgggtaa tgcttattat  1980
aaacaaggtg attatcaaaa agctattgaa tattatcaaa aagctttgga attggatcca  2040
aataatgcta aagcttggta tagaagaggt aatgcttatt ataaacaagg tgattatcaa  2100
aaagctattg aagattatca aaaagctttg gaattggatc caaataatag atctagatct  2160
gctggtggtg gtggttctgg tggtggtggt tctggtggtg gtggtgcttc tttgggtcca  2220
ttgccaccag gttgggaagt tagatctact gtttctggta gaatttattt tgttgatcat  2280
aataatagaa ctactcaatt tactgatcca agattgcatg gttctgctgg ttctgctgct  2340
ggttctggtg aatttggttc tgctgaagct gctgctaaag aagctgctgc taaagctggt  2400
tctgctggtt ctgctgctgg ttctggtgaa tttggttctg gtgctatggg tccattgcca  2460
ccaggttggg aaaaaagaac tgattctaat ggtagagttt attttgttaa tcataatact  2520
agaattactc aatgggaaga tccaagatct                                  2550
```

```
SEQ ID NO: 148          moltype = DNA  length = 2478
FEATURE                 Location/Qualifiers
source                  1..2478
                        mol_type = other DNA
                        organism = synthetic construct
SEQUENCE: 148
atggttgcgg tacgtaggaa ggctctttca attttggcag aagctcctgt attagcatct  60
gatcgtttac catataaaaa ttatgactac gaccgcgtat ttggcgcttg ttgtgaaaat  120
gttataggtt acatgccttt gcccgttggt gttataggcc ccttggttat cgatggtaca  180
tcttatcata taccaatggc aactacagag ggttgtttgg tagcttctgc catgcgtggc  240
tgtaaggcaa tcaatgctgg cggtggtgca acaactgttt taactaagga tggtatgaca  300
agaggcccag tagtccgttt cccaactttg aaaagatctg gtgcctgtaa gatatggtta  360
gactcagaag agggacaaaa cgcaattaaa aaagctttta actctacatc aagatttgca  420
cgtctgcaac atattcaaac ttgtctagca ggagatttac tcttcatgag atttagaaca  480
actactggtg acgcaatggg tatgaatatg atttctaaag gtgtcgaata ctcattaaag  540
caaatggtag aagagtatgg ctgggaagat atggaggttg tctccgtttc tggtaactac  600
tgtaccgaca aaaaaccagc tgccatcaac tggatcgaag gtcgtggtaa gagtgtcgtc  660
gcagaagcta ctattcctgg tgatgttgtc agaaaagtgt taaaaagtga tgtttccgca  720
ttggttgagt tgaacattgc taagaatttg gttggatctg caatggctgg gtctgttggt  780
ggatttaacg cacatgcagc taatttagtg acagctgttt tcttggcatt aggacaagat  840
cctgcacaaa atgttgaaag ttccaactgt ataacattga tgaaagaagt ggacggtgat  900
ttgagaattt ccgtatccat gccatccatc gaagtaggta ccatcggtgg tggtactgtt  960
ctagaaccac aaggtgccat gttggactta ttaggtgtaa gaggcccgca tgctaccgct  1020
cctggtacca acgcacgtca attagcaaga atagttgcct gtgccgtctt ggcaggtgaa  1080
ttatccttat gtgctgccct agcagccggc catttggttc aaagtcatat gacccacaac  1140
aggaaattgt ctggtggtgg tggttctggt ggtggtggtt ctggtggtgg tggttctgct  1200
gaagcttggt ataatttggg taatgcttat tataaacaag gtgattatca aaaagctatt  1260
gaatattatc aaaaagcttt ggaattggat ccaaataatg ctgaagcttg gtataatttg  1320
ggtaatgctt attataaaca aggtgattat caaaaagcta ttgaatatta tcaaaaagct  1380
ttggaattgg atccaaataa tgctgaagct tggtataatt tgggtaatgc ttattataaa  1440
caaggtgatt atcaaaaagc tattgaagat tatcaaaaag ctttggaatt ggatccaaat  1500
aatttgcaag ctgaagcttg gaaaaatttg ggtaatgctt attataaaca aggtgattat  1560
caaaaagcta ttgaatatta tcaaaaagct ttggaattgg atccaaataa tgcttctgct  1620
tggtataatt tgggtaatgc ttattataaa caaggtgatt atcaaaaagc tattgaatat  1680
tatcaaaaag ctttggaatt ggatccaaat aatgctaaag cttggtatag aagaggtaat  1740
gcttattata aacaaggtga ttatcaaaaa gctattgaag attatcaaaa agctttggaa  1800
ttggatccaa ataatagatc tagatctgct ggtggtggtg gttctggtgg tggtggttct  1860
ggtggtggtg gtgcttcttc ttattatcat catcatcatc atcatttgga atctacttct  1920
ttgtataaaa aagctggttc tgaatttttt agaagagaaa gaaataaaat ggctgctgct  1980
aaatgtagaa atagaagaag agaattgact gatactttgc aagctgaaac tgatcaattg  2040
```

```
gaagatgaaa aatctgcttt gcaaactgaa attgctaatt tgttgaaaga aaaagaaaaa  2100
ttggaattta ttttggctgc tcatagacca gcttgtaaaa ttccagatga tttgggtttt  2160
ccagaagaaa tgtctttgga aggttctgct ggttctgctg ctggttctgg tgaatttggt  2220
tctgctgaag ctgctgctaa agaagctgct gctaaagctg gttctgctgg ttctgctgct  2280
ggttctggtg aatttggttc ttcttattat catcatcatc atcatcattt ggaatctact  2340
tctttgtata aaaaagctgg ttctggttct caaaaagttg aatctttgaa acaaaaaatt  2400
gaagaattga aacaaagaaa agctcaattg aaaaatgata ttgctaattt ggaaaaagaa  2460
attgcttatg ctgaaact                                                2478

SEQ ID NO: 149         moltype = DNA  length = 3141
FEATURE                Location/Qualifiers
source                 1..3141
                       mol_type = other DNA
                       organism = synthetic construct
SEQUENCE: 149
atgtcattac cgttcttaac ttctgcaccg ggaaaggtta ttatttttgg tgaacactct  60
gctgtgtaca acaagcctgc cgtcgctgct agtgtgtctg cgttgagaac ctacctgcta  120
ataagcgagt catctgcacc agatactatt gaattggact tcccggacat tagctttaat  180
cataagtggt ccatcaatga tttcaatgcc atcaccgagg atcaagtaaa ctcccaaaaa  240
ttggccaagg ctcaacaagc caccgatggc ttgtctcagg aactcgttag tcttttggat  300
ccgttgttag ctcaactatc cgaatccttc cactaccatg cagcgttttg tttcctgtat  360
atgtttgttt gcctatgccc ccatgccaag aatattaagt tttctttaaa gtctacttta  420
cccatcggtg ctgggttggg ctcaagcgcc tctatttctg tatcactggc cttagctatg  480
gcctacttgg gggggttaat aggatctaat gacttggaaa agctgtcaga aaacgataag  540
catatagtga atcaatgggc cttcataggt gaaaagtgta ttcacggtac cccttcagga  600
atagataacg ctgtggccac ttatggtaat gccctgctat ttgaaaaaga ctcacataat  660
ggaacaataa acacaaacaa ttttaagttc ttagatgatt tcccagccat tccaatgatc  720
ctaacctata ctagaattcc aaggtctaca aaagatcttg ttgctcgcgt tcgtgtgttg  780
gtcaccgaga aatttcctga agttatgaag ccaattctag atgccatggg tgaatgtgcc  840
ctacaaggct tagagatcat gactaagtta agtaaatgta aaggcaccga tgacgaggct  900
gtagaaacta ataatgaact gtatgaacaa ctattggaat tgataagaat aaatcatgga  960
ctgcttgtct caatcggtgt ttctcatcct ggattagaac ttattaaaaa tctgagcgat  1020
gatttgagaa ttggctccac aaaacttacc ggtgctggtg gcggcggttg ctctttgact  1080
ttgttacgaa gagacattac tcaagagcaa attgacagct tcaaaaagaa attgcaagat  1140
gattttagtt acgagacatt tgaaacagac ttgggtggga ctggctgctg tttgttaagc  1200
gcaaaaaatt tgaataaaga tcttaaaatc aaatccctag tattccaatt atttgaaaat  1260
aaaactacca caaagcaaca aattgacgat ctattattgc caggaaacac gaatttacca  1320
tggacttcat aaaaattgtc tggtggtggt ggttctggtg gtggtggttc tggtggtggt  1380
ggttctgctg aagcttggta taatttgggt aatgcttatt ataaacaagg tgattatcaa  1440
aaagctattg aatattatca aaaagctttg gaattggatc caaataatgc tgaagcttgg  1500
tataatttgg gtaatgctta ttataaacaa ggtgattatc aaaaagctat tgaatattat  1560
caaaaagctt tggaattgga tccaaataat gctgaagctt ggtataattt gggtaatgct  1620
tattataaac aaggtgatta tcaaaaagct attgaagatt atcaaaaagc tttggaattg  1680
gatccaaata atttgcaagc tgaagcttgg aaaaatttgg gtaatgctta ttataaacaa  1740
ggtgattatc aaaaagctat tgaatattat caaaaagctt tggaattgga tccaaataat  1800
gcttctgctt ggtataattt gggtaatgct tattataaac aaggtgatta tcaaaaagct  1860
attgaatatt atcaaaaagc tttggaattg gatccaaata atgctaaagc ttggtataga  1920
agaggtaatg cttattataa acaaggtgat tatcaaaaag ctattgaaga ttatcaaaaa  1980
gctttggaat tggatccaaa taatagatct agatctgctg gtggtggtgg ttctggtggt  2040
ggtggttctg gtggtggtgg tgcttctatg gaaccagcta tggaaccaga aactttggaa  2100
gctagaatta atagagctac taatccattg aataaagaat tggattgggc ttctattaat  2160
ggtttttgtg aacaattgaa tgaagatttt gaaggtccac cattggctac tagattgttg  2220
gctcataaaa ttcaatctcc acaagaatgg gaagctattc aagctttgac tgttttggaa  2280
acttgtatga aatcttgtgg taaaagattt catgatgaag ttggtaaatt tagattttttg  2340
aatgaattga ttaaagttgt ttctccaaaa tatttgggtt ctagaacttc tgaaaaagtt  2400
aaaaataaaa ttttggaatt gttgtattct tggactgttg gtttgccaga agaagttaaa  2460
attgctgaag cttatcaaat gttgaaaaaa caaggtattg ttaaatctgg ttctgctggt  2520
tctgctgctg gttctggtga atttggttct gctgaagctg ctgctaaaga agctgctgct  2580
aaagctggtt ctgctggttc tgctgctggt tctggtgaat ttggttctgg tgctatgggt  2640
tctatggctg aagctgaagg tgaatctttg gaatcttggt tgaataaagc tactaatcca  2700
tctaatagac aagaagattg ggaatatatt attggttttt gtgatcaaat taataaagaa  2760
ttggaaggtc cacaaattgc tgttagattg ttggctcata aaattcaatc tccacaagaa  2820
tgggaagctt tgcaagcttt gactgttttg gaagcttgta tgaaaaattg tggtagaaga  2880
tttcataatg aagttggtaa atttagattt ttgaatgaat tgattaaagt tgtttctcca  2940
aaatatttgg gtgatagagt ttctgaaaaa gttaaaacta aagttattga attgttgtat  3000
tcttggacta tggctttgcc agaagaagct aaaattaaag atgcttatca tatgttgaaa  3060
agacaaggta ttgttcaatc tgatccacca attccagttg atagaacttt gattccatct  3120
ccaccaccaa gaccaaaaaa t                                            3141

SEQ ID NO: 150         moltype = DNA  length = 2604
FEATURE                Location/Qualifiers
source                 1..2604
                       mol_type = other DNA
                       organism = synthetic construct
SEQUENCE: 150
atgtcagagt tgagagcctt cagtgcccca gggaaagcgt tactagctgg tggatattta  60
gttttagata caaaatatga agcatttgta gtcggattat cggcaagaat gcatgctgta  120
gcccatcctt acggttcatt gcaagggtct gataagtttg aagtgcgtgt gaaaagtaaa  180
caatttaaag atggggagtg gctgtaccat ataagtccta aaagtggctt cattcctgtt  240
```

```
tcgataggcg gatctaagaa ccctttcatt gaaaaagtta tcgctaacgt atttagctac  300
tttaaaccta acatggacga ctactgcaat agaaacttgt tcgttattga tattttctct  360
gatgatgcct accattctca ggaggatagc gttaccgaac atcgtggcaa cagaagattg  420
agttttcatt cgcacagaat tgaagaagtt cccaaaacag ggctgggctc ctcggcaggt  480
ttagtcacag ttttaactac agctttggcc tcctttttg tatcggacct ggaaaataat  540
gtagacaaat atagagaagt tattcataat ttagcacaag ttgctcattg tcaagctcag  600
ggtaaaattg gaagcgggtt tgatgtagcg gcggcagcat atggatctat cagatataga  660
agattcccac ccgcattaat ctctaatttg ccagatattg gaagtgctac ttacggcagt  720
aaactggcgc atttggttga tgaagaagac tggaatatta cgattaaaag taaccattta  780
ccttcgggat taactttatg gatgggcgat attaagaatg gttcagaaac agtaaaactg  840
gtccagaagg taaaaaattg gtatgattcg catatgccag aaagcttgaa aatatataca  900
gaactcgatc atgcaaattc tagatttatg gatggactat ctaaactaga tcgcttacac  960
gagactcatg acgattacag cgatcagata tttgagtctc ttgagaggaa tgactgtacc  1020
tgtcaaaagt atcctgaaat cacagaagtt agagatgcag ttgccacaat tagacgttcc  1080
tttagaaaaa taactaaaga atctggtgcc gatatcgaac ctcccgtaca aactagctta  1140
ttggatgatt gccagacctt aaaaggagtt cttacttgct taatacctgg tgctggtggt  1200
tatgacgcca ttgcagtgat tactaagcaa gatgttgatc ttagggctca aaccgctaat  1260
gacaaaagat tttctaaggt tcaatggctg gatgtaactc aggctgactg gggtgttagg  1320
aaagaaaaag atccggaaac ttatcttgat aaataaaaat tgtctggtgg tggtggttct  1380
ggtggtggtg gttctggtgg tggtggttct gctgaagctt ggtataattt gggtaatgct  1440
tattataaac aaggtgatta tcaaaaagct attgaatatt atcaaaaagc tttggaattg  1500
gatccaaata atgctgaagc ttggtataat ttgggtaatg cttattataa acaaggtgat  1560
tatcaaaaag ctattgaata ttatcaaaaa gctttggaat tggatccaaa taatgctgaa  1620
gcttggtata atttgggtaa tgcttattat aaacaaggtg attatcaaaa agctattgaa  1680
gattatcaaa aagctttgga attggatcca aataatttgc aagctgaagc ttggaaaaat  1740
ttgggtaatg cttattataa acaaggtgat tatcaaaaag ctattgaata ttatcaaaaa  1800
gctttggaat tggatccaaa taatgcttct gcttggtata atttgggtaa tgcttattat  1860
aaacaaggtg attatcaaaa agctattgaa tattatcaaa aagctttgga attggatcca  1920
aataatgcta aagcttggta tagaagaggt aatgcttatt ataaacaagg tgattatcaa  1980
aaagctattg aagattatca aaaagctttg gaattggatc caaataatag atctagatct  2040
gctggtggtg gtggttctgg tggtggtggt tctggtggtg gtggtgcttc ttcttattat  2100
catcatcatc atcatcattt ggaatctact tctttgtata aaaaagctgg ttctggttct  2160
caaaaagttg aagaattgaa aaataaaatt gctgaattgg aaaatagaaa tgctgttaaa  2220
aaaaatagag ttgctcattt gaaacaagaa attgcttatt tgaaagatga attggctgct  2280
catgaatttg aaggttctgc tggttctgct gctggttctg gtgaatttgg ttctgctgaa  2340
gctgctgcta aagaagctgc tgctaaagct ggttctgctg gttctgctgc tggttctggt  2400
gaatttggtt cttcttatta tcatcatcat catcatcatt tggaatctac ttctttgtat  2460
aaaaaagctg gttctggttc ttttgaaaat gttactcatg aatttatttt ggctactttg  2520
gaaaatgaaa atgctaaatt gagaagattg gaagctaaat tggaaagaga attggctaga  2580
ttgagaaatg aagttgcttg gttg                                    2604

SEQ ID NO: 151          moltype = DNA  length = 3027
FEATURE                 Location/Qualifiers
source                  1..3027
                        mol_type = other DNA
                        organism = synthetic construct
SEQUENCE: 151
atgaccgttt acacagcatc cgttaccgca cccgtcaaca tcgcaaccct taagtattgg  60
gggaaaaggg acacgaagtt gaatctgccc accaattcgt ccatatcagt gactttatcg  120
caagatgacc tcagaacgtt gacctctgcg gctactgcac ctgagtttga acgcgacact  180
ttgtggttaa atggagaacc acacagcatc gacaatgaaa gaactcaaaa ttgtctgcgc  240
gacctacgcc aattaagaaa ggaaatggaa tcgaaggacg cctcattgcc cacattatct  300
caatggaaac tccacattgt ctccgaaaat aactttccta cagcagctgg tttagcttcc  360
tccgctgctg gctttgctgc attggtctct gcaattgcta agttatacca attaccacag  420
tcaacttcag aaatatctag aatagcaaga aaggggtctg gttcagcttg tagatcgttg  480
tttggcggat acgtggcctg ggaaatggga aaagctgaag atggtcatga ttccatggca  540
gtacaaatcg cagacagctc tgactggcct cagatgaaag cttgtgtcct agttgtcagc  600
gatattaaaa aggatgtgag ttccactcag ggtatgcaat tgaccgtggc aacctccgaa  660
ctatttaaag aaagaattga acatgtcgta ccaaagagat ttgaagtcat gcgtaaagcc  720
attgttgaaa aagatttcgc caccttgca aaggaaacaa tgatggattc caactctttc  780
catgccacat gtttggactc tttccctcca atattctaca tgaatgacac ttccaagcgt  840
atcatcagtt ggtgccacac cattaatcag ttttacggag aaacaatcgt tgcatacacg  900
tttgatgcag gtccaaatgc tgtgttgtac tacttagctg aaaatgagtc gaaactcttt  960
gcatttatct ataaattgtt tggctctgtt cctggatggg acaagaaatt tactactgag  1020
cagcttgagg ctttcaacca tcaatttgaa tcatctaact ttactgcacg tgaattggat  1080
cttgagttgc aaaaggatgt tgccagagtg attttaactc aagtcggttc aggcccacaa  1140
gaaacaaacg aatctttgat tgacgcaaag actggtctac caaaggaata aaaattgtct  1200
ggtggtggtg gttctggtgg tggtggttct ggtggtggtg gttctgctga agcttggtat  1260
aatttgggta atgcttatta taaacaaggt gattatcaaa aagctattga atattatcaa  1320
aaagctttgg aattggatcc aaataatgct gaagcttggt ataatttggg taatgcttat  1380
tataaacaag gtgattatca aaaagctatt gaatattatc aaaaagcttt ggaattggat  1440
ccaaataatg ctgaagcttg gtataatttg ggtaatgctt attataaaca aggtgattat  1500
caaaaagcta ttgaagatta tcaaaaagct ttggaattgg atccaaataa tttgcaagct  1560
gaagcttgga aaaatttggg taatgcttat tataaacaag gtgattatca aaaagctatt  1620
gaatattatc aaaaagcttt ggaattggat ccaaataatg cttctgcttg gtataatttg  1680
ggtaatgctt attataaaca aggtgattat caaaaagcta ttgaatatta tcaaaaagct  1740
ttggaattgg atccaaataa tgctaaagct tggtatagaa gaggtaatgc ttattataaa  1800
caaggtgatt atcaaaaagc tattgaagat tatcaaaaag ctttggaatt ggatccaaat  1860
aatagatcta gatctgctgg tggtggtggt tctggtggtg gtggttctgg tggtggtggt  1920
```

-continued

```
gcttctgcta tggctgattt ggaacaaaaa gttttggaaa tggaagcttc tacttatgat  1980
ggtgttttta tttggaaaat ttctgatttt ccaagaaaaa gacaagaagc tgttgctggt  2040
agaattccag ctattttttc tccagctttt tatacttcta gatatggtta taaaatgtgt  2100
ttgagaattt atttgaatgg tgatggtact ggtagaggta ctcatttgtc tttgtttttt  2160
gttgttatga aaggtccaaa tgatgctttg ttgagatggc catttaatca aaaagttact  2220
ttgatgttgt tggatcaaaa taatagagaa catgttattg atgcttttag accagatgtt  2280
acttcttctt cttttcaaag accagttaat gatatgaata ttgcttctgg ttgtccattg  2340
ttttgtccag tttctaaaat ggaagctaaa aattcttatg ttagagatga tgctattttt  2400
attaaagcta ttgttgattt gactggtttg ggttctgctg gttctgctgc tggttctggt  2460
gaatttggtt ctgctgaagc tgctgctaaa gaagctgctg ctaaagctgg ttctgctggt  2520
tctgctgctg gttctggtga atttggttct gcttctatta aattgcaatc ttctgatggt  2580
gaaatttttg aagttgatgt tgaaattgct aaacaatctg ttactattaa aactatgttg  2640
gaagatttgg gtatggatga tgaaggtgat gatgatccag ttccattgcc aaatgttaat  2700
gctgctattt tgaaaaaagt tattcaatgg tgtactcatc ataaagatga tccaccacca  2760
ccagaagatg atgaaaataa agaaaaaaga actgatgata ttccagtttg ggatcaagaa  2820
tttttgaaag ttgatcaagg tactttgttt gaattgattt tggctgctaa ttatttggat  2880
attaaaggtt tgttggatgt tacttgtaaa actgttgcta atatgattaa aggtaaaact  2940
ccagaagaaa ttagaaaaac ttttaatatt aaaaatgatt ttactgaaga agaagaagct  3000
caagttagaa aagaaaatca atggtgt                                      3027

SEQ ID NO: 152          moltype = DNA  length = 2154
FEATURE                 Location/Qualifiers
source                  1..2154
                        mol_type = other DNA
                        organism = synthetic construct
SEQUENCE: 152
atgactgccg acaacaatag tatgccccat ggtgcagtat ctagttacgc caaattagtg  60
caaaaccaaa cacctgaaga cattttggaa gagtttcctg aaattattcc attacaacaa  120
agacctaata cccgatctag tgagacgtca aatgacgaaa gcggagaaac atgtttttct  180
ggtcatgatg aggagcaaat taagttaatg aatgaaaatt gtattgtttt ggattgggac  240
gataatgcta ttggtgccgg taccaagaaa gtttgtcatt taatggaaaa tattgaaaag  300
ggtttactac atcgtgcatt ctccgtcttt attttcaatg aacaaggtga attactttta  360
caacaaagag ccactgaaaa aataactttc cctgatcttt ggactaacac atgctgctct  420
catccactat gtattgatga cgaattaggt ttgaagggta agctagacga taagattaag  480
ggcgctatta ctgcggcggt gagaaaacta gatcatgaat taggtattcc agaagatgaa  540
actaagacaa ggggtaagtt tcactttttta aacagaatcc attacatggc accaagcaat  600
gaaccatggg gtgaacatga aattgattac atcctatttt ataagatcaa cgctaaagaa  660
aacttgactg tcaacccaaa cgtcaatgaa gttagagact tcaaatgggt ttcaccaaat  720
gatttgaaaa ctatgtttgc tgacccaagt tacaagttta cgccttggtt taagattatt  780
tgcgagaatt acttattcaa ctggtgggag caattagatg acctttctga agtggaaaat  840
gacaggcaaa ttcatagaat gctataaaaa ttgtctggtg gtggtggttc tggtggtggt  900
ggttctggtg gtggtggttc tgctgaagct tggtataatt tgggtaatgc ttattataaa  960
caaggtgatt atcaaaaagc tattgaatat tatcaaaaag ctttggaatt ggatccaaat  1020
aatgctgaag cttggtataa tttgggtaat gcttattata aacaaggtga ttatcaaaaa  1080
gctattgaat attatcaaaa agctttggaa ttggatccaa ataatgctga agcttggtat  1140
aatttgggta atgcttatta taaacaaggt gattatcaaa aagctattga agattatcaa  1200
aaagctttgg aattggatcc aaataatttg caagctgaag cttggaaaaa tttgggtaat  1260
gcttattata aacaaggtga ttatcaaaaa gctattgaat attatcaaaa agctttggaa  1320
ttggatccaa ataatgcttc tgcttggtat aatttgggta atgcttatta taaacaaggt  1380
gattatcaaa aagctattga atattatcaa aaagctttgg aattggatcc aaataatgct  1440
aaagcttggt atagaagagg taatgcttat tataaacaag gtgattatca aaaagctatt  1500
gaagattatc aaaaagcttt ggaattggat ccaaataata gatctagatc tgctggtggt  1560
ggtggttctg gtggtggtgg ttctggtggt ggtggtgctt cttcttatta tcatcatcat  1620
catcatcatt tggaatctac ttctttgtat aaaaaagctg gttctggttc taatactgtt  1680
aaagaattga aaaattatat tcaagaattg gaagaaagaa atgctgaatt gaaaaatttg  1740
aaagaacatt tgaaatttgc taaagctgaa ttggaatttg aattggctgc tcataaattt  1800
gaaggttctg ctggttctgc tgctggttct ggtgaatttg gttctgctga agctgctgct  1860
aaagaagctg ctgctaaagc tggttctgct ggttctgctg ctggttctgg tgaatttggt  1920
tcttcttatt atcatcatca tcatcatcat ttggaatcta cttctttgta taaaaaagct  1980
ggttctggtt ctcaaaaagt tgctcaattg aaaaatagag ttgcttataa attgaaagaa  2040
aatgctaaat tggaaaatat tgttgctaga ttggaaaatg ataatgctaa tttggaaaaa  2100
gatattgcta atttggaaaa agatattgct aatttggaaa gagatgttgc taga        2154

SEQ ID NO: 153          moltype = DNA  length = 2448
FEATURE                 Location/Qualifiers
source                  1..2448
                        mol_type = other DNA
                        organism = synthetic construct
SEQUENCE: 153
atggcttcag aaaaggaaat aagaagagaa agattcttga acgtattccc aaagttagtt  60
gaagaattga acgctagttt gttagcttat ggtatgccta aagaagcctg cgattggtat  120
gctcactctt taaactacaa tactccaggt ggtaaattga atagaggttt gagtgtagtt  180
gatacttatg ctatcttgtc taacaaaacc gttgaacaat taggtcaaga agaatacgaa  240
aaggtcgcta tcttgggttg gtgtattgaa ttgttgcaag catacttttt ggttgccgat  300
gacatgatgg ataagtctat aacaagaaga ggtcaaccat gctggtacaa agttccagaa  360
gttggtgaaa tagccataaa tgatgctttt atgttggaag ccgctatcta taaattgttg  420
aagtcacatt tcagaaacga aaagtactac atcgatatta ccgaattatt ccacgaagtt  480
actttccaaa cagaattggg tcaattgatg gatttgataa ctgcacctga agataaagtt  540
gacttgtcaa agttttcctt gaagaaacat tcattcatcg tcacctttga aactgcttat  600
```

-continued

```
tactccttct atttgccagt cgccttggct atgtacgtag ctggtattac tgatgaaaaa  660
gacttgaagc aagcaagaga tgttttgata cctttgggtg aatacttcca aatccaagat  720
gactacttag actgtttcgg tactccagaa caaataggta aaatcggtac agatattcaa  780
gacaataagt gcagttgggt tattaacaag gctttggaat tagcatctgc cgaacaaaga  840
aagactttgg atgaaaacta cggtaaaaag gactcagttg ctgaagcaaa gtgtaagaaa  900
atttttaatg atttgaagat tgaacaattg taccatgaat acgaagaatc catcgctaaa  960
gacttaaagg caaagattag tcaagttgat gaatcaagag gttttaaagc cgacgttttg  1020
acagctttct tgaataaggt ctacaagaga tcaaagtaga aattgtctgg tggtggtggt  1080
tctggtggtg gtggttctgg tggtggtggt tctgctgaag cttggtataa tttgggtaat  1140
gcttattata aacaaggtga ttatcaaaaa gctattgaat attatcaaaa agctttggaa  1200
ttggatccaa ataatgctga agcttggtat aatttgggta atgcttatta taaacaaggt  1260
gattatcaaa aagctattga atattatcaa aaagctttgg aattggatcc aaataatgct  1320
gaagcttggt ataatttggg taatgcttat tataaacaag gtgattatca aaaagctatt  1380
gaagattatc aaaaagcttt ggaattggat ccaaataatt tgcaagctga agcttggaaa  1440
aatttgggta atgcttatta taaacaaggt gattatcaaa aagctattga atattatcaa  1500
aaagctttgg aattggatcc aaataatgct tctgcttggt ataatttggg taatgcttat  1560
tataaacaag gtgattatca aaaagctatt gaatattatc aaaaagcttt ggaattggat  1620
ccaaataatg ctaaagcttg gtatagaaga ggtaatgctt attataaaca aggtgattat  1680
caaaaagcta ttgaagatta tcaaaaagct ttggaattgg atccaaataa tagatctaga  1740
tctgctggtg gtggtggttc tggtggtggt ggttctggtg gtggtggtgc ttctttgtgt  1800
actatgaaaa aaggtccatc tggttatggt tttaatttgc attctgataa atctaaacca  1860
ggtcaattta ttagatctgt tgatccagat tctccagctg aagcttctgg tttgagagct  1920
caagatagaa ttgttgaagt taatggtgtt tgtatggaag gtaaacaaca tggtgatgtt  1980
gtttctgcta ttagagctgg tggtgatgaa actaaattgt tggttgttga tagagaaggt  2040
tctgctggtt ctgctgctgg ttctggtgaa tttggttctg ctgaagctgc tgctaaagaa  2100
gctgctgcta aagctggttc tgctggttct gctgctggtt ctggtgaatt tggttcttct  2160
tctggtgcta ttatttatac tgttgaattg aaaagatatg gtggtccatt gggtattact  2220
atttctggta ctgaagaacc atttgatcca attattattt cttctttgac taaaggtggt  2280
ttggctgaaa gaactggtgc tattcatatt ggtgatagaa ttttggctat taattcttct  2340
tctttgaaag gtaaaccatt gtctgaagct attcatttgt tgcaaatggc tggtgaaact  2400
gttactttga aaattaaaaa acaaactgat gctcaaccag cttcttct              2448
```

```
SEQ ID NO: 154         moltype = DNA  length = 2649
FEATURE                Location/Qualifiers
source                 1..2649
                       mol_type = other DNA
                       organism = synthetic construct
SEQUENCE: 154
atgaatcatt tgagagctga aggtccagct tctgttttgg ctattggtac tgctaatcca  60
gaaaatattt tgttgcaaga tgaatttcca gattattatt ttagagttac taaatctgaa  120
catatgactc aattgaaaga aaaatttaga aaaatttgtg ataaatctat gattagaaaa  180
agaaattgtt ttttgaatga agaacatttg aaacaaaatc caagattggt tgaacatgaa  240
atgcaaactt tggatgctag acaagatatg ttggttgttg aagttccaaa attgggtaaa  300
gatgcttgtg ctaaagctat taaagaatgg ggtcaaccaa aatctaaaat tactcatttg  360
atttttactt ctgcttctac tactgatatg ccaggtgctg attatcattg tgctaaattg  420
ttgggtttgt ctccatctgt taaaagagtt atgatgtatc aattgggttg ttatggtggt  480
ggtactgttt tgagaattgc taaagatatt gctgaaaata ataaaggtgc tagagttttg  540
gctgtttgtt gtgatattat ggcttgtttg tttagaggtc catctgaatc tgatttggaa  600
ttgttggttg gtcaagctat ttttggtgat ggtgctgctg ctgttattgt tggtgctgaa  660
ccagatgaat ctgttggtga aagaccaatt tttgaattgg tttctactgg tcaaactatt  720
ttgccaaatt ctgaaggtac tattggtggt catattagag aagctggttt gatttttgat  780
ttgcataaag atgttccaat gttgatttct aataatattg aaaaatgttt gattgaagct  840
tttactccaa ttggtatttc tgattggaat tctatttttt ggattactca tccaggtggt  900
aaagctattt tggataaagt tgaagaaaaa ttgcatttga aatctgataa atttgttgat  960
tctagacatg ttttgtctga acatggtaat atgtcttctt ctactgtttt gtttgttatg  1020
gatgaattga gaaaaagatc tttggaagaa ggtaaatcta ctactggtga tggttttgaa  1080
tggggtgttt tgtttggttt tggtccaggt ttgactgttg aaagagttgt tgttagatct  1140
gttccaatta aatataaatt gtctggtggt ggtggttctg gtggtggtgg ttctggtggt  1200
ggtggttctg ctgaagcttg gtataatttg ggtaatgctt attataaaca aggtgattat  1260
caaaaagcta ttgaatatta tcaaaaagct ttggaattgg atccaaataa tgctgaagct  1320
tggtataatt tgggtaatgc ttattataaa caaggtgatt atcaaaaagc tattgaatat  1380
tatcaaaaag ctttggaatt ggatccaaat aatgctgaag cttggtataa tttgggtaat  1440
gcttattata aacaaggtga ttatcaaaaa gctattgaag attatcaaaa agctttggaa  1500
ttggatccaa ataatttgca agctgaagct tggaaaaatt tgggtaatgc ttattataaa  1560
caaggtgatt atcaaaaagc tattgaatat tatcaaaaag ctttggaatt ggatccaaat  1620
aatgcttctg cttggtataa tttgggtaat gcttattata aacaaggtga ttatcaaaaa  1680
gctattgaat attatcaaaa agctttggaa ttggatccaa ataatgctaa agcttggtat  1740
agaagaggta atgcttatta taaacaaggt gattatcaaa aagctattga agattatcaa  1800
aaagctttgg aattggatcc aaataataga tctagatctg ctggtggtgg tggttctggt  1860
ggtggtggtt ctggtggtgg tggtgcttct ggtaataatt tggaaactta tgaatggtat  1920
aataaatcta tttctagaga taaagctgaa aaattgttgt tggatactgg taaagaaggt  1980
gcttttatgg ttagagattc tagaactcca ggtacttata ctgtttctgt ttttactaaa  2040
gctattattt ctgaaaatcc atgtattaaa cattatcata ttaaagaaac taatgattct  2100
ccaaaaaagat attatgttgc tgaaaaatat gtttttgatt ctattccatt gttgattcaa  2160
tatcatcaat ataatggtgg tggtttggtt actagattga gatatccagt ttgtggtggt  2220
tctgctggtt ctgctgctgg ttctggtgaa tttggttctg ctgaagctgc tgctaaagaa  2280
gctgctgcta aagctggttc tgctggttct gctgctggtt ctggtgaatt tggttctggt  2340
tctcatccat ggtttttttgg taaaattcca agagctaaag ctgaagaaat gttgtctaaa  2400
caaagacatg atggtgcttt tttgattaga gaatctgaat ctgctccagg tgatttttct  2460
```

-continued

```
ttgtctgtta aatttggtaa tgatgttcaa cattttaaag ttttgagaga tggtgctggt  2520
aaatattttt tgtgggttgt taaatttaat tctttgaatg aattggttga ttatcataga  2580
tctacttctg tttctagaaa tcaacaaatt tttttgagag atattgaaca agttccacaa  2640
caaccaact                                                          2649

SEQ ID NO: 155         moltype = DNA  length = 1995
FEATURE                Location/Qualifiers
source                 1..1995
                       mol_type = other DNA
                       organism = synthetic construct
SEQUENCE: 155
atggctgtta aacatttgat tgttttgaaa tttaaagatg aaattactga agctcaaaaa  60
gaagaatttt ttaaaactta tgttaatttg gttaatatta ttccagctat gaaagatgtt  120
tattggggta aagatgttac tcaaaaaaat aaagaagaag gttatactca tattgttgaa  180
gttacttttg aatctgttga aactattcaa gattatatta ttcatccagc tcatgttggt  240
tttggtgatg tttatagatc tttttgggaa aaattgttga tttttgatta tactccaaga  300
aaaaaattgt ctggtggtgg tggttctggt ggtggtggtt ctggtggtgg tggttctgct  360
gaagcttggt ataatttggg taatgcttat tataaacaag gtgattatca aaaagctatt  420
gaatattatc aaaaagcttt ggaattggat ccaaataatg ctgaagcttg gtataatttg  480
ggtaatgctt attataaaca aggtgattat caaaaagcta ttgaatatta tcaaaaagct  540
ttggaattgg atccaaataa tgctgaagct tggtataatt tgggtaatgc ttattataaa  600
caaggtgatt atcaaaaagc tattgaagat tatcaaaaag ctttggaatt ggatccaaat  660
aatttgcaag ctgaagcttg gaaaaatttg ggtaatgctt attataaaca aggtgattat  720
caaaaagcta ttgaatatta tcaaaaagct ttggaattgg atccaaataa tgcttctgct  780
tggtataatt tgggtaatgc ttattataaa caaggtgatt atcaaaaagc tattgaatat  840
tatcaaaaag ctttggaatt ggatccaaat aatgctaaag cttggtatag aagaggtaat  900
gcttattata aacaaggtga ttatcaaaaa gctattgaag attatcaaaa agctttggaa  960
ttggatccaa ataatagatc tagatctgct ggtggtggtg gttctggtgg tggtggttct  1020
ggtggtggtg gtgcttctgg tcaagataga tctgaagcta ctttgattaa aagatttaaa  1080
ggtgaaggtg ttagatataa agctaaattg attggtattg atgaagtttc tgctgctaga  1140
ggtgataaat tgtgtcaaga ttctatgatg aaattgaaag gtgttgttgc tggtgctaga  1200
tctaaaggtg aacataaaca aaaaattttt ttgactattt cttttggtgg tattaaaatt  1260
tttgatgaaa aaactggtgc tttgcaacat catcatgctg ttcatgaaat ttcttatatt  1320
gctaaagata ttactgatca tagagctttt ggttatgttt gtggtaaaga aggtaatcat  1380
agatttgttg ctattaaaac tgctcaagct gctgaaccag ttattttgga tttgagagat  1440
ttgtttcaat tgatttatga attgaaacaa agagaagaat tggaaaaaaa agctggttct  1500
gctggttctg ctgctggttc tggtgaattt ggttctgctg aagctgctgc taaagaagct  1560
gctgctaaag ctggttctgc tggttctgct gctggttctg gtgaatttgg ttctggttct  1620
catatgggtt ctcaattttg ggttacttct caaaaaactg aagcttctga aagatgtggt  1680
ttgcaaggtt cttatatttt gagagttgaa gctgaaaaat tgactttgtt gactttgggt  1740
gctcaatctc aaattttgga accattgttg ttttggccat atactttgtt gagaagatat  1800
ggtagagata aagttatgtt ttcttttgaa gctggtagaa gatgtccatc tggtccaggt  1860
acttttactt ttcaaacttc tcaaggtaat gatatttttc aagctgttga agctgctatt  1920
caacaacaaa aagctcaagg taaagttggt caagctcaag atattttgag attggaacat  1980
catcatcatc atcat                                                   1995

SEQ ID NO: 156         moltype = DNA  length = 2391
FEATURE                Location/Qualifiers
source                 1..2391
                       mol_type = other DNA
                       organism = synthetic construct
SEQUENCE: 156
atgggtttgt cttctgtttg tacttttttct tttcaaacta attatcatac tttgttgaat  60
ccacataata ataatccaaa aacttctttg ttgtgttata gacatccaaa aactccaatt  120
aaatattctt ataataattt tccatctaaa cattgttcta ctaaatcttt tcatttgcaa  180
aataaatgtt ctgaatcttt gtctattgct aaaaattcta ttagagctgc tactactaat  240
caaactgaac caccagaatc tgataatcat tctgttgcta ctaaaatttt gaattttggt  300
aaagcttgtt ggaaattgca aagaccatat actattattg ctttttacttc ttgtgcttgt  360
ggtttgtttg gtaaagaatt gttgcataat actaatttga tttcttggtc tttgatgttt  420
aaagcttttt ttttttggt tgctattttg tgtattgctt cttttactac tactattaat  480
caaatttatg atttgcatat tgatagaatt aataaaccag atttgccatt ggcttctggt  540
gaaatttctg ttaatactgc ttggattatg tctattattg ttgctttgtt tggtttgatt  600
attactatta aaatgaaagg tggtccattg tatatttttg gttattgttt tggtattttt  660
ggtggtattg tttattctgt tccaccattt agatggaaac aaaatccatc tactgctttt  720
ttgttgaatt ttttggctca tattattact aattttactt tttattatgc ttctagagct  780
gctttgggtt tgccatttga attgagacca tcttttactt ttttgttggc ttttatgaaa  840
tctatgggtt ctgctttggc tttgattaaa gatgcttctg atgttgaagg tgatactaaa  900
tttggtattt ctactttggc ttctaaatat ggttctagaa atttgacttt gttttgttct  960
ggtattgttt tgttgtctta tgttgctgct attttggctg gtattatttg gccacaagct  1020
tttaattcta atgttatgtt gttgtctcat gctattttgg ctttttggtt gattttgcaa  1080
actagagatt ttgctttgac taattatgat ccagaagctg gtagaagatt ttatgaattt  1140
atgtggaaat tgtattatgc tgaatatttg gtttatgttt ttattaaatt gtctggtggt  1200
ggtggttctg gtggtggtgg ttctggtggt ggtggttctg ctgaagcttg gtataatttg  1260
ggtaatgctt attataaaca aggtgattat caaaaagcta ttgaatatta tcaaaaagct  1320
ttggaattgg atccaaataa tgctgaagct tggtataatt tgggtaatgc ttattataaa  1380
caaggtgatt atcaaaaagc tattgaatat tatcaaaaag ctttggaatt ggatccaaat  1440
aatgctgaag cttggtataa tttgggtaat gcttattata aacaaggtga ttatcaaaaa  1500
gctattgaag attatcaaaa agctttggaa ttggatccaa ataatttgca agctgaagct  1560
tggaaaaatt tgggtaatgc ttattataaa caaggtgatt atcaaaaagc tattgaatat  1620
```

-continued

```
tatcaaaaag ctttggaatt ggatccaaat aatgcttctg cttggtataa tttgggtaat  1680
gcttattata aacaaggtga ttatcaaaaa gctattgaat attatcaaaa agctttggaa  1740
ttggatccaa ataatgctaa agcttggtat agaagaggta atgcttatta taaacaaggt  1800
gattatcaaa aagctattga agattatcaa aaagctttgg aattggatcc aaataataga  1860
tctagatctg ctggtggtgg tggttctggt ggtggtggtt ctggtggtgg tggtgcttct  1920
gctgaatatg ttagagcttt gtttgatttt aatggtaatg atgaagaaga tttgccattt  1980
aaaaaaggtg atattttgag aattagagat aaaccagaag aacaatggtg gaatgctgaa  2040
gattctgaag gtaaaagagg tatgattcca gttccatatg ttgaaaaata tggttctgct  2100
ggttctgctg ctggttctgg tgaatttggt tctgctgaag ctgctgctaa agaagctgct  2160
gctaaagctg gttctgctgg ttctgctgct ggttctggtg aatttggttc tttgattaaa  2220
catatgagag ctgaagcttt gtttgatttt actggtaatt ctaaattgga attgaatttt  2280
aaagctggtg atgttatttt tttgttgtct agaattaata aagattggtt ggaaggtact  2340
gttagaggtg ctactggtat ttttccattg tcttttgtta aaattttgaa a           2391

SEQ ID NO: 157          moltype = DNA  length = 8226
FEATURE                 Location/Qualifiers
source                  1..8226
                        mol_type = other DNA
                        organism = synthetic construct
SEQUENCE: 157
atgagcgaag aaagcttatt cgagtcttct ccacagaaga tggagtacga aattacaaac  60
tactcagaaa gacatacaga acttccaggt catttcattg gcctcaatac agtagataaa  120
ctagaggagt ccccgttaag ggactttgtt aagagtcacg gtggtcacac ggtcatatcc  180
aagatcctga tagcaaataa tggtattgcc gccgtgaaag aaattagatc cgtcagaaaa  240
tgggcatacg agacgttcgg cgatgacaga accgtccaat tcgtcgccat ggccacccca  300
gaagatctgg aggccaacgc agaatatatc cgtatggccg atcaatacat tgaagtgcca  360
ggtggtacta ataataacaa ctacgctaac gtagacttga tcgtagacat cgccgaaaga  420
gcagacgtag acgccgtatg ggctggctgg ggtcacgcct ccgagaatcc actattgcct  480
gaaaaattgt cccagtctaa gaggaaagtc atctttattg ggcctccagg taacgccatg  540
aggtctttag gtgataaaat ctcctctacc attgtcgctc aaagtgctaa agtcccatgt  600
attccatggt ctggtaccgg tgttgacacc gttcacgtgg acgagaaaac cggtctggtc  660
tctgtcgacg atgacatcta tcaaaagggt tgttgtacct ctcctgaaga tggtttacaa  720
aaggccaagc gtattggttt tcctgtcatg attaaggcat ccgaaggtgg tggtggtaaa  780
ggtatcagac aagttgaacg tgaagaagat ttcatcgctt tataccacca ggcagccaac  840
gaaattccag gctcccccat tttcatcatg aagttggccg gtagagcgcg tcacttggaa  900
gttcaactgc tagcagatca gtacggtaca aatatttcct tgttcggtag agactgttcc  960
gttcagagac gtcatcaaaa aattatcgaa gaagcaccag ttacaattgc caaggctgaa  1020
acatttcacg agatggaaaa ggctgccgtc agactgggga aactagtcgg ttatgtctct  1080
gccggtaccg tggagtatct atattctcat gatgatggaa aattctactt tttagaattg  1140
aacccaagat tacaagtcga gcatccaaca acggaaatgg tctccggtgt taacttacct  1200
gcagctcaat tacaaatcgc tatgggtatc cctatgcata gaataagtga cattagaact  1260
ttatatggta tgaatcctca ttctgcctca gaaatcgatt tcgaattcaa aactcaagat  1320
gccaccaaga aacaaagaag acctattcca aagggtcatt gtaccgcttg tcgtatcaca  1380
tcagaagatc caaacgatgg attcaagcca tcgggtggta ctttgcatga actaaacttc  1440
cgttcttcct ctaatgtttg gggttacttc tccgtgggta acaatggtaa tattcactcc  1500
ttttcggact ctcagttcgg ccatattttt gcttttggtg aaaatagaca agcttccagg  1560
aaacacatgg ttgttgccct gaaggaattg tccattaggg gtgatttcag aactactgtg  1620
gaatacttga tcaaactttt ggaaactgaa gatttcgagg ataacactat taccaccggt  1680
tggttggacg atttgattac tcataaaatg accgctgaaa agcctgatcc aactcttgcc  1740
gtcatttgcg gtgccgctac aaaggctttc ttagcatctg aagaagcccg ccacaagtat  1800
atcgaatcct tacaaaaggg acaagttcta tctaaagacc tactgcaaac tatgttccct  1860
gtagatttta tccatgaggg taaaagatac aagttcaccg tagctaaatc cggtaatgac  1920
cgttacacat tatttatcaa tggttctaaa tgtgatatca tactgcgtca actatctgat  1980
ggtggtcttt tgattgccat aggcggtaaa tcgcatacca tctattggaa agaagaagtt  2040
gctgctacaa gattatccgt tgactctatg actactttgt tggaagttga aaacgatcca  2100
acccagttgc gtactccatc ccctggtaaa ttggttaaat tcttggtgga aaatggtgaa  2160
cacattatca agggccaacc atatgcagaa attgaagtta tgaaaatgca aatgcctttg  2220
gtttctcaag aaaatggtat cgtccagtta ttaaagcaac ctggttctac cattgttgca  2280
ggtgatatca tggctattat gactcttgac gatccatcca aggtcaagca cgctctacca  2340
tttgaaggta tgctgccaga ttttggttct ccagttatcg aaggaaccaa acctgcctat  2400
aaattcaagt cattagtgtc tactttggaa aacattttga agggttatga caaccaagtt  2460
attatgaacg cttccttgca acaattgata gaggttttga gaaatccaaa actgccttac  2520
tcagaatgga aactacacat ctctgcttta cattcaagat tgcctgctaa gctagatgaa  2580
caaatggaag agttagttgc acgttctttg agacgtggtg ctgttttccc agctagacaa  2640
ttaagtaaat tgattgatat ggccgtgaag aatcctgaat acaaccccga caaattgctg  2700
ggcgccgtcg tggaaccatt ggcggatatt gctcataagt actctaacgg gttagaagcc  2760
catgaacatt ctatatttgt ccatttcttg gaagaatatt acgaagttga aaagttattc  2820
aatggtccaa atgttcgtga ggaaaatatc attctgaaat tgcgtgatga aaaccctaaa  2880
gatctagata aagttgcgct aactgttttg tctcattcga aagtttcagc gaagaataac  2940
ctgatcctag ctatcttgaa acattatcaa ccattgtgca agttatcttc taaagtttct  3000
gccattttct ctactcctct acaacatatt gttgaactag aatctaaggc taccgctaag  3060
gtcgctctac aagcaagaga aattttgatt caaggcgctt taccttcggt caaggaaaga  3120
actgaacaaa ttgaacatat cttaaaatcc tctgttgtga aggttgccta tggctcatcc  3180
aatccaaagc gctctgaacc agatttgaat atcttgaagg acttgatcga ttctaattac  3240
gttgtgttcg atgttttact tcaattccta acccatcaag acccagttgt gactgctgca  3300
gctgctcaag tctatattcg tcgtgcttat cgtgcttaca ccataggaga tattagagtt  3360
cacgaaggtg tcacagttcc aattgttgaa tggaaattcc aactaccttc agctgcgttc  3420
tccacctttc caactgttaa atctaaaatg ggtatgaaca gggctgtttc tgtttcagat  3480
ttgtcatatg ttgcaaacag tcagtcatct ccgttaagag aaggtatttt gatggctgtg  3540
```

-continued

```
gatcatttag atgatgttga tgaaattttg tcacaaagtt tggaagttat tcctcgtcac  3600
caatcttctt ctaacggacc tgctcctgat cgttctggta gctccgcatc gttgagtaat  3660
gttgctaatg tttgtgttgc ttctacagaa ggtttcgaat ctgaagagga aattttggta  3720
aggttgagag aaattttgga tttgaataag caggaattaa tcaatgcttc tatccgtcgt  3780
atcacattta tgttcggttt taaagatggg tcttatccaa agtattatac ttttaacggt  3840
ccaaattata acgaaaatga aacaattcgt cacattgagc cggctttggc cttccaactg  3900
gaattaggaa gattgtccaa cttcaacatt aaaccaattt tcactgataa tagaaacatc  3960
catgtctacg aagctgttag taagacttct ccattggata agagattctt tacaagaggt  4020
attattagaa cgggtcatat ccgtgatgac atttctattc aagaatatct gacttctgaa  4080
gctaacagat tgatgagtga tatattggat aatttagaag tcaccgacac ttcaaattct  4140
gatttgaatc atatcttcat caacttcatt gcggtgtttg atatctctcc agaagatgtc  4200
gaagccgcct tcggtggttt cttagaaaga tttggtaaga gattgttgag attgcgtgtt  4260
tcttctgccg aaattagaat catcatcaaa gatcctcaaa caggtgcccc agtaccattg  4320
cgtgccttga tcaataacgt ttctggttat gttatcaaaa cagaaatgta caccgaagtc  4380
aagaacgcaa aaggtgaatg ggtatttaag tctttgggta aacctggatc catgcattta  4440
agacctattg ctactcctta ccctgttaag gaatggttgc aaccaaaacg ttataaggca  4500
cacttgatgg gtaccacata tgtctatgac ttcccagaat tattccgcca agcatcgtca  4560
tcccaatgga aaaatttctc tgcagatgtt aagttaacag atgatttctt tatttccaac  4620
gagttgattg aagatgaaaa cggcgaatta actgaggtgg aaagagaacc tggtgccaac  4680
gctattggta tggttgcctt taagattact gtaaagactc ctgaatatcc aagaggccgt  4740
caatttgttg ttgttgctaa cgatatcaca ttcaagatcg gttcctttgg tccacaagaa  4800
gacgaattct tcaataaggt tactgaatat gctagaaagc gtggtatccc aagaatttac  4860
ttggctgcaa actcaggtgc cagaattggt atggctgaag agattgttcc actatttcaa  4920
gttgcatgga atgatgctgc caatccggac aagggcttcc aatacttata cttaacaagt  4980
gaaggtatgg aaactttaaa gaaatttgac aaagaaaatt ctgttctcac tgaacgtact  5040
gttataaacg gtgaagaaag atttgtcatc aagacaatta ttggttctga agatgggtta  5100
ggtgtcgaat gtctacgtgg atctggttta attgctggtg caacgtcaag ggcttaccac  5160
gatatcttca ctatcacctt agtcacttgt agatccgtcg gtatcggtgc ttatttggtt  5220
cgtttgggtc aaagagctat tcaggtcgaa ggccagccaa ttattttaac tggtgctcct  5280
gcaatcaaca aaatgctggg tagagaagtt tatacttcta acttacaatt gggtggtact  5340
caaatcatgt ataacaacgg tgtttcacat ttgactgctg ttgacgattt agctggtgta  5400
gagaagattg ttgaatggat gtcttatgtt ccagccaagc gtaatatgcc agttcctatc  5460
ttggaaacta aagacacatg ggatagacca gttgatttca ctccaactaa tgatgaaact  5520
tacgatgtaa gatggatgat tgaaggtcgt gagactgaaa gtggatttga atatggtttg  5580
tttgataaag ggtctttctt tgaaactttg tcaggatggg ccaaaggtgt tgtcgttggt  5640
agagcccgtc ttggtggtat tccactgggt gttattggtg ttgaaacaag aactgtcgag  5700
aacttgattc ctgctgatcc agctaatcca aatagtgctg aaacattaat tcaagaacct  5760
ggtcaagttt ggcatccaaa ctccgccttc aagactgctc aagctatcaa tgactttaac  5820
aacggtgaac aattgccaat gatgattttg gccaactgga gaggtttctc tggtggtcaa  5880
cgtgatatgt tcaacgaagt cttgaagtat ggttcgttta ttgttgacgc attggtggat  5940
tacaaacaac caattattat ctatatccca cctaccggtg aactaagagg tggttcatgg  6000
gttgttgtcg atccaactat caacgctgac caaatggaaa tgtatgccga cgtcaacgct  6060
agagctggtg ttttggaacc acaaggtatg gttggtatca agttccgtag agaaaaattg  6120
ctggacacca tgaacagatt ggatgacaag tacagagaat tgagatctca attatccaac  6180
aagagtttgg ctccagaagt acatcagcaa atatccaagc aattagctga tcgtgagaga  6240
gaactattgc caatttacgg acaaatcagt cttcaatttg ctgatttgca cgataggtct  6300
tcacgtatgg tggccaaggg tgttatttct aaggaactgg aatggaccga ggcacgtcgt  6360
ttcttcttct ggagattgag aagaagattg aacgaagaat atttgattaa aaggttgagc  6420
catcaggtag gcgaagcatc aagattagaa aagatcgcaa gaattagatc gtggtaccct  6480
gcttcagtgg accatgaaga tgataggcaa gtcgcaacat ggattgaaga aaactacaaa  6540
actttggacg ataaactaaa gggtttgaaa ttagagtcat tcgctcaaga cttagctaaa  6600
aagatcagaa gcgaccatga caatgctatt gatggattat ctgaagttat caagatgtta  6660
tctaccgatg ataaagaaaa attgttgaag actttgaaat aaaaattgtc tggtggtggt  6720
ggttctggtg gtggtggttc tggtggtggt ggttctgctg aagcttggta taatttgggt  6780
aatgcttatt ataaacaagg tgattatcaa aaagctattg aatattatca aaaagctttg  6840
gaattggatc caaataatgc tgaagcttgg tataatttgg gtaatgctta ttataaacaa  6900
ggtgattatc aaaaagctat tgaatattat caaaaagctt tggaattgga tccaaataat  6960
gctgaagctt ggtataattt gggtaatgct tattataaac aaggtgatta tcaaaaagct  7020
attgaagatt atcaaaaagc tttggaattg gatccaaata atttgcaagc tgaagcttgg  7080
aaaaatttgg gtaatgctta ttataaacaa ggtgattatc aaaaagctat tgaatattat  7140
caaaaagctt tggaattgga tccaaataat gcttctgctt ggtataattt gggtaatgct  7200
tattataaac aaggtgatta tcaaaaagct attgaatatt atcaaaaagc tttggaattg  7260
gatccaaata atgctaaagc ttggtataga agaggtaatg cttattataa acaaggtgat  7320
tatcaaaaag ctattgaaga ttatcaaaaa gctttggaat tggatccaaa taatagatct  7380
agatctgctg gtggtggtgg ttctggtggt ggtggttctg gtggtggtgg tgcttctggt  7440
tctcatatga gattgggtgc tcaatctatt caaccaactg ctaatttgga tagaactgat  7500
gatttggttt atttgaatgt tatggaattg gttagagctg ttttggaatt gaaaaatgaa  7560
ttggctcaat tgccaccaga aggttatgtt gttgttgtta aaaatgttgg tttgactttg  7620
agaaaattga ttggttctgt tgatgatttg ttgccatctt tgccatcttc ttctagaact  7680
gaaattgaag gtactcaaaa attgttgaat aaagatttgg ctgaattgat taataaaatg  7740
agattggctc aacaaaatgc tgttacttct ttgtctgaag aatgtaaaag acaaatgttg  7800
actgcttctc atactttggc tgttgatgct aaaaatttgt tggatgctgt tgatcaagct  7860
aaagttttgg ctaatttggc tcatccacca gctgaaggtt ctgctggttc tgctgctggt  7920
tctggtgaat ttggttctgc tgaagctgct gctaaagaag ctgctgctaa agctggttct  7980
gctggttctg ctgctggttc tggtgaattt ggttctggtg ctatggctac tccaggttct  8040
gaaaatgttt tgccaagaga accattgatt gctactgctg ttaaattttt gcaaaattct  8100
agagttagac aatctccatt ggctactaga agagcttttt tgaaaaaaaa aggtttgact  8160
gatgaagaaa ttgatatggc ttttcaacaa tctggtactg ctgctgatga accatcttct  8220
ttgtgg                                                              8226
```

```
SEQ ID NO: 158          moltype = DNA  length = 10860
FEATURE                 Location/Qualifiers
source                  1..10860
                        mol_type = other DNA
                        organism = synthetic construct
SEQUENCE: 158
atgggttctg ctggttctgc tgctggttct ggtgaatttg gttctgctgg ttctgctgct  60
ggttctggtg aatttggttc tgctggttct gctgctggtt ctggtgaatt ttcttattat  120
catcatcatc atcatcattt ggaatctact tctttgtata aaaaagctgg ttctggttct  180
gctagaaatg cttatttgag aaaaaaaatt gctagattga aaaaagataa tttgcaattg  240
gaaagagatg aacaaaattt ggaaaaaatt attgctaatt tgagagatga aattgctaga  300
ttggaaaatg aagttgcttc tcatgaacaa ggttctgctg gttctgctgc tggttctggt  360
gaatttgctg aagctgctgc taaagaagct gctgctaaag ctggttctgc tggttctgct  420
gctggttctg gtgaattttc ttattatcat catcatcatc atcatttgga atctacttct  480
ttgtataaaa aagctggttc tggttctaat ttggttgctc aattggaaaa tgaagttgct  540
tctttggaaa atgaaaatga aactttgaaa aaaaaaaatt tgcataaaaa agatttgatt  600
gcttatttgg aaaaagaaat tgctaatttg agaaaaaaaa ttgaagaagg ttctgctggt  660
tctgctgctg gttctggtga atttggttct gctgaagctg ctgctaaaga agctgctgct  720
aaagaagctg ctgctaaaga agctgctgct aaagctggtt ctgctggttc tgctgctggt  780
tctggtgaat ttggttcttc ttattatcat catcatcatc atcatttgga atctacttct  840
ttgtataaaa aagctggttc tggttctcaa aaagttgctg aattgaaaaa tagagttgct  900
gttaaattga atagaaatga acaattgaaa aataaagttg aagaattgaa aaatagaaat  960
gcttatttga aaaatgaatt ggctactttg gaaaatgaag ttgctagatt ggaaaatgat  1020
gttgctgaag gttctgctgg ttctgctgct ggttctggtg aatttgctga agctgctgct  1080
aaagaagctg ctgctaaagc tggttctgct ggttctgctg ctggttctgg tgaattttct  1140
tattatcatc atcatcatca tcatttggaa tctacttctt tgtataaaaa agctggttct  1200
ggttctaatg aagttactac tttggaaaat gatgctgctt ttattgaaaa tgaaaatgct  1260
tatttggaaa aagaaattgc tagattgaga aaagaaaaag ctgctttgag aaatagattg  1320
gctcataaaa aaggttctgc tggttctgct gctggttctg gtgaatttgg ttctgctgaa  1380
gctgctgcta aagaagctgc tgctaaagaa gctgctgcta aagaagctgc tgctaaagct  1440
ggttctgctg gttctgctgc tggttctggt gaatttggtt ctagaccacc aactatttct  1500
aatccaccac cattgatttc ttctgctaaa catccatctg ttggttctgc tggttctgct  1560
gctggttctg gtgaatttgc tgaagctgct gctaaagaag ctgctgctaa agctggttct  1620
gctggttctg ctgctggttc tggtgaattt aattttttgc aatctagacc agaaccaact  1680
gctccaccag aagaatcttt tagatctggt ggttctgctg gttctgctgc tggttctggt  1740
gaatttggtt ctgctgaagc tgctgctaaa gaagctgctg ctaaagaagc tgctgctaaa  1800
gaagctgctg ctaaagctgg ttctgctggt tctgctgctg gttctggtga atttggttct  1860
tctaaaggta ctggtttgaa tccaaatgct aaagtttggc aagaaattgc tccaggtaat  1920
ggttctgctg gttctgctgc tggttctggt gaatttgctg aagctgctgc taaagaagct  1980
gctgctaaag ctggttctgc tggttctgct gctggttctg gtgaatttcc agatggtggt  2040
actacttttg aacatttgtg gtcttctttg gaaccagatt ctacttatgg ttctgctggt  2100
tctgctgctg gttctggtga atttggttct gctgaagctg ctgctaaaga agctgctgct  2160
aaagaagctg ctgctaaaga agctgctgct aaagctggtt ctgctggttc tgctgctggt  2220
tctggtgaat ttggttcttc ttattatcat catcatcatc atcatttgga atctacttct  2280
ttgtataaaa aagctggttc tggttctaaa agaattgctt atttgagaaa aaaaattgct  2340
gctttgaaaa aagataatgc taatttggaa aaagatattg ctaatttgga aaatgaaatt  2400
gaaagattga ttaaagaaat taaaactttg gaaaatgaag ttgcttctca tgaacaaggt  2460
tctgctggtt ctgctgctgg ttctggtgaa tttgctgaag ctgctgctaa agaagctgct  2520
gctaaagctg gttctgctgg ttctgctgct ggttctggtg aattttctta ttatcatcat  2580
catcatcatc atttggaatc tacttctttg tataaaaaag ctggttctgg ttctaatttg  2640
ttggctactt tgagatctac tgctgctgtt ttggaaaatg aaaatcatgt tttggaaaaa  2700
gaaaaagaaa aattgagaaa agaaaaagaa caattgttga ataaattgga agcttataaa  2760
ggttctgctg gttctgctgc tggttctggt gaatttggtt ctgctgaagc tgctgctaaa  2820
gaagctgctg ctaaagaagc tgctgctaaa gaagctgctg ctaaagctgg ttctgctggt  2880
tctgctgctg gttctggtga atttggttct ccagctactt ctcaacatcc accaccacca  2940
ccaggtcata gatctcaagc tccatctcat ggttctgctg gttctgctgc tggttctggt  3000
gaatttgctg aagctgctgc taaagaagct gctgctaaag ctggttctgc tggttctgct  3060
gctggttctg gtgaatttga attgaattct ttgttgattt tgttggaagc tgctgaatat  3120
ttggaaagaa gagatagagg ttctgctggt tctgctgctg gttctggtga atttggttct  3180
gctgaagctg ctgctaaaga agctgctgct aaagaagctg ctgctaaaga agctgctgct  3240
aaagctggtt ctgctggttc tgctgctggt tctggtgaat ttggttctag accaccaact  3300
atttctaatc caccaccatt gatttcttct gctaaacatc catctgttgg ttctgctggt  3360
tctgctgctg gttctggtga atttgctgaa gctgctgcta aagaagctgc tgctaaagct  3420
ggttctgctg gttctgctgc tggttctggt gaatttaatt ttttgcaatc tagaccagaa  3480
ccaactgctc caccagaaga atcttttaga tctggtggtt ctgctggttc tgctgctggt  3540
tctggtgaat ttggttctgc tgaagctgct gctaaagaag ctgctgctaa agaagctgct  3600
gctaaagaag ctgctgctaa agctggttct gctggttctg ctgctggttc tggtgaattt  3660
ggttcttcta aaggtactgg tttgaatcca aatgctaaag tttggcaaga aattgctcca  3720
ggtaatggtt ctgctggttc tgctgctggt tctggtgaat ttgctgaagc tgctgctaaa  3780
gaagctgctg ctaaagctgg ttctgctggt tctgctgctg gttctggtga atttccagat  3840
ggtggtacta cttttgaaca tttgtggtct tctttggaac cagattctac ttatggttct  3900
gctggttctg ctgctggttc tggtgaattt ggttctgctg aagctgctgc taaagaagct  3960
gctgctaaag aagctgctgc taaagaagct gctgctaaag ctggttctgc tggttctgct  4020
gctggttctg gtgaatttgg ttcttcttat tatcatcatc atcatcatca tttggaatct  4080
acttctttgt ataaaaaagc tggttctggt tctaaaagaa ttgcttattt gagaaaaaaa  4140
attgctgctt tgaaaaaaga taatgctaat ttggaaaaag atattgctaa tttggaaaat  4200
gaaattgaaa gattgattaa agaaattaaa actttggaaa atgaagttgc ttctcatgaa  4260
caaggttctg ctggttctgc tgctggttct ggtgaatttg ctgaagctgc tgctaaagaa  4320
```

```
gctgctgcta aagctggttc tgctggttct gctgctggtt ctggtgaatt ttcttattat  4380
catcatcatc atcatcattt ggaatctact tctttgtata aaaaagctgg ttctggttct  4440
aatttgttgg ctactttgag atctactgct gctgttttgg aaaatgaaaa tcatgttttg  4500
gaaaaagaaa aagaaaaatt gagaaaagaa aaagaacaat tgttgaataa attggaagct  4560
tataaaggtt ctgctggttc tgctgctggt tctggtgaat ttggttctgc tgaagctgct  4620
gctaaagaag ctgctgctaa agaagctgct gctaaagaag ctgctgctaa agctggttct  4680
gctggttctg ctgctggttc tggtgaattt ggttctgctt tggttgatga tgctgctgat  4740
tatgaaccac caccatctaa taatgaagaa gctttgggtt ctgctggttc tgctgctggt  4800
tctggtgaat ttgctgaagc tgctgctaaa gaagctgctg ctaaagctgg ttctgctggt  4860
tctgctgctg gttctggtga atttagagaa ttgtttgatg atccatctta tgttaatgtt  4920
caaaatttgg ataaagctag acaaggttct gctggttctg ctgctggttc tggtgaattt  4980
ggttctgctg aagctgctgc taaagaagct gctgctaaag aagctgctgc taaagaagct  5040
gctgctaaag ctggttctgc tggttctgct gctggttctg gtgaatttgg ttctaaaaat  5100
actaaatcta tgaattttga taatccagtt tatagaaaaa ctactgaaga agaaggttct  5160
gctggttctg ctgctggttc tggtgaattt gctgaagctg ctgctaaaga agctgctgct  5220
aaagctggtt ctgctggttc tgctgctggt tctggtgaat ttagatcttt gccatctact  5280
tggattgaaa ataaattgta tggtatgtct gatccaaatt ggggttctgc tggttctgct  5340
gctggttctg gtgaatttgg ttctgctgaa gctgctgcta aagaagctgc tgctaaagaa  5400
gctgctgcta aagaagctgc tgctaaagct ggttctgctg gttctgctgc tggttctggt  5460
gaatttggtt ctgttgttga taattctcca ccaccagctt tgccaccaaa aaaaagacaa  5520
tctgctccat ctggttctgc tggttctgct gctggttctg gtgaatttgc tgaagctgct  5580
gctaaagaag ctgctgctaa agctggttct gctggttctg ctgctggttc tggtgaattt  5640
actcaaagat ctaaaccaca accagctgtt ccaccaagac catctgctga tttgattttg  5700
ggttctgctg gttctgctgc tggttctggt gaatttggtt ctgctgaagc tgctgctaaa  5760
gaagctgctg ctaaagaagc tgctgctaaa gaagctgctg ctaaagctgg ttctgctggt  5820
tctgctgctg gttctggtga atttggttct actgatgaag aaagagaaga aactgaagaa  5880
gaagtttatt tgttgaattc tactactttg ggttctgctg gttctgctgc tggttctggt  5940
gaatttgctg aagctgctgc taaagaagct gctgctaaag ctggttctgc tggttctgct  6000
gctggttctg gtgaatttga tggtaatgtt tctggtactc aaagattgga ttctgctact  6060
gttagaactt attcttgtgg ttctgctggt tctgctgctg gttctggtga atttggttct  6120
gctgaagctg ctgctaaaga agctgctgct aaagaagctg ctgctaaaga agctgctgct  6180
aaagctggtt ctgctggttc tgctgctggt tctggtgaat ttggttcttc ttattatcat  6240
catcatcatc atcatttgga atctacttct ttgtataaaa aagctggttc tggttctcaa  6300
aaagttgctc aattgaaaaa tagagttgct tataaattga aagaaaatgc taaattggaa  6360
aatattgttg ctagattgga aaatgataat gctaatttgg aaaaagatat tgctaatttg  6420
gaaaaagata ttgctaattt ggaaagagat gttgctagag gttctgctgg ttctgctgct  6480
ggttctggtg aatttgctga agctgctgct aaagaagctg ctgctaaagc tggttctgct  6540
ggttctgctg ctggttctgg tgaattttct tattatcatc atcatcatca tcatttggaa  6600
tctacttctt tgtataaaaa agctggttct ggttctaata ctgttaaaga attgaaaaat  6660
tatattcaag aattggaaga aagaaatgct gaattgaaaa atttgaaaga acatttgaaa  6720
tttgctaaag ctgaattgga atttgaattg gctgctcata aatttgaagg ttctgctggt  6780
tctgctgctg gttctggtga atttggttct gctgaagctg ctgctaaaga agctgctgct  6840
aaagaagctg ctgctaaaga agctgctgct aaagctggtt ctgctggttc tgctgctggt  6900
tctggtgaat ttggttctca tgatgattct ttgccacatc cacaacaagc tactgatgat  6960
tctggtcatg aatctgatgg ttctgctggt tctgctgctg gttctggtga atttgctgaa  7020
gctgctgcta aagaagctgc tgctaaagct ggttctgctg gttctgctgc tggttctggt  7080
gaatttggtt ctccaaatgc tggttctgtt gaacaaactc caaaaaaacc aggtttgaga  7140
agaagaggtt ctgctggttc tgctgctggt tctggtgaat ttggttctgc tgaagctgct  7200
gctaaagaag ctgctgctaa agaagctgct gctaaagaag ctgctgctaa agctggttct  7260
gctggttctg ctgctggttc tggtgaattt ggttcttctt attatcatca tcatcatcat  7320
catttggaat ctacttcttt gtataaaaaa gctggttctg gttcttttga aaatgttact  7380
catgaattta ttttggctac tttggaaaat gaaaatgcta aattgagaag attggaagct  7440
aaattggaaa gagaattggc tagattgaga aatgaagttg cttggttggg ttctgctggt  7500
tctgctgctg gttctggtga atttgctgaa gctgctgcta aagaagctgc tgctaaagct  7560
ggttctgctg gttctgctgc tggttctggt gaattttctt attatcatca tcatcatcat  7620
catttggaat ctacttcttt gtataaaaaa gctggttctg gttctcaaaa agttgaagaa  7680
ttgaaaaata aaattgctga attggaaaat agaaatgctg ttaaaaaaaa tagagttgct  7740
catttgaaac aagaaattgc ttatttgaaa gatgaattgg ctgctcatga atttgaaggt  7800
tctgctggtt ctgctgctgg ttctggtgaa tttggttctg ctgaagctgc tgctaaagaa  7860
gctgctgcta aagaagctgc tgctaaagaa gctgctgcta aagctggttc tgctggttct  7920
gctgctggtt ctggtgaatt tggttctgtt tcttctacta aattggtttc ttttcatgat  7980
gattctgatg aagatttgtt gcatattggt tctgctggtt ctgctgctgg ttctggtgaa  8040
tttgctgaag ctgctgctaa agaagctgct gctaaagctg gttctgctgg ttctgctgct  8100
ggttctggtg aatttgctgc tgctactcca atttctactt ttcatgatga ttctgatgaa  8160
gatttgttgc atgttggttc tgctggttct gctgctggtt ctggtgaatt tggttctgct  8220
gaagctgctg ctaaagaagc tgctgctaaa gaagctgctg ctaaagaagc tgctgctaaa  8280
gctggttctg ctggttctgc tgctggttct ggtgaatttg gttcttctta ttatcatcat  8340
catcatcatc atttggaatc tacttctttg tataaaaaag ctggttctgg ttctcaaaaa  8400
gttgaatctt tgaaacaaaa aattgaagaa ttgaaacaaa gaaaagctca attgaaaaat  8460
gatattgcta atttggaaaa agaaattgct tatgctgaaa ctggttctgc tggttctgct  8520
gctggttctg gtgaatttgc tgaagctgct gctaaagaag ctgctgctaa agctggttct  8580
gctggttctg ctgctggttc tggtgaattt tcttattatc atcatcatca tcatcatttg  8640
gaatctactt ctttgtataa aaaagctggt tctgaatttt ttagaagaga aagaaataaa  8700
atggctgctg ctaaatgtag aaatagaaga agagaattga ctgatacttt gcaagctgaa  8760
actgatcaat tggaagatga aaaatctgct ttgcaaactg aaattgctaa tttgttgaaa  8820
gaaaaagaaa aattggaatt tattttggct gctcatagac cagcttgtaa aattccagat  8880
gatttgggtt ttccagaaga aatgtctttg gaaggttctg ctggttctgc tgctggttct  8940
ggtgaatttg gttctgctga agctgctgct aaagaagctg ctgctaaaga agctgctgct  9000
aaagaagctg ctgctaaagc tggttctgct ggttctgctg ctggttctgg tgaatttggt  9060
```

```
tcttttcaaa tgccagctga tactccacca ccagcttatt tgccaccaga agatccaatg  9120
actggttctg ctggttctgc tgctggttct ggtgaatttg ctgaagctgc tgctaaagaa  9180
gctgctgcta aagctggttc tgctggttct gctgctggtt ctggtgaatt tgaaagagaa  9240
tctaatgaag aaccaccacc accatatgaa gatccatatt ggggtaatgg tggttctgct  9300
ggttctgctg ctggttctgg tgaatttggt tctgctgaag ctgctgctaa agaagctgct  9360
gctaaagaag ctgctgctaa agaagctgct gctaaagctg gttctgctgg ttctgctgct  9420
ggttctggtg aatttggttc ttcttattat catcatcatc atcatcattt ggaatctact  9480
tctttgtata aaaaagctgg ttctggttct caaaaagttg ctgaattgaa aaatagagtt  9540
gctgttaaat tgaatagaaa tgaacaattg aaaaataaag ttgaagaatt gaaaaataga  9600
aatgcttatt tgaaaaatga attggctact ttggaaaatg aagttgctag attggaaaat  9660
gatgttgctg aaggttctgc tggttctgct gctggttctg gtgaatttgc tgaagctgct  9720
gctaaagaag ctgctgctaa agctggttct gctggttctg ctgctggttc tggtgaattt  9780
tcttattatc atcatcatca tcatcatttg gaatctactt ctttgtataa aaaagctggt  9840
tctggttcta atgaagttac tactttggaa aatgatgctg cttttattga aaatgaaaat  9900
gcttatttgg aaaaagaaat tgctagattg agaaaaagaaa aagctgcttt gagaaataga  9960
ttggctcata aaaaatctta ttatcatcat catcatcatc atttggaatc tacttctttg  10020
tataaaaaag ctggttctgg ttctgctaga aatgcttatt tgagaaaaaa aattgctaga  10080
ttgaaaaaag ataatttgca attggaaaga gatgaacaaa atttggaaaa aattattgct  10140
aatttgagag atgaaattgc tagattggaa aatgaagttg cttctcatga acaaggttct  10200
gctggttctg ctgctggttc tggtgaattt gctgaagctg ctgctaaaga agctgctgct  10260
aaagctggtt ctgctggttc tgctgctggt tctggtgaat ttcttattta tcatcatcat  10320
catcatcatt tggaatctac ttctttgtat aaaaaagctg gttctggttc taatttggtt  10380
gctcaattgg aaaatgaagt tgcttctttg gaaaatgaaa atgaaacttt gaaaaaaaaa  10440
aatttgcata aaaaagattt gattgcttat ttggaaaaag aaattgctaa tttgagaaaa  10500
aaaattgaag aaggttctgc tggttctgct gctggttctg gtgaatttgg ttctgctgaa  10560
gctgctgcta aagaagctgc tgctaaagaa gctgctgcta aagaagctgc tgctaaagct  10620
ggttctgctg gttctgctgc tggttctggt gaatttggtt ctgaacaaaa attgatttct  10680
gaagaagatt tggaacaaaa attgatttct gaagaagatt tggaacaaaa attgatttct  10740
gaagaagatt tgggttctgc tggttctgct gctggttctg gtgaatttgg ttctgctggt  10800
tctgctgctg gttctggtga atttggttct gctggttctg ctgctggttc tggtgaattt  10860

SEQ ID NO: 159         moltype = DNA  length = 1356
FEATURE                Location/Qualifiers
source                 1..1356
                       mol_type = other DNA
                       organism = synthetic construct
SEQUENCE: 159
atgggttctg ctggttctgc tgctggttct ggtgaatttg gttctgctgg ttctgctgct  60
ggttctggtg aatttggttc tgctggttct gctgctggtt ctggtgaatt ttcttattat  120
catcatcatc atcatcattt ggaatctact tctttgtata aaaaagctgg ttctggttct  180
gctagaaatg cttatttgag aaaaaaaatt gctagattga aaaaagataa tttgcaattg  240
gaaagagatg aacaaaattt ggaaaaaatt attgctaatt tgagagatga aattgctaga  300
ttggaaaatg aagttgcttc tcatgaacaa ggttctgctg gttctgctgc tggttctggt  360
gaatttgctg aagctgctgc taaagaagct gctgctaaag ctggttctgc tggttctgct  420
gctggttctg gtgaattttc ttattatcat catcatcatc atcatttgga atctacttct  480
ttgtataaaa aagctggttc tggttctaat ttggttgctc aattggaaaa tgaagttgct  540
tctttggaaa atgaaaatga aactttgaaa aaaaaaaatt tgcataaaaa agatttgatt  600
gcttatttgg aaaaagaaat tgctaatttg agaaaaaaaa ttgaagaagg ttctgctggt  660
tctgctgctg gttctggtga atttggttct gctgaagctg ctgctaaaga agctgctgct  720
aaagaagctg ctgctaaaga agctgctgct aaagctggtt ctgctggttc tgctgctggt  780
tctggtgaat ttggttcttc tgctactaga gaattggatg aattgatggc ttctttgtct  840
gattttaaaa ttcaaggtgg ttctgctggt tctgctgctg gttctggtga atttgctgaa  900
gctgctgcta aagaagctgc tgctaaagct ggttctgctg gttctgctgc tggttctggt  960
gaatttgatt tggctttgtc tgaaaattgg gctcaagaat ttttggctgc tggtgatgct  1020
gttgatggtt ctgctggttc tgctgctggt tctggtgaat ttggttctgc tgaagctgct  1080
gctaaagaag ctgctgctaa agaagctgct gctaaagaag ctgctgctaa agctggttct  1140
gctggttctg ctgctggttc tggtgaattt ggttctgatt ataaagatga tgatgataaa  1200
gattataaag atgatgatga taaagattat aaagatgatg atgataaagg ttctgctggt  1260
tctgctgctg gttctggtga atttggttct gctggttctg ctgctggttc tggtgaattt  1320
ggttctgctg gttctgctgc tggttctggt gaattt                            1356

SEQ ID NO: 160         moltype = AA  length = 1532
FEATURE                Location/Qualifiers
source                 1..1532
                       mol_type = protein
                       organism = synthetic construct
SEQUENCE: 160
MSAKAISEQT GKELLYKFIC TTSAIQNRFK YARVTPDTDW ARLLQDHPWL LSQNLVVKPD  60
QLIKRRGKLG LVGVNLTLDG VKSWLKPRLG QEATVGKATG FLKNFLIEPF VPHSQAEEFY  120
VCIYATREGD YVLFHHEGGV DVGDVDAKAQ KLLVGVDEKL NPEDIKKHLL VHAPEDKKEI  180
LASFISGLFN FYEDLYFTYL EINPLVVTKD GVYVLDLAAK VDATADYICK VKWGDIEFPP  240
PFGREAYPEE AYIADLDAKS GASLKLTLLN PKGRIWTMVA GGGASVVYSD TICDLGGVNE  300
LANYGEYSGA PSEQQTYDYA KTILSLMTRE KHPDGKILII GGSIANFTNV AATFKGIVRA  360
IRDYQGPLKE HEVTIFVRRG GPNYQEGLRV MGEVGKTTGI PIHVFGTETH MTAIVGMALG  420
HRPIPNQPPT AAHTANFLLN ASGSTSTPAP SRTASFSESR ADEVAPAKKA KPAMPQDSVP  480
SPRSLQGKST TLFSRHTKAI VWGMQTRAVQ GMLDFDYVCS RDEPSVAAMV YPFTGDHKQK  540
FYWGHKEILI PVFKNMADAM RKHPEVDVLI NFASLRSAYD STMETMNYAQ IRTIAIIAEG  600
IPEALTRKLI KKADQKGVTI IGPATVGGIK PGCFKIGNTG GMLDNILASK LYRPGSVAYV  660
SRSGGMSNEL NNIISRTTDG VYEGVAIGGD RYPGSTFMDH VLRYQDTPGV KMIVVLGEIG  720
```

-continued

```
GTEEYKICRG IKEGRLTKPI VCWCIGTCAT MFSSEVQFGH AGACANQASE TAVAKNQALK  780
EAGVFVPRSF DELGEIIQSV YEDLVANGVI VPAQEVPPPT VPMDYSWARE LGLIRKPASF  840
MTSICDERGQ ELIYAGMPIT EVFKEEMGIG GVLGLLWFQK RLPKYSCQFI EMCLMVTADH  900
GPAVSGAHNT IICARAGKDL VSSLTSGLLT IGDRFGGALD AAAKMFSKAF DSGIIPMEFV  960
NKMKKEGKLI MGIGHRVKSI NNPDMRVQIL KDYVRQHFPA TPLLDYALEV EKITTSKKPN  1020
LILNVDGLIG VAFVDMLRNC GSFTREEADE YIDIGALNGI FVLGRSMGFI GHYLDQKRLK  1080
QGLYRHPWDD ISYVLPEHMS MKLSGGGGSG GGGSGGGGSA EAWYNLGNAY YKQGDYQKAI  1140
EYYQKALELD PNNAEAWYNL GNAYYKQGDY QKAIEYYQKA LELDPNNAEA WYNLGNAYYK  1200
QGDYQKAIED YQKALELDPN NLQAEAWKNL GNAYYKQGDY QKAIEYYQKA LELDPNNASA  1260
WYNLGNAYYK QGDYQKAIEY YQKALELDPN NAKAWYRRGN AYYKQGDYQK AIEDYQKALE  1320
LDPNNRSRSA GGGGSGGGGS GGGGASSYYH HHHHHLESTS LYKKAGSGSN LVAQLENEVA  1380
SLENENETLK KKNLHKKDLI AYLEKEIANL RKKIEEGSAG SAAGSGEFGS AEAAAKEAAA  1440
KAGSAGSAAG SGEFGSSYYH HHHHHLESTS LYKKAGSGSA RNAYLRKKIA RLKKDNLQLE  1500
RDEQNLEKII ANLRDEIARL ENEVASHEQG SG                              1532

SEQ ID NO: 161         moltype = AA  length = 824
FEATURE                Location/Qualifiers
source                 1..824
                       mol_type = protein
                       organism = synthetic construct
SEQUENCE: 161
MKNCVIVSAV RTAIGSFNGS LASTSAIDLG ATVIKAAIER AKIDSQHVDE VIMGNVLQAG  60
LGQNPARQAL LKSGLAETVC GFTVNKVCGS GLKSVALAAQ AIQAGQAQSI VAGGMENMSL  120
APYLLDAKAR SGYRLGDGQV YDVILRDGLM CATHGYHMGI TAENVAKEYG ITREMQDELA  180
LHSQRKAAAA IESGAFTAEI VPVNVVTRKK TFVFSQDEFP KANSTAEALG ALRPAFDKAG  240
TVTAGNASGI NDGAAALVIM EESAALAAGL TPLARIKSYA SGGVPPALMG MGPVPATQKA  300
LQLAGLQLAD IDLIEANEAF AAQFLAVGKN LGFDSEKVNV NGGAIALGHP IGASGARILV  360
TLLHAMQARD KTLGLATLCI GGGQGIAMVI ERLNKLSGGG GSGGGGSGGG GSAEAWYNLG  420
NAYYKQGDYQ KAIEYYQKAL ELDPNNAEAW YNLGNAYYKQ GDYQKAIEYY QKALELDPNN  480
AEAWYNLGNA YYKQGDYQKA IEDYQKALEL DPNNLQAEAW KNLGNAYYKQ GDYQKAIEYY  540
QKALELDPNN ASAWYNLGNA YYKQGDYQKA IEYYQKALEL DPNNAKAWYR RGNAYYKQGD  600
YQKAIEDYQK ALELDPNNRS RSAGGGGSGG GGSGGGGASS YYHHHHHHLE STSLYKKAGS  660
GSNEVTTLEN DAAFIENENA YLEKEIARLR KEKAALRNRL AHKKGSAGSA AGSGEFGSAE  720
AAAKEAAAKA GSAGSAAGSG EFGSSYYHHH HHHLESTSLY KKAGSGSQKV AELKNRVAVK  780
LNRNEQLKNK VEELKNRNAY LKNELATLEN EVARLENDVA EGSG                  824

SEQ ID NO: 162         moltype = AA  length = 779
FEATURE                Location/Qualifiers
source                 1..779
                       mol_type = protein
                       organism = synthetic construct
SEQUENCE: 162
MKKVCVIGAG TMGSGIAQAF AAKGFEVVLR DIKDEFVDRG LDFINKNLSK LVKKGKIEEA  60
TKVEILTRIS GTVDLNMAAD CDLVIEAAVE RMDIKKQIFA DLDNICKPET ILASNTSSLS  120
ITEVASATKR PDKVIGMHFF NPAPVMKLVE VIRGIATSQE TFDAVKETSI AIGKDPVEVA  180
EAPGFVVNRI LIPMINEAVG ILAEGIASVE DIDKAMKLGA NHPMGPLELG DFIGLDICLA  240
IMDVLYSETG DSKYRPHTLL KKYVRAGWLG RKSGKGFYDY SKKLSGGGGS GGGGSGGGGS  300
AEAWYNLGNA YYKQGDYQKA IEYYQKALEL DPNNAEAWYN LGNAYYKQGD YQKAIEYYQK  360
ALELDPNNAE AWYNLGNAYY KQGDYQKAIE DYQKALELDP NNLQAEAWKN LGNAYYKQGD  420
YQKAIEYYQK ALELDPNNAS AWYNLGNAYY KQGDYQKAIE YYQKALELDP NNAKAWYRRG  480
NAYYKQGDYQ KAIEDYQKAL ELDPNNRSRS AGGGGSGGGG SGGGGASENL YFQGENLYFQ  540
GDSSESCWNC GRKASETCSG CNTARYCGSF CQHKDWEKHH HICGQTLQAQ QGSAGSAAGS  600
GEFGSAEAAA KEAAAKAGSA GSAAGSGEFG SMAVSESQLK KMVSKYKYRD LTVRETVNVI  660
TLYKDLKPVL DSYVFNDGSS RELMNLTGTI PVPYRGNTYN IPICLWLLDT YPYNPPICFV  720
KPTSSMTIKT GKHVDANGKI YLPYLHEWKH PQSDLLGLIQ VMIVVFGDEP PVFSRPGSG   779

SEQ ID NO: 163         moltype = AA  length = 744
FEATURE                Location/Qualifiers
source                 1..744
                       mol_type = protein
                       organism = synthetic construct
SEQUENCE: 163
MELNNVILEK EGKVAVVTIN RPKALNALNS DTLKEMDYVI GEIENDSEVL AVILTGAGEK  60
SFVAGADISE MKEMNTIEGR KFGILGNKVF RRLELLEKPV IAAVNGFALG GGCEIAMSCD  120
IRIASSNARF GQPEVGLGIT PGFGGTQRLS RLVGMGMAKQ LIFTAQNIKA DEALRIGLVN  180
KVVEPSELMN TAKEIANKIV SNAPVAVKLS KQAINRGMQC DIDTALAFES EAFGECFSTE  240
DQKDAMTAFI EKRKIEGFKN RKLSGGGGSG GGGSGGGGSA EAWYNLGNAY YKQGDYQKAI  300
EYYQKALELD PNNAEAWYNL GNAYYKQGDY QKAIEYYQKA LELDPNNAEA WYNLGNAYYK  360
QGDYQKAIED YQKALELDPN NLQAEAWKNL GNAYYKQGDY QKAIEYYQKA LELDPNNASA  420
WYNLGNAYYK QGDYQKAIEY YQKALELDPN NAKAWYRRGN AYYKQGDYQK AIEDYQKALE  480
LDPNNRSRSA GGGGSGGGGS GGGGASGPLG SPLTASMLAS APPQEQKQML GERLFPLIQA  540
MHPTLAGKIT GMLLEIDNSE LLHMLESPES LRSKVDEAVA VLQAHQAKEA AQKAGSAGSA  600
AGSGEFGSAE AAAKEAAAKA GSAGSAAGSG EFGSNTNMSV PTDGAVTTSQ IPASEQETLV  660
RPKPLLLKLL KSVGAQKDTY TMKEVLFYLG QYIMTKRLYD EKQQHIVYCS NDLLGDLFGV  720
PSFSVKEHRK IYTMIYRNLV VGSG                                        744

SEQ ID NO: 164         moltype = AA  length = 823
FEATURE                Location/Qualifiers
source                 1..823
```

```
                        mol_type = protein
                        organism = synthetic construct
SEQUENCE: 164
MIVKPMVRNN ICLNAHPQGC KKGVEDQIEY TKKRITAEVK AGAKAPKNVL VLGCSNGYGL  60
ASRITAAFGY GAATIGVSFE KAGSETKYGT PGWYNNLAFD EAAKREGLYS VTIDGDAFSD  120
EIKAQVIEEA KKKGIKFDLI VYSLASPVRT DPDTGIMHKS VLKPFGKTFT GKTVDPFTGE  180
LKEISAEPAN DEEAAATVKV MGGEDWERWI KQLSKEGLLE EGCITLAYSY IGPEATQALY  240
RKGTIGKAKE HLEATAHRLN KENPSIRAFV SVNKGLVTRA SAVIPVIPLY LASLFKVMKE  300
KGNHEGCIEQ ITRLYAERLY RKDGTIPVDE ENRIRIDDWE LEEDVQKAVS ALMEKVTGEN  360
AESLTDLAGY RHDFLASNGF DVEGINYEAE VERFDRIKLS GGGGSGGGGS GGGGSAEAWY  420
NLGNAYYKQG DYQKAIEYYQ KALELDPNNA EAWYNLGNAY YKQGDYQKAI EYYQKALELD  480
PNNAEAWYNL GNAYYKQGDY QKAIEDYQKA LELDPNNLQA EAWKNLGNAY YKQGDYQKAI  540
EYYQKALELD PNNASAWYNL GNAYYKQGDY QKAIEYYQKA LELDPNNAKA WYRRGNAYYK  600
QGDYQKAIED YQKALELDPN NRSRSAGGGG SGGGGSGGGG ASSYYHHHHH HLESTSLYKK  660
AGSGSNLLAT LRSTAAVLEN ENHVLEKEKE KLRKEKEQLL NKLEAYKGSA GSAAGSGEFG  720
SAEAAAKEAA AKAGSAGSAA GSGEFGSSYY HHHHHHLEST SLYKKAGSGS KRIAYLRKKI  780
AALKKDNANL EKDIANLENE IERLIKEIKT LENEVASHEQ GSG                   823

SEQ ID NO: 165          moltype = AA  length = 829
FEATURE                 Location/Qualifiers
source                  1..829
                        mol_type = protein
                        organism = synthetic construct
SEQUENCE: 165
MTREVVVVSG VRTAIGTFGG SLKDVAPAEL GALVVREALA RAQVSGDDVG HVVFGNVIQT  60
EPRDMYLGRV AAVNGGVTIN APALTVNRLC GSGLQAIVSA AQTILLGDTD VAIGGGAESM  120
SRAPYLAPAA RWGARMGDAG LVDMMLGALH DPFHRIHMGV TAENVAKEYD ISRAQQDEAA  180
LESHRRASAA IKAGYFKDQI VPVVSKGRKG DVTFDTDEHV RHDATIDDMT KLRPVFVKEN  240
GTVTAGNASG LNDAAAAVVM MERAEAERRG LKPLARLVSY GHAGVDPKAM GIGPVPATKI  300
ALERAGLQVS DLDVIEANEA FAAQACAVTK ALGLDPAKVN PNGSGISLGH PIGATGALIT  360
VKALHELNRV QGRYALVTMC IGGGQGIAAI FERIKLSGGG GSGGGGSGGG GSAEAWYNLG  420
NAYYKQGDYQ KAIEYYQKAL ELDPNNAEAW YNLGNAYYKQ GDYQKAIEYY QKALELDPNN  480
AEAWYNLGNA YYKQGDYQKA IEDYQKALEL DPNNLQAEAW KNLGNAYYKQ GDYQKAIEYY  540
QKALELDPNN ASAWYNLGNA YYKQGDYQKA IEYYQKALEL DPNNAKAWYR RGNAYYKQGD  600
YQKAIEDYQK ALELDPNNRS RSAGGGGSGG GGSGGGGASD VMWEYKWENT GDAELYGPFT  660
SAQMQTWVSE GYFPDGVYCR KLDPPGGQFY NSKRIDFDLY TGSAGSAAGS GEFGSAEAAA  720
KEAAAKAGSA GSAAGSGEFG SESDSVEFNN AISYVNKIKT RFLDHPEIYR SFLEILHTYQ  780
KEQLHTKGRP FRGMSEEEVF TEVANLFRGQ EDLLSEFGQF LPEAKRGSG             829

SEQ ID NO: 166          moltype = AA  length = 852
FEATURE                 Location/Qualifiers
source                  1..852
                        mol_type = protein
                        organism = synthetic construct
SEQUENCE: 166
MKLSTKLCWC GIKGRLRPQK QQQLHNTNLQ MTELKKQKTA EQKTRPQNVG IKGIQIYIPT  60
QCVNQSELEK FDGVSQGKYT IGLGQTNMSF VNDREDIYSM SLTVLSKLIK SYNIDTNKIG  120
RLEVGTETLI DKSKSVKSVL MQLFGENTDV EGIDTLNACY GGTNALFNSL NWIESNAWDG  180
RDAIVVCGDI AIYDKGAARP TGGAGTVAMW IGPDAPIVFD SVRASYMEHA YDFYKPDFTS  240
EYPYVDGHFS LTCYVKALDQ VYKSYSKKAI SKGLVSDPAG SDALNVLKYF DYNVFHVPTC  300
KLVTKSYGRL LYNDFRANPQ LFPEVDAELA TRDYDESLTD KNIEKTFVNV AKPFHKERVA  360
QSLIVPTNTG NMYTASVYAA FASLLNYVGS DDLQGKRVGL FSYGSGLAAS LYSCKIVGDV  420
QHIIKELDIT NKLAKRITET PKDYEAAIEL RENAHLKKNF KPQGSIEHLQ SGVYYLTNID  480
DKFRRSYDVK KLSGGGGSG GGGSGGGGSA EAWYNLGNAY YKQGDYQKAI EYYQKALELD  540
PNNAEAWYNL GNAYYKQGDY QKAIEYYQKA LELDPNNAEA WYNLGNAYYK QGDYQKAIED  600
YQKALELDPN NLQAEAWKNL GNAYYKQGDY QKAIEYYQKA LELDPNNASA WYNLGNAYYK  660
QGDYQKAIEY YQKALELDPN NAKAWYRRGN AYYKQGDYQK AIEDYQKALE LDPNNRSRSA  720
GGGGSGGGGS GGGGASLGPL PPGWEVRSTV SGRIYFVDHN NRTTQFTDPR LHGSAGSAAG  780
SGEFGSAEAA AKEAAAKAGS AGSAAGSGEF GSGAMGPLPP GWEKRTDSNG RVYFVNHNTR  840
ITQWEDPRSG SG                                                     852

SEQ ID NO: 167          moltype = AA  length = 829
FEATURE                 Location/Qualifiers
source                  1..829
                        mol_type = protein
                        organism = synthetic construct
SEQUENCE: 167
MVAVRRKALS ILAEAPVLAS DRLPYKNYDY DRVFGACCEN VIGYMPLPVG VIGPLVIDGT  60
SYHIPMATTE GCLVASAMRG CKAINAGGGA TTVLTKDGMT RGPVVRFPTL KRSGACKIWL  120
DSEEGQNAIK KAFNSTSRFA RLQHIQTCLA GDLLFMRFRT TTGDAMGMNM ISKGVEYSLK  180
QMVEEYGWED MEVVSVSGNY CTDKKPAAIN WIEGRGKSVV AEATIPGDVV RKVLKSDVSA  240
LVELNIAKNL VGSAMAGSVG GFNAHAANLV TAVFLALGQD PAQNVESSNC ITLMKEVDGD  300
LRISVSMPSI EVGTIGGGTV LEPQGAMLDL LGVRGPHATA PGTNARQLAR IVACAVLAGE  360
LSLCAALAAG HLVQSHMTHN RKLSGGGGSG GGGSGGGGSA EAWYNLGNAY YKQGDYQKAI  420
EYYQKALELD PNNAEAWYNL GNAYYKQGDY QKAIEYYQKA LELDPNNAEA WYNLGNAYYK  480
QGDYQKAIED YQKALELDPN NLQAEAWKNL GNAYYKQGDY QKAIEYYQKA LELDPNNASA  540
WYNLGNAYYK QGDYQKAIEY YQKALELDPN NAKAWYRRGN AYYKQGDYQK AIEDYQKALE  600
LDPNNRSRSA GGGGSGGGGS GGGGASSYYH HHHHHLESTS LYKKAGSEFF RRERNKMAAA  660
KCRNRRRELT DTLQAETDQL EDEKSALQTE IANLLKEKEK LEFILAAHRP ACKIPDDLGF  720
```

-continued

```
PEEMSLEGSA GSAAGSGEFG SAEAAAKEAA AKAGSAGSAA GSGEFGSSYY HHHHHHLEST  780
SLYKKAGSGS QKVESLKQKI EELKQRKAQL KNDIANLEKE IAYAETGSG              829

SEQ ID NO: 168          moltype = AA  length = 1049
FEATURE                 Location/Qualifiers
REGION                  1..1049
                        note = chimeric enzyme
source                  1..1049
                        mol_type = protein
                        organism = synthetic construct
SEQUENCE: 168
MSLPFLTSAP GKVIIFGEHS AVYNKPAVAA SVSALRTYLL ISESSAPDTI ELDFPDISFN  60
HKWSINDFNA ITEDQVNSQK LAKAQQATDG LSQELVSLLD PLLAQLSESF HYHAAFCFLY  120
MFVCLCPHAK NIKFSLKSTL PIGAGLGSSA SISVSLALAM AYLGGLIGSN DLEKLSENDK  180
HIVNQWAFIG EKCIHGTPSG IDNAVATYGN ALLFEKDSHN GTINTNNFKF LDDFPAIPMI  240
LTYTRIPRST KDLVARVRVL VTEKFPEVMK PILDAMGECA LQGLEIMTKL SKCKGTDDEA  300
VETNNELYEQ LLELIRINHG LLVSIGVSHP GLELIKNLSD DLRIGSTKLT GAGGGGCSLT  360
LLRRDITQEQ IDSFKKKLQD DFSYETFETD LGGTGCCLLS AKNLNKDLKI KSLVFQLFEN  420
KTTTKQQIDD LLLPGNTNLP WTSKLSGGGG SGGGGSGGGG SAEAWYNLGN AYYKQGDYQK  480
AIEYYQKALE LDPNNAEAWY NLGNAYYKQG DYQKAIEYYQ KALELDPNNA EAWYNLGNAY  540
YKQGDYQKAI EDYQKALELD PNNLQAEAWK NLGNAYYKQG DYQKAIEYYQ KALELDPNNA  600
SAWYNLGNAY YKQGDYQKAI EYYQKALELD PNNAKAWYRR GNAYYKQGDY QKAIEDYQKA  660
LELDPNNRSR SAGGGGSGGG GSGGGGASME PAMEPETLEA RINRATNPLN KELDWASING  720
FCEQLNEDFE GPPLATRLLA HKIQSPQEWE AIQALTVLET CMKSCGKRFH DEVGKFRFLN  780
ELIKVVSPKY LGSRTSEKVK NKILELLYSW TVGLPEEVKI AEAYQMLKKQ GIVKSGSAGS  840
AAGSGEFGSA EAAAKEAAAK AGSAGSAAGS GEFGSGAMGS MAEAEGESLE SWLNKATNPS  900
NRQEDWEYII GFCDQINKEL EGPQIAVRLL AHKIQSPQEW EALQALTVLE ACMKNCGRRF  960
HNEVGKFRFL NELIKVVSPK YLGDRVSEKV KTKVIELLYS WTMALPEEAK IKDAYHMLKR  1020
QGIVQSDPPI PVDRTLIPSP PPRPKNGSG                                    1049

SEQ ID NO: 169          moltype = AA  length = 871
FEATURE                 Location/Qualifiers
source                  1..871
                        mol_type = protein
                        organism = synthetic construct
SEQUENCE: 169
MSELRAFSAP GKALLAGGYL VLDTKYEAFV VGLSARMHAV AHPYGSLQGS DKFEVRVKSK  60
QFKDGEWLYH ISPKSGFIPV SIGGSKNPFI EKVIANVFSY FKPNMDDYCN RNLFVIDIFS  120
DDAYHSQEDS VTEHRGNRRL SFHSHRIEEV PKTGLGSSAG GLVTVLTTAL ASFFVSDLEN  180
NVDKYREVIH NLAQVAHCQA QGKIGSGFDV AAAAYGSIRY RRFPPALISN LPDIGSATYG  240
SKLAHLVDEE DWNITIKSNH LPSGLTLWMG DIKNGSETVK LVQKVKNWYD SHMPESLKIY  300
TELDHANSRF MDGLSKLDRL HETHDDYSDQ IFESLERNDC TCQKYPEITE VRDAVATIRR  360
SFRKITKESG ADIEPPVQTS LLDDCQTLKG VLTCLIPGAG GYDAIAVITK QDVDLRAQTA  420
NDKRFSKVQW LDVTQADWGV RKEKDPETYL DKKLSGGGGS GGGGSGGGGS AEAWYNLGNA  480
YYKQGDYQKA IEYYQKALEL DPNNAEAWYN LGNAYYKQGD YQKAIEYYQK ALELDPNNAE  540
AWYNLGNAYY KQGDYQKAIE DYQKALELDP NNLQAEAWKN LGNAYYKQGD YQKAIEYYQK  600
ALELDPNNAS AWYNLGNAYY KQGDYQKAIE YYQKALELDP NNAKAWYRRG NAYYKQGDYQ  660
KAIEDYQKAL ELDPNNRSRS AGGGGSGGGG SGGGGASSYY HHHHHHLEST SLYKKAGSGS  720
QKVEELKNKI AELENRNAVK KNRVAHLKQE IAYLKDELAA HEFEGSAGSA AGSGEFGSAE  780
AAAKEAAAKA GSAGSAAGSG EFGSSYYHHH HHHLESTSLY KKAGSGSFEN VTHEFILATL  840
ENENAKLRRL EAKLERELAR LRNEVAWLGS G                                 871

SEQ ID NO: 170          moltype = AA  length = 1011
FEATURE                 Location/Qualifiers
source                  1..1011
                        mol_type = protein
                        organism = synthetic construct
SEQUENCE: 170
MTVYTASVTA PVNIATLKYW GKRDTKLNLP TNSSISVTLS QDDLRTLTSA ATAPEFERDT  60
LWLNGEPHSI DNERTQNCLR DLRQLRKEME SKDASLPTLS QWKLHIVSEN NFPTAAGLAS  120
SAAGFAALVS AIAKLYQLPQ STSEISRIAR KGSGSACRSL FGGYVAWEMG KAEDGHDSMA  180
VQIADSSDWP QMKACVLVVS DIKKDVSSTQ GMQLTVATSE LFKERIEHVV PKRFEVMRKA  240
IVEKDFATFA KETMMDSNSF HATCLDSFPP IFYMNDTSKR IISWCHTINQ FYGETIVAYT  300
FDAGPNAVLY YLAENESKLF AFIYKLFGSV PGWDKKFTTE QLEAFNHQFE SSNFTARELD  360
LELQKDVARV ILTQVGSGPQ ETNESLIDAK TGLPKEKLSG GGGSGGGGSG GGGSAEAWYN  420
LGNAYYKQGD YQKAIEYYQK ALELDPNNAE AWYNLGNAYY KQGDYQKAIE YYQKALELDP  480
NNAEAWYNLG NAYYKQGDYQ KAIEDYQKAL ELDPNNLQAE AWKNLGNAYY KQGDYQKAIE  540
YYQKALELDP NNASAWYNLG NAYYKQGDYQ KAIEYYQKAL ELDPNNAKAW YRRGNAYYKQ  600
GDYQKAIEDY QKALELDPNN RSRSAGGGGS GGGGSGGGGA SAMADLEQKV LEMEASTYDG  660
VFIWKISDFP RKRQEAVAGR IPAIFSPAFY TSRYGYKMCL RIYLNGDGTG RGTHLSLFFV  720
VMKGPNDALL RWPFNQKVTL MLLDQNNREH VIDAFRPDVT SSSFQRPVND MNIASGCPLF  780
CPVSKMEAKN SYVRDDAIFI KAIVDLTGLG SAGSAAGSGE FGSAEAAAKE AAAKAGSAGS  840
AAGSGEFGSA SIKLQSSDGE IFEVDVEIAK QSVTIKTMLE DLGMDDEGDD DPVPLPNVNA  900
AILKKVIQWC THHKDDPPPP EDDENKEKRT DDIPVWDQEF LKVDQGTLFE LILAANYLDI  960
KGLLDVTCKT VANMIKGKTP EEIRKTFNIK NDFTEEEEAQ VRKENQWCGS G           1011

SEQ ID NO: 171          moltype = AA  length = 720
FEATURE                 Location/Qualifiers
source                  1..720
```

```
                        mol_type = protein
                        organism = synthetic construct
SEQUENCE: 171
MTADNNSMPH GAVSSYAKLV QNQTPEDILE EFPEIIPLQQ RPNTRSSETS NDESGETCFS  60
GHDEEQIKLM NENCIVLDWD DNAIGAGTKK VCHLMENIEK GLLHRAFSVF IFNEQGELLL  120
QQRATEKITF PDLWTNTCCS HPLCIDDELG LKGKLDDKIK GAITAAVRKL DHELGIPEDE  180
TKTRGKFHFL NRIHYMAPSN EPWGEHEIDY ILFYKINAKE NLTVNPNVNE VRDFKWVSPN  240
DLKTMFADPS YKFTPWFKII CENYLFNWWE QLDDLSEVEN DRQIHRMLKL SGGGGSGGGG  300
SGGGGSAEAW YNLGNAYYKQ GDYQKAIEYY QKALELDPNN AEAWYNLGNA YYKQGDYQKA  360
IEYYQKALEL DPNNAEAWYN LGNAYYKQGD YQKAIEDYQK ALELDPNNLQ AEAWKNLGNA  420
YYKQGDYQKA IEYYQKALEL DPNNASAWYN LGNAYYKQGD YQKAIEYYQK ALELDPNNAK  480
AWYRRGNAYY KQGDYQKAIE DYQKALELDP NNRSRSAGGG GSGGGGSGGG GASSYYHHHH  540
HHLESTSLYK KAGSGSNTVK ELKNYIQELE ERNAELKNLK EHLKFAKAEL EFELAAHKFE  600
GSAGSAAGSG EFGSAEAAAK EAAAKAGSAG SAAGSGEFGS SYYHHHHHHL ESTSLYKKAG  660
SGSQKVAQLK NRVAYKLKEN AKLENIVARL ENDNANLEKD IANLEKDIAN LERDVARGSG  720

SEQ ID NO: 172          moltype = AA  length = 801
FEATURE                 Location/Qualifiers
source                  1..801
                        mol_type = protein
                        organism = synthetic construct
SEQUENCE: 172
MEAKIDELIN NDPVWSSQNE SLISKPYNHI LLKPGKNFRL NLIVQINRVM NLPKDQLAIV  60
SQIVELLHNS SLLIDDIEDN APLRRGQTTS HLIWGVPSTI NTANYMYFRA MQLVSQLTTK  120
EPLYHWLITI FNEELINLHR GQGLDIYWRD FLPEIIPTQE MYLNMVMNKT GGLFRLTLRL  180
MEALSPSSHH GHSLVPFINL LGIIYQIRDD YLNLKDFQMS SEKGFAEDIT EGKLSFPIVH  240
ALNFTKTKGQ TEQHNEILRI LLLRTSDKDI KLKLIQILEF DTNSLAYTKN FINQLVNMIK  300
NDNENKYLPD LASHSDTATN LHDELLYIID HLSELKLSGG GGSGGGGSGG GGSAEAWYNL  360
GNAYYKQGDY QKAIEYYQKA LELDPNNAEA WYNLGNAYYK QGDYQKAIEY YQKALELDPN  420
NAEAWYNLGN AYYKQGDYQK AIEDYQKALE LDPNNLQAEA WKNLGNAYYK QGDYQKAIEY  480
YQKALELDPN NASAWYNLGN AYYKQGDYQK AIEYYQKALE LDPNNAKAWY RRGNAYYKQG  540
DYQKAIEDYQ KALELDPNNR SRSAGGGGSG GGGSGGGGAS LCTMKKGPSG YGFNLHSDKS  600
KPGQFIRSVD PDSPAEASGL RAQDRIVEVN GVCMEGKQHG DVVSAIRAGG DETKLLVVDR  660
EGSAGSAAGS GEFGSAEAAA KEAAAKAGSA GSAAGSGEFG SSSGAIIYTV ELKRYGGPLG  720
ITISGTEEPF DPIIISSLTK GGLAERTGAI HIGDRILAIN SSSLKGKPLS EAIHLLQMAG  780
ETVTLKIKKQ TDAQPASSGS G                                            801

SEQ ID NO: 173          moltype = AA  length = 547
FEATURE                 Location/Qualifiers
source                  1..547
                        mol_type = protein
                        organism = synthetic construct
SEQUENCE: 173
MKCSTFSFWF VCKIIFFFFS FNIQTSIANP RENFLKCFSQ YIPNNATNLK LVYTQNNPLY  60
MSVLNSTIHN LRFTSDTTPK PLVIVTPSHV SHIQGTILCS KKVGLQIRTR SGGHDSEGMS  120
YISQVPFVIV DLRNMRSIKI DVHSQTAWVE AGATLGEVYY WVNEKNENLS LAAGYCPTVC  180
AGGHFGGGGY GPLMRNYGLA ADNIIDAHLV NVHGKVLDRK SMGEDLFWAL RGGGAESFGI  240
IVAWKIRLVA VPKSTMFSVK KIMEIHELVK LVNKWQNIAY KYDKDLLLMT HFITRNITDN  300
QGKNKTAIHT YFSSVFLGGV DSLVDLMNKS FPELGIKKTD CRQLSWIDTI IFYSGVVNYD  360
TDNFNKEILL DRSAGQNGAF KIKLDYVKKP IPESVFVQIL EKLYEEDIGA GMYALYPYGG  420
IMDEISESAI PFPHRAGILY ELWYICSWEK QEDNEKHLNW IRNIYNFMTP YVSKNPRLAY  480
LNYRDLDIGI NDPKNPNNYT QARIWGEKYF GKNFDRLVKV KTLVDPNNFF RNEQSIPPLP  540
RHRHGSG                                                            547

SEQ ID NO: 174          moltype = AA  length = 548
FEATURE                 Location/Qualifiers
source                  1..548
                        mol_type = protein
                        organism = synthetic construct
SEQUENCE: 174
MNCSTFSFWF VCKIIFFFLS FNIQISIANP QENFLKCFSE YIPNNPANPK FIYTQHDQLY  60
MSVLNSTIQN LRFTSDTTPK PLVIVTPSNV SHIQASILCS KKVGLQIRTR SGGHDAEGLS  120
YISQVPFAIV DLRNMHTVKV DIHSQTAWVE AGATLGEVYY WINEMNENFS FPGGYCPTVG  180
VGGHFSGGGY GALMRNYGLA ADNIIDAHLV NVDGKVLDRK SMGEDLFWAI RGGGGENFGI  240
IAACKIKLVV VPSKATIFSV KKNMEIHGLV KLFNKWQNIA YKYDKDLMLT THFRTRNITD  300
NHGKNKTTVH GYFSSIFLGG VDSLVDLMNK SFPELGIKKT DCKELSWIDT TIFYSGVVNY  360
NTANFKKEIL LDRSAGKKTA FSIKLDYVKK LIPETAMVKI LEKLYEEEVG VGMYVLYPYG  420
GIMDEISESA IPFPHRAGIM YELWYTATWE KQEDNEKHIN WVRSVYNFTT PYVSQNPRLA  480
YLNYRDLDLG KTNPESPNNY TQARIWGEKY FGKNFNRLVK VKTKADPNNF FRNEQSIPPL  540
PPRHHGSG                                                           548

SEQ ID NO: 175          moltype = AA  length = 886
FEATURE                 Location/Qualifiers
source                  1..886
                        mol_type = protein
                        organism = synthetic construct
SEQUENCE: 175
MNHLRAEGPA SVLAIGTANP ENILLQDEFP DYYFRVTKSE HMTQLKEKFR KICDKSMIRK  60
RNCFLNEEHL KQNPRLVEHE MQTLDARQDM LVVEVPKLGK DACAKAIKEW GQPKSKITHL  120
```

```
IFTSASTTDM PGADYHCAKL LGLSPSVKRV MMYQLGCYGG GTVLRIAKDI AENNKGARVL  180
AVCCDIMACL FRGPSESDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LHLKSDKFVD SRHVLSEHGN MSSSTVLFVM DELRKRSLEE GKSTTGDGFE  360
WGVLFGFGPG LTVERVVVRS VPIKYKLSGG GGSGGGGSGG GGSAEAWYNL GNAYYKQGDY  420
QKAIEYYQKA LELDPNNAEA WYNLGNAYYK QGDYQKAIEY YQKALELDPN NAEAWYNLGN  480
AYYKQGDYQK AIEDYQKALE LDPNNLQAEA WKNLGNAYYK QGDYQKAIEY YQKALELDPN  540
NASAWYNLGN AYYKQGDYQK AIEYYQKALE LDPNNAKAWY RRGNAYYKQG DYQKAIEDYQ  600
KALELDPNNR SRSAGGGGSG GGGSGGGGAS GNNLETYEWY NKSISRDKAE KLLLDTGKEG  660
AFMVRDSRTP GTYTVSVFTK AIISENPCIK HYHIKETNDS PKRYYVAEKY VFDSIPLLIQ  720
YHQYNGGGLV TRLRYPVCGG SAGSAAGSGE FGSAEAAAKE AAAKAGSAGS AAGSGEFGSG  780
SHPWFFGKIP RAKAEEMLSK QRHDGAFLIR ESESAPGDFS LSVKFGNDVQ HFKVLRDGAG  840
KYFLWVVKFN SLNELVDYHR STSVSRNQQI FLRDIEQVPQ QPTGSG                886

SEQ ID NO: 176          moltype = AA  length = 668
FEATURE                 Location/Qualifiers
source                  1..668
                        mol_type = protein
                        organism = synthetic construct
SEQUENCE: 176
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR KKLSGGGGSG GGGSGGGGSA  120
EAWYNLGNAY YKQGDYQKAI EYYQKALELD PNNAEAWYNL GNAYYKQGDY QKAIEYYQKA  180
LELDPNNAEA WYNLGNAYYK QGDYQKAIED YQKALELDPN NLQAEAWKNL GNAYYKQGDY  240
QKAIEYYQKA LELDPNNASA WYNLGNAYYK QGDYQKAIEY YQKALELDPN NAKAWYRRGN  300
AYYKQGDYQK AIEDYQKALE LDPNNRSRSA GGGGSGGGGS GGGGASGQDR SEATLIKRFK  360
GEGVRYKAKL IGIDEVSAAR GDKLCQDSMM KLKGVVAGAR SKGEHKQKIF LTISFGGIKI  420
FDEKTGALQH HHAVHEISYI AKDITDHRAF GYVCGKEGNH RFVAIKTAQA AEPVILDLRD  480
LFQLIYELKQ REELEKKAGS AGSAAGSGEF GSAEAAAKEA AAKAGSAGSA AGSGEFGSGS  540
HMGSQFWVTS QKTEASERCG LQGSYILRVE AEKLTLLTLG AQSQILEPLL FWPYTLLRRY  600
GRDKVMFSFE AGRRCPSGPG TFTFQTSQGN DIFQAVEAAI QQQKAQGKVG QAQDILRLEH  660
HHHHHGSG                                                         668

SEQ ID NO: 177          moltype = AA  length = 800
FEATURE                 Location/Qualifiers
source                  1..800
                        mol_type = protein
                        organism = synthetic construct
SEQUENCE: 177
MGLSSVCTFS FQTNYHTLLN PHNNNPKTSL LCYRHPKTPI KYSYNNFPSK HCSTKSFHLQ  60
NKCSESLSIA KNSIRAATTN QTEPPESDNH SVATKILNFG KACWKLQRPY TIIAFTSCAC  120
GLFGKELLHN TNLISWSLMF KAFFFLVAIL CIASFTTTIN QIYDLHIDRI NKPDLPLASG  180
EISVNTAWIM SIIVALFGLI ITIKMKGGPL YIFGYCFGIF GGIVYSVPPF RWKQNPSTAF  240
LLNFLAHIIT NFTFYYASRA ALGLPFELRP SFTFLLAFMK SMGSALALIK DASDVEGDTK  300
FGISTLASKY GSRNLTLFCS GIVLLSYVAA ILAGIIWPQA FNSNVMLLSH AILAFWLILQ  360
TRDFALTNYD PEAGRRFYEF MWKLYYAEYL VYVFIKLSGG GGSGGGGSGG GGSAEAWYNL  420
GNAYYKQGDY QKAIEYYQKA LELDPNNAEA WYNLGNAYYK QGDYQKAIEY YQKALELDPN  480
NAEAWYNLGN AYYKQGDYQK AIEDYQKALE LDPNNLQAEA WKNLGNAYYK QGDYQKAIEY  540
YQKALELDPN NASAWYNLGN AYYKQGDYQK AIEYYQKALE LDPNNAKAWY RRGNAYYKQG  600
DYQKAIEDYQ KALELDPNNR SRSAGGGGSG GGGSGGGGAS AEYVRALFDF NGNDEEDLPF  660
KKGDILRIRD KPEEQWWNAE DSEGKRGMIP VPYVEKYGSA GSAAGSGEFG SAEAAAKEAA  720
AKAGSAGSAA GSGEFGSLIK HMRAEALFDF TGNSKLELNF KAGDVIFLLS RINKDWLEGT  780
VRGATGIFPL SFVKILKGSG                                             800

SEQ ID NO: 178          moltype = AA  length = 2744
FEATURE                 Location/Qualifiers
source                  1..2744
                        mol_type = protein
                        organism = synthetic construct
SEQUENCE: 178
MSEESLFESS PQKMEYEITN YSERHTELPG HFIGLNTVDK LEESPLRDFV KSHGGHTVIS  60
KILIANNGIA AVKEIRSVRK WAYETFGDDR TVQFVAMATP EDLEANAEYI RMADQYIEVP  120
GGTNNNNYAN VDLIVDIAER ADVDAVWAGW GHASENPLLP EKLSQSKRKV IFIGPPGNAM  180
RSLGDKISST IVAQSAKVPC IPWSGTGVDT VHVDEKTGLV SVDDDIYQKG CCTSPEDGLQ  240
KAKRIGFPVM IKASEGGGGK GIRQVEREED FIALYHQAAN EIPGSPIFIM KLAGRARHLE  300
VQLLADQYGT NISLFGRDCS VQRRHQKIIE EAPVTIAKAE TFHEMEKAAV RLGKLVGYVS  360
AGTVEYLYSH DDGKFYFLEL NPRLQVEHPT TEMVSGVNLP AAQLQIAMGI PMHRISDIRT  420
LYGMNPHSAS EIDFEFKTQD ATKKQRRPIP KGHCTACRIT SEDPNDGFKP SGGTLHELNF  480
RSSSNVWGYF SVGNNGNIHS FSDSQFGHIF AFGENRQASR KHMVVALKEL SIRGDFRTTV  540
EYLIKLLETE DFEDNTITTG WLDDLITHKM TAEKPDPTLA VICGAATKAF LASEEARHKY  600
IESLQKGQVL SKDLLQTMFP VDFIHEGKRY KFTVAKSGND RYTLFINGSK CDIILRQLSD  660
GGLLIAIGGK SHTIYWKEEV AATRLSVDSM TTLLEVENDP TQLRTPSPGK LVKFLVENGE  720
HIIKGQPYAE IEVMKMQMPL VSQENGIVQL LKQPGSTIVA GDIMAIMTLD DPSKVKHALP  780
FEGMLPDFGS PVIEGTKPAY KFKSLVSTLE NILKGYDNQV IMNASLQQLI EVLRNPKLPY  840
SEWKLHISAL HSRLPAKLDE QMEELVARSL RRGAVFPARQ LSKLIDMAVK NPEYNPDKLL  900
GAVVEPLADI AHKYSNGLEA HEHSIFVHFL EEYYEVEKLF NGPNVREENI ILKLRDENPK  960
DLDKVALTVL SHSKVSAKNN LILAILKHYQ PLCKLSSKVS AIFSTPLQHI VELESKATAK  1020
VALQAREILI QGALPSVKER TEQIEHILKS SVVKAVYGSS NPKRSEPDLN ILKDLIDSNY  1080
VVFDVLLQFL THQDPVVTAA AAQVYIRRAY RAYTIGDIRV HEGVTVPIVE WKFQLPSAAF  1140
```

```
STFPTVKSKM GMNRAVSVSD LSYVANSQSS PLREGILMAV DHLDDVDEIL SQSLEVIPRH 1200
QSSSNGPAPD RSGSSASLSN VANVCVASTE GFESEEEILV RLREILDLNK QELINASIRR 1260
ITFMFGFKDG SYPKYYTFNG PNYNENETIR HIEPALAFQL ELGRLSNFNI KPIFTDNRNI 1320
HVYEAVSKTS PLDKRFFTRG IIRTGHIRDD ISIQEYLTSE ANRLMSDILD NLEVTDTSNS 1380
DLNHIFINFI AVFDISPEDV EAAFGGFLER FGKRLLRLRV SSAEIRIIIK DPQTGAPVPL 1440
RALINNVSGY VIKTEMYTEV KNAKGEWVFK SLGKPGSMHL RPIATPYPVK EWLQPKRYKA 1500
HLMGTTYVYD FPELFRQASS SQWKNFSADV KLTDDFFISN ELIEDENGEL TEVEREPGAN 1560
AIGMVAFKIT VKTPEYPRGR QFVVVANDIT FKIGSFGPQE DEFFNKVTEY ARKRGIPRIY 1620
LAANSGARIG MAEEIVPLFQ VAWNDAANPD KGFQYLYLTS EGMETLKKFD KENSVLTERT 1680
VINGEERFVI KTIIGSEDGL GVECLRGSGL IAGATSRAYH DIFTITLVTC RSVGIGAYLV 1740
RLGQRAIQVE GQPIILTGAP AINKMLGREV YTSNLQLGGT QIMYNNGVSH LTAVDDLAGV 1800
EKIVEWMSYV PAKRNMPVPI LETKDTWDRP VDFTPTNDET YDVRWMIEGR ETESGFEYGL 1860
FDKGSFFETL SGWAKGVVVG RARLGGIPLG VIGVETRTVE NLIPADPANP NSAETLIQEP 1920
GQVWHPNSAF KTAQAINDFN NGEQLPMMIL ANWRGFSGGQ RDMFNEVLKY GSFIVDALVD 1980
YKQPIIIYIP PTGELRGGSW VVVDPTINAD QMEMYADVNA RAGVLEPQGM VGIKFRREKL 2040
LDTMNRLDDK YRELRSQLSN KSLAPEVHQQ ISKQLADRER ELLPIYGQIS LQFADLHDRS 2100
SRMVAKGVIS KELEWTEARR FFFWRLRRRL NEEYLIKRLS HQVGEASRLE KIARIRSWYP 2160
ASVDHEDDRQ VATWIEENYK TLDDKLKGLK LESFAQDLAK KIRSDHDNAI DGLSEVIKML 2220
STDDKEKLLK TLKKLSGGGG SGGGGSGGGG SAEAWYNLGN AYYKQGDYQK AIEYYQKALE 2280
LDPNNAEAWY NLGNAYYKQG DYQKAIEYYQ KALELDPNNA EAWYNLGNAY YKQGDYQKAI 2340
EDYQKALELD PNNLQAEAWK NLGNAYYKQG DYQKAIEYYQ KALELDPNNA SAWYNLGNAY 2400
YKQGDYQKAI EYYQKALELD PNNAKAWYRR GNAYYKQGDY QKAIEDYQKA LELDPNNRSR 2460
SAGGGGSGGG GSGGGGASGS HMRLGAQSIQ PTANLDRTDD LVYLNVMELV RAVLELKNEL 2520
AQLPPEGYVV VVKNVGLTLR KLIGSVDDLL PSLPSSSRTE IEGTQKLLNK DLAELINKMR 2580
LAQQNAVTSL SEECKRQMLT ASHTLAVDAK NLLDAVDQAK VLANLAHPPA EGSAGSAAGS 2640
GEFGSAEAAA KEAAAKAGSA GSAAGSGEFG SGAMATPGSE NVLPREPLIA TAVKFLQNSR 2700
VRQSPLATRR AFLKKKGLTD EEIDMAFQQS GTAADEPSSL WGSG                2744

SEQ ID NO: 179        moltype = AA   length = 3623
FEATURE               Location/Qualifiers
source                1..3623
                      mol_type = protein
                      organism = synthetic construct
SEQUENCE: 179
MGSAGSAAGS GEFGSAGSAA GSGEFGSAGS AAGSGEFSYY HHHHHHLEST SLYKKAGSGS 60
ARNAYLRKKI ARLKKDNLQL ERDEQNLEKI IANLRDEIAR LENEVASHEQ GSAGSAAGSG 120
EFAEAAAKEA AAKAGSAGSA AGSGEFSYYH HHHHHLESTS LYKKAGSGSN LVAQLENEVA 180
SLENENETLK KKNLHKKDLI AYLEKEIANL RKKIEEGSAG SAAGSGEFGS AEAAAKEAAA 240
KEAAAKEAAA KAGSAGSAAG SGEFGSSYYH HHHHHLESTS LYKKAGSGSQ KVAELKNRVA 300
VKLNRNEQLK NKVEELKNRN AYLKNELATL ENEVARLEND VAEGSAGSAA GSGEFAEAAA 360
KEAAAKAGSA GSAAGSGEFS YYHHHHHHLE STSLYKKAGS GSNEVTTLEN DAAFIENENA 420
YLEKEIARLR KEKAALRNRL AHKKGSAGSA AGSGEFGSAE AAAKEAAAKE AAAKEAAAKA 480
GSAGSAAGSG EFGSRPPTIS NPPPLISSAK HPSVGSAGSA AGSGEFAEAA AKEAAAKAGS 540
AGSAAGSGEF NFLQSRPEPT APPEESFRSG GSAGSAAGSG EFGSAEAAAK EAAAKEAAAK 600
EAAAKAGSAG SAAGSGEFGS SKGTGLNPNA KVWQEIAPGN GSAGSAAGSG EFAEAAAKEA 660
AAKAGSAGSA AGSGEFPDGG TTFEHLWSSL EPDSTYGSAG SAAGSGEFGS AEAAAKEAAA 720
KEAAAKEAAA KAGSAGSAAG SGEFGSSYYH HHHHHLESTS LYKKAGSGSK RIAYLRKKIA 780
ALKKDNANLE KDIANLENEI ERLIKEIKTL ENEVASHEQG SAGSAAGSGE FAEAAAKEAA 840
AKAGSAGSAA GSGEFSYYHH HHHHLESTSL YKKAGSGSNL LATLRSTAAV LENENHVLEK 900
EKEKLRKEKE QLLNKLEAYK GSAGSAAGSG EFGSAEAAAK EAAAKEAAAK EAAAKAGSAG 960
SAAGSGEFGS PATSQHPPPP PGHRSQAPSH GSAGSAAGSG EFAEAAAKEA AAKAGSAGSA 1020
AGSGEFELNS LLILLEAAEY LERRDRGSAG SAAGSGEFGS AEAAAKEAAA KEAAAKEAAA 1080
KAGSAGSAAG SGEFGSRPPT ISNPPPLISS AKHPSVGSAG SAAGSGEFAE AAAKEAAAKA 1140
GSAGSAAGSG EFNFLQSRPE PTAPPEESFR SGGSAGSAAG SGEFGSAEAA AKEAAAKEAA 1200
AKEAAAKAGS AGSAAGSGEF GSSKGTGLNP NAKVWQEIAP GNGSAGSAAG SGEFAEAAAK 1260
EAAAKAGSAG SAAGSGEFPD GGTTFEHLWS SLEPDSTYGS AGSAAGSGEF GSAEAAAKEA 1320
AAKEAAAKEA AAKAGSAGSA AGSGEFGSSY YHHHHHHLES TSLYKKAGSG SKRIAYLRKK 1380
IAALKKDNAN LEKDIANLEN EIERLIKEIK TLENEVASHE QGSAGSAAGS GEFAEAAAKE 1440
AAAKAGSAGS AAGSGEFSYY HHHHHHLEST SLYKKAGSGS NLLATLRSTA AVLENENHVL 1500
EKEKEKLRKE KEQLLNKLEA YKGSAGSAAG SGEFGSAEAA AKEAAAKEAA AKEAAAKAGS 1560
AGSAAGSGEF GSALVDDAAD YEPPPSNNEE ALGSAGSAAG SGEFAEAAAK EAAAKAGSAG 1620
SAAGSGEFRE LFDDPSYVNV QNLDKARQGS AGSAAGSGEF GSAEAAAKEA AAKEAAAKEA 1680
AAKAGSAGSA AGSGEFGSKN TKSMNFDNPV YRKTTEEEGS AGSAAGSGEF AEAAAKEAAA 1740
KAGSAGSAAG SGEFRSLPST WIENKLYGMS DPNWGSAGSA AGSGEFGSAE AAAKEAAAKE 1800
AAAKEAAAKA GSAGSAAGSG EFGSVVDNSP PPALPPKKRQ SAPSGSAGSA AGSGEFAEAA 1860
AKEAAAKAGS AGSAAGSGEF TQRSKPQPAV PPRPSADLIL GSAGSAAGSG EFGSAEAAAK 1920
EAAAKEAAAK EAAAKAGSAG SAAGSGEFGS TDEEREETEE EVYLLNSTTL GSAGSAAGSG 1980
EFAEAAAKEA AAKAGSAGSA AGSGEFDGNV SGTQRLDSAT VRTYSCGSAG SAAGSGEFGS 2040
AEAAAKEAAA KEAAAKEAAA KAGSAGSAAG SGEFGSSYYH HHHHHLESTS LYKKAGSGSQ 2100
KVAQLKNRVA YKLKENAKLE NIVARLENDN ANLEKDIANL EKDIANLERD VARGSAGSAA 2160
GSGEFAEAAA KEAAAKAGSA GSAAGSGEFS YYHHHHHHLE STSLYKKAGS GSNTVKELKN 2220
YIQELEERNA ELKNLKEHLK FAKAELEFEL AAHKFEGSAG SAAGSGEFGS AEAAAKEAAA 2280
KEAAAKEAAA KAGSAGSAAG SGEFGSHDDS LPHPQQATDD SGHESDGSAG SAAGSGEFAE 2340
AAAKEAAAKA GSAGSAAGSG EFGSPNAGSV EQTPKKPGLR RRGSAGSAAG SGEFGSAEAA 2400
AKEAAAKEAA AKEAAAKAGS AGSAAGSGEF GSSYYHHHHH HLESTSLYKK AGSGSFENVT 2460
HEFILATLEN ENAKLRRLEA KLERELARLR NEVAWLGSAG SAAGSGEFAE AAAKEAAAKA 2520
GSAGSAAGSG EFSYYHHHHH HLESTSLYKK AGSGSQKVEE LKNKIAELEN RNAVKKNRVA 2580
HLKQEIAYLK DELAAHEFEG SAGSAAGSGE FGSAEAAAKE AAAKEAAAKE AAAKAGSAGS 2640
AAGSGEFGSV SSTKLVSFHD DSDEDLLHIG SAGSAAGSGE FAEAAAKEAA AKAGSAGSAA 2700
```

-continued

```
GSGEFAAATP ISTFHDDSDE DLLHVGSAGS AAGSGEFGSA EAAAKEAAAK EAAAKEAAAK  2760
AGSAGSAAGS GEFGSSYYHH HHHHLESTSL YKKAGSGSQK VESLKQKIEE LKQRKAQLKN  2820
DIANLEKEIA YAETGSAGSA AGSGEFAEAA AKEAAAKAGS AGSAAGSGEF SYYHHHHHHL  2880
ESTSLYKKAG SEFFRRERNK MAAAKCRNRR RELTDTLQAE TDQLEDEKSA LQTEIANLLK  2940
EKEKLEFILA AHRPACKIPD DLGFPEEMSL EGSAGSAAGS GEFGSAEAAA KEAAAKEAAA  3000
KEAAAKAGSA GSAAGSGEFG SFQMPADTPP PAYLPPEDPM TGSAGSAAGS GEFAEAAAKE  3060
AAAKAGSAGS AAGSGEFERE SNEEPPPPYE DPYWGNGGSA GSAAGSGEFG SAEAAAKEAA  3120
AKEAAAKEAA AKAGSAGSAA GSGEFGSSYY HHHHHHLEST SLYKKAGSGS QKVAELKNRV  3180
AVKLNRNEQL KNKVEELKNR NAYLKNELAT LENEVARLEN DVAEGSAGSA AGSGEFAEAA  3240
AKEAAAKAGS AGSAAGSGEF SYYHHHHHHL ESTSLYKKAG SGSNEVTTLE NDAAFIENEN  3300
AYLEKEIARL RKEKAALRNR LAHKKSYYHH HHHHLESTSL YKKAGSGSAR NAYLRKKIAR  3360
LKKDNLQLER DEQNLEKIIA NLRDEIARLE NEVASHEQGS AGSAAGSGEF AEAAAKEAAA  3420
KAGSAGSAAG SGEFSYYHHH HHHLESTSLY KKAGSGSNLV AQLENEVASL ENENETLKKK  3480
NLHKKDLIAY LEKEIANLRK KIEEGSAGSA AGSGEFGSAE AAAKEAAAKE AAAKEAAAKA  3540
GSAGSAAGSG EFGSEQKLIS EEDLEQKLIS EEDLEQKLIS EEDLGSAGSA AGSGEFGSAG  3600
SAAGSGEFGS AGSAAGSGEF GSG                                          3623

SEQ ID NO: 180         moltype = AA  length = 455
FEATURE                Location/Qualifiers
source                 1..455
                       mol_type = protein
                       organism = synthetic construct
SEQUENCE: 180
MGSAGSAAGS GEFGSAGSAA GSGEFGSAGS AAGSGEFSYY HHHHHHLEST SLYKKAGSGS  60
ARNAYLRKKI ARLKKDNLQL ERDEQNLEKI IANLRDEIAR LENEVASHEQ GSAGSAAGSG  120
EFAEAAAKEA AAKAGSAGSA AGSGEFSYYH HHHHHLESTS LYKKAGSGSN LVAQLENEVA  180
SLENENETLK KKNLHKKDLI AYLEKEIANL RKKIEEGSAG SAAGSGEFGS AEAAAKEAAA  240
KEAAAKEAAA KAGSAGSAAG SGEFGSSATR ELDELMASLS DFKIQGGSAG SAAGSGEFAE  300
AAAKEAAAKA GSAGSAAGSG EFDLALSENW AQEFLAAGDA VDGSAGSAAG SGEFGSAEAA  360
AKEAAAKEAA AKEAAAKAGS AGSAAGSGEF GSDYKDDDDK DYKDDDDKDY KDDDDKGSAG  420
SAAGSGEFGS AGSAAGSGEF GSAGSAAGSG EFGSG                             455

SEQ ID NO: 181         moltype = DNA  length = 4596
FEATURE                Location/Qualifiers
source                 1..4596
                       mol_type = other DNA
                       organism = synthetic construct
SEQUENCE: 181
atgagtgcta aggcaatttc tgaacaaact ggtaaagaat tgttgtacaa gtttatttgt  60
actacatcag ccatccaaaa tagattcaaa tacgctagag ttaccccaga tactgactgg  120
gctagattgt tacaagatca tccatggttg ttatctcaaa acttggttgt caaacctgac  180
caattaatta agagaagagg taaattgggt ttagtaggtg ttaatttgac attggatggt  240
gtaaagtctt ggttgaaacc aagattaggt caagaagcca cagttggtaa agctaccggt  300
ttcttgaaaa atttcttgat cgaaccattt gtccctcatt cacaagccga agaattctat  360
gtatgtatct acgctactag agagggtgac tatgttttat ttcatcacga aggtggtgtc  420
gacgtaggtg acgttgacgc caaggctcaa aagttgttgg ttggtgtcga tgaaaagttg  480
aacccagaag acattaaaaa gcatttgttg gttcacgcac ctgaagataa aaaggaaata  540
ttggcctcct ttataagtgg tttgtttaat ttctacgaag atttgtactt cacctacttg  600
gaaattaacc cattagtagt tactaaggat ggtgtatatg ttttggactt agctgcaaaa  660
gttgatgcaa cagccgacta catttgtaag gtcaaatggg gtgacatcga atttccacct  720
ccattcggta gagaagctta tccagaagaa gcctacattg ctgatttgga cgctaagtct  780
ggtgcatcat tgaagttgac attgttgaac cctaaaggta gaatttggac catggttgct  840
ggtggtggtg ctagtgtcgt atattctgat actatatgcg acttgggtgg tgttaacgaa  900
ttggcaaact acggtgaata ctcaggtgcc ccatccgaac aacaaacata cgattacgct  960
aagaccatct tgtccttaat gactagagaa aagcatcctg atggtaaaat cttgatcatc  1020
ggtggtagta tcgcaaattt tactaacgtt gccgctacat tcaagggtat cgtcagagct  1080
ataagagatt accaaggtcc attgaaggaa cacgaagtaa caatattcgt tagaagaggt  1140
ggtcctaact accaagaagg tttgagagtc atgggtgaag taggtaaaac cactggtata  1200
ccaatccatg tctttggtac agaaacccac atgactgcaa tagttggtat ggccttaggt  1260
catagaccaa tccctaatca acctccaacc gcagcccaca ctgcaaattt cttgttaaac  1320
gcctctggtt caacttccac accagctcct tctagaacag caagtttctc tgaatcaaga  1380
gctgatgaag tcgctccagc taagaaagca aaaccagcca tgcctcaaga ctccgttcca  1440
agtcctagat ctttgcaggg taaatctact actttgtttt ctagacatac taaggctata  1500
gtatggggta tgcaaacaag agcagttcaa ggcatgttgg atttcgacta tgtttgtagt  1560
agagatgaac catctgttgc tgcaatggtc tatcctttta ctggtgacca taagcaaaaa  1620
ttctactggg gtcacaagga aatattgatc ccagttttta agaacatggc cgatgctatg  1680
agaaaacatc ctgaagtcga cgtattgatt aacttcgcct cattaagatc cgcttacgat  1740
tctacaatgg aaaccatgaa ctacgctcaa ataagaacca tcgctatcat tgcagaaggt  1800
attccagaag ccttgactag aaagttgatt aagaaagctg atcaaaaagg tgtcacaata  1860
atcggtccag ctaccgtagg tggtattaag cctggttgtt tcaagatcgg taacactggt  1920
ggtatgttgg ataacatatt ggcatctaag ttgtatagac caggttcagt cgcttacgta  1980
tccagaagtg gtggtatgtc caacgaattg aacaacatca tcagtagaac tacagatggt  2040
gtatacgaag gtgttgctat tggtggtgac agatacccag gttctacttt tatggatcat  2100
gtattgagat atcaagacac acctggtgtt aaaatgattg ttgtcttggg tgaaataggt  2160
ggtactgaag aatacaagat atgcagaggt atcaaagaag gtagattgac aaagccaatc  2220
gtttgttggt gcattggtac ttgtgcaaca atgttttctt cagaagttca attcggtcat  2280
gcaggtgcct gcgctaatca agcttcagaa acagcagttg ccaagaacca agcattaaaa  2340
gaagccggtg tttttgtccc tagatctttc gatgaattag gtgaaatcat tcaatcagtc  2400
tatgaagact tggtagctaa tggtgtaatt gttccagcac aagaagttcc tccacctact  2460
```

-continued

```
gtccctatgg attactcttg ggcaagagaa ttgggtttaa ttagaaagcc agctagtttt  2520
atgacctcta tatgtgatga aagaggtcaa gaattgatct atgctggtat gcctattact  2580
gaagtattca aagaagaaat gggtatcggt ggtgttttag gtttgttgtg gttccaaaag  2640
agattgccaa agtactcttg tcaattcatt gaaatgtgct taatggttac agctgatcat  2700
ggtcctgctg tctcaggtgc acacaatacc ataatctgcg ctagagctgg taaagatttg  2760
gtttcttctt tgacctcagg tttgttaact attggtgaca gatttggtgg tgcattagac  2820
gccgctgcaa agatgtttct aaaagctttc gattccggta taatcccaat ggaattcgtt  2880
aataagatga aaaaggaggg taaattgata atgggtatcg gtcatcgtgt taagtctatc  2940
aataaccctg atatgagagt acaaatcttg aaggactatg ttagacaaca ctttccagcc  3000
acacctttgt tagattacgc tttggaagtt gaaaagatta ccacttctaa aaagccaaat  3060
ttgatcttga acgttgatgg tttaattggt gttgcttttg tcgacatgtt gagaaactgt  3120
ggttccttca ctagagaaga agctgatgaa tatatcgaca ttggtgcatt gaatggtatc  3180
tttgttttag gtagatctat gggtttcatt ggtcattact tggatcaaaa gagattaaag  3240
caaggtttgt acagacatcc atgggatgac atttcttacg ttttacctga acacatgtca  3300
atgaaattgt ctggtggtgg tggttctggt ggtggtggtt ctggtggtgg tggtagtgcc  3360
gaagcttggt acaatttggg taacgcatac tacaagcagg gtgactacca aaaggcaatt  3420
gaatattacc aaaaggcctt ggaattagac ccaaataacg cagaagcctg gtataatttg  3480
ggtaatgctt attataaaca gggtgactat caaaaggcta tcgaatacta ccaaaaggca  3540
ttggaattag accctaataa cgctgaagca tggtataatt tgggtaacgc ttattataag  3600
cagggtgact atcaaaaagc catcgaagac taccaaaagg ctttggaatt agatccaaat  3660
aacttacaag ccgaagcttg gaagaatttg ggtaacgctt actataaaca gggtgactac  3720
caaaaagcaa ttgaatacta tcaaaaagct ttagaattgg accctaataa cgcatcagcc  3780
tggtacaatt tgggtaatgc ttactataag cagggtgact atcagaaggc cattgaatac  3840
tatcaaaagg ctttagaatt ggatccaaat aacgctaaag catggtacag acgtggtaac  3900
gcttattaca aacagggtga ctaccagaaa gccattgaag attatcaaaa ggctttggaa  3960
ttggatccta acaacagatc tagatcagct ggtggtggtg gttctggtgg tggtggttct  4020
ggtggtggtg gtgcttcttc atattaccat caccatcacc atcacttgga atccacaagt  4080
ttatacaaaa aggctggttc tggttcaaat ttggtcgcac aattggaaaa cgaagtagcc  4140
tctttagaaa atgaaaacga aaccttgaaa aagaaaaact tacataagaa agatttgatc  4200
gcttatttgg aaaaggaaat cgcaaatttg agaaagaaaa ttgaagaagg tagtgcaggt  4260
tctgccgctg gttctggtga atttggttca gctgaagcag ccgctaagga agcagccgct  4320
aaagccggtt cagctggttc cgcagccggt tctggtgaat tcggttccag ttactatcac  4380
catcaccatc atcacttgga atccactagt ttatataaga aagcaggttc tggttcagca  4440
agaaatgcct acttgagaaa gaaaatagct agattaaaga aagataactt gcaattggaa  4500
agagatgaac aaaatttgga aaagattatc gccaacttaa gagatgaaat cgctagattg  4560
gaaaatgaag ttgcatccca tgaacaaggt agtggt                           4596
```

```
SEQ ID NO: 182         moltype = DNA  length = 2472
FEATURE                Location/Qualifiers
source                 1..2472
                       mol_type = other DNA
                       organism = synthetic construct
SEQUENCE: 182
atgaaaaact gtgtaatcgt ttctgctgtt agaactgcaa ttggttcctt taatggtagt  60
ttggcctcta catcagctat tgatttgggt gctaccgtca tcaaagctgc aattgaaaga  120
gcaaagattg attctcaaca tgtcgacgaa gtaataatgg gtaacgtttt gcaagctggt  180
ttaggtcaaa atccagcaag acaagccttg ttaaaatctg gtttagcaga aactgtatgt  240
ggtttcacag ttaataaggt ctgcggttct ggtttgaagt cagttgcttt agccgctcaa  300
gctatacaag caggtcaagc ccaatctatc gtcgctggtg gtatggaaaa tatgtcattg  360
gcaccttatt tgttagatgc aaaagccaga tcaggttata gattaggtga cggtcaagta  420
tacgacgtta ttttgagaga tggtttaatg tgcgctactc atggttatca catgggtatt  480
acagcagaaa atgttgccaa agaatacggt ataaccagag aaatgcaaga tgaattggca  540
ttacattccc aaagaaaggc agccgctgca atcgaaagtg gtgcttttac tgcagaaatt  600
gtcccagtaa acgttgtcac aagaaagaaa actttcgttt tctcccaaga tgaattccca  660
aaagctaata gtaccgctga agcattgggt gctttaagac ctgcattcga caaggccggt  720
accgtaactg ccggtaatgc ttctggtata aacgatggtg ccgctgcatt ggttatcatg  780
gaagaatcag ccgctttagc agccggtttg acacctttag ctagaattaa atcttatgca  840
tcaggtggtg ttccacctgc tttgatgggt atgggtccag tccctgctac ccaaaaggca  900
ttgcaattag ccggtttgca attggctgat atcgacttaa tcgaagcaaa cgaagccttt  960
gctgcacaat tcttggcagt tggtaaaaat ttgggtttcg actccgaaaa ggttaatgtc  1020
aacggtggtg ccattgcttt gggtcatcca ataggtgctt caggtgcaag aatcttggtt  1080
acattgttgc atgccatgca agctagagat aaaaccttgg gtttagctac tttgtgtatc  1140
ggtggtggtc aaggtatcgc aatggttatc gaaagattga ataagttgtc tggtggtggt  1200
ggttctggtg gtggtggttc tggtggtggt ggtagtgcag aagcctggta caatttgggt  1260
aacgcttact acaagcaggg tgactaccaa aaggcaatcg aatactacca aaaggccttg  1320
gaattagatc caaataacgc tgaagcatgg tataatttgg gtaatgccta ttataaacag  1380
ggtgactatc aaaaagctat tgaatattac caaaaggcat tggaattaga tcctaataac  1440
gccgaagctt ggtataattt gggtaacgcc tattataagc agggtgacta tcaaaaggcc  1500
atcgaagatt accaaaaggc tttggaattg gatccaaaca acttgcaagc agaagcctgg  1560
aagaatttgg gtaacgctta ttacaaacag ggtgactacc aaaaagctat tgaatactat  1620
caaaaagcct tagaattgga tcctaataac gcttctgcat ggtacaattt gggtaatgcc  1680
tactataaac agggtgacta ccagaaggct attgaatact accaaaaagc attagaattg  1740
gatccaaata acgccaaggc ttggtacaga cgtggtaatg cctattacaa gcagggtgac  1800
taccagaaag ccatagaaga ctatcaaaaa gccttggaat tggatcctaa caacagatcc  1860
agaagtgctg gtggtggtgg ttctggtggt ggtggttctg gtggtggtgg tgcttcttca  1920
tattaccatc accatcacca tcacttggaa tctacatcat tatacaaaaa ggctggttcc  1980
ggtagtaatg aagttactac attggaaaac gatgccgctt ttatcgaaaa cgaaaacgca  2040
tacttggaaa aggaaatcgc cagattaaga aaggaaaagg cagccttgag aaatagatta  2100
gcccataaaa agggttccgc tggtagtgct gcaggttctg gtgaatttgg ttcagctgaa  2160
```

```
gccgctgcaa aagaagccgc tgcaaaggca ggttctgccg gttcagccgc tggttctggt  2220
gaattcggtt ccagttacta tcaccatcac catcatcact tggaatctac ttcattatat  2280
aaaaaggccg gttccggtag tcaaaaagtc gctgaattaa agaacagagt agctgttaag  2340
ttgaacagaa acgaacaatt gaaaaataag gtagaagaat tgaaaaatag aaacgcctac  2400
ttaaagaatg aattggcaac attggaaaac gaagtcgcta gattggaaaa tgatgtagca  2460
gaaggttctg gt                                                      2472

SEQ ID NO: 183         moltype = DNA  length = 2337
FEATURE                Location/Qualifiers
source                 1..2337
                       mol_type = other DNA
                       organism = synthetic construct
SEQUENCE: 183
atgaaaaagg tttgtgtcat tggtgctggt accatgggtt ctggtatagc acaagccttt  60
gctgcaaaag gtttcgaagt tgtcttgaga gatatcaagg acgaattcgt tgatagaggt  120
ttggacttca tcaataagaa cttgtctaag ttggttaaaa agggtaaaat cgaagaagct  180
acaaaggtag aaatcttgac cagaatttca ggtactgttg atttgaatat ggccgctgat  240
tgtgacttgg taatcgaagc agccgttgaa agaatggata ttaagaaaca aatcttcgca  300
gatttggaca acatctgcaa acctgaaaca atcttagcct caaacacctc ttcattgtcc  360
attactgaag tcgctagtgc aacaaaaaga ccagataagg taataggcat gcatttcttt  420
aatccagctc ctgttatgaa gttggtagaa gttattagag gtatagcaac atctcaagaa  480
acctttgacg ctgttaagga aacttcaata gcaatcggta aagatccagt cgaagtagcc  540
gaagctcctg gtttcgtagt taacagaatc ttgataccta tgatcaacga agctgttggt  600
atcttggctg aaggtattgc atctgtcgaa gatattgaca aagccatgaa gttaggtgct  660
aatcacccaa tgggtccttt ggaattgggt gactttattg gtttggacat atgtttagct  720
atcatggacg ttttgtattc cgaaacaggt gacagtaaat acagaccaca taccttgttg  780
aagaaatatg ttagagcagg ttggttaggt agaaagtctg gtaaaggttt ctacgattac  840
tctaaaaagt tgtctggtgg tggtggttct ggtggtggtg gttctggtgg tggtggtagt  900
gcagaagcct ggtacaattt gggtaacgct tactacaagc agggtgacta ccaaaaggcc  960
atagaatact accaaaaggc tttggaattg gatcctaata acgctgaagc atggtataat  1020
ttgggtaatg catattataa acagggtgac tatcaaaagg caatcgaata ctaccaaaag  1080
gccttggaat tagatccaaa taacgccgaa gcttggtata atttgggtaa cgcctattat  1140
aagcagggtg actatcaaaa agctatcgaa gattaccaaa aggcattgga attggatcct  1200
aacaacttac aagcagaagc ctggaagaat ttgggtaacg catattacaa acagggtgac  1260
taccaaaaag ccattgaata ttatcaaaaa gctttggaat tggatccaaa taacgcttca  1320
gcatggtaca atttgggtaa tgcctattac aagcagggtg actatcagaa agctattgaa  1380
tattatcaaa aggctttgga attagatcct aataacgcca aggcttggta cagacgtggt  1440
aatgcctatt acaagcaggg tgactaccag aaggccattg aagactatca aaaagccttg  1500
gaattggatc caaacaacag atctagatca gctggtggtg gtggttctgg tggtggtggt  1560
tctggtggtg gtggtgcttc cgaaaatttg tacttccaag gtgaaaactt gtacttccag  1620
ggtgactcca gtgaaagttg ttggaattgc ggtagaaaag cctccgaaac ctgtagtggt  1680
tgcaacactg ctagatattg tggttctttt tgccaacaca aagattggga aaagcatcac  1740
catatttgtg gtcaaacatt acaagcacaa caaggttctg ccggttcagc tgcaggttct  1800
ggtgaatttg gttccgctga agccgctgca aaagaagccg ctgcaaaggc aggttccgcc  1860
ggtagtgccg ctggtagtgg tgaattcggt tctatggcag tttccgaaag tcaattgaag  1920
aaaatggttt ctaagtacaa gtacagagat ttgactgtta gagaaacagt taacgtcatc  1980
actttgtaca aggatttgaa gccagtcttg gactcatacg tttttaatga tggttcttca  2040
agagaattga tgaacttaac tggtacaata ccagttcctt accgtggtaa cacttacaac  2100
atcccaatct gtttgtggtt gttagataca tatccttaca atccacctat ctgcttcgtc  2160
aaaccaacat ccagtatgac cattaaaact ggtaaacatg ttgatgctaa cggtaaaata  2220
tatttgccat acttacacga atggaagcat cctcaatcag acttgttggg tttaatccaa  2280
gtaatgatcg tcgtatttgg tgacgaacca cctgttttct ctagaccagg ttcaggt     2337

SEQ ID NO: 184         moltype = DNA  length = 2232
FEATURE                Location/Qualifiers
source                 1..2232
                       mol_type = other DNA
                       organism = synthetic construct
SEQUENCE: 184
atggaattga acaacgttat attggaaaag gagggtaaag tcgctgttgt cactataaat  60
agaccaaagg cattgaacgc cttgaactct gatacattga aggaaatgga ctacgttatc  120
ggtgaaattg aaaacgattc agaagtctta gcagtaattt tgaccggtgc cggtgaaaaa  180
tcctttgttg ccggtgctga tatcagtgaa atgaaggaaa tgaacactat cgaaggtaga  240
aagttcggta tcttgggtaa caaggttttc agaagattgg aattgttgga aaagcctgtt  300
atagctgcag tcaatggttt cgctttgggt ggtggttgtg aaatcgcaat gtcctgcgat  360
attagaatag cttcttcaaa cgcaagattt ggtcaaccag aagtcggttt aggtattaca  420
cctggtttcg gtggtaccca aagattatct agattggttg gtatgggtat ggccaagcaa  480
ttgattttta ctgctcaaaa catcaaggct gatgaagcat tgagaatcgg tttggttaat  540
aaggtagttg aaccatctga attgatgaac accgccaagg aaatcgctaa taagattgtt  600
tctaatgctc cagttgctgt caagttgagt aagcaagcta taaatcgtgg tatgcaatgt  660
gatatcgaca ctgcattggc cttcgaatct gaagcatttg gtgaatgctt ctcaacagaa  720
gatcaaaaag acgcaatgac cgcctttatc gaaaagagaa agatagaagg tttcaaaaac  780
agaaagttat ctggtggtgg tggttctggt ggtggtggtt ctggtggtgg tggtagtgct  840
gaagcatggt acaatttggg taacgcttac tacaagcagg gtgactacca aaaggcaatc  900
gaatactacc aaaaggcctt ggaattggac ccaaataacg ccgaagcttg gtataatttg  960
ggtaatgcct attataaaca gggtgactat caaaaagcta tagaatacta ccaaaaggca  1020
ttggaattgg accctaataa cgcagaagcc tggtataatt tgggtaacgc ctattataag  1080
cagggtgact atcaaaaggc catagaagac taccaaaagg ctttggaatt ggatccaaac  1140
aacttacaag ctgaagcatg gaagaatttg ggtaacgctt attacaaaca gggtgactac  1200
```

-continued

```
caaaaagcta ttgaatatta tcaaaaagct ttagaattag accctaataa cgcctctgct  1260
tggtacaatt tgggtaatgc ctactataaa cagggtgact accagaaggc tattgaatat  1320
taccaaaaag ctttagaatt ggatccaaat aacgcaaagg cctggtacag acgtggtaat  1380
gcctattaca agcagggtga ctaccagaaa gccattgaag attatcaaaa agctttggaa  1440
ttggatccta acaacagatc cagaagtgct ggtggtggtg gttctggtgg tggtggttct  1500
ggtggtggtg gtgcttctgg tccattgggt tcccctttga ctgcatcaat gttagcttcc  1560
gcaccacctc aagaacaaaa gcaaatgttg ggtgaaagat tattcccatt gatacaagct  1620
atgcatccta ctttagcagg taaaatcaca ggcatgttgt tggaaatcga taactctgaa  1680
ttgttacaca tgttagaatc cccagaaagt ttgagatcta aagttgacga agccgtagct  1740
gttttgcaag ctcatcaagc aaaagaagcc gctcaaaagg ccggttcagc tggttccgca  1800
gccggtagtg gtgaatttgg ttctgctgaa gctgcagcca aagaagctgc agccaaggca  1860
ggtagtgccg gttctgctgc aggttctggt gaattcggtt ccaataccaa catgagtgtc  1920
ccaactgatg gtgctgtaac tacatctcaa attcctgcat cagaacaaga aactttagtt  1980
agaccaaagc ctttgttgtt gaagttgttg aagtcagtag gtgctcaaaa agatacctac  2040
actatgaagg aagttttatt ttatttgggt caatacatca tgacaaagag attatacgat  2100
gaaaagcaac aacatatcgt ttactgttca aacgatttgt tgggtgactt gtttggtgta  2160
ccatctttct cagttaagga acacagaaag atctatacaa tgatatacag aaatttggtc  2220
gtaggttctg gt                                                      2232

SEQ ID NO: 185         moltype = DNA  length = 2469
FEATURE                Location/Qualifiers
source                 1..2469
                       mol_type = other DNA
                       organism = synthetic construct
SEQUENCE: 185
atgatcgtaa agccaatggt tagaaacaac atctgtttga acgctcatcc tcaaggttgc  60
aaaaagggtg tagaagatca aatcgaatac accaaaaaga gaatcactgc agaagttaaa  120
gccggtgcta aagcacctaa gaatgttttg gtcttaggtt gttccaacgg ttatggtttg  180
gctagtagaa taacagctgc atttggttac ggtgccgcta ccatcggtgt ttccttcgaa  240
aaggctggta gtgaaaccaa atatggtact ccaggttggt acaataactt ggcatttgat  300
gaagcagcca agagagaagg tttatactct gtcactatag atggtgacgc tttctcagat  360
gaaatcaagg cacaagttat tgaagaagcc aaaaagaaag gtataaaatt cgatttgatc  420
gtttactcct tagcaagtcc agtcagaaca gatcctgaca ccggtataat gcataagtct  480
gttttgaagc cattcggtaa aactttcaca ggtaaaacag tcgatccttt caccggtgaa  540
ttgaaagaaa tatctgctga accagcaaat gatgaagaag ctgcagccac agtaaaagtt  600
atgggtggtg aagactggga aagatggatc aagcaattgt ccaaagaagg tttgttggaa  660
gaaggttgta tcaccttagc ttattcatac attggtcctg aagccactca agctttgtat  720
agaaaaggta caatcggtaa agctaaagaa catttggaag ccaccgctca cagattaaat  780
aaggaaaacc catctatcag agcatttgtt tctgtaaata agggtttagt tactagagca  840
tccgccgtta tcccagtcat tcctttgtat ttggctagtt tgtttaaggt tatgaaggaa  900
aagggtaacc atgaaggttg catagaacaa atcactagat tgtacgcaga aagattatac  960
agaaaggatg gtacaattcc agttgacgaa gaaaacagaa tcagaatcga tgactgggaa  1020
ttggaagaag atgtccaaaa ggcagtatct gccttaatgg aaaaagttac cggtgaaaac  1080
gctgaatcat tgactgattt ggcaggttat agacacgact tttagcctc taatggtttc  1140
gatgtcgaag gtattaacta cgaagcagaa gtagaaagat tcgacagaat taaattgtct  1200
ggtggtggtg gttctggtgg tggtggttct ggtggtggtg gtagtgctga agcatggtat  1260
aatttgggta acgcttatta caagcagggt gactaccaaa aggccatcga atactaccaa  1320
aaggctttgg aattggaccc taataacgcc gaagcttggt acaatttggg taatgcctac  1380
tataaacagg gtgactatca aaaagcaatt gaatattacc aaaaggcctt ggaattagac  1440
ccaaataacg cagaagcctg gtacaatttg ggtaacgcct actataagca gggtgactat  1500
caaaaggcta ttgaagacta ccaaaaggca ttggaattag atcctaataa cttgcaagct  1560
gaagcatgga aaaatttggg taatgcctat tataaacagg gtgactacca aaaagctatt  1620
gaatactatc aaaaagcttt ggaattggac ccaaataacg cctcagcttg gtataatttg  1680
ggtaatgcat actacaaaca gggtgactat cagaaggcaa tagaatacta tcaaaaagcc  1740
ttagaattgg atcctaataa cgcaaaagcc tggtatagac gtggtaatgc ctactacaag  1800
cagggtgact atcagaaggc gatagaagat tatcaaaagg cattggaatt ggatccaaac  1860
aacagatcta gatcagctgg tggtggtggt tctggtggtg gtggttctgg tggtggtggt  1920
gcttcttcat attaccatca ccatcaccat cacttggaat ccacaagttt atataagaaa  1980
gcaggttctg gttcaaattt gttagccact ttgagatcaa cagctgcagt attggaaaac  2040
gaaaaccatg ttttggaaaa agaaaaggaa aagttgagaa aggaaaagga acaattgttg  2100
aataagttgg aagcctacaa aggttctgct ggttcagccg ctggttccgg tgaattcggt  2160
agtgctgaag cagccgctaa ggaagcagcc gctaaagctg gttccgcagg tagtgcagcc  2220
ggttctggtg aatttggttc cagttactat caccatcacc atcatcactt ggaatccact  2280
agtttatata agaaagctgg ttctggttca aagagaatcg catacttgag aaagaaaatc  2340
gctgcattaa agaaagataa cgccaacttg gaaaaggaca tcgctaattt ggaaaacgaa  2400
atcgaaagat tgattaaaga aattaaaaca ttagaaaatg aagttgcttc tcatgaacaa  2460
ggttcaggt                                                          2469

SEQ ID NO: 186         moltype = DNA  length = 2487
FEATURE                Location/Qualifiers
source                 1..2487
                       mol_type = other DNA
                       organism = synthetic construct
SEQUENCE: 186
atgactagag aagttgtcgt agttagtggt gttagaacag ctattggtac ctttggtggt  60
tctttaaaag atgttgcacc agccgaattg ggtgcattag tcgtaagaga agctttggca  120
agagcccaag tttcaggtga cgatgtcggt catgttgtct tcggtaacgt tatccaaaca  180
gaaccaagag atatgtattt gggtagagta gctgcagtta atggtggtgt taccataaac  240
gctcctgcat taactgtcaa cagattgtgt ggtagtggtt tacaagctat tgtttctgcc  300
```

-continued

```
gctcaaacaa tattgttagg tgacaccgac gttgctatcg gtggtggtgc tgaatctatg  360
tcaagagccc catacttagc tcctgcagcc agatggggtg ccagaatggg tgacgctggt  420
ttggttgaca tgatgttggg tgctttgcat gatccattcc atagaatcca catgggtgta  480
actgcagaaa acgttgccaa ggaatacgat atctcaagag cacaacaaga cgaagctgca  540
ttagaatcac acagaagagc atccgccgct attaaagccg gttactttaa ggatcaaata  600
gttccagtag tttctaaagg tagaaagggt gacgttacct tcgatactga cgaacatgtt  660
agacacgacg ctactattga tgacatgaca aagttaagac ctgttttcgt caaggaaaat  720
ggtactgtta cagctggtaa tgcatctggt ttgaacgatg cagccgctgc agtcgtaatg  780
atggaaagag ccgaagctga aagaagaggt ttgaaaccat tagctagatt ggtttcttat  840
ggtcatgctg gtgtcgatcc taaagcaatg ggtataggtc cagttcctgc tactaagatc  900
gcattggaaa gagccggttt acaagtctct gatttggacg taattgaagc caatgaagct  960
tttgccgctc aagcatgtgc cgttacaaaa gccttgggtt tagatccagc taaggtcaat  1020
cctaacggta gtggtatctc tttaggtcat ccaattggtg caaccggtgc cttgataact  1080
gttaaggctt tgcacgaatt gaacagagta caaggtagat atgcattagt tacaatgtgc  1140
atcggtggtg gtcaaggtat tgcagccata ttcgaaagaa ttaagttgtc tggtggtggt  1200
ggttctggtg gtggtggttc tggtggtggt ggtagtgctg aagcatggta caatttgggt  1260
aacgcttact acaagcaggg tgactaccaa aaggcaatcg aatattacca aaaagccttg  1320
gaattagacc caaataacgc cgaagcttgg tataatttgg gtaatgccta ttataaacag  1380
ggtgactatc aaaaagctat agaatactac caaaaggcat tggaattaga ccctaataac  1440
gcagaagcct ggtataattt gggtaacgcc tattataagc agggtgacta tcaaaaggcc  1500
atagaagact accaaaaggc tttggaattg gatccaaaca acttacaagc tgaagcatgg  1560
aagaatttgg gtaacgctta ttacaaacag ggtgactacc aaaaagctat tgaatactat  1620
caaaaggctt tagaattgga ccctaataac gcctctgctt ggtacaattt gggtaatgcc  1680
tactataaac agggtgacta ccagaaggct atcgaatatt atcaaaaagc tttagaattg  1740
gacccaaata acgcaaaggc ctggtacaga cgtggtaatg cctattacaa gcagggtgac  1800
taccagaaag ctattgaaga ttatcaaaag gcattggaat tggatcctaa caacagatcc  1860
agaagtgctg gtggtggtgg ttctggtggt ggtggttctg gtggtggtgg tgcttctgat  1920
gttatgtggg aatataagtg ggaaaataca ggtgacgctg aattatacgg tccttttact  1980
tcagcacaaa tgcaaacatg ggtatccgaa ggttatttcc ctgatggtgt ttactgcaga  2040
aaattagacc cacctggtgg tcaattctac aactcaaaga gaatagattt cgacttgtac  2100
accggttcag ctggttccgc tgcaggttct ggtgaatttg gttccgcaga agccgctgca  2160
aaagaagccg ctgcaaaggc tggtagtgca ggttctgccg ctggtagtgg tgaatttggt  2220
tctgaatcag attccgtcga attcaataac gctatatctt acgtaaataa gattaaaacc  2280
agatttttag atcatccaga aatctataga tcattcttag aaatcttgca tacataccaa  2340
aaagaacaat tgcacaccaa gggtagacct ttcagaggca tgtccgaaga agaagtcttt  2400
actgaagtag ctaatttgtt tagaggtcaa gaagatttgt tgtcagaatt cggtcaattc  2460
ttgccagaag caaaaagagg ttccggt                                    2487

SEQ ID NO: 187         moltype = DNA  length = 2169
FEATURE                Location/Qualifiers
source                 1..2169
                       mol_type = other DNA
                       organism = synthetic construct
SEQUENCE: 187
atgggtaaaa attacaagtc attggattcc gttgtcgcaa gtgactttat tgccttgggt  60
ataacttctg aagtcgcaga aacattgcat ggtagattag ccgaaattgt atgtaactac  120
ggtgctgcaa ccccacaaac ttggatcaac atagcaaacc atatcttgtc accagatttg  180
cctttctcct tgcaccaaat gttgttttat ggttgctaca aggatttcgg tcctgctcca  240
cctgcatgga ttccagaccc tgaaaaggtt aagtcaacta atttgggtgc tttgttagaa  300
aagagaggta aagaattctt gggtgttaag tacaaggatc caatctcttc tttttctcac  360
ttccaagaat tttctgtcag aaaccctgaa gtatactgga gaacagtttt gatggatgaa  420
atgaaaataa gtttctctaa ggacccagaa tgtatcttga gaagagatga catcaacaac  480
ccaggtggtt ctgaatggtt gccaggtggt tatttgaact cagctaaaaa ttgcttgaac  540
gttaactcca ataagaaatt gaatgatact atgattgtct ggagagatga aggcaacgat  600
gacttgccat tgaataagtt gacattggat caattgagaa agagagtttg gttggtcggt  660
tacgcattag aagaaatggg tttggaaaaa ggttgtgcca tagctatcga tatgcctatg  720
catgtagacg ctgtagttat ctatttggct attgttttag caggttacgt cgtagtttct  780
atagctgatt cattttccgc accagaaatc tcaactagat tgagattatc caaagcaaag  840
gccatattca cacaagatca catcatcaga ggtaaaaaga gaatcccttt atactcaaga  900
gtcgtagaag ccaaatcccc aatggctata gttatccctt gtagtggttc taacattggt  960
gcagaattaa gagatggtga catatcttgg gattactttt tggaaagagc caaagaattc  1020
aagaattgcg aattcactgc cagagaacaa ccagttgatg cttacactaa catttttgttc  1080
tccagtggta ctacaggtga accaaaagca ataccttgga cacaagccac ccctttaaag  1140
gccgctgcag atggttggtc acatttggat attagaaaag gtgacgtcat agtatggcca  1200
actaatttgg gttggatgat gggtccttgg ttggtttatg ctagtttgtt aaatggtgcc  1260
tctattgctt tatacaacgg tagtccattg gtttctggtt tcgctaaatt tgtccaagat  1320
gcaaaagtaa caatgttggg tgttgtccct tcaatcgtta gaagttggaa gtctacaaat  1380
tgtgtctcag gttatgattg gtccaccatc agatgctttt cttcatccgg tgaagcctct  1440
aatgtcgacg aatatttgtg gttaatgggt agagctaact acaagccagt tatcgaaatg  1500
tgtggtggta ccgaaattgg tggtgcattc tcagccggtt cctttttaca agctcaatca  1560
ttgagttctt tttcatccca atgtatgggt tgcacattgt acatcttgga taagaacggt  1620
tacccaatgc ctaaaaataa gccaggtatt ggtgaattgg ctttaggtcc tgttatgttc  1680
ggtgcatcta aaacattgtt gaacggtaac catcacgatg tatacttcaa gggtatgcca  1740
accttaaatg gtgaagtttt gagaagacat ggtgacatat tcgaattaac ctcaaacggt  1800
tactaccatg cccacggtag agctgatgac actatgaaca tcggtggtat caaaatcagt  1860
tctatcgaaa tcgaaagagt atgtaacgaa gttgatgaca gagtctttga aaccactgca  1920
attggtgttc caccattggg tggtggtcca gaacaattag taatcttttt cgttttgaag  1980
gattctaacg acacaaccat agatttgaac caattgagat tatcttttaa cttgggttta  2040
caaaagaaat tgaacccatt attcaaagtt actagagtag ttccattgtc atccttacct  2100
```

-continued

```
agaactgcta caaacaagat tatgagaaga gtcttgagac aacaattcag tcattttgaa  2160
ggttctggt                                                          2169

SEQ ID NO: 188          moltype = DNA  length = 2556
FEATURE                 Location/Qualifiers
source                  1..2556
                        mol_type = other DNA
                        organism = synthetic construct
SEQUENCE: 188
atgaagttat ctactaaatt gtgttggtgc ggtattaagg gtagattaag accacaaaag  60
caacaacaat tgcataacac aaacttgcaa atgaccgaat tgaagaaaca aaagactgct  120
gaacaaaaga ctagaccaca aaacgttggt attaaaggta tccaaatcta tatccctaca  180
caatgtgtca atcaatctga attggaaaag tttgatggtg tatcacaggg taaatacact  240
atcggtttag gtcaaacaaa catgtctttc gtaaacgata gagaagacat ctattctatg  300
tcattgactg ttttgtccaa gttgataaaa agttacaaca tcgatacaaa caagattggt  360
agattggaag ttggtaccga aactttgatc gataagtcca agagtgtcaa gtctgtattg  420
atgcaattgt tcggtgaaaa taccgatgtt gaaggtatcg acactttaaa tgcttgttat  480
ggtggtacta acgcattatt caattcattg aactggatcg aatccaatgc ctgggatggt  540
agagatgcta ttgttgtctg cggtgacatc gctatctatg acaaaggtgc tgcaagacca  600
accggtggtg caggtactgt tgccatgtgg ataggtccag atgcacctat cgtttttgac  660
tctgtcagag catcatacat ggaacatgcc tacgatttct acaaaccaga cttcacctcc  720
gaatatcctt acgttgatgg tcacttttct ttgacttgtt acgtcaaggc tttggaccaa  780
gtatacaagt cttactctaa gaaagcaata tctaagggtt tggtttcaga tccagctggt  840
tccgacgcat taaacgtctt gaagtacttc gattacaacg ttttccatgt ccctacatgc  900
aagttggtta ccaagtctta cggtagattg ttgtacaacg atttcagagc taacccacaa  960
ttgttccctg aagtcgacgc tgaattagca actagagatt acgacgaatc tttgacagat  1020
aagaacatcg aaaagacttt cgtaaacgtt gcaaagccat tccacaaaga aagagttgcc  1080
caatcattaa ttgtccctac aaataccggt aacatgtata cagcctcagt ttacgccgct  1140
tttgcttcct tgttaaatta tgtaggtagt gatgacttgc aaggtaaaag agttggttta  1200
ttctcctatg gtagtggttt agcagcctct ttgtactctt gtaagattgt aggtgacgtt  1260
caacacatta ttaaggaatt ggacatcact aataagttgg ctaagagaat cactgaaaca  1320
ccaaaggatt atgaagctgc aatcgaattg agagaaaacg cacatttgaa gaaaaatttc  1380
aaacctcaag gtagtataga acacttgcaa tctggtgtct actacttaac aaacatcgat  1440
gacaaattca gaagatcata cgatgttaaa aagaaattgt ctggtggtgg tggttctggt  1500
ggtggtggtt ctggtggtgg tggtagtgct gaagcatggt ataatttggg taacgcttat  1560
tacaagcagg gtgactacca aaaagcaatc gaatattacc aaaaggcctt ggaattagac  1620
ccaaataacg ccgaagcttg gtacaatttg ggtaatgcat actataaaca gggtgactat  1680
caaaaggcta tcgaatacta ccaaaaggca ttggaattag accctaataa cgcagaagcc  1740
tggtacaatt tgggtaacgc ctactataag cagggtgact atcaaaaagc catagaagac  1800
taccaaaagg ctttggaatt agatccaaat aacttgcaag ctgaagcatg gaaaaatttg  1860
ggtaatgcct actacaaaca gggtgactac caaaaggcaa ttgaatatta tcaaaaagcc  1920
ttggaattag atcctaataa cgcctcagct tggtataatt tgggtaatgc ctattataag  1980
cagggtgact accagaaagc cattgaatat tatcaaaagg ctttagaatt ggatccaaat  2040
aacgcaaaag cctggtatag acgtggtaat gcctactaca agcagggtga ctatcagaag  2100
gctattgaag attatcaaaa agctttggaa ttggatccaa acaacagatc cagaagtgct  2160
ggtggtggtg gttctggtgg tggtggttct ggtggtggtg gtgcttcttt gggtcctttg  2220
ccacctggtt gggaagtaag atccacagtt agtggtagaa tctatttcgt tgatcataac  2280
aacagaacta cacaattcac cgacccaaga ttgcacggtt ctgctggttc agccgctggt  2340
tctggtgaat ttggttccgc agaagcagcc gctaaggaag cagccgctaa agccggttcc  2400
gctggtagtg cagccggtag tggtgaattt ggttctggtg ctatgggtcc attaccacct  2460
ggttgggaaa agagaacaga ttctaacggt agagtctact tcgtaaacca taataccaga  2520
attactcaat gggaagatcc tagatctggt tcaggt                            2556

SEQ ID NO: 189          moltype = DNA  length = 2487
FEATURE                 Location/Qualifiers
source                  1..2487
                        mol_type = other DNA
                        organism = synthetic construct
SEQUENCE: 189
atggtagccg ttagaagaaa ggctttgtct atcttagccg aagctccagt tttggcatca  60
gatagattac cttacaagaa ctacgattac gacagagtat ttggtgcttg ttgcgaaaac  120
gttattggtt atatgccatt gcctgtcggt gtaatcggtc cattagttat tgatggtaca  180
tcttaccata tccctatggc aactacagaa ggttgtttgg ttgcatcagc catgagaggt  240
tgcaaggcaa ttaatgctgg tggtggtgct accactgttt taaccaaaga tggtatgact  300
agaggtccag ttgtcagatt tcctactttg aagagatccg gtgcttgtaa aatatggtta  360
gatagtgaag aaggtcaaaa tgccatcaaa aaggctttta actccactag tagattcgca  420
agattgcaac atattcaaac atgcttagcc ggtgacttgt tgtttatgag attcagaaca  480
accactggtg acgctatggg tatgaatatg atatctaagg gtgtcgaata ctcattgaag  540
caaatggtag aagaatacgg ttgggaagat atggaagtag tttctgtttc aggcaactac  600
tgtactgaca aaaagccagc tgcaattaac tggatagaag gtcgtggtaa atctgtcgta  660
gctgaagcaa caatacctgg tgacgttgtt agaaaggttt tgaaatctga cgtatcagct  720
ttggttgaat tgaacatcgc taaaaatttg gttggttccg ccatggctgg tagtgtcggt  780
ggttttaatg cacatgccgc taacttagtt acagcagtct tcttggcctt aggtcaagat  840
ccagctcaaa acgtagaatc ttcaaactgt atcaccttga tgaaagaagt tgatggtgac  900
ttaagaatat ccgttagtat gccatcaata gaagtcggta caatcggtgg tggtaccgtc  960
ttggaacctc aaggtgcaat gttagatttg ttaggtgtta gaggtccaca tgcaactgcc  1020
cctggtacaa atgctagaca attggcaaga attgtcgctt gtgcagtatt agctggtgaa  1080
ttgtccttat gcgcagcctt ggctgcaggt cacttagttc aaagtcatat gacacacaac  1140
agaaagttgt ctggtggtgg tggttctggt ggtggtggtt ctggtggtgg tggtagtgcc  1200
```

```
gaagcttggt ataatttggg taacgcatat tacaagcagg gtgactacca aaaggccatc  1260
gaatactacc aaaaggcttt ggaattggac ccaaataacg cagaagcctg gtacaatttg  1320
ggtaatgctt actataaaca gggtgactat caaaaggcaa ttgaatatta ccaaaaggcc  1380
ttggaattag accctaataa cgctgaagca tggtacaatt tgggtaacgc ctactataag  1440
cagggtgact atcaaaaagc tattgaagac taccaaaagg cattggaatt agatccaaat  1500
aacttgcaag ccgaagcttg gaaaaatttg ggtaacgctt actacaaaca gggtgactac  1560
caaaaagcta ttgaatacta tcaaaaagct ttggaattgg accctaataa cgcatctgcc  1620
tggtataatt tgggtaatgc ttattataaa cagggtgact accagaaggc aatagaatac  1680
tatcaaaaag ccttggaatt agacccaaat aacgctaaag catggtatag acgtggtaat  1740
gcttactata agcagggtga ctaccagaaa gctatagaag attatcaaaa ggcattggaa  1800
ttggatccta acaacagatc tagatcagct ggtggtggtg gttctggtgg tggtggttct  1860
ggtggtggtg gtgcttccag ttattaccat caccatcacc atcacttgga atccactagt  1920
ttatacaaaa aggcaggttc agaatttttc agaagagaaa gaaataagat ggccgctgca  1980
aaatgtagaa acagaagaag agaattgaca gataccttac aagctgaaac cgatcaattg  2040
gaagacgaaa agtctgcatt gcaaactgaa atagccaatt tgttgaagga aaaggaaaag  2100
ttggaattca ttttagccgc tcatagacca gcttgcaaaa ttcctgatga cttgggtttc  2160
ccagaagaaa tgtctttaga aggttccgca ggtagtgcag ccggttccgg tgaatttggt  2220
agtgctgaag ctgcagccaa ggaagctgca gccaaagctg gttctgcagg ttcagctgca  2280
ggttccggtg aattcggttc ttcatactat caccatcacc atcatcactt ggaatctacc  2340
tcattataca aaaaggctgg ttccggtagt caaaaggttg aatctttgaa gcaaaagatt  2400
gaagaattga agcaaagaaa agcccaattg aagaatgata tcgctaactt agaaaaggaa  2460
atcgcctacg ctgaaactgg ttctggt                                     2487

SEQ ID NO: 190         moltype = DNA  length = 3147
FEATURE                Location/Qualifiers
source                 1..3147
                       mol_type = other DNA
                       organism = synthetic construct
SEQUENCE: 190
atgagtttac catttttgac atctgctcct ggtaaagtta ttatattcgg tgaacatagt  60
gccgtctata ataagccagc tgtcgctgca tctgtatcag ctttgagaac atacttgttg  120
atctctgaat cttcagcacc tgataccatc gaattggatt tcccagacat ctcattcaat  180
cacaagtggt ccattaatga tttcaacgct atcaccgaag accaagtaaa ctcacaaaag  240
ttggccaaag ctcaacaagc aactgatggt ttgtcacaag aattagtttc cttgttagac  300
ccattgttgg ctcaattgtc cgaaagtttc cattaccacg ccgctttctg tttcttgtac  360
atgttcgttt gtttatgccc tcatgctaag aatatcaaat tttctttgaa gtctactttg  420
ccaattggtg caggtttagg ttccagtgcc tctatatcag tttccttagc attggccatg  480
gcttatttgg gtggtttgat aggtagtaac gatttggaaa agttgtctga aaacgacaag  540
catatcgtca accaatgggc attcatcggt gaaaaatgca ttcacggtac tcctagtggt  600
atagataatg cagttgccac atatggtaac gctttgttat tcgaaaagga ctctcataac  660
ggtaccatca acactaacaa cttcaagttc ttggatgact ttcctgcaat accaatgatc  720
ttgacttaca caagaattcc aagatctact aaagatttgg tagctagagt cagagtattg  780
gttacagaaa agttccctga agttatgaag ccaatcttgg atgcaatggg tgaatgtgcc  840
ttgcaaggtt tggaaatcat gacaaagttg tcaaagtgca agggtactga tgacgaagct  900
gttgaaacaa ataacgaatt gtacgaacaa ttgttggaat tgatcagaat caatcatggt  960
ttgttagttt caattggtgt ctcccaccca ggtttagaat tgataaagaa cttgtcagat  1020
gacttaagaa tcggttccac aaaattgacc ggtgctggtg gtggtggttg ttctttgacc  1080
ttgttaagaa gagatatcac tcaagaacaa atcgacagtt ttaaaaagaa attgcaagat  1140
gacttctctt acgaaacttt cgaaacagat ttgggtggta ctggttgttg cttgttgtca  1200
gctaagaatt tgaacaaaga tttgaagatt aaatccttgg ttttccaatt gttcgaaaat  1260
aagactacaa ccaagcaaca aatcgatgac ttgttgttgc ctggtaatac aaacttgcca  1320
tggacctcaa aattatctgg tggtggtggt tctggtggtg gtggttctgg tggtggtggt  1380
agtgctgaag catggtataa tttgggtaac gcatattaca agcagggtga ctaccaaaag  1440
gctatcgaat actaccaaaa ggcattggaa ttggacccta ataacgccga agcttggtac  1500
aatttgggta atgcttacta taaacagggt gactatcaaa aggccattga atattaccaa  1560
aaggctttgg aattggaccc aaataacgca gaagcctggt acaatttggg taacgcttac  1620
tataagcagg gtgactatca aaaagcaatt gaagactacc aaaaggcctt agaattggat  1680
cctaataact tgcaagctga agcatggaaa aatttgggta acgcttatta taaacagggt  1740
gactaccaaa aagccattga atactatcaa aaagcattgg aattggatcc aaataacgcc  1800
tctgcttggt ataatttggg taatgcttat tataagcagg gtgactacca gaaagccata  1860
gaatactatc aaaaagcttt ggaattagac cctaataacg caaaagcctg gtatagacgt  1920
ggtaatgctt actacaaaca gggtgactat cagaaggcaa tagaagatta tcaaaaagct  1980
ttagaattag acccaaataa cagaagtaga tctgctggtg gtggtggttc tggtggtggt  2040
ggttctggtg gtggtggtgc ttctatggaa cctgcaatgg aaccagaaac attggaagcc  2100
agaatcaata gagctaccaa tcctttgaac aaggaattgg attgggcttc tattaatggt  2160
ttctgtgaac aattgaacga agacttcgaa ggtccacctt tagcaacaag attattggcc  2220
cataaaattc aatcaccaca agaatgggaa gcaatacaag ccttaaccgt cttggaaact  2280
tgtatgaagt cctgcggtaa aagattccac gatgaagttg gtaaattcag atttttgaac  2340
gaattgatca aggttgtctc acctaagtat ttgggtagta gaacatctga aaaggttaaa  2400
aacaagatct tggaattgtt gtactcctgg accgtaggtt taccagaaga agttaagatc  2460
gctgaagcat accaaatgtt gaagaaacaa ggtattgtta agtcaggttc cgccggtagt  2520
gcagccggtt ctggtgaatt cggttctgca gaagctgcag ccaaggaagc tgcagccaaa  2580
gctggttcag caggttccgc tgcaggttct ggtgaatttg gttcaggtgc aatgggttcc  2640
atggccgaag ctgaaggtga aagtttggaa tcttggttaa ataaggctac aaatccatca  2700
aacagacaag aagattggga atatatcatt ggtttctgtg accaaatcaa taaggaattg  2760
gaaggtcctc aaatagctgt tagattattg gcacataaga tccaatctcc acaagaatgg  2820
gaagccttac aagctttgac tgttttagaa gcttgtatga agaattgcgg tagaagattt  2880
cacaacgaag tcggtaaatt cagatttttg aatgaattaa ttaaggtagt tagtccaaaa  2940
tacttaggtg acagagtttc tgaaaaggtt aagaccaaag tcatagaatt gttgtactct  3000
```

```
tggactatgg ccttgcctga agaagctaag atcaaagatg cataccatat gttgaagaga  3060
caaggtatag tccaatcaga tccacctatc ccagtagaca gaactttgat tccatctcca  3120
ccaccaagac ctaaaaatgg ttccggt                                      3147

SEQ ID NO: 191         moltype = DNA  length = 2610
FEATURE                Location/Qualifiers
source                 1..2610
                       mol_type = other DNA
                       organism = synthetic construct
SEQUENCE: 191
atgtccgaat taagagcttt tagtgcacct ggtaaagcct tgttagctgg tggttatttg  60
gttttggata caaagtacga agcattcgtt gtcggtttgt cagccagaat gcatgcagtc  120
gcccaccctt acggttcttt acaaggttct gataagttcg aagtaagagt caagtctaag  180
caattcaagg acggtgaatg gttataccat atatctccaa agtcaggttt tattcctgtt  240
tccataggtg gtagtaaaaa tccattcatc gaaaaggtta ttgcaaacgt cttttcttac  300
ttcaagccta acatggatga ctactgtaac agaaacttgt tcgtcatcga tatattctct  360
gatgacgctt atcattctca agaagactca gtaactgaac acagaggtaa tagaagattg  420
tcctttcata gtcacagaat tgaagaagtt ccaaaaaccg gtttaggttc ttcagctggt  480
ggtttagtca ctgtattgac tacagcttta gcatcctttt tcgttagtga tttggaaaac  540
aacgtagaca agtacagaga agttattcat aatttggcac aagtagccca ctgccaagca  600
caaggtaaaa tcggttccgg ttttgatgtt gctgcagccg cttatggttc aattagatac  660
agaagattcc cacctgcttt gatatctaat ttgccagata tcggttctgc tacatatggt  720
tcaaagttgg cacatttggt tgatgaagaa gactggaaca tcacaattaa atccaaccat  780
ttgcctagtg gtttgacctt atggatgggt gacattaaga atggttctga aactgttaag  840
ttggtccaaa aagtaaagaa ctggtacgat tctcatatgc cagaatcatt gaagatctac  900
acagaattag accatgctaa ttccagattc atggatggtt tgagtaaatt agacagattg  960
catacccacg atgactactc tgatcaaatc ttcgaatcat tggaaagaaa cgactgtact  1020
tgccaaaaat acccagaaat cacagaagta agagatgccg ttgctaccat aagaagatct  1080
tttagaaaga tcactaagga atcaggtgca gatatcgaac cacctgttca aacatctttg  1140
ttagatgact gtcaaacctt gaagggtgtc ttaacttgct tgattccagg tgctggtggt  1200
tatgatgcaa tagccgtcat cactaaacaa gatgtagact tgagagctca aacagcaaac  1260
gataagagat tttcaaaggt ccaatggtta gatgtaaccc aagctgactg gggtgttaga  1320
aaagaaaagg atcctgaaac ttacttggac aaaaagttat ctggtggtgg tggttctggt  1380
ggtggtggtt ctggtggtgg tggtagtgct gaagcatggt acaatttggg taacgcatac  1440
tacaagcagg gtgactacca aaaggccata gaatactacc aaaaggcttt ggaattggac  1500
ccaaataacg ccgaagcttg gtataatttg ggtaatgctt attataaaca gggtgactat  1560
caaaaggcaa tcgaatacta ccaaaaggcc ttggaattag accctaataa cgcagaagcc  1620
tggtataatt tgggtaacgc ttattataag cagggtgact atcaaaaagc tatcgaagac  1680
taccaaaagg cattggaatt agatccaaat aacttgcaag ctgaagcatg gaagaatttg  1740
ggtaacgctt actataaaca gggtgactac caaaaagcca ttgaatatta tcaaaaagct  1800
ttggaattgg atcctaataa cgcctctgct tggtacaatt tgggtaatgc ttactataag  1860
cagggtgact atcagaaggc tattgaatat tatcaaaagg ctttagaatt ggaccctaat  1920
aacgcaaagg cctggtacag acgtggtaac gcttattaca aacagggtga ctaccagaaa  1980
gctattgaag attatcaaaa ggcattggaa ttggatccta acaacagatc cagaagtgct  2040
ggtggtggtg gttctggtgg tggtggttct ggtggtggtg gtgcttccag ttattaccat  2100
caccatcacc atcacttgga atctacatca ttatacaaaa aggctggttc cggtagtcaa  2160
aaggttgaag aattgaaaaa taagatagcc gaattggaaa acagaaacgc tgttaaaaag  2220
aacagagtcg cacatttgaa acaagaaata gcctacttga aggatgaatt agcagcccat  2280
gaatttgaag gttctgccgg ttcagctgca ggttctggtg aattcggttc agctgaagcc  2340
gctgcaaaag aagccgctgc aaaggccggt tccgctggta gtgccgctgg ttctggtgaa  2400
tttggttctt catactatca ccatcaccat catcacttgg aatctacttc attatataaa  2460
aaggccggtt ccggtagttt cgaaaacgtt acacatgaat tcattttggc taccttggaa  2520
aacgaaaacg caaagttaag aagattggaa gccaagttgg aaagagaatt agctagattg  2580
agaaatgaag ttgcatggtt aggttctggt                                   2610

SEQ ID NO: 192         moltype = DNA  length = 3033
FEATURE                Location/Qualifiers
source                 1..3033
                       mol_type = other DNA
                       organism = synthetic construct
SEQUENCE: 192
atgacagttt ataccgcttc tgtcaccgca cctgtaaata ttgctacttt gaaatactgg  60
ggtaaaagag atactaagtt gaatttgcca acaaactctt caatctcagt tacattgtcc  120
caagatgact taagaacctt gacttctgct gcaactgctc ctgaattcga aagagataca  180
ttgtggttga atggtgaacc acattctatc gacaacgaaa gaactcaaaa ctgtttgaga  240
gatttgagac aattgagaaa ggaaatggag agtaaggatg cttctttgcc tacattgagt  300
caatggaagt tgcacatagt ttctgaaaac aacttcccaa ccgccgctgg tttggcatcc  360
agtgcagccg gtttcgctgc attagtctct gcaatcgcca agttgtacca attgccacaa  420
agtacatctg aaatcagtag aatcgctaga aaaggttcag gttccgcatg tagatcttta  480
tttggtggtt acgtcgcatg ggaaatgggt aaagccgaag acggtcatga ttcaatggcc  540
gtacaaatag ctgactcttc agattggcct caaatgaaag cttgcgtctt ggttgtctca  600
gacatcaaaa aggatgtatc cagtacacaa ggcatgcaat tgactgttgc aacatccgaa  660
ttgtttaaag aaagaatcga acacgtagtt ccaaaaagat tcgaagtcat gagaaaggct  720
atcgtagaaa aggatttcgc caccttcgct aaggaaacta tgatggacag taactctttc  780
catgcaactt gtttggattc atttccacct attttctata tgaacgacac ctcaaagaga  840
ataatctcct ggtgccacac tatcaaccaa ttctacggtg aaacaatcgt tgcttacacc  900
ttcgatgcag gtcctaatgc cgtcttgtat tacttagccg aaaacgaatc aaagttgttc  960
gcttttatat ataagttgtt tggttccgtt ccaggttggg ataaaaagtt cactacagaa  1020
caattggaag cttttaatca tcaattcgaa tcttcaaact ttactgccag agaattggac  1080
```

-continued

```
ttagaattgc aaaaggatgt agctagagtt atcttgaccc aagttggttc aggtcctcaa  1140
gaaactaacg aatccttgat agatgctaag acaggtttgc caaaagaaaa attgtctggt  1200
ggtggtggtt ctggtggtgg tggttctggt ggtggtggta gtgctgaagc atggtataat  1260
ttgggtaacg cttattacaa gcagggtgac taccaaaagg ccatcgaata ctaccaaaag  1320
gctttggaat tggaccctaa taacgccgaa gcttggtaca atttgggtaa tgcctactat  1380
aaacagggtg actatcaaaa agcaattgaa tattaccaaa aggccttgga attggaccca  1440
aataacgcag aagcctggta caatttgggt aacgcctact ataagcaggg tgactatcaa  1500
aaggctatcg aagattacca aaaggcatta gaattggatc ctaataactt gcaagctgaa  1560
gcatggaaaa atttgggtaa tgcctattat aaacagggtg actaccaaaa agctattgaa  1620
tactatcaaa aagctttaga attagaccca aataacgcct cagcttggta taatttgggt  1680
aatgcatact acaaacaggg tgactatcag aaggcaattg aatactatca aaaggcatta  1740
gaattagatc ctaataacgc aaaagcctgg tatagacgtg gtaatgccta ctacaagcag  1800
ggtgactatc agaaggcgat tgaagactac caaaaggcat tggaattgga tccaaacaac  1860
agatcaagat ccgctggtgg tggtggttct ggtggtggtg gttctggtgg tggtggtgct  1920
tctgcaatgg ccgatttgga acaaaaggta ttggaaatgg aagctagtac atatgacggt  1980
gtttttattt ggaagatctc tgatttccca agaaaaagac aagaagctgt tgcaggtaga  2040
atccctgcta tttttagtcc agcattctac acctctagat acggttacaa gatgtgtttg  2100
agaatatatt tgaatggtga cggtactggt agaggtactc atttgtcttt gtttttcgtc  2160
gtaatgaagg gtcctaatga tgctttgttg agatggcctt ttaatcaaaa ggttaccttg  2220
atgttgttgg atcaaaacaa cagagaacac gttatcgacg cttttagacc tgatgtcact  2280
tccagttctt tccaaagacc agttaatgat atgaacattg cttctggttg tcctttgttt  2340
tgcccagtct caaagatgga agctaaaaat tcctatgtta gagatgacgc catcttcatt  2400
aaggctatcg ttgatttgac tggtttaggt tcagcaggtt ccgccgctgg ttctggtgaa  2460
tttggttccg ccgaagcagc cgctaaggaa gcagccgcta aagcaggtag tgccggttct  2520
gcagccggct ctggcgaatt tggtagtgcc tctattaaat tgcaatcatc cgacggtgaa  2580
atcttcgaag ttgatgtcga aatagcaaag caatctgtta ccataaaaac tatgttggaa  2640
gatttgggta tggatgacga aggtgacgat gatccagttc ctttgccaaa tgtcaacgct  2700
gcaatattga agaaagttat tcaatggtgc acacatcaca aggacgatcc acctccacct  2760
gaagacgatg aaaataagga aaagagaact gacgatattc cagtatggga ccaagaattc  2820
ttgaaggttg atcaaggtac attgttcgaa ttgatcttgg ccgctaacta tttggacatc  2880
aagggtttgt tagatgtaac atgtaaaacc gttgctaaca tgatcaaggg taaaacacca  2940
gaagaaatca gaaagacctt taatattaag aatgatttca ctgaagaaga agaagcacaa  3000
gttagaaagg aaaaccaatg gtgcggttct ggt                               3033
```

```
SEQ ID NO: 193          moltype = DNA  length = 2160
FEATURE                 Location/Qualifiers
source                  1..2160
                        mol_type = other DNA
                        organism = synthetic construct
SEQUENCE: 193
atgactgctg ataataactc tatgccacat ggtgccgtat cttcatacgc taagttggtt  60
caaaaccaaa cacctgaaga tatcttggaa gaattcccag aaatcatccc tttgcaacaa  120
agaccaaaca ctagatccag tgaaacatcc aacgatgaaa gtggtgaaac ctgtttttca  180
ggtcatgacg aagaacaaat taaattgatg aacgaaaact gcatcgtatt ggattgggat  240
gacaatgcaa taggtgccgg tactaagaaa gtttgtcatt tgatggaaaa catagaaaag  300
ggtttgttgc acagagcttt ctccgttttt atattcaatg aacagggtga attgttattg  360
caacaaagag caacagaaaa gatcaccttt ccagatttgt ggactaatac atgttgctct  420
catcctttgt gcattgatga cgaattaggt ttgaagggta aattggatga caaaattaag  480
ggtgctataa ctgctgcagt cagaaaatta gatcatgaat tgggtatacc agaagacgaa  540
accaagactc gtggtaaatt ccatttctta aacagaatcc actatatggc tccatctaac  600
gaaccttggg gtgaacatga aatcgattac atcttatttt acaagattaa tgcaaaggaa  660
aacttgacag ttaacccaaa cgttaatgaa gtcagagatt tcaaatgggt ttctcctaat  720
gatttgaaga ccatgtttgc tgacccatca tataagttta ctccttggtt caagatcatc  780
tgtgaaaact acttgtttaa ctggtgggaa caattagatg acttgtctga agttgaaaac  840
gatagacaaa tccatagaat gttgaaattg tctggtggtg gtggttctgg tggtggtggt  900
tctggtggtg gtggtagtgc cgaagcttgg tacaatttgg gtaacgctta ctacaagcag  960
ggtgactacc aaaaggcaat cgaatactac caaaaggcct tggaattgga cccaaataac  1020
gcagaagcct ggtataattt gggtaatgca tattataaac agggtgacta tcaaaaggct  1080
attgaatatt accaaaaggc attggaattg gaccctaata acgctgaagc atggtataat  1140
ttgggtaacg cctattataa gcagggtgac tatcaaaaag ccatcgaaga ctaccaaaag  1200
gctttggaat tggatccaaa caacttacaa gccgaagctt ggaagaattt gggtaacgct  1260
tattacaaac agggtgacta ccaaaaagct attgaatact atcaaaaagc cttagaatta  1320
gaccctaata acgcatctgc ctggtacaat ttgggtaatg cctattacaa gcagggtgac  1380
tatcagaagg ctattgaata ctaccaaaaa gcattggaat tggatccaaa taacgctaag  1440
gcatggtaca gacgtggtaa tgcctattac aagcagggtg actatcaaaa ggcgattgaa  1500
gattatcaaa aagctttgga attggatcct aacaacagat ctagatcagc tggtggtggt  1560
ggttctggtg gtggtggttc tggtggtggt ggtgcttctt catattacca tcaccatcac  1620
catcacttag aatccacaag tttgtacaaa aaggctggtt ctggttcaaa caccgttaag  1680
gaattaaaga actacatcca agaattggaa gaaagaaacg cagaattgaa aaatttgaag  1740
gaacatttga agtttgccaa ggctgaatta gaattcgaat tggccgctca caaatttgaa  1800
ggttccgctg gtagtgcagc cggttccggt gaattcggta gtgcagaagc tgcagccaaa  1860
gaagctgcag ccaaggctgg ttctgcaggt tcagctgcag gttctggtga atttggttcc  1920
agttactatc accatcacca tcatcactta gaatccacta gtttgtataa aaaggccggt  1980
tctggttcac aaaaagtcgc acaattaaag aatagagtag cctacaagtt gaaggaaaac  2040
gctaagttgg aaaacattgt cgcaagatta gaaaacgata atgccaactt ggaaaaagac  2100
atcgctaatt tggaaaagga tattgcaaac ttggaaagag atgttgccag aggttctggt  2160
```

```
SEQ ID NO: 194          moltype = DNA  length = 2403
FEATURE                 Location/Qualifiers
```

```
source                  1..2403
                        mol_type = other DNA
                        organism = synthetic construct
SEQUENCE: 194
atggaagcta agatagatga attgataaat aacgacccag tttggtcttc acaaaacgaa  60
tccttgatca gtaagccata caaccatatc ttgttaaaac ctggtaaaaa tttcagatta  120
aatttgatcg tacaaatcaa cagagttatg aatttgccta aggatcaatt ggctatcgtt  180
tctcaaatag tcgaattgtt gcataactcc agtttgttga tcgatgacat cgaagataac  240
gcaccattga gaagaggtca aactacatcc cacttaattt ggggtgtccc tagtactatt  300
aataccgcaa actacatgta cttcagagcc atgcaattgg tatcacaatt gaccactaag  360
gaaccattgt accattggtt gatcacaatt tttaacgaag aattgattaa tttgcacaga  420
ggtcaaggtt tggatatcta ttggagagac ttcttaccag aaattatacc tacccaagaa  480
atgtacttga acatggtaat gaataagact ggtggtttgt ttagattgac cttgagatta  540
atggaagctt tgtctccatc ttcacatcac ggtcattcat tggttccttt cataaacttg  600
ttgggtatca tctatcaaat cagagatgac tacttgaatt tgaaggattt ccaaatgtcc  660
agtgaaaagg gtttcgcaga agacataact gagggtaaat tgtcattccc aatcgtccat  720
gccttaaact tcacaaaaac caagggtcaa accgaacaac acaatgaaat cttaagaatt  780
ttgttattga gaacttctga taaggacata aagttgaagt tgatccaaat cttggaattc  840
gataccaact cattggctta cactaagaac ttcatcaacc aattggttaa catgattaag  900
aatgataacg aaaataagta cttgccagat ttggcctccc atagtgacac tgctacaaat  960
ttgcacgatg aattgttgta catcatcgac catttgtccg aattgaaatt atctggtggt  1020
ggtggttctg gtggtggtgg ttctggtggt ggtggtagtg cagaagcctg gtacaacttg  1080
ggtaacgctt actacaagca gggtgactac caaaaggcta tcgaatacta ccaaaaggca  1140
ttggaattag acccaaataa cgctgaagca tggtacaact taggcaacgc atattataaa  1200
cagggtgact atcaaaaggc catagaatac taccaaaagg ctttggaatt ggaccctaat  1260
aacgccgaag cttggtacaa cttgggtaat gcttattaca agcagggtga ctatcaaaaa  1320
gcaattgaag actaccaaaa agccttggaa ttagatccaa ataacttgca agcagaagcc  1380
tggaagaact taggcaacgc atactataaa cagggtgact accaaaaagc cattgaatat  1440
tatcaaaaag ctttggaatt agaccctaat aacgcttctg cttggtataa cttaggcaat  1500
gcctattata agcagggtga ctatcagaaa gctattgaat attatcaaaa ggccttggaa  1560
ttggacccaa ataacgccaa ggcttggtac agacgtggta acgcatacta caaacagggt  1620
gactatcaga aggctatcga agattatcaa aaagcattag aattagatcc taataacaga  1680
tctagatcag ctggtggtgg tggttctggt ggtggtggtt ctggtggtgg tggtgcttct  1740
ttgtgtacta tgaaaaaggg tccatctggt tacggtttta atttgcattc tgataagtca  1800
aagcctggtc aattcataag atcagttgat ccagactccc ctgcagaagc cagtggtttg  1860
agagctcaag atagaattgt cgaagtaaat ggtgtctgca tggaaggtaa acaacacggt  1920
gacgttgttt ctgctattag agctggtggt gacgaaacta agttattggt agttgacaga  1980
gaaggttccg ccggtagtgc tgcaggttct ggtgaatttg gttcagctga agccgctgca  2040
aaagaagccg ctgcaaaggc cggttctgct ggttcagccg ctggttctgg tgaattcggt  2100
tcttcatccg gtgctataat ctatacagtt gaattgaaga gatacggtgg tccattaggt  2160
attactatat ctggtacaga agaaccattc gatcctatca tcatcagttc tttgactaag  2220
ggtggtttag ctgaaagaac aggtgcaatc catattggtg acagaatatt ggctatcaat  2280
tcatccagtt tgaaaggtaa accattgtca gaagctatcc acttattgca aatggcaggt  2340
gaaaccgtta ctttgaaaat caaaaagcaa acagatgcac aacctgcctc ttcaggttct  2400
ggt                                                                2403

SEQ ID NO: 195          moltype = DNA  length = 2658
FEATURE                 Location/Qualifiers
source                  1..2658
                        mol_type = other DNA
                        organism = synthetic construct
SEQUENCE: 195
atgaatcatt tgagagccga aggaccagct tctgtcttag caataggtac tgccaatcca  60
gagaacatct tgttacaaga tgaatttcct gactattact tcagagttac caaatccgag  120
catatgacgc agttgaagga aaagtttaga aagatctgtg ataagagtat gatcagaaag  180
aggaactgct tcttaaacga agagcatttg aagcaaaatc ctagattagt ggaacacgag  240
atgcaaacat tggatgctag gcaggacatg ttagttgtcg aagttcctaa attgggtaaa  300
gatgcatgtg ccaaagctat taaggaatgg ggtcaaccca agtctaagat aactcatttg  360
atttttacta gtgctagcac tacagatatg cctggtgcag actatcactg tgccaaacta  420
cttggtttat cgccctctgt gaagagagtt atgatgtatc aactaggttg ctacggtggt  480
ggtactgtac ttagaatcgc taaagacatt gcagaaaata acaagggtgc cagggtcttg  540
gctgtatgtt gcgatattat ggcttgcttg tttagaggtc catcagaatc cgatttggag  600
ctgttggttg gtcaagctat tttcggtgac ggtgctgcag ctgttattgt tggtgcagaa  660
cctgatgagt cagtcggtga aagaccaatc tttgaattgg tttctaccgg tcaaacgatt  720
ttaccaaata gtgaaggtac aataggtggt catatcagag aagctggttt gatattcgat  780
ttgcacaaag acgttcctat gctaatatct aacaacatcg aaaagtgtct gatcgaggct  840
tttacccccca tcggtatttc cgattggaat agtatattct ggatcacgca tccaggtggt  900
aaagcaatcc tggataaggt tgaagagaag ctgcatttga agtctgataa gtttgtcgac  960
agcagacatg tattgtcgga acacggtaac atgtcttcat ccacagtgct gttcgttatg  1020
gatgaactta gaaagagatc tttggaagag ggtaaaagca ccacgggtga cggttttgaa  1080
tggggtgttc tttttggatt cggccccggt ttgaccgtcg aaagagtagt tgttagatct  1140
gtaccaatta aatacaagtt gtctggtggt ggtggttctg gtggtggtgg ttctggtggt  1200
ggtggtagtg cagaagcctg gtacaatttg ggtaacgctt actacaagca gggtgactac  1260
cagaaggcta tcgagtatta ccaaaaagca cttgaactgg atccaaataa cgctgaggca  1320
tggtataatt tgggcaacgc atattacaaa cagggtgact atcaaaaggc catagaatac  1380
taccaaaagg ctttggagct ggatcctaat aacgccgaag cttggtacaa tttgggaaat  1440
gcctattata agcagggtga ctatcagaag gcaatagagg actaccaaaa agccctagaa  1500
cttgatccaa ataatttgca ggcagaagcc tggaagaatt tgggtaatgc ttactataaa  1560
cagggtgact atcagaaagc tattgaatac taccaaaaag cactggaatt ggatcctaat  1620
```

-continued

```
aacgcttctg cttggtacaa tttgggcaac gcttactaca aacagggtga ctaccaaaaa  1680
gctatcgaat attatcaaaa ggctctggaa ctagatccaa ataacgccaa ggcttggtat  1740
agaaggggaa atgcttatta taaacagggt gactaccaga aagcaattga agactaccaa  1800
aaagcccttg aactggatcc taataacaga tctagaagcg ctggtggtgg tggttctggt  1860
ggtggtggtt ctggtggtgg tggtgcttct ggtaacaact tagaaacata cgagtggtac  1920
aataagtcta tttctagaga taaggccgaa aagttactac ttgacaccgg taaagaaggt  1980
gcttttatgg ttagagattc tagaactcca ggtacttata cagtctctgt attcacaaag  2040
gctatcatct cagaaaaccc atgtatcaag cattaccaca tcaaggaaac caacgactct  2100
cctaaaagat attacgtggc agaaaagtac gtttttgatt caatcccact gttgattcaa  2160
tatcatcagt acaatggtgg tggtttggtg actagattga ggtatcctgt ttgcggtggt  2220
agcgcaggtt cggctgcagg atcaggcgaa tttggttccg ccgaggccgc tgcaaaagaa  2280
gccgctgcaa aggctggatc tgcaggctca gccgctggtt ctggagaatt tggttctggt  2340
tctcatccct ggtttttcgg taaaattcca agagcaaagg ccgaagaaat gttgtctaaa  2400
caaagacacg acggtgcatt tttgataagg gaaagtgaga gcgcacctgg tgacttttcg  2460
ttgtctgtta aattcggtaa tgatgtccaa catttcaagg tattgagaga tggtgctggt  2520
aaatactttt tgtgggtcgt aaagttcaat tccttgaacg aattagtgga ttaccataga  2580
tcaacttccg ttagtaggaa ccaacagatt ttcttgagag atatcgaaca agttccacaa  2640
cagcctacag gttctgga                                                 2658
```

```
SEQ ID NO: 196         moltype = DNA  length = 2004
FEATURE                Location/Qualifiers
source                 1..2004
                       mol_type = other DNA
                       organism = synthetic construct
SEQUENCE: 196
atggctgtaa agcatttgat cgtgttgaaa ttcaaggatg aaatcacaga ggcacaaaag  60
gaagagtttt tcaagaccta cgttaatttg gtcaacataa tcccagctat gaaagatgta  120
tactggggta aagacgtgac ccaaaagaat aaggaagagg gttataccca tatagtagaa  180
gtgacgttcg aatcagttga aactatccaa gattacatca tacaccctgc tcatgttggc  240
tttggtgacg tctacagatc cttctgggaa aagttgctga tcttcgatta cactccaaga  300
aagaaattgt ctggtggtgg tggttctggt ggtggtggtt ctggtggtgg tggtagtgca  360
gaagcctggt ataatttggg aaacgcttat tacaaacagg gtgactacca aaaggccatc  420
gagtattacc aaaaagctct tgaactggac ccaaataacg ctgaggcatg gtataatttg  480
ggtaacgcat actataagca aggtgactac caaaaggcaa ttgaatatta ccaaaaggcc  540
ttggagttag accctaataa cgccgaagct tggtacaatt tggtaatgc ctactataaa  600
cagggtgact atcaaaaggc tatagaggac taccagaaag cactagaact tgatcccaat  660
aacttgcaag cagaagcctg gaagaatttg ggtaatgcct attataagca aggtgactat  720
caaaaagcta ttgaatacta ccaaaaagct ctggaattgg accctaataa cgcttctgct  780
tggtataatt tgggtaatgc atactacaag caaggtgact accagaaggc aatagagtat  840
taccaaaaag ccttagaact agacccaaat aacgccaagg cttggtacag aaggggtaat  900
gcctactaca agcagggtga ctaccaaaaa gctattgagg actaccaaaa agcacttgaa  960
ctggatccta ataacagatc tagatcagct ggtggtggtg gttctggtgg tggtggttct  1020
ggtggtggtg gtgcttccgg tcaagataga agtgaagcca cattgattaa aagattcaaa  1080
ggagaaggtg ttagatacaa ggctaagctg atcggtatcg atgaagtttc tgctgctaga  1140
ggtgacaaat tgtgtcaaga ctctatgatg aagctgaagg gcgttgtcgc aggtgccaga  1200
tctaagggtg aacataagca aaagatattt ttgacgatct cattcggtgg tattaaaatc  1260
ttcgatgaaa agactggtgc tttacaacat caccatgcag tacacgaaat ctcttacatc  1320
gctaaggata tcacagacca tagagcattc ggttacgttt gcggtaaaga aggcaatcat  1380
agatttgtcg ctattaaaac cgcccaagcc gctgaaccag tcatcttgga tttgagagac  1440
ttattccagc taatctatga actaaagcaa agagaagaat tggaaaagaa agctggtagc  1500
gcaggatcgg cagccggtag cggagaattt ggttctgctg aggctgcagc caaagaagct  1560
gcagccaagg ccggctctgc tggttcagct gcaggctctg gtgaatttgg ttctggttct  1620
catatgggtt ctcaattttg ggtaacttct caaaagactg aagcttccga gagatgtggt  1680
ttgcaaggct cctatatttt aagggtggaa gccgagaagc ttaccctact tacgctgggt  1740
gcacagagtc aaatattgga acccctgttg ttctggccat atactttatt gagaagatac  1800
ggtagagata aagttatgtt cagtttcgaa gctggtagaa gatgcccaag cggtcctgga  1860
acttttacat tccagacatc acaaggcaat gatatctttc aggcagttga agccgctatt  1920
caacagcaaa aagcccaggg taaagtcgga caggctcaag acattctaag attggaacac  1980
catcaccatc atcatggttc tggt                                          2004
```

```
SEQ ID NO: 197         moltype = DNA  length = 2400
FEATURE                Location/Qualifiers
source                 1..2400
                       mol_type = other DNA
                       organism = synthetic construct
SEQUENCE: 197
atgggtttgt cttcagtttg tacattctct ttccaaacga actaccatac tttgctgaac  60
cctcacaaca acaatcccaa aacttctttg ctttgctaca gacatccaaa aacccctatt  120
aagtatagct acaacaattt cccatcgaaa cattgtagta ctaagagctt ccatttgcaa  180
aataagtgct ccgaatcttt gtctatcgct aagaactcaa ttagagctgc aactacaaat  240
cagacggaac cacctgagtc ggataatcac tctgtagcca ccaaaatttt gaactttggt  300
aaagcttgtt ggaagctgca aagaccatac acaataatag ccttcacctc ctgtgcttgc  360
ggtttgtttg gtaaagaact gttgcataac acaaatttga tttcgtggtc tttgatgttc  420
aaggcatttt tctttttggt tgcaatcctt tgcatcgcct cttttaccac gactattaat  480
caaatctatg atttgcacat cgacagaatt aataagcccg atttgccact agcttcaggt  540
gaaatctccg ttaatactgc atggattatg tcaatcattg tcgccttgtt cggtttaatc  600
atcacaatta aatgaaagg tggtccattg tacatcttcg gctactgttt cggtatattc  660
ggtggtatag tatattccgt tccacctttt agatggaaac aaaaccccag taccgctttc  720
ttactaaatt tcttggcaca tatcatcaca aacttcacct tctactacgc ttctagagct  780
```

```
gctttgggtt tgccattcga attaagacca tcttttacat ttttgctggc ttttatgaaa  840
tcgatgggtt ctgcattggc cttgattaaa gatgcatctg acgttgaagg tgacacaaaa  900
ttcggcatca gtaccttggc tagcaagtac ggttctagaa atttgacttt gttttgttca  960
ggtatcgtat tgttatccta cgtggcagcc attttagccg gtatcatttg gccacaagct  1020
tttaacagta atgtcatgct acttagccac gcaatattgg ccttctggct gatcttgcag  1080
acgagagatt ttgctttaac taattatgac cctgaggcag gtagaagatt ctacgaattc  1140
atgtggaagc tgtactacgc tgaatatttg gtttacgtct ttattaagtt gtctggtggt  1200
ggtggttctg gtggtggtgg ttctggtggt ggtggtagtg ctgaagcatg gtacaactta  1260
ggcaacgcat actacaagca gggtgactac cagaaggcaa ttgagtatta ccaaaaagcc  1320
ttagaactag acccaaacaa tgccgaggct tggtataact tgggcaatgc ttattacaaa  1380
cagggtgact atcaaaaggc tatagaatat taccaaaagg cacttgagct ggaccctaac  1440
aatgcagaag cctggtataa cttaggcaat gcttattaca agcagggtga ctatcagaag  1500
gccatcgagg actaccaaaa ggctttggaa ctggatccaa acaatttgca ggctgaagca  1560
tggaagaatt tgggtaacgc ttactataaa cagggtgact atcagaaagc aatagaatac  1620
taccaaaaag ccctagaact tgaccctaac aatgcctctg cttggtacaa cttgggtaat  1680
gcttactata agcagggtga ctaccaaaaa gctatcgaat attaccaaaa agcactggaa  1740
ttggacccaa acaatgcaaa ggcctggtat agaagaggta acgcctacta caaacagggt  1800
gactaccaaa aggctattga agattaccaa aaggctctgg aactagatcc taacaacaga  1860
tctagatccg ctggtggtgg tggttctggt ggtggtggtt ctggtggtgg tggtgcttct  1920
gcagaatacg ttagagctct gttcgatttc aacggtaacg atgaagagga cttgcctttt  1980
aagaaaggtg acattttgag aatcagggac aaaccagaag agcaatggtg gaatgctgaa  2040
gattctgagg gtaaaagagg aatgattcct gttccctatg tcgaaaagta cggctcagca  2100
ggttccgctg caggatctgg cgaattcggt tcagccgagg ccgctgcaaa agaagccgct  2160
gcaaaggctg gaagtgcagg cagcgccgct ggttccggag aatttggtag tttgattaaa  2220
catatgagag ccgaagcttt attcgatttt actggtaact ccaaacttga actgaatttc  2280
aaggcaggtg acgttatttt cttgttgagt agaattaata aggactggtt ggaaggtact  2340
gttagaggtg ctactggaat attcccactt tcttttgtga aaatcctgaa gggctcaggt  2400

SEQ ID NO: 198         moltype = DNA  length = 1641
FEATURE                Location/Qualifiers
source                 1..1641
                       mol_type = other DNA
                       organism = synthetic construct
SEQUENCE: 198
atgaaatgta gcactttttc tttctggttc gtttgcaaga tcattttctt tttcttttct  60
tttaatatcc aaacttcgat cgcaaatcca agagaaaact tcttaaagtg tttctcacaa  120
tacattccta ataacgccac gaatttgaag ctggtataca ctcagaacaa cccactgtac  180
atgagcgtgc taaactcgac aatccataat ttgagattca cttccgatac tacacccaaa  240
ccattagtaa tcgtgacacc ttctcatgtt tcacacattc aaggaaccat actatgctct  300
aagaaagtcg gtttgcagat tagaacaagg tctggtggtc atgatagtga aggcatgtcc  360
tacatcagtc aagttccatt cgttatcgtc gatttgagaa acatgaggtc tatcaaaata  420
gacgttcact cacagacggc ttgggtcgag gcaggtgcca ctttgggaga agtttactac  480
tgggtcaacg aaaagaatga aaatttgtct cttgctgcag gttactgtcc aactgtctgc  540
gctggtggtc attttggtgg tggtggttat ggacctctta tgagaaacta cggtttggcc  600
gctgataata tcattgacgc acatttggta aatgtgcacg gtaaagttct agatagaaag  660
tcaatgggtg aagatttgtt ttgggcattg agaggtggtg gtgctgaatc ctttggtata  720
atcgtagctt ggaaaaattag attggttgca gtcccaaagt ctacaatgtt ctcagttaag  780
aaaattatgg aaatccatga gctggtaaag ttggtgaata agtggcaaaa catcgcttac  840
aagtacgata aggacttgct gctaatgacc catttcatca cgagaaacat cactgataac  900
cagggtaaaa ataagacagc aatacacacc tacttctctt cagttttctt gggtggtgtt  960
gattccttag tggatttgat gaataagagt ttccctgaac tgggtattaa gaaaactgat  1020
tgtagacaat tgagctggat cgacacaatc atattctata gtggtgttgt caactacgat  1080
actgacaact tcaacaaaga aatccttctg gatagaagtg ccggacaaaa tggcgctttc  1140
aaaattaagt tggactacgt taaaaagcct atacccgagt cagtatttgt gcagatcctt  1200
gaaaaactgt atgaagagga tattggtgct ggaatgtacg cattatatcc atacggtggt  1260
ataatggatg aaatctccga gagtgccata ccattccctc atagagctgg tatcttgtac  1320
gaactgtggt acatatgttc ttgggaaaaa caagaggata acgaaaagca cttaaactgg  1380
atcaggaaca tctataactt catgactcct tacgtttcta aaaaccccag attggcttat  1440
ttgaattaca gagatttgga cataggtatc aacgatccta aaaatccaaa caactacaca  1500
caagcaagaa tttggggtga aaagtacttc ggtaaaaatt tcgatagatt ggttaaagtc  1560
aagaccttag ttgaccccaa caactttttc agaaacgaac aatctattcc acctttgcct  1620
agacataggc acggctctgg t                                            1641

SEQ ID NO: 199         moltype = DNA  length = 1644
FEATURE                Location/Qualifiers
source                 1..1644
                       mol_type = other DNA
                       organism = synthetic construct
SEQUENCE: 199
atgaactgta gcactttttc tttttggttc gtttgcaaga taatattttt ctttttgtcc  60
tttaatatcc aaatcagtat cgccaaccca caggaaaact tttaaagtg tttctctgag  120
tacatcccca acaacccagc taaccctaag tttatatata cacaacatga tcagctgtac  180
atgagcgtat tgaactcgac cattcaaaat ttgagattca cttctgacac tacacctaag  240
cccttggtca tagtaactcc ttctaatgtc tcacatatac aagcttctat cttgtgctct  300
aagaaagttg gtttgcagat tagaacaagg tctggtggtc acgatgcaga aggtttatcc  360
tatattagtc aagtcccatt tgccatagta gatttgagaa atatgcatac tgtgaaagtt  420
gacatacact cacagactgc ttgggtggaa gcaggtgcca cattgggaga ggtttactac  480
tggatcaacg agatgaacga aaactttagt ttcccaggtg gttactgtcc cacagtcggt  540
gttggtggtc atttttctgg tggtggttat ggagctttaa tgagaaacta cggtttggct  600
```

```
gcagataata tcattgacgc acatttggtg aacgttgatg gtaaagttct tgacagaaaa  660
tcaatgggtg aagatttgtt ttgggctatc agaggtggtg gtggtgaaaa tttcggtata  720
atcgccgctt gcaaaattaa gttggttgtc gtacctagca aagctactat ttctctgtc  780
aaaaagaaca tggaaatcca tggtttagta aagttgttta ataagtggca aaacatcgca  840
tacaagtacg ataaggattt gatgcttacc acgcatttca gaactaggaa catcacagat  900
aaccatggta aaaataagac tacagttcac ggatacttct cttcaatttt cttgggtggt  960
gttgattctc ttgttgattt gatgaataag tcattcccag aactgggtat taaaaagaca  1020
gattgtaagg aactgagctg gatcgacacc acgattttct atagtggtgt ggttaattac  1080
aacaccgcca acttcaaaaa ggaaatcttg ctggatagat ccgctggtaa aaagaccgct  1140
ttttctatta aacttgacta cgttaagaaa ctgatccctg aaactgcaat ggttaagata  1200
ttggagaagc tgtacgaaga ggaagtcggc gtaggcatgt acgttttgta tccatacggt  1260
ggtataatgg atgagatctc cgaaagtgcc ataccatttc ctcatagagc tggtatcatg  1320
tatgaattat ggtacaccgc tacgtgggag aagcaagaag ataacgagaa acacataaac  1380
tgggtcagat ctgtatacaa cttcactaca ccttacgttt ctcagaaccc aagattggca  1440
tatttgaact acagagattt ggacttgggt aaaaccaacc ccgaatctcc aaataactat  1500
acgcaagcaa gaatttgggg tgaaaagtac ttcggtaaaa atttcaacag attggtgaag  1560
gttaagacaa aagccgatcc aaacaacttc tttagaaacg aacaatctat tccaccattg  1620
ccaccaagac atcatggttc cggc                                       1644

SEQ ID NO: 200         moltype = DNA  length = 8232
FEATURE                Location/Qualifiers
source                 1..8232
                       mol_type = other DNA
                       organism = synthetic construct
SEQUENCE: 200
atgtcagaag agtccttatt tgaatcttca ccacaaaaga tggagtacga aatcactaac  60
tactctgaga gacatacaga attgcctgga cacttcatcg gtttgaacac agttgacaag  120
ctggaagagt ctccattgag agatttcgtc aagtcccatg gtggtcacac cgtaattagt  180
aagatcttga tagctaacaa cggtatcgct gcagtcaagg aaattagatc tgttagaaag  240
tgggcatatg aaacctttgg tgacgataga acggtccaat tcgtagctat ggcaactcct  300
gaagacttgg aggccaatgc tgaatatatc agaatggccg atcaatacat tgaagttcca  360
ggtggtacaa ataacaataa ctacgctaat gtcgacttaa tagtagatat cgctgaaaga  420
gcagacgtgg atgccgtttg ggctggttgg ggacatgctt ccgaaaaccc tttgttaccc  480
gaaaaattgt ctcagagtaa gagaaaagtt atttttattg gtccacctgg aaatgcaatg  540
agatcattag gtgacaagat atccagtact atcgtggcac aatcagccaa agttccatgt  600
attccttggt ccggcaccgg tgttgacacg gtgcatgttg atgaaaagac tggtttggtt  660
tctgtagatg acgatatcta tcagaaggga tgttgcactt cacctgaaga tggtttgcaa  720
aaggctaaga gaatcggttt cccagttatg atcaaggcat cagaaggtgg tggtggtaaa  780
ggtatcaggc aggtcgaaag agaagaggat ttcatcgctc tgtaccatca agccgctaat  840
gaaatacccg gttctccaat tttcataatg aaactagctg gaagggcaag acatttggaa  900
gttcagctac ttgctgacca atacggcact aatatttcct tgttcggtag agattgcagt  960
gttcaaagaa gacatcaaaa gattatcgaa gaggcaccag tcactatagc aaaagccgaa  1020
acatttcacg agatggaaaa ggcagctgtt agattgggta aattggtcgg atatgtaagt  1080
gctggaacag tcgaatattt gtacagccat gacgatggta aattctactt tttggaactt  1140
aacccaagat tacaagttga gcaccctact acagaaatgg tttctggtgt taatttgcca  1200
gctgcacaac tgcagattgc tatgggtatc cctatgcata gaatcagtga tatcaggact  1260
ctgtacggta tgaatccaca cagcgcttcg gagattgact tcgaattcaa aactcaggat  1320
gcaactaaga aacaaagaag accaatccca aagggtcatt gtaccgcttg cagaattacg  1380
tccgaagacc ccaatgatgg ttttaaacca tctggtggta ctttgcacga actaaacttt  1440
agaagctcgt ctaatgtctg gggttatttc tcagtaggca acaacggtaa catccattct  1500
ttttcagatt cccagttcgg tcacatcttc gcatttggag aaaataggca agcctctaga  1560
aagcatatgg ttgtcgctct taaagaactg tcaatcagag gtgacttcag aaccacggtt  1620
gaatacttaa ttaaactgtt ggaaactgaa gacttcgaag ataatacgat tactacaggt  1680
tggttggacg atttgataac ccataagatg acggcagaaa aacctgatcc caccttggcc  1740
gttatctgtg gtgccgctac gaaggccttt ttagcttctg aagaggctag acataagtac  1800
atagaaagcc tgcaaaaggg tcaggtacta tcgaaagact tactacaaac aatgtttcct  1860
gtggatttca tccacgaagg taaaagatac aagtttactg ttgctaagtc tggcaacgat  1920
aggtacacgt tgttcattaa tggtagcaag tgcgacatca ttctaagaca actttcagat  1980
ggtggtttgc tgatcgcaat tggtggtaaa tcacatacta tctattggaa ggaagaggtc  2040
gcagccacaa gattgagtgt agacagcatg accacgttgt tagaggttga aaacgatcca  2100
actcaattaa gaacaccatc tcctggtaaa cttgtgaaat ttctggttga aaatggcgag  2160
catataatca agggtcaacc ctacgctgag attgaagtta tgaaaatgca gatgccattg  2220
gtttctcaag aaaacggtat agttcaacta cttaaacagc ctggatcaac catagtagct  2280
ggtgacatca tggcaattat gacgttagac gatccatcca aggtgaaaca tgctcttcct  2340
tttgagggta tgctgcccga tttcggttct ccagttattg aaggcactaa accagcatac  2400
aagtttaaat cgttggtttc tacactggaa aacatcctaa agggttacga taaccaagtt  2460
attatgaatg cttctttgca acagttgata gaagtcttga gaaatcctaa gttaccctat  2520
tcagaatgga aattgcatat tagcgctctt cactcgagat tgcctgcaaa attggatgaa  2580
caaatggaag agctagtcgc tagatctttg agaagaggtg ctgtatttcc agcaaggcaa  2640
ttgagtaagc taattgacat ggcagttaaa aacccagaat acaaccctga taaactgttg  2700
ggtgccgtag tggaaccatt ggcagatatt gcccataagt actctaatgg tttagaagct  2760
catgagcact caatcttcgt gcatttcttg gaagagtact acgaggttga aaaattgttc  2820
aacggtccta acgtcagaga agagaacatc atcctgaagt tgagagatga aaacccaaag  2880
gacttggata aagtcgctct tactgtactg agtcatagca aggtttctgc caaaaataac  2940
ttaatcctag ctatcctgaa gcactaccaa cctttgtgta agctgtcatc caaagtttct  3000
gcaatatttt caactccatt gcaacatatc gtagagcttg aatctaaggc taccgcaaaa  3060
gtggctttgc aggcaagaga aattttgatc caaggtgctt tgccatcagt taaagaaaga  3120
acagagcaaa tagaacacat cctgaagagt agcgttgtca aagtcgcata cggttcgtct  3180
aatcctaaga gatctgaacc cgatttgaat atacttaagg atttgatcga ttcaaattac  3240
```

-continued

```
gtagtgtttg acgttttact acagttctta actcatcaag atcctgttgt cacagctgca  3300
gccgctcaag tctatataag aagggcctat agagcttaca ctatcggtga cattagggta  3360
cacgaaggcg tgacagttcc aatcgtggaa tggaaatttc aattgccctc cgcagccttt  3420
agtaccttcc caacggtaaa gtcaaaaatg ggtatgaaca gagctgtttc tgtttctgat  3480
ttgagctatg tggctaattc gcaatcatcc cctttaagag aaggtattct aatggctgtg  3540
gaccatttgg acgatgttga tgaaattttg tctcaatctt tggaagttat tccaagacac  3600
caaagtagct cgaatggtcc cgctccagat aggtctggat cttcagcaag tttaagcaac  3660
gtagccaatg tgtgtgttgc ttccactgag ggttttgaaa gtgaagagga aatcttggtt  3720
agattgagag aaattttgga tttgaacaaa caagaattga ttaatgcttc catcagaagg  3780
atcacattca tgttcggttt taaagatggt agttacccta agtactacac ctttaatggt  3840
cccaactaca acgagaacga aactatcaga catatcgaac ctgccttagc tttccaattg  3900
gaactgggta gattgtcaaa cttcaacatc aagccaattt tcactgataa cagaaacatc  3960
catgtgtacg aagctgtttc aaagacatcc ccattagata agagattttt caccagaggc  4020
atcattagga cgggtcacat tagagatgat attagcatac aagagtactt gacttcggaa  4080
gctaacagat taatgtctga catcctagat aatttggaag ttaccgacac gtcgaactct  4140
gatttgaacc atatctttat taacttcatc gcagtgttcg acatatctcc tgaggatgtt  4200
gaagctgcat ttggtggttt cttggaaaga ttcggtaaaa gattgctgag attgagagtc  4260
tccagtgctg aaatcagaat catcattaag gatccacaaa ctggtgcccc tgtacccctg  4320
agagctttga tcaataatgt ttctggttac gtaattaaaa ccgagatgta cacggaagtc  4380
aagaatgcta agggtgaatg ggtattcaag agcttgggta aacccggctc gatgcactta  4440
agaccaattg caacaccata tcctgtcaaa gaatggttgc aacctaagag atacaaagcc  4500
cacttaatgg gtactacata cgtttacgat ttcccagaat tgttcagaca ggcttcttct  4560
tctcaatgga agaatttttc cgccgacgtt aagctgactg acgatttctt tatcagtaac  4620
gaactaatcg aggatgaaaa tggtgaactt acagaggttg aaagagagcc aggagcaaat  4680
gccattggca tggtcgcttt taagatcact gtaaagacac cagaatatcc taggggtaga  4740
caattcgtag tggttgcaaa cgacatcacc tttaaaattg gttctttcgg acctcaagaa  4800
gatgagtttt tcaataaggt tactgaatac gctaggaaaa gaggtatacc aagaatctac  4860
ttggccgcta attctggagc aaggattggc atggccgagg aaatagtgcc tttatttcag  4920
gttgcatgga acgacgcagc caacccagat aagggattcc aatatttgta tttgacttct  4980
gagggtatgg aaacattgaa aaagttcgat aaggaaaact cagtgctgac cgagagaact  5040
gttattaatg gagaggaaag gttcgtaatc aaaactataa tcggttctga agatggtttg  5100
ggcgtggagt gtctgagagg tagcggtttg attgctggtg caacttctag agcttaccat  5160
gatattttta ctatcacact ggtcacttgc agatctgtag gcataggtgc ttatttggtt  5220
agattgggtc aaagggccat ccaggtcgaa ggccaaccta ttatattgac tggtgccccc  5280
gctataaaca aaatgctggg tagagaagtt tatacctcca atttgcagtt gggtggtacg  5340
caaatcatgt acaataacgg tgtttctcat ttgacagctg tagacgattt ggctggtgtg  5400
gaaaagattg ttgaatggat gtcatatgtg ccagctaaaa gaaacatgcc cgttccaata  5460
ttggaaacta aggacacatg ggatagacca gtagatttta cccctacgaa tgacgaaacc  5520
tatgatgtga gatggatgat tgagggtagg gaaactgagt ctggttttga atacggtttg  5580
ttcgataagg gttctttctt tgaaacatta tcaggctggg ccaagggtgt cgtagtggga  5640
agagctagat tgggtggtat tcctctaggt gttattggtg tagaaactag aacagttgaa  5700
aatttgatcc ccgcagatcc agccaaccct aattctgctg aaactttaat tcaggaacct  5760
ggtcaagttt ggcatcccaa ctcagctttt aaaaccgcac aggccattaa tgatttcaac  5820
aacggtgaac aattgccaat gatgatactg gctaactgga gaggtttttc tggtggtcaa  5880
agggatatgt tcaacgaagt tttgaagtac ggtagtttta tcgtcgacgc actggtagat  5940
tacaagcaac ctatcataat atacattcca ccaactggtg aattaagagg tggttcttgg  6000
gttgtcgtag acccaaccat taacgcagat cagatggaaa tgtacgccga tgtgaatgct  6060
agagcaggtg ttttggaacc acaaggaatg gttggtatta agtttagaag agaaaaattg  6120
ctggatacta tgaacagatt agacgataag tacagggaat tgagatctca actgagcaat  6180
aagtctttgg ctccagaagt tcatcaacag atctctaagc aactggctga tagggaaaga  6240
gaattgttgc caatatacgg tcagatctca ttgcaatttg ccgacttaca cgataggtca  6300
tccagaatgg tggctaaggg tgttatttca aaagaattag agtggacaga agctagaaga  6360
tttttctttt ggagattgag aagaagattg aacgaggaat atttgattaa aagattgtca  6420
catcaagttg gcgaggcttc tagattggaa aagatcgcaa ggattagatc ttggtatcca  6480
gcatcagtcg atcacgaaga cgatagacaa gtagccactt ggattgagga aaattacaag  6540
acactggacg ataagttgaa gggtttaaag ctagaatcct ttgcccaaga cttggctaaa  6600
aagattagaa gtgaccatga taatgctatc gatggtttga gtgaagttat taaaatgctt  6660
agcactgacg ataaggaaaa actgttgaag acattgaaga aactgtctgg tggtggtggt  6720
tctggtggtg gtggttctgg tggtggtggt agtgccgaag cttggtataa cttgggaaat  6780
gcttattaca agcagggtga ctaccaaaag gccatagaat actaccaaaa ggctcttgag  6840
ctggatccta ataacgcaga agcctggtat aacttaggca atgcatacta taaacaaggt  6900
gactaccaaa aggcaataga gtactaccaa aaggccttgg aattagatcc aaataacgct  6960
gaggcatggt ataacttggg caacgcctac tataaacagg gtgactatca aaaggctata  7020
gaagattacc agaaggcact agagcttgat cctaataact tgcaagccga agcttggaag  7080
aacttaggaa atgcatacta taagcaaggt gactatcaaa aagctattga atattaccaa  7140
aaggctctgg agttggatcc aaataacgca tctgcttggt acaacttagg caacgcctac  7200
tataagcagg gtgactatca aaaagcaatt gaatattatc aaaaggcctt agagctagat  7260
cctaataacg ctaaagcatg gtataggaga ggcaatgcat actacaaaca gggtgactac  7320
caaaaagcta tagaagatta ccaaaaggca cttgaactgg atccaaataa cagatctaga  7380
tccgctggtg gtggtggttc tggtggtggt ggttctggtg gtggtggtgc ttctggttct  7440
catatgagat tgggagccca atctattcag ccaaccgcta acttagatag aacggacgat  7500
ttggtctatt tgaatgtaat ggaattggtt agagctgttt tggagttgaa aaatgaacta  7560
gcacaattgc caccagaagg ttacgtggtt gtcgtaaaga atgttggttt gactcttaga  7620
aagttgatag gctcggtcga cgatttgcta ccatctttgc catcttcttc tagaactgaa  7680
atagagggta cacaaaagct tctgaacaaa gatttggctg aattgattaa taagatgaga  7740
ttggcacaac agaacgccgt tacttctttg tctgaggagt gtaagagaca aatgctaact  7800
gcttctcata ctttggctgt tgatgcaaag aacttgttag acgctgtgga tcaagcaaaa  7860
gttttagcca atttggctca cccacctgcc gaaggttctg ctggatcagc tgcaggatcc  7920
ggcgaatttg gttctgctga agccgctgca aaagaggctg ctgcaaaagc tggatctgca  7980
```

-continued

```
ggtagtgctg ctggtagcgg agaatttggt tctggtgcca tggctactcc tggttcagaa  8040
aacgttctac caagagaacc attgattgca acagccgtga agttcttgca gaactctaga  8100
gttagacaat ctccattggc aactagaaga gcatttttga aaaagaaagg tttgaccgac  8160
gaggaaattg atatggcttt ccaacagtcc ggtactgcag ccgatgaacc atcttcattg  8220
tggggaagtg gc                                                      8232

SEQ ID NO: 201         moltype = DNA  length = 10869
FEATURE                Location/Qualifiers
source                 1..10869
                       mol_type = other DNA
                       organism = synthetic construct
SEQUENCE: 201
atgggttctg ctggttcagc tgcaggttct ggtgaattcg gttccgctgg tagtgccgct  60
ggttctggtg aatttggttc tgctggttca gcagccggtt ctggtgaatt ctcctattac  120
catcaccatc accatcactt ggaatctact tcattataca aaaggctgg ttccggtagt  180
gccagaaacg cttacttgag aaagaaaatt gctagattga agaaagataa tttgcaattg  240
gaaagagatg aacaaaactt ggaaaagatt atcgctaatt tgagagatga aatagcaaga  300
ttggaaaatg aagttgcttc tcatgaacaa ggttccgcag gtagtgccgc cggttctggt  360
gaatttgctg aagccgctgc aaaggaagcc gctgcaaaag caggttctgc cggttcagcc  420
gctggtagtg gtgaattttc ttactatcac catcaccatc atcacttgga atctacctca  480
ttatataaaa aggccggttc cggtagtaac ttggttgctc aattagaaaa tgaagtcgca  540
tcattggaaa acgaaaacga aactttgaaa aagaaaaact tacataagaa agatttgatc  600
gcttacttag aaaaggaaat agcaaatttg agaaaagaaa tagaagaagg ttccgctggt  660
agtgcagccg gtagtggtga attcggttct gctgaagctg cagccaagga agctgcagcc  720
aaagaagccg ctgctaaaga agctgcagcc aaagctggtt ctgcaggttc tgccgcaggt  780
tccggtgaat ttggttcttc atactatcac catcaccacc accacttgga atctacctca  840
ttatacaaga aagctggttc cggtagtcaa aaggtcgctg aattgaaaaa cagagtagct  900
gttaagttga acagaaacga acaattgaaa aataaggtag aagaattgaa aaatagaaac  960
gcttacttga aaaacgaatt ggcaactttg gaaaacgaag tagctagatt agaaaacgat  1020
gttgctgaag gttctgctgg ttctgctgct ggttctggtg aattcgctga agcagccgct  1080
aaggaagcag ccgctaaagc cggttccgcc ggttctgctg cgggctctgg tgaattttcc  1140
tactatcacc atcatcatca ccacttggaa tctacatcat tatataagaa agccggttcc  1200
ggtagtaatg aagttactac attggaaaac gatgctgctt ttattgaaaa cgaaaacgca  1260
tacttagaaa aggaaatcgc tagattgaga aaggaaaagg ccgctttgag aaatagatta  1320
gctcataaga aaggttctgc tggtagcgct gctggctctg gtgaatttgg ttccgccgaa  1380
gccgctgcta aggaagccgc tgccaaagaa gccgctgcca aggaagccgc tgctaaggct  1440
ggttccgccg gttcagctgc aggctctggt gaattcggtt ctagaccacc taccatctct  1500
aatccacctc cattgatttc cagtgctaaa catccatccg tcggtagtgc aggttccgct  1560
gccggctctg gcgaatttgc cgaagctgct gccaaagaag cagccgctaa agctggttca  1620
gcaggttccg ctgccggatc tggcgaattc aatttcttgc aatctagacc agaacctact  1680
gctcctccag aagaaagttt cagatctggt ggttcagctg gttccgccgc aggatctggc  1740
gaatttggtt ccgcagaagc tgccgctaaa gaagctgctg caaaagaagc agccgccaaa  1800
gaagctgctg caaaagccgg tagtgctggt tcagctgccg gttccggtga attcggttct  1860
tcaaaaggta ccggtttaaa tccaaacgct aaagtttggc aagaaattgc tcctggtaac  1920
ggttctgcag gttccgcagc tggttccggt gaattcgccg aggccgctgc taaggaagca  1980
gcagccaaag caggtagtgc tggttccgca gctggttcag gtgaattccc agacggtggt  2040
accactttcg aacatttgtg gtccagttta gaacctgatt ctacatacgg ttctgccggt  2100
tctgcagcag gcagcggtga attcggttct gccgaagctg ctgctaaaga agctgctgcc  2160
aaggaagctg ctgctaagga agctgctgcc aaagccggta gtgcaggttc tgctgccggt  2220
tcaggtgaat ttggttcttc ttactatcac caccaccacc atcacttgga atctacatca  2280
ttatacaaga aagccggttc tggtagtaag agaatcgcat acttaagaaa gaaaatcgct  2340
gcattgaaga aagataacgc aaacttagaa aaggacatcg ctaacttgga aaacgaaatc  2400
gaaagattga ttaaagaaat caaaaccttg gaaaatgaag ttgcatctca tgaacaaggt  2460
tcagccggtt ctgcagcggg ctccggtgaa tttgccgaag ctgcagcaaa agaagctgcc  2520
gctaaggctg gtagtgctgg ttctgctgca ggcagcggtg aattttctta ctaccaccat  2580
caccaccatc acttggaatc tacttcatta tataagaaag caggttctgg tagtaacttg  2640
ttagcaacat taagatctac cgctgcagtc ttggaaaacg aaaaccatgt attggaaaaa  2700
gaaaaggaaa aattgagaaa ggaaaaagaa caattgttga ataagttgga agcttacaaa  2760
ggttcagcag gttctgcagc gggctctggc gaattcggtt ccgccgaagc tgcagcaaag  2820
gaagctgcag ctaaagaggc cgctgcaaaa gaagctgctg ccaaagcagg tagtgcaggt  2880
tccgcagccg gctccggcga atttggttca ccagctacat cccaacatcc tccacctcca  2940
cctggtcata gatctcaagc tccttcacat ggttccgcag gtagtgcagc tggatctggc  3000
gaattcgccg aagctgccgc taaggaagct gctgcaaaag ctggttccgc tggttcagca  3060
gcaggttccg gtgaattcga attgaattct ttgttgatat tgttagaagc agccgaatat  3120
ttggaaagaa gagatagagg ttctgccggt agtgctgcag gtagcggcga atttggttct  3180
gcagaagcag ccgccaagga agcagctgca aaagaagcag cagctaaaga agcagctgca  3240
aaagccggtt ctgctggttc agccgcagga tctggagaat tcggttccag accacctaca  3300
atttccaatc cacctccatt gatctcttct gccaagcatc catccgttgg tagtgcaggt  3360
tcagctgccg gtagtggtga atttgccgaa gccgccgcta aggaagccgc cgccaaagca  3420
ggttcagccg gttccgccgc aggttcaggt gaattcaatt tcttgcagtc aagaccagaa  3480
cctaccgctc ctccagagga gagtttcaga tctggtggta gtgccggttc agctgccggc  3540
tctggagaat ttggttctgc agaggctgct gccaaggaag ccgcagctaa agaagccgct  3600
gcgaaagaag ccgccgctaa agctggtagt gcaggtagtg ctgcgggatc tggcgaattc  3660
ggttcttcta agggtactgg tttgaaccct aatgccaagg tctggcaaga aatcgcccct  3720
ggtaacggtt ccgcaggttc cgccgcaggt agtggtgaat tcgccgaggc tgccgccaag  3780
gaagccgccg ctaaggcagg tagtgctggt tcagcggccg gctctggtga atttccagac  3840
ggtggtacaa cctttgagca tttgtggtcc agtttagaac ctgattctac gtacggttct  3900
gctggttccg ctgcaggatc tggcgaattc ggttccgcgg aagccgccgc aaaagaagcc  3960
gccgccaaag aagccgccgc aaaggaagcc gcagcaaagg caggtagtgc cggctccgcc  4020
```

-continued

```
gctggcagtg gcgaatttgg ttcttcatat tatcaccatc atcatcatca cttggaatct  4080
acttcattat acaagaaagc aggttccggt tctaaaagaa ttgcttactt aagaaagaaa  4140
atcgcggctt tgaagaaaga caatgctaac ttagaaaaag atattgccaa cttggaaaat  4200
gaaatcgaaa gattaattaa ggaaattaaa acattggaaa acgaagttgc atcacatgaa  4260
caaggttcag ctggttccgc tgcagggtcc ggcgaatttg cagaagccgc cgccaaggaa  4320
gccgcagcca aagctggtag tgcaggttct gccgctggct ctggcgaatt ttcttactat  4380
catcatcacc atcaccactt ggaatctact tcattataca agaaagcggg ttcaggttct  4440
aacttgttag caactttaag atctacagcc gctgttttag aaaatgaaaa ccatgtctta  4500
gaaaaagaaa aggaaaagtt gagaaaggaa aaggaacaat tattaaataa gttagaagcc  4560
tacaagggtt cagcaggttc cgcagcaggc tcaggcgaat ttggttctgc agaagcggct  4620
gctaaggaag ctgccgcaaa ggaagcagct gctaaggagg ccgctgcaaa ggctggttct  4680
gctggttccg ccgcgggctc tggagaattc ggttccgctt tggttgatga cgccgctgat  4740
tatgaacctc caccttcaaa taacgaagaa gctttaggtt ccgctggttc cgctgcaggt  4800
tccggcgagt tcgcagaagc cgcagcaaaa gaagccgcag ctaaggcagg tagtgccgga  4860
tccgccgctg gcagtggaga attcagagaa ttgttcgatg acccatctta cgtcaacgta  4920
caaaatttgg ataaagctag acaaggttcc gccggttctg cagcgggatc tggggaattt  4980
ggttctgcag aagctgccgc caaagaagct gcagctaaag aagccgcagc caaagaagct  5040
gctgctaagg ccggttctgc tggttctgcc gcaggatctg gggaattcgg ttccaagaat  5100
actaagagta tgaacttcga taacccagtt tacagaaaga ctacagaaga agaaggttca  5160
gccggttcag ccgccggttc cggtgaattt gcagaggctg ccgctaaaga ggctgccgct  5220
aaggccggta gtgctggttc tgcagccggc tccggagaat tcagatcttt gccatccaca  5280
tggattgaaa acaaattata cggcatgtca gaccctaatt ggggttctgc aggttcagct  5340
gcgggatctg gtgaattcgg ttcagcagaa gccgcagcca aggaagccgc tgcaaaggag  5400
gccgctgcca aagaagcagc tgctaaggct ggttcagccg gttccgcagc cggcagtggt  5460
gaatttggta gtgttgtcga taattctcca cctccagctt tgcctccaaa gaaaagacaa  5520
tctgctccat ctggttcagc aggttcagcc gctggttcag gtgaatttgc cgaagcagct  5580
gccaaggaag ctgccgccaa ggcgggcagt gcaggttcgg ctgcggggtc tggtgaattc  5640
actcaaagat ctaaaccaca acctgcagtt cctccaagac catctgctga cttgatttta  5700
ggttccgccg gttccgcagc tggctctggc gaattcggtt ccgctgaggc tgccgctaaa  5760
gaagcggccg ctaaagaggc agccgctaaa gaggcggccg ctaaagcagg ttctgcaggt  5820
tcagcagcag gtagtggtga atttggttct acagatgaag aaagagaaga aaccgaagaa  5880
gaagtttatt tgttgaactc taccactttg ggttcagctg gttctgctgc gggttctggc  5940
gaatttgcag aagcagctgc taaggaagcc gcggcaaagg ctggttctgc gggctccgcc  6000
gcaggttctg gtgaatttga tggtaatgta tctggtactc aaagattaga ctcagctacc  6060
gttagaactt attcatgcgg ttctgccggt agtgcagcgg gctctgggga attcggttcc  6120
gcagaagccg ctgcaaaaga agccgctgca aaagaagccg ctgcgaagga ggctgctgct  6180
aaggcaggtt ccgccggtag tgctgcgggt tccggcgaat ttggttccag ttactatcac  6240
catcatcacc accacttgga atccacaagt ttatataaga aagctggttc tggttcacaa  6300
aaggtagctc aattgaaaaa tagagttgca tacaagttga aggaaaacgc taagttggaa  6360
aacatagtag caagattaga aaacgataac gctaatttgg aaaaggacat cgcaaatttg  6420
gaaaaggata tagctaactt ggaaagagat gttgctagag gttctgctgg tagtgccgca  6480
ggctctggcg aattcgctga agctgccgct aaagaggctg cggctaaagc tggttcagct  6540
ggttctgcag cggggtctgg tgaattttct tattatcacc atcatcacca tcacttggaa  6600
tccaccagtt tatacaagaa agccggctct ggttcaaaca ctgttaagga attgaaaaat  6660
tacattcaag aattggaaga aagaaacgct gaattgaaaa atttgaagga acatttgaag  6720
tttgcaaaag ccgaattgga attcgaatta gcagcccata aatttgaagg ttctgccggt  6780
tctgccgccg gatctggaga atttggttct gcggaggctg ccgctaaaga agccgccgct  6840
aaagaggctg cagctaagga agctgcagca aaggctggtt ctgccggttc cgctgccggc  6900
tccggcgaat ttggttcaca tgatgactcc ttgccacatc ctcaacaagc tacagatgac  6960
tctggtcatg aatccgacgg ttccgcaggc tctgctgccg gctccggcga gtttgctgaa  7020
gccgctgcta aagaggctgc tgctaaagcc ggttctgccg gttcagcagc tggatctgga  7080
gaatttggtt ccccaaatgc tggtagtgtt gaacaaaccc caaagaaacc tggtttgaga  7140
agaagaggta gtgctggttc tgccgctggc tccggagaat ttggttcagc cgaagctgcg  7200
gccaaagagg ctgctgcaaa ggaggctgcg gctaaggaag ccgccgctaa agccggttca  7260
gctggttccg cggcaggctc cggggaattt ggttcttctt attatcacca ccaccaccat  7320
cacttggaat ccactagttt atacaagaaa gcaggctctg gttcattcga aaacgtcact  7380
catgaattca ttttggcaac cttagaaaac gaaaacgcta agttgagaag attagaagca  7440
aagttggaaa gagaattggc tagattaaga aatgaagtag cttggttggg ttctgcgggc  7500
tcggccgctg gctctggtga attcgccgaa gctgcggcca aggaggctgc cgcaaaggcc  7560
ggttctgccg gttccgcagc gggatccggc gaattttctt actaccatca tcaccatcac  7620
cacttggaat ccacaagttt atacaagaaa gcgggttctg gttcacaaaa agttgaagaa  7680
ttgaaaaata agatagcaga attggaaaac agaaacgctg taaagaaaaa tagagttgca  7740
catttgaagc aagaaatcgc ttacttgaag gatgaattag cagcccatga attcgaaggt  7800
agtgccggtt ccgctgctgg ctcaggcgaa tttggtagtg cagaagctgc cgctaaggag  7860
gctgccgcca aagaagcagc cgcaaaagaa gctgccgcaa aagccggttc tgcgggctct  7920
gctgccggat ccggcgaatt cggttcagtc tccagtacta aattagtatc ctttcatgat  7980
gacagtgatg aagacttgtt acatatcggt tctgcaggct cagccgctgg ctctggagag  8040
tttgcagagg cagctgctaa agaagccgcc gcaaaggcag gttctgcagg ttctgcagct  8100
ggtagtggtg aattcgctgc tgcaacccca atatctactt ttcatgatga ctcagacgaa  8160
gacttgttgc atgtcggttc cgcaggttca gcagcgggat ccggtgaatt tggttcagca  8220
gaagctgccg ccaaggaggc cgctgctaaa gaagcagcag ccaaggaagc agcagcaaag  8280
gccggctctg ctggttctgc tgccgggtcc ggcgaatttg gttcttctta ttaccaccat  8340
catcatcacc acttggaatc cactagttta tataagaaag ccggttctgg ttcacaaaag  8400
gtggaatcat taaaacaaaa gattgaagaa ttgaagcaaa gaaaagcaca attgaaaaat  8460
gatattgcca atttggaaaa ggaaatcgct tacgcagaaa caggtagtgc cggttcagcc  8520
gcgggctctg gtgaattcgc agaagctgcc gcaaaagaag ctgcagcaaa agccggttct  8580
gcaggctctg ctgctggctc tggcgaattt tcctactatc atcatcatca tcatcacttg  8640
gaatccacaa gtttatacaa gaaagcgggt agtgaatttt tcagaagaga aagaaacaag  8700
atggcagccg ctaagtgtag aaacagaaga agagaattga ctgatacatt acaagctgaa  8760
```

-continued

```
acagatcaat tagaagacga aaaatcagct ttgcaaaccg aaatcgcaaa tttgttgaaa  8820
gaaaaagaaa aattggaatt cattttagca gcccatagac cagcttgcaa aatacctgat  8880
gacttgggtt ttccagaaga aatgtcttta gaaggtagtg ccggtagtgc cgctggctca  8940
ggtgaatttg gtagtgcaga agctgccgcg aaagaagccg cagctaaaga agctgccgcc  9000
aaagaggcag ccgcaaaggc aggttcagca ggttcagctg ccgggtccgg ggaatttggt  9060
tcattccaaa tgccagctga cactcctcca cctgcatatt tgccacctga agatcctatg  9120
acaggtagtg ccggttctgc tgccgggtct ggcgaattcg ctgaagccgc tgctaaggag  9180
gctgcagcta aggccggctc tgcaggttcc gctgcaggtt caggtgaatt tgaaagagaa  9240
tctaacgaag aaccacctcc accttatgaa gatccatact ggggtaatgg tggttctgcc  9300
ggtagtgccg ccggctcagg cgaatttggt tctgcggagg ctgctgcaaa ggaagctgcg  9360
gccaaggaag ctgccgcaaa agaggctgct gccaaggccg gttcagcagg ttcagcagct  9420
gggtccggtg aatttggttc cagttattat caccaccatc atcaccactt ggaatctacc  9480
tcattatata agaaagcggg ttccggtagt caaaaagttg cagaattgaa aaacagagtt  9540
gctgtcaaat taaatagaaa tgagcagttg aaaaataagg tcgaggagtt gaaaaataga  9600
aacgcatact tgaaaaatga attggctact ttggaaaacg aagtcgcaag attagaaaat  9660
gatgtagctg aaggctctgc tggttccgca gcgggctcag gtgaattcgc cgaagcagcc  9720
gcaaaggaag ctgccgctaa ggccggctca gcaggttctg ccgccggaag cggtgaattt  9780
tcttattacc accaccacca tcaccacttg gaatctactt cattatacaa gaaagcgggg  9840
tccggtagta acgaagtcac aaccttagaa aatgatgcag cctttataga aaacgaaaat  9900
gcctacttag aaaaagaaat tgcaagattg agaaaggaaa aagctgcatt gagaaacaga  9960
ttagcccaca agaaatctta ctatcaccac catcatcatc acttggaatc tacatcatta  10020
tacaagaaag cgggctccgg tagtgctaga aatgcctact taagaaagaa aatagccaga  10080
ttgaagaaag acaatttgca attagagaga gatgaacaga acttagaaaa gattatagcc  10140
aatttgagag atgaaattgc tagattagaa aatgaagtag cttctcatga acaaggtagt  10200
gctggctccg ctgccggctc cggagaattt gccgaagctg ccgccaagga agccgcggcc  10260
aaggctggtt ccgctggttc tgctgccgga tctggagaat ttcctctatta ccatcatcat  10320
catcatcatt tggaatctac atcattatac aagaaagcgg gatctggttc taacttggtc  10380
gcccaattgg agaacgaagt cgcatcattg gagaacgaaa acgaaacctt gaagaaaaag  10440
aacttacaca aaaaggattt gatagcttac ttagaaaaag aaatcgctaa tttgagaaag  10500
aaaattgaag aaggtagtgc aggttcagcc gctggctccg gtgaatttgg ttcagcggag  10560
gctgccgcta aggaggcagc cgctaaagaa gcagccgcta aggaggctgc agcaaaagca  10620
ggttccgcag gttctgcagc gggttccgga gaatttggtt ctgaacaaaa gttgatctct  10680
gaagaagatt tggaacaaaa gttgatatct gaagaagact tggaacaaaa attaatatca  10740
gaagaagatt tgggtagtgc aggttcagca gctggttctg gagaatttgg ttcagcaggt  10800
tctgccgctg gaagtggcga attcggtagt gccggctccg ctgctggctc tggcgaattt  10860
ggttctggt                                                        10869
```

```
SEQ ID NO: 202         moltype = DNA  length = 1365
FEATURE                Location/Qualifiers
source                 1..1365
                       mol_type = other DNA
                       organism = synthetic construct
SEQUENCE: 202
atgggttctg ctggttcagc tgcaggttct ggtgaatttg gttccgcagg tagtgccgct  60
ggttctggtg aattcggttc tgctggttca gcagccggtt ctggtgaatt ttcatattac  120
catcaccatc accatcactt ggaatccacc agtttataca aaaaggctgg ttctggttca  180
gctagaaacg catatttgag aaagaaaatt gctagattga agaaagataa cttgcaattg  240
gaaagagatg aacaaaattt ggaaaagatt atcgccaact taagagatga aatagcaaga  300
ttggaaaacg aagtagcttc tcatgaacaa ggttccgcag gtagtgcagc tggttctggt  360
gaatttgctg aagccgctgc aaaggaagcc gctgcaaaag ctggttccgc tggttcagcc  420
gctggttccg gtgaattcag ttactatcac catcaccatc atcacttgga atccactagt  480
ttatataaaa aggccggttc tggttcaaat ttggttgctc aattagaaaa cgaagtcgca  540
tctttagaaa acgaaaacga aacattgaaa aagaaaaatt tgcataagaa agatttgatc  600
gcttatttgg aaaaggaaat cgcaaacttg agaaagaaaa tagaagaagg ttccgctggt  660
tctgctgctg gttccggtga atttggttca gctgaagctg cagccaagga agctgcagcc  720
aaagaagccg ctgctaaaga agctgcagcc aaagcaggtt ctgccggttc tgccgcaggt  780
tccggtgaat tcggttcttc agctactaga gaattggatg aattgatggc atccttaagt  840
gacttcaaga tacaaggtgg ttccgctggt tctgcagccg gctctggcga attcgcagaa  900
gcagccgcta aggaagcagc cgctaaagct ggttctgcag gttctgctgc cggttctggt  960
gaattcgatt tggctttgtc tgaaaactgg gcacaagaat tcttggctgc aggtgacgct  1020
gttgatggtt ctgctggtag tgctgccggt tcaggtgaat ttggtagtgc tgaagctgct  1080
gccaaagaag cagccgctaa agaagctgct gccaaggaag ctgccgctaa agcaggttcc  1140
gccggttctg ccgccggctc cggcgaattt ggttcagatt ataaggatga cgatgacaag  1200
gattacaaag acgatgatga caaggattat aaagatgacg atgacaaagg ttccgctggt  1260
agtgccgccg gctctggaga attcggttct gccggttcag ctgccggctc cggagaattt  1320
ggttccgctg gtagtgcagc cggttcaggt gaattcggtt ctggt                1365
```

```
SEQ ID NO: 203         moltype = DNA  length = 19104
FEATURE                Location/Qualifiers
source                 1..19104
                       mol_type = other DNA
                       organism = synthetic construct
SEQUENCE: 203
atgagtgcta aggcaatttc tgaacaaact ggtaaagaat tgttgtacaa gtttatttgt  60
actacatcag ccatccaaaa tagattcaaa tacgctagag ttaccccaga tactgactgg  120
gctagattgt tacaagatca tccatggttg ttatctcaaa acttggttgt caaacctgac  180
caattaatta agagaagagg taaattgggt ttagtaggtg ttaatttgac attggatggt  240
gtaaagtctt ggttgaaacc aagattaggt caagaagcca cagttggtaa agctaccggt  300
ttcttgaaaa atttcttgat cgaaccattt gtccctcatt cacaagccga agaattctat  360
```

-continued gtatgtatct acgctactag agagggtgac tatgttttat ttcatcacga aggtggtgtc 420
gacgtaggtg acgttgacgc caaggctcaa aagttgttgg ttggtgtcga tgaaaagttg 480
aacccagaag acattaaaaa gcatttgttg gttcacgcac ctgaagataa aaaggaaata 540
ttggcctcct ttataagtgg tttgtttaat ttctacgaag atttgtactt cacctacttg 600
gaaattaacc cattagtagt tactaaggat ggtgtatatg ttttggactt agctgcaaaa 660
gttgatgcaa cagccgacta catttgtaag gtcaaatggg gtgacatcga atttccacct 720
ccattcggta gagaagctta tccagaagaa gcctacattg ctgatttgga cgctaagtct 780
ggtgcatcat tgaagttgac attgttgaac cctaaaggta gaatttggac catggttgct 840
ggtggtggtg ctagtgtcgt atattctgat actatatgcg acttgggtgg tgttaacgaa 900
ttggcaaact acggtgaata ctcaggtgcc ccatccgaac aacaaacata cgattacgct 960
aagaccatct tgtccttaat gactagagaa aagcatcctg atggtaaaat cttgatcatc 1020
ggtggtagta tcgcaaattt tactaacgtt gccgctacat tcaagggtat cgtcagagct 1080
ataagagatt accaaggtcc attgaaggaa cacgaagtaa caatattcgt tagaagaggt 1140
ggtcctaact accaagaagg tttgagagtc atgggtgaag taggtaaaac cactggtata 1200
ccaatccatg tctttggtac agaaacccac atgactgcaa tagttggtat ggccttaggt 1260
catagaccaa tccctaatca acctccaacc gcagcccaca ctgcaaattt cttgttaaac 1320
gcctctggtt caacttccac accagctcct tctagaacag caagtttctc tgaatcaaga 1380
gctgatgaag tcgctccagc taagaaagca aaaccagcca tgcctcaaga ctccgttcca 1440
agtcctagat ctttgcaggg taaatctact actttgtttt ctagacatac taaggctata 1500
gtatggggta tgcaaacaag agcagttcaa ggcatgttgg atttcgacta tgtttgtagt 1560
agagatgaac catctgttgc tgcaatggtc tatcctttta ctggtgacca taagcaaaaa 1620
ttctactggg gtcacaagga aatattgatc ccagttttta agaacatggc cgatgctatg 1680
agaaaacatc ctgaagtcga cgtattgatt aacttcgcct cattaagatc cgcttacgat 1740
tctacaatgg aaaccatgaa ctacgctcaa ataagaacca tcgctatcat tgcagaaggt 1800
attccagaag ccttgactag aaagttgatt aagaaagctg atcaaaaagg tgtcacaata 1860
atcggtccag ctaccgtagg tggtattaag cctggttgtt tcaagatcgg taacactggt 1920
ggtatgttgg ataacatatt ggcatctaag ttgtatagac caggttcagt cgcttacgta 1980
tccagaagtg gtggtatgtc caacgaattg aacaacatca tcagtagaac tacagatggt 2040
gtatacgaag gtgttgctat tggtggtgac agatacccag gttctacttt tatggatcat 2100
gtattgagat atcaagacac acctggtgtt aaaatgattg ttgtcttggg tgaaataggt 2160
ggtactgaag aatacaagat atgcagaggt atcaaagaag gtagattgac aaagccaatc 2220
gtttgttggt gcattggtac ttgtgcaaca atgttttctt cagaagttca attcggtcat 2280
gcaggtgcct gcgctaatca agcttcagaa acagcagttg ccaagaacca agcattaaaa 2340
gaagccggtg tttttgtccc tagatctttc gatgaattag gtgaaatcat tcaatcagtc 2400
tatgaagact tggtagctaa tggtgtaatt gttccagcac aagaagttcc tccacctact 2460
gtccctatgg attactcttg ggcaagagaa ttgggtttaa ttagaaagcc agctagtttt 2520
atgacctcta tatgtgatga aagaggtcaa gaattgatct atgctggtat gcctattact 2580
gaagtattca aagaagaaat gggtatcggt ggtgttttag gtttgttgtg gttccaaaag 2640
agattgccaa agtactcttg tcaattcatt gaaatgtgct taatggttac agctgatcat 2700
ggtcctgctg tctcaggtgc acacaatacc ataatctgcg ctagagctgg taaagatttg 2760
gtttcttctt tgacctcagg tttgttaact attggtgaca gatttggtgg tgcattagac 2820
gccgctgcaa agatgttttc aaaagctttc gattccggta taatcccaat ggaattcgtt 2880
aataagatga aaaaggaggg taaattgata atgggtatcg gtcatcgtgt taagtctatc 2940
aataaccctg atatgagagt acaaatcttg aaggactatg ttagacaaca ctttccagcc 3000
acacctttgt tagattacgc tttggaagtt gaaaagatta ccacttctaa aaagccaaat 3060
ttgatcttga acgttgatgg tttaattggt gttgcttttg tcgacatgtt gagaaactgt 3120
ggttccttca ctagagaaga agctgatgaa tatatcgaca ttggtgcatt gaatggtatc 3180
tttgttttag gtagatctat gggtttcatt ggtcattact tggatcaaaa gagattaaag 3240
caaggtttgt acagacatcc atgggatgac atttcttacg ttttacctga acacatgtca 3300
atgaaattgt ctggtggtgg tggttctggt ggtggtggtt ctggtggtgg tggtagtgcc 3360
gaagcttggt acaatttggg taacgcatac tacaagcagg gtgactacca aaaggcaatt 3420
gaatattacc aaaaggcctt ggaattagac ccaaataacg cagaagcctg gtataatttg 3480
ggtaatgctt attataaaca gggtgactat caaaaggcta tcgaatacta ccaaaaggca 3540
ttggaattag accctaataa cgctgaagca tggtataatt tgggtaacgc ttattataag 3600
cagggtgact atcaaaaagc catcgaagac taccaaaagg ctttggaatt agatccaaat 3660
aacttacaag ccgaagcttg gaagaatttg ggtaacgctt actataaaca gggtgactac 3720
caaaaagcaa ttgaatacta tcaaaaagct ttagaattgg accctaataa cgcatcagcc 3780
tggtacaatt tgggtaatgc ttactataag cagggtgact atcagaaggc cattgaatac 3840
tatcaaaagg ctttagaatt ggatccaaat aacgctaaag catggtacag acgtggtaac 3900
gcttattaca aacagggtga ctaccagaaa gccattgaag attatcaaaa ggctttggaa 3960
ttggatccta acaacagatc tagatcagct ggtggtggtg gttctggtgg tggtggttct 4020
ggtggtggtg gtgcttcttc atattaccat caccatcacc atcacttgga atccacaagt 4080
ttatacaaaa aggctggttc tggttcaaat ttggtcgcac aattggaaaa cgaagtagcc 4140
tctttagaaa atgaaaacga aaccttgaaa aagaaaaact tacataagaa agatttgatc 4200
gcttatttgg aaaaggaaat cgcaaatttg agaaagaaaa ttgaagaagg tagtgcaggt 4260
tctgccgctg gttctggtga atttggttca gctgaagcag ccgctaagga agcagccgct 4320
aaagccggtt cagctggttc cgcagccggt tctggtgaat tcggttccag ttactatcac 4380
catcaccatc atcacttgga atccacaagt ttatataaga aagcaggttc tggttcagca 4440
agaaatgcct acttgagaaa gaaaatagct agattaaaga aagataactt gcaattggaa 4500
agagatgaac aaaatttgga aaagattatc gccaacttaa gagatgaaat cgctagattg 4560
gaaaatgaag ttgcatccca tgaacaaggt agtggtgcta ctaacttctc tttgttgaag 4620
caagcaggtg acgttgaaga aaatccaggt ccaatgaaaa actgtgtaat cgtttctgct 4680
gttagaactg caattggttc ctttaatggt agtttggcct ctacatcagc tattgatttg 4740
ggtgctaccg tcatcaaagc tgcaattgaa agagcaaaga ttgattctca acatgtcgac 4800
gaagtaataa tgggtaacgt tttgcaagct ggtttaggtc aaaatccagc aagacaagcc 4860
ttgttaaaat ctggtttagc agaaactgta tgtggtttca cagttaataa ggtctgcggt 4920
tctggtttga agtcagttgc tttagccgct caagctatac aagcaggtca agcccaatct 4980
atcgtcgctg gtggtatgga aaatatgtca ttggcacctt atttgttaga tgcaaaagcc 5040
agatcaggtt atagattagg tgacggtcaa gtatacgacg ttattttgag agatggttta 5100

-continued

```
atgtgcgcta ctcatggtta tcacatgggt attacagcag aaaatgttgc caaagaatac  5160
ggtataacca gagaaatgca agatgaattg gcattacatt cccaaagaaa ggcagccgct  5220
gcaatcgaaa gtggtgcttt tactgcagaa attgtcccag taaacgttgt cacaagaaag  5280
aaaactttcg ttttctccca agatgaattc ccaaaagcta atagtaccgc tgaagcattg  5340
ggtgctttaa gacctgcatt cgacaaggcc ggtaccgtaa ctgccggtaa tgcttctggt  5400
ataaacgatg gtgccgctgc attggttatc atggaagaat cagccgcttt agcagccggt  5460
ttgacacctt tagctagaat taaatcttat gcatcaggtg gtgttccacc tgctttgatg  5520
ggtatgggtc cagtccctgc tacccaaaag gcattgcaat tagccggttt gcaattggct  5580
gatatcgact taatcgaagc aaacgaagcc tttgctgcac aattcttggc agttggtaaa  5640
aatttgggtt tcgactccga aaaggttaat gtcaacggtg gtgccattgc tttgggtcat  5700
ccaataggtg cttcaggtgc aagaatcttg gttacattgt tgcatgccat gcaagctaga  5760
gataaaacct tgggtttagc tactttgtgt atcggtggtg gtcaaggtat cgcaatggtt  5820
atcgaaagat tgaataagtt gtctggtggt ggtggttctg gtggtggtgg ttctggtggt  5880
ggtggtagtg cagaagcctg gtacaatttg ggtaacgctt actacaagca gggtgactac  5940
caaaaggcaa tcgaatacta ccaaaaggcc ttggaattag atccaaataa cgctgaagca  6000
tggtataatt tgggtaatgc ctattataaa cagggtgact atcaaaaagc tattgaatat  6060
taccaaaagg cattggaatt agatcctaat aacgccgaag cttggtataa tttgggtaac  6120
gcctattata agcagggtga ctatcaaaag gccatcgaag attaccaaaa ggctttggaa  6180
ttggatccaa acaacttgca agcagaagcc tggaagaatt tgggtaacgc ttattacaaa  6240
cagggtgact accaaaaagc tattgaatac tatcaaaaag ccttagaatt ggatcctaat  6300
aacgcttctg catggtacaa tttgggtaat gcctactata aacagggtga ctaccagaag  6360
gctattgaat actaccaaaa agcattagaa ttggatccaa ataacgccaa ggcttggtac  6420
agacgtggta atgcctatta caagcagggt gactaccaga aagccataga agactatcaa  6480
aaagccttgg aattggatcc taacaacaga tccagaagtg ctggtggtgg tggttctggt  6540
ggtggtggtt ctggtggtgg tggtgcttct tcatattacc atcaccatca ccatcacttg  6600
gaatctacat cattatacaa aaaggctggt tccggtagta atgaagttac tacattggaa  6660
aacgatgccg cttttatcga aaacgaaaac gcatacttgg aaaaggaaat cgccagatta  6720
agaaaggaaa aggcagcctt gagaaataga ttagcccata aaaagggttc cgctggtagt  6780
gctgcaggtt ctggtgaatt tggttcagct gaagccgctg caaaagaagc cgctgcaaag  6840
gcaggttctg ccggttcagc cgctggttct ggtgaattcg gttccagtta ctatcaccat  6900
caccatcatc acttggaatc tacttcatta tataaaaagg ccggttccgg tagtcaaaaa  6960
gtcgctgaat taaagaacag agtagctgtt aagttgaaca gaaacgaaca attgaaaaat  7020
aaggtagaag aattgaaaaa tagaaacgcc tacttaaaga atgaattggc aacattggaa  7080
aacgaagtcg ctagattgga aaatgatgta gcagaaggtt ctggtgctac taacttctct  7140
ttgttgaagc aagcaggtga cgttgaagaa aatccaggtc caatgaaaaa ggtttgtgtc  7200
attggtgctg gtaccatggg ttctggtata gcacaagcct ttgctgcaaa aggtttcgaa  7260
gttgtcttga gagatatcaa ggacgaattc gttgatagag gtttggactt catcaataag  7320
aacttgtcta agttggttaa aaagggtaaa atcgaagaag ctacaaaggt agaaatcttg  7380
accagaattt caggtactgt tgatttgaat atggccgctg attgtgactt ggtaatcgaa  7440
gcagccgttg aaagaatgga tattaagaaa caaatcttcg cagatttgga caacatctgc  7500
aaacctgaaa caatcttagc ctcaaacacc tcttcattgt ccattactga agtcgctagt  7560
gcaacaaaaa gaccagataa ggtaataggc atgcatttct ttaatccagc tcctgttatg  7620
aagttggtag aagttattag aggtatagca acatctcaag aaacctttga cgctgttaag  7680
gaaacttcaa tagcaatcgg taaagatcca gtcgaagtag ccgaagctcc tggtttcgta  7740
gttaacagaa tcttgatacc tatgatcaac gaagctgttg gtatcttggc tgaaggtatt  7800
gcatctgtcg aagatattga caaagccatg aagttaggtg ctaatcaccc aatgggtcct  7860
ttggaattgg gtgactttat tggtttggac atatgtttag ctatcatgga cgtttttgtat  7920
tccgaaacag gtgacagtaa atacagacca catacttgt tgaagaaata tgttagagca  7980
ggttggttag gtagaaagtc tggtaaaggt ttctacgatt actctaaaaa gttgtctggt  8040
ggtggtggtt ctggtggtgg tggttctggt ggtggtggta gtgcagaagc ctggtacaat  8100
ttgggtaacg cttactacaa gcagggtgac taccaaaagg ccatagaata ctaccaaaag  8160
gctttggaat tggatcctaa taacgctgaa gcatggtata atttgggtaa tgcatattat  8220
aaacagggtg actatcaaaa ggcaatcgaa tactaccaaa aggccttgga attagatcca  8280
aataacgccg aagcttggta taatttgggt aacgcctatt ataagcaggg tgactatcaa  8340
aaagctatcg aagattacca aaaggcattg gaattggatc ctaacaactt acaagcagaa  8400
gcctggaaga atttgggtaa cgcatattac aaacagggtg actaccaaaa agccattgaa  8460
tattatcaaa aagctttgga attggatcca aataacgctt cagcatggta caatttgggt  8520
aatgcctatt acaagcaggg tgactatcag aaagctattg aatattatca aaaggctttg  8580
gaattagatc ctaataacgc caaggcttgg tacagacgtg gtaatgccta ttacaagcag  8640
ggtgactacc agaaggccat tgaagactat caaaaagcct tggaattgga tccaaacaac  8700
agatctagat cagctggtgg tggtggttct ggtggtggtg gttctggtgg tggtggtgct  8760
tccgaaaatt tgtacttcca aggtgaaaac ttgtacttcc agggtgactc cagtgaaagt  8820
tgttggaatt gcggtagaaa agcctccgaa acctgtagtg gttgcaacac tgctagatat  8880
tgtggttctt tttgccaaca caaagattgg gaaaagcatc accatatttg tggtcaaaca  8940
ttacaagcac aacaaggttc tgccggttca gctgcaggtt ctggtgaatt tggttccgct  9000
gaagccgctg caaaagaagc cgctgcaaag gcaggttccg ccggtagtgc cgctggtagt  9060
ggtgaattcg gttctatggc agtttccgaa agtcaattga agaaaatggt ttctaagtac  9120
aagtacagag atttgactgt tagagaaaca gttaacgtca tcactttgta caaggatttg  9180
aagccagtct tggactcata cgtttttaat gatggttctt caagagaatt gatgaactta  9240
actggtacaa taccagttcc ttaccgtggt aacacttaca acatcccaat ctgtttgtgg  9300
ttgttagata catatcctta caatccacct atctgcttcg tcaaaccaac atccagtatg  9360
accattaaaa ctggtaaaca tgttgatgct aacggtaaaa tatatttgcc atacttacac  9420
gaatggaagc atcctcaatc agacttgttg ggtttaatcc aagtaatgat cgtcgtattt  9480
ggtgacgaac cacctgtttt ctctagacca ggttcaggtg ctactaactt ctctttgttg  9540
aagcaagcag gtgacgttga agaaaatcca ggtccaatgg aattgaacaa cgttatattg  9600
gaaaaggagg gtaaagtcgc tgttgtcact ataaatagac caaaggcatt gaacgccttg  9660
aactctgata cattgaagga aatggactac gttatcggtg aaattgaaaa cgattcagaa  9720
gtcttagcag taattttgac cggtgccggt gaaaaatcct ttgttgccgg tgctgatatc  9780
agtgaaatga aggaaatgaa cactatcgaa ggtagaaagt tcggtatctt gggtaacaag  9840
```

-continued

```
gttttcagaa gattggaatt gttggaaaag cctgttatag ctgcagtcaa tggtttcgct  9900
ttgggtggtg gttgtgaaat cgcaatgtcc tgcgatatta gaatagcttc ttcaaacgca  9960
agatttggtc aaccagaagt cggtttaggt attacacctg gtttcggtgg tacccaaaga  10020
ttatctagat tggttggtat gggtatggcc aagcaattga tttttactgc tcaaaacatc  10080
aaggctgatg aagcattgag aatcggtttg gttaataagg tagttgaacc atctgaattg  10140
atgaacaccg ccaaggaaat cgctaataag attgtttcta atgctccagt tgctgtcaag  10200
ttgagtaagc aagctataaa tcgtggtatg caatgtgata tcgacactgc attggccttc  10260
gaatctgaag catttggtga atgcttctca acagaagatc aaaaagacgc aatgaccgcc  10320
tttatcgaaa agagaaagat agaaggtttc aaaaacagaa agttatctgg tggtggtggt  10380
tctggtggtg gtggttctgg tggtggtggt agtgctgaag catggtacaa tttgggtaac  10440
gcttactaca agcagggtga ctaccaaaag gcaatcgaat actaccaaaa ggccttggaa  10500
ttggacccaa ataacgccga agcttggtat aatttgggta atgcctatta taaacagggt  10560
gactatcaaa aagctataga atactaccaa aaggcattgg aattggaccc taataacgca  10620
gaagcctggt ataatttggg taacgcctat tataagcagg gtgactatca aaaggccata  10680
gaagactacc aaaaggcttt ggaattggat ccaaacaact tacaagctga agcatggaag  10740
aatttgggta acgcttatta caaacagggt gactaccaaa aagctattga atattatcaa  10800
aaagctttag aattagaccc taataacgcc tctgcttggt acaatttggg taatgcctac  10860
tataaacagg gtgactacca gaaggctatt gaatattacc aaaaagcttt agaattggat  10920
ccaaataacg caaaggcctg gtacagacgt ggtaatgcct attacaagca gggtgactac  10980
cagaaagcca ttgaagatta tcaaaaagct ttggaattgg atcctaacaa cagatccaga  11040
agtgctggtg gtggtggttc tggtggtggt ggttctggtg gtggtggtgc ttctggtcca  11100
ttgggttccc ctttgactgc atcaatgtta gcttccgcac cacctcaaga acaaaagcaa  11160
atgttgggtg aaagattatt cccattgata caagctatgc atcctacttt agcaggtaaa  11220
atcacaggca tgttgttgga aatcgataac tctgaattgt tacacatgtt agaatcccca  11280
gaaagtttga gatctaaagt tgacgaagcc gtagctgttt tgcaagctca tcaagcaaaa  11340
gaagccgctc aaaaggccgg ttcagctggt tccgcagccg gtagtggtga atttggttct  11400
gctgaagctg cagccaaaga agctgcagcc aaggcaggta gtgccggttc tgctgcaggt  11460
tctggtgaat tcggttccaa taccaacatg agtgtcccaa ctgatggtgc tgtaactaca  11520
tctcaaattc ctgcatcaga acaagaaact ttagttagac caaagccttt gttgttgaag  11580
ttgttgaagt cagtaggtgc tcaaaaagat acctacacta tgaaggaagt tttattttat  11640
ttgggtcaat acatcatgac aaagagatta tacgatgaaa agcaacaaca tatcgtttac  11700
tgttcaaacg atttgttggg tgacttgttt ggtgtaccat ctttctcagt taaggaacac  11760
agaaagatct atacaatgat atacagaaat ttggtcgtag gttctggtgc tactaacttc  11820
tctttgttga agcaagcagg tgacgttgaa gaaaatccag gtccaatgat cgtaaagcca  11880
atggttagaa acaacatctg tttgaacgct catcctcaag gttgcaaaaa gggtgtagaa  11940
gatcaaatcg aatacaccaa aaagagaatc actgcagaag ttaaagccgg tgctaaagca  12000
cctaagaatg ttttggtctt aggttgttcc aacggttatg gtttggctag tagaataaca  12060
gctgcatttg gttacggtgc cgctaccatc ggtgtttcct tcgaaaaggc tggtagtgaa  12120
accaaatatg gtactccagg ttggtacaat aacttggcat ttgatgaagc agccaagaga  12180
gaaggtttat actctgtcac tatagatggt gacgctttct cagatgaaat caaggcacaa  12240
gttattgaag aagccaaaaa gaaaggtata aaattcgatt tgatcgttta ctccttagca  12300
agtccagtca gaacagatcc tgacaccggt ataatgcata agtctgtttt gaagccattc  12360
ggtaaaactt tcacaggtaa aacagtcgat cctttcaccg gtgaattgaa agaaatatct  12420
gctgaaccag caaatgatga agaagctgca gccacagtaa aagttatggg tggtgaagac  12480
tgggaaagat ggatcaagca attgtccaaa gaaggtttgt tggaagaagg ttgtatcacc  12540
ttagcttatt catacattgg tcctgaagcc actcaagctt tgtatagaaa aggtacaatc  12600
ggtaaagcta aagaacattt ggaagccacc gctcacagat taaataagga aaacccatct  12660
atcagagcat ttgtttctgt aaataagggt ttagttacta gagcatccgc cgttatccca  12720
gtcattcctt tgtatttggc tagtttgttt aaggttatga aggaaaaggg taaccatgaa  12780
ggttgcatag aacaaatcac tagattgtac gcagaaagat tatacagaaa ggatggtaca  12840
attccagttg acgaagaaaa cagaatcaga atcgatgact gggaattgga agaagatgtc  12900
caaaaggcag tatctgcctt aatggaaaaa gttaccggtg aaaacgctga atcattgact  12960
gatttggcag gttatagaca cgacttttta gcctctaatg gtttcgatgt cgaaggtatt  13020
aactacgaag cagaagtaga aagattcgac agaattaaat tgtctggtgg tggtggttct  13080
ggtggtggtg gttctggtgg tggtggtagt gctgaagcat ggtataattt gggtaacgct  13140
tattacaagc agggtgacta ccaaaaggcc atcgaatact accaaaaggc tttggaattg  13200
gaccctaata acgccgaagc ttggtacaat ttgggtaatg cctactataa acagggtgac  13260
tatcaaaaag caattgaata ttaccaaaag gccttggaat tagacccaaa taacgcagaa  13320
gcctggtaca atttgggtaa cgcctactat aagcagggtg actatcaaaa ggctattgaa  13380
gactaccaaa aggcattgga attagatcct aataacttgc aagctgaagc atggaaaaat  13440
ttgggtaatg cctattataa acagggtgac taccaaaaag ctattgaata ctatcaaaaa  13500
gctttggaat tggacccaaa taacgcctca gcttggtata atttgggtaa tgcatactac  13560
aaacagggtg actatcagaa ggcaatagaa tactatcaaa aagccttaga attggatcct  13620
aataacgcaa aagcctggta tagacgtggt aatgcctact acaagcaggg tgactatcag  13680
aaggcgatag aagattatca aaaggcattg gaattggatc caaacaacag atctagatca  13740
gctggtggtg gtggttctgg tggtggtggt tctggtggtg gtggtgcttc ttcatattac  13800
catcaccatc accatcactt ggaatccaca agtttatata agaaagcagg ttctggttca  13860
aatttgttag ccactttgag atcaacagct gcagtattgg aaaacgaaaa ccatgttttg  13920
gaaaaagaaa aggaaaagtt gagaaaggaa aaggaacaat tgttgaataa gttggaagcc  13980
tacaaaggtt ctgctggttc agccgctggt tccggtgaat tcggtagtgc tgaagcagcc  14040
gctaaggaag cagccgctaa agctggttcc gcaggtagtg cagccggttc tggtgaattt  14100
ggttccagtt actatcacca tcaccatcat cacttggaat ccacaagttt atataagaaa  14160
gctggttctg gttcaaagag aatcgcatac ttgagaaaga aaatcgctgc attaaagaaa  14220
gataacgcca acttggaaaa ggacatcgct aatttggaaa acgaaatcga aagattgatt  14280
aaagaaatta aaacattaga aaatgaagtt gcttctcatg aacaaggttc aggtgctact  14340
aacttctctt tgttgaagca agcaggtgac gttgaagaaa atccaggtcc aatgactaga  14400
gaagttgtcg tagttagtgg tgttagaaca gctattggta cctttggtgg ttctttaaaa  14460
gatgttgcac cagccgaatt gggtgcatta gtcgtaagag aagctttggc aagagcccaa  14520
gtttcaggtg acgatgtcgg tcatgttgtc ttcggtaacg ttatccaaac agaaccaaga  14580
```

-continued

```
gatatgtatt tgggtagagt agctgcagtt aatggtggtg ttaccataaa cgctcctgca  14640
ttaactgtca acagattgtg tggtagtggt ttacaagcta ttgtttctgc cgctcaaaca  14700
atattgttag gtgacaccga cgttgctatc ggtggtggtg ctgaatctat gtcaagagcc  14760
ccatacttag ctcctgcagc cagatggggt gccagaatgg gtgacgctgg tttggttgac  14820
atgatgttgg gtgctttgca tgatccattc catagaatcc acatgggtgt aactgcagaa  14880
aacgttgcca aggaatacga tatctcaaga gcacaacaag acgaagctgc attagaatca  14940
cacagaagag catccgccgc tattaaagcc ggttacttta aggatcaaat agttccagta  15000
gtttctaaag gtagaaaggg tgacgttacc ttcgatactg acgaacatgt tagacacgac  15060
gctactattg atgacatgac aaagttaaga cctgttttcg tcaaggaaaa tggtactgtt  15120
acagctggta atgcatctgg tttgaacgat gcagccgctg cagtcgtaat gatggaaaga  15180
gccgaagctg aaagaagagg tttgaaacca ttagctagat tggtttctta tggtcatgct  15240
ggtgtcgatc ctaaagcaat gggtataggt ccagttcctg ctactaagat cgcattggaa  15300
agagccggtt tacaagtctc tgatttggac gtaattgaag ccaatgaagc ttttgccgct  15360
caagcatgtg ccgttacaaa agccttgggt ttagatccag ctaaggtcaa tcctaacggt  15420
agtggtatct ctttaggtca tccaattggt gcaaccggtg ccttgataac tgttaaggct  15480
ttgcacgaat tgaacagagt acaaggtaga tatgcattag ttacaatgtg catcggtggt  15540
ggtcaaggta ttgcagccat attcgaaaga attaagttgt ctggtggtgg tggttctggt  15600
ggtggtggtt ctggtggtgg tggtagtgct gaagcatggt acaatttggg taacgcttac  15660
tacaagcagg gtgactacca aaaggcaatc gaatattacc aaaaagcctt ggaattagac  15720
ccaaataacg ccgaagcttg gtataatttg ggtaatgcct attataaaca gggtgactat  15780
caaaaagcta tagaatacta ccaaaaggca ttggaattag accctaataa cgcagaagcc  15840
tggtataatt tgggtaacgc ctattataag cagggtgact atcaaaaggc catagaagac  15900
taccaaaagg ctttggaatt ggatccaaac aacttacaag ctgaagcatg gaagaatttg  15960
ggtaacgctt attacaaaca gggtgactac caaaaagcta ttgaatacta tcaaaaggct  16020
ttagaattgg accctaataa cgcctctgct tggtacaatt tgggtaatgc ctactataaa  16080
cagggtgact accagaaggc tatcgaatat tatcaaaaag ctttagaatt ggacccaaat  16140
aacgcaaagg cctggtacag acgtggtaat gcctattaca agcagggtga ctaccagaaa  16200
gctattgaag attatcaaaa ggcattggaa ttggatccta acaacagatc cagaagtgct  16260
ggtggtggtg gttctggtgg tggtggttct ggtggtggtg gtgcttctga tgttatgtgg  16320
gaatataagt gggaaaatac aggtgacgct gaattatacg gtccttttac ttcagcacaa  16380
atgcaaacat gggtatccga aggttatttc cctgatggtg tttactgcag aaaattagac  16440
ccacctggtg gtcaattcta caactcaaag agaatagatt tcgacttgta caccggttca  16500
gctggttccg ctgcaggttc tggtgaattt ggttccgcag aagccgctgc aaaagaagcc  16560
gctgcaaagg ctggtagtgc aggttctgcc gctggtagtg gtgaatttgg ttctgaatca  16620
gattccgtcg aattcaataa cgctatatct tacgtaaata agattaaaac cagattttta  16680
gatcatccag aaatctatag atcattctta gaaatcttgc atacatacca aaaagaacaa  16740
ttgcacacca agggtagacc tttcagaggc atgtccgaag aagaagtctt tactgaagta  16800
gctaatttgt ttagaggtca agaagatttg ttgtcagaat tcggtcaatt cttgccagaa  16860
gcaaaaagag gttccggtgc tactaacttc tctttgttga agcaagcagg tgacgttgaa  16920
gaaaatccag gtccaatggg taaaaattac aagtcattgg attccgttgt cgcaagtgac  16980
tttattgcct tgggtataac ttctgaagtc gcagaaacat tgcatggtag attagccgaa  17040
attgtatgta actacggtgc tgcaacccca caaacttgga tcaacatagc aaaccatatc  17100
ttgtcaccag atttgccttt ctccttgcac caaatgttgt tttatggttg ctacaaggat  17160
ttcggtcctg ctccacctgc atggattcca gaccctgaaa aggttaagtc aactaatttg  17220
ggtgctttgt tagaaaagag aggtaaagaa ttcttgggtg ttaagtacaa ggatccaatc  17280
tcttcttttt ctcacttcca agaattttct gtcagaaacc ctgaagtata ctggagaaca  17340
gttttgatgg atgaaatgaa aataagtttc tctaaggacc cagaatgtat cttgagaaga  17400
gatgacatca acaacccagg tggttctgaa tggttgccag gtggttattt gaactcagct  17460
aaaaattgct tgaacgttaa ctccaataag aaattgaatg atactatgat tgtctggaga  17520
gatgaaggca acgatgactt gccattgaat aagttgacat tggatcaatt gagaaagaga  17580
gtttggttgg tcggttacgc attagaagaa atgggtttgg aaaaaggttg tgccatagct  17640
atcgatatgc ctatgcatgt agacgctgta gttatctatt tggctattgt tttagcaggt  17700
tacgtcgtag tttctatagc tgattcattt tccgcaccag aaatctcaac tagattgaga  17760
ttatccaaag caaaggccat attcacacaa gatcacatca tcagaggtaa aaagagaatc  17820
cctttatact caagagtcgt agaagccaaa tccccaatgg ctatagttat cccttgtagt  17880
ggttctaaca ttggtgcaga attaagagat ggtgacatat cttgggatta ctttttggaa  17940
agagccaaag aattcaagaa ttgcgaattc actgccagag aacaaccagt tgatgcttac  18000
actaacattt tgttctccag tggtactaca ggtgaaccaa aagcaatacc ttggacacaa  18060
gccacccctt taaaggccgc tgcagatggt tggtcacatt tggatattag aaaaggtgac  18120
gtcatagtat ggccaactaa tttgggttgg atgatgggtc cttggttggt ttatgctagt  18180
ttgttaaatg gtgcctctat tgctttatac aacggtagtc cattggtttc tggtttcgct  18240
aaatttgtcc aagatgcaaa agtaacaatg ttgggtgttg tcccttcaat cgttagaagt  18300
tggaagtcta caaattgtgt ctcaggttat gattggtcca ccatcagatg cttttcttca  18360
tccggtgaag cctctaatgt cgacgaatat ttgtggttaa tgggtagagc taactacaag  18420
ccagttatcg aaatgtgtgg tggtaccgaa attggtggtg cattctcagc cggttccttt  18480
ttacaagctc aatcattgag ttctttttca tcccaatgta tgggttgcac attgtacatc  18540
ttggataaga acggttaccc aatgcctaaa aataagccag gtattggtga attggcttta  18600
ggtcctgtta tgttcggtgc atctaaaaca ttgttgaacg gtaaccatca cgatgtatac  18660
ttcaagggta tgccaacctt aaatggtgaa gttttgagaa gacatggtga catattcgaa  18720
ttaacctcaa acggttacta ccatgcccac ggtagagctg atgacactat gaacatcggt  18780
ggtatcaaaa tcagttctat cgaaatcgaa agagtatgta acgaagttga tgacagagtc  18840
tttgaaacca ctgcaattgg tgttccacca ttgggtggtg gtccagaaca attagtaatc  18900
tttttcgttt tgaaggattc taacgacaca accatagatt tgaaccaatt gagattatct  18960
tttaacttgg gtttacaaaa gaaattgaac ccattattca aagttactag agtagttcca  19020
ttgtcatcct tacctagaac tgctacaaac aagattatga gaagagtctt gagacaacaa  19080
ttcagtcatt ttgaaggttc tggt                                        19104
```

SEQ ID NO: 204 moltype = DNA length = 18738
FEATURE Location/Qualifiers

```
source                  1..18738
                        mol_type = other DNA
                        organism = synthetic construct
SEQUENCE: 204
atgaagttat ctactaaatt gtgttggtgc ggtattaagg gtagattaag accacaaaag  60
caacaacaat tgcataacac aaacttgcaa atgaccgaat tgaagaaaca aaagactgct  120
gaacaaaaga ctagaccaca aaacgttggt attaaaggta tccaaatcta tatccctaca  180
caatgtgtca atcaatctga attggaaaag tttgatggtg tatcacaggg taaatacact  240
atcggtttag gtcaaacaaa catgtctttc gtaaacgata gagaagacat ctattctatg  300
tcattgactg ttttgtccaa gttgataaaa agttacaaca tcgatacaaa caagattggt  360
agattggaag ttggtaccga aactttgatc gataagtcca agagtgtcaa gtctgtattg  420
atgcaattgt tcggtgaaaa taccgatgtt gaaggtatcg acactttaaa tgcttgttat  480
ggtggtacta acgcattatt caattcattg aactggatcg aatccaatgc ctgggatggt  540
agagatgcta ttgttgtctg cggtgacatc gctatctatg acaaaggtgc tgcaagacca  600
accggtggtg caggtactgt tgccatgtgg ataggtccag atgcacctat cgtttttgac  660
tctgtcagag catcatacat ggaacatgcc tacgatttct acaaaccaga cttcacctcc  720
gaatatcctt acgttgatgg tcacttttct ttgacttgtt acgtcaaggc tttggaccaa  780
gtatacaagt cttactctaa gaaagcaata tctaagggtt tggtttcaga tccagctggt  840
tccgacgcat taaacgtctt gaagtacttc gattacaacg ttttccatgt ccctacatgc  900
aagttggtta ccaagtctta cggtagattg ttgtacaacg atttcagagc taacccacaa  960
ttgttccctg aagtcgacgc tgaattagca actagagatt acgacgaatc tttgacagat  1020
aagaacatcg aaaagacttt cgtaaacgtt gcaaagccat tccacaaaga aagagttgcc  1080
caatcattaa ttgtccctac aaataccggt aacatgtata cagcctcagt ttacgccgct  1140
tttgcttcct tgttaaatta tgtaggtagt gatgacttgc aaggtaaaag agttggttta  1200
ttctcctatg gtagtggttt agcagcctct ttgtactctt gtaagattgt aggtgacgtt  1260
caacacatta ttaaggaatt ggacatcact aataagttgg ctaagagaat cactgaaaca  1320
ccaaaggatt atgaagctgc aatcgaattg agagaaaacg cacatttgaa gaaaaatttc  1380
aaacctcaag gtagtataga acacttgcaa tctggtgtct actacttaac aaacatcgat  1440
gacaaattca gaagatcata cgatgttaaa aagaaattgt ctggtggtgg tggttctggt  1500
ggtggtggtt ctggtggtgg tggtagtgct gaagcatggt ataatttggg taacgcttat  1560
tacaagcagg gtgactacca aaaagcaatc gaatattacc aaaaggcctt ggaattagac  1620
ccaaataacg ccgaagcttg gtacaatttg ggtaatgcat actataaaca gggtgactat  1680
caaaaggcta tcgaatacta ccaaaaggca ttggaattag accctaataa cgcagaagcc  1740
tggtacaatt tgggtaacgc ctactataag cagggtgact atcaaaaagc catagaagac  1800
taccaaaagg ctttggaatt agatccaaat aacttgcaag ctgaagcatg gaaaaatttg  1860
ggtaatgcct actacaaaca gggtgactac caaaaggcaa ttgaatatta tcaaaaagcc  1920
ttggaattag atcctaataa cgcctcagct tggtataatt tgggtaatgc ctattataag  1980
cagggtgact accagaaagc cattgaatat tatcaaaagg ctttagaatt ggatccaaat  2040
aacgcaaaag cctggtatag acgtggtaat gcctactaca agcagggtga ctatcagaag  2100
gctattgaag attatcaaaa agctttggaa ttggatccaa acaacagatc cagaagtgct  2160
ggtggtggtg gttctggtgg tggtggttct ggtggtggtg gtgcttcttt gggtcctttg  2220
ccacctggtt gggaagtaag atccacagtt agtggtagaa tctatttcgt tgatcataac  2280
aacagaacta cacaattcac cgacccaaga ttgcacggtt ctgctggttc agccgctggt  2340
tctggtgaat ttggttccgc agaagcagcc gctaaggaag cagccgctaa agccggttcc  2400
gctggtagtg cagccggtag tggtgaattt ggttctggtg ctatgggtcc attaccacct  2460
ggttgggaaa agagaacaga ttctaacggt agagtctact tcgtaaacca taataccaga  2520
attactcaat gggaagatcc tagatctggt tcaggtgcta ctaacttctc tttgttgaag  2580
caagcaggtg acgttgaaga aaatccaggt ccaatggtag ccgttagaag aaaggctttg  2640
tctatcttag ccgaagctcc agttttggca tcagatagat taccttacaa gaactacgat  2700
tacgacagag tatttggtgc ttgttgcgaa aacgttattg gttatatgcc attgcctgtc  2760
ggtgtaatcg gtccattagt tattgatggt acatcttacc atatccctat ggcaactaca  2820
gaaggttgtt tggttgcatc agccatgaga ggttgcaagg caattaatgc tggtggtggt  2880
gctaccactg ttttaaccaa agatggtatg actagaggtc cagttgtcag atttcctact  2940
ttgaagagat ccggtgcttg taaaatatgg ttagatagtg aagaaggtca aaatgccatc  3000
aaaaaggctt ttaactccac aagtagattc gcaagattgc aacatattca aacatgctta  3060
gccggtgact tgttgtttat gagattcaga acaaccactg gtgacgctat gggtatgaat  3120
atgatatcta agggtgtcga atactcattg aagcaaatgg tagaagaata cggttgggaa  3180
gatatggaag tagtttctgt ttcaggcaac tactgtactg acaaaaagcc agctgcaatt  3240
aactggatag aaggtcgtgg taaatctgtc gtagctgaag caacaatacc tggtgacgtt  3300
gttagaaagg ttttgaaatc tgacgtatca gctttggttg aattgaacat cgctaaaaat  3360
ttggttggtt ccgccatggc tggtagtgtc ggtggtttta atgcacatgc cgctaactta  3420
gttacagcag tcttcttggc cttaggtcaa gatccagctc aaaacgtaga atcttcaaac  3480
tgtatcacct tgatgaaaga agttgatggt gacttaagaa tatccgttag tatgccatca  3540
atagaagtcg gtacaatcgg tggtggtacc gtcttggaac ctcaaggtgc aatgttagat  3600
ttgttaggtg ttagaggtcc acatgcaact gcccctggta caaatgctag acaattggca  3660
agaattgtcg cttgtgcagt attagctggt gaattgtcct tatgcgcagc cttggctgca  3720
ggtcacttag ttcaaagtca tatgacacac aacagaaagt tgtctggtgg tggtggttct  3780
ggtggtggtg gttctggtgg tggtggtagt gccgaagctt ggtataattt gggtaacgca  3840
tattacaagc agggtgacta ccaaaaggcc atcgaatact accaaaaggc tttggaattg  3900
gacccaaata acgcagaagc ctggtacaat ttgggtaatg cttactataa acagggtgac  3960
tatcaaaagg caattgaata ttaccaaaag gccttggaat tagaccctaa taacgctgaa  4020
gcatggtaca atttgggtaa cgcctactat aagcagggtg actatcaaaa agctattgaa  4080
gactaccaaa aggcattgga attagatcca aataacttgc aagccgaagc ttggaaaaat  4140
ttgggtaacg cttactacaa acagggtgac taccaaaaag ctattgaata ctatcaaaaa  4200
gctttggaat tggaccctaa taacgcatct gcctggtata atttgggtaa tgcttattat  4260
aaacagggtg actaccagaa ggcaatagaa tactatcaaa aagccttgga attagaccca  4320
aataacgcta aagcatggta tagacgtggt aatgcttact ataagcaggg tgactaccag  4380
aaagctatag aagattatca aaaggcattg gaattggatc ctaacaacag atctagatca  4440
gctggtggtg gtggttctgg tggtggtggt tctggtggtg gtggtgcttc cagttattac  4500
```

-continued

```
catcaccatc accatcactt ggaatccaca agtttataca aaaaggcagg ttcagaattt  4560
ttcagaagag aaagaaataa gatggccgct gcaaaatgta gaaacagaag aagagaattg  4620
acagatacct tacaagctga aaccgatcaa ttggaagacg aaaagtctgc attgcaaact  4680
gaaatagcca atttgttgaa ggaaaaggaa aagttggaat tcattttagc cgctcataga  4740
ccagcttgca aaattcctga tgacttgggt ttcccagaag aaatgtcttt agaaggttcc  4800
gcaggtagtg cagccggttc cggtgaattt ggtagtgctg aagctgcagc caaggaagct  4860
gcagccaaag ctggttctgc aggttcagct gcaggttccg gtgaattcgg ttcttcatac  4920
tatcaccatc accatcatca cttggaatct acctcattat acaaaaaggc tggttccggt  4980
agtcaaaagg ttgaatcttt gaagcaaaag attgaagaat tgaagcaaag aaaagcccaa  5040
ttgaagaatg atatcgctaa cttagaaaag gaaatcgcct acgctgaaac tggttctggt  5100
gctactaact tctctttgtt gaagcaagca ggtgacgttg aagaaaatcc aggtccaatg  5160
agtttaccat ttttgacatc tgctcctggt aaagttatta tattcggtga acatagtgcc  5220
gtctataata agccagctgt cgctgcatct gtatcagctt tgagaacata cttgttgatc  5280
tctgaatctt cagcacctga taccatcgaa ttggatttcc cagacatctc attcaatcac  5340
aagtggtcca ttaatgattt caacgctatc accgaagacc aagtaaactc acaaaagttg  5400
gccaaagctc aacaagcaac tgatggtttg tcacaagaat tagtttcctt gttagaccca  5460
ttgttggctc aattgtccga aagtttccat taccacgccg ctttctgttt cttgtacatg  5520
ttcgtttgtt tatgccctca tgctaagaat atcaaatttt ctttgaagtc tactttgcca  5580
attggtgcag gtttaggttc cagtgcctct atatcagttt ccttagcatt ggccatggct  5640
tatttgggtg gtttgatagg tagtaacgat ttggaaaagt tgtctgaaaa cgacaagcat  5700
atcgtcaacc aatgggcatt catcggtgaa aaatgcattc acggtactcc tagtggtata  5760
gataatgcag ttgccacata tggtaacgct ttgttattcg aaaaggactc tcataacggt  5820
accatcaaca ctaacaactt caagttcttg gatgactttc ctgcaatacc aatgatcttg  5880
acttacacaa gaattccaag atctactaaa gatttggtag ctagagtcag agtattggtt  5940
acagaaaagt tccctgaagt tatgaagcca atcttggatg caatgggtga atgtgccttg  6000
caaggtttgg aaatcatgac aaagttgtca aagtgcaagg gtactgatga cgaagctgtt  6060
gaaacaaata acgaattgta cgaacaattg ttggaattga tcagaatcaa tcatggtttg  6120
ttagtttcaa ttggtgtctc ccacccaggt ttagaattga taaagaactt gtcagatgac  6180
ttaagaatcg gttccacaaa attgaccggt gctggtggtg gtggttgttc tttgaccttg  6240
ttaagaagag atatcactca agaacaaatc gacagtttta aaaagaaatt gcaagatgac  6300
ttctcttacg aaactttcga aacagatttg ggtggtactg gttgttgctt gttgtcagct  6360
aagaatttga acaaagattt gaagattaaa tccttggttt tccaattgtt cgaaaataag  6420
actacaacca agcaacaaat cgatgacttg ttgttgcctg gtaatacaaa cttgccatgg  6480
acctcaaaat tatctggtgg tggtggttct ggtggtggtg gttctggtgg tggtggtagt  6540
gctgaagcat ggtataattt gggtaacgca tattacaagc agggtgacta ccaaaaggct  6600
atcgaatact accaaaaggc attggaattg gaccctaata acgccgaagc ttggtacaat  6660
ttgggtaatg cttactataa acagggtgac tatcaaaagg ccattgaata ttaccaaaag  6720
gctttggaat tggacccaaa taacgcagaa gcctggtaca atttgggtaa cgcttactat  6780
aagcagggtg actatcaaaa agcaattgaa gactaccaaa aggccttaga attggatcct  6840
aataacttgc aagctgaagc atggaaaaat ttgggtaacg cttattataa acagggtgac  6900
taccaaaaag ccattgaata ctatcaaaaa gcattggaat tggatccaaa taacgcctct  6960
gcttggtata atttgggtaa tgcttattat aagcagggtg actaccagaa agccatagaa  7020
tactatcaaa aagctttgga attagaccct aataacgcaa aagcctggta tagacgtggt  7080
aatgcttact acaaacaggg tgactatcag aaggcaatag aagattatca aaaagcttta  7140
gaattagacc caaataacag aagtagatct gctggtggtg gtggttctgg tggtggtggt  7200
tctggtggtg gtggtgcttc tatggaacct gcaatggaac cagaaacatt ggaagccaga  7260
atcaatagag ctaccaatcc tttgaacaag gaattggatt gggcttctat taatggtttc  7320
tgtgaacaat tgaacgaaga cttcgaaggt ccacctttag caacaagatt attggcccat  7380
aaaattcaat caccacaaga atgggaagca atacaagcct taaccgtctt ggaaacttgt  7440
atgaagtcct gcggtaaaag attccacgat gaagttggta aattcagatt tttgaacgaa  7500
ttgatcaagg ttgtctcacc taagtatttg ggtagtagaa catctgaaaa ggttaaaaac  7560
aagatcttgg aattgttgta ctcctggacc gtaggtttac cagaagaagt taagatcgct  7620
gaagcatacc aaatgttgaa gaaacaaggt attgttaagt caggttccgc cggtagtgca  7680
gccggttctg gtgaattcgg ttctgcagaa gctgcagcca aggaagctgc agccaaagct  7740
ggttcagcag gttccgctgc aggttctggt gaatttggtt caggtgcaat gggttccatg  7800
gccgaagctg aaggtgaaag tttggaatct tggttaaata aggctacaaa tccatcaaac  7860
agacaagaag attgggaata tatcattggt ttctgtgacc aaatcaataa ggaattggaa  7920
ggtcctcaaa tagctgttag attattggca cataagatcc aatctccaca agaatgggaa  7980
gccttacaag ctttgactgt tttagaagct tgtatgaaga attgcggtag aagatttcac  8040
aacgaagtcg gtaaattcag atttttgaat gaattaatta aggtagttag tccaaaatac  8100
ttaggtgaca gagtttctga aaaggttaag accaaagtca tagaattgtt gtactcttgg  8160
actatggcct tgcctgaaga agctaagatc aaagatgcat accatatgtt gaagagacaa  8220
ggtatagtcc aatcagatcc acctatccca gtagacagaa ctttgattcc atctccacca  8280
ccaagaccta aaaatggttc cggtgctact aacttctctt tgttgaagca agcaggtgac  8340
gttgaagaaa atccaggtcc aatgtccgaa ttaagagctt ttagtgcacc tggtaaagcc  8400
ttgttagctg gtggttattt ggttttggat acaaagtacg aagcattcgt tgtcggtttg  8460
tcagccagaa tgcatgcagt cgcccaccct tacggttctt tacaaggttc tgataagttc  8520
gaagtaagag tcaagtctaa gcaattcaag gacggtgaat ggttatacca tatatctcca  8580
aagtcaggtt ttattcctgt ttccataggt ggtagtaaaa atccattcat cgaaaaggtt  8640
attgcaaacg tcttttctta cttcaagcct aacatggatg actactgtaa cagaaacttg  8700
ttcgtcatcg atatattctc tgatgacgct tatcattctc aagaagactc agtaactgaa  8760
cacagaggta atagaagatt gtcctttcat agtcacagaa ttgaagaagt tccaaaaacc  8820
ggtttaggtt cttcagctgg tggtttagtc actgtattga ctacagcttt agcatccttt  8880
ttcgttagtg atttggaaaa caacgtagac aagtacagag aagttattca taatttggca  8940
caagtagccc actgccaagc acaaggtaaa atcggttccg gttttgatgt tgctgcagcc  9000
gcttatggtt caattagata cagaagattc ccacctgctt tgatatctaa tttgccagat  9060
atcggttctg ctacatatgg ttcaaagttg gcacatttgg ttgatgaaga agactggaac  9120
atcacaatta aatccaacca tttgcctagt ggtttgacct tatggatggg tgacattaag  9180
aatggttctg aaactgttaa gttggtccaa aaagtaaaga actggtacga ttctcatatg  9240
```

-continued

```
ccagaatcat tgaagatcta cacagaatta gaccatgcta attccagatt catggatggt  9300
ttgagtaaat tagacagatt gcatacccac gatgactact ctgatcaaat cttcgaatca  9360
ttggaaagaa acgactgtac ttgccaaaaa tacccagaaa tcacagaagt aagagatgcc  9420
gttgctacca taagaagatc ttttagaaag atcactaagg aatcaggtgc agatatcgaa  9480
ccacctgttc aaacatcttt gttagatgac tgtcaaacct tgaagggtgt cttaacttgc  9540
ttgattccag gtgctggtgg ttatgatgca atagccgtca tcactaaaca agatgtagac  9600
ttgagagctc aaacagcaaa cgataagaga ttttcaaagg tccaatggtt agatgtaacc  9660
caagctgact ggggtgttag aaaagaaaag gatcctgaaa cttacttgga caaaaagtta  9720
tctggtggtg gtggttctgg tggtggtggt tctggtggtg gtggtagtgc tgaagcatgg  9780
tacaatttgg gtaacgcata ctacaagcag ggtgactacc aaaaggccat agaatactac  9840
caaaaggctt tggaattgga cccaaataac gccgaagctt ggtataattt gggtaatgct  9900
tattataaac agggtgacta tcaaaaggca atcgaatact accaaaaggc cttggaatta  9960
gaccctaata acgcagaagc ctggtataat ttgggtaacg cttattataa gcagggtgac  10020
tatcaaaaag ctatcgaaga ctaccaaaag gcattggaat tagatccaaa taacttgcaa  10080
gctgaagcat ggaagaattt gggtaacgct tactataaac agggtgacta ccaaaaagcc  10140
attgaatatt atcaaaaagc tttggaattg gatcctaata acgcctctgc ttggtacaat  10200
ttgggtaatg cttactataa gcagggtgac tatcagaagg ctattgaata ttatcaaaag  10260
gctttagaat tggaccctaa taacgcaaag gcctggtaca gacgtggtaa cgcttattac  10320
aaacagggtg actaccagaa agctattgaa gattatcaaa aggcattgga attggatcct  10380
aacaacagat ccagaagtgc tggtggtggt ggttctggtg gtggtggttc tggtggtggt  10440
ggtgcttcca gttattacca tcaccatcac catcacttgg aatctacatc attatacaaa  10500
aaggctggtt ccggtagtca aaaggttgaa gaattgaaaa ataagatagc cgaattggaa  10560
aacagaaacg ctgttaaaaa gaacagagtc gcacatttga aacaagaaat agcctacttg  10620
aaggatgaat tagcagccca tgaatttgaa ggttctgccg gttcagctgc aggttctggt  10680
gaattcggtt cagctgaagc cgctgcaaaa gaagccgctg caaaggccgg ttccgctggt  10740
agtgccgctg gttctggtga atttggttct tcatactatc accatcacca tcatcacttg  10800
gaatctactt cattatataa aaaggccggt tccggtagtt tcgaaaacgt tacacatgaa  10860
ttcattttgg ctaccttgga aaacgaaaac gcaaagttaa gaagattgga agccaagttg  10920
gaaagagaat tagctagatt gagaaatgaa gttgcatggt taggttctgg tgctactaac  10980
ttctctttgt tgaagcaagc aggtgacgtt gaagaaaatc caggtccaat gacagtttat  11040
accgcttctg tcaccgcacc tgtaaatatt gctactttga aatactgggg taaaagagat  11100
actaagttga atttgccaac aaactcttca atctcagtta cattgtccca agatgactta  11160
agaaccttga cttctgctgc aactgctcct gaattcgaaa gagatacatt gtggttgaat  11220
ggtgaaccac attctatcga caacgaaaga actcaaaact gtttgagaga tttgagacaa  11280
ttgagaaagg aaatggagag taaggatgct tctttgccta cattgagtca atggaagttg  11340
cacatagttt ctgaaaacaa cttcccaacc gccgctggtt tggcatccag tgcagccggt  11400
ttcgctgcat tagtctctgc aatcgccaag ttgtaccaat tgccacaaag tacatctgaa  11460
atcagtagaa tcgctagaaa aggttcaggt tccgcatgta gatctttatt tggtggttac  11520
gtcgcatggg aaatgggtaa agccgaagac ggtcatgatt caatggccgt acaaatagct  11580
gactcttcag attggcctca aatgaaagct tgcgtcttgg ttgtctcaga catcaaaaag  11640
gatgtatcca gtacacaagg catgcaattg actgttgcaa catccgaatt gtttaaagaa  11700
agaatcgaac acgtagttcc aaaaagattc gaagtcatga gaaaggctat cgtagaaaag  11760
gatttcgcca ccttcgctaa ggaaactatg atggacagta actctttcca tgcaacttgt  11820
ttggattcat ttccacctat tttctatatg aacgacacct caaagagaat aatctcctgg  11880
tgccacacta tcaaccaatt ctacggtgaa acaatcgttg cttacacctt cgatgcaggt  11940
cctaatgccg tcttgtatta cttagccgaa aacgaatcaa agttgttcgc ttttatatat  12000
aagttgtttg gttccgttcc aggttgggat aaaaagttca ctacagaaca attggaagct  12060
tttaatcatc aattcgaatc ttcaaacttt actgccagag aattggactt agaattgcaa  12120
aaggatgtag ctagagttat cttgacccaa gttggttcag gtcctcaaga aactaacgaa  12180
tccttgatag atgctaagac aggtttgcca aaagaaaaat tgtctggtgg tggtggttct  12240
ggtggtggtg gttctggtgg tggtggtagt gctgaagcat ggtataattt gggtaacgct  12300
tattacaagc agggtgacta ccaaaaggcc atcgaatact accaaaaggc tttggaattg  12360
gaccctaata acgccgaagc ttggtacaat ttgggtaatg cctactataa acagggtgac  12420
tatcaaaaag caattgaata ttaccaaaag gccttggaat tggacccaaa taacgcagaa  12480
gcctggtaca atttgggtaa cgcctactat aagcagggtg actatcaaaa ggctatcgaa  12540
gattaccaaa aggcattaga attggatcct aataacttgc aagctgaagc atggaaaaat  12600
ttgggtaatg cctattataa acagggtgac taccaaaaag ctattgaata ctatcaaaaa  12660
gctttagaat tagacccaaa taacgcctca gcttggtata atttgggtaa tgcatactac  12720
aaacagggtg actatcagaa ggcaattgaa tactatcaaa aggcattaga attagatcct  12780
aataacgcaa aagcctggta tagacgtggt aatgcctact acaagcaggg tgactatcag  12840
aaggcgattg aagactacca aaaggcattg gaattggatc caaacaacag atcaagatcc  12900
gctggtggtg gtggttctgg tggtggtggt tctggtggtg gtggtgcttc tgcaatggcc  12960
gatttggaac aaaaggtatt ggaaatggaa gctagtacat atgacggtgt ttttatttgg  13020
aagatctctg atttcccaag aaaaagacaa gaagctgttg caggtagaat ccctgctatt  13080
tttagtccag cattctacac ctctagatac ggttacaaga tgtgtttgag aatatatttg  13140
aatggtgacg gtactggtag aggtactcat ttgtctttgt ttttcgtcgt aatgaagggt  13200
cctaatgatg ctttgttgag atggcctttt aatcaaaagg ttaccttgat gttgttggat  13260
caaaacaaca gagaacacgt tatcgacgct tttagacctg atgtcacttc cagttctttc  13320
caaagaccag ttaatgatat gaacattgct tctggttgtc ctttgtttg cccagtctca  13380
aagatggaag ctaaaaattc ctatgttaga gatgacgcca tcttcattaa ggctatcgtt  13440
gatttgactg gtttaggttc agcaggttcc gccgctggtt ctggtgaatt tggttccgcc  13500
gaagcagccg ctaaggaagc agccgctaaa gcaggtagtg ccggttctgc agccggctct  13560
ggcgaatttg gtagtgcctc tattaaattg caatcatccg acggtgaaat cttcgaagtt  13620
gatgtcgaaa tagcaaagca atctgttacc ataaaaacta tgttggaaga tttgggtatg  13680
gatgacgaag gtgacgatga tccagttcct ttgccaaatg tcaacgctgc aatattgaag  13740
aaagttattc aatggtgcac acatcacaag gacgatccac ctccacctga agacgatgaa  13800
aataaggaaa agagaactga cgatattcca gtatgggacc aagaattctt gaaggttgat  13860
caaggtacat tgttcgaatt gatcttggcc gctaactatt tggacatcaa gggtttgtta  13920
gatgtaacat gtaaaaccgt tgctaacatg atcaagggta aaacaccaga agaaatcaga  13980
```

-continued aagaccttta atattaagaa tgatttcact gaagaagaag aagcacaagt tagaaaggaa 14040
aaccaatggt gcggttctgg tgctactaac ttctctttgt tgaagcaagc aggtgacgtt 14100
gaagaaaatc caggtccaat gactgctgat aataactcta tgccacatgg tgccgtatct 14160
tcatacgcta agttggttca aaaccaaaca cctgaagata tcttggaaga attcccagaa 14220
atcatccctt tgcaacaaag accaaacact agatccagtg aaacatccaa cgatgaaagt 14280
ggtgaaacct gtttttcagg tcatgacgaa gaacaaatta aattgatgaa cgaaaactgc 14340
atcgtattgg attgggatga caatgcaata ggtgccggta ctaagaaagt ttgtcatttg 14400
atggaaaaca tagaaaaggg tttgttgcac agagctttct ccgtttttat attcaatgaa 14460
cagggtgaat tgttattgca acaaagagca acagaaaaga tcacctttcc agatttgtgg 14520
actaatacat gttgctctca tcctttgtgc attgatgacg aattaggttt gaagggtaaa 14580
ttggatgaca aaattaaggg tgctataact gctgcagtca gaaaattaga tcatgaattg 14640
ggtataccag aagacgaaac caagactcgt ggtaaattcc atttcttaaa cagaatccac 14700
tatatggctc catctaacga accttggggt gaacatgaaa tcgattacat cttattttac 14760
aagattaatg caaaggaaaa cttgacagtt aacccaaacg ttaatgaagt cagagatttc 14820
aaatgggttt ctcctaatga tttgaagacc atgtttgctg acccatcata taagtttact 14880
ccttggttca agatcatctg tgaaaactac ttgtttaact ggtgggaaca attagatgac 14940
ttgtctgaag ttgaaaacga tagacaaatc catagaatgt tgaaattgtc tggtggtggt 15000
ggttctggtg gtggtggttc tggtggtggt ggtagtgccg aagcttggta caatttgggt 15060
aacgcttact acaagcaggg tgactaccaa aaggcaatcg aatactacca aaaggccttg 15120
gaattggacc caaataacgc agaagcctgg tataatttgg gtaatgcata ttataaacag 15180
ggtgactatc aaaaggctat tgaatattac caaaaggcat tggaattgga ccctaataac 15240
gctgaagcat ggtataattt gggtaacgcc tattataagc agggtgacta tcaaaaagcc 15300
atcgaagact accaaaaggc tttggaattg gatccaaaca acttacaagc cgaagcttgg 15360
aagaatttgg gtaacgctta ttacaaacag ggtgactacc aaaaagctat tgaatactat 15420
caaaaagcct tagaattaga ccctaataac gcatctgcct ggtacaattt gggtaatgcc 15480
tattacaagc agggtgacta tcagaaggct attgaatact accaaaaagc attggaattg 15540
gatccaaata acgctaaggc atggtacaga cgtggtaatg cctattacaa gcagggtgac 15600
tatcaaaagg cgattgaaga ttatcaaaaa gctttggaat tggatcctaa caacagatct 15660
agatcagctg gtggtggtgg ttctggtggt ggtggttctg gtggtggtgg tgcttcttca 15720
tattaccatc accatcacca tcacttagaa tccacaagtt tgtacaaaaa ggctggttct 15780
ggttcaaaca ccgttaagga attaaagaac tacatccaag aattggaaga aagaaacgca 15840
gaattgaaaa atttgaagga acatttgaag tttgccaagg ctgaattaga attcgaattg 15900
gccgctcaca aatttgaagg ttccgctggt agtgcagccg gttccggtga attcggtagt 15960
gcagaagctg cagccaaaga agctgcagcc aaggctggtt ctgcaggttc agctgcaggt 16020
tctggtgaat ttggttccag ttactatcac catcaccatc atcacttaga atccacaagt 16080
ttgtataaaa aggccggttc tggttcacaa aaagtcgcac aattaaagaa tagagtagcc 16140
tacaagttga aggaaaacgc taagttggaa aacattgtcg caagattaga aaacgataat 16200
gccaacttgg aaaaagacat cgctaatttg gaaaaggata ttgcaaactt ggaaaagagat 16260
gttgccagag gttctggtgc tactaacttc tctttgttga agcaagcagg tgacgttgaa 16320
gaaaatccag gtccaatgga agctaagata gatgaattga taaataacga cccagtttgg 16380
tcttcacaaa acgaatcctt gatcagtaag ccatacaacc atatcttgtt aaaacctggt 16440
aaaaatttca gattaaattt gatcgtacaa atcaacagag ttatgaattt gcctaaggat 16500
caattggcta tcgtttctca aatagtcgaa ttgttgcata actccagttt gttgatcgat 16560
gacatcgaag ataacgcacc attgagaaga ggtcaaacta catcccactt aatttggggt 16620
gtccctagta ctattaatac cgcaaactac atgtacttca gagccatgca attggtatca 16680
caattgacca ctaaggaacc attgtaccat tggttgatca caatttttaa cgaagaattg 16740
attaatttgc acagaggtca aggtttggat atctattgga gagacttctt accagaaatt 16800
atacctaccc aagaaatgta cttgaacatg gtaatgaata agactggtgg tttgtttaga 16860
ttgaccttga gattaatgga agctttgtct ccatcttcac atcacggtca ttcattggtt 16920
cctttcataa acttgttggg tatcatctat caaatcagag atgactactt gaatttgaag 16980
gatttccaaa tgtccagtga aaagggtttc gcagaagaca taactgaggg taaattgtca 17040
ttcccaatcg tccatgcctt aaacttcaca aaaaccaagg gtcaaaccga acaacacaat 17100
gaaatcttaa gaattttgtt attgagaact tctgataagg acataaagtt gaagttgatc 17160
caaatcttgg aattcgatac caactcattg gcttacacta agaacttcat caaccaattg 17220
gttaacatga ttaagaatga taacgaaaat aagtacttgc cagatttggc ctcccatagt 17280
gacactgcta caaatttgca cgatgaattg ttgtacatca tcgaccattt gtccgaattg 17340
aaattatctg gtggtggtgg ttctggtggt ggtggttctg gtggtggtgg tagtgcagaa 17400
gcctggtaca acttgggtaa cgcttactac aagcagggtg actaccaaaa ggctatcgaa 17460
tactaccaaa aggcattgga attagaccca aataacgctg aagcatggta caacttaggc 17520
aacgcatatt ataaacaggg tgactatcaa aaggccatag aatactacca aaaggctttg 17580
gaattggacc ctaataacgc cgaagcttgg tacaacttgg gtaatgctta ttacaagcag 17640
ggtgactatc aaaaagcaat tgaagactac caaaaagcct tggaattaga tccaaataac 17700
ttgcaagcag aagcctggaa gaacttaggc aacgcatact ataaacaggg tgactaccaa 17760
aaagccattg aatattatca aaaagctttg gaattagacc ctaataacgc ttctgcttgg 17820
tataacttag gcaatgccta ttataagcag ggtgactatc agaaagctat tgaatattat 17880
caaaaggcct tggaattgga cccaaataac gccaaggctt ggtacagacg tggtaacgca 17940
tactacaaac agggtgacta tcagaaggct atcgaagatt atcaaaaagc attagaatta 18000
gatcctaata acagatctag atcagctggt ggtggtggtt ctggtggtgg tggttctggt 18060
ggtggtggtg cttctttgtg tactatgaaa aagggtccat ctggttacgg ttttaatttg 18120
cattctgata agtcaaagcc tggtcaattc ataagatcag ttgatccaga ctcccctgca 18180
gaagccagtg gtttgagagc tcaagataga attgtcgaag taaatggtgt ctgcatggaa 18240
ggtaaacaac acggtgacgt tgtttctgct attagagctg gtggtgacga aactaagtta 18300
ttggtagttg acagagaagg ttccgccggt agtgctgcag gttctggtga atttggttca 18360
gctgaagccg ctgcaaaaga agccgctgca aaggccggtt ctgctggttc agccgctggt 18420
tctggtgaat tcggttcttc atccggtgct ataatctata cagttgaatt gaagagatac 18480
ggtggtccat taggtattac tatatctggt acagaagaac cattcgatcc tatcatcatc 18540
agttctttga ctaagggtgg tttagctgaa agaacaggtg caatccatat tggtgacaga 18600
atattggcta tcaattcatc cagtttgaaa ggtaaaccat tgtcagaagc tatccactta 18660
ttgcaaatgg caggtgaaac cgttactttg aaaatcaaaa agcaaacaga tgcacaacct 18720

-continued

```
gcctcttcag gttctggt                                              18738

SEQ ID NO: 205          moltype = DNA  length = 18864
FEATURE                 Location/Qualifiers
source                  1..18864
                        mol_type = other DNA
                        organism = synthetic construct
SEQUENCE: 205
atgaatcatt tgagagccga aggaccagct tctgtcttag caataggtac tgccaatcca  60
gagaacatct tgttacaaga tgaatttcct gactattact tcagagttac caaatccgag  120
catatgacgc agttgaagga aaagtttaga aagatctgtg ataagagtat gatcagaaag  180
aggaactgct tcttaaacga agagcatttg aagcaaaatc ctagattagt ggaacacgag  240
atgcaaacat tggatgctag gcaggacatg ttagttgtcg aagttcctaa attgggtaaa  300
gatgcatgtg ccaaagctat taaggaatgg ggtcaaccca agtctaagat aactcatttg  360
atttttacaa gtgctagcac tacagatatg cctggtgcag actatcactg tgccaaacta  420
cttggtttat cgccctctgt gaagagagtt atgatgtatc aactaggttg ctacggtggt  480
ggtactgtac ttagaatcgc taaagacatt gcagaaaata acaagggtgc cagggtcttg  540
gctgtatgtt gcgatattat ggcttgcttg tttagaggtc catcagaatc cgatttggag  600
ctgttggttg gtcaagctat tttcggtgac ggtgctgcag ctgttattgt tggtgcagaa  660
cctgatgagt cagtcggtga aagaccaatc tttgaattgg tttctaccgg tcaaacgatt  720
ttaccaaata gtgaaggtac aataggtggt catatcagag aagctggttt gatattcgat  780
ttgcacaaag acgttcctat gctaatatct aacaacatcg aaaagtgtct gatcgaggct  840
tttacccccca tcggtatttc cgattggaat agtatattct ggatcacgca tccaggtggt  900
aaagcaatcc tggataaggt tgaagagaag ctgcatttga agtctgataa gtttgtcgac  960
agcagacatg tattgtcgga acacggtaac atgtcttcat ccacagtgct gttcgttatg  1020
gatgaactta gaaagagatc tttggaagag ggtaaaagca ccacgggtga cggttttgaa  1080
tggggtgttc tttttggatt cggccccggt ttgaccgtcg aaagagtagt tgttagatct  1140
gtaccaatta aatacaagtt gtctggtggt ggtggttctg gtggtggtgg ttctggtggt  1200
ggtggtagtg cagaagcctg gtacaatttg ggtaacgctt actacaagca gggtgactac  1260
cagaaggcta tcgagtatta ccaaaaagca cttgaactgg atccaaataa cgctgaggca  1320
tggtataatt tgggcaacgc atattacaaa cagggtgact atcaaaaggc catagaatac  1380
taccaaaagg ctttggagct ggatcctaat aacgccgaag cttggtacaa tttgggaaat  1440
gcctattata agcagggtga ctatcagaag gcaatagagg actaccaaaa agccctagaa  1500
cttgatccaa ataatttgca ggcagaagcc tggaagaatt tgggtaatgc ttactataaa  1560
cagggtgact atcagaaagc tattgaatac taccaaaaag cactggaatt ggatcctaat  1620
aacgcttctg cttggtacaa tttgggcaac gcttactaca aacagggtga ctaccaaaaa  1680
gctatcgaat attatcaaaa ggctctggaa ctagatccaa ataacgccaa ggcttggtat  1740
agaaggggaa atgcttatta taaacagggt gactaccaga aagcaattga agactaccaa  1800
aaagcccttg aactggatcc taataacaga tctagaagcg ctggtggtgg tggttctggt  1860
ggtggtggtt ctggtggtgg tggtgcttct ggtaacaact tagaaacata cgagtggtac  1920
aataagtcta tttctagaga taaggccgaa aagttactac ttgacaccgg taaagaaggt  1980
gcttttatgg ttagagattc tagaactcca ggtacttata cagtctctgt attcacaaag  2040
gctatcatct cagaaaaccc atgtatcaag cattaccaca tcaaggaaac caacgactct  2100
cctaaaagat attacgtggc agaaaagtac gtttttgatt caatcccact gttgattcaa  2160
tatcatcagt acaatggtgg tggtttggtg actagattga ggtatcctgt ttgcggtggt  2220
agcgcaggtt cggctgcagg atcaggcgaa tttggttccg ccgaggccgc tgcaaaagaa  2280
gccgctgcaa aggctggatc tgcaggctca gccgctggtt ctggagaatt tggttctggt  2340
tctcatccct ggtttttcgg taaaattcca agagcaaagg ccgaagaaat gttgtctaaa  2400
caaagacacg acggtgcatt tttgataagg gaaagtgaga gcgcacctgg tgacttttcg  2460
ttgtctgtta aattcggtaa tgatgtccaa catttcaagg tattgagaga tggtgctggt  2520
aaatactttt tgtgggtcgt aaagttcaat tccttgaacg aattagtgga ttaccataga  2580
tcaacttccg ttagtaggaa ccaacagatt ttcttgagag atatcgaaca agttccacaa  2640
cagcctacag gttctggagc tactaacttc tctttgttga agcaagcagg tgacgttgaa  2700
gaaaatccag gtccaatggc tgtaaagcat ttgatcgtgt tgaaattcaa ggatgaaatc  2760
acagaggcac aaaaggaaga gtttttcaag acctacgtta atttggtcaa cataatccca  2820
gctatgaaag atgtatactg ggtaaagac gtgacccaaa agaataagga agagggttat  2880
acccatatag tagaagtgac gttcgaatca gttgaaacta tccaagatta catcatacac  2940
cctgctcatg ttggctttgg tgacgtctac agatccttct gggaaaagtt gctgatcttc  3000
gattacactc caagaaagaa attgtctggt ggtggtggtt ctggtggtgg tggttctggt  3060
ggtggtggta gtgcagaagc ctggtataat ttgggaaacg cttattacaa acagggtgac  3120
taccaaaagg ccatcgagta ttaccaaaaa gctcttgaac tggacccaaa taacgctgag  3180
gcatggtata atttgggtaa cgcatactat aagcaaggtg actaccaaaa ggcaattgaa  3240
tattaccaaa aggccttgga gttagaccct aataacgccg aagcttggta caatttgggt  3300
aatgcctact ataaacaggg tgactatcaa aaggctatag aggactacca gaaagcacta  3360
gaacttgatc ccaataactt gcaagcagaa gcctggaaga atttgggtaa tgcctattat  3420
aagcaaggtg actatcaaaa agctattgaa tactaccaaa aagctctgga attggaccct  3480
aataacgctt ctgcttggta taatttgggt aatgcatact acaagcaagg tgactaccag  3540
aaggcaatag agtattacca aaaagcctta gaactagacc caaataacgc caaggcttgg  3600
tacagaaggg gtaatgccta ctacaagcag ggtgactacc aaaaagctat tgaggactac  3660
caaaaagcac ttgaactgga tcctaataac agatctagat cagctggtgg tggtggttct  3720
ggtggtggtg gttctggtgg tggtggtgct tccggtcaag atagaagtga agccacattg  3780
attaaaagat tcaaaggaga aggtgttaga tacaaggcta agctgatcgg tatcgatgaa  3840
gtttctgctg ctagaggtga caaattgtgt caagactcta tgatgaagct gaagggcgtt  3900
gtcgcaggtg ccagatctaa gggtgaacat aagcaaaaga tatttttgac gatctcattc  3960
ggtggtatta aaatcttcga tgaaaagact ggtgctttac aacatcacca tgcagtacac  4020
gaaatctctt acatcgctaa ggatatcaca gaccatagag cattcggtta cgtttgcggt  4080
aaagaaggca atcatagatt tgtcgctatt aaaaccgccc aagccgctga accagtcatc  4140
ttggatttga gagacttatt ccagctaatc tatgaactaa agcaaagaga agaattggaa  4200
aagaaagctg gtagcgcagg atcggcagcc ggtagcggag aatttggttc tgctgaggct  4260
```

-continued

```
gcagccaaag aagctgcagc caaggccggc tctgctggtt cagctgcagg ctctggtgaa  4320
tttggttctg gttctcatat gggttctcaa ttttgggtaa cttctcaaaa gactgaagct  4380
tccgagagat gtggtttgca aggctcctat attttaaggg tggaagccga gaagcttacc  4440
ctacttacgc tgggtgcaca gagtcaaata ttggaacccc tgttgttctg gccatatact  4500
ttattgagaa gatacggtag agataaagtt atgttcagtt tcgaagctgg tagaagatgc  4560
ccaagcggtc ctggaacttt tacattccag acatcacaag gcaatgatat ctttcaggca  4620
gttgaagccg ctattcaaca gcaaaaagcc cagggtaaag tcggacaggc tcaagacatt  4680
ctaagattgg aacaccatca ccatcatcat ggttctggtg ctactaactt ctctttgttg  4740
aagcaagcag gtgacgttga agaaaatcca ggtccaatgg gtttgtcttc agtttgtaca  4800
ttctctttcc aaacgaacta ccatactttg ctgaaccctc acaacaacaa tcccaaaact  4860
tctttgcttt gctacagaca tccaaaaacc cctattaagt atagctacaa caatttccca  4920
tcgaaacatt gtagtactaa gagcttccat ttgcaaaata agtgctccga atctttgtct  4980
atcgctaaga actcaattag agctgcaact acaaatcaga cggaaccacc tgagtcggat  5040
aatcactctg tagccaccaa aattttgaac tttggtaaag cttgttggaa gctgcaaaga  5100
ccatacacaa taatagcctt cacctcctgt gcttgcggtt tgtttggtaa agaactgttg  5160
cataacacaa atttgatttc gtggtctttg atgttcaagg catttttctt tttggttgca  5220
atcctttgca tcgcctcttt taccacgact attaatcaaa tctatgattt gcacatcgac  5280
agaattaata agcccgattt gccactagct tcaggtgaaa tctccgttaa tactgcatgg  5340
attatgtcaa tcattgtcgc cttgttcggt ttaatcatca caattaaaat gaaaggtggt  5400
ccattgtaca tcttcggcta ctgtttcggt atattcggtg gtatagtata ttccgttcca  5460
ccttttagat ggaaacaaaa ccccagtacc gctttcttac taaatttctt ggcacatatc  5520
atcacaaact tcaccttcta ctacgcttct agagctgctt tgggtttgcc attcgaatta  5580
agaccatctt ttacattttt gctggctttt atgaaatcga tgggttctgc attggccttg  5640
attaaagatg catctgacgt tgaaggtgac acaaaattcg gcatcagtac cttggctagc  5700
aagtacggtt ctagaaattt gactttgttt tgttcaggta tcgtattgtt atcctacgtg  5760
gcagccattt tagccggtat catttggcca caagctttta acagtaatgt catgctactt  5820
agccacgcaa tattggcctt ctggctgatc ttgcagacga gagattttgc tttaactaat  5880
tatgaccctg aggcaggtag aagattctac gaattcatgt ggaagctgta ctacgctgaa  5940
tatttggttt acgtctttat taagttgtct ggtggtggtg gttctggtgg tggtggttct  6000
ggtggtggtg gtagtgctga agcatggtac aacttaggca acgcatacta caagcagggt  6060
gactaccaga aggcaattga gtattaccaa aaagccttag aactagaccc aaacaatgcc  6120
gaggcttggt ataacttggg caatgcttat tacaaacagg gtgactatca aaaggctata  6180
gaatattacc aaaaggcact tgagctggac cctaacaatg cagaagcctg gtataactta  6240
ggcaatgctt attacaagca gggtgactat cagaaggcca tcgaggacta ccaaaaggct  6300
ttggaactgg atccaaacaa tttgcaggct gaagcatgga agaatttggg taacgcttac  6360
tataaacagg gtgactatca gaaagcaata gaatactacc aaaaagccct agaacttgac  6420
cctaacaatg cctctgcttg gtacaacttg ggtaatgctt actataagca gggtgactac  6480
caaaaagcta tcgaatatta ccaaaaagca ctggaattgg acccaaacaa tgcaaaggcc  6540
tggtatagaa gaggtaacgc ctactacaaa cagggtgact accaaaaggc tattgaagat  6600
taccaaaagg ctctggaact agatcctaac aacagatcta gatccgctgg tggtggtggt  6660
tctggtggtg gtggttctgg tggtggtggt gcttctgcag aatacgttag agctctgttc  6720
gatttcaacg gtaacgatga agaggacttg ccttttaaga aaggtgacat tttgagaatc  6780
agggacaaac cagaagagca atggtggaat gctgaagatt ctgagggtaa aagaggaatg  6840
attcctgttc cctatgtcga aaagtacggc tcagcaggtt ccgctgcagg atctggcgaa  6900
ttcggttcag ccgaggccgc tgcaaaagaa gccgctgcaa aggctggaag tgcaggcagc  6960
gccgctggtt ccggagaatt tggtagtttg attaaacata tgagagccga agctttattc  7020
gattttactg gtaactccaa acttgaactg aatttcaagg caggtgacgt tatttcttg   7080
ttgagtagaa ttaataagga ctggttggaa ggtactgtta gaggtgctac tggaatattc  7140
ccactttctt ttgtgaaaat cctgaagggc tcaggtgcta ctaacttctc tttgttgaag  7200
caagcaggtg acgttgaaga aaatccaggt ccaatgaaat gtagcacttt ttctttctgg  7260
ttcgtttgca agatcatttt cttttttctt tcttttaata tccaaacttc gatcgcaaat  7320
ccaagagaaa acttcttaaa gtgtttctca caatacattc ctaataacgc cacgaatttg  7380
aagctggtat acactcagaa caacccactg tacatgagcg tgctaaactc gacaatccat  7440
aatttgagat tcacttccga tactacaccc aaaccattag taatcgtgac accttctcat  7500
gtttcacaca ttcaaggaac catactatgc tctaagaaag tcggtttgca gattagaaca  7560
aggtctggtg gtcatgatag tgaaggcatg tcctacatca gtcaagttcc attcgttatc  7620
gtcgatttga gaaacatgag gtctatcaaa atagacgttc actcacagac ggcttgggtc  7680
gaggcaggtg ccactttggg agaagtttac tactgggtca acgaaaagaa tgaaaatttg  7740
tctcttgctg caggttactg tccaactgtc tgcgctggtg gtcattttgg tggtggtggt  7800
tatggacctc ttatgagaaa ctacggtttg gccgctgata atatcattga cgcacatttg  7860
gtaaatgtgc acggtaaagt tctagataga aagtcaatgg gtgaagattt gttttgggca  7920
ttgagaggtg gtggtgctga atcctttggt ataatcgtag cttggaaaat tagattggtt  7980
gcagtcccaa agtctacaat gttctcagtt aagaaaatta tggaaatcca tgagctggta  8040
aagttggtga ataagtggca aaacatcgct tacaagtacg ataaggactt gctgctaatg  8100
acccatttca tcacgagaaa catcactgat aaccagggta aaaataagac agcaatacac  8160
acctacttct cttcagtttt cttgggtggt gttgattcct tagtggattt gatgaataag  8220
agtttccctg aactgggtat taagaaaact gattgtagac aattgagctg gatcgacaca  8280
atcatattct atagtggtgt tgtcaactac gatactgaca acttcaacaa agaaatcctt  8340
ctggatagaa gtgccggaca aaatggcgct ttcaaaatta agttggacta cgttaaaaag  8400
cctatacccg agtcagtatt tgtgcagatc cttgaaaaac tgtatgaaga ggatattggt  8460
gctggaatgt acgcattata tccatacggt ggtataatgg atgaaatctc cgagagtgcc  8520
ataccattcc ctcatagagc tggtatcttg tacgaactgt ggtacatatg ttcttgggaa  8580
aaacaagagg ataacgaaaa gcacttaaac tggatcagga acatctataa cttcatgact  8640
ccttacgttt ctaaaaaccc cagattggct tatttgaatt acagagattt ggacataggt  8700
atcaacgatc ctaaaaatcc aaacaactac acacaagcaa gaatttgggg tgaaaagtac  8760
ttcggtaaaa atttcgatag attggttaaa gtcaagacct tagttgaccc caacaacttt  8820
ttcagaaacg aacaatctat tccacctttg cctagacata ggcacggctc tggtgctact  8880
aacttctctt tgttgaagca agcaggtgac gttgaagaaa atccaggtcc aatgaactgt  8940
agcacttttt ctttttggtt cgtttgcaag ataatatttt tctttttgtc ctttaatatc  9000
```

-continued

```
caaatcagta tcgccaaccc acaggaaaac tttttaaagt gtttctctga gtacatcccc  9060
aacaacccag ctaaccctaa gtttatatat acacaacatg atcagctgta catgagcgta  9120
ttgaactcga ccattcaaaa tttgagattc acttctgaca ctacacctaa gcccttggtc  9180
atagtaactc cttctaatgt ctcacatata caagcttcta tcttgtgctc taagaaagtt  9240
ggtttgcaga ttagaacaag gtctggtggt cacgatgcag aaggtttatc ctatattagt  9300
caagtcccat ttgccatagt agatttgaga aatatgcata ctgtgaaagt tgacatacac  9360
tcacagactg cttgggtgga agcaggtgcc acattgggag aggtttacta ctggatcaac  9420
gagatgaacg aaaactttag tttcccaggt ggttactgtc ccacagtcgg tgttggtggt  9480
catttttctg gtggtggtta tggagcttta atgagaaact acggtttggc tgcagataat  9540
atcattgacg cacatttggt gaacgttgat ggtaaagttc ttgacagaaa atcaatgggt  9600
gaagatttgt tttgggctat cagaggtggt ggtggtgaaa atttcggtat aatcgccgct  9660
tgcaaaatta agttggttgt cgtacctagc aaagctacta ttttctctgt caaaaagaac  9720
atggaaatcc atggtttagt aaagttgttt aataagtggc aaaacatcgc atacaagtac  9780
gataaggatt tgatgcttac cacgcatttc agaactagga acatcacaga taaccatggt  9840
aaaaataaga ctacagttca cggatacttc tcttcaattt tcttgggtgg tgttgattct  9900
cttgttgatt tgatgaataa gtcattccca gaactgggta ttaaaaagac agattgtaag  9960
gaactgagct ggatcgacac cacgatttc tatagtggtg tggttaatta caacaccgcc  10020
aacttcaaaa aggaaatctt gctggataga tccgctggta aaaagaccgc tttttctatt  10080
aaacttgact acgttaagaa actgatccct gaaactgcaa tggttaagat attggagaag  10140
ctgtacgaag aggaagtcgg cgtaggcatg tacgttttgt atccatacgg tggtataatg  10200
gatgagatct ccgaaagtgc cataccattt cctcatagag ctggtatcat gtatgaatta  10260
tggtacaccg ctacgtggga gaagcaagaa gataacgaga aacacataaa ctgggtcaga  10320
tctgtataca acttcactac accttacgtt tctcagaacc caagattggc atatttgaac  10380
tacagagatt tggacttggg taaaaccaac cccgaatctc caaataacta tacgcaagca  10440
agaatttggg gtgaaaagta cttcggtaaa aatttcaaca gattggtgaa ggttaagaca  10500
aaagccgatc caaacaactt ctttagaaac gaacaatcta ttccaccatt gccaccaaga  10560
catcatggtt ccggcgctac taacttctct ttgttgaagc aagcaggtga cgttgaagaa  10620
aatccaggtc caatgtcaga agagtcctta tttgaatctt caccacaaaa gatggagtac  10680
gaaatcacta actactctga gagacataca gaattgcctg gacacttcat cggtttgaac  10740
acagttgaca agctggaaga gtctccattg agagatttcg tcaagtccca tggtggtcac  10800
accgtaatta gtaagatctt gatagctaac aacggtatcg ctgcagtcaa ggaaattaga  10860
tctgttagaa agtgggcata tgaaaccttt ggtgacgata gaacggtcca attcgtagct  10920
atggcaactc ctgaagactt ggaggccaat gctgaatata tcagaatggc cgatcaatac  10980
attgaagttc caggtggtac aaataacaat aactacgcta atgtcgactt aatagtagat  11040
atcgctgaaa gagcagacgt ggatgccgtt tggcgctggtt ggggacatgc ttccgaaaac  11100
cctttgttac ccgaaaaatt gtctcagagt aagagaaaag ttatttttat tggtccacct  11160
ggaaatgcaa tgagatcatt aggtgacaag atatccagta ctatcgtggc acaatcagcc  11220
aaagttccat gtattccttg gtccggcacc ggtgttgaca cggtgcatgt tgatgaaaag  11280
actggtttgg tttctgtaga tgacgatatc tatcagaagg gatgttgcac ttcacctgaa  11340
gatggtttgc aaaaggctaa gagaatcggt ttcccagtta tgatcaaggc atcagaaggt  11400
ggtggtggta aaggtatcag gcaggtcgaa agagaagagg atttcatcgc tctgtaccat  11460
caagccgcta atgaaatacc cggttctcca attttcataa tgaaactagc tggaagggca  11520
agacatttgg aagttcagct acttgctgac caatacggca ctaatatttc cttgttcggt  11580
agagattgca gtgttcaaag aagacatcaa aagattatcg aagaggcacc agtcactata  11640
gcaaaagccg aaacatttca cgagatggaa aaggcagctg ttagattggg taaattggtc  11700
ggatatgtaa gtgctggaac agtcgaatat ttgtacagcc atgacgatgg taaattctac  11760
tttttggaac ttaacccaag attacaagtt gagcaccccta ctacagaaat ggtttctggt  11820
gttaatttgc cagctgcaca actgcagatt gctatgggta tccctatgca tagaatcagt  11880
gatatcagga ctctgtacgg tatgaatcca cacagcgctt cggagattga cttcgaattc  11940
aaaactcagg atgcaactaa gaaacaaaga agaccaatcc caaagggtca ttgtaccgct  12000
tgcagaatta cgtccgaaga ccccaatgat ggttttaaac catctggtgg tactttgcac  12060
gaactaaact ttagaagctc gtctaatgtc tggggttatt tctcagtagg caacaacggt  12120
aacatccatt ctttttcaga ttcccagttc ggtcacatct tcgcatttgg agaaaatagg  12180
caagcctcta gaaagcatat ggttgtcgct cttaaagaac tgtcaatcag aggtgacttc  12240
agaaccacgg ttgaatactt aattaaactg ttggaaactg aagacttcga agataatacg  12300
attactacag gttggttgga cgatttgata acccataaga tgacggcaga aaaacctgat  12360
cccaccttgg ccgttatctg tggtgccgct acgaaggcct ttttagcttc tgaagaggct  12420
agacataagt acatagaaag cctgcaaaag ggtcaggtac tatcgaaaga cttactacaa  12480
acaatgtttc ctgtggattt catccacgaa ggtaaaagat acaagtttac tgttgctaag  12540
tctggcaacg ataggtacac gttgttcatt aatggtagca agtgcgacat cattctaaga  12600
caactttcag atggtggttt gctgatcgca attggtggta aatcacatac tatctattgg  12660
aaggaagagg tcgcagccac aagattgagt gtagacagca tgaccacgtt gttagaggtt  12720
gaaaacgatc caactcaatt aagaacacca tctcctggta aacttgtgaa atttctggtt  12780
gaaaatggcg agcatataat caagggtcaa ccctacgctg agattgaagt tatgaaaatg  12840
cagatgccat tggtttctca agaaaacggt atagttcaac tacttaaaca gcctggatca  12900
accatagtag ctggtgacat catggcaatt atgacgttag acgatccatc caaggtgaaa  12960
catgctcttc cttttgaggg tatgctgccc gatttcggtt ctccagttat tgaaggcact  13020
aaaccagcat acaagtttaa atcgttggtt tctacactgg aaaacatcct aaagggttac  13080
gataaccaag ttattatgaa tgcttctttg caacagttga tagaagtctt gagaaatcct  13140
aagttaccct attcagaatg gaaattgcat attagcgctc ttcactccag attgcctgca  13200
aaattggatg aacaaatgga agagctagtc gctagatctt tgagaagagg tgctgtattt  13260
ccagcaaggc aattgagtaa gctaattgac atggcagtta aaaacccaga atacaaccct  13320
gataaactgt tgggtgccgt agtggaacca ttggcagata ttgcccataa gtactctaat  13380
ggtttagaag ctcatgagca ctcaatcttc gtgcatttct tggaagagta ctacgaggtt  13440
gaaaaattgt tcaacggtcc taacgtcaga gaagagaaca tcatcctgaa gttgagagat  13500
gaaaacccaa aggacttgga taaagtcgct cttactgtac tgagtcatag caaggtttct  13560
gccaaaaata acttaatcct agctatcctg aagcactacc aacctttgtg taagctgtca  13620
tccaaagttt ctgcaatatt ttcaactcca ttgcaacata tcgtagagct tgaatctaag  13680
gctaccgcaa aagtggcttt gcaggcaaga gaaattttga tccaaggtgc tttgccatca  13740
```

```
gttaaagaaa gaacagagca aatagaacac atcctgaaga gtagcgttgt caaagtcgca  13800
tacggttcgt ctaatcctaa gagatctgaa cccgatttga atatacttaa ggatttgatc  13860
gattcaaatt acgtagtgtt tgacgtttta ctacagttct taactcatca agatcctgtt  13920
gtcacagctg cagccgctca agtctatata agaagggcct atagagctta cactatcggt  13980
gacattaggg tacacgaagg cgtgacagtt ccaatcgtgg aatggaaatt tcaattgccc  14040
tccgcagcct ttagtacctt cccaacggta aagtcaaaaa tgggtatgaa cagagctgtt  14100
tctgtttctg atttgagcta tgtggctaat tcgcaatcat cccctttaag agaaggtatt  14160
ctaatggctg tggaccattt ggacgatgtt gatgaaattt tgtctcaatc tttggaagtt  14220
attccaagac accaaagtag ctcgaatggt cccgctccag ataggtctgg atcttcagca  14280
agtttaagca acgtagccaa tgtgtgtgtt gcttccactg agggttttga aagtgaagag  14340
gaaatcttgg ttagattgag agaaattttg gatttgaaca aacaagaatt gattaatgct  14400
tccatcagaa ggatcacatt catgttcggt tttaaagatg gtagttaccc taagtactac  14460
acctttaatg gtcccaacta caacgagaac gaaactatca gacatatcga acctgcctta  14520
gctttccaat tggaactggg tagattgtca aacttcaaca tcaagccaat tttcactgat  14580
aacagaaaca tccatgtgta cgaagctgtt tcaaagacat ccccattaga taagagattt  14640
ttcaccagag gcatcattag gacgggtcac attagagatg atattagcat acaagagtac  14700
ttgacttcgg aagctaacag attaatgtct gacatcctag ataatttgga agttaccgac  14760
acgtcgaact ctgatttgaa ccatatcttt attaacttca tcgcagtgtt cgacatatct  14820
cctgaggatg ttgaagctgc atttggtggt ttcttggaaa gattcggtaa aagattgctg  14880
agattgagag tctccagtgc tgaaatcaga atcatcatta aggatccaca aactggtgcc  14940
cctgtacccc tgagagcttt gatcaataat gtttctggtt acgtaattaa aaccgagatg  15000
tacacggaag tcaagaatgc taagggtgaa tgggtattca agagcttggg taaacccggc  15060
tcgatgcact taagaccaat tgcaacacca tatcctgtca aagaatggtt gcaacctaag  15120
agatacaaag cccacttaat gggtactaca tacgtttacg atttcccaga attgttcaga  15180
caggcttctt cttctcaatg gaagaatttt tccgccgacg ttaagctgac tgacgatttc  15240
tttatcagta acgaactaat cgaggatgaa aatggtgaac ttacagaggt tgaaagagag  15300
ccaggagcaa atgccattgg catggtcgct tttaagatca ctgtaaagac accagaatat  15360
cctaggggta gacaattcgt agtggttgca aacgacatca cctttaaaat tggttctttc  15420
ggacctcaag aagatgagtt tttcaataag gttactgaat acgctaggaa aagaggtata  15480
ccaagaatct acttggccgc taattctgga gcaaggattg gcatggccga ggaaatagtg  15540
cctttatttc aggttgcatg gaacgacgca gccaacccag ataagggatt ccaatatttg  15600
tatttgactt ctgagggtat ggaaacattg aaaaagttcg ataaggaaaa ctcagtgctg  15660
accgagagaa ctgttattaa tggagaggaa aggttcgtaa tcaaaactat aatcggttct  15720
gaagatggtt tgggcgtgga gtgtctgaga ggtagcggtt tgattgctgg tgcaacttct  15780
agagcttacc atgatatttt tactatcaca ctggtcactt gcagatctgt aggcataggt  15840
gcttatttgg ttagattggg tcaaagggcc atccaggtcg aaggccaacc tattatattg  15900
actggtgccc ccgctataaa caaaatgctg ggtagagaag tttatacctc caatttgcag  15960
ttgggtggta cgcaaatcat gtacaataac ggtgtttctc atttgacagc tgtagacgat  16020
ttggctggtg tggaaaagat tgttgaatgg atgtcatatg tgccagctaa aagaaacatg  16080
cccgttccaa tattggaaac taaggacaca tgggatagac cagtagattt taccccctacg  16140
aatgacgaaa cctatgatgt gagatggatg attgagggta gggaaactga gtctggtttt  16200
gaatacggtt tgttcgataa gggttctttc tttgaaacat tatcaggctg ggccaagggt  16260
gtcgtagtgg gaagagctag attgggtggt attcctctag gtgttattgg tgtagaaact  16320
agaacagttg aaaatttgat ccccgcagat ccagccaacc ctaattctgc tgaaacttta  16380
attcaggaac ctggtcaagt ttggcatccc aactcagctt ttaaaaccgc acaggccatt  16440
aatgatttca acaacggtga acaattgcca atgatgatac tggctaactg gagaggtttt  16500
tctggtggtc aaagggatat gttcaacgaa gttttgaagt acggtagttt tatcgtcgac  16560
gcactggtag attacaagca acctatcata atatacattc caccaactgg tgaattaaga  16620
ggtggttctt gggttgtcgt agacccaacc attaacgcag atcagatgga aatgtacgcc  16680
gatgtgaatg ctagagcagg tgttttggaa ccacaaggaa tggttggtat taagtttaga  16740
agagaaaaat tgctggatac tatgaacaga ttagacgata agtacaggga attgagatct  16800
caactgagca ataagtcttt ggctccagaa gttcatcaac agatctctaa gcaactggct  16860
gatagggaaa gagaattgtt gccaatatac ggtcagatct cattgcaatt tgccgactta  16920
cacgataggt catccagaat ggtggctaag ggtgttattt caaaagaatt agagtggaca  16980
gaagctagaa gatttttctt ttggagattg agaagaagat tgaacgagga atatttgatt  17040
aaaagattgt cacatcaagt tggcgaggct tctagattgg aaaagatcgc aaggattaga  17100
tcttggtatc cagcatcagt cgatcacgaa gacgatagac aagtagccac ttggattgag  17160
gaaaattaca agacactgga cgataagttg aagggtttaa agctagaatc ctttgcccaa  17220
gacttggcta aaaagattag aagtgaccat gataatgcta tcgatggttt gagtgaagtt  17280
attaaaatgc ttagcactga cgataaggaa aaactgttga agacattgaa gaaactgtct  17340
ggtggtggtg gttctggtgg tggtggttct ggtggtggtg gtagtgccga agcttggtat  17400
aacttgggaa atgcttatta caagcagggt gactaccaaa aggccataga atactaccaa  17460
aaggctcttg agctggatcc taataacgca gaagcctggt ataacttagg caatgcatac  17520
tataaacaag gtgactacca aaaggcaata gagtactacc aaaaggcctt ggaattagat  17580
ccaaataacg ctgaggcatg gtataacttg ggcaacgcct actataaaca gggtgactat  17640
caaaaggcta tagaagatta ccagaaggca ctagagcttg atcctaataa cttgcaagcc  17700
gaagcttgga agaacttagg aaatgcatac tataagcaag gtgactatca aaaagctatt  17760
gaatattacc aaaaggctct ggagttggat ccaaataacg catctgcttg gtacaactta  17820
ggcaacgcct actataagca gggtgactat caaaaagcaa ttgaatatta tcaaaaggcc  17880
ttagagctag atcctaataa cgctaaagca tggtatagga gaggcaatgc atactacaaa  17940
cagggtgact accaaaaagc tatagaagat taccaaaagg cacttgaact ggatccaaat  18000
aacagatcta gatccgctgg tggtggtggt tctggtggtg gtggttctgg tggtggtggt  18060
gcttctggtt ctcatatgag attgggagcc caatctattc agccaaccgc taacttagat  18120
agaacggacg atttggtcta tttgaatgta atggaattgg ttagagctgt tttggagttg  18180
aaaaatgaac tagcacaatt gccaccagaa ggttacgtgg ttgtcgtaaa gaatgttggt  18240
ttgactctta gaaagttgat aggctcggtc gacgatttgc taccatcttt gccatcttct  18300
tctagaactg aaatagaggg tacacaaaag cttctgaaca aagatttggc tgaattgatt  18360
aataagatga gattggcaca acagaacgcc gttacttctt tgtctgagga gtgtaagaga  18420
caaatgctaa ctgcttctca tactttggct gttgatgcaa agaacttgtt agacgctgtg  18480
```

-continued

```
gatcaagcaa aagttttagc caatttggct cacccacctg ccgaaggttc tgctggatca  18540
gctgcaggat ccggcgaatt tggttctgct gaagccgctg caaaagaggc tgctgcaaaa  18600
gctggatctg caggtagtgc tgctggtagc ggagaatttg gttctggtgc catggctact  18660
cctggttcag aaaacgttct accaagagaa ccattgattg caacagccgt gaagttcttg  18720
cagaactcta gagttagaca atctccattg gcaactagaa gagcattttt gaaaaagaaa  18780
ggtttgaccg acgaggaaat tgatatggct ttccaacagt ccggtactgc agccgatgaa  18840
ccatcttcat tgtggggaag tggc                                         18864

SEQ ID NO: 206          moltype = DNA  length = 19473
FEATURE                 Location/Qualifiers
source                  1..19473
                        mol_type = other DNA
                        organism = synthetic construct
SEQUENCE: 206
atgggttctg ctggttcagc tgcaggttct ggtgaattcg gttccgctgg tagtgccgct  60
ggttctggtg aatttggttc tgctggttca gcagccggtt ctggtgaatt ctcctattac  120
catcaccatc accatcactt ggaatctact tcattataca aaaaggctgg ttccggtagt  180
gccagaaacg cttacttgag aaagaaaatt gctagattga agaaagataa tttgcaattg  240
gaaagagatg aacaaaactt ggaaaagatt atcgctaatt tgagagatga aatagcaaga  300
ttggaaaatg aagttgcttc tcatgaacaa ggttccgcag gtagtgccgc cggttctggt  360
gaatttgctg aagccgctgc aaaggaagcc gctgcaaaag caggttctgc cggttcagcc  420
gctggtagtg gtgaattttc ttactatcac catcaccatc atcacttgga atctacctca  480
ttatataaaa aggccggttc cggtagtaac ttggttgctc aattagaaaa tgaagtcgca  540
tcattggaaa acgaaaacga aactttgaaa aagaaaaact tacataagaa agatttgatc  600
gcttacttag aaaaggaaat agcaaatttg agaaagaaaa tagaagaagg ttccgctggt  660
agtgcagccg gtagtggtga attcggttct gctgaagctg cagccaagga agctgcagcc  720
aaagaagccg ctgctaaaga agctgcagcc aaagctggtt ctgcaggttc tgccgcaggt  780
tccggtgaat ttggttcttc atactatcac catcaccacc accacttgga atctacctca  840
ttatacaaga aagctggttc cggtagtcaa aaggtcgctg aattgaaaaa cagagtagct  900
gttaagttga acagaaacga acaattgaaa aataaggtag aagaattgaa aaatagaaac  960
gcttacttga aaaacgaatt ggcaactttg gaaaacgaag tagctagatt agaaaacgat  1020
gttgctgaag gttctgctgg ttctgctgct ggttctggtg aattcgctga agcagccgct  1080
aaggaagcag ccgctaaagc cggttccgcc ggttctgctg cgggctctgg tgaattttcc  1140
tactatcacc atcatcatca ccacttggaa tctacatcat tatataagaa agccggttcc  1200
ggtagtaatg aagttactac attggaaaac gatgctgctt ttattgaaaa cgaaaacgca  1260
tacttagaaa aggaaatcgc tagattgaga aaggaaaagg ccgctttgag aaatagatta  1320
gctcataaga aaggttctgc tggtagcgct gctggctctg gtgaatttgg ttccgccgaa  1380
gccgctgcta aggaagccgc tgccaaagaa gccgctgcca aggaagccgc tgctaaggct  1440
ggttccgccg gttcagctgc aggctctggt gaattcggtt ctagaccacc taccatctct  1500
aatccacctc cattgatttc cagtgctaaa catccatccg tcggtagtgc aggttccgct  1560
gccggctctg gcgaatttgc cgaagctgct gccaaagaag cagccgctaa agctggttca  1620
gcaggttccg ctgccggatc tggcgaattc aatttcttgc aatctagacc agaacctact  1680
gctcctccag aagaaagttt cagatctggt ggttcagctg gttccgccgc aggatctggc  1740
gaatttggtt ccgcagaagc tgccgctaaa gaagctgctg caaaagaagc agccgccaaa  1800
gaagctgctg caaaagccgg tagtgctggt tcagctgccg gttccggtga attcggttct  1860
tcaaaaggta ccggtttaaa tccaaacgct aaagtttggc aagaaattgc tcctggtaac  1920
ggttctgcag gttccgcagc tggttccggt gaattcgccg aggccgctgc taaggaagca  1980
gcagccaaag caggtagtgc tggttccgca gctggttcag gtgaattccc agacggtggt  2040
accactttcg aacatttgtg gtccagttta gaacctgatt ctacatacgg ttctgccggt  2100
tctgcagcag gcagcggtga attcggttct gccgaagctg ctgctaaaga agctgctgcc  2160
aaggaagctg ctgctaagga agctgctgcc aaagccggta gtgcaggttc tgctgccggt  2220
tcaggtgaat ttggttcttc ttactatcac caccaccacc atcacttgga atctacatca  2280
ttatacaaga aagccggttc tggtagtaag agaatcgcat acttaagaaa gaaaatcgct  2340
gcattgaaga aagataacgc aaacttagaa aaggacatcg ctaacttgga aaacgaaatc  2400
gaaagattga ttaaagaaat caaaaccttg gaaaatgaag ttgcatctca tgaacaaggt  2460
tcagccggtt ctgcagcggg ctccggtgaa tttgccgaag ctgcagcaaa agaagctgcc  2520
gctaaggctg gtagtgctgg ttctgctgca ggcagcggtg aattttctta ctaccaccat  2580
caccaccatc acttggaatc tacttcatta tataagaaag caggttctgg tagtaacttg  2640
ttagcaacat taagatctac cgctgcagtc ttggaaaacg aaaaccatgt attggaaaaa  2700
gaaaaggaaa aattgagaaa ggaaaaagaa caattgttga ataagttgga agcttacaaa  2760
ggttcagcag gttctgcagc gggctctggc gaattcggtt ccgccgaagc tgcagcaaag  2820
gaagctgcag ctaaagaggc cgctgcaaaa gaagctgctg ccaaagcagg tagtgcaggt  2880
tccgcagccg gctccggcga atttggttca ccagctacat cccaacatcc tccacctcca  2940
cctggtcata gatctcaagc tccttcacat ggttccgcag gtagtgcagc tggatctggc  3000
gaattcgccg aagctgccgc taaggaagct gctgcaaaag ctggttccgc tggttcagca  3060
gcaggttccg gtgaattcga attgaattct ttgttgatat tgttagaagc agccgaatat  3120
ttggaaagaa gagatagagg ttctgccggt agtgctgcag gtagcggcga atttggttct  3180
gcagaagcag ccgccaagga agcagctgca aaagaagcag cagctaaaga agcagctgca  3240
aaagccggtt ctgctggttc agccgcagga tctggagaat tcggttccag accacctaca  3300
atttccaatc cacctccatt gatctcttct gccaagcatc catccgttgg tagtgcaggt  3360
tcagctgccg gtagtggtga atttgccgaa gccgccgcta aggaagccgc cgccaaagca  3420
ggttcagccg gttccgccgc aggttcaggt gaattcaatt tcttgcagtc aagaccagaa  3480
cctaccgctc ctccagagga gagtttcaga tctggtggta gtgccggttc agctgccggc  3540
tctggagaat ttggttctgc agaggctgct gccaaggaag ccgcagctaa agaagccgct  3600
gcgaaagaag ccgccgctaa agctggtagt gcaggtagtg ctgcgggatc tggcgaattc  3660
ggttcttcta agggtactgg tttgaaccct aatgccaagg tctggcaaga aatcgcccct  3720
ggtaacggtt ccgcaggttc cgccgcaggt agtggtgaat tcgccgaggc tgccgccaag  3780
gaagccgccg ctaaggcagg tagtgctggt tcagcggccg gctctggtga atttccagac  3840
ggtggtacaa cctttgagca tttgtggtcc agtttagaac ctgattctac gtacggttct  3900
```

-continued

```
gctggttccg ctgcaggatc tggcgaattc ggttccgcgg aagccgccgc aaaagaagcc  3960
gccgccaaag aagccgccgc aaaggaagcc gcagcaaagg caggtagtgc cggctccgcc  4020
gctggcagtg gcgaatttgg ttcttcatat tatcaccatc atcatcatca cttggaatct  4080
acttcattat acaagaaagc aggttccggt tctaaaagaa ttgcttactt aagaaagaaa  4140
atcgcggctt tgaagaaaga caatgctaac ttagaaaaag atattgccaa cttggaaaat  4200
gaaatcgaaa gattaattaa ggaaattaaa acattggaaa acgaagttgc atcacatgaa  4260
caaggttcag ctggttccgc tgcagggtcc ggcgaatttg cagaagccgc cgccaaggaa  4320
gccgcagcca aagctggtag tgcaggttct gccgctggct ctggcgaatt ttcttactat  4380
catcatcacc atcaccactt ggaatctact tcattataca agaaagcggg ttcaggttct  4440
aacttgttag caactttaag atctacagcc gctgttttag aaaatgaaaa ccatgtctta  4500
gaaaaagaaa aggaaaagtt gagaaaggaa aaggaacaat tattaaataa gttagaagcc  4560
tacaagggtt cagcaggttc cgcagcaggc tcaggcgaat ttggttctgc agaagcggct  4620
gctaaggaag ctgccgcaaa ggaagcagct gctaaggagg ccgctgcaaa ggctggttct  4680
gctggttccg ccgcgggctc tggagaattc ggttccgctt tggttgatga cgccgctgat  4740
tatgaacctc caccttcaaa taacgaagaa gctttaggtt ccgctggttc cgctgcaggt  4800
tccggcgagt tcgcagaagc cgcagcaaaa gaagccgcag ctaaggcagg tagtgccgga  4860
tccgccgctg gcagtggaga attcagagaa ttgttcgatg acccatctta cgtcaacgta  4920
caaaatttgg ataaagctag acaaggttcc gccggttctg cagcgggatc tggggaattt  4980
ggttctgcag aagctgccgc caaagaagct gcagctaaag aagccgcagc caaagaagct  5040
gctgctaagg ccggttctgc tggttctgcc gcaggatctg ggaattcgg ttccaagaat  5100
actaagagta tgaacttcga taacccagtt tacagaaaga ctacagaaga agaaggttca  5160
gccggttcag ccgccggttc cggtgaattt gcagaggctg ccgctaaaga ggctgccgct  5220
aaggccggta gtgctggttc tgcagccggc tccggagaat tcagatcttt gccatccaca  5280
tggattgaaa acaaattata cggcatgtca gaccctaatt ggggttctgc aggttcagct  5340
gcgggatctg gtgaattcgg ttcagcagaa gccgcagcca aggaagccgc tgcaaaggag  5400
gccgctgcca aagaagcagc tgctaaggct ggttcagccg gttccgcagc cggcagtggt  5460
gaatttggta gtgttgtcga taattctcca cctccagctt tgcctccaaa gaaaagacaa  5520
tctgctccat ctggttcagc aggttcagcc gctggttcag gtgaatttgc cgaagcagct  5580
gccaaggaag ctgccgccaa ggcgggcagt gcaggttcgg ctgcggggtc tggtgaattc  5640
actcaaagat ctaaaccaca acctgcagtt cctccaagac catctgctga cttgatttta  5700
ggttccgccg gttccgcagc tggctctggc gaattcggtt ccgctgaggc tgccgctaaa  5760
gaagcggccg ctaaagaggc agccgctaaa gaggcggccg ctaaagcagg ttctgcaggt  5820
tcagcagcag gtagtggtga atttggttct acagatgaag aaagagaaga aaccgaagaa  5880
gaagtttatt tgttgaactc taccactttg ggttcagctg gttctgctgc gggttctggc  5940
gaatttgcag aagcagctgc taaggaagcc gcggcaaagg ctggttctgc gggctccgcc  6000
gcaggttctg gtgaatttga tggtaatgta tctggtactc aaagattaga ctcagctacc  6060
gttagaactt attcatgcgg ttctgccggt agtgcagcgg gctctgggga attcggttcc  6120
gcagaagccg ctgcaaaaga agccgctgca aaagaagccg ctgcgaagga ggctgctgct  6180
aaggcaggtt ccgccggtag tgctgcgggt tccggcgaat ttggttccag ttactatcac  6240
catcatcacc accacttgga atccacaagt ttatataaga aagctggttc tggttcacaa  6300
aaggtagctc aattgaaaaa tagagttgca tacaagttga aggaaaacgc taagttggaa  6360
aacatagtag caagattaga aaacgataac gctaatttgg aaaaggacat cgcaaatttg  6420
gaaaaggata tagctaactt ggaaagagat gttgctagag gttctgctgg tagtgccgca  6480
ggctctggcg aattcgctga agctgccgct aaagaggctg cggctaaagc tggttcagct  6540
ggttctgcag cggggtctgg tgaattttct tattatcacc atcatcacca tcacttggaa  6600
tccaccagtt tatacaagaa agccggctct ggttcaaaca ctgttaagga attgaaaaat  6660
tacattcaag aattggaaga aagaaacgct gaattgaaaa atttgaagga acatttgaag  6720
tttgcaaaag ccgaattgga attcgaatta gcagcccata aatttgaagg ttctgccggt  6780
tctgccgccg gatctggaga atttggttct gcggaggctg ccgctaaaga agccgccgct  6840
aaagaggctg cagctaagga agctgcagca aaggctggtt ctgccggttc cgctgccggc  6900
tccggcgaat ttggttcaca tgatgactcc ttgccacatc ctcaacaagc tacagatgac  6960
tctggtcatg aatccgacgg ttccgcaggc tctgctgccg gctccggcga gtttgctgaa  7020
gccgctgcta aagaggctgc tgctaaagcc ggttctgccg gttcagcagc tggatctgga  7080
gaatttggtt ccccaaatgc tggtagtgtt gaacaaaccc caaagaaacc tggtttgaga  7140
agaagaggta gtgctggttc tgccgctggc tccggagaat ttggttcagc cgaagctgcg  7200
gccaaagagg ctgctgcaaa ggaggctgcg gctaaggaag ccgccgctaa agccggttca  7260
gctggttccg cggcaggctc cggggaattt ggttcttctt attatcacca ccaccaccat  7320
cacttggaat ccacaagttt atacaagaaa gcaggctctg gttcattcga aaacgtcact  7380
catgaattca ttttggcaac cttagaaaac gaaaacgcta agttgagaag attagaagca  7440
aagttggaaa gagaattggc tagattaaga aatgaagtag cttggttggg ttctgcgggc  7500
tcggccgctg gctctggtga attcgccgaa gctgcggcca aggaggctgc cgcaaaggcc  7560
ggttctgccg gttccgcagc gggatccggc gaattttctt actaccatca tcaccatcac  7620
cacttggaat ccacaagttt atacaagaaa gcgggttctg gttcacaaaa agttgaagaa  7680
ttgaaaaata agatagcaga attggaaaac agaaacgctg taaagaaaaa tagagttgca  7740
catttgaagc aagaaatcgc ttacttgaag gatgaattag cagcccatga attcgaaggt  7800
agtgccggtt ccgctgctgg ctcaggcgaa tttggtagtg cagaagctgc cgctaaggag  7860
gctgccgcca aagaagcagc cgcaaaagaa gctgccgcaa aagccggttc tgcgggctct  7920
gctgccggat ccggcgaatt cggttcagtc tccagtacta aattagtatc ctttcatgat  7980
gacagtgatg aagacttgtt acatatcggt tctgcaggct cagccgctgg ctctggagag  8040
tttgcagagg cagctgctaa agaagccgcc gcaaaggcag gttctgcagg ttctgcagct  8100
ggtagtggtg aattcgctgc tgcaacccca atatctactt ttcatgatga ctcagacgaa  8160
gacttgttgc atgtcggttc cgcaggttca gcagcgggat ccggtgaatt tggttcagca  8220
gaagctgccg ccaaggaggc cgctgctaaa gaagcagcag ccaaggaagc agcagcaaag  8280
gccggctctg ctggttctgc tgccgggtcc ggcgaatttg gttcttctta ttaccaccat  8340
catcatcacc acttggaatc cacaagttta tataagaaag ccggttctgg ttcacaaaag  8400
gtggaatcat taaaacaaaa gattgaagaa ttgaagcaaa gaaaagcaca attgaaaaat  8460
gatattgcca atttggaaaa ggaaatcgct tacgcagaaa caggtagtgc cggttcagcc  8520
gcgggctctg gtgaattcgc agaagctgcc gcaaaagaag ctgcagcaaa agccggttct  8580
gcaggctctg ctgctggctc tggcgaattt tcctactatc atcatcatca tcatcacttg  8640
```

-continued

```
gaatccacaa gtttatacaa gaaagcgggt agtgaatttt tcagaagaga aagaaacaag  8700
atggcagccg ctaagtgtag aaacagaaga agagaattga ctgatacatt acaagctgaa  8760
acagatcaat tagaagacga aaaatcagct ttgcaaaccg aaatcgcaaa tttgttgaaa  8820
gaaaaagaaa aattggaatt cattttagca gcccatagac cagcttgcaa aatacctgat  8880
gacttgggtt ttccagaaga aatgtcttta gaaggtagtg ccggtagtgc cgctggctca  8940
ggtgaatttg gtagtgcaga agctgccgcg aaagaagccg cagctaaaga agctgccgcc  9000
aaagaggcag ccgcaaaggc aggttcagca ggttcagctg ccgggtccgg ggaatttggt  9060
tcattccaaa tgccagctga cactcctcca cctgcatatt tgccacctga agatcctatg  9120
acaggtagtg ccggttctgc tgccgggtct ggcgaattcg ctgaagccgc tgctaaggag  9180
gctgcagcta aggccggctc tgcaggttcc gctgcaggtt caggtgaatt tgaaagagaa  9240
tctaacgaag aaccacctcc accttatgaa gatccatact ggggtaatgg tggttctgcc  9300
ggtagtgccg ccggctcagg cgaatttggt tctgcggagg ctgctgcaaa ggaagctgcg  9360
gccaaggaag ctgccgcaaa agaggctgct gccaaggccg gttcagcagg ttcagcagct  9420
gggtccggtg aatttggttc cagttattat caccaccatc atcaccactt ggaatctacc  9480
tcattatata agaaagcggg ttccggtagt caaaaagttg cagaattgaa aaacagagtt  9540
gctgtcaaat taaatagaaa tgagcagttg aaaaataagg tcgaggagtt gaaaaataga  9600
aacgcatact tgaaaaatga attggctact ttggaaaacg aagtcgcaag attagaaaat  9660
gatgtagctg aaggctctgc tggttccgca gcgggctcag gtgaattcgc cgaagcagcc  9720
gcaaaggaag ctgccgctaa ggccggctca gcaggttctg ccgccggaag cggtgaattt  9780
tcttattacc accaccacca tcaccacttg gaatctactt cattatacaa gaaagcgggg  9840
tccggtagta acgaagtcac aaccttagaa aatgatgcag cctttataga aaacgaaaat  9900
gcctacttag aaaaagaaat tgcaagattg agaaaggaaa aagctgcatt gagaaacaga  9960
ttagcccaca agaaatctta ctatcaccac catcatcatc acttggaatc tacatcatta  10020
tacaagaaag cgggctccgg tagtgctaga aatgcctact taagaaagaa aatagccaga  10080
ttgaagaaag acaatttgca attagagaga gatgaacaga acttagaaaa gattatagcc  10140
aatttgagag atgaaattgc tagattagaa aatgaagtag cttctcatga acaaggtagt  10200
gctggctccg ctgccggctc cggagaattt gccgaagctg ccgccaagga agccgcggcc  10260
aaggctggtt ccgctggttc tgctgccgga tctggagaat tttcctatta ccatcatcat  10320
catcatcatt tggaatctac atcattatac aagaaagcgg gatctggttc taacttggtc  10380
gcccaattgg agaacgaagt cgcatcattg gagaacgaaa acgaaacctt gaagaaaaag  10440
aacttacaca aaaaggattt gatagcttac ttagaaaaag aaatcgctaa tttgagaaag  10500
aaaattgaag aaggtagtgc aggttcagcc gctggctccg gtgaatttgg ttcagcggag  10560
gctgccgcta aggaggcagc cgctaaagaa gcagccgcta aggaggctgc agcaaaagca  10620
ggttccgcag gttctgcagc gggttccgga gaatttggtt ctgaacaaaa gttgatctct  10680
gaagaagatt tggaacaaaa gttgatatct gaagaagact tggaacaaaa attaatatca  10740
gaagaagatt tgggtagtgc aggttcagca gctggttctg gagaatttgg ttcagcaggt  10800
tctgccgctg gaagtggcga attcggtagt gccggctccg ctgctggctc tggcgaattt  10860
ggttctggtg ctactaactt ctctttgttg aagcaagcag gtgacgttga agaaaatcca  10920
ggtccaatgg gttctgctgg ttcagctgca ggttctggtg aatttggttc cgcaggtagt  10980
gccgctggtt ctggtgaatt cggttctgct ggttcagcag ccggttctgg tgaattttca  11040
tattaccatc accatcacca tcacttggaa tccaccagtt tatacaaaaa ggctggttct  11100
ggttcagcta gaaacgcata tttgagaaag aaaattgcta gattgaagaa agataacttg  11160
caattggaaa gagatgaaca aaatttggaa aagattatcg ccaacttaag agatgaaata  11220
gcaagattgg aaaacgaagt agcttctcat gaacaaggtt ccgcaggtag tgcagctggt  11280
tctggtgaat ttgctgaagc cgctgcaaag gaagccgctg caaaagctgg ttccgctggt  11340
tcagccgctg gttccggtga attcagttac tatcaccatc accatcatca cttggaatcc  11400
acaagtttat ataaaaaggc cggttctggt tcaaatttgg ttgctcaatt agaaaacgaa  11460
gtcgcatctt tagaaaacga aaacgaaaca ttgaaaaaga aaaatttgca taagaaagat  11520
ttgatcgctt atttggaaaa ggaaatcgca aacttgagaa agaaaataga agaaggttcc  11580
gctggttctg ctgctggttc cggtgaattt ggttcagctg aagctgcagc caaggaagct  11640
gcagccaaag aagccgctgc taaagaagct gcagccaaag caggttctgc cggttctgcc  11700
gcaggttccg gtgaattcgg ttcttcagct actagagaat tggatgaatt gatggcatcc  11760
ttaagtgact tcaagataca aggtggttcc gctggttctg cagccggctc tggcgaattc  11820
gcagaagcag ccgctaagga agcagccgct aaagctggtt ctgcaggttc tgctgccggt  11880
tctggtgaat tcgatttggc tttgtctgaa aactgggcac aagaattctt ggctgcaggt  11940
gacgctgttg atggttctgc tggtagtgct gccggttcag gtgaatttgg tagtgctgaa  12000
gctgctgcca aagaagcagc cgctaaagaa gctgctgcca aggaagctgc cgctaaagca  12060
ggttccgccg gttctgccgc cggctccggc gaatttggtt cagattataa ggatgacgat  12120
gacaaggatt acaaagacga tgatgacaag gattataaag atgacgatga caaaggttcc  12180
gctggtagtg ccgccggctc tggagaattc ggttctgccg gttcagctgc cggctccgga  12240
gaatttggtt ccgctggtag tgcagccggt tcaggtgaat tcggttctgg tgctactaac  12300
ttctctttgt tgaagcaagc aggtgacgtt gaagaaaatc caggtccaat gagtgctaag  12360
gcaatttctg aacaaactgg taaagaattg ttgtacaagt ttatttgtac tacatcagcc  12420
atccaaaata gattcaaata cgctagagtt accccagata ctgactgggc tagattgtta  12480
caagatcatc catggttgtt atctcaaaac ttggttgtca aacctgacca attaattaag  12540
agaagaggta aattgggttt agtaggtgtt aatttgacat tggatggtgt aaagtcttgg  12600
ttgaaaccaa gattaggtca agaagccaca gttggtaaag ctaccggttt cttgaaaaat  12660
ttcttgatcg aaccatttgt ccctcattca caagccgaag aattctatgt atgtatctac  12720
gctactagag agggtgacta tgttttattt catcacgaag gtggtgtcga cgtaggtgac  12780
gttgacgcca aggctcaaaa gttgttggtt ggtgtcgatg aaaagttgaa cccagaagac  12840
attaaaaagc atttgttggt tcacgcacct gaagataaaa aggaaatatt ggcctccttt  12900
ataagtggtt tgtttaattt ctacgaagat ttgtacttca cctacttgga aattaaccca  12960
ttagtagtta ctaaggatgg tgtatatgtt ttggacttag ctgcaaaagt tgatgcaaca  13020
gccgactaca tttgtaaggt caaatggggt gacatcgaat ttccacctcc attcggtaga  13080
gaagcttatc cagaagaagc ctacattgct gatttggacg ctaagtctgg tgcatcattg  13140
aagttgacat tgttgaaccc taaaggtaga atttggacca tggttgctgg tggtggtgct  13200
agtgtcgtat attctgatac tatatgcgac ttgggtggtg ttaacgaatt ggcaaactac  13260
ggtgaatact caggtgcccc atccgaacaa caaacatacg attacgctaa gaccatcttg  13320
tccttaatga ctagagaaaa gcatcctgat ggtaaaatct tgatcatcgg tggtagtatc  13380
```

-continued

```
gcaaatttta ctaacgttgc cgctacattc aagggtatcg tcagagctat aagagattac  13440
caaggtccat tgaaggaaca cgaagtaaca atattcgtta gaagaggtgg tcctaactac  13500
caagaaggtt tgagagtcat gggtgaagta ggtaaaacca ctggtatacc aatccatgtc  13560
tttggtacag aaacccacat gactgcaata gttggtatgg ccttaggtca tagaccaatc  13620
cctaatcaac ctccaaccgc agcccacact gcaaatttct tgttaaacgc ctctggttca  13680
acttccacac cagctccttc tagaacagca agtttctctg aatcaagagc tgatgaagtc  13740
gctccagcta agaaagcaaa accagccatg cctcaagact ccgttccaag tcctagatct  13800
ttgcagggta aatctactac tttgttttct agacatacta aggctatagt atggggtatg  13860
caaacaagag cagttcaagg catgttggat ttcgactatg tttgtagtag agatgaacca  13920
tctgttgctg caatggtcta tcctttttact ggtgaccata agcaaaaatt ctactggggt  13980
cacaaggaaa tattgatccc agtttttaag aacatggccg atgctatgag aaaacatcct  14040
gaagtcgacg tattgattaa cttcgcctca ttaagatccg cttacgattc tacaatggaa  14100
accatgaact acgctcaaat aagaaccatc gctatcattg cagaaggtat tccagaagcc  14160
ttgactagaa agttgattaa gaaagctgat caaaaaggtg tcacaataat cggtccagct  14220
accgtaggtg gtattaagcc tggttgtttc aagatcggta acactggtgg tatgttggat  14280
aacatattgg catctaagtt gtatagacca ggttcagtcg cttacgtatc cagaagtggt  14340
ggtatgtcca acgaattgaa caacatcatc agtagaacta cagatggtgt atacgaaggt  14400
gttgctattg gtggtgacag atacccaggt tctactttta tggatcatgt attgagatat  14460
caagacacac ctggtgttaa aatgattgtt gtcttgggtg aaataggtgg tactgaagaa  14520
tacaagatat gcagaggtat caaagaaggt agattgacaa agccaatcgt ttgttggtgc  14580
attggtactt gtgcaacaat gttttcttca gaagttcaat tcggtcatgc aggtgcctgc  14640
gctaatcaag cttcagaaac agcagttgcc aagaaccaag cattaaaaga agccggtgtt  14700
tttgtcccta gatctttcga tgaattaggt gaaatcattc aatcagtcta tgaagacttg  14760
gtagctaatg gtgtaattgt tccagcacaa gaagttcctc cacctactgt ccctatggat  14820
tactcttggg caagagaatt gggtttaatt agaaagccag ctagttttat gacctctata  14880
tgtgatgaaa gaggtcaaga attgatctat gctggtatgc ctattactga agtattcaaa  14940
gaagaaatgg gtatcggtgg tgttttaggt ttgttgtggt tccaaaagag attgccaaag  15000
tactcttgtc aattcattga aatgtgctta atggttacag ctgatcatgg tcctgctgtc  15060
tcaggtgcac acaataccat aatctgcgct agagctggta aagatttggt ttcttctttg  15120
acctcaggtt tgttaactat tggtgacaga tttggtggtg cattagacgc cgctgcaaag  15180
atgttttcaa aagctttcga ttccggtata atcccaatgg aattcgttaa taagatgaaa  15240
aaggagggta aattgataat gggtatcggt catcgtgtta agtctatcaa taaccctgat  15300
atgagagtac aaatcttgaa ggactatgtt agacaacact ttccagccac acctttgtta  15360
gattacgctt tggaagttga aaagattacc acttctaaaa agccaaattt gatcttgaac  15420
gttgatggtt taattggtgt tgcttttgtc gacatgttga gaaactgtgg ttccttcact  15480
agagaagaag ctgatgaata tatcgacatt ggtgcattga atggtatctt tgttttaggt  15540
agatctatgg gtttcattgg tcattacttg gatcaaaaga gattaaagca aggtttgtac  15600
agacatccat gggatgacat ttcttacgtt ttacctgaac acatgtcaat gaaattgtct  15660
ggtggtggtg gttctggtgg tggtggttct ggtggtggtg gtagtgccga agcttggtac  15720
aatttgggta acgcatacta caagcagggt gactaccaaa aggcaattga atattaccaa  15780
aaggccttgg aattagaccc aaataacgca gaagcctggt ataatttggg taatgcttat  15840
tataaacagg gtgactatca aaaggctatc gaatactacc aaaaggcatt ggaattagac  15900
cctaataacg ctgaagcatg gtataatttg ggtaacgctt attataagca gggtgactat  15960
caaaaagcca tcgaagacta ccaaaaggct ttggaattag atccaaataa cttacaagcc  16020
gaagcttgga agaatttggg taacgcttac tataaacagg gtgactacca aaaagcaatt  16080
gaatactatc aaaaagcttt agaattggac cctaataacg catcagcctg gtacaatttg  16140
ggtaatgctt actataagca gggtgactat cagaaggcca ttgaatacta tcaaaaggct  16200
ttagaattgg atccaaataa cgctaaagca tggtacagac gtggtaacgc ttattacaaa  16260
cagggtgact accagaaagc cattgaagat tatcaaaagg ctttggaatt ggatcctaac  16320
aacagatcta gatcagctgg tggtggtggt tctggtggtg gtggttctgg tggtggtggt  16380
gcttcttcat attaccatca ccatcaccat cacttggaat ccacaagttt atacaaaaag  16440
gctggttctg gttcaaattt ggtcgcacaa ttggaaaacg aagtagcctc tttagaaaat  16500
gaaaacgaaa ccttgaaaaa gaaaaactta cataagaaag atttgatcgc ttatttggaa  16560
aaggaaatcg caaatttgag aaagaaaatt gaagaaggta gtgcaggttc tgccgctggt  16620
tctggtgaat ttggttcagc tgaagcagcc gctaaggaag cagccgctaa agccggttca  16680
gctggttccg cagccggttc tggtgaattc ggttccagtt actatcacca tcaccatcat  16740
cacttggaat ccacaagttt atataagaaa gcaggttctg gttcagcaag aaatgcctac  16800
ttgagaaaga aaatagctag attaaagaaa gataacttgc aattggaaag agatgaacaa  16860
aatttggaaa agattatcgc caacttaaga gatgaaatcg ctagattgga aaatgaagtt  16920
gcatcccatg aacaaggtag tggtgctact aacttctctt tgttgaagca agcaggtgac  16980
gttgaagaaa atccaggtcc aatgaaaaac tgtgtaatcg tttctgctgt tagaactgca  17040
attggttcct ttaatggtag tttggcctct acatcagcta ttgatttggg tgctaccgtc  17100
atcaaagctg caattgaaag agcaaagatt gattctcaac atgtcgacga agtaataatg  17160
ggtaacgttt tgcaagctgg tttaggtcaa aatccagcaa gacaagcctt gttaaaatct  17220
ggtttagcag aaactgtatg tggtttcaca gttaataagg tctgcggttc tggtttgaag  17280
tcagttgctt tagccgctca agctatacaa gcaggtcaag cccaatctat cgtcgctggt  17340
ggtatggaaa atatgtcatt ggcaccttat ttgttagatg caaaagccag atcaggttat  17400
agattaggtg acggtcaagt atacgacgtt attttgagag atggtttaat gtgcgctact  17460
catggttatc acatgggtat tacagcagaa aatgttgcca aagaatacgg tataaccaga  17520
gaaatgcaag atgaattggc attacattcc caaagaaagg cagccgctgc aatcgaaagt  17580
ggtgctttta ctgcagaaat tgtcccagta aacgttgtca caagaaagaa aactttcgtt  17640
ttctcccaag atgaattccc aaaagctaat agtaccgctg aagcattggg tgctttaaga  17700
cctgcattcg acaaggccgg taccgtaact gccggtaatg cttctggtat aaacgatggt  17760
gccgctgcat tggttatcat ggaagaatca gccgctttag cagccggttt gacacctttta  17820
gctagaatta aatcttatgc atcaggtggt gttccacctg ctttgatggg tatgggtcca  17880
gtccctgcta cccaaaaggc attgcaatta gccggtttgc aattggctga tatcgactta  17940
atcgaagcaa acgaagcctt tgctgcacaa ttcttggcag ttggtaaaaa tttgggtttc  18000
gactccgaaa aggttaatgt caacggtggt gccattgctt tgggtcatcc aataggtgct  18060
tcaggtgcaa gaatcttggt tacattgttg catgccatgc aagctagaga taaaaccttg  18120
```

-continued

```
ggtttagcta ctttgtgtat cggtggtggt caaggtatcg caatggttat cgaaagattg  18180
aataagttgt ctggtggtgg tggttctggt ggtggtggtt ctggtggtgg tggtagtgca  18240
gaagcctggt acaatttggg taacgcttac tacaagcagg gtgactacca aaaggcaatc  18300
gaatactacc aaaaggcctt ggaattagat ccaaataacg ctgaagcatg gtataatttg  18360
ggtaatgcct attataaaca gggtgactat caaaaagcta ttgaatatta ccaaaaggca  18420
ttggaattag atcctaataa cgccgaagct tggtataatt tgggtaacgc ctattataag  18480
cagggtgact atcaaaaggc catcgaagat taccaaaagg ctttggaatt ggatccaaac  18540
aacttgcaag cagaagcctg gaagaatttg ggtaacgctt attacaaaca gggtgactac  18600
caaaaagcta ttgaatacta tcaaaaagcc ttagaattgg atcctaataa cgcttctgca  18660
tggtacaatt tgggtaatgc ctactataaa cagggtgact accagaaggc tattgaatac  18720
taccaaaaag cattagaatt ggatccaaat aacgccaagg cttggtacag acgtggtaat  18780
gcctattaca agcagggtga ctaccagaaa gccatagaag actatcaaaa agccttggaa  18840
ttggatccta acaacagatc cagaagtgct ggtggtggtg gttctggtgg tggtggttct  18900
ggtggtggtg gtgcttcttc atattaccat caccatcacc atcacttgga atctacatca  18960
ttatacaaaa aggctggttc cggtagtaat gaagttacta cattggaaaa cgatgccgct  19020
tttatcgaaa acgaaaacgc atacttggaa aaggaaatcg ccagattaag aaaggaaaag  19080
gcagccttga gaaatagatt agcccataaa aagggttccg ctggtagtgc tgcaggttct  19140
ggtgaatttg gttcagctga agccgctgca aaagaagccg ctgcaaaggc aggttctgcc  19200
ggttcagccg ctggttctgg tgaattcggt tccagttact atcaccatca ccatcatcac  19260
ttggaatcta cttcattata taaaaaggcc ggttccggta gtcaaaaagt cgctgaatta  19320
aagaacagag tagctgttaa gttgaacaga aacgaacaat tgaaaaataa ggtagaagaa  19380
ttgaaaaata gaaacgccta cttaaagaat gaattggcaa cattggaaaa cgaagtcgct  19440
agattggaaa atgatgtagc agaaggttct ggt                                19473
```

```
SEQ ID NO: 207          moltype = DNA  length = 7125
FEATURE                 Location/Qualifiers
source                  1..7125
                        mol_type = other DNA
                        organism = synthetic construct
SEQUENCE: 207
atgagtgcta aggcaatttc tgaacaaact ggtaaagaat tgttgtacaa gtttatttgt  60
actacatcag ccatccaaaa tagattcaaa tacgctagag ttaccccaga tactgactgg  120
gctagattgt tacaagatca tccatggttg ttatctcaaa acttggttgt caaacctgac  180
caattaatta agagaagagg taaattgggt ttagtaggtg ttaatttgac attggatggt  240
gtaaagtctt ggttgaaacc aagattaggt caagaagcca cagttggtaa agctaccggt  300
ttcttgaaaa atttcttgat cgaaccattt gtccctcatt cacaagccga agaattctat  360
gtatgtatct acgctactag agagggtgac tatgttttat ttcatcacga aggtggtgtc  420
gacgtaggtg acgttgacgc caaggctcaa aagttgttgg ttggtgtcga tgaaaagttg  480
aacccagaag acattaaaaa gcatttgttg gttcacgcac ctgaagataa aaaggaaata  540
ttggcctcct ttataagtgg tttgtttaat ttctacgaag atttgtactt cacctacttg  600
gaaattaacc cattagtagt tactaaggat ggtgtatatg ttttggactt agctgcaaaa  660
gttgatgcaa cagccgacta catttgtaag gtcaaatggg gtgacatcga atttccacct  720
ccattcggta gagaagctta tccagaagaa gcctacattg ctgatttgga cgctaagtct  780
ggtgcatcat tgaagttgac attgttgaac cctaaaggta gaatttggac catggttgct  840
ggtggtggtg ctagtgtcgt atattctgat actatatgcg acttgggtgg tgttaacgaa  900
ttggcaaact acggtgaata ctcaggtgcc ccatccgaac aacaaacata cgattacgct  960
aagaccatct tgtccttaat gactagagaa aagcatcctg atggtaaaat cttgatcatc  1020
ggtggtagta tcgcaaattt tactaacgtt gccgctacat tcaagggtat cgtcagagct  1080
ataagagatt accaaggtcc attgaaggaa cacgaagtaa caatattcgt tagaagaggt  1140
ggtcctaact accaagaagg tttgagagtc atgggtgaag taggtaaaac cactggtata  1200
ccaatccatg tctttggtac agaaacccac atgactgcaa tagttggtat ggccttaggt  1260
catagaccaa tccctaatca acctccaacc gcagcccaca ctgcaaattt cttgttaaac  1320
gcctctggtt caacttccac accagctcct tctagaacag caagtttctc tgaatcaaga  1380
gctgatgaag tcgctccagc taagaaagca aaaccagcca tgcctcaaga ctccgttcca  1440
agtcctagat ctttgcaggg taaatctact actttgtttt ctagacatac taaggctata  1500
gtatggggta tgcaaacaag agcagttcaa ggcatgttgg atttcgacta tgtttgtagt  1560
agagatgaac catctgttgc tgcaatggtc tatcctttta ctggtgacca taagcaaaaa  1620
ttctactggg gtcacaagga aatattgatc ccagttttta agaacatggc cgatgctatg  1680
agaaaacatc ctgaagtcga cgtattgatt aacttcgcct cattaagatc cgcttacgat  1740
tctacaatgg aaaccatgaa ctacgctcaa ataagaacca tcgctatcat tgcagaaggt  1800
attccagaag ccttgactag aaagttgatt aagaaagctg atcaaaaagg tgtcacaata  1860
atcggtccag ctaccgtagg tggtattaag cctggttgtt tcaagatcgg taacactggt  1920
ggtatgttgg ataacatatt ggcatctaag ttgtatagac caggttcagt cgcttacgta  1980
tccagaagtg gtggtatgtc caacgaattg aacaacatca tcagtagaac tacagatggt  2040
gtatacgaag gtgttgctat tggtggtgac agatacccag gttctacttt tatggatcat  2100
gtattgagat atcaagacac acctggtgtt aaaatgattg ttgtcttggg tgaaataggt  2160
ggtactgaag aatacaagat atgcagaggt atcaaagaag gtagattgac aaagccaatc  2220
gtttgttggt gcattggtac ttgtgcaaca atgttttctt cagaagttca attcggtcat  2280
gcaggtgcct gcgctaatca agcttcagaa acagcagttg ccaagaacca agcattaaaa  2340
gaagccggtg tttttgtccc tagatctttc gatgaattag gtgaaatcat tcaatcagtc  2400
tatgaagact tggtagctaa tggtgtaatt gttccagcac aagaagttcc tccacctact  2460
gtccctatgg attactcttg ggcaagagaa ttgggtttaa ttagaaagcc agctagtttt  2520
atgacctcta tatgtgatga aagaggtcaa gaattgatct atgctggtat gcctattact  2580
gaagtattca aagaagaaat gggtatcggt ggtgttttag gtttgttgtg gttccaaaag  2640
agattgccaa agtactcttg tcaattcatt gaaatgtgct taatggttac agctgatcat  2700
ggtcctgctg tctcaggtgc acacaatacc ataatctgcg ctagagctgg taaagatttg  2760
gtttcttctt tgacctcagg tttgttaact attggtgaca gatttggtgg tgcattagac  2820
gccgctgcaa agatgttttc aaaagctttc gattccggta taatcccaat ggaattcgtt  2880
aataagatga aaaaggaggg taaattgata atgggtatcg gtcatcgtgt taagtctatc  2940
```

-continued

```
aataaccctg atatgagagt acaaatcttg aaggactatg ttagacaaca ctttccagcc  3000
acacctttgt tagattacgc tttggaagtt gaaaagatta ccacttctaa aaagccaaat  3060
ttgatcttga acgttgatgg tttaattggt gttgcttttg tcgacatgtt gagaaactgt  3120
ggttccttca ctagagaaga agctgatgaa tatatcgaca ttggtgcatt gaatggtatc  3180
tttgttttag gtagatctat gggtttcatt ggtcattact tggatcaaaa gagattaaag  3240
caaggtttgt acagacatcc atgggatgac atttcttacg ttttacctga acacatgtca  3300
atgaaattgt ctggtggtgg tggttctggt ggtggtggtt ctggtggtgg tggtagtgcc  3360
gaagcttggt acaatttggg taacgcatac tacaagcagg gtgactacca aaaggcaatt  3420
gaatattacc aaaaggcctt ggaattagac ccaaataacg cagaagcctg gtataatttg  3480
ggtaatgctt attataaaca gggtgactat caaaaggcta tcgaatacta ccaaaaggca  3540
ttggaattag accctaataa cgctgaagca tggtataatt tgggtaacgc ttattataag  3600
cagggtgact atcaaaaagc catcgaagac taccaaaagg ctttggaatt agatccaaat  3660
aacttacaag ccgaagcttg gaagaatttg ggtaacgctt actataaaca gggtgactac  3720
caaaaagcaa ttgaatacta tcaaaaagct ttagaattgg accctaataa cgcatcagcc  3780
tggtacaatt tgggtaatgc ttactataag cagggtgact atcagaaggc cattgaatac  3840
tatcaaaagg ctttagaatt ggatccaaat aacgctaaag catggtacag acgtggtaac  3900
gcttattaca aacagggtga ctaccagaaa gccattgaag attatcaaaa ggctttggaa  3960
ttggatccta acaacagatc tagatcagct ggtggtggtg gttctggtgg tggtggttct  4020
ggtggtggtg gtgcttcttc atattaccat caccatcacc atcacttgga atccacaagt  4080
ttatacaaaa aggctggttc tggttcaaat ttggtcgcac aattggaaaa cgaagtagcc  4140
tctttagaaa atgaaaacga aaccttgaaa aagaaaaact tacataagaa agatttgatc  4200
gcttatttgg aaaaggaaat cgcaaatttg agaaagaaaa ttgaagaagg tagtgcaggt  4260
tctgccgctg gttctggtga atttggttca gctgaagcag ccgctaagga agcagccgct  4320
aaagccggtt cagctggttc cgcagccggt tctggtgaat tcggttccag ttactatcac  4380
catcaccatc atcacttgga atccacaagt ttatataaga aagcaggttc tggttcagca  4440
agaaatgcct acttgagaaa gaaaatagct agattaaaga aagataactt gcaattggaa  4500
agagatgaac aaaatttgga aaagattatc gccaacttaa gagatgaaat cgctagattg  4560
gaaaatgaag ttgcatccca tgaacaaggt agtggtgcta ctaacttctc tttgttgaag  4620
caagcaggtg acgttgaaga aaatccaggt ccaatgaaaa actgtgtaat cgtttctgct  4680
gttagaactg caattggttc ctttaatggt agtttggcct ctacatcagc tattgatttg  4740
ggtgctaccg tcatcaaagc tgcaattgaa agagcaaaga ttgattctca acatgtcgac  4800
gaagtaataa tgggtaacgt tttgcaagct ggtttaggtc aaaatccagc aagacaagcc  4860
ttgttaaaat ctggtttagc agaaactgta tgtggtttca cagttaataa ggtctgcggt  4920
tctggtttga agtcagttgc tttagccgct caagctatac aagcaggtca agcccaatct  4980
atcgtcgctg gtggtatgga aaatatgtca ttggcacctt atttgttaga tgcaaaagcc  5040
agatcaggtt atagattagg tgacggtcaa gtatacgacg ttattttgag agatggttta  5100
atgtgcgcta ctcatggtta tcacatgggt attacagcag aaaatgttgc caaagaatac  5160
ggtataacca gagaaatgca agatgaattg gcattacatt cccaaagaaa ggcagccgct  5220
gcaatcgaaa gtggtgcttt tactgcagaa attgtcccag taaacgttgt cacaagaaag  5280
aaaactttcg ttttctccca agatgaattc ccaaaagcta atagtaccgc tgaagcattg  5340
ggtgctttaa gacctgcatt cgacaaggcc ggtaccgtaa ctgccggtaa tgcttctggt  5400
ataaacgatg gtgccgctgc attggttatc atggaagaat cagccgcttt agcagccggt  5460
ttgacacctt tagctagaat taaatcttat gcatcaggtg gtgttccacc tgctttgatg  5520
ggtatgggtc cagtccctgc tacccaaaag gcattgcaat tagccggttt gcaattggct  5580
gatatcgact taatcgaagc aaacgaagcc tttgctgcac aattcttggc agttggtaaa  5640
aatttgggtt tcgactccga aaaggttaat gtcaacggtg gtgccattgc tttgggtcat  5700
ccaataggtg cttcaggtgc aagaatcttg gttacattgt tgcatgccat gcaagctaga  5760
gataaaacct tgggtttagc tactttgtgt atcggtggtg gtcaaggtat cgcaatggtt  5820
atcgaaagat tgaataagtt gtctggtggt ggtggttctg gtggtggtgg ttctggtggt  5880
ggtggtagtg cagaagcctg gtacaatttg ggtaacgctt actacaagca gggtgactac  5940
caaaaggcaa tcgaatacta ccaaaaggcc ttggaattag atccaaataa cgctgaagca  6000
tggtataatt tgggtaatgc ctattataaa cagggtgact atcaaaaagc tattgaatat  6060
taccaaaagg cattggaatt agatcctaat aacgccgaag cttggtataa tttgggtaac  6120
gcctattata agcagggtga ctatcaaaag gccatcgaag attaccaaaa ggctttggaa  6180
ttggatccaa acaacttgca agcagaagcc tggaagaatt tgggtaacgc ttattacaaa  6240
cagggtgact accaaaaagc tattgaatac tatcaaaaag ccttagaatt ggatcctaat  6300
aacgcttctg catggtacaa tttgggtaat gcctactata aacagggtga ctaccagaag  6360
gctattgaat actaccaaaa agcattagaa ttggatccaa ataacgccaa ggcttggtac  6420
agacgtggta atgcctatta caagcagggt gactaccaga aagccataga agactatcaa  6480
aaagccttgg aattggatcc taacaacaga tccagaagtg ctggtggtgg tggttctggt  6540
ggtggtggtt ctggtggtgg tggtgcttct tcatattacc atcaccatca ccatcacttg  6600
gaatctacat cattatacaa aaaggctggt tccggtagta atgaagttac tacattggaa  6660
aacgatgccg cttttatcga aaacgaaaac gcatacttgg aaaaggaaat cgccagatta  6720
agaaaggaaa aggcagcctt gagaaataga ttagcccata aaaagggttc cgctggtagt  6780
gctgcaggtt ctggtgaatt tggttcagct gaagccgctg caaaagaagc cgctgcaaag  6840
gcaggttctg ccggttcagc cgctggttct ggtgaattcg gttccagtta ctatcaccat  6900
caccatcatc acttggaatc tacttcatta tataaaaagg ccggttccgg tagtcaaaaa  6960
gtcgctgaat taaagaacag agtagctgtt aagttgaaca gaaacgaaca attgaaaaat  7020
aaggtagaag aattgaaaaa tagaaacgcc tacttaaaga atgaattggc aacattggaa  7080
aacgaagtcg ctagattgga aaatgatgta gcagaaggtt ctggt                 7125
```

```
SEQ ID NO: 208          moltype = AA  length = 7
FEATURE                 Location/Qualifiers
source                  1..7
                        mol_type = protein
                        organism = synthetic construct
SEQUENCE: 208
GVKESLV                                                             7
```

```
SEQ ID NO: 209         moltype = AA  length = 723
FEATURE                Location/Qualifiers
source                 1..723
                       mol_type = protein
                       organism = synthetic construct
SEQUENCE: 209
MGKNYKSLDS VVASDFIALG ITSEVAETLH GRLAEIVCNY GAATPQTWIN IANHILSPDL  60
PFSLHQMLFY GCYKDFGPAP PAWIPDPEKV KSTNLGALLE KRGKEFLGVK YKDPISSFSH  120
FQEFSVRNPE VYWRTVLMDE MKISFSKDPE CILRRDDINN PGGSEWLPGG YLNSAKNCLN  180
VNSNKKLNDT MIVWRDEGND DLPLNKLTLD QLRKRVWLVG YALEEMGLEK GCAIAIDMPM  240
HVDAVVIYLA IVLAGYVVVS IADSFSAPEI STRLRLSKAK AIFTQDHIIR GKKRIPLYSR  300
VVEAKSPMAI VIPCSGSNIG AELRDGDISW DYFLERAKEF KNCEFTAREQ PVDAYTNILF  360
SSGTTGEPKA IPWTQATPLK AAADGWSHLD IRKGDVIVWP TNLGWMMGPW LVYASLLNGA  420
SIALYNGSPL VSGFAKFVQD AKVTMLGVVP SIVRSWKSTN CVSGYDWSTI RCFSSSGEAS  480
NVDEYLWLMG RANYKPVIEM CGGTEIGGAF SAGSFLQAQS LSSFSSQCMG CTLYILDKNG  540
YPMPKNKPGI GELALGPVMF GASKTLLNGN HHDVYFKGMP TLNGEVLRRH GDIFELTSNG  600
YYHAHGRADD TMNIGGIKIS SIEIERVCNE VDDRVFETTA IGVPPLGGGP EQLVIFFVLK  660
DSNDTTIDLN QLRLSFNLGL QKKLNPLFKV TRVVPLSSLP RTATNKIMRR VLRQQFSHFE  720
GSG                                                                723

SEQ ID NO: 210         moltype = AA  length = 127
FEATURE                Location/Qualifiers
source                 1..127
                       mol_type = protein
                       organism = synthetic construct
SEQUENCE: 210
GSHMGSQFWV TSQKTEASER CGLQGSYILR VEAEKLTLLT LGAQSQILEP LLFWPYTLLR  60
RYGRDKVMFS FEAGRRCPSG PGTFTFQTSQ GNDIFQAVEA AIQQQKAQGK VGQAQDILRL  120
EHHHHHH                                                            127

SEQ ID NO: 211         moltype = AA  length = 2741
FEATURE                Location/Qualifiers
source                 1..2741
                       mol_type = protein
                       organism = synthetic construct
SEQUENCE: 211
MSEESLFESS PQKMEYEITN YSERHTELPG HFIGLNTVDK LEESPLRDFV KSHGGHTVIS  60
KILIANNGIA AVKEIRSVRK WAYETFGDDR TVQFVAMATP EDLEANAEYI RMADQYIEVP  120
GGTNNNNYAN VDLIVDIAER ADVDAVWAGW GHASENPLLP EKLSQSKRKV IFIGPPGNAM  180
RSLGDKISST IVAQSAKVPC IPWSGTGVDT VHVDEKTGLV SVDDDIYQKG CCTSPEDGLQ  240
KAKRIGFPVM IKASEGGGGK GIRQVEREED FIALYHQAAN EIPGSPIFIM KLAGRARHLE  300
VQLLADQYGT NISLFGRDCS VQRRHQKIIE EAPVTIAKAE TFHEMEKAAV RLGKLVGYVS  360
AGTVEYLYSH DDGKFYFLEL NPRLQVEHPT TEMVSGVNLP AAQLQIAMGI PMHRISDIRT  420
LYGMNPHSAS EIDFEFKTQD ATKKQRRPIP KGHCTACRIT SEDPNDGFKP SGGTLHELNF  480
RSSSNVWGYF SVGNNGNIHS FSDSQFGHIF AFGENRQASR KHMVVALKEL SIRGDFRTTV  540
EYLIKLLETE DFEDNTITTG WLDDLITHKM TAEKPDPTLA VICGAATKAF LASEEARHKY  600
IESLQKGQVL SKDLLQTMFP VDFIHEGKRY KFTVAKSGND RYTLFINGSK CDIILRQLSD  660
GGLLIAIGGK SHTIYWKEEV AATRLSVDSM TTLLEVENDP TQLRTPSPGK LVKFLVENGE  720
HIIKGQPYAE IEVMKMQMPL VSQENGIVQL LKQPGSTIVA GDIMAIMTLD DPSKVKHALP  780
FEGMLPDFGS PVIEGTKPAY KFKSLVSTLE NILKGYDNQV IMNASLQQLI EVLRNPKLPY  840
SEWKLHISAL HSRLPAKLDE QMEELVARSL RRGAVFPARQ LSKLIDMAVK NPEYNPDKLL  900
GAVVEPLADI AHKYSNGLEA HEHSIFVHFL EEYYEVEKLF NGPNVREENI ILKLRDENPK  960
DLDKVALTVL SHSKVSAKNN LILAILKHYQ PLCKLSSKVS AIFSTPLQHI VELESKATAK  1020
VALQAREILI QGALPSVKER TEQIEHILKS SVVKVAYGSS NPKRSEPDLN ILKDLIDSNY  1080
VVFDVLLQFL THQDPVVTAA AAQVYIRRAY RAYTIGDIRV HEGVTVPIVE WKFQLPSAAF  1140
STFPTVKSKM GMNRAVSVSD LSYVANSQSS PLREGILMAV DHLDDVDEIL SQSLEVIPRH  1200
QSSSNGPAPD RSGSSASLSN VANVCVASTE GFESEEEILV RLREILDLNK QELINASIRR  1260
ITFMFGFKDG SYPKYYTFNG PNYNENETIR HIEPALAFQL ELGRLSNFNI KPIFTDNRNI  1320
HVYEAVSKTS PLDKRFFTRG IIRTGHIRDD ISIQEYLTSE ANRLMSDILD NLEVTDTSNS  1380
DLNHIFINFI AVFDISPEDV EAAFGGFLER FGKRLLRLRV SSAEIRIIIK DPQTGAPVPL  1440
RALINNVSGY VIKTEMYTEV KNAKGEWVFK SLGKPGSMHL RPIATPYPVK EWLQPKRYKA  1500
HLMGTTYVYD FPELFRQASS SQWKNFSADV KLTDDFFISN ELIEDENGEL TEVEREPGAN  1560
AIGMVAFKIT VKTPEYPRGR QFVVVANDIT FKIGSFGPQE DEFFNKVTEY ARKRGIPRIY  1620
LAANSGARIG MAEEIVPLFQ VAWNDAANPD KGFQYLYLTS EGMETLKKFD KENSVLTERT  1680
VINGEERFVI KTIIGSEDGL GVECLRGSGL IAGATSRAYH DIFTITLVTC RSVGIGAYLV  1740
RLGQRAIQVE GQPIILTGAP AINKMLGREV YTSNLQLGGT QIMYNNGVSH LTAVDDLAGV  1800
EKIVEWMSYV PAKRNMPVPI LETKDTWDRP VDFTPTNDET YDVRWMIEGR ETESGFEYGL  1860
FDKGSFFETL SGWAKGVVVG RARLGGIPLG VIGVETRTVE NLIPADPANP NSAETLIQEP  1920
GQVWHPNSAF KTAQAINDFN NGEQLPMMIL ANWRGFSGGQ RDMFNEVLKY GSFIVDALVD  1980
YKQPIIIYIP PTGELRGGSW VVVDPTINAD QMEMYADVNA RAGVLEPQGM VGIKFRREKL  2040
LDTMNRLDDK YRELRSQLSN KSLAPEVHQQ ISKQLADRER ELLPIYGQIS LQFADLHDRS  2100
SRMVAKGVIS KELEWTEARR FFFWRLRRRL NEEYLIKRLS HQVGEASRLE KIARIRSWYP  2160
ASVDHEDDRQ VATWIEENYK TLDDKLKGLK LESFAQDLAK KIRSDHDNAI DGLSEVIKML  2220
STDDKEKLLK TLKKLSGGGG SGGGGSGGGG SAEAWYNLGN AYYKQGDYQK AIEYYQKALE  2280
LDPNNAEAWY NLGNAYYKQG DYQKAIEYYQ KALELDPNNA EAWYNLGNAY YKQGDYQKAI  2340
EDYQKALELD PNNLQAEAWK NLGNAYYKQG DYQKAIEYYQ KALELDPNNA SAWYNLGNAY  2400
YKQGDYQKAI EYYQKALELD PNNAKAWYRR GNAYYKQGDY QKAIEDYQKA LELDPNNRSR  2460
SAGGGGSGGG GSGGGGASGS HMRLGAQSIQ PTANLDRTDD LVYLNVMELV RAVLELKNEL  2520
AQLPPEGYVV VVKNVGLTLR KLIGSVDDLL PSLPSSSRTE IEGTQKLLNK DLAELINKMR  2580
```

-continued

```
LAQQNAVTSL SEECKRQMLT ASHTLAVDAK NLLDAVDQAK VLANLAHPPA EGSAGSAAGS  2640
GEFGSAEAAA KEAAAKAGSA GSAAGSGEFG SGAMATPGSE NVLPREPLIA TAVKFLQNSR  2700
VRQSPLATRR AFLKKKGLTD EEIDMAFQQS GTAADEPSSL W                      2741

SEQ ID NO: 212          moltype = DNA  length = 57
FEATURE                 Location/Qualifiers
source                  1..57
                        mol_type = other DNA
                        organism = synthetic construct
SEQUENCE: 212
gctactaact tctctttgtt gaagcaagca ggtgacgttg aagaaaatcc aggtcca     57
```

BIDIRECTIONAL MULTI-ENZYMATIC SCAFFOLDS FOR BIOSYNTHESIZING CANNABINOIDS

CROSS-REFERENCE TO RELATED APPLICATIONS

This application is a continuation of U.S. application Ser. No. 16/694,417, filed Nov. 25, 2019, which claims priority to U.S. Application Serial Nos. 62/836,265, filed on Apr. 19, 2019 and 62/771,839, filed on Nov. 27, 2018. The disclosures of the prior applications are considered part of (and are incorporated by reference in) the disclosure of this application.

TECHNICAL FIELD

This document relates to methods and materials for biosynthesizing cannabinoids, and more particularly to using bidirectional multi-enzymatic scaffolds to biosynthesize cannabinoids.

SEQUENCE LISTING

This application contains a Sequence Listing that has been submitted electronically as an XML file named "47300-0003002_SL_ST26.XML." The XML file, created on May 12, 2023, is 487,591 bytes in size. The material in the XML file is hereby incorporated by reference in its entirety.

BACKGROUND

The emerging therapeutic potential of cannabinoids warrants industrial-scale production to meet compounding future demands. Traditional cannabinoid production efforts rely on large-scale farming of *Cannabis sativa* L. However, agricultural cannabinoid production is problematic due to issues such as uncontrollable environmental factors and scaling limitations.

SUMMARY

This document is based, at least in part, on the discovery that a bidirectional, multi-enzymatic scaffold can be engineered to allow high-throughput cannabinoid production in recombinant host cells. By controlling the localization, spatial orientation, and stoichiometry of enzymes catalyzing the biosynthesis of cannabinoids and cannabinoid precursors, the multi-enzymatic scaffolds described herein allow flux-optimized cannabinoid biosynthesis in genetically-engineered host cells.

In one aspect, this document features a host cell capable of producing one or more cannabinoids selected from the group consisting of cannabigerolic acid, cannabidiolic acid, and cannabichromenic acid. The host cell includes at least three different exogenous nucleic acids, wherein the first and the second exogenous nucleic acids each encode a plurality of engineered enzymes selected from the group consisting of acetyl-CoA acetyltransferase, a 3-hydroxybutyryl-CoA dehydrogenase, an enoyl-CoA hydratase, a beto-ketothiolase, a trans-enoyl-CoA reductase, an HMG-CoA synthetase, an HMG-CoA reductase, a mevalonate kinase, a phosphomevalonate kinase, a diphosphomevalonate decarboxylase, an isopentenyl-diphosphate delta isomerase, a geranyl-diphosphate synthase, an olivetol synthase, an olivetolic acid cyclase, and a CBGA synthase; wherein each of the engineered enzymes includes a heterologous interaction domain, wherein the heterologous interaction domain comprises a first and a second peptide motif, and wherein each heterologous interaction domain is different from each other; and wherein the third exogenous nucleic acid encodes a polypeptide scaffold comprising a plurality of peptide ligands, wherein each peptide ligand comprises an amino acid sequence that can bind to the first or the second peptide motif of one of the heterologous interaction domains. The plurality of engineered enzymes further can include an ATP citrate lyase and an acetyl-CoA carboxylase. The host cell further can include an exogenous nucleic acid encoding a cannabidiolic acid synthase (CBDAS) and a cannabichromenic acid synthase (CBCAS). The host cell can include an exogenous CBDAS. The host cell can include an exogneous CBCAS. The host cell can include an exogenous CBDAS and an exogenous CBCAS. The host cell can include an exogenous hexanoyl-CoA synthetase. The host cell can include at least four different exogenous nucleic acids, wherein the first, second, and fourth nucleic acids each encode a plurality of the engineered enzymes. The host cell can include at least five different exogenous nucleic acids, wherein the first, second, fourth, and fifth nucleic acid each encode a plurality of the engineered enzymes. The host cell can include at least six different exogenous nucleic acids, wherein the first, second, fourth, fifth, and sixth nucleic acids each encode a plurality of the engineered enzymes. Each exogenous nucleic acid can include a constitutive promoter operably linked to the sequence encoding the engineered enzyme or polypeptide scaffold or an inducible promoter operably linked to the sequence encoding the engineered enzyme or polypeptide scaffold. In some embodiments, the promoter is a GAL1-10 promoter. In some embodiments, a constitutive promoter used to express the polypeptide scaffold has weaker constitutive activity level than a constitutive promoter used to express the engineered enzymes. In some embodiments, a constitutive promoter is used to express the engineered enzymes and an inducible promoter is used to express the polypeptide scaffold. In some embodiments, an inducible promoter is used to express the engineered enzymes and a constitutive promoter is used to express the polypeptide scaffold.

Any of the host cells can be bacterial, yeast, algae, or plant cells. A bacterial cell can be selected from the group consisting of *Escherichia coli, Bacillus, Brevibacterium, Streptomyces*, and *Pseudomonas* cells. A yeast cell can be selected from the group consisting of *Pichia pastoris, Saccharomyces cerevisiae, Yarrowia lipolytica, Kluyveromyces marxianus*, and Komagataella phaffii cells. An algae cell can be *Dunaliella* sp., *Chlorella variabilis, Euglena mutabilis*, or *Chlamydomonas reinhardtii* cells. A plant cell can be a *Cannabis* or tobacco cell.

In some embodiments, each of the engineered enzymes is of the formula: enzyme—$linker_1$–spacer–$linker_2$– $motif_1$–$linker_3$–$motif_2$, where linkers 1, 2, and 3 can be the same or different, motif 1 and motif 2 can be the same or different, and where motif 1 and motif 2 form the heterologous interaction domain. A scaffold polypeptide can be of the formula: N-terminus—[Ligand 1–linker–Ligand 2–Spacer] n–(optionally-tagged)C-terminus, where n is the number of heterologous interaction domains, and where ligand 1 and ligand 2 bind motif 1 and motif 2, respectively, of the heterologous interaction domain. The scaffold polypeptide can be tagged with a MYC tag, FLAG tag, or HA tag. The host cell further can include a nucleic acid encoding a second polypeptide scaffold comprising a plurality of peptide ligands, wherein each peptide ligand comprises an amino acid sequence that can bind to a different motif of the heterologous interaction domain. The linker can have a flexible GS-rich sequence flanking a rigid α-helical moiety. The spacer can be the cTPR6 spacer.

This document also features a method of producing one or more cannabinoids selected from the group consisting of cannabigerolic acid, cannabidiolic acid, and cannabichromenic acid. The method can include culturing any of the host cells described herein under conditions wherein the host cell produces the one or more cannabinoids. The host cells can be cultured in a culture medium supplemented with citrate, glucose, hexanoic acid, and/or other carbon source, and/or in a culture medium supplemented with malonyl-CoA. The method further can include extracting the one or more cannabinoids from the host cells.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 6A contains the amino acid sequence of each of the following enzymes: an ATP citrate lyase (SEQ ID NO:83), acetyl-CoA acetyltransferase (atoB) (SEQ ID NO:84), a 3-hydroxybutyryl-CoA dehydrogenase (SEQ ID NO:85), an enoyl-CoA hydratase (SEQ ID NO:86), a trans-enoyl-CoA reductase (SEQ ID NO:88), a beta-ketothiolase (bktB) (SEQ ID NO:87), an HMG-CoA synthase (SEQ ID NO:90), a truncated HMG-CoA reductase (SEQ ID NO:91), a mevalonate kinase (SEQ ID NO:92), a phosphomevalonate kinase (SEQ ID NO:93), a diphosphomevalonate decarboxylase (SEQ ID NO:94), an isopentenyl-diphosphate delta isomerase (SEQ ID NO:95), a mutant geranyl-diphosphate synthase ($ERG20^{WW}$) (SEQ ID NO:96), an olivetol synthase (SEQ ID NO:98), an olivetolic acid cyclase (SEQ ID NO:99), a CBGA synthase (SEQ ID NO:100), an acetyl-CoA carboxylase (SEQ ID NO:97), a CBDA synthase (SEQ ID NO:101), a CBCA synthase (SEQ ID NO:102), and a hexanoyl-CoA synthetase (SEQ ID NO:89).

FIG. 6B contains the amino acid sequence of engineered enzymes of the formula Enzyme–Enzyme Linker–cTPR6 Spacer–ID Linker–ID Motif #1–ID Motif Linker– ID Motif #2, where the linkers (enzyme linker, ID linker, and ID motif linker) can be the same or different, and ID motif #1 and ID motif #2 can be the same or different. The amino acid sequence of the following engineered enzymes are provided: ATP citrate lyase (ID1) (SEQ ID NO:103), an acetyl-CoA acetyltransferase (atoB) (ID2) (SEQ ID NO:104), a 3-hydroxybutyryl-CoA dehydrogenase (ID3) (SEQ ID NO:105), an enoyl-CoA hydratase (ID4) (SEQ ID NO:106), a trans-enoyl-CoA reductase (ID5) (SEQ ID NO:107), a beto-ketothiolase (bktB) (ID6) (SEQ ID NO:108), an HMG-CoA synthase (ID7) (SEQ ID NO:109), a truncated HMG-CoA reductase (ID8) (SEQ ID NO:110), a mevalonate kinase (ID9) (SEQ ID NO:111), a phosphomevalonate kinase (ID10) (SEQ ID NO:112), a diphosphomevalonate decarboxylase (ID11) (SEQ ID NO:113), an isopentenyl-diphosphate delta isomerase (ID12) (SEQ ID NO:114), a mutant geranyl-diphosphate synthase (ERG20$^{WW}$) (ID13) (SEQ ID NO:115), an olivetol synthase (ID14) (SEQ ID NO:116), an olivetolic acid cyclase (ID15) (SEQ ID NO:117), a CBGA synthase (ID16) (SEQ ID NO:118), and an acetyl-CoA carboxylase (ID17) (SEQ ID NO:211).

FIG. 6C contains the amino acid sequence of a polypeptide scaffold of the formula: N-terminus– [Ligand #1– ID Motif #1 Ligand–Linker– ID Motif #2 Ligand—Scaffolded ID-binding Site Spacer]n– (Myc)3-tagged C-terminus, where n is 16 and the ID motif ligands correspond to the motifs for IDs 1-16 as shown in Table 2. See SEQ ID NO:119.

FIG. 6D contains the amino acid sequence of a polypeptide scaffold of the formula: N-terminus–[Ligand #1–ID Motif #1 Ligand–Linker–ID Motif #2 Ligand—Scaffolded ID-binding Site Spacer]n–(FLAG)3-tagged C-terminus, where n is 2 and the ID motif ligands correspond to the motifs for IDs 1 and 17 as shown in Table 2. See SEQ ID NO:120.

FIG. 12A contains the nucleotide sequences encoding each of the following: an ATP citrate lyase (SEQ ID NO:121), an acetyl-CoA acetyltransferase (atoB) (SEQ ID NO:122), a 3-hydroxybutyryl-CoA dehydrogenase (SEQ ID NO:123), an enoyl-CoA hydratase (SEQ ID NO:124), a trans-enoyl-CoA reductase (SEQ ID NO:125), a beto-ketothiolase (bktB) (SEQ ID NO:126), an HMG-CoA synthase (SEQ ID NO:127), a truncated HMG-CoA reductase (SEQ ID NO:128), a mevalonate kinase (SEQ ID NO:129), a phosphomevalonate kinase (SEQ ID NO:130), a diphosphomevalonate decarboxylase (SEQ ID NO:131), an isopentenyl-diphosphate delta isomerase (SEQ ID NO:132), a geranyl-diphosphate synthase (ERG20$^{WW}$) (SEQ ID NO:133), an olivetol synthase (SEQ ID NO:134), an olivetolic acid cyclase (SEQ ID NO:135), a CBGA synthase (SEQ ID NO:136), an acetyl-CoA carboxylase (SEQ ID NO:137), a CBDA synthase (SEQ ID NO:138), a CBCA synthase (SEQ ID NO:139), and a hexanoyl-CoA synthetase (SEQ ID NO:140).

FIG. 12B contains the nucleotide sequences encoding engineered enzymes of the formula: Enzyme–Enzyme Linker–cTPR6 Spacer– ID Linker– ID Motif #1– ID Motif Linker– ID Motif #2, where the Enzyme Linker, ID Linker, and ID Motif Linker can be the same or different, and where ID Motif #1 and ID Motif #2 can be the same or different. The nucleotide sequences encoding the following engineered enzymes are provided: ATP citrate lyase (ID1) (SEQ ID NO:141), an acetyl-CoA acetyltransferase (atoB) (ID2) (SEQ ID NO:142), a 3-hydroxybutyryl-CoA dehydrogenase (ID3) (SEQ ID NO:143), an enoyl-CoA hydratase (ID4) (SEQ ID NO:144), a trans-enoyl-CoA reductase (ID5) (SEQ ID NO:145), a bktB (ID6) (SEQ ID NO:146), an HMG-CoA synthase (ID7) (SEQ ID NO:147), a truncated HMG-CoA reductase (ID8) (SEQ ID NO:148), a mevalonate kinase (ID9) (SEQ ID NO:149), a phosphomevalonate kinase (ID10) (SEQ ID NO:150), a diphosphomevalonate decarboxylase (ID11) (SEQ ID NO:151), an isopentenyl-diphosphate delta isomerase (ID12) (SEQ ID NO:152), a mutant geranyl-diphosphate synthase (ERG20$^{WW}$) (ID13) (SEQ ID NO:153), an olivetol synthase (ID14) (SEQ ID NO:154), an olivetolic acid cyclase (ID15) (SEQ ID NO:155), a CBGA synthase (ID16) (SEQ ID NO:156), and an acetyl-CoA carboxylase (ID17) (SEQ ID NO:157).

FIG. 12C contains the nucleotide sequence (SEQ ID NO:158) encoding a scaffold polypeptide that contains the peptide ligands corresponding to IDs 1-16 as shown in Table 2 and a triplicate myc tag on the C-terminus.

FIG. 12D contains the nucleic acid sequence (SEQ ID NO:159) encoding a scaffold polypeptide that contains the peptide ligands corresponding to IDs 1 and 17, and a triplicate FLAG tag on the C-terminus.

FIG. 13A contains the amino acid sequence of scaffold-binding engineered enzymes and a soluble hexanoyl-CoA synthetase (HCS) (SEQ ID NO:209) encoded by the HCA gene cassette. The scaffold-binding engineered enzymes are ATP Citrate Lyase (ACL) (ACL— Enzyme Linker—cTPR6 Spacer— ID Linker— ID1) (SEQ ID NO:160); Acetyl-CoAAcetyltransferase (atoB) (atoB— Enzyme Linker—cTPR6 Spacer— ID Linker— ID2) (SEQ ID NO:161); 3-Hydroxybutyryl-CoA Dehydrogenase (BHBD) (BHBD—Enzyme Linker—cTPR6 Spacer— ID Linker— ID3) (SEQ ID NO:162); Enoyl-CoA Hydratase (ECH) (ECH— Enzyme Linker—cTPR6 Spacer— ID Linker— ID4) (SEQ ID NO:163); Trans-Enoyl-CoA Reductase (ECR) (ECR—Enzyme Linker—cTPR6 Spacer— ID Linker— ID5) (SEQ ID NO:164); and Beta-Ketothiolase (bktB) (bktB—Enzyme Linker—cTPR6 Spacer— ID Linker— ID6) (SEQ ID NO:165).

FIG. 13B contains the amino acid sequences of scaffold-binding engineered enzymes encoded by the GPP gene cassette. The scaffold-binding engineered enzymes are HMG-CoA Synthase (HMGS) (HMGS— Enzyme Linker—cTPR6 Spacer— ID Linker— ID7) (SEQ ID NO:166); truncated HMG-CoA Reductase (tHMGR) (tHMGR—Enzyme Linker—cTPR6 Spacer— ID Linker— ID8) (SEQ ID NO:167); Mevalonate Kinase (ERG12) (ERG12— Enzyme Linker—cTPR6 Spacer— ID Linker— ID9) (SEQ ID NO:168); Phosphomevalonate Kinase (ERG8) (ERG8—Enzyme Linker—cTPR6 Spacer—ID Linker— ID10) (SEQ ID NO:169); Diphosphomevalonate Decarboxylase (MVD1) (MVD1— Enzyme Linker—cTPR6 Spacer— ID Linker— ID11) (SEQ ID NO:170); Isopentenyl-Diphosphate Delta-Isomerase (IDI1) (IDI1— Enzyme Linker—cTPR6 Spacer— ID Linker— ID12) (SEQ ID NO:171); and Geranyl-Diphosphate Synthase (ERG20$^{WW}$) (ERG20$^{WW}$—Enzyme Linker—cTPR6 Spacer— ID Linker— ID13) (SEQ ID NO:172).

FIG. 13C contains the amino acid sequences of scaffold-binding engineered enzymes, a soluble CBDA synthase (SEQ ID NO:173), and a soluble CBCA synthase (SEQ ID NO:174) encoded by the CAN gene cassette. The scaffold-binding engineered enzymes are Olivetol Synthase (OS) (OS— Enzyme Linker—cTPR6 Spacer— ID Linker— ID14) SEQ ID NO:175); Olivetolic Acid Cyclase (OAC) (OAC— Enzyme Linker—cTPR6 Spacer— ID Linker— ID15) (SEQ ID NO:176); CBGA Synthase (CBGAS— Enzyme Linker—cTPR6 Spacer— ID Linker— ID16) (SEQ ID NO:177); and Acetyl-CoA Carboxylase (ACC) (ACC— Enzyme Linker—cTPR6 Spacer— ID Linker— ID17) (SEQ ID NO:178).

FIG. 13D contains the amino acid sequences of the Cannabinoidergic Metabolon Scaffold (CBSCFLD)—(Myc)3 (SEQ ID NO:179) and the Malonyl-CoA Metabolon Scaffold (MCASCFLD)— (FLAG)3 (SEQ ID NO:180).

FIG. 14A contains codon-optimized nucleotide sequences (SEQ ID NOs:181-187) encoding the enzymes of FIG. 13A.

FIG. 14B contains the codon-optimized nucleotide sequences (SEQ ID NOs:188-194) encoding the enzymes of FIG. 13B.

FIG. 14C contains the codon-optimized nucleotide sequences (SEQ ID NOs:195-200) encoding the enzymes of FIG. 13C.

FIG. 14D contains the codon-optimized nucleotide sequences (SEQ ID NO:201 and SEQ ID NO:202) encoding the scaffolds of FIG. 13D.

FIG. 15A contains the nucleotide sequence of the HCA gene cassette (SEQ ID NO:203).

FIG. 15B contains the nucleotide sequence of the GPP gene cassette (SEQ ID NO:204).

FIG. 15C contains the nucleotide sequence of the CAN gene cassette (SEQ ID NO:205).

FIG. 15D contains the nucleotide sequence of the SCF gene cassette (SEQ ID NO:206).

FIG. 15E contains the nucleotide sequence of the SOL gene cassette (SEQ ID NO:207).

FIG. 16 is a map of the pCCI-Brick plasmid construct.

FIG. 17 is a map of a pESC-TRP ("vHCA") vector construct. In this map, the vector contains a TRP gene allowing selection in tryptophan deficient media. Similar vectors also were made in which the TRP gene was replaced with a LEU gene allowing selection in leucine deficient media, a HIS3 gene allowing selection in histidine deficient media, or a URA3 gene allowing selection in uracil deficient media.

FIG. 18 is a graph of the proliferation curves for yCBSCF and yCBSOL cultures. Line plots depicting cell proliferation curves were fitted via nonlinear regression of cell density measurements ($OD_{600nm}$) recorded in 12-hour intervals over a 48-hour incubation period for yCBSCF and yCBSOL cultures. Initial cell densities for all cultures were standardized to $OD_{600mn}$=0.3. For all measures, n=3 biological replicates for yCBSCF and yCBSOL cultures. Floating data points depict means with 95% confidence intervals. Dotted lines represent 95% confidence intervals for regression curve fits.

FIGS. 19A-19E show a comparison of cannabinoid and precursor titers for scaffolded and soluble cannabinoid biosynthesis. Representative mass spectra of target analytes isolated from (FIG. 19A) yCBSOL and (FIG. 19B) yCBSCF cultures incubated for 48 hours in basal culture media. Bar plots depicting (FIG. 19C) Total (aggregate) cannabinoid (CBGA+CBDA+CBCA+CBG+CBD+CBC) titers, (FIG. 19D) cannabinoid precursor (OVA) titers and summated parent and decarboxylation derivative (CBGA+CBG, CBDA+CBD, and CBCA+CBC) cannabinoid titers, and (FIG. 19E) separated parent (COO(H)) cannabinoid (CBGA, CBDA, and CBCA) and decarboxylation derivative (ACOOH) cannabinoid (CBG, CBD, and CBC) titers for 48-hour yCBSOL (left) and yCBSCF (right) cultures grown in basal culture media. For all measures, n=3 biological replicates for yCBSCF and yCBSOL cultures. CB, cannabinoid; Cannabigerolic acid, CBGA; cannabigerol, CBG; cannabidiolic acid, CBDA; cannabidiol, CBD; cannabichromenic acid, CBCA; cannabichromene, CBC; olivetolic acid, OVA. Floating asterisks indicate statistically significant (determined by Bonferroni's multiple comparisons post-hoc test; a=0.05) between-strain differences for yCBSCF versus yCBSOL cultures. Bar plots depict means with 95% confidence intervals. *p<0.05; p<0.01; *p<0.001; ****p<0.0001.

FIG. 20 is a bar plot of the impact of citrate and hexanoate supplementation on scaffolded and soluble cannabinoid biosynthesis. Total cannabinoid (CBGA+CBDA+CBCA+CBG+CBD+CBC) titers are shown for yCBSOL and yCBSCF cultures incubated for 48 hours in basal, hexanoate (300 mg/L)-supplemented, and buffered (pH 6.0) citrate (300 mg/L)-supplemented culture media. Floating asterisks indicate statistically significant (determined by Bonferroni's multiple comparisons post-hoc test; a=0.05) between-strain differences for yCBSCF versus yCBSOL cultures. Lines with asterisks indicate statistically significant (determined by Bonferroni's multiple comparisons post-hoc test; a=0.05) within-strain differences for basal media total cannabinoid titers versus citrate-supplemented media total cannabinoid titers for yCBSCF cultures. Bar plots depict means with 95% confidence intervals. *p<0.05; p<0.01; *p<0.001; ****p<0.0001.

FIGS. 21A and 21B show concentration-response parameterization of scaffolded and soluble cannabinoid biosynthesis from citrate. In FIG. 21A, line plots are shown depicting eight-point concentration ([citrate])—response (total cannabinoid titers) curves fitted via asymmetric sigmoidal (five-parameter) logistic regression and in FIG. 21B, bar graphs are shown depicting concentration-response parameter estimates ($CB_{Max}$, the estimated maximum total cannabinoid titers and citrate $EC_{50}$, the estimated citrate concentration yielding half-maximal total cannabinoid titers) for 48-hour yCBSCF and $yCB_{SOL}$ cultures incubated for 48 hours in culture media supplemented with 0, 10, 30, 100, 300, 1000, 3000, or 10000 mg/L buffered (pH 6.0) citrate. For all measures, n=3 biological replicates for yCBSCF and $yCB_{SOL}$ cultures. Floating asterisks indicate statistically significant (determined by Bonferroni's multiple comparisons post-hoc test; $\alpha$=0.05) between-strain differences for yCBSCF versus $yCB_{SOL}$ cultures. Floating data points and bar plots depict means with 95% confidence intervals. Dotted lines represent 95% confidence intervals for regression curve fits *p<0.05; p<0.01; *p<0.001; ****p<0.0001.

DETAILED DESCRIPTION

This document provides methods and materials for producing cannabinoids in host cells or in vitro using a bidirectional, multi-enzymatic scaffold, which can control the localization and stoichiometry of enzymes catalyzing the biosynthesis of cannabinoids and cannabinoid precursors. As described herein, one or more cannabinoids including cannabigerolic acid (CBGA), cannabidiolic acid (CBDA), cannabichromenic acid (CBCA), and tetrahydrocannabinolic acid, can be produced using a bidirectional, multi-enzymatic scaffold and one or more soluble cannabinoid synthesis enzymes, and the conjugate bases, cannabigerolate, cannabidiolate, cannabichromenate, and tetrahydrocannabinolate, respectively, and decarboxylation products, cannabigerol (CBG), cannabidiol (CBD), cannabichromene (CBC), and tetrahydrocannabinol, respectively, of these cannabinoids also can be produced, as can the tetrahydrocannabinolic acid oxidation product cannabinolic acid and its decararboxylation product cannabinol. The bidirectional, multi-enzymatic scaffold described herein results in significant increases in cannabinoid production in recombinant hosts, including total cannabinoid, CBGA, CBG, CBDA, CBD, CBCA, CBC, and olivetolic acid precursor production, as compared with cannabinoid production in recombinant hosts using the same enzymes that are not bound to a scaffold. As used herein, enzymes that are not bound to a scaffold are referred to as soluble or non-scaffolded. While one particular form of a cannabinoid or other compound may be referenced herein, it is understood that any of its neutral or ionized forms, including any salt forms thereof or decarboxylation derivatives thereof (e.g., produced in the presence of heat and light), are included unless otherwise indicated. It is understood by those skilled in the art that the specific form will depend on factors such as pH and carboxylation status.

Figure 1A:
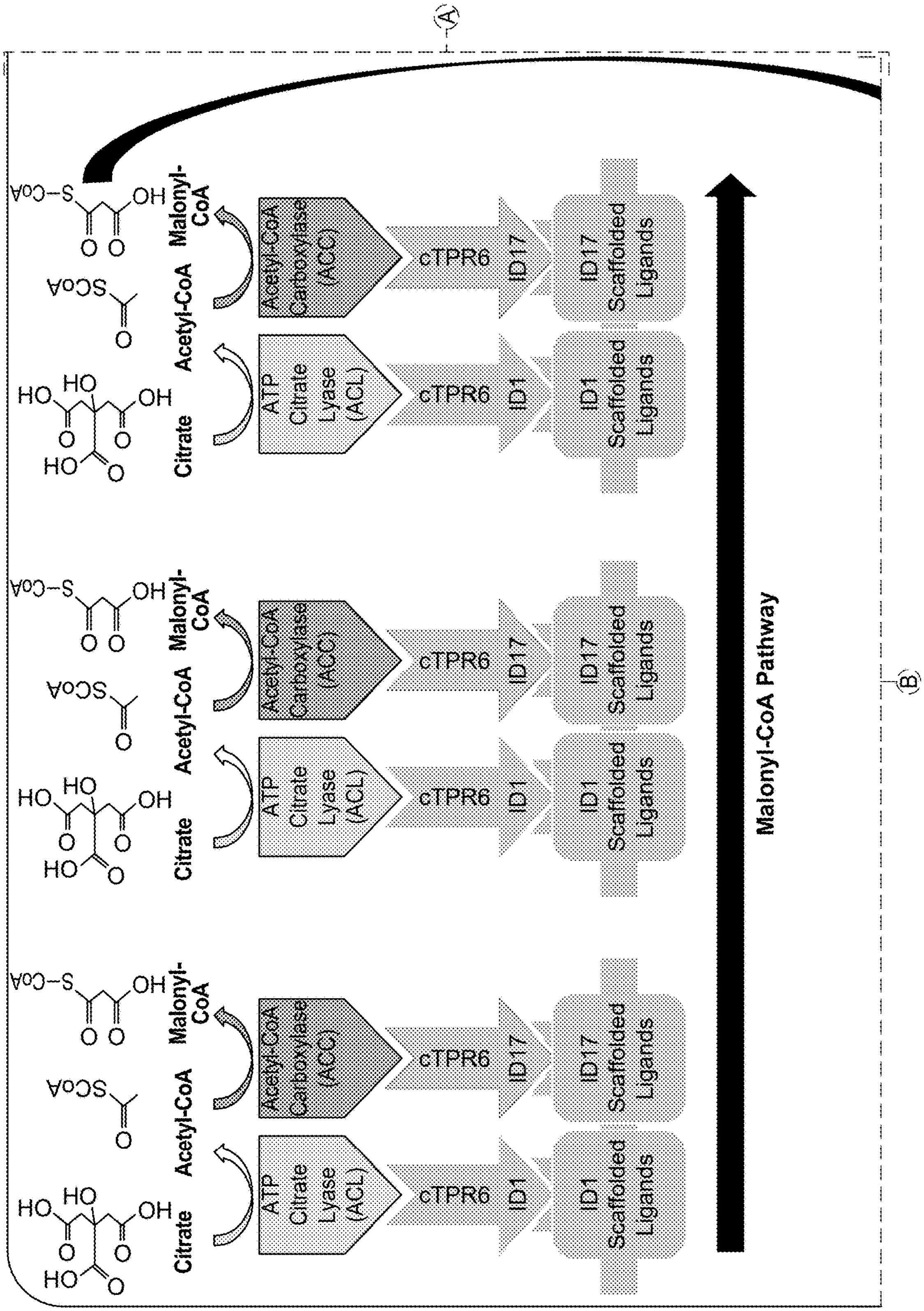
FIG. 1A is a schematic of one representative embodiment of a multi-enzymatic cannabinoidergic scaffold within a cell. The multi-enzymatic scaffold includes enzymes of the hexanoyl-CoA pathway, enzymes of the upper cannabinoid pathway, and enzymes of the mevalonate pathway. The schematic also depicts a second scaffold according to one embodiment containing enzymes of the malonyl-CoA pathway and depicts a non-scaffolded cannabidiolic acid synthase (CBDAS) and a non-scaffolded cannabichromenic acid synthase (CBCAS). ID refers to enzyme-linked interaction domain; cTPR6 refers to a spacer sequence; scaffolded ligands refer to the tandem peptide ligands that form the scaffold-binding sites specific for each enzyme-linked ID. The target products cannabigerolic acid (CBGA), cannabigerol (CBG), cannabidiolic acid (CBDA), cannabidiol (CBD), cannabichromenic acid (CBCA), and cannabichromene (CBC), are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.
Figure 1A:
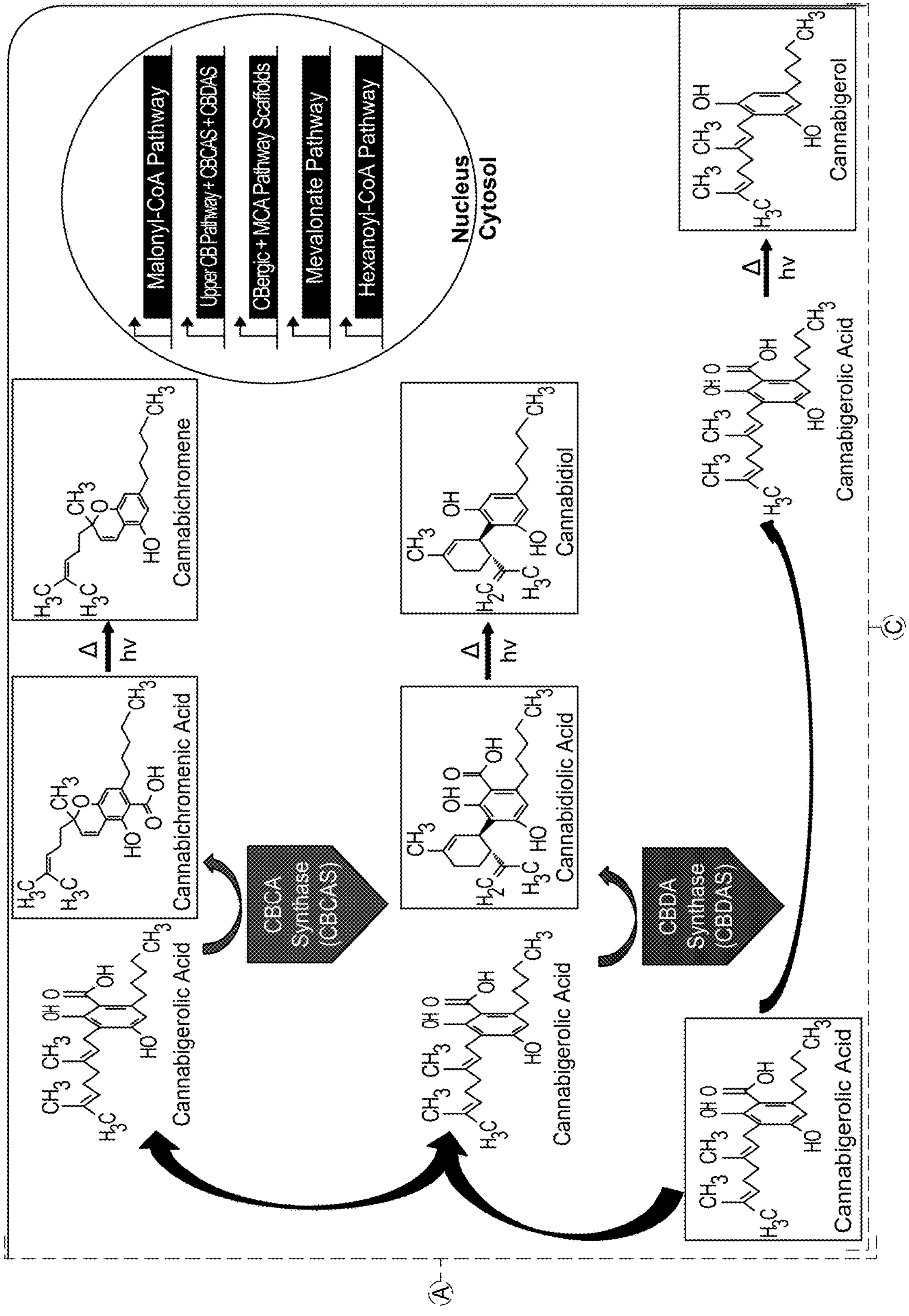
Figure 1A:
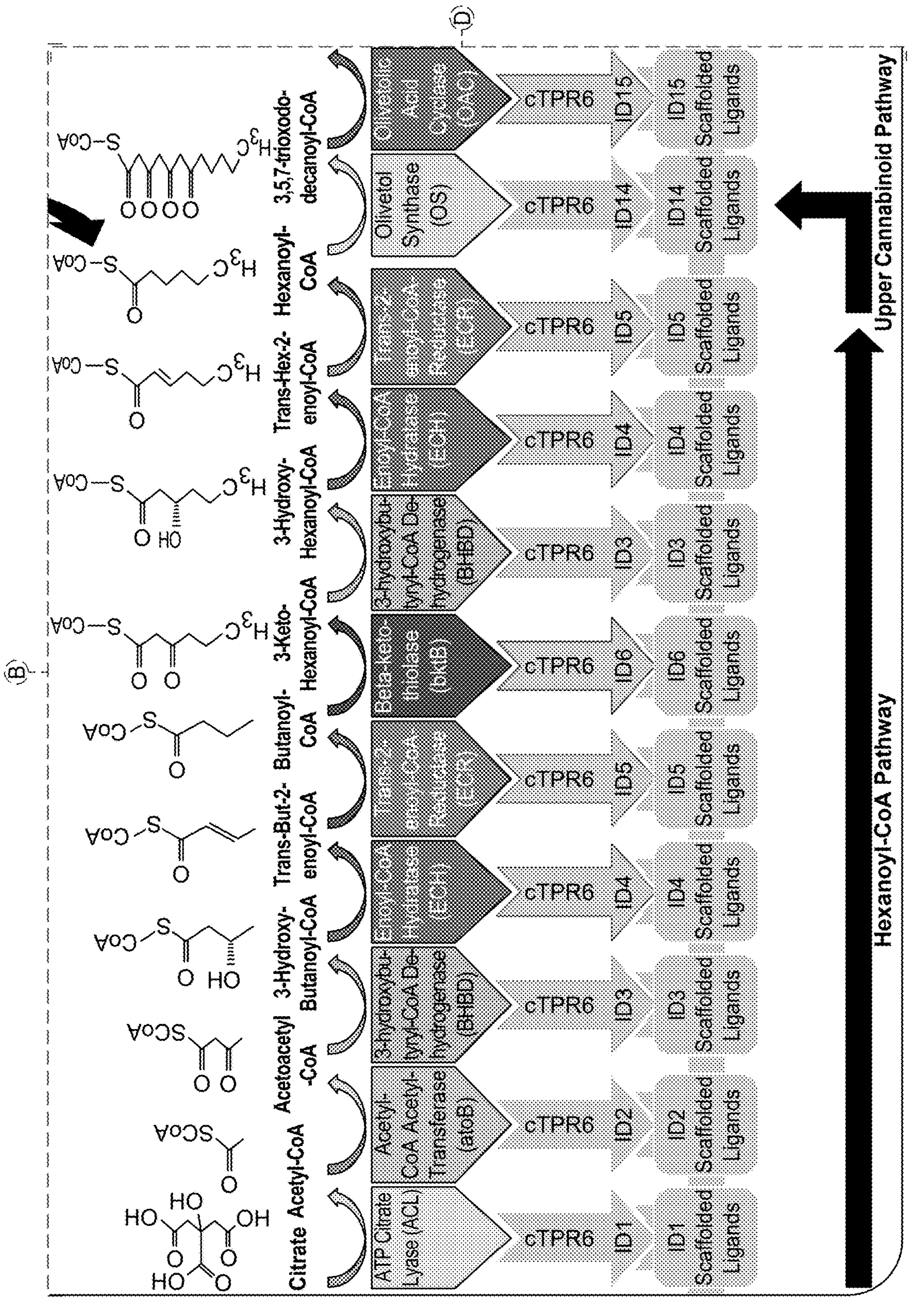
Figure 1A:
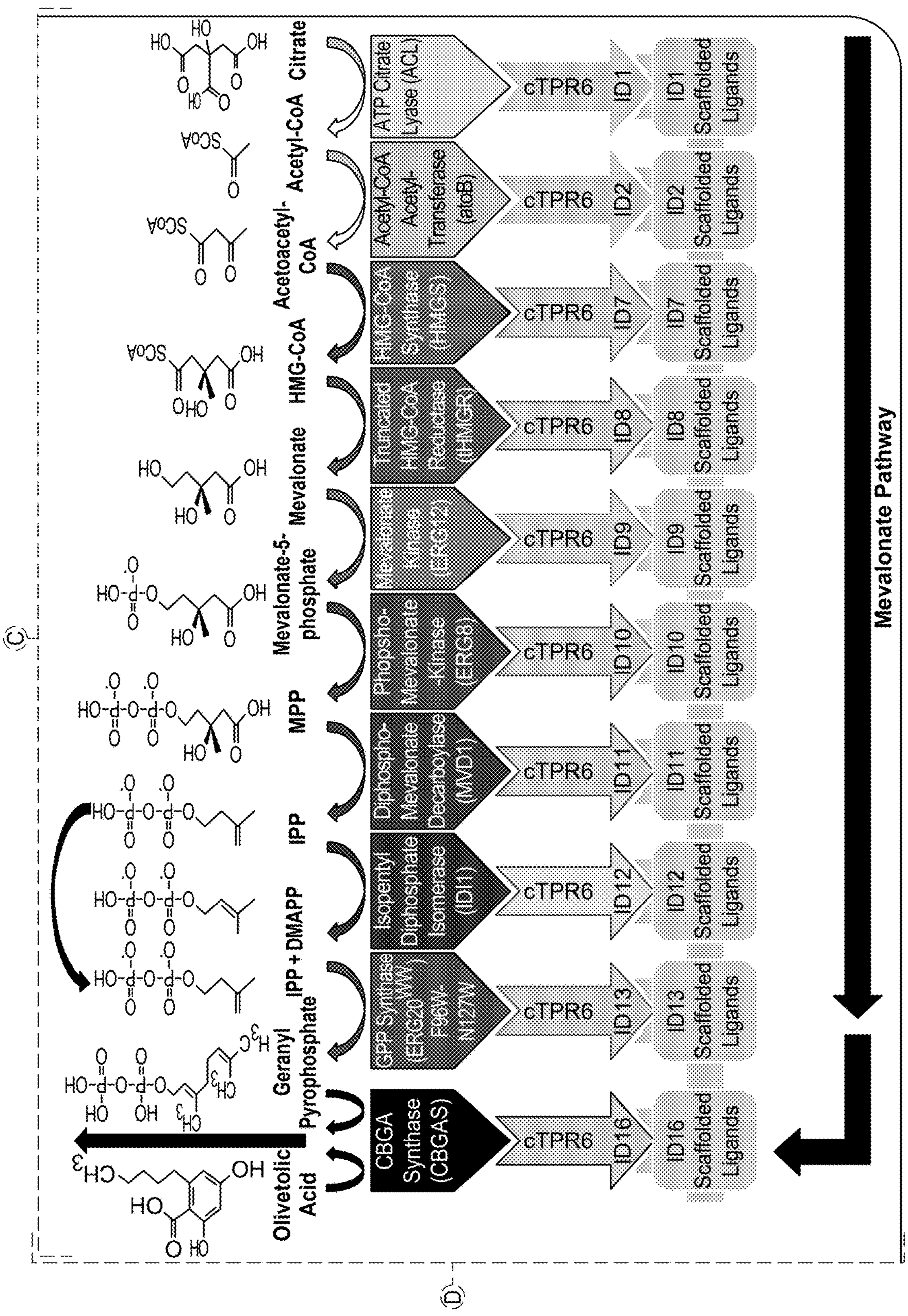
Figure 1B:
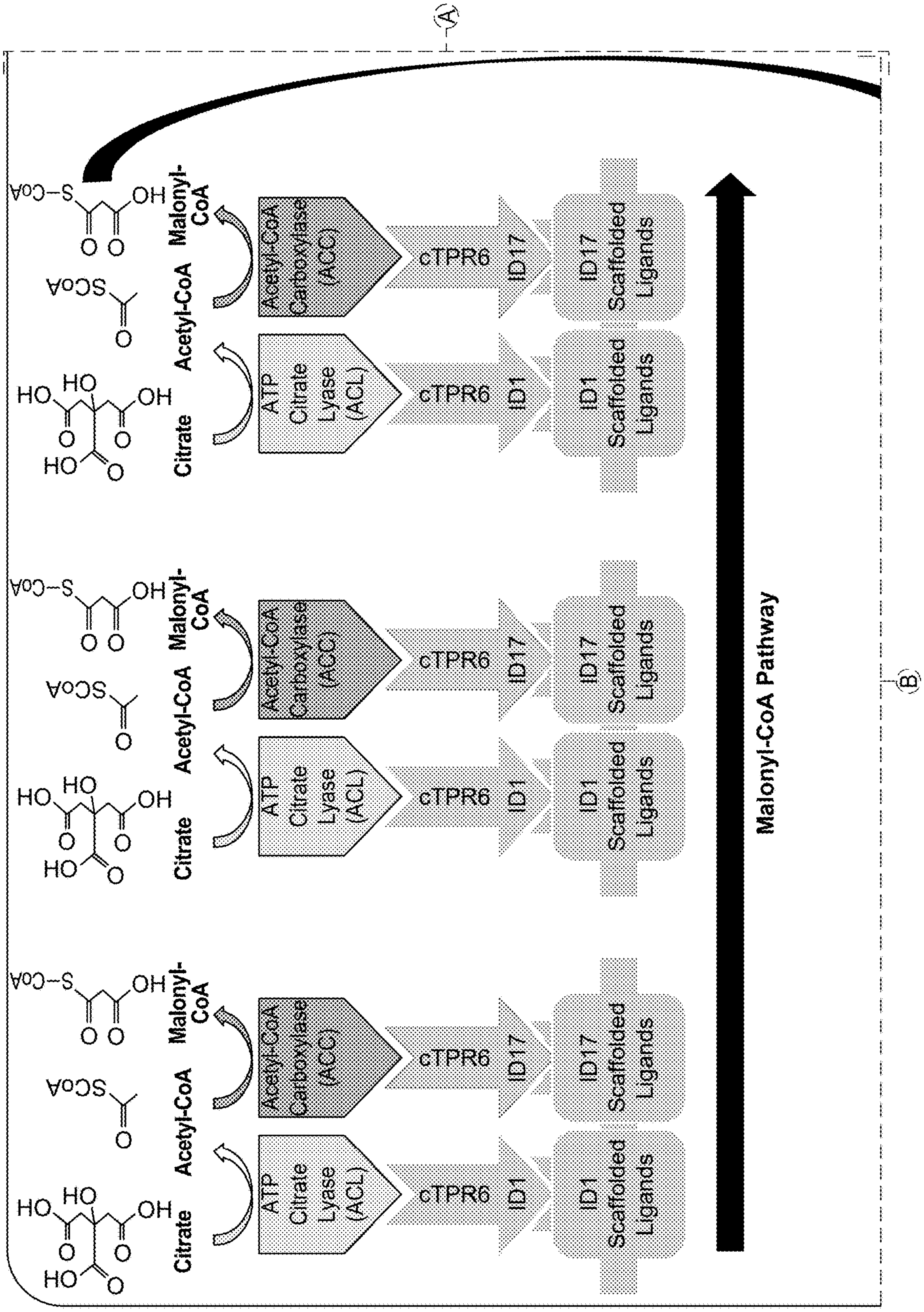
FIG. 1B is a schematic of one representative embodiment of a bidirectional, multi-enzymatic scaffold within a cell (e.g., a yeast cell). The multi-enzymatic scaffold (referred to as SCF gene cassette in the nucleus) includes enzymes of the hexanoyl-CoA pathway (referred to as HCA cassette in nucleus), enzymes of the upper cannabinoid pathway (referred to as CAN cassette in nucleus), and enzymes of the mevalonate pathway (referred to as GPP cassette in nucleus). The schematic also depicts a second scaffold according to one embodiment containing enzymes of the malonyl-CoA pathway and depicts a non-scaffolded CBDAS and a non-scaffolded CBCAS. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.
Figure 1B:
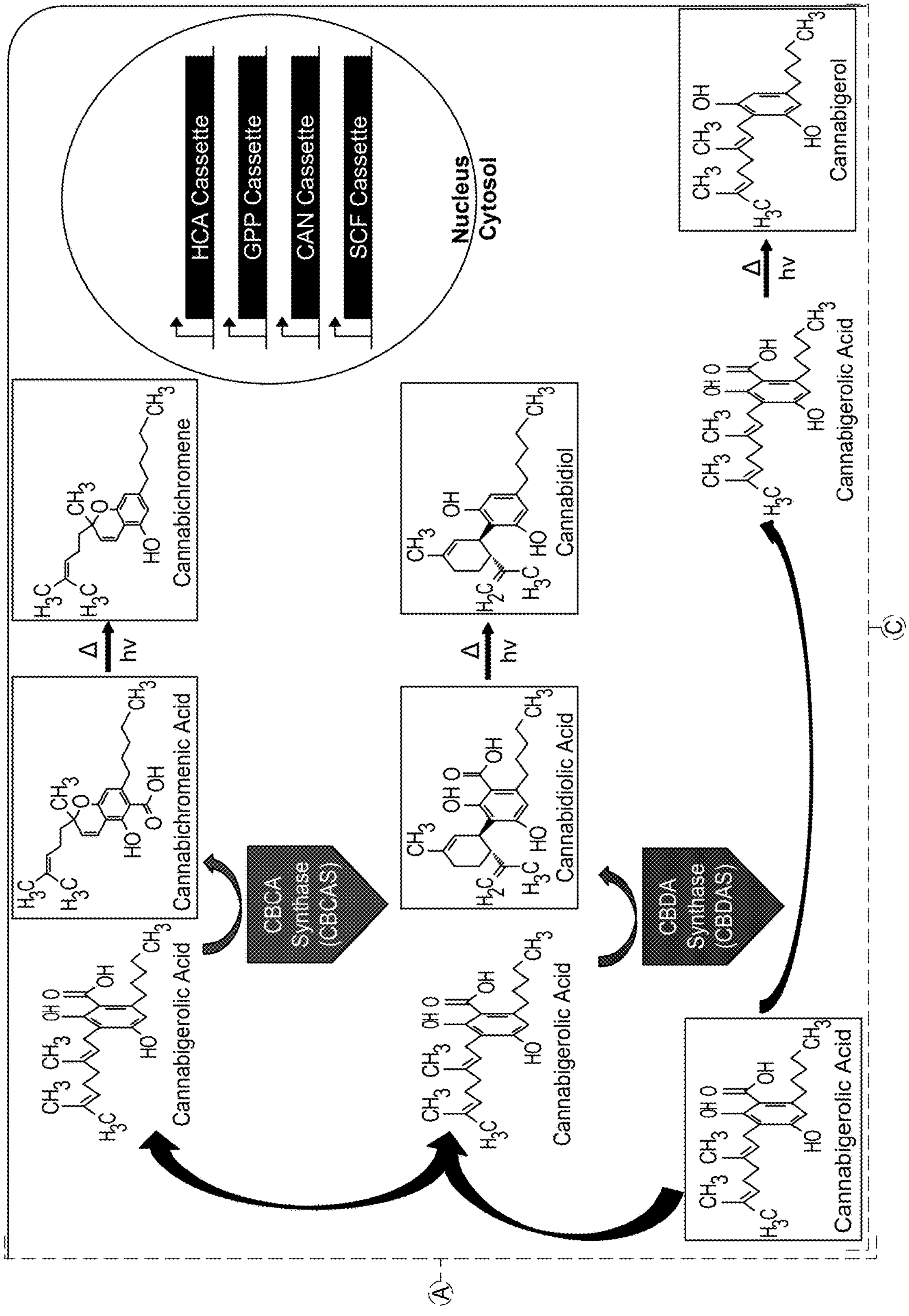
Figure 1B:
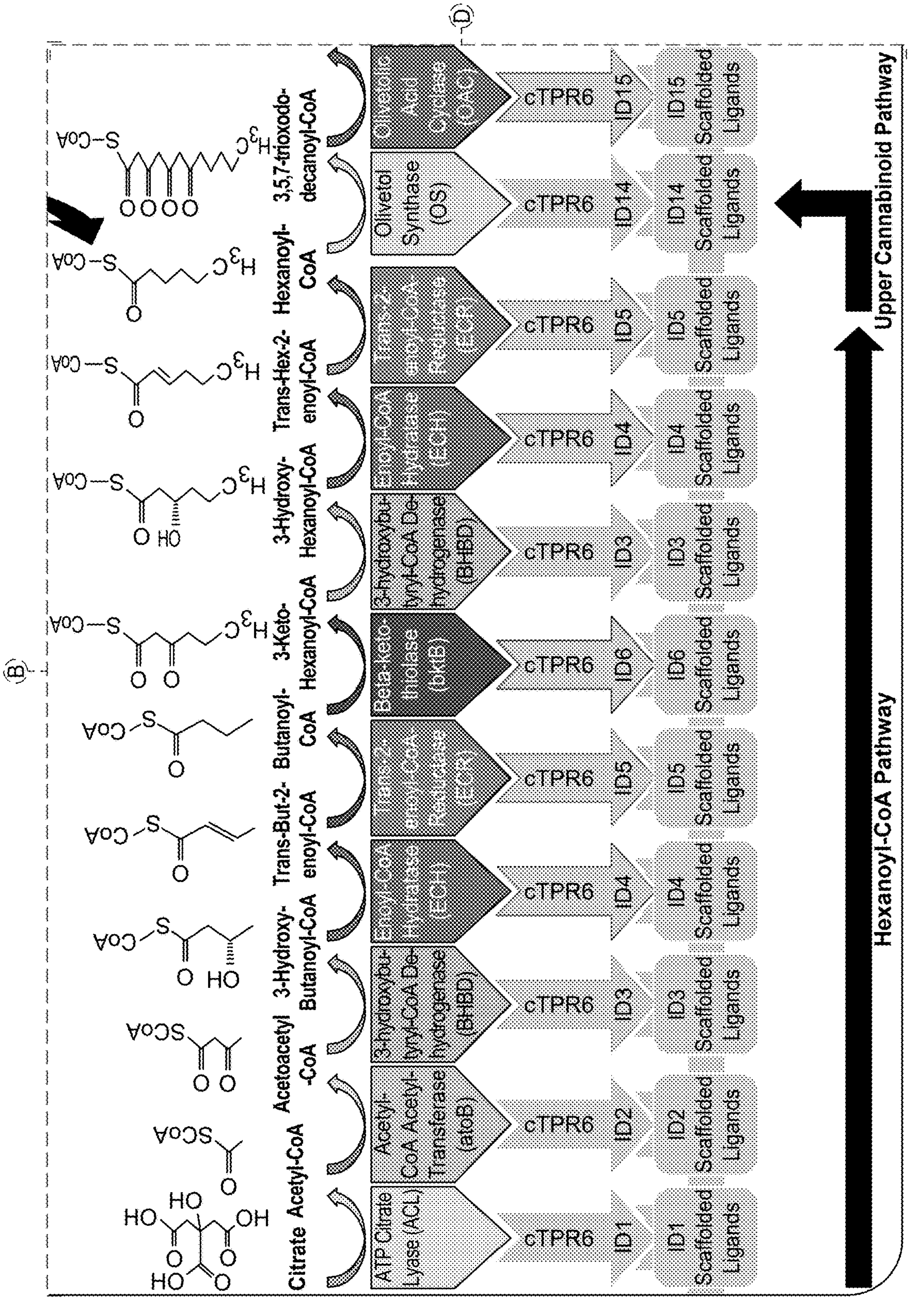
Figure 1B:
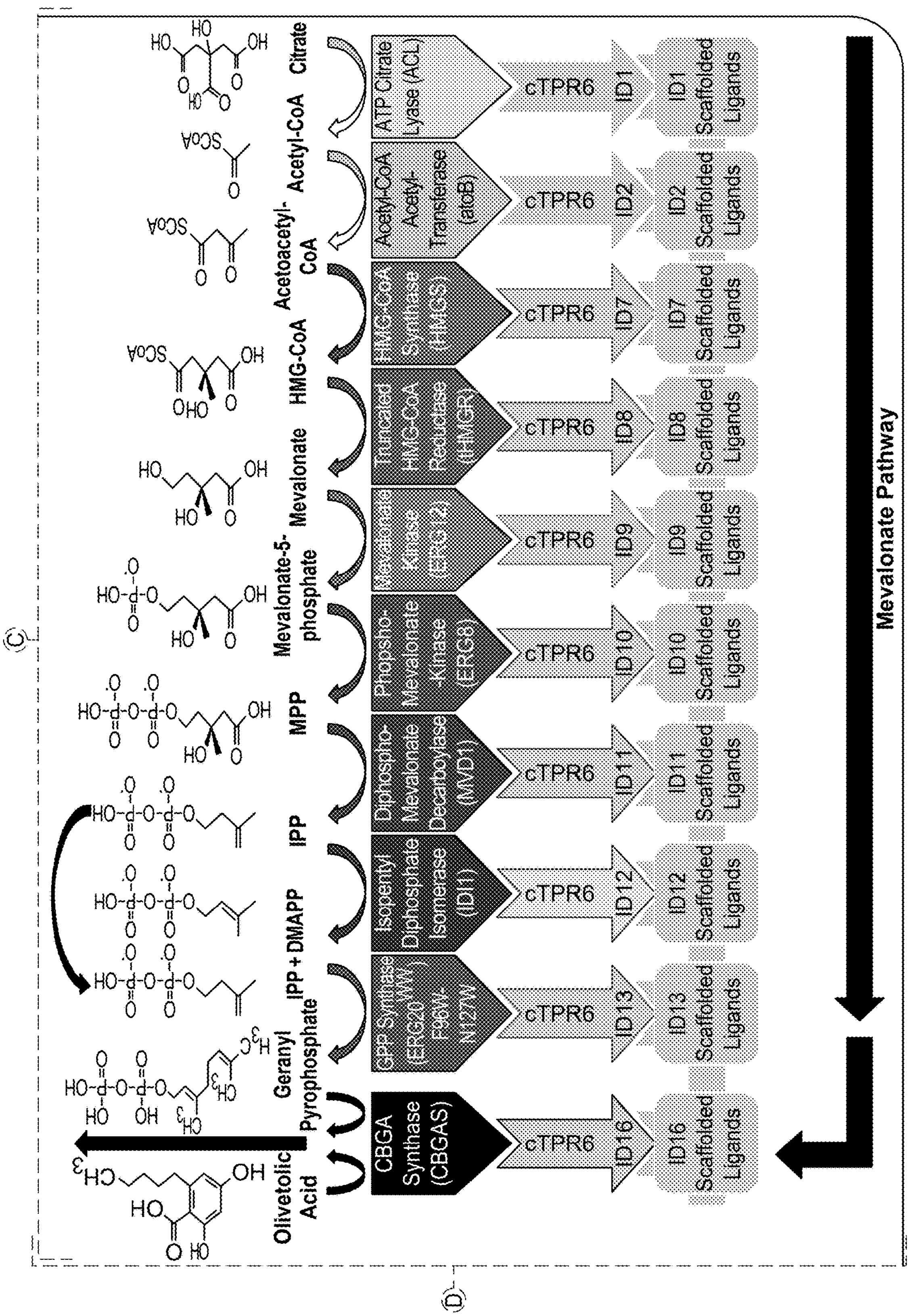

In general, enzymes described herein, which can be co-localized on one or more scaffolds and used for producing cannabinoids or cannabinoid precursors, are engineered to contain an interaction domain (ID), which can be separated from the enzyme by an amino acid spacer sequence at the N- or C-terminus of the enzyme. The ID can be composed of two or more scaffold-binding motifs. The engineered enzymes also can include one or more linkers between the enzyme, spacer, and/or ID. The engineered enzymes can bind to a scaffold, which is a polypeptide that contains unique ID-binding domains, i.e., tandem peptide ligands, as shown in FIG. 1A and FIG. 1B, such that the enzymes are co-localized to the scaffold. In other words, each enzyme can be engineered to contain a protein-protein interaction domain that is specific for ligand or ligands (binding site) on the scaffold such that the enzyme can be localized to a discrete location along the scaffold via non-covalent interactions. In some cases, the engineered enzymes can be chimeric enzymes. The scaffolded ligands can be separated using amino acid linkers or spacers. See, for example, Horn and Sticht, *Frontiers in Bioengineering and Biotechnology,* 2015, volume 3, article 191; Whitaker and Dueber, *Methods in Enzymology*, Chapter 19, "Metabolic Pathway Flux Enhancement by Synthetic Protein Scaffolding," Volume 497, 2011, for descriptions of IDs, binding domains, linkers and spacers. IDs also can be referred to as adaptor domains.

Typically, each interaction domain consists of two tandem scaffold-binding motifs that continue/extend from the C-terminus of the engineered enzyme and that can bind to their corresponding scaffolded peptide ligands, which are constructed in tandem along the scaffold. Dual-binding of enzymes to the scaffold ensures fixed spatial orientation, increases binding specificity for each ID-scaffold interaction, and better tethers each enzyme to the scaffold, all of which can improve pathway flux by enabling substrate channeling through each enzymatic step in the scaffolded biosynthetic pathways.

In some embodiments, there are more than two, e.g., three, four, five, six, seven, eight, nine, or ten, or more molecules of each enzyme localized to the scaffold. In addition, the ratio of any given enzyme in a biosynthetic pathway to any other enzyme in the biosynthetic pathway can be varied. For example, the ratio of one engineered enzyme in a pathway to a second engineered enzyme in the same pathway can be varied, e.g., from about 1:5 to about 5:1, e.g., from about 1:5 to about 2:5, from about 2:5 to about 3:5, from about 3:5 to about 5:5, from about 5:5 to about 5:3, from about 5:3 to about 5:2, or from about 5:2 to about 5:1.

The peptide ligands are typically short peptide sequences, ranging in length from 3 to 50 amino acid residues. For example, a peptide ligand can be 3-10, 7-15, 10-20, 15-25, 20-30, 25-35, 30-40, 35-45, or 40-50 amino acids in length. There is a database of over 200 different motifs available on the web at elm. eu.org that can be used as described herein. See, for example, Dinkel et al., *Nucleic Acids Res.* 2014; 42(Database issue): D259—D266.

An ID can be a peptide sequence ranging in length 3 to 200 amino acid residues. For example, the ID can be 3-10, 7-15, 10-20, 15-25, 20-30, 25-35, 30-40, 35-45, 40-50, 45-55, 50-60, 65-75, 70-80, 85-95, 90-100, 100-110, 105-115, 110-120, 115-125, 120-130, 125-135, 130-140, 135-145, 140-150, 135-145, 140-150, 145-155, 150-160, 165-175, 170-180, 175-185, 180-190, 185-195, or 190-200 amino acids in length. For example, an ID can be a SH2 domain, a SH3 domain, a PDZ domain, a GTPase binding domain (GBD), a leucine zipper domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, a bZIP domain, a fibronectin receptor domain, a FNDC domain, a SAMD domain, a WBP domain, and/or a SASH domain. See, e.g., U.S. Pat. No. 9,856,460 for a list of domains that can be uses as an ID as described herein.

For example, an ID can be a "Src homology2" (SH2) or a "Src homology3" (SH3) domain. SH2 domains are highly conserved structures of approximately 100 amino acid residues that comprise two α-helices and seven β-strands. The SH2 domain can have a promiscuous or strict specificity for a 3-5 amino acid motif flanking a phosphorylated tyrosine. See, Horn and Sticht, 2015, *supra*. For example, a SH2 domain that can be used as an ID as described herein can be residues 5-122 of a mouse Ct10 regulator of kinase adaptor (Crk) protein having GenBank Accession No. AAH31149.

SH3 domains are small modules of approximately 60 residues that bind proline-rich ligands, which bind to the domain surface at three shallow grooves formed by conserved aromatic residues and exhibit two different binding orientations. See, Horn and Sticht, 2015, *supra*. In some embodiments, the proline-rich ligand can have a core PXXP motif flanked by a positively charged residue. Class I PZP domains recognize ligands conforming to the consensus +XXPXXP (where + is either Arg or Lys), while Class II domains recognize PXXPX+ motifs and bind to ligands in the opposite orientation. See, Teyra, et al., *FEBS Lett.*, 2012 586(17):2631-7. Individual SH3 domains do not measurably interact with other SH3 domain family ligands within an organism, minimizing cross-talk and increasing the number of domain/ligand pairs available for simultaneous use. See, Whitaker and Dueber, 2011, *supra*. For example, a SH3 domain that can be used as an ID as described herein can be residues 134-190 of a mouse Crk protein having GenBank Accession No. AAH31149 and its peptide ligand can be (SEQ ID NO: 1)
PPPALPPKRRR.

For example, an ID can be a PDZ (PSD-95/Discs-large/ZO1) domain. PDZ domains are approximately 100 amino acid residues in length and target specific motifs at the C-terminus of the binding partner. The peptide ligand adopts a β-strand and extends an existing β-sheet within the PDZ domain upon binding. At least four different classes of ligands are known for PDZ domains exhibiting a distinct binding specificity. See, Horn and Sticht, 2015, *supra*. For example, grouped PDZ domains into two main specificity classes based on distinct ligand signatures: Class I PDZ domains recognize a (X[T/S]XϕCOOH) motif, Class II PDZ domains recognize a (XϕXϕINCOOH) motif, and Class III PDZ domains recognize a X[ED]XϕCOOH motif, where X is any residue and ϕ is a hydrophobic amino acid. See, Teyra, et al., 2012, *supra*. PDZ and SH3 domains are found throughout eukaryotic and eubacterial genomes. For example, a PDZ domain that can be used as an ID as described herein can be residues 77-171 of a mouse α-syntrophin protein having GenBank Accession No. EDL06069 and the peptide ligand can be (SEQ ID NO: 208)
GVKESLV.

For example, an ID can be a GBD domain from a protein such as the Wiskott-Aldrich syndrome-like protein (N-WASP). Isolated GBD domains do not adopt a single, discrete structure under physiological conditions but rather exhibit multiple, loosely packed conformations in solution. The corresponding peptide ligand has been deduced from the autoinhibited form of the GBD. See, Horn and Sticht, 2015, *supra*. For example, a GBD domain that can be used as an ID described herein can include residues 196 to 274 of a rat N-WASP protein having GenBank Accession No. BAA21534, and its peptide ligand, which can be LVGALMHVMQKRSRAIHSSDEGEDQAGDEDED (SEQ ID NO:2), can be used as a peptide ligand as described herein.

For example, an ID can have a leucine zipper or synthetic coiled-coil domain. A leucine zipper domain can include multiple interspersed leucine residues approximately seven amino acid residues apart. Havranek, and Harbury ((2003), *Nat. Struct. Biol.* 10, 45-52) identified new pairs of homodimers or heterodimers by altering residues between leucine zipper pairs based on computational prediction. Reinke, et al. ((2010). *J. Am. Chem. Soc.* 132, 6025-6031) identified three pairs of synthetic coiled coils that do not exhibit measurable self-association. See, Whitaker and Dueber, 2011, *supra*. One example of an ID that can be used as described herein can be ITIRAAFLEKENTALRTEIAELEKEVGRCENIVSKYETRYGPL (SEQ ID NO:3), and its peptide ligand for use as described herein can be (SEQ ID NO: 4)
LEIRAAFLEKENTALRTRAAELRKRVGRCRNIVSKYETRYGPL.

For example, an ID can be a dockerin polypeptide, which can localize to a specific cohesion polypeptide on a scaffold described herein. Cohesion-dockerin pairs are particularly useful for ex vivo applications as binding is calcium dependent. See, Whitaker and Dueber, 2011, *supra.*

Combinations of IDs that have high affinity for their peptide ligands and high specificity, i.e., minimal cross-reactivity, can be used as described herein to allow for binding of multiple, different enzymes to a scaffold provided herein. For example, at least three different enzymes can be localized on a scaffold. In some embodiments, at least four different enzymes can be localized on a scaffold. In some embodiments, at least five different enzymes can be localized on a scaffold. In some embodiments, at least six different enzymes can be localized on a scaffold. In some embodiments, at least seven different enzymes can be localized on a scaffold. In some embodiments, at least eight different enzymes can be localized on a scaffold. In some embodiments, at least nine different enzymes can be localized on a scaffold. In some embodiments, at least ten different enzymes can be localized on a scaffold. In some embodiments, at least eleven different enzymes can be localized on a scaffold. In some embodiments, at least twelve different enzymes can be localized on a scaffold. In some embodiments, at least fifteen different enzymes can be localized on a scaffold. In some embodiments, at least seventeen different enzymes can be localized on a scaffold. In some embodiments, at least eighteen different enzymes can be localized on a scaffold. In some embodiments, at least twenty different enzymes can be localized on a scaffold. In some embodiments, at least twenty-one different enzymes can be localized on a scaffold.

Table 1 provide exemplary combinations of heterologous IDs, i.e., IDs that are different from each other, that can be used in seventeen different engineered enzymes and Table 2 provides the corresponding exemplary combinations of peptide ligands that can be used to localize the seventeen different enzymes to one or more scaffolds. In the embodiments shown in Tables 1 and 2, each ID is composed of two tandem peptide motifs as are the corresponding peptide ligands, which interact with the tandem peptide motifs. It will be appreciated that any one of the enzymes listed in Tables 1 and 2 can be used in combination with any of the listed combinations of IDs and corresponding peptide ligands.

TABLE 1

Interaction Domain Motif Sequences in Engineered Enzymes

| Enzyme | ID # | ID Motif #1 | ID Motif #1 Amino Acid Sequence | ID Motif #2 | ID Motif #2 Amino Acid Sequence |
|---|---|---|---|---|---|
| ATP Citrate Lyase | 1 | SYNZIP1 | SYYHHHHHHLESTSLYKKAGSGSNLVAQLENEVASLENENETLKKKNLHKKDLIAYLEKEIANLRKKIEE ((SEQ ID NO: 5)) | SYNZIP2 | SYYHHHHHHLESTSLYKKAGSGSARNAYLRKKIARLKKDNLQLERDEQNLEKIIANLRDEIARLENEVASHEQ (SEQ ID NO: 6) |
| Acetyl-CoA Acetyltransferase (atoB) | 2 | SYNZIP3 | SYYHHHHHHLESTSLYKKAGSGSNEVTTLENDAAFIENENAYLEKEIARLRKEKAALRNRLAHKK (SEQ ID NO: 7) | SYNZIP4 | SYYHHHHHHLESTSLYKKAGSGSQKVAELKNRVAVKLNRNEQLKNKVEELKNRNAYLKNELATLENEVARLENDVAE (SEQ ID NO: 8) |
| 3-hydroxybutyryl-CoA Dehydrogenase | 3 | MYND | ENLYFQGENLYFQGDSSESCWNCGRKASETCSGCNTARYCGSFCQHKDWEKHHHICGQTLQAQQ (SEQ ID NO: 9) | UEV | MAVSESQLKKMVSKYKYRDLTVRETVNVITLYKDLKPVLDSYVFNDGSSRELMNLTGTIPVPYRGNTYNIPICLWLLDTYPYNPPICFVKPTSSMTIKTGKHVDANGKIYLPYLHEWKHPQSDLLGLIQVMIVVFGDEPPVFSRP (SEQ ID NO: 10) |
| Enoyl-CoA Hydratase | 4 | PABP | GPLGSPLTASMLASAPPQEQKQMLGERLFPLIQAMHPTLAGKITGMLLEIDNSELLHMLESPESLRSKVDEAVAVLQAHQAKEAAQKA (SEQ ID NO: 11) | MDM2 | NTNMSVPTDGAVTTSQIPASEQETLVRPKPLLLKLLKSVGAQKDTYTMKEVLFYLGQYIMTKRLYDEKQQHIVYCSNDLLGDLFGVPSFSVKEHRKIYTMIYRNLVV (SEQ ID NO: 12) |
| Trans-Enoyl-CoA Reductase | 5 | SYNZIP10 | SYYHHHHHHLESTSLYKKAGSGSNLLATLRSTAAVLENENHVLEKEKEKLRKEKEQLLNKLEAYK (SEQ ID NO: 13) | SYNZIP22 | SYYHHHHHHLESTSLYKKAGSGSKRIAYLRKKIAALKKDNANLEKDIANLENEIERLIKEIKTLENEVASHEQ (SEQ ID NO: 14) |
| Beta-ketothiolase (bktB) | 6 | GYF | DVMWEYKWENTGDAELYGPFTSAQMQTWVSEGYFPDGVYCRKLDPPGGQFYNSKRIDFDLYT (SEQ ID NO: 15) | PAH | ESDSVEFNNAISYVNKIKTRFLDHPEIYRSFLEILHTYQKEQLHTKGRPFRGMSEEEVFTEVANLFRGQEDLLSEFGQFLPEAKR (SEQ ID NO: 16) |
| HMG-COA Synthase | 7 | WW1A | LGPLPPGWEVRSTVSGRIYFVDHNNRTTQFTDPRLH (SEQ ID NO: 17) | WW1B | GAMGPLPPGWEKRTDSNGRVYFVNHNTRITQWEDPRS (SEQ ID NO: 18) |
| HMG-COA Reductase | 8 | FOS | SYYHHHHHHLESTSLYKKAGSEFFRRERNKMAAAKCRNRRRELTDTLQAETDQLEDEKSALQTEIANLLKEKEKLEFILAAHRPACKIPDDLGFPEEMSLE (SEQ ID NO: 19) | SYNZIP9 | SYYHHHHHHLESTSLYKKAGSGSQKVESLKQKIEELKQRKAQLKNDIANLEKEIAYAET (SEQ ID NO: 20) |

TABLE 1-continued

Interaction Domain Motif Sequences in Engineered Enzymes

| Enzyme | ID # | ID Motif #1 | ID Motif #1 Amino Acid Sequence | ID Motif #2 | ID Motif #2 Amino Acid Sequence |
|---|---|---|---|---|---|
| Mevalonate Kinase | 9 | VHS1 | MEPAMEPETLEARINRATNPLN KELDWASINGFCEQLNEDFEGP PLATRLLAHKIQSPQEWEAIQAL TVLETCMKSCGKRFHDEVGKFR FLNELIKVVSPKYLGSRTSEKVK NKILELLYSWTVGLPEEVKIAEA YQMLKKQGIVKS (SEQ ID NO: 21) | VHS2 | GAMGSMAEAEGESLESWLNKATN PSNRQEDWEYIIGFCDQINKELEGP QIAVRLLAHKIQSPQEWEALQALT VLEACMKNCGRRFHNEVGKFRFL NELIKVVSPKYLGDRVSEKVKTKV IELLYSWTMALPEEAKIKDAYHML KRQGIVQSDPPIPVDRTLIPSPPPRP KN (SEQ ID NO: 22) |
| Phosphomevalonate Kinase | 10 | SYNZIP13 | SYYHHHHHHLESTSLYKKAGSG SQKVEELKNKIAELENRNAVKK NRVAHLKQEIAYLKDELAAHEF E (SEQ ID NO: 23) | SYNZIP15 | SYYHHHHHHLESTSLYKKAGSGSF ENVTHEFILATLENENAKLRRLEA KLERELARLRNEVAWL (SEQ ID NO: 24) |
| Diphospho-mevalonate Decarboxylase | 11 | MATH | AMADLEQKVLEMEASTYDGVFI WKISDFPRKRQEAVAGRIPAIFS PAFYTSRYGYKMCLRIYLNGDG TGRGTHLSLFFVVMKGPNDALL RWPFNQKVTLMLLDQNNREHV IDAFRPDVTSSSFQRPVNDMNIA SGCPLFCPVSKMEAKNSYVRDD AIFIKAIVDLTGL (SEQ ID NO: 25) | SKP1 | ASIKLQSSDGEIFEVDVEIAKQSVTI KTMLEDLGMDDEGDDDPVPLPNV NAAILKKVIQWCTHHKDDPPPPED DENKEKRTDDIPVWDQEFLKVDQ GTLFELILAANYLDIKGLLDVTCKT VANMIKGKTPEEIRKTFNIKNDFTE EEEAQVRKENQWC (SEQ ID NO: 26) |
| Isopentenyl-Diphosphate Delta-Isomerase | 12 | SYNZIP5 | SYYHHHHHHLESTSLYKKAGSG SNTVKELKNYIQELEERNAELK NLKEHLKFAKAELEFELAAHKF E (SEQ ID NO: 27) | SYNZIP6 | SYYHHHHHHLESTSLYKKAGSGS QKVAQLKNRVAYKLKENAKLENI VARLENDNANLEKDIANLEKDIAN LERDVAR (SEQ ID NO: 28) |
| Geranyl-Diphosphate Synthase | 13 | PDZ1 | LCTMKKGPSGYGFNLHSDKSKP GQFIRSVDPDSPAEASGLRAQDR IVEVNGVCMEGKQHGDVVSAIR AGGDETKLLVVDRE (SEQ ID NO: 29) | PDZ2 | SSGALIYTVELKRYGGPLGITISGTE EPFDPIIISSLTKGGLAERTGAIHIG DRILAINSSSLKGKPLSEAIHLLQM AGETVTLKIKKQTDAQPASS (SEQ ID NO: 30) |
| Olivetol Synthase | 14 | SH2A | GNNLETYEWYNKSISRDKAEKL LLDTGKEGAFMVRDSRTPGTYT VSVFTKAIISENPCIKHYHIKET NDSPKRYYVAEKYVFDSIPLLIQ YHQYNGGGLVTRLRYPVCG (SEQ ID NO: 31) | SH2B | GSHPWFFGKIPRAKAEEMLSKQRH DGAFLIRESESAPGDFSLSVKFGND VQHFKVLRDGAGKYFLWVVKFNS LNELVDYHRSTSVSRNQQIFLRDIE QVPQQPT (SEQ ID NO: 32) |
| Olivetolic Acid Cyclase | 15 | PTB1 | GQDRSEATLIKRFKGEGVRYKA KLIGIDEVSAARGDKLCQDSMM KLKGVVAGARSKGEHKQKIFLT ISFGGIKIFDEKTGALQHHHAVH EISYIAKDITDHRAFGYVCGKEG NHRFVAIKTAQAAEPVILDLRDL FQLIYELKQREELEKKA (SEQ ID NO: 33) | PTB2 | GSHMGSQFWVTSQKTEASERCGL QGSYILRVEAEKLTLLTLGAQSQIL EPLLFWPYTLLRRYGRDKVMFSFE AGRRCPSGPGTFTFQTSQGNDIFQ AVEAAIQQQKAQGKVGQAQDILR LEHHHHHH (SEQ ID NO: 210) |
| CBGA Synthase | 16 | SH3A | AEYVRALFDFNGNDEEDLPFKK GDILRIRDKPEEQWWNAEDSEG KRGMIPVPYVEKY (SEQ ID NO: 34) | SH3B | LIKHMRAEALFDFTGNSKLELNFK AGDVIFLLSRINKDWLEGTVRGAT GIFPLSFVKILK (SEQ ID NO: 35) |
| Acetyl-CoA Carboxylase | 17 | FAT | GSHMRLGAQSIQPTANLDRTDD LVYLNVMELVRAVLELKNELA QLPPEGYVVVVKNVGLTLRKLI GSVDDLLPSLPSSSRTEIEGTQK LLNKDLAELINKMRLAQQNAVTS LSEECKRQMLTASHTLAVDAKN LLDAVDQAKVLANLAHPPAE (SEQ ID NO: 36) | PEX | GAMATPGSENVLPREPLIATAVKF LQNSRVRQSPLATRRAFLKKKGLT DEEIDMAFQQSGTAADEPSSLW (SEQ ID NO: 37) |

TABLE 2

Tandem Peptide Ligand Sequences in Scaffold

| Enzyme | ID # | ID Motif #1 | ID Motif #1 Scaffolded Ligand Amino Acid Sequence | ID Motif #2 | ID Motif #2 Scaffolded Ligand Amino Acid Sequence |
|---|---|---|---|---|---|
| ATP Citrate Lyase | 1 | SYNZIP1 | SYYHHHHHHLESTSLYKKAGS GSARNAYLRKKIARLKKDNLQ LERDEQNLEKIIANLRDEIARLE NEVASHEQ (SEQ ID NO: 6) | SYNZIP2 | SYYHHHHHHLESTSLYKKAGSGS NLVAQLENEVASLENENETLKKK NLHKKDLIAYLEKEIANLRKKIEE (SEQ ID NO: 5) |
| Acetyl-CoA Acetyltransferase (atoB) | 2 | SYNZIP3 | SYYHHHHHHLESTSLYKKAGS GSQKVAELKNRVAVKLNRNEQ LKNKVEELKNRNAYLKNELAT LENEVARLENDVAE (SEQ ID NO: 8) | SYNZIP4 | SYYHHHHHHLESTSLYKKAGSGS NEVTTLENDAAFIENENAYLEKEI ARLRKEKAALRNRLAHKK (SEQ ID NO: 7) |
| 3-hydroxybutyryl-CoA Dehydrogenase | 3 | MYND | RPPTISNPPPLISSAKHPSV (SEQ ID NO: 38) | UEV | NFLQSRPEPTAPPEESFRSG (SEQ ID NO: 39) |
| Enoyl-CoA Hydratase | 4 | PABP | SKGTGLNPNAKVWQEIAPGN (SEQ ID NO: 40) | MDM2 | PDGGTTFEHLWSSLEPDSTY (SEQ ID NO: 41) |
| Trans-Enoyl-CoA Reductase | 5 | SYNZIP10 | SYYHHHHHHLESTSLYKKAGS GSKRIAYLRKKIAALKKDNAN LEKDIANLENEIERLIKEIKTLE NEVASHEQ (SEQ ID NO: 14) | SYNZIP22 | SYYHHHHHHLESTSLYKKAGSGS NLLATLRSTAAVLENENHVLEKEK EKLRKEKEQLLNKLEAYK (SEQ ID NO: 13) |
| Beta-Ketothiolase (bktB) | 6 | GYF | PATSQHPPPPPGHRSQAPSH (SEQ ID NO: 42) | PAH | ELNSLLILLEAAEYLERRDR (SEQ ID NO: 43) |
| HMG-COA Synthase | 7 | WW1A | FQMPADTPPPAYLPPEDPMT (SEQ ID NO: 44) | WW1B | ERESNEEPPPPYEDPYWGNG (SEQ ID NO: 45) |
| HMG-COA Reductase | 8 | FOS | SYYHHHHHHLESTSLYKKAGS GSQKVESLKQKIEELKQRKAQL KNDIANLEKEIAYAET (SEQ ID NO: 20) | SYNZIP9 | SYYHHHHHHLESTSLYKKAGSEFF RRERNKMAAAKCRNRRRELTDTL QAETDQLEDEKSALQTEIANLLKE KEKLEFILAAHRPACKIPDDLGFPE EMSLE (SEQ ID NO: 19) |
| Mevalonate Kinase | 9 | VHS1 | VSSTKLVSFHDDSDEDLLHI (SEQ ID NO: 46) | VHS2 | AAATPISTFHDDSDEDLLHV (SEQ ID NO: 47) |
| Phosphomevalonate Kinase | 10 | SYNZIP13 | SYYHHHHHHLESTSLYKKAGS GSFENVTHEFILATLENENAKL RRLEAKLERELARLRNEVAWL (SEQ ID NO: 24) | SYNZIP15 | SYYHHHHHHLESTSLYKKAGSGS QKVEELKNKIAELENRNAVKKNR VAHLKQEIAYLKDELAAHEFE (SEQ ID NO: 23) |
| Diphosphomevalonate Decarboxylase | 11 | MATH | HDDSLPHPQQATDDSGHESD (SEQ ID NO: 48) | SKP1 | GSPNAGSVEQTPKKPGLRRR (SEQ ID NO: 49) |
| Isopentenyl-Diphosphate Delta-Isomerase | 12 | SYNZIP5 | SYYHHHHHHLESTSLYKKAGS GSQKVAQLKNRVAYKLKENA KLENIVARLENDNANLEKDIAN LEKDIANLERDVAR (SEQ ID NO: 28) | SYNZIP6 | SYYHHHHHHLESTSLYKKAGSGS NTVKELKNYIQELEERNAELKNLK EHLKFAKAELEFELAAHKFE (SEQ ID NO: 27) |
| Geranyl-Diphosphate Synthase | 13 | PDZ1 | TDEEREETEEEVYLLNSTTL (SEQ ID NO: 50) | PDZ2 | DGNVSGTQRLDSATVRTYSC (SEQ ID NO: 51) |
| Olivetol Synthase | 14 | SH2A | ALVDDAADYEPPPSNNEEAL (SEQ ID NO: 52) | SH2B | RELFDDPSYVNVQNLDKARQ (SEQ ID NO: 53) |
| Olivetolic Acid Cyclase | 15 | PTB1 | KNTKSMNFDNPVYRKTTEEE (SEQ ID NO: 54) | PTB2 | RSLPSTWIENKLYGMSDPNW (SEQ ID NO: 55) |
| CBGA Synthase | 16 | SH3A | VVDNSPPPALPPKKRQSAPS (SEQ ID NO: 56) | SH3B | TORSKPQPAVPPRPSADLIL (SEQ ID NO: 57) |
| Acetyl-CoA Carboxylase | 17 | FAT | SATRELDELMASLSDFKIQG (SEQ ID NO: 58) | PEX | DLALSENWAQEFLAAGDAVD (SEQ ID NO: 59) |

The spacers or linkers connecting an enzyme and ID, as well as a binding domain on a scaffold, can be peptide sequences ranging in length from 6 to 250 amino acid residues. The term “spacer” typically refers to a longer and more structurally-rigid peptide sequence and the term “linker” typically refers to a shorter and more structurally-flexible peptide sequence. In embodiments in which both terms are used, linker typically refers to a sequence that is about 3 to about 50 amino acids in length and spacer typically refers to a sequence that is longer (e.g., about 36 to about 250 amino acids in length). For example, a linker can be 6-15, 10-20, 15-25, 20-30, 25-35, 30-40, 35-45, or 40-50 amino acids in length. A spacer can be, for example, 36-40, 40-50, 45-55, 50-60, 55-65, 60-70, 65-75, 70-80, 75-85, 90-100, 95-105, 100-110, 105-115, 110-120, 115-125, 120-130, 125-135, 130-140, 135-145, 140-150, 145-155, 150-160, 165-175, 170-180, 175-185, 180-190, 185-195, 190-200, 195-205, 200-210, 205-215, 210-220, 215-225, 220-230, 225-235, 230-240, 235-245, or 240-250 amino acids in length. See, for example, Chen, et al., *Adv Drug Deliv Rev.* 2013 65(10): 1357-1369. In either case, the linker/spacer can be a series of small and/or hydrophilic and/or other amino acid residues that can adapt flexible and/or rigid structures. For example, the linker can be a series of glycine residues, a series of alanine residues, a series of serine residues, or a series of alternating glycine and serine (or threonine) residues such as $(G\text{-}S)_8$ (SEQ ID NO:60), $(G\text{-}S)_{10}$ (SEQ ID NO:61), or $(G\text{-}S)_{15}$ (SEQ ID NO:62), or contain mainly glycine residues such as $(GGGGS)_3$ (SEQ ID NO:63) or $(GGGGS)_4$ (SEQ ID NO:64), or contain any other series of canonical or non-canonical amino acid residues or combinations thereof. In some embodiments, a linker can include glutamic acid, alanine, and lysine residues such as $(EAAAK)_2$ (SEQ ID NO:65), $(EAAAK)_3$ (SEQ ID NO:66), or $(EAAAK)_4$ (SEQ ID NO:67). See, Horn and Sticht, 2015, *supra*. In some embodiments, a linker can be a combination of glycine, alanine, proline and methionine residues, such as AAAGGM (SEQ ID NO:68), AAAGGMPPAAAGGM (SEQ ID NO:69), AAAGGM (SEQ ID NO:70), or PPAAAGGMM (SEQ ID NO:71). See, e.g., U.S. Pat. No. 9,856,460.

Based on amino acid composition, linkers or spacers can be either structured or intrinsically unstructured. For example, in some embodiments, a spacer can have a sequence that adopts a more structurally-rigid α-helical conformation and a linker can have a GS-rich peptide sequence that is more structurally-flexible. For example, in some embodiments, a linker can include flexible GS-rich sequences flanking one or more rigid α-helical moieties, e.g., GS-rich sequences flanking duplicate, triplicate, or quadruplicate α-helical moieties. For example, in some embodiments, a linker or spacer can have the sequence GSAGSAAGSGEF (SEQ ID NO:72), KLSGGGGSGGGGSGGGGS (SEQ ID NO:73), GSAGSAAGSGEFGSAEAAAKEAAAK-AGSAGSAAGSGEFGS (SEQ ID NO:74), GSAGSAAGSGEFAEAAAKEAAAK-AGSAGSAAGSGEF (SEQ ID NO:75), or GSAGSAAGSGEFG-SAEAAAKEAAAKEAAAKEAAAK-AGSAGSAAGSGEFGS (SEQ ID NO:76).

In some embodiments, the ligands on the scaffold can be separated by linkers that are 20-50 amino acid residues in length (e.g., 20, 21, 22, 23, 24, 25, 26, 27, 28, 29, 30, 31, 32, 33. 34, 35, 36, 37, 38, 39, 40, 41, 42, 43, 44, 45, 46, 47, 48, 49, or 50 amino acid residues in length). In some embodiments, the IDs engineered at the C-terminus or N-terminus of each scaffolded enzyme can contain a linker (e.g., a flexible linker) of 15 to (e.g., 20) amino acid residues in length flanking a spacer of 15 to 50 (e.g. 36) amino acid residues. In some embodiments, the ID can be separated from the enzyme by a spacer sequence such as the cTPR6 spacer, which includes sextuplicate rigid α-helical moieties and can have the sequence:

(SEQ ID NO: 77)
AEAWYNLGNAYYKQGDYQKAIEYYQKALELDPNNAEAWYNLGNAYYKQ
GDYQKAIEYYQKALELDPNNAEAWYNLGNAYYKQGDYQKAIEDYQKAL
ELDPNNLQAEAWKNLGNAYYKQGDYQKAIEYYQKALELDPNNASAWYN
LGNAYYKQGDYQKAIEYYQKALELDPNNAKAWYRRGNAYYKQGDYQKA
IEDYQKALELDPNNRSRSA.

In some embodiments, the engineered enzyme can be of a formula: enzyme $-linker_1-spacer-linker_2-motif_1-linker_3-motif_2$, where linkers 1, 2, and 3 can be the same or different, and motif 1 and motif 2 can be the same or different. In some embodiments, linker 1 can be referred to as the enzyme linker, i.e., it connects the enzyme to the spacer such as cTPR6 spacer, and can include flexible GS-rich moieties flanking a rigid α-helical moiety such as KLSGGGGSGGGGSGGGGS (SEQ ID NO:73). In some embodiments, linker 2 can be referred to as the ID linker and can include, for example, flexible GS-rich moieties flanking a rigid α-helical moiety such as GGGGSGGGGSGGGGAS (SEQ ID NO:78). In some embodiments, linker 3 can be referred to as the motif linker and can include flexible GS-rich moieties flanking a rigid α-helical moiety such as (SEQ ID NO: 74)
GSAGSAAGSGEFGSAEAAAKEAAAKAGSAGSAAGSGEFGS.

Figure 3:
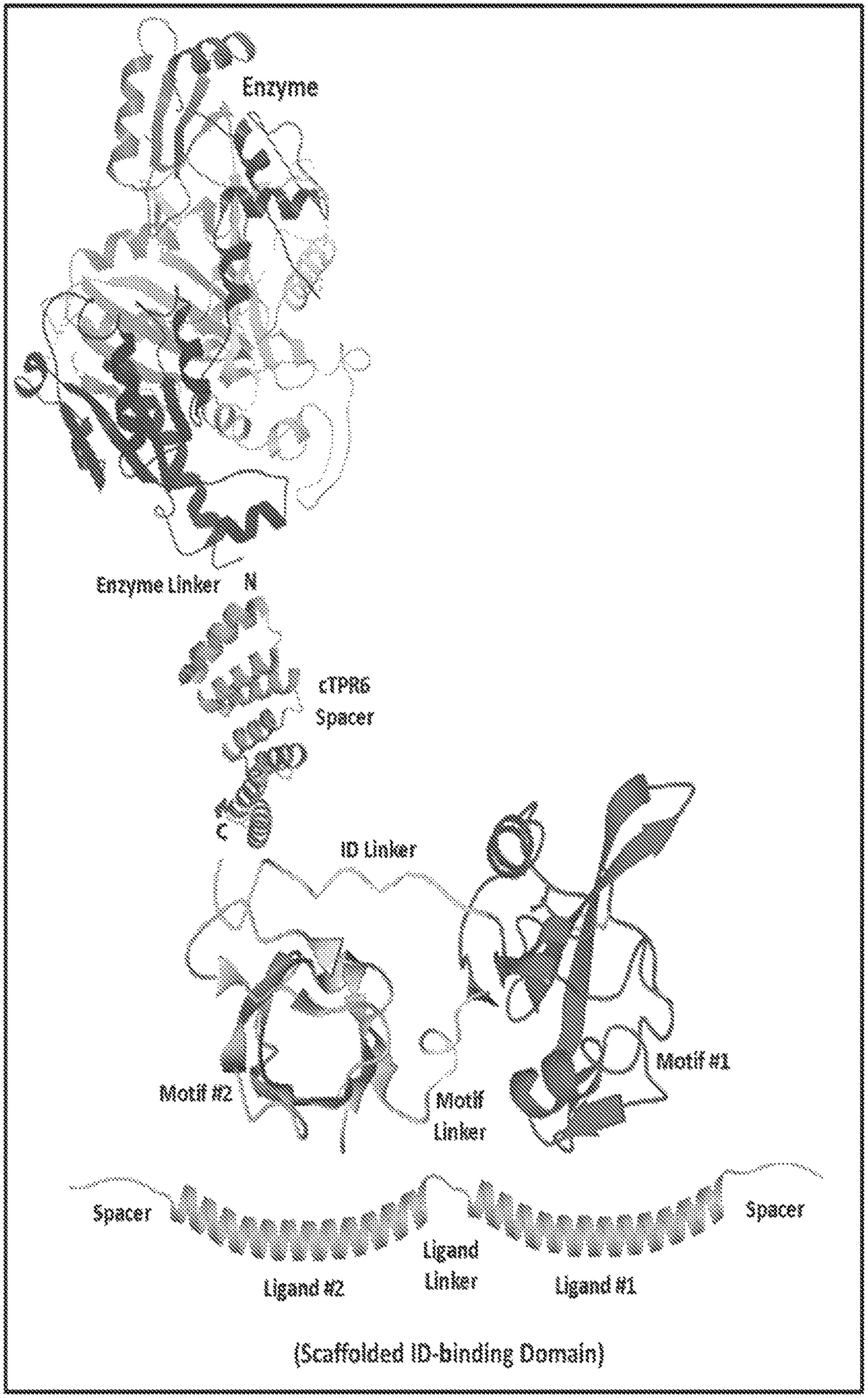
FIG. 3 is an example of an enzyme-scaffold complex.

Table 1 provides non-limiting examples of motifs 1 and motifs 2, which are used together to form heterologous IDs. FIG. 3 contains a schematic of an exemplary engineered enzyme of this formula complexed with a scaffold. FIG. 6B and FIGS. 13A-C contain the amino acid sequence of an ATP citrate lyase, atoB, a 3-hydroxybutyryl-CoA dehydrogenase, an enoyl-CoA hydratase, a trans-enoyl-CoA reductase, a beto-ketothiolase (bktB), an HMG-CoA synthase, a truncated HMG-CoA reductase, a mevalonate kinase, a phosphomevalonate kinase, a diphosphomevalonate decarboxylase, an isopentenyl-diphosphate delta isomerase, a geranyl-diphosphate synthase ($ERG20^{WW}$), an olivetol synthase, an olivetolic acid cyclase, a CBGA synthase, and an acetyl-CoA carboxylase according to this formula. In some embodiments, linkers 1 and 2 can be $(G_4S)_3$, the spacer can be the cTPR6 sequence, and linker 3 can be $(GS)_8$.

In some embodiments, a scaffold can be of a formula: N-terminus–[Ligand #1– linker–Ligand #2–Spacer]n–(optionally-tagged)C-terminus, where n is the number of interaction domains. The linker can be referred to as a scaffolded ligand linker and can be used to connect and separate paired motif-binding ligands that recruit/localize each enzyme to its scaffold-binding site. Such a linker can include flexible GS-rich moieties flanking a rigid α-helical moiety and have a sequence such as GSAGSAAGSGEFAEAAAKEAAAK-AGSAGSAAGSGEF (SEQ ID NO:75). The spacer can be referred to as a scaffolded ID-binding site spacer and can be used to connect and separate the scaffold-binding sites (composed of the paired motif binding ligands) for each enzyme. Such a spacer can include flexible GS-rich moieties flanking a rigid α-helical moiety and have a sequence such as GSAGSAAGSGEFG-SAEAAAKEAAAKEAAAKEAAAK-AGSAGSAAGSGEFGS (SEQ ID NO:76). The N-terminus can include a flexible GS-rich sequence to help stabilize and solubilize the scaffold. For example, the N-terminus can have the sequence GSAGSAAGSGEFGSAGSAAGSGEFGSAGSAAGSGEF (SEQ ID NO:79). The C-terminus can include a flexible GS rich sequence flanking a rigid α-helical moiety to stabilize and solubilize the scaffold and can be optionally tagged (e.g., with a MYC tag, a FLAG tag, or other tag described below) to ease purification or detection of the scaffold. For example, a C-terminal sequence with a triplicate MYC tag can have the sequence GSAGSAAGSGEFG-SAEAAAKEAAAKEAAAKEAAAK-AGSAGSAAGSGEFGSEQK LISEEDLEQKLISEED-LEQKLISEEDLGSAGSAAGSGEFGSAGSAAGSGEFGSAGSAAGSGEF (SEQ ID NO:80). For example, a C-terminal sequence with a triplicate FLAG tag can have the sequence GSAGSAAGSGEFG-SAEAAAKEAAAKEAAAKEAAAK-AGSAGSAAGSGEFGSDYK DDDDKDYKDDDDKDYKDDDDKGSAGSAAGSGEF GSAGSAAGSGEFGSAGSAA GSGEF (SEQ ID NO:81). FIG. 6C and FIG. 13D each contain an example of a scaffold polypeptide of this formula that contains the peptide ligands corresponding to IDS 1-16 as shown in Table 2, and a triplicate MYC tag on the C-terminus. For example, FIG. 13D contains an example of a scaffold polypeptide (see SCF gene cassette of FIG. 2B) containing a triplicate MYC tag. FIG. 6D and FIG. 13D each contain an example of a scaffold polypeptide that contains the peptide ligands corresponding to IDs 1 and 17 as shown in Table 2 and a triplicate FLAG tag on the C-terminus. Accordingly, the amino acid sequence of a scaffold can depend on the sequence of the peptide ligands that can bind to the selected ID motif of the enzymes.

In some embodiments, any one of the enzymes can be engineered to include an N-terminal or C-terminal linker motif that allows covalent (isopeptide) bonding to the scaffold. See, for example, the SpyTag and SpyCatcher system described by Zakeri, et al., *Proc. Natl. Acad. Sci.,* 2012 109 (12) E690-E697.

In some embodiments involving multi-enzymatic scaffolds described herein, the first engineered enzyme of a biosynthetic pathway can produce a first product that can be a substrate for the second engineered enzyme of the biosynthetic pathway, the second engineered enzyme of the biosynthetic pathway can produce a second product that can be a substrate for the third engineered enzyme of the biosynthetic pathway, and so forth. In some cases, the second engineered enzyme can be immobilized on the scaffold such that it is positioned adjacent to or very close to the first engineered enzyme. The third engineered enzyme can be immobilized on the scaffold such that it is positioned adjacent or very close the second engineered enzyme. In this way, the effective concentration of the first product can be high, and the second engineered enzyme can act efficiently on the first product, the third engineered enzyme can act efficiently on the second product, and so forth.

As shown in FIGS. 1A and 1B, one example of a multi-enzymatic scaffold contains enzymes of the hexanoyl-CoA pathway on the N-terminus of the scaffold, enzymes of the mevalonate pathway on the C-terminus of the scaffold, and enzymes of the upper cannabinoid pathway in between. Within any of the pathways, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL (see below).

A fully-assembled multi-enzymatic scaffold provided herein can adopt stoichiometry and a spatial arrangement that can help maximize pathway flux and minimize accumulation of pathway intermediates and by-products. Such scaffolds can facilitate substrate channeling both within and between cannabinoid and cannabinoid precursor pathways. Specifically, this scaffolding system can facilitate unidirectional flux through each of the primary cannabinoid precursor pathways, and converging near the midpoint of the scaffold. The hexanoyl-CoA/olivetolic acid (OVA) pathway can begin at the N-terminus of the scaffold, and the mevalonate or MEP pathway can begin at the C-terminus of the scaffold. The enzyme catalyzing the rate-limiting/committed step in cannabinoid biosynthesis, a CBGA synthase, can be localized at the intersection of these precursor pathways near the scaffold midpoint.

By this design, the two primary precursors for cannabinoid biosynthesis, hexanoyl-CoA/olivetolic acid and geranyl pyrophosphate, can be bi-directionally delivered to a CBGA synthase at this intersection. The CBGA synthase can catalyze biosynthesis of CBGA, the primary cannabinoid from which all other cannabinoids are derived. Substrate channeling within and between the scaffolded pathways can accelerate the kinetics of the composite pathway in accordance with the law of mass action.

In the embodiment shown in FIGS. 1A and 1B, the N-terminal hexanoyl-CoA pathway can include an ATP citrate lyase (ACL) (also can be referred to as an ATP citrate synthase), an acetyl-CoA acetyltransferase (atoB), two 3-hydroxy-acyl-CoA dehydrogenases (BHBDs), two enoyl-CoA hydratases (ECHs), a beta-ketothiolase (bktB), and two trans-2-enoyl-CoA-reductases (ECRs).

In the hexanoyl-CoA pathway shown in FIGS. 1A and 1B, citrate, from cellular metabolism and/or supplemented in the growth medium, can be used as a substrate for ACL-catalyzed acetyl-CoA synthesis. ACL is classified under EC 2.3.3.8. Acetyl-CoA can be used as a substrate for atoB-catalyzed acetoacetyl-CoA synthesis. atoB is classified under EC 2.3.1.9. Acetoacetyl-CoA can serve as the substrate for BHBD-catalyzed 3-hydroxybutanoyl-CoA synthesis. BHBD is classified under EC 1.1.1.157. 3-hydroxybutanoyl-CoA can serve as the substrate for ECH-catalyzed trans-but-2-enoyl-CoA synthesis. ECH is classified under EC 4.2.1.17. Trans-but-2-enoyl-CoA can serve as the substrate for ECR-catalyzed butanoyl-CoA synthesis. ECR is classified under EC 1.3.8.1. Butanoyl-CoA can serve as the substrate for bktB-catalyzed 3-keto-hexanoyl-CoA synthesis. bktB is classified under EC 2.3.1.9. The bktB catalyzing the production of 3-ketohexanoyl CoA from butanoyl-CoA can be the same as, or different from, the atoB used to catalyze the production of acetoacetyl-CoA from acetyl-CoA. 3-ketohexanoyl-CoA is the substrate for BHBD-catalyzed 3-hydroxyhexanoyl-CoA synthesis. BHBD is classified under EC 1.1.1.157. The BHBD catalyzing the production of 3-hydroxyhexanoyl-CoA can be the same as, or different from, the BHBD used to catalyze the production of 3-hydroxybutanoyl-CoA. 3-hydroxyhexanoyl-CoA can be the substrate for ECH-catalyzed trans-hex-2-enoyl-CoA synthesis. ECH is classified under 4.2.1.17. The ECH catalyzing the production of trans-hex-2-enoyl-CoA can be the same as, or different from, the ECH used to catalyze the production of trans-but-2-enoyl-CoA. Trans-hex-2-enoyl-CoA can be the substrate for ECR-catalyzed hexanoyl-CoA synthesis. ECR is classified under EC 1.3.1.38 or EC 1.3.1.44. The ECR catalyzing the production of hexanoyl-CoA can be the same as, or different from, the ECR used to catalyze the production of butanoyl-CoA In some embodiments, a hexanoyl-CoA synthetase (HCS) enzyme can be substituted for the scaffolded enzymes of the hexanoyl-CoA pathway or can be included in a soluble form in addition to the scaffolded enzymes of the hexanoyl-CoA pathway, and in some embodiments, hexanoic acid can be added to the growth media as a substrate for HCS-catalyzed hexanoyl-CoA production. The HCS can be included on the scaffold, N-terminal to the upper cannabinoid pathway in FIGS. 1A and 1B, and/or it can be non-scaffolded (soluble).

In the embodiment shown in FIGS. 1A and 1B, the C-terminal mevalonate pathway can include an ACL, an atoB, a hydroxymethylglutaryl-CoA, an HMG-CoA synthase (HMGS), an HMG-CoA reductase (HMGR), a mevalonate kinase (ERG12), a phosphomevalonate kinase (ERGS), a diphospho mevalonate decarboxylase (MVD1), an isopentyl diphosphate isomerase (IDI1), and a mutant GPP synthase (mGPPS). In the mevalonate pathway shown in FIGS. 1A and 1B, citrate from cellular metabolism and/or supplemented in the growth medium, can be used as a substrate for ACL-catalyzed acetyl-CoA synthesis. ACL is classified under EC 2.3.3. Acetyl-CoA can be used as a substrate for bktB-catalyzed acetoacetyl-CoA synthesis. bktB is classified under EC 2.3.1.9. Acetoacetyl-CoA can be the substrate for HMGS-catalyzed HMG-CoA synthesis. HMG-CoA can be the substrate for HMGR catalyzed mevalonate synthesis. HMGR is classified under EC 1.1.1.88 or 1.1.1.34. Mevalonate can be the substrate for mevalonate kinase-catalyzed mevalonate-5 phosphate synthesis. Mevalonate kinase is classified under EC 2.7.1.36. Mevalonate-5-phosphate can be the substrate for phosphomevalonate kinase-catalyzed mevalonate pyrophosphate synthesis. Phosphomevalonate kinase is classified under EC 2.7.4.2. Mevalonate pyrophosphate can be the substrate for diphosphomevalonate decarboxylase-catalyzed isopentyl pyrophosphate synthesis. Diphosphomevalonate decarboxylase is classified under EC 4.1.1.33. Isopentyl pyrophosphate can be the substrate for isopentyl diphosphate isomerase-catalyzed dimethylallyl pyrophosphate synthesis. Isopentyl diphosphate isomerase is classified under EC. 5.3.3.2. Dimethylallyl pyrophosphate can be the substrate for geranyl pyrophosphate synthase (GPPS)-catalyzed geranyl pyrophosphate synthesis. GPPS is classified under EC 2.5.1.1.

As acetyl-CoA can be the initial substrate for the hexanoyl-CoA, mevalonate/geranyl pyrophosphate, and malonyl-CoA cannabinoid precursor biosynthetic pathways, the inclusion of ACL at both the N-terminus and C-terminus of the multi-enzymatic scaffold in FIGS. 1A and 1B can directly couple the scaffolded pathways to cellular metabolism via ACL-catalyzed production of acetyl-CoA from citric acid cycle-derived citrate. The citrate also can be supplemented into the culture medium (e.g., as buffered citrate). In some embodiments, the ACL enzyme is included only at the N-terminus of the scaffold. In some embodiments, the ACL enzyme is included only at the C-terminus of the scaffold. In some embodiments, the ACL enzyme is included in soluble form.

Figure 5:
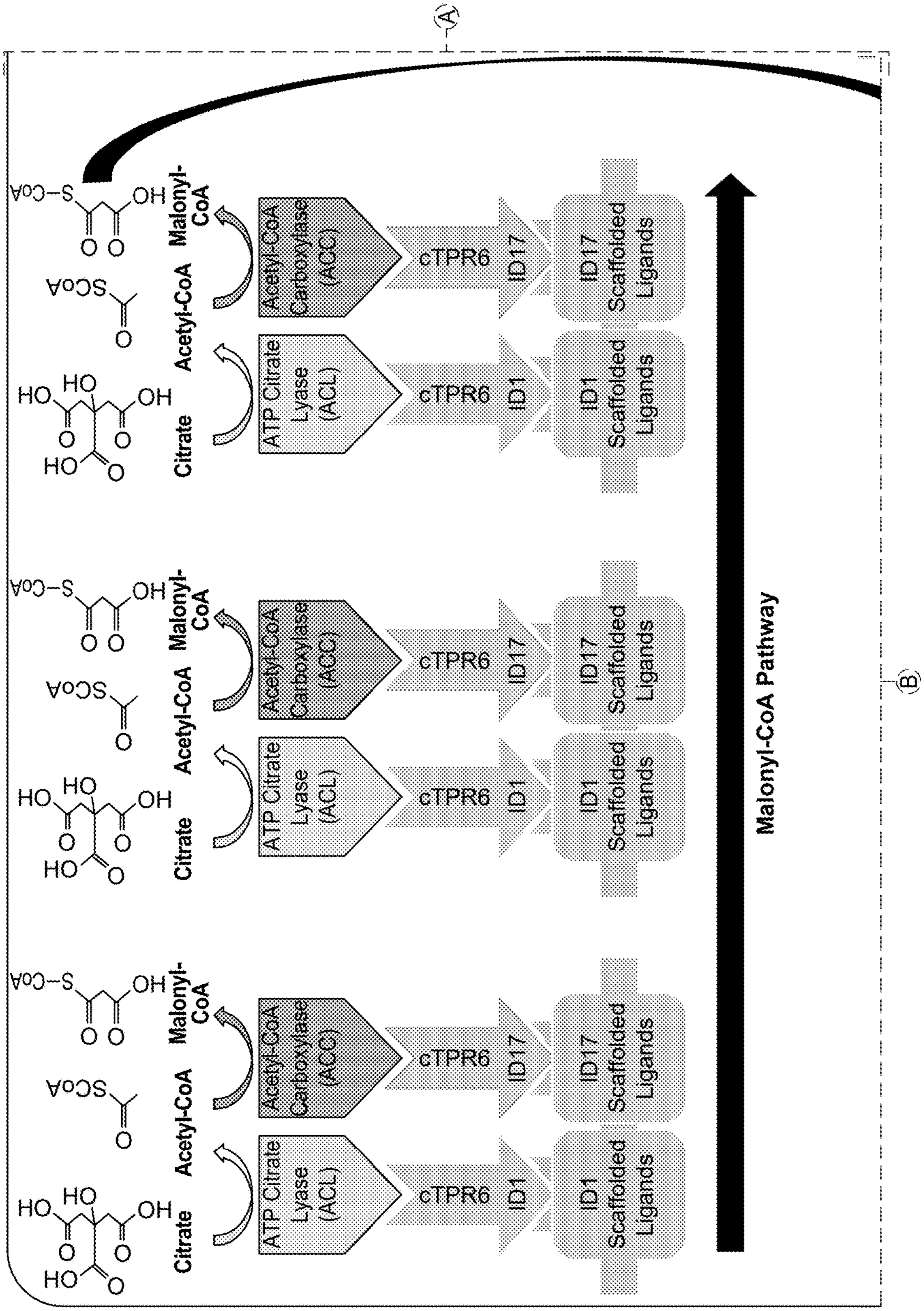
FIG. 5 is a schematic of one representative embodiment of a multi-enzymatic cannabinoidergic scaffold within a cell. The multi-enzymatic scaffold includes enzymes of the hexanoyl-CoA pathway, enzymes of the upper cannabinoid pathway, and enzymes of the MEP (2-C-methylerythritol 4-phosphate) pathway. The schematic also depicts a second scaffold according to one embodiment containing enzymes of the malonyl-CoA pathway and depicts a non-scaffolded CBDAS and a non-scaffolded CBCAS. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.
Figure 5:
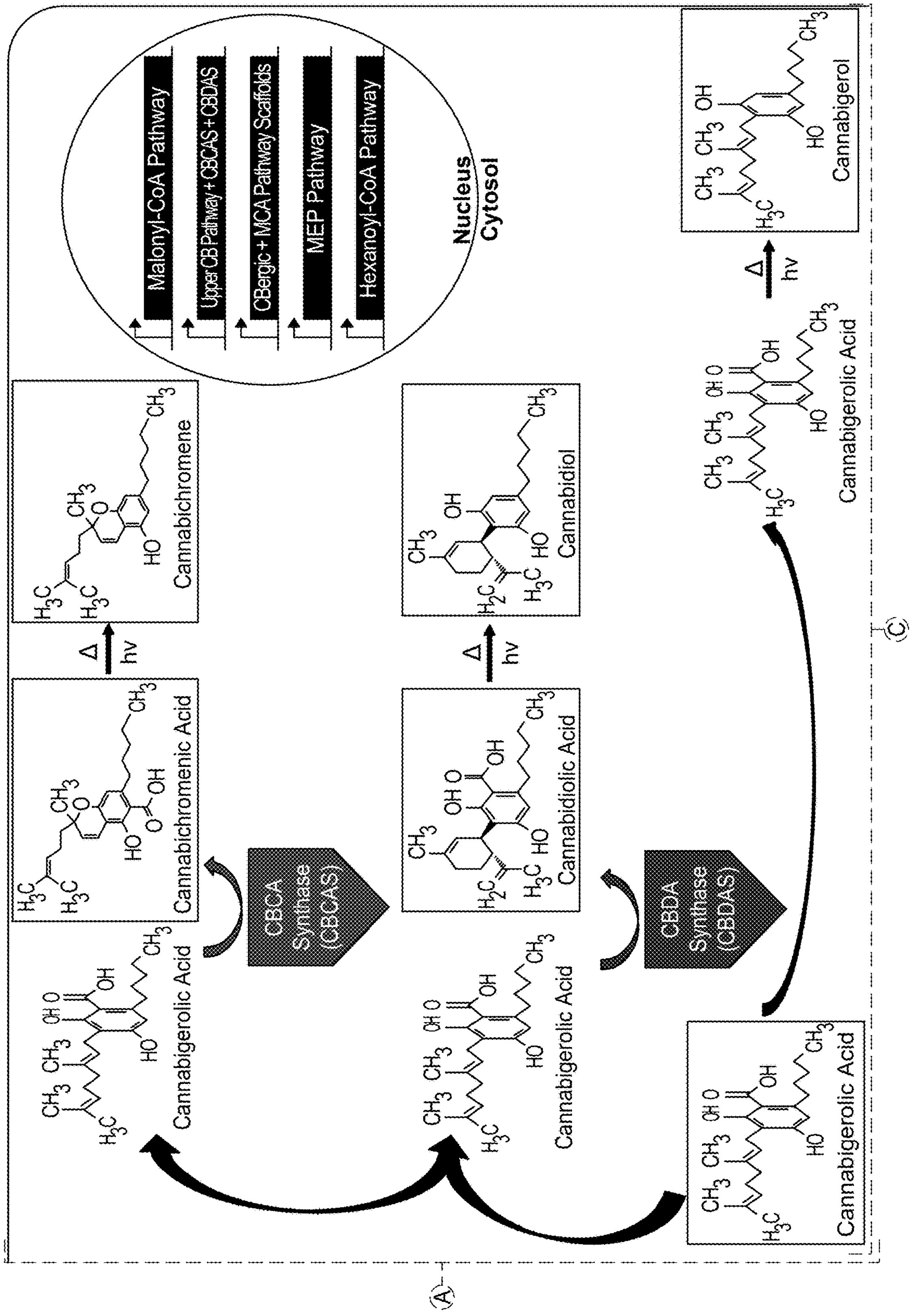
Figure 5:
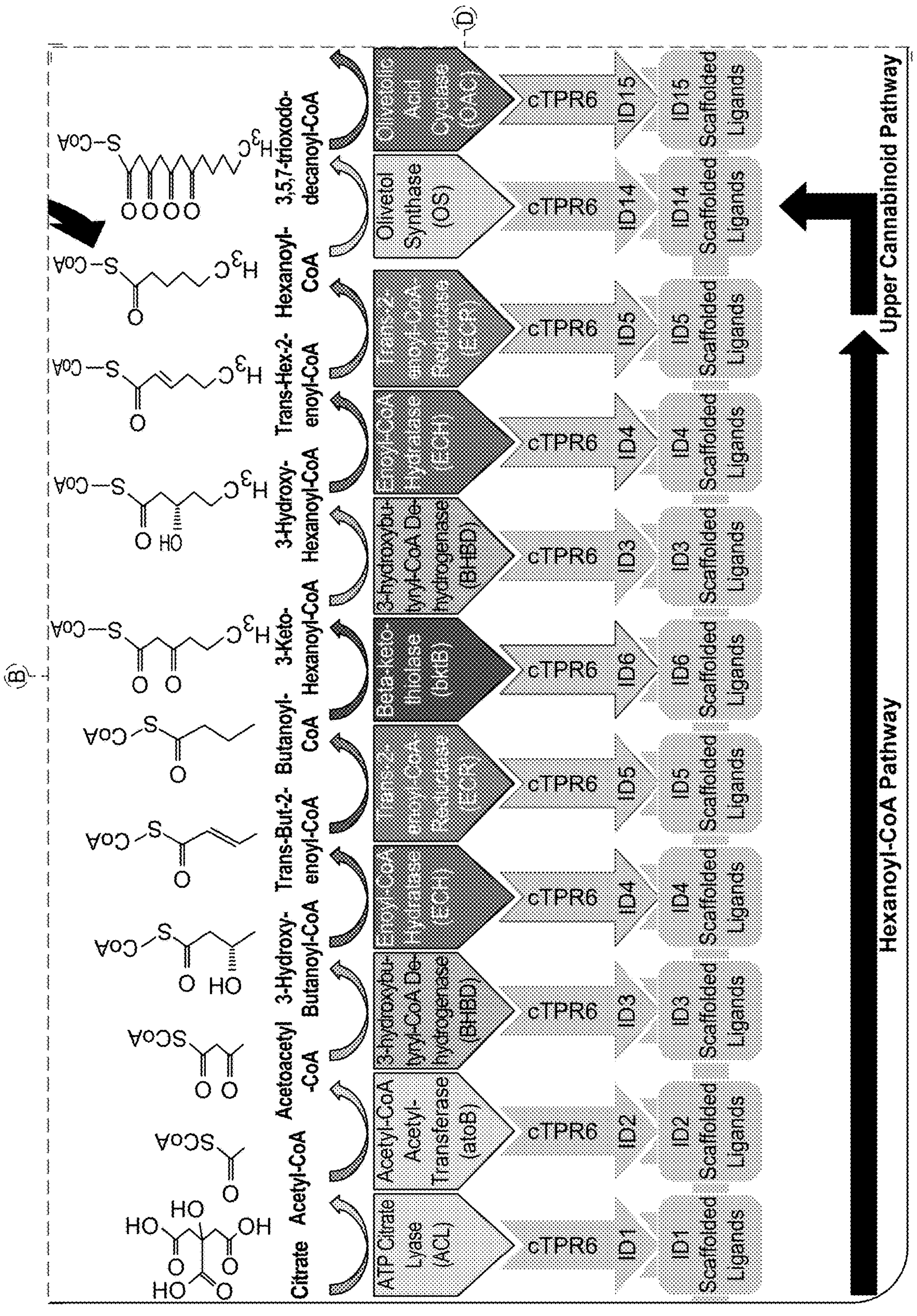
Figure 5:
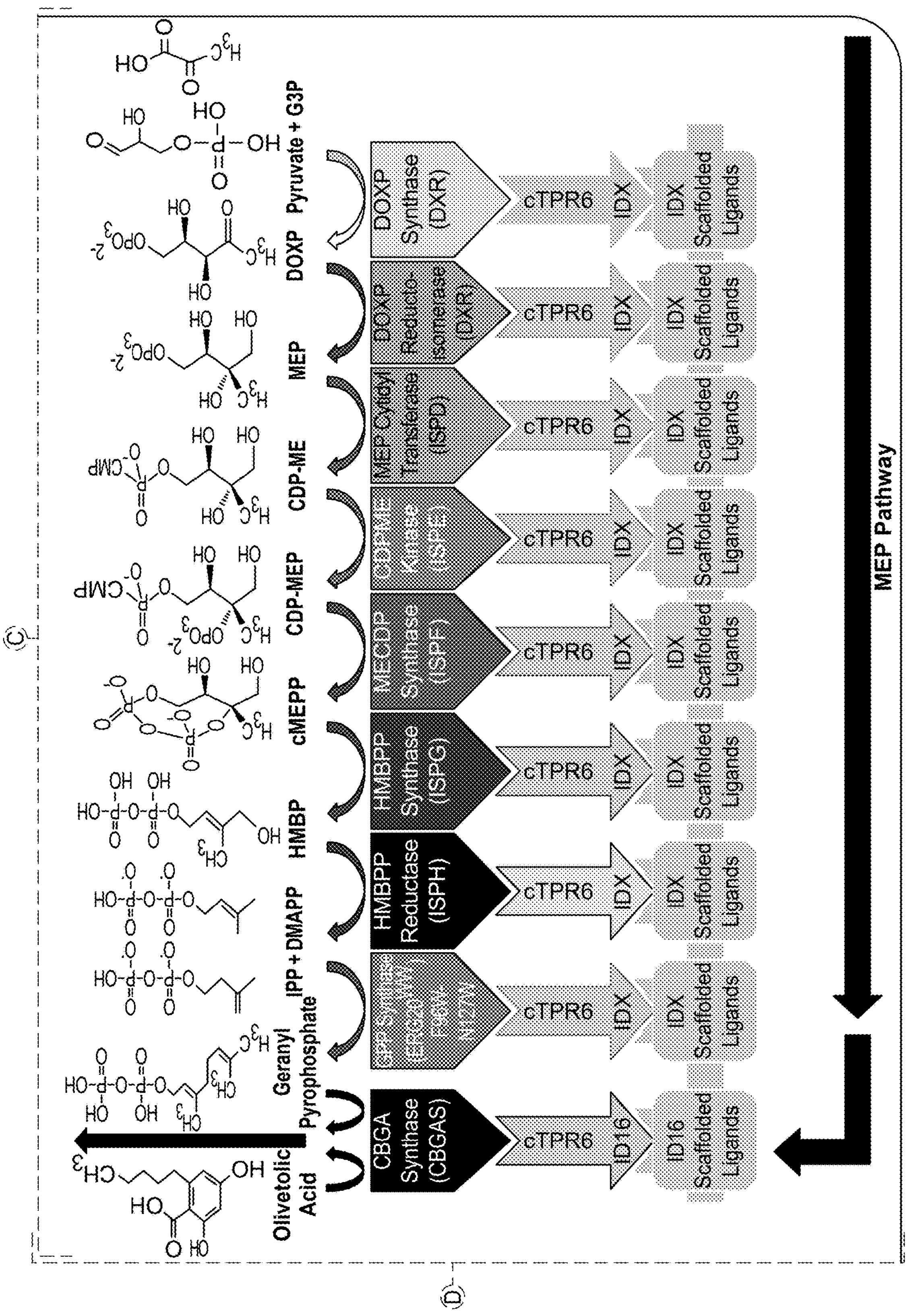

In some embodiments, the 2-C-methylerythritol 4-phosphate (MEP) pathway, which also can produce geranyl pyrophosphate, can be substituted for the scaffolded mevalonate pathway at the C-terminus of the scaffold or can be included in a soluble form in addition to the scaffolded mevalonate pathway. For example, as shown in FIG. 5, the C-terminus of the scaffold can include a 1-deoxy-D-xylulose-5-phosphate (DOXP) synthase, a DOXP reductoisomerase, a MEP cytidyl transferase, a 4-diphosphocytidyl-2-C-methylerythritol (CDPME) kinase, a 2-C-methyl-D-erythritol 2,4-cyclodiphosphate (MECDP) synthase, a 4-hydroxy-3-methyl-but-2-enyl pyrophosphate (HIVIBPP) synthase, a HMBPP reductase, and a GPPS. Pyruvate and glyceraldehyde-3-phosphate (G3P) can be used as substrates for DOXP-synthase-catalyzed DOXP synthesis. DOXP is classified under EC 2.2.1.7. DOXP can be the substrate for DOXP reductoisomerase (DXR)-catalyzed MEP synthesis. DXR is classified under EC 1.1.1.267. MEP can be the substrate for 2-C-methyl-D-erythritol 4-phosphate cytidylyltransferase (ISPD)-catalyzed 4-diphosphocytidyl-2-C-methylerythritol (CDP-ME) synthesis. ISPD is classified under EC 2.7.7.60. CDP-ME can be the substrate for 4-diphosphocytidyl-2-C-methyl-D-erythritol kinase (ISPE)-catalyzed 4-diphosphocytidyl-2-C-methyl-D-erythritol 2-phosphate (CDP-MEP) synthesis. ISPE is classified under EC 2.7.1.148. CDP-MEP can be the substrate for 2-C-methyl-D-erythritol 2,4-cyclodiphosphate synthase (ISPF)-catalyzed 2-C-methyl-D-erythritol 2,4-cyclodiphosphate (cMEPP) synthesis. ISPF is classified under EC 4.6.1.12. cMEPP can be the substrate for HMB-PP synthase (ISPG)-catalyzed (E)-4-Hydroxy-3-methyl-but-2-enyl pyrophosphate (HMBPP) synthesis. ISPG is classified under EC 1.17.7.1. HMBPP can be the substrate for 4-hydroxy-3-methylbut-2-enyl diphosphate reductase (ISPH)-catalyzed isopentenyl pyrophosphate (IPP) and dimethylallyl pyrophosphate (DMAPP) synthesis. ISPH is classified under EC 1.17.1.2. IPP and DMAPP can be substrates for GPPS-catalyzed geranyl pyrophosphate synthesis. GPPS is classified under EC 2.5.1.1.

In some embodiments, the mevalonate pathway can be substituted for the scaffolded MEP pathway at the C-terminus of the scaffold or can be included in a soluble form in addition to the scaffolded MEP pathway.

In the embodiment shown in FIG. 1A and FIG. 1B, a second multi-enzymatic scaffold can be co-expressed to enhance cytosolic titers of malonyl-CoA, another secondary substrate which can be used in cannabinoid biosynthesis. Such a scaffold can include an ATP citrate lyase (ACL) and acetyl-CoA carboxylase (ACC) in tandem. In some embodiments, the ACL and ACC are paired in duplicate or triplicate along the scaffold. If the ACL and ACC are paired in duplicate or triplicate, the two or three ACLs on the scaffold can be the same or different, and the two or three ACCs can be the same or different. In any of the embodiments, malonyl-CoA can be supplemented into the growth media instead of, or in addition to, being supplied by a scaffolded malonyl-CoA pathway.

Figure 4:
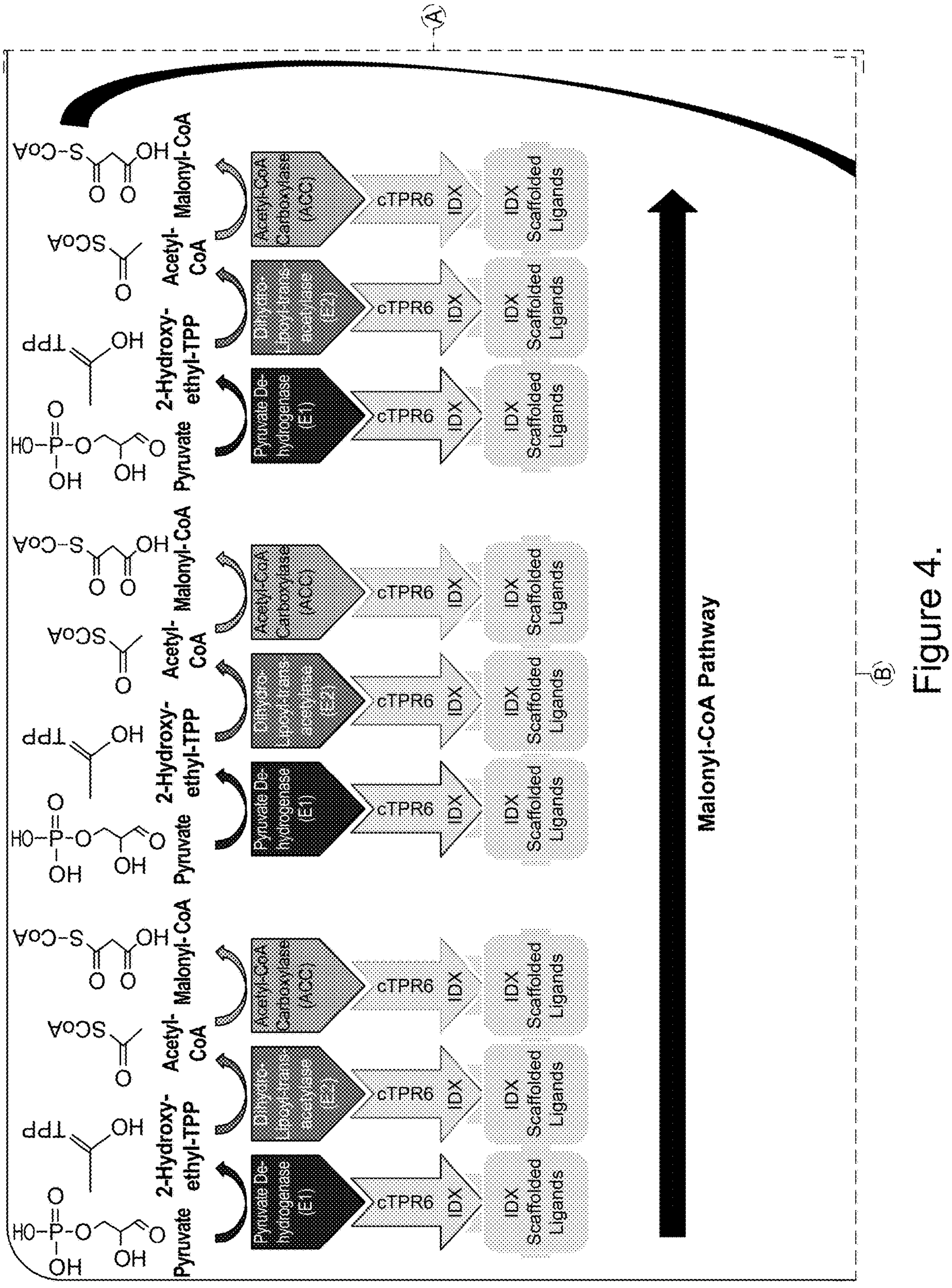
FIG. 4 is a schematic of one representative embodiment of a multi-enzymatic cannabinoidergic scaffold within a cell. The multi-enzymatic scaffold includes enzymes of the hexanoyl-CoA pathway, enzymes of the upper cannabinoid pathway, and enzymes of the mevalonate pathway. The schematic also depicts a second scaffold according to one embodiment containing enzymes of the malonyl-CoA pathway and depicts a non-scaffolded CBDAS and a non-scaffolded CBCAS. Pyruvate dehydrogenase (E1) and dihydrolipoyl transacetylase (E2) are substituted for ATP citrate lyase in both of the depicted scaffolds. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.
Figure 4:
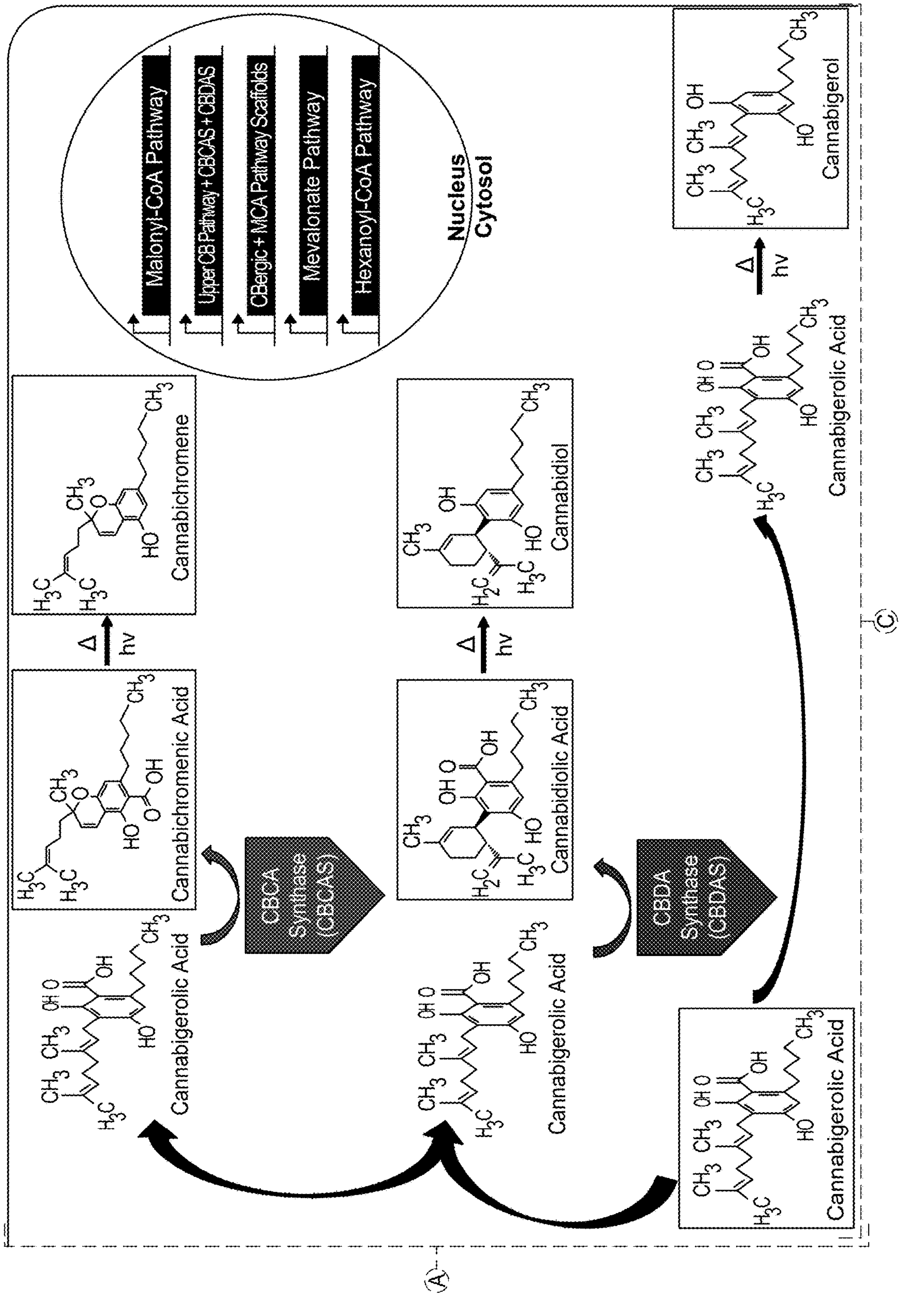
Figure 4:
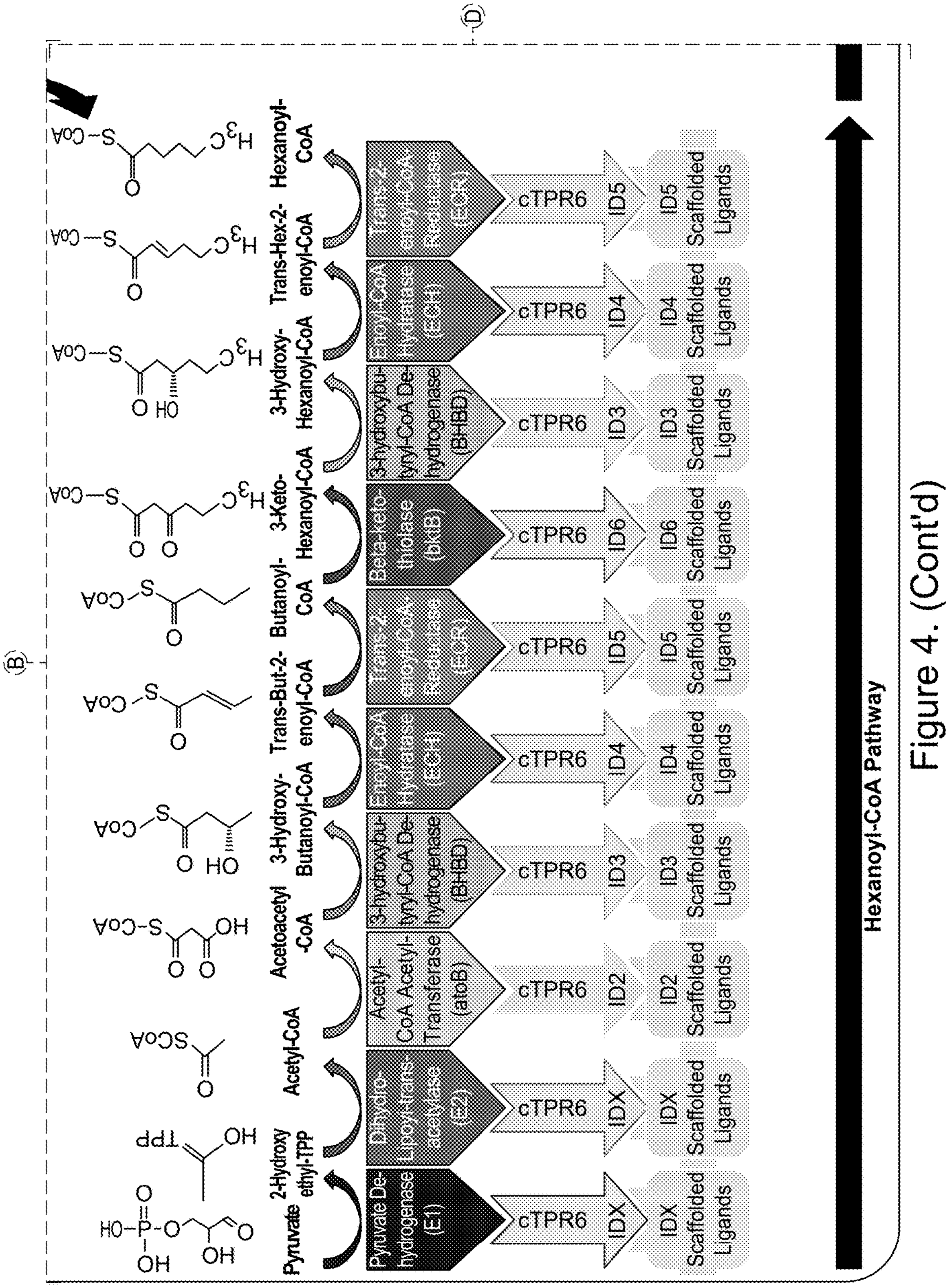
Figure 4:
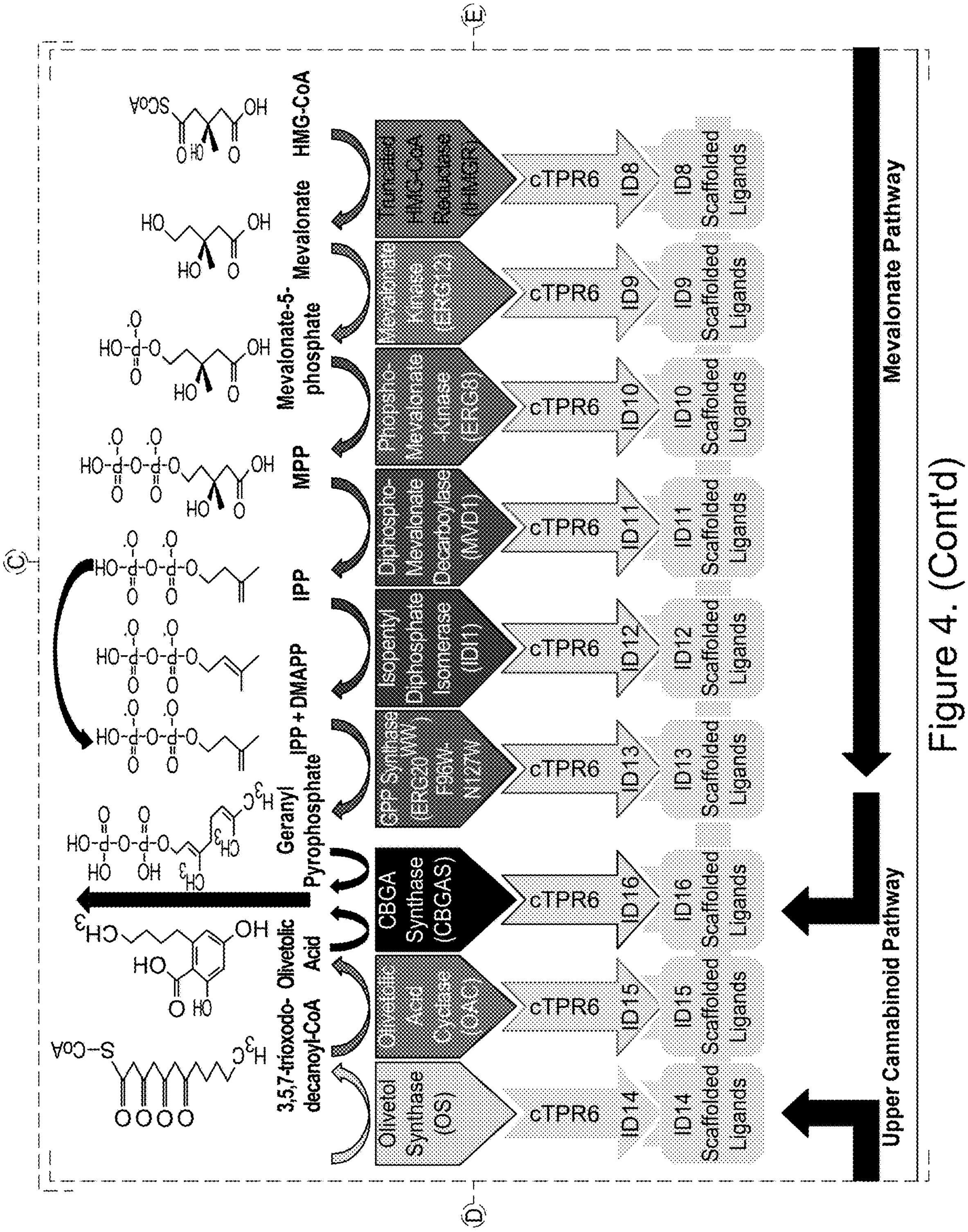
Figure 4:
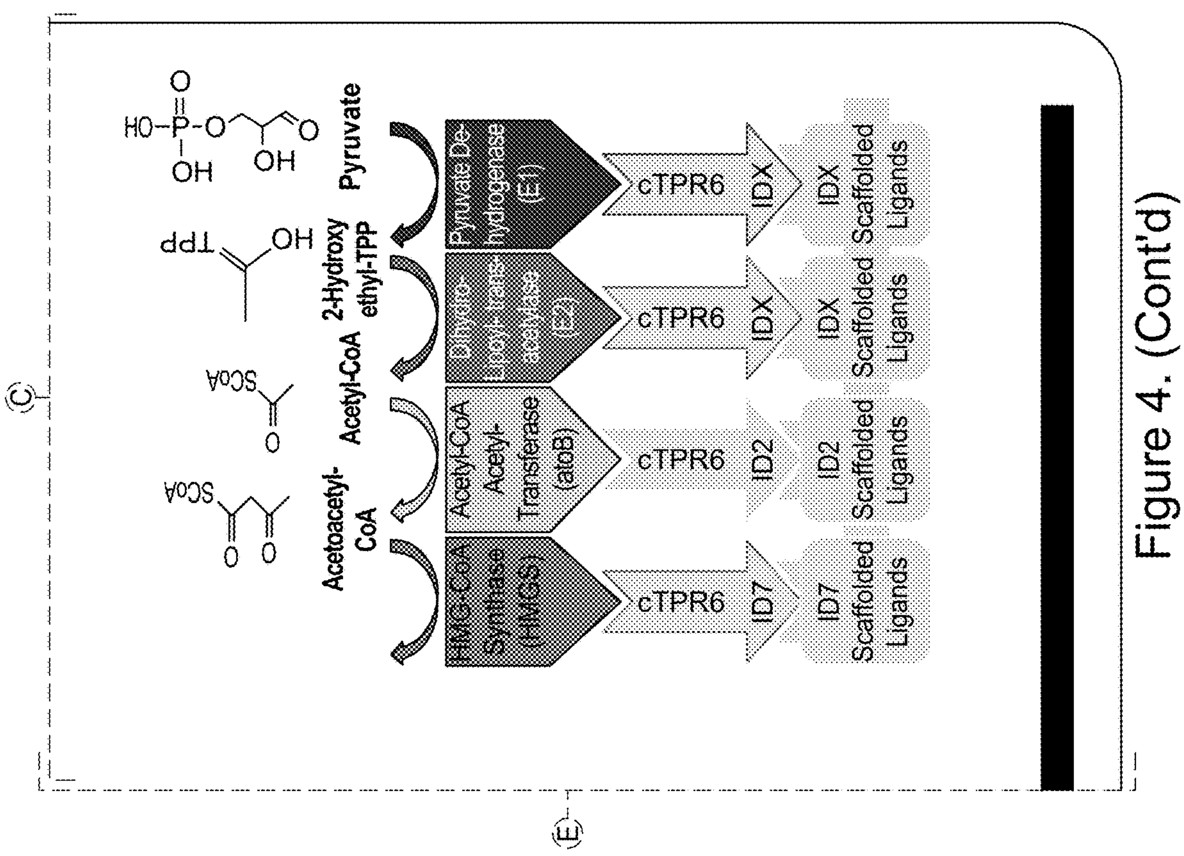

In any of the embodiments in which an ACL enzyme is used, a pyruvate dehydrogenase (E1) and a dihydrolipoyl transacetylase (E2) can be substituted for the ACL. For example, as shown in FIG. 4, a pyruvate dehydrogenase (E1) and a dihydrolipoyl transacetylase (E2) can be substituted upstream of scaffolded mevalonate, hexanoyl-CoA, and malonyl-CoA pathways. Using both a pyruvate dehydrogenase (E1) and a dihydrolipoyl transacetylase can allow acetyl-CoA to be produced using pyruvate rather than citrate as the primary substrate. In such embodiments, pyruvate also can be supplemented in the growth media. Pyruvate dehydrogenases and dihydrolipoyl transacetylases are constituents of the multi-enzyme pyruvate dehydrogenase complex that catalyze acetyl-CoA production from pyruvate. E1 and E2 are found in bacteria and eukaryotes.

As shown in FIG. 1A and FIG. 1B, the co-scaffolded upper cannabinoid pathway can include an olivetol synthase (OS), an olivetolic acid cyclase (OAC), and an aromatic prenyl-transferase (APT) such as a CBGA synthase (CBGAS). The upper cannabinoid pathway can begin using hexanoyl-CoA and three malonyl CoAs as the substrate for olivetol synthase-catalyzed 3,5,7-trioxododecanoyl-CoA synthesis. Olivetol synthase is classified under EC 2.3.1.206.

3,5,7-trioxododecanoyl-CoA can be used as a substrate for OAC-catalyzed olivetolic acid synthesis. OAC is classified under EC 4.4.1.26.

At the flux intersection of the converging N-terminal hexanoyl-CoA/upper cannabinoid and C-terminal mevalonate/MEP pathways (near the scaffold midpoint), an APT such as CBGAS can use olivetolic acid from the hexanoyl-CoA/upper cannabinoid pathways and geranyl pyrophosphate from the mevalonate or MEP pathway as substrates for cannabigerolate synthesis. A suitable APT is classified under EC 2.5.1.102.

Figure 7:
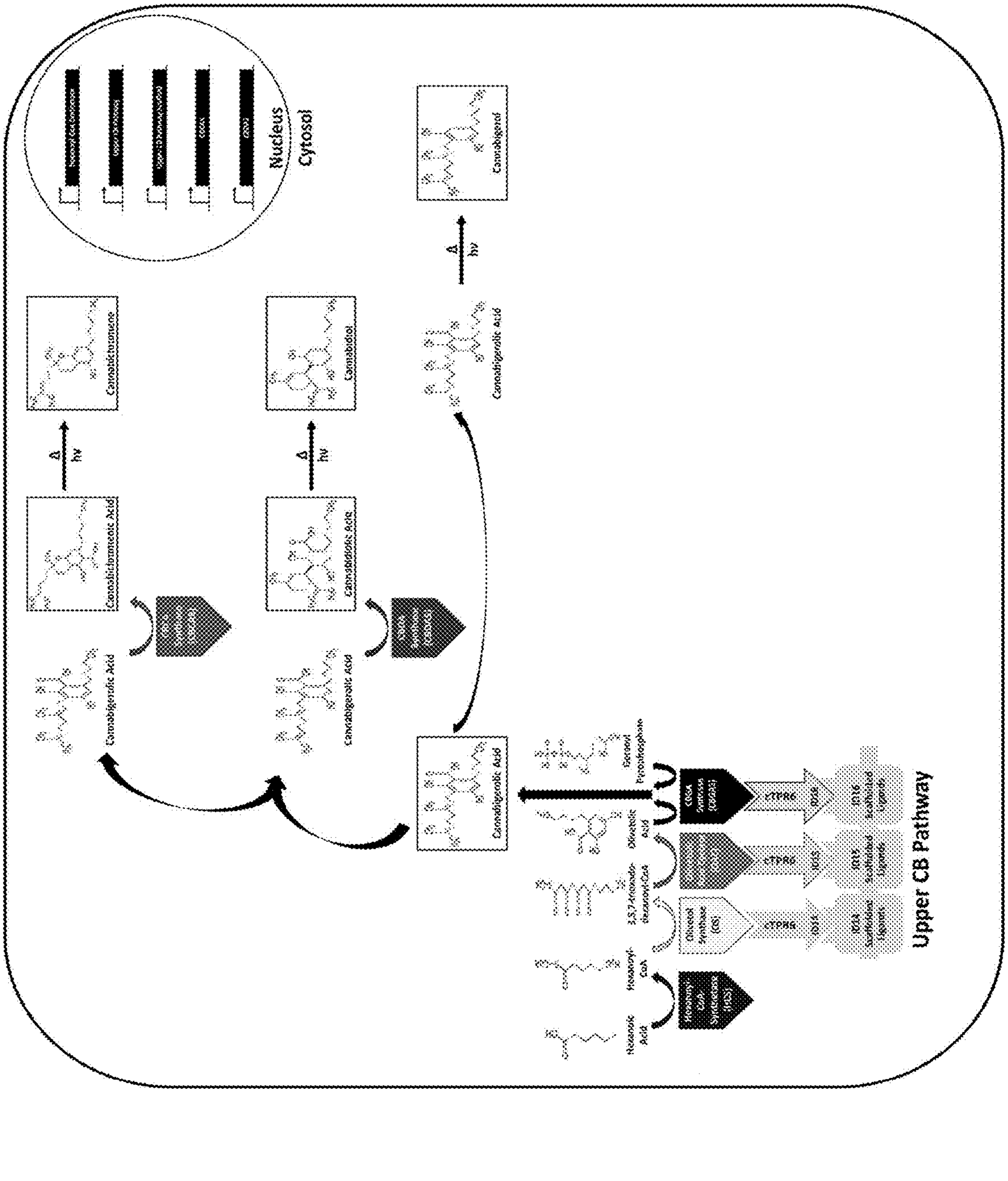
FIG. 7 is a schematic of one representative embodiment of a scaffold with the minimal requirements for cannabigerolic acid synthesis. The scaffold contains enzymes of the upper cannabinoid pathway. In this embodiment, a non-scaffolded hexanoyl-CoA synthetase (HCS), a non-scaffolded CBDAS, and a non-scaffolded CBCAS also are used. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.

In some embodiments, enzymes in the upper cannabinoid pathway can be scaffolded with a hexanoyl-CoA synthetase (HCS) to biosynthesize cannabigerolate. In some embodiments, a soluble HCS can be used with scaffolded enzymes of the upper cannabinoid pathway to biosynthesize cannabigerolate as shown in FIG. 7. Suitable enzymes for the upper cannabinoid pathway are described above.

Figure 8:
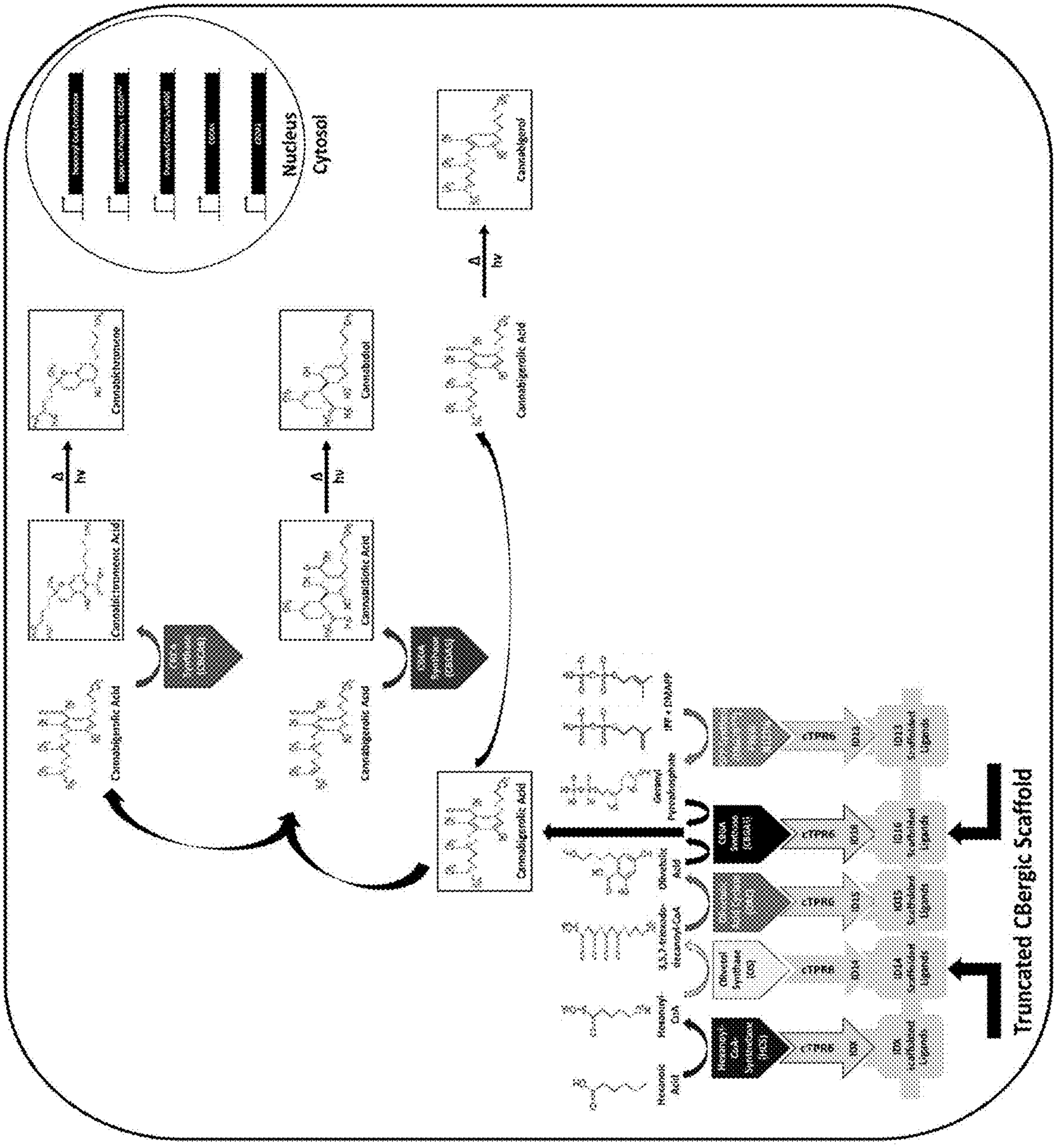
FIG. 8 is a schematic of one representative embodiment of a bi-directional scaffold containing a HCS on the N-terminus of the scaffold, a geranyl pyrophosphate synthase (GPPS) on the C-terminus of the scaffold, and the enzymes of the upper cannabinoid pathway between the HCS and GPPS. In this embodiment, a non-scaffolded CBDAS and a non-scaffolded CBCAS also can be used. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.

In some embodiments, a minimal bidirectional scaffold, such as the one depicted in FIG. 8, can be used in which HCS is on the N-terminus of the scaffold, a GPPS is on the C-terminus of the scaffold, and enzymes in the upper cannabinoid pathway are scaffolded between the HCS and GPPS.

Figure 9:
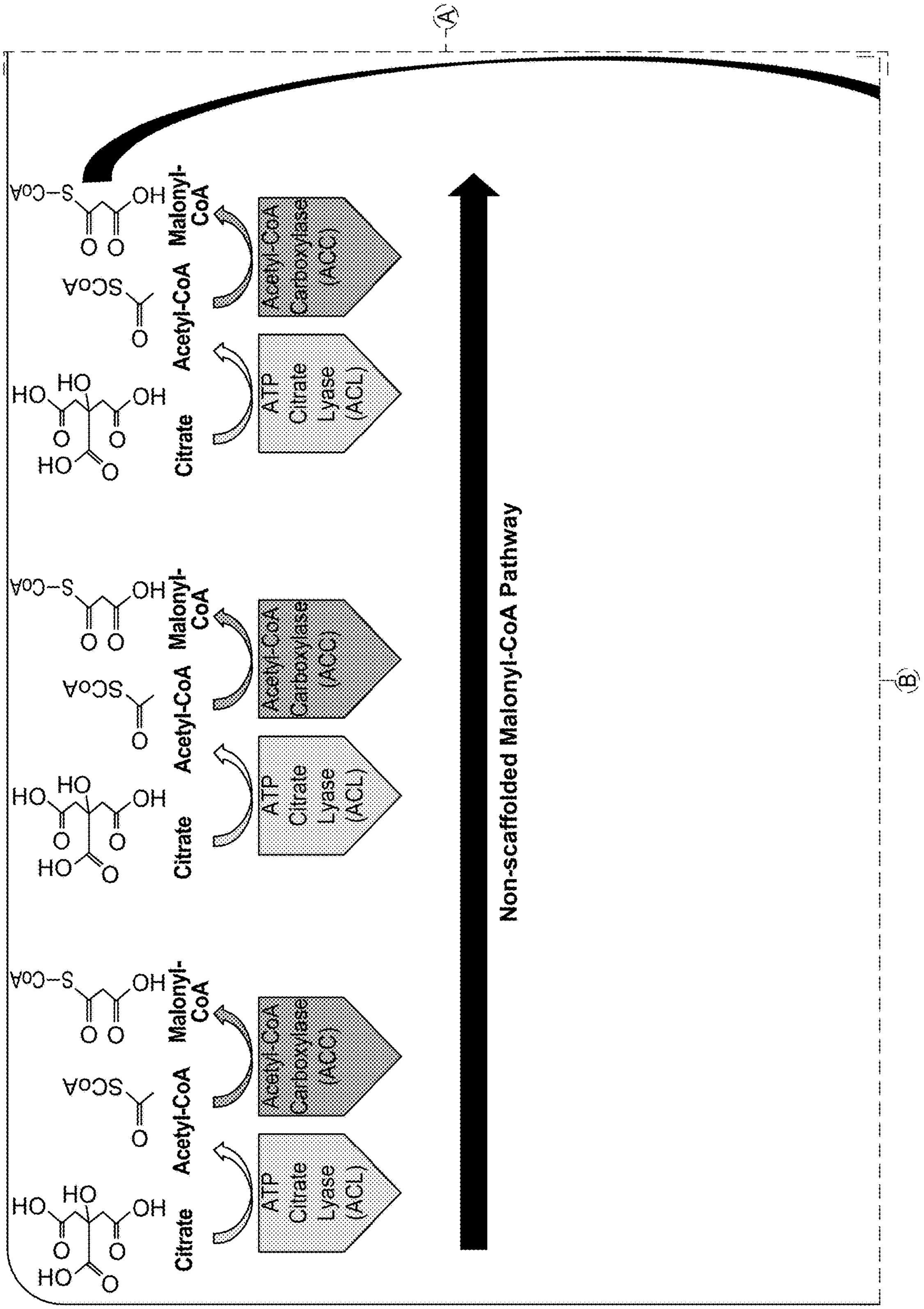
FIG. 9 is a schematic of one representative embodiment of a unidirectional scaffold containing enzymes of the upper cannabinoid pathway, shown with soluble enzymes from the precursor pathways (hexanoyl-CoA pathway, mevalonate pathway, and malonyl-CoA pathway), and soluble CBDAS and CBCAS. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.
Figure 9:
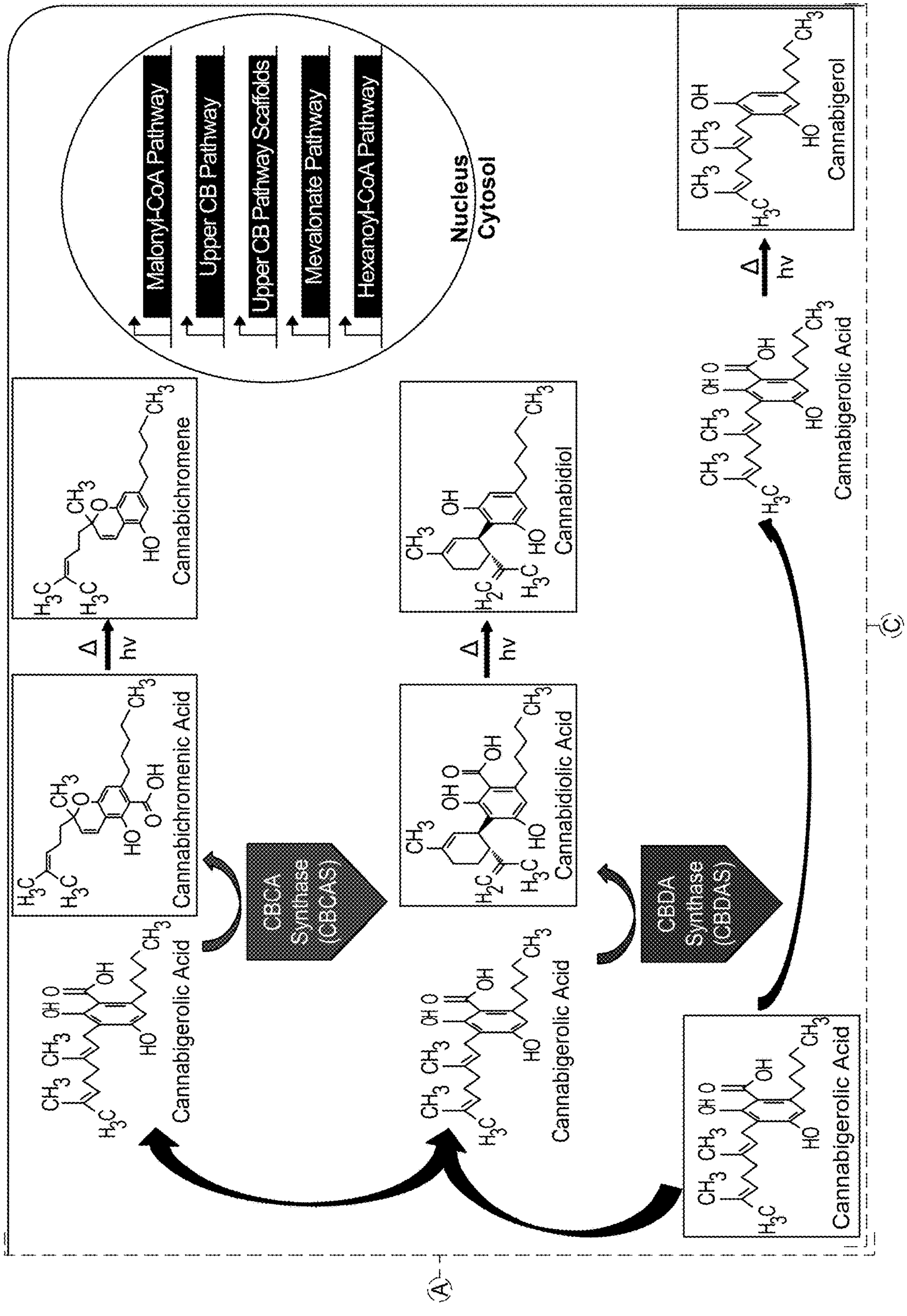
Figure 9:
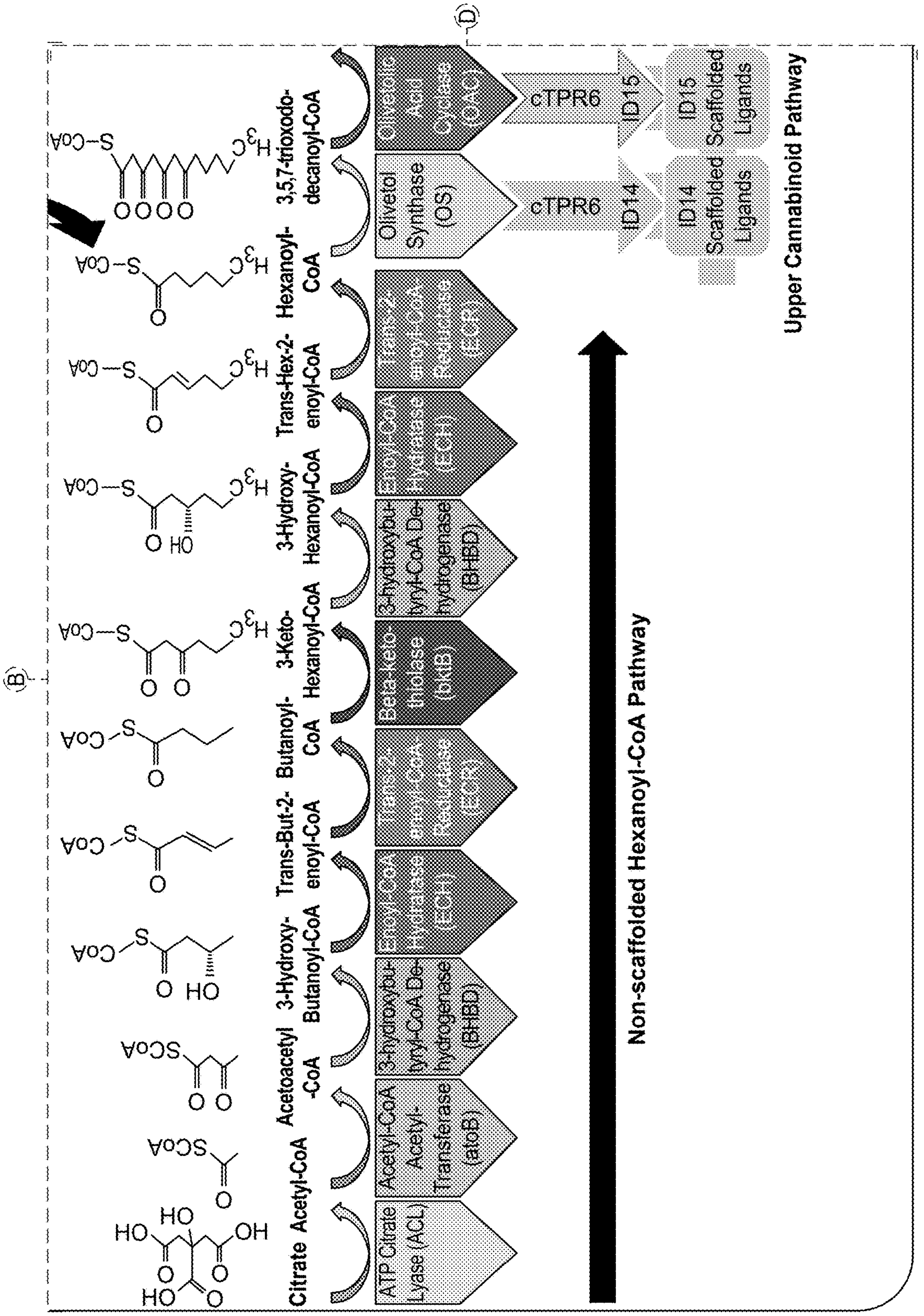
Figure 9:
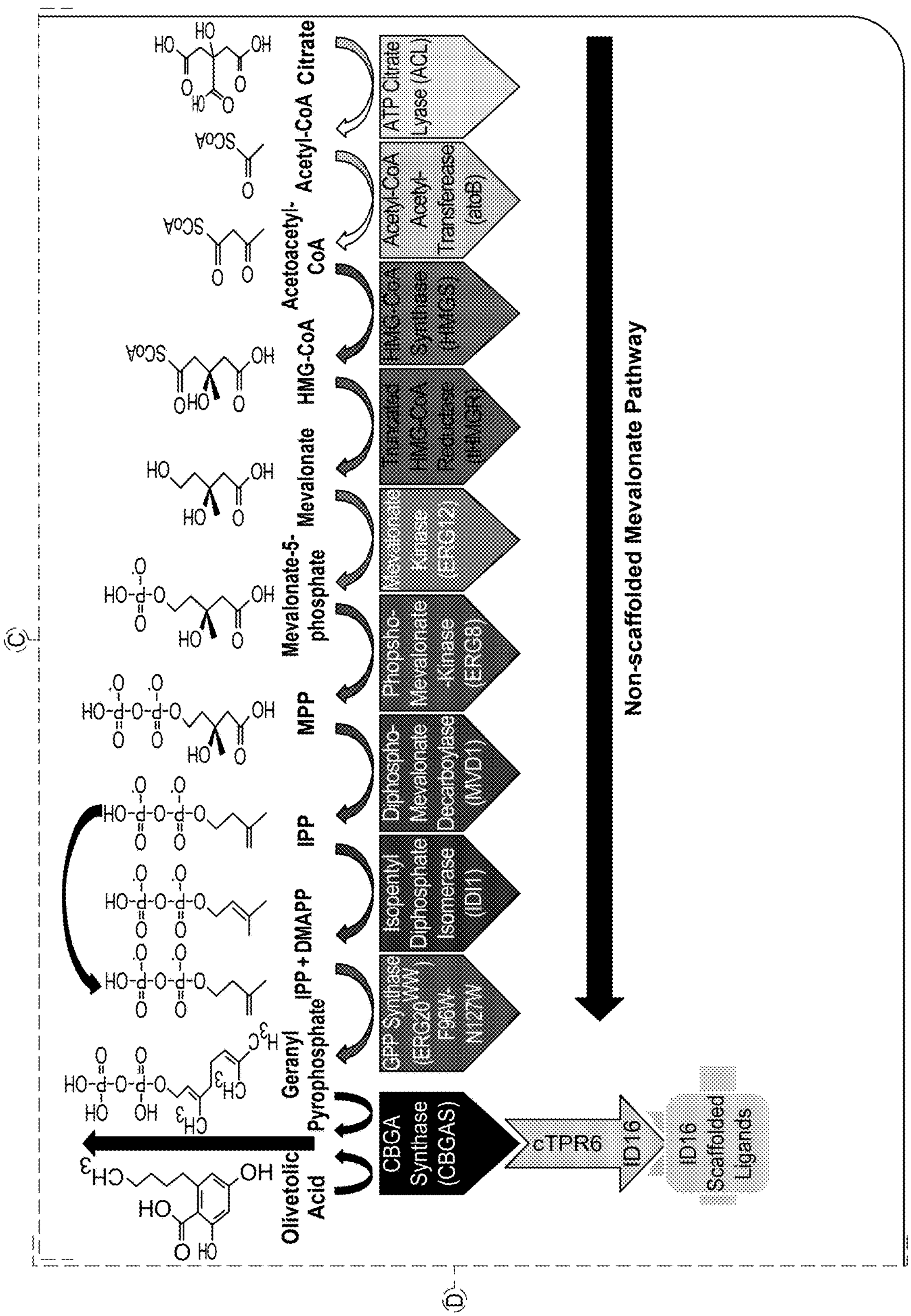

In some embodiments, such as the embodiment shown in FIG. 9, the enzymes in the upper cannabinoid pathway can be scaffolded, while the enzymes in the hexanoyl-CoA pathway, enzymes in the mevalonate pathway, and enzymes in the malonyl-CoA pathway can be soluble. In some embodiments, the enzymes in the upper cannabinoid pathway can be scaffolded, while the enzymes in the hexanoyl-CoA pathway, enzymes in the MEP pathway, and enzymes in the malonyl-CoA pathway can be soluble. In such embodiments, HCS can be substituted for the soluble forms of the enzymes of the hexanoyl-CoA pathway. Suitable enzymes for each of these pathways are described above.

In some embodiments, the enzymes in the upper cannabinoid pathway can be scaffolded, while a hexanoyl-CoA synthase, enzymes in the mevalonate or MEP pathway, and enzymes in the malonyl-CoA pathway can be soluble. Suitable enzymes for each of these pathways are described above.

In some embodiments, a HCS can be scaffolded N-terminally relative to the scaffolded enzymes in the upper cannabinoid pathway, while enzymes in the mevalonate or MEP pathway, and enzymes in the malonyl-CoA pathway can be soluble. Suitable enzymes for each of these pathways are described above.

In some embodiments, the enzymes in the upper cannabinoid pathway can be scaffolded, while the enzymes in the hexanoyl-CoA pathway or a hexanoyl-CoA synthase and enzymes in the mevalonate or MEP pathways can be soluble. In some embodiments, the enzymes in the hexanoyl-CoA pathway or a hexanoyl-CoA synthase can be scaffolded N-terminal to the enzymes in the upper cannabinoid pathway, and enzymes in the mevalonate or MEP pathways can be soluble. In such embodiments, malonyl-CoA can be supplemented. Suitable enzymes for each of these pathways are described above.

Figure 10:
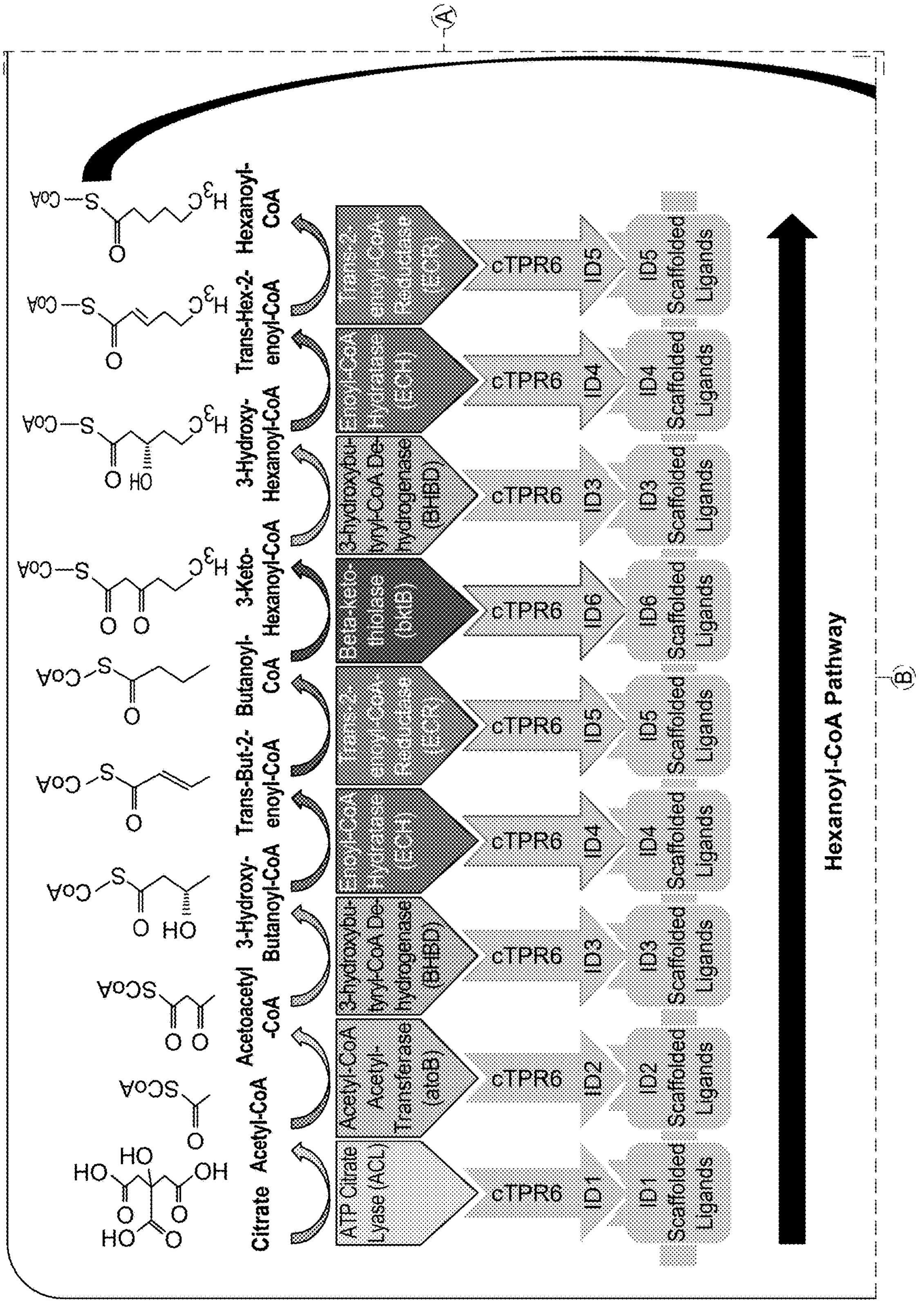
FIG. 10 is a schematic of one representative embodiment of a multi-enzymatic cannabinoidergic scaffold within a cell. The multi-enzymatic scaffold includes enzymes of the malonyl-CoA (MCA) pathway, enzymes of the upper cannabinoid pathway, and enzymes of the mevalonate pathway. The schematic also depicts a separate scaffold according to one embodiment containing enzymes of the hexanoyl-CoA pathway and depicts a non-scaffolded CBDAS and a non-scaffolded CBCAS. ID refers to enzyme-linked interaction domain; cTPR6 refers to a spacer sequence; scaffolded ligands refer to the tandem peptide ligands that form the scaffold-binding sites specific for each enzyme-linked ID. The target products CBGA, CBG, CBDA, CBD, CBCA, and CBC are boxed for emphasis. CBG can be produced by decarboxylation of CBGA, CBD can be produced by decarboxylation of CBDA, and CBC can be produced by decarboxylation of CBCA. For each decarboxylation, the 'Δ' symbols represent heat and the 'hv' symbols represent light.
Figure 10:
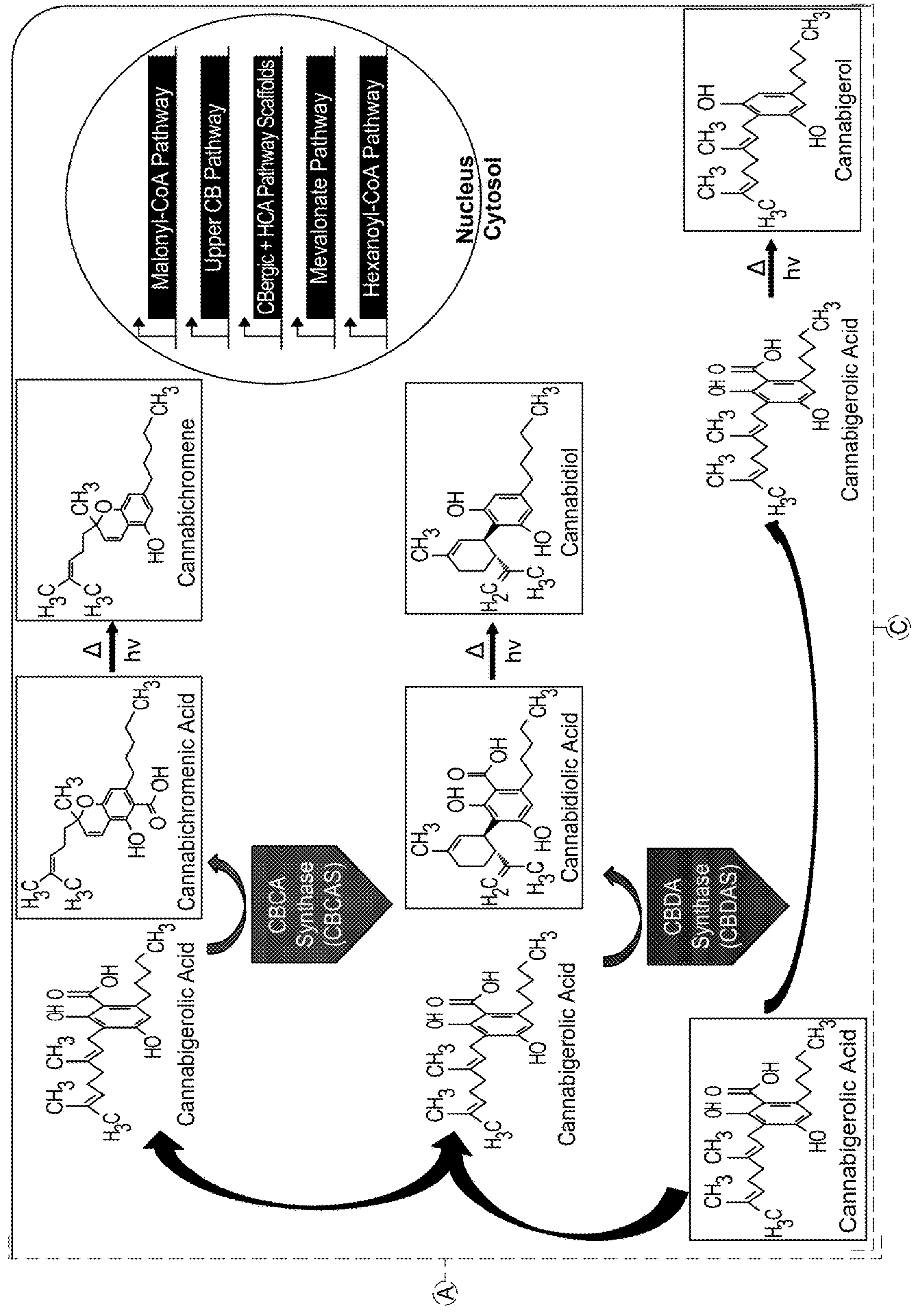
Figure 10:
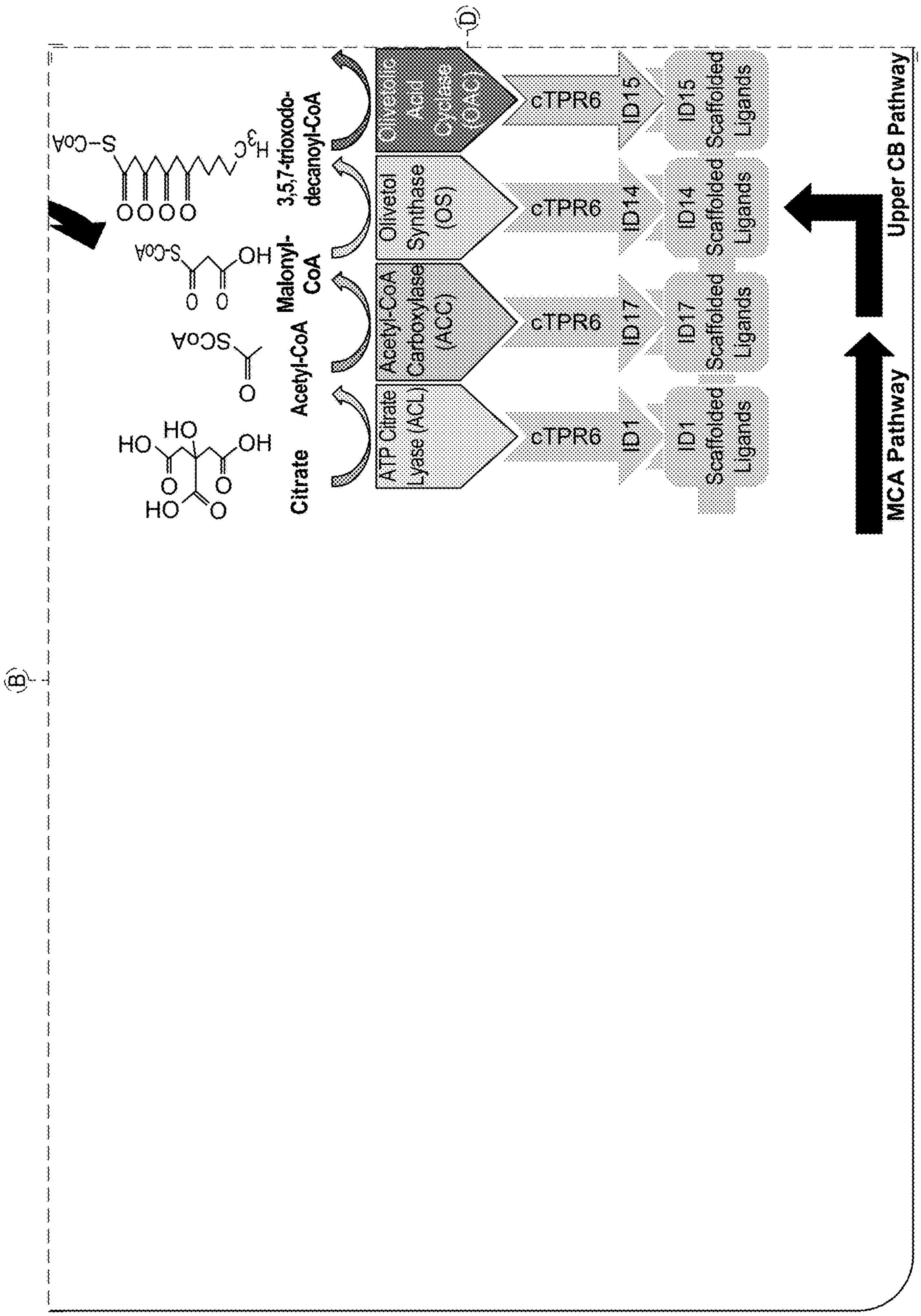
Figure 10:
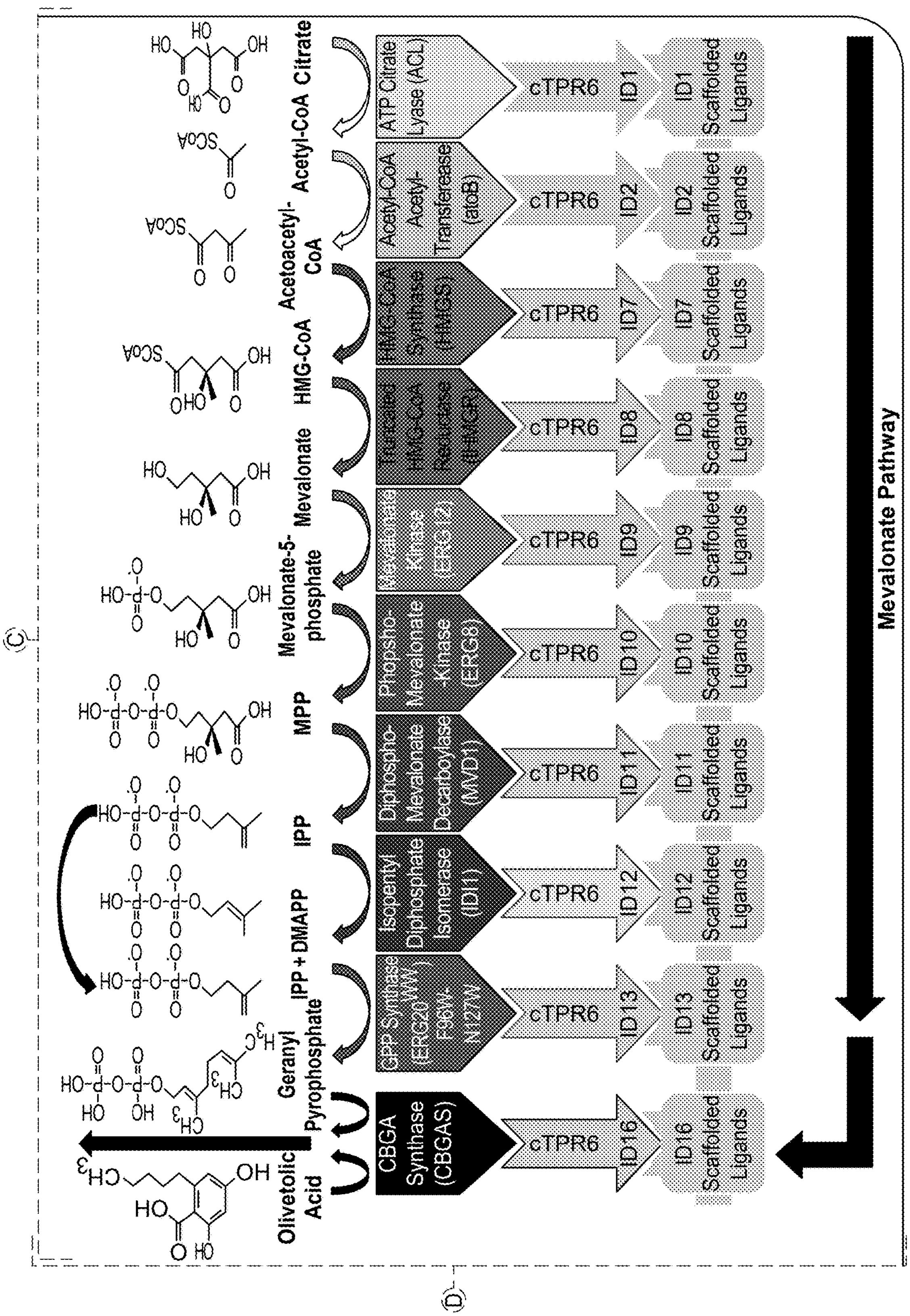

In some embodiments, such as the embodiment shown in FIG. 10, a bi-directional scaffold can include enzymes of the malonyl-CoA (MCA) pathway on the N-terminus of the scaffold, enzymes of the mevalonate pathway on the C-terminus of the scaffold, and enzymes in the upper cannabinoid pathway in between. In some embodiments, a bi-directional scaffold can include enzymes of the malonyl-CoA pathway on the N-terminus of the scaffold, enzymes of the MEP pathway on the C-terminus of the scaffold, and enzymes in the upper cannabinoid pathway in between. In such embodiments, enzymes of the hexanoyl-CoA pathway can be on a separate scaffold or can be soluble. In some embodiments, HCS can be substituted for scaffolded or soluble enzymes of the hexanoyl-CoA pathway.

In some embodiments, each of the pathways are on separate scaffolds. For example, in one embodiment, enzymes of the upper cannabinoid pathway can be on one scaffold, enzymes of the mevalonate or MEP pathway can be localized on one scaffold, enzymes of the hexanoyl-CoA pathway can be localized on one scaffold, and enzymes of the malonyl-CoA pathway can be localized on another scaffold.

Cannabigerolic acid biosynthesized in any of the embodiments described herein can be isolated and/or can be used as a substrate for synthesis of other secondary and tertiary cannabinoids using downstream cannabinoid synthases. In order to generate a more diverse profile of cannabinoids, the downstream cannabinoid synthases typically are not scaffolded, as scaffolding would favor production of the terminal cannabinoid. In some embodiments, however, one or more of the downstream cannabinoid synthases can be included on a scaffold described herein.

For example, one or more of cannabidiolic acid synthase (CBDAS), cannabichromenic acid synthase (CBCAS), tetrahydrocannabinolic acid synthase (THCAS), or other cannabinoid synthases can be used to produce additional cannabigerolate-derived cannabinoids. For example, a CBDAS; a CBCAS; a THCAS; a CBDAS and a CBCAS; a CBDAS and a THCAS; a CBCAS and a THCAS; or a CBDAS, CBCAS, and THCAS can be used to produce additional cannabigerolate-derived cannabinoids such as one or more of cannabiodiolic acid, cannabichromenic acid, and delta-9 tetrahydrocannabinolic acid. CBDAS is classified under EC 1.21.3.8 and can catalyze the synthesis of cannabidiolic acid from cannabigerolic acid. CBCAS is classified under EC 1.3.3—and can catalyze the synthesis of cannabichromenic acid from cannabigerolic acid. THCAS is classified under EC 1.21.3.7 and can catalyze the synthesis of delta-9 tetrahydrocannabinolic acid from cannabigerolic acid.

Host Cells for Producing Cannabinoids

Cannabinoids can be produced in host cells or in vitro using a multi-enzymatic scaffold as described herein. Suitable host cells include any microorganism, eukaryotic or prokaryotic, such as bacteria (e.g., *Escherichia coli, Bacillus, Brevibacterium, Streptomyces*, or *Pseudomonas*), yeast (e.g., *Pichia pastoris, Saccharomyces cerevisiae, Yarrowia lipolytica, Kluyveromyces marxianus*, or Komagataella phaffii) and other fungi (e.g., *Neurospora crassa*), and green algae (e.g., *Dunaliella* sp., *Chlorella variabilis, Euglena mutabilis*, or *Chlamydomonas reinhardtii*), as well as plant cells (e.g., tobacco, *Cannabis*, or other photosynthetic plant cells) that can be maintained in culture or, in the case of plant cells such as those from tobacco or *cannabis* plants, can be engineered in culture and cultivated as intact transgenic plants. Such host cells or plant may or may not naturally produce cannabinoids.

A host cell can be modified to contain one or more exogenous nucleic acids that encode a scaffold as described herein and one or more exogenous nucleic acids that encode the engineered enzymes. The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "exogenous" as used herein with reference to nucleic acid and a particular host cell refers to any nucleic acid that does not originate from that particular host cell as found in nature. Thus, non-naturally-occurring nucleic acid is considered to be exogenous to a host cell once introduced into the host cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

A nucleic acid that is naturally-occurring can be exogenous to a particular cell. For example, an entire chromosome isolated from a cell of organism X is an exogenous nucleic acid with respect to a cell of organism Y once that chromosome is introduced into Y's cell.

It is noted that a host cell can be given an exogenous nucleic acid molecule that encodes a polypeptide having an enzymatic activity that catalyzes the production of a compound not normally produced by that host cell. Alternatively, or additionally, a host cell can be given an exogenous nucleic acid molecule that encodes a polypeptide having an enzymatic activity that catalyzes the production of a compound that is normally produced by that host cell. In this case, the recombinant host cell can produce more of the compound, or can produce the compound more efficiently, than a similar host cell not having the genetic modification.

An enzyme having a particular enzymatic activity can be a polypeptide that is either naturally-occurring or non-naturally-occurring. A naturally-occurring polypeptide is any polypeptide having an amino acid sequence as found in nature, including wild-type and polymorphic polypeptides. Such naturally-occurring polypeptides can be obtained from any species including, without limitation, animal (e.g., mammalian), plant, fungal, and bacterial species. A non-naturally-occurring polypeptide is any polypeptide having an amino acid sequence that is not found in nature. Thus, a non-naturally-occurring polypeptide can be a mutated version of a naturally-occurring polypeptide, or an engineered polypeptide such as the engineered enzymes described herein that contain IDs. For example, a non-naturally-occurring polypeptide having geranyl pyrophosphate synthase activity can be a mutated version of a naturally-occurring polypeptide having geranyl pyrophosphate synthase activity. For example, the GPPS encoded by Erg20 may include a substitution of a tryptophan for phenylalanine at position 96 and a substitution of a tryptophan for asparagine at position 127 (referred to as $Erg20^{WW}$). $Erg20^{WW}$ favors production of geranyl pyrophosphate over farnesyl pyrophosphate. See, Jiang, et al., *Metab Eng.* 2017, 41:57-66. For example, a truncated HMGR (tHMGR) such as an N-terminally truncated HMGR that includes the catalytic domain but not the transmembrane or regulatory domains of HMGR can be used. For example, the HMGR from *A. thaliana* (GenBank Accession No. J04537) or a HMGR from *S. cerevisiae* (which contains only residues 646-1025) can be truncated to remove the transmembrane and/or regulatory domains and used in a scaffold described herein to remove a bottleneck in the mevalonate pathway. HMGR catalyzes the rate-limiting step in the mevalonate pathway (see, e.g., Song et al., 2017, *Scientific reports*, doi:10.1038/s41598-017-15005-4). For example, the nucleic acid encoding an atoB from *S. cerevisiae* can be modified to contain a synthetic 5' UTR (such as the synthetic 5' UTR sequence: 5'-cggcacccctacaaacagaaggaatataaa-3' (SEQ ID NO:82)) and can be used in the scaffold as it alters atoB expression to facilitate flux-rebalancing in favor of production of acetoacetyl-CoA over the reverse reaction product butyryl-CoA (see Kim et al., 2018, *Bioresour Technol*, doi: 10.1016/j.biortech. 2017.10.014). A polypeptide can be mutated by, for example, sequence additions, deletions, substitutions, or combinations thereof.

Any of the enzymes described herein that can be used to produce one or more cannabinoids can have at least 70% sequence identity (e.g., at least 75%, 80%, 85%, 90%, 95%, 97%, 98%, 99%, or 100%) to the amino acid sequence of the corresponding wild-type enzyme. It will be appreciated that the sequence identity can be determined on the basis of the mature enzyme (e.g., with any signal sequence removed).

For example, an ACL can have at least 70% sequence identity (e.g., at least 75%, 80%, 85%, 90%, 95%, 97%, 98%, 99%, or 100%) to the amino acid sequence of a *Homo sapiens* ACL (see SEQ ID NO:83, FIG. 6A), or an ACL from *Rattus norvegicus, Mus musculus*, or *Ciona intestinalis*, e.g., GenBank Accession Nos. AAA74463, AAK56081, and BAB00624, respectively.

For example, an acetyl-CoA acetyltransferase (atoB) can have at least 70% sequence identity (e.g., at least 75%, 80%, 85%, 90%, 95%, 97%, 98%, 99%, or 100%) to the amino acid sequence of an *Escherichia coli* atoB (see SEQ ID NO:84, FIG. 6A), or an atoB from *Cupriavidus necator, Clostridium acetobutylicum*, or *Arabidopsis thaliana*, e.g., GenBank Accession Nos. CAJ92573, AAK80816, and AAM67058, respectively. In some embodiments, a malonyl-CoA acyl carrier protein transacylase from *Saccharomyces cerevisiae, Homo sapiens, Serratia plymuthica*, or *Dickeya paradisiaca* can be substituted for atoB, e.g., GenBank Accession Nos. DAA10992, AAH30985, AG055277, and ACS85236, respectively.

For example, a 3-hydroxy-butyryl-CoA dehydrogenase (BHBD) can have at least 70% sequence identity (e.g., at least 75%, 80%, 85%, 90%, 95%, 97%, 98%, 99%, or 100%) to the amino acid sequence of a *Clostridium acetobutylicum* BHBD (see SEQ ID NO:85, FIG. 6A), or a BHBD from *Escherichia coli, Treponema denticola*, or *Arabidopsis thaliana*, e.g., GenBank Accession Nos. AIZ91493, AAS11105, and AAN17431, respectively.

For example, an enoyl-CoA hydratase (ECH) can have at least 70% sequence identity (e.g., at least 75%, 80%, 85%, 90%, 95%, 97%, 98%, 99%, or 100%) to the amino acid sequence of a *Clostridium acetobutylicum* ECH (see SEQ ID NO:86, FIG. 6A), or an ECH from *Acinetobacter oleivorans, Cupriavidus necator*, or *Acinetobacter baumannii*, e.g., GenBank Accession Nos. ADI91469, CAJ91294, and ACJ57023, respectively.

For example, a beta-ketothiolase (bktB) can have at least 70% sequence identity (e.g., at least 75%, 80%, 85%, 90%, 95%, 97%, 98%, 99%, or 100%) to the amino acid sequence of a *Cupriavidus necator* bktB (see SEQ ID NO:87, FIG. 6A), or a bktB from *Escherichia coli, Lactobacillus casei*, or *Clostridium acetobutylicum*, e.g., GenBank Accession Nos. ALI39443, CAQ67083, and AAK80816, respectively.

For example, a trans-2-enoyl-CoA-reductase (ECR) can have at least 70% sequence identity (e.g., at least 75%, 80%, 85%, 90%, 95%, 97%, 98%, 99%, or 100%) to the amino acid sequence of a *Treponema denticola* ECR (see SEQ ID NO:88, FIG. 6A), or an ECR from *Cupriavidus necator, Saccharomyces cerevisiae*, or *Klebsiella michiganensis*, e.g., GenBank Accession Nos. AAP86010, DAA07148, and AIE72439, respectively.

For example, a hexanoyl-CoA synthetase (HCS), which is a type of acyl-activating enzyme (AAE), can have at least 70% sequence identity (e.g., at least 75%, 80%, 85%, 90%, 95%, 97%, 98%, 99%, or 100%) to the amino acid sequence of a *C. sativa* AAE1 (see SEQ ID NO:89, FIG. 6A, GenBank Accession No. AFD33345) or *C. sativa* AAE3 (GenBank Accession No. AFD33347). The *C. sativa* AAE1 and AAE3 each can use hexanoate as a substrate. See, Stout, et al., *Plant* 1, 71(3): 353-365 (2012). In some embodiments, the AAE encoded by CsAAE1 can be used. See, GenBank Accession No. JN717233 for the coding sequence. In some embodiments, the AAE encoded by CsAAE3 can be used. See, GenBank Accession No. JN717233 for the coding sequence. In some embodiments, both CsAAE1 and CsAAE3 can be used.

For example, an HMG-CoA synthase (HMGS) can have at least 70% sequence identity (e.g., at least 75%, 80%, 85%, 90%, 95%, 97%, 98%, 99%, or 100%) to the amino acid sequence of a *S. cerevisiae* HMGS (see SEQ ID NO:90, FIG. 6A), or an HMGS from *Arabidopsis thaliana, Lactobacillus casei*, or *Homo sapiens*, e.g., GenBank Accession Nos. AEE83052, CAQ67081, and AAA62411, respectively.

For example, an HMG-CoA reductase (HMGR), N-terminally truncated or canonical, can have at least 70% sequence identity (e.g., at least 75%, 80%, 85%, 90%, 95%, 97%, 98%, 99%, or 100%) to the amino acid sequence of a *S. cerevisiae* HMGS (see SEQ ID NO:91, FIG. 6A), or an HMGR from *Arabidopsis thaliana, Lactobacillus casei*, or *Homo sapiens*, e.g., GenBank Accession Nos. AEE35849, CAQ67082, and AAA52679, respectively.

For example, a mevalonate kinase can have at least 70% sequence identity (e.g., at least 75%, 80%, 85%, 90%, 95%, 97%, 98%, 99%, or 100%) to the amino acid sequence of a *S. cerevisiae* mevalonate kinase (see SEQ ID NO:92, FIG. 6A), or a mevalonate kinase from *Arabidopsis thaliana, Lactobacillus casei*, or *Homo sapiens*, e.g., GenBank Accession Nos. AAD31719, CAQ66794, and AAF82407, respectively.

For example, a phosphomevalonate kinase can have at least 70% sequence identity (e.g., at least 75%, 80%, 85%, 90%, 95%, 97%, 98%, 99%, or 100%) to the amino acid sequence of a *S. cerevisiae* phosphomevalonate kinase (see SEQ ID NO:93, FIG. 6A), or a mevalonate kinase from *Scheffersomyces stipitis, Lactobacillus casei*, or *Homo sapiens*, e.g., GenBank Accession Nos. EAZ63544, CAQ66339, and AAH06089, respectively.

For example, a diphosphomevalonate decarboxylase can have at least 70% sequence identity (e.g., at least 75%, 80%, 85%, 90%, 95%, 97%, 98%, 99%, or 100%) to the amino acid sequence of a *S. cerevisiae* diphosphomevalonate decarboxylase (see SEQ ID NO:94, FIG. 6A), or a diphosphomevalonate decarboxylase from *Arabidopsis thaliana, Lactobacillus casei*, or *Homo sapiens*, e.g., GenBank Accession Nos. AAC67348, CAQ66795, and AAC50440, respectively.

For example, an isopentyl diphosphate isomerase can have at least 70% sequence identity (e.g., at least 75%, 80%, 85%, 90%, 95%, 97%, 98%, 99%, or 100%) to the amino acid sequence of a *S. cerevisiae* isopentyl diphosphate isomerase (see SEQ ID NO:95, FIG. 6A), or an isopentyl diphosphate isomerase from *Arabidopsis thaliana, Lactobacillus casei*, or *Homo sapiens*, e.g., GenBank Accession Nos. AAC49920, CAQ66796, and AAP35407, respectively.

For example, a geranyl pyrophosphate synthase (GPPS) (also known as a geranyl-diphospate synthase) can have at least 70% sequence identity (e.g., at least 75%, 80%, 85%, 90%, 95%, 97%, 98%, 99%, or 100%) to the amino acid sequence of the *S. cerevisiae* GPS or a GPPS from *Acinetobacter baumannii, Lactobacillus casei*, or *Homo sapiens*, e.g., GenBank Accession Nos. ACJ56139, CAQ66932, and AAH10004, respectively. In some embodiments, a mutant GPPS can be used. For example, the GPPS encoded by Erg20 may include a substitution of a tryptophan for phenylalanine at position 96 and a substitution of a tryptophan for asparagine at position 127 (referred to as $Erg20^{WW}$) (see SEQ ID NO:96, FIG. 6A). $Erg20^{WW}$ favors production of geranyl pyrophosphate over farnesyl pyrophosphate. See, Jiang, et al., *Metab Eng.* 2017 41:57-66. In some cases, substituting a glutamic acid for lysine at position 179 of Erg20 ($Erg20^{K179E}$) can be used to produce a GPPS that favors production of geranyl pyrophosphate. See, WO2016010827A1.

For example, a DOXP synthase can have at least 70% sequence identity (e.g., at least 75%, 80%, 85%, 90%, 95%, 97%, 98%, 99%, or 100%) to the amino acid sequence of an *Escherichia coli, Clostridium acetobutylicum, Treponema denticola*, or *Arabidopsis thaliana* DOXP synthase, e.g., GenBank Accession Nos. CDH63925, AAK80036, AAS12424, and ANM65835, respectively.

For example, a DOXP reductoisomerase can have at least 70% sequence identity (e.g., at least 75%, 80%, 85%, 90%, 95%, 97%, 98%, 99%, or 100%) to the amino acid sequence of an *Escherichia coli, Clostridium acetobutylicum, Treponema denticola*, or *Arabidopsis thaliana* DOXP reductoisomerase, e.g., GenBank Accession Nos. CDH63708, AAK79760, AAS12860, and AAM61343, respectively.

For example, a MEP cytidyl transferase can have at least 70% sequence identity (e.g., at least 75%, 80%, 85%, 90%, 95%, 97%, 98%, 99%, or 100%) to the amino acid sequence of an *Escherichia coli, Clostridium acetobutylicum, Treponema denticola*, or *Arabidopsis thaliana* MEP cytidyl transferase, e.g., GenBank Accession Nos. CDH66380, AAK81121, AAS12810, and BAB21592, respectively.

For example, a CDPME kinase can have at least 70% sequence identity (e.g., at least 75%, 80%, 85%, 90%, 95%, 97%, 98%, 99%, or 100%) to the amino acid sequence of an *Escherichia coli, Clostridium acetobutylicum, Treponema denticola*, or *Arabidopsis thaliana* CDPME kinase, e.g., GenBank Accession Nos. CDH64802, AAK80844, AAS11855, and AEC07908, respectively.

For example, a MECDP synthase can have at least 70% sequence identity (e.g., at least 75%, 80%, 85%, 90%, 95%, 97%, 98%, 99%, or 100%) to the amino acid sequence of an *Escherichia coli, Nicotiana tabacum, Treponema denticola*, or *Acinetobacter baumannii* MECDP synthase, e.g., GenBank Accession Nos. CDH66379, AHM22925, AAS12811, and ACJ59227, respectively.

For example, an HMBPP synthase can have at least 70% sequence identity (e.g., at least 75%, 80%, 85%, 90%, 95%, 97%, 98%, 99%, or 100%) to the amino acid sequence of an *Escherichia coli, Acinetobacter baumannii, Treponema denticola*, or *Arabidopsis thaliana* HMBPP synthase, e.g., GenBank Accession Nos. AAN81487, ACJ58210, AAS11783, and AED97354, respectively.

For example, an HMBPP reductase can have at least 70% sequence identity (e.g., at least 75%, 80%, 85%, 90%, 95%, 97%, 98%, 99%, or 100%) to the amino acid sequence of an *Escherichia coli, Acinetobacter baumannii, Treponema denticola*, or *Arabidopsis thaliana* HMBPP reductase, e.g., GenBank Accession Nos. CDH63564, ACJ57384, AAS11585, and AEE86362, respectively.

For example, an acetyl-CoA carboxylase (ACC) can have at least 70% sequence identity (e.g., at least 75%, 80%, 85%, 90%, 95%, 97%, 98%, 99%, or 100%) to the amino acid sequence of a *S. cerevisiae* acetyl-CoA carboxylase (see SEQ ID NO:97, FIG. 6A), or an acetyl-CoA carboxylase from *Homo sapiens, Treponema denticola*, or *Cupriavidus necator*, e.g., GenBank Accession Nos. AAP94122, AAS11086, and CAQ67359, respectively.

For example, a pyruvate dehydrogenase (E1) and dihydrolipoyl transacetylase (E2) can have at least 70% sequence identity (e.g., at least 75%, 80%, 85%, 90%, 95%, 97%, 98%, 99%, or 100%) to the amino acid sequence of a *Saccharomyces cerevisiae, Escherichia coli, Clostridium acetobutylicum*, or *Cupriavidus necator* E1 and E2, e.g., GenBank Accession Nos. DAA07337, AMC97367, CAQ66617, and CAJ92510 for E1, and DAA10474, AUG14916, CAQ66619, and CAJ92511 for E2, respectively.

For example, an olivetol synthase (OS) can have at least 70% sequence identity (e.g., at least 75%, 80%, 85%, 90%, 95%, 97%, 98%, 99%, or 100%) to the amino acid sequence of an OS from *C. sativa* set forth in SEQ ID NO:98 (FIG. 6A) or the OS from *C. sativa* having GenBank Accession No. BAG14339. See, for example, Taura, et al., *FEBS Letters* 583 (2009) 2061-2066.

For example, an olivetolic acid cyclase (OAC) can have at least 70% sequence identity (e.g., at least 75%, 80%, 85%, 90%, 95%, 97%, 98%, 99%, or 100%) to the amino acid sequence of an OAC from *C. sativa* set forth in SEQ ID NO:99 (FIG. 6A) or the OAC from *C. sativa* having GenBank Accession No. AFN42527. See, for example, Gagne, et al., *Proc. Natl. Acad. Sci. USA,* 2012 109 (31) 12811-12816.

For example, a CBGAS can have at least 70% sequence identity (e.g., at least 75%, 80%, 85%, 90%, 95%, 97%, 98%, 99%, or 100%) to the amino acid sequence of an aromatic prenyl-transferase (APT) from *Cannabis sativa* such as the CBGAS set forth in SEQ ID NO:100 (FIG. 6A). See, for example, U.S. Patent Publication No. 20120144523A1 and U.S. Pat. No. 8,884,100B2. In some embodiments, a soluble APT from *Streptomyces* (e.g., NphB) can be used. See, for example, Carvalho et al., *FEMS Yeast Research,* 17, 2017, fox037.

For example, a cannabidiolic acid synthase (CBDAS) can have at least 70% sequence identity (e.g., at least 75%, 80%, 85%, 90%, 95%, 97%, 98%, 99%, or 100%) to the amino acid sequence of a CBDAS from *C. sativa* set forth in SEQ ID NO:101 (FIG. 6A) or the amino acid sequence of a CBDAS from *C. sativa* having GenBank Accession No. BAF65033. See, for example, Taura, et al., *FEBS Lett.* 581 (16), 2929-2934 (2007).

For example, a cannabichromenic acid synthase (CBCAS) can have at least 70% sequence identity (e.g., at least 75%, 80%, 85%, 90%, 95%, 97%, 98%, 99%, or 100%) to the amino acid sequence of a CBCAS from *C. sativa* set forth in SEQ ID NO:102 (FIG. 6A) or the amino acid sequence of a CBCAS from *C. sativa* as set forth in SEQ ID NO:2 of WO 2015/196275 A1. SEQ ID NO:2 of WO 2015/196275 A1 includes an N-terminal 28 amino acid signal peptide. All or a portion of the signal peptide can be removed from the sequence. The CBDAS from *C. indica* or *C. ruderalis* also can be used. In some embodiments, an *Escherichia coli* or yeast optimized nucleic acid sequence encoding a *C. sativa* CBCAS as set forth in SEQ ID NOs: 8 and 9, respectively, of WO 2015/196275 A1 can be used.

For example, a tetrahydrocannabinolic acid synthase (THCAS) can have at least 70% sequence identity (e.g., at least 75%, 80%, 85%, 90%, 95%, 97%, 98%, 99%, or 100%) to the amino acid sequence of a THCAS from *C. sativa* having GenBank Accession No. BAC41356. See, for example, Sirikantaramas, et al., *J. Biol. Chem.* 279 (38), 39767-39774 (2004).

The percent identity (homology) between two amino acid sequences can be determined as follows. First, the amino acid sequences are aligned using the BLAST 2 Sequences (B12seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C: \seq1.txt); -j is set to a file containing the second amino acid sequence to be compared (e.g., C: \seq2.txt); -p is set to blastp; -o is set to any desired file name (e.g., C: \output.txt); and all other options are left at their default setting. For example, the following command can be used to generate an output file containing a comparison between two amino acid sequences: C: \B12seq-i c: \seq1.txt-j c: \seq2.txt-p blastp-o c: \output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) can be attained, using appropriate codon bias tables for that species. For example, the nucleotide sequences set forth in FIG. 12A are the nucleic acid sequences encoding an ATP citrate lyase, an atoB, a 3-hydroxbutyryl-CoA dehydrogenase, an enoyl-CoA hydratase, a beto-ketothiolase (bktB), a trans-enoyl-CoA reductase, an HMG-CoA synthase, an HMG-CoA reductase, a mevalonate kinase, a phosphomevalonate kinase, a diphosphomevalonate decarboxylase, an isopentenyl-diphosphate delta isomerase, a geranyl-diphosphate synthase ($ERG20^{WW}$), an olivetol synthase, an olivetolic acid cyclase, a CBGA synthase, a CBDA synthase, a CBCA synthase, an acetyl-CoA carboxylase, and a hexanoyl-CoA synthetase. The nucleic acid sequences for the ATP citrate lyase, atoB, 3-hydroxybutyryl-CoA dehydrogenase, enoyl-CoA hydratase, trans-enoyl-CoA reductase, bktB, olivetol synthase, olivetolic acid cyclase, CBGA synthase, CBDA synthase, and CBCA synthase have been codon optimized for expression in yeast. FIGS. 14A-14C contain codon optimized (for expression in yeast) nucleic acid sequences encoding the engineered enzymes of FIGS. 13A-13C.

In addition to sequence similarity, it will be appreciated that enzymes and scaffolds with structural and/or functional similarity to the enzymes and scaffolds described herein are also encompassed within the scope of the document.

Figure 2A:
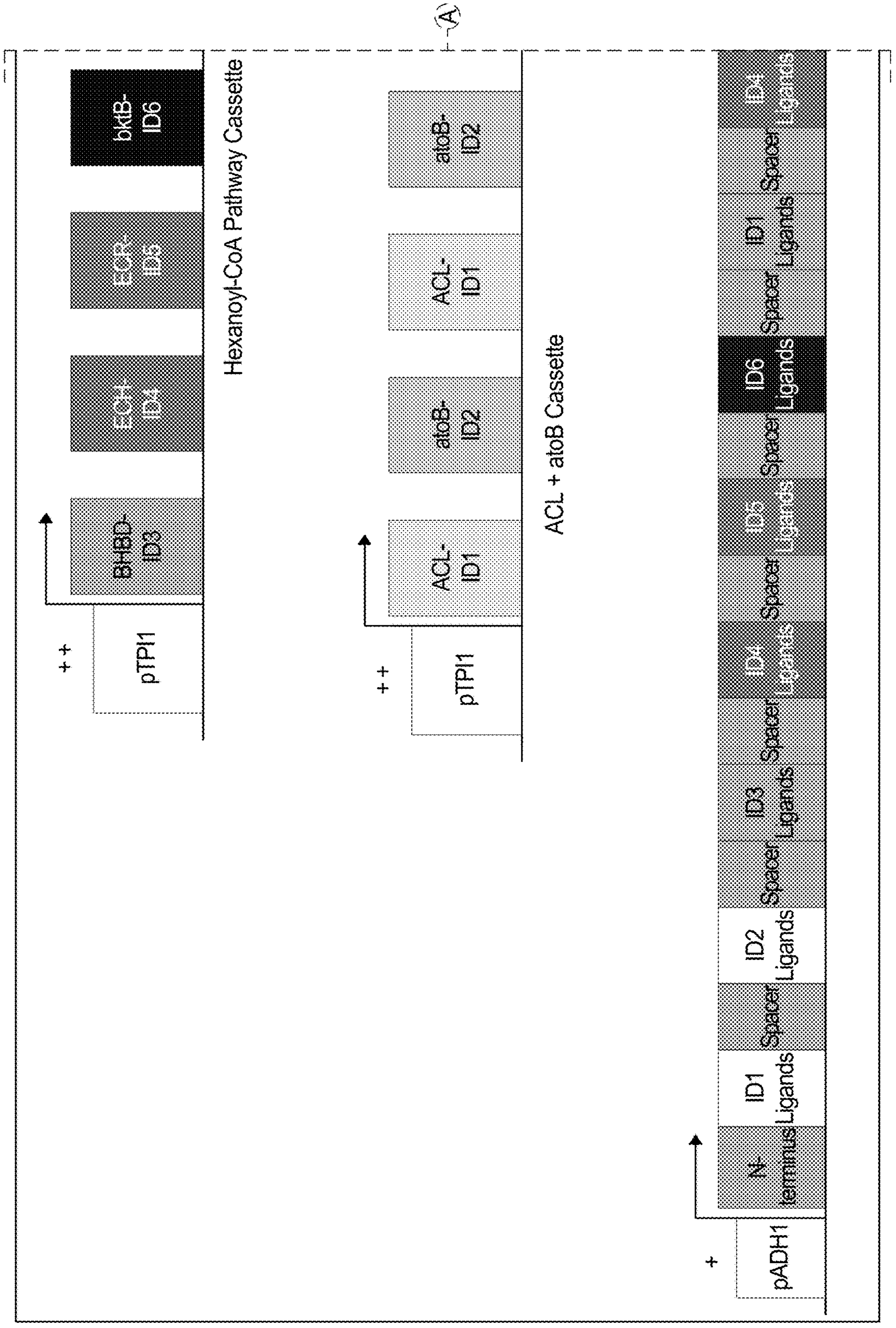
FIG. 2A is a schematic of gene cassettes according to one embodiment for the engineering of cannabinoidergic cells.
Figure 2A:
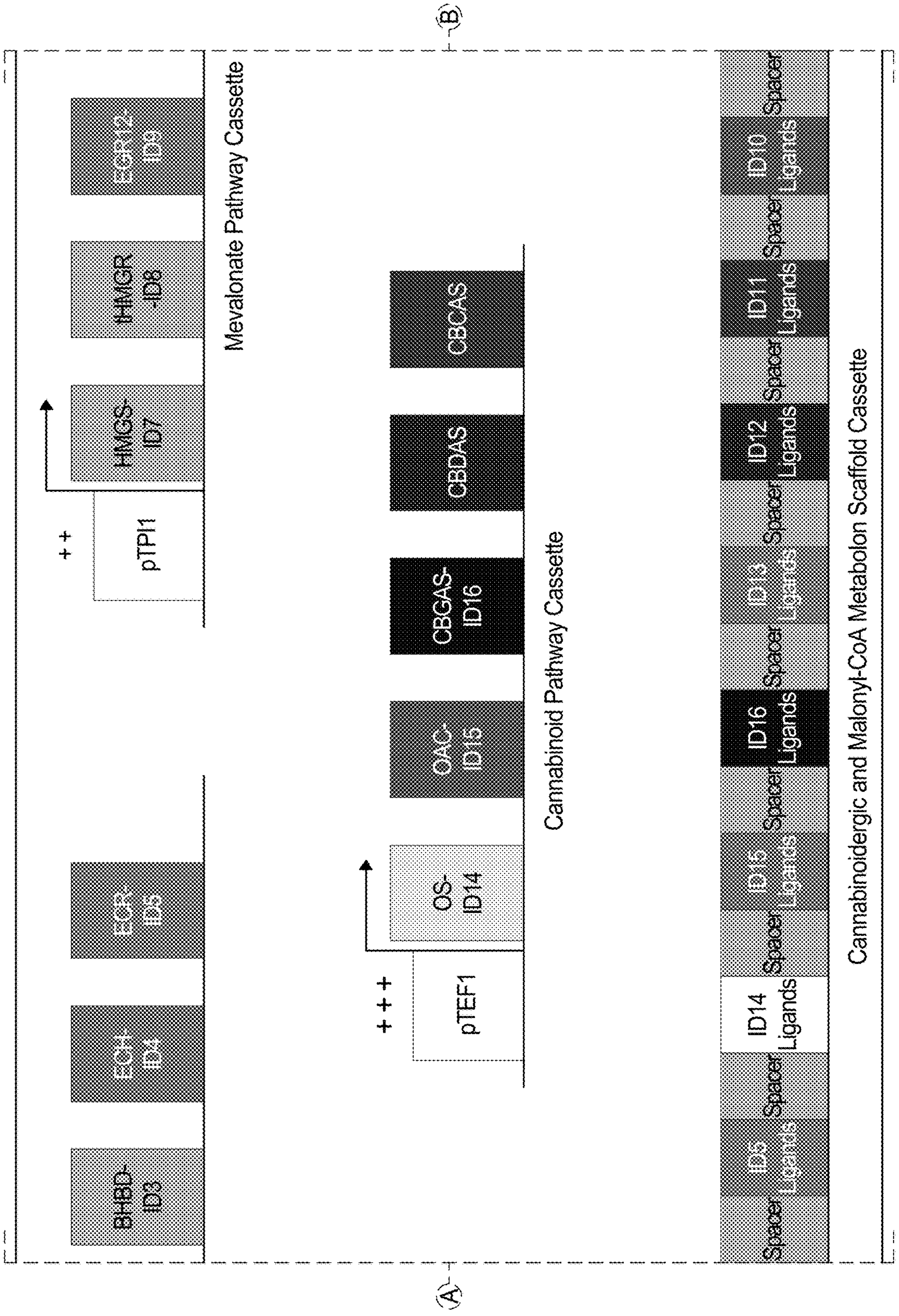
Figure 2A:
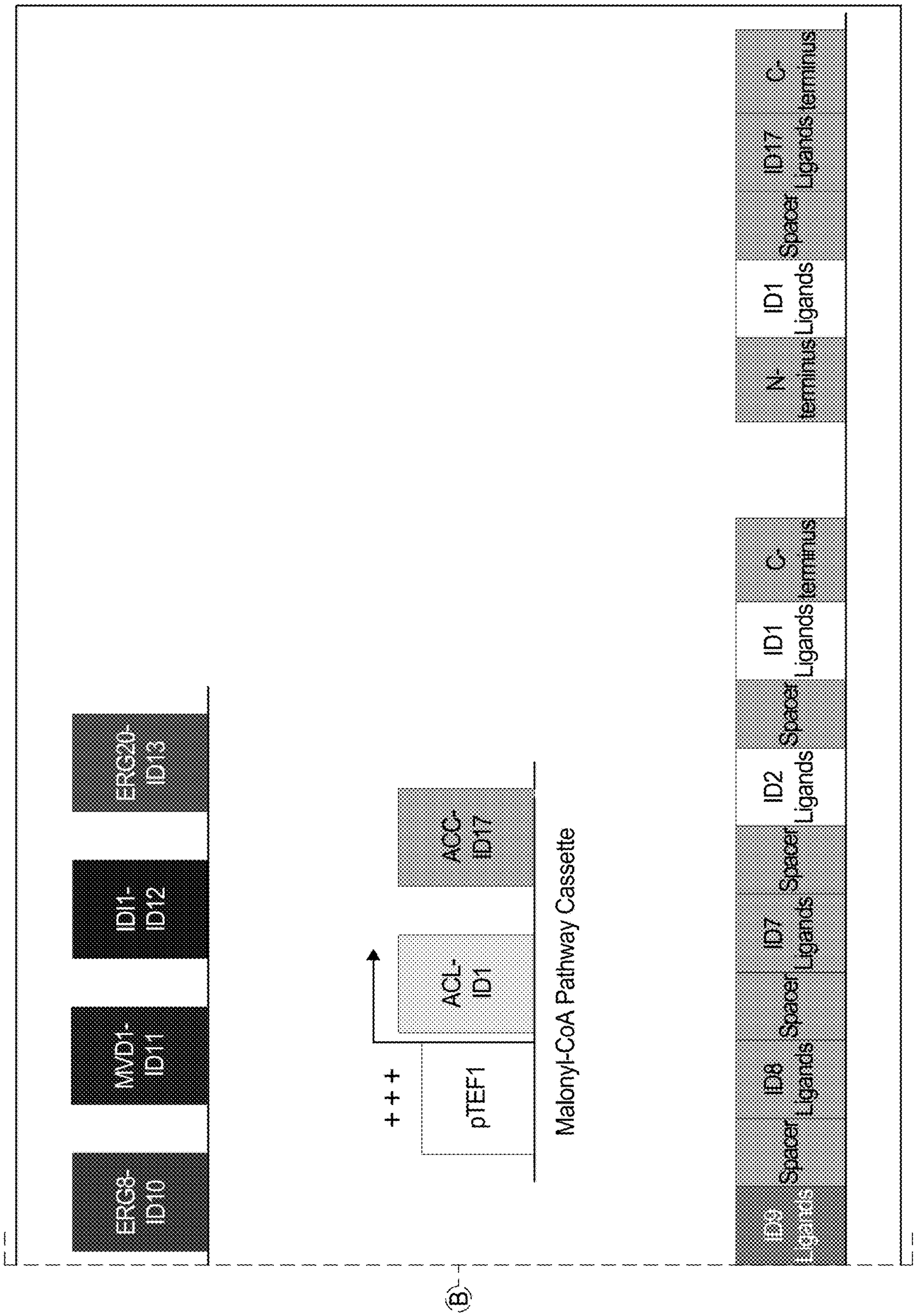
Figure 2B:
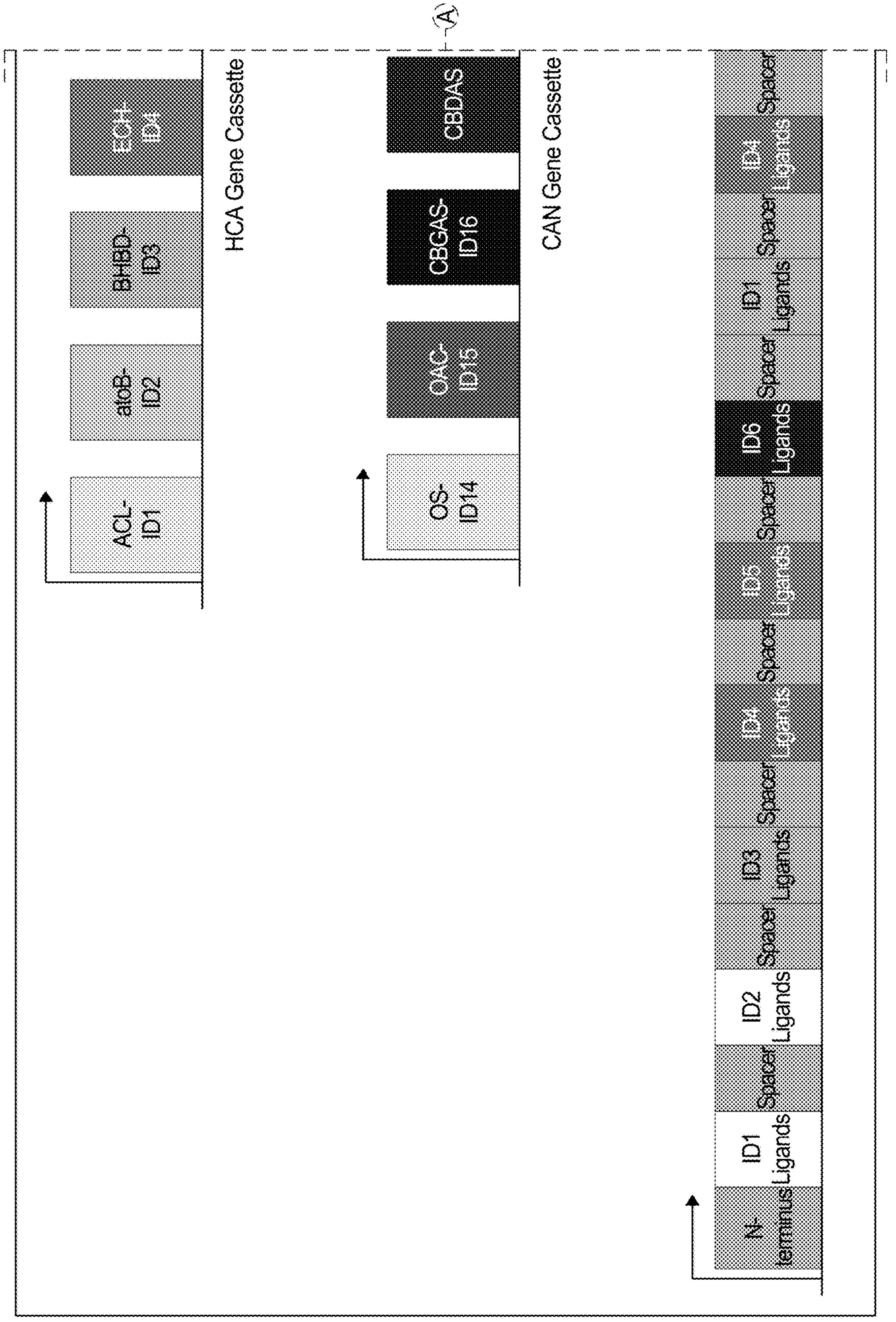
FIG. 2B is a schematic of gene cassettes used in Examples 2-4 for biosynthesizing cannabinoids in yeast.
Figure 2B:
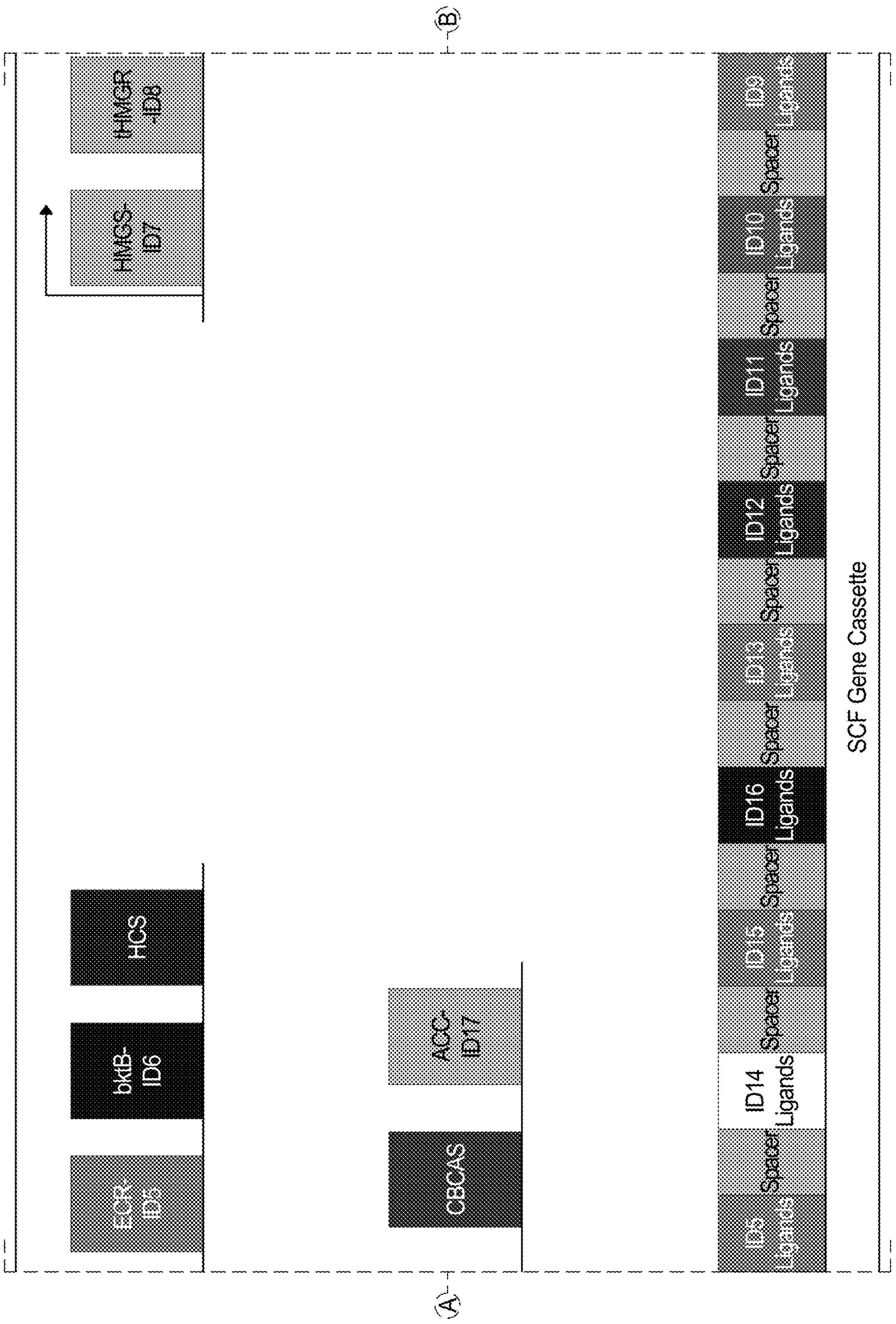
Figure 2B:
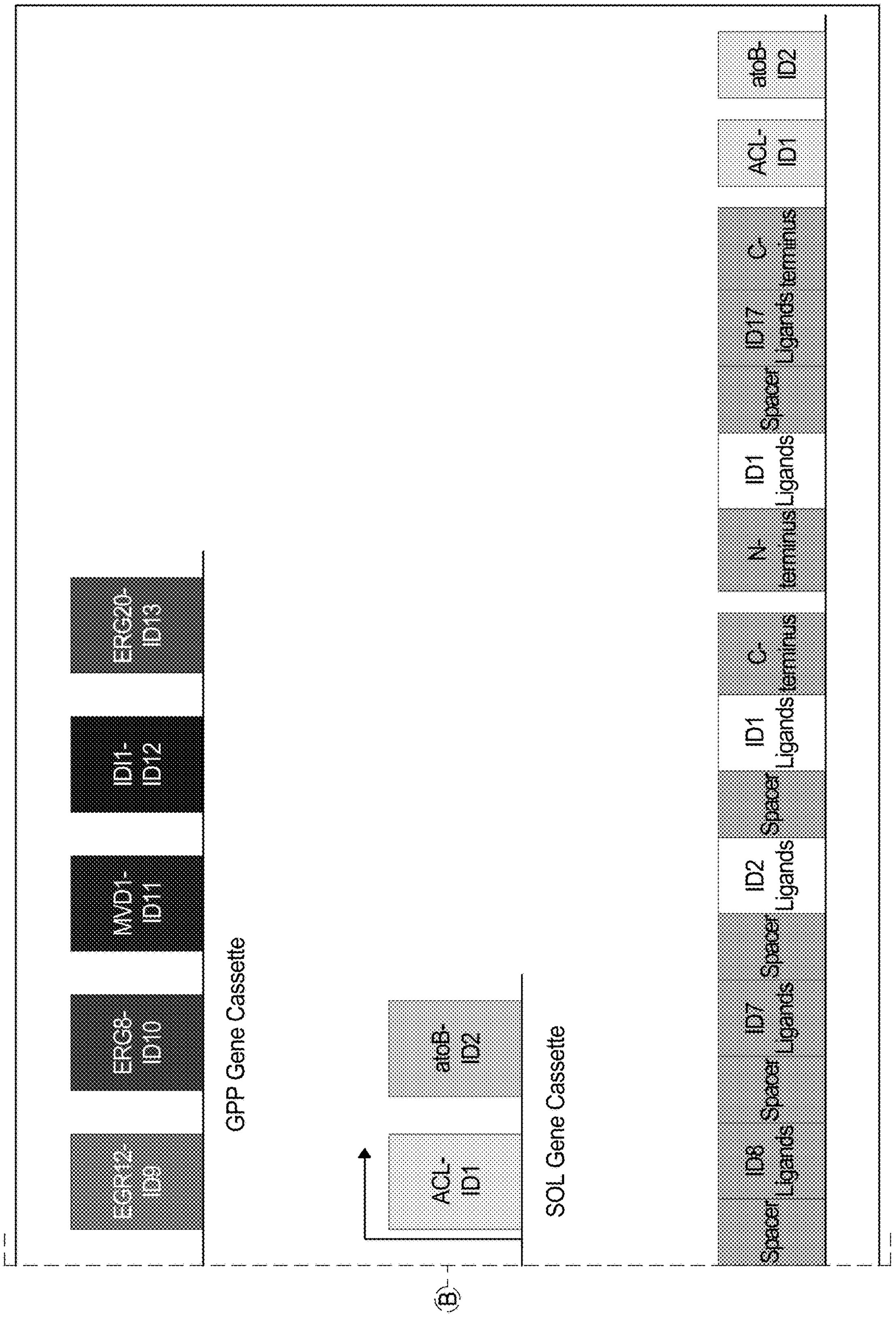

This document provides recombinant host cells that can be used to produce one or more cannabinoids as described herein. For example, an individual host cell can contain exogenous nucleic acid such that the scaffold polypeptide and each of the enzymes to be immobilized on the scaffold are expressed. It is important to note that such host cells can contain any number and/or combination of exogenous nucleic acid molecules. For example, a particular host cell can contain an exogenous nucleic acid encoding the scaffold, and additional exogenous nucleic acids encoding the enzymes of the malonyl-CoA pathway, enzymes of the hexanoyl-CoA pathway or encoding a HCS, and enzymes of the mevalonate or MEP pathway. A single exogenous nucleic acid can encode one enzyme or more than one enzyme (e.g., one or more copies of from one to ten (or more) enzymes, from one to eight, from one to seven, from one to six, from one to five, from one to four, or from two to three enzymes). Thus, the number of different exogenous nucleic acids needed to produce the engineered enzymes to be localized on the scaffold will depend on the design of the scaffold and/or the particular embodiment. FIG. 2A and FIG. 2B each provide a non-limiting schematic of suitable gene cassettes for expressing the scaffolds and enzymes. FIG. 12C provides the nucleic acid sequence encoding a scaffold polypeptide containing the peptide ligands corresponding to IDs 1-16 as shown in Table 2 and a triplicate MYC tag. See also FIG. 14D for the codon-optimized nucleic acid sequence encoding the scaffold polypeptide of FIG. 13D. FIG. 12D provides the nucleic acid sequence encoding a scaffold polypeptide that contains the peptide ligands corresponding to IDs 1 and 17, and a triplicate FLAG tag. See also FIG. 14D.

In some embodiments, multiple nucleic acids encoding polypeptides (e.g., the nucleic acids of a gene cassette such as in FIG. 2A or FIG. 2B) can be linked together using a nucleic acid sequence encoding a self-cleaving peptide. During translation of the transcripts, the growing polypeptide can be cleaved at the 2A peptide with translation continuing through to the next polypeptide. When designing a vector to express the polypeptides as a polycistronic unit, the nucleic acid encoding the polypeptides and the self-cleaving peptide (e.g., a 2A peptide) can be designed such that they are in translational frame with each other. Examples of 2A peptides that can be used as described herein include, without limitation, a 2A peptide of foot-and-mouth disease virus (FMDV), a 2A peptide of equine rhinitis A virus (ERAVO), a 2A peptide of Thosea asigna virus (TaV), or a 2A peptide of porcine teschovirus-1 (PTV-1) or porcine teschovirus-2 (PTV-2). The 2A peptides from PTV-1 and PTV-2 are referred to as P2A peptides. See, e.g., SEQ ID NO:212 for a codon-optimized nucleotide sequence (for *S. cerevisiae*) encoding a P2A peptide.

Further, the cells described herein can contain a single copy or multiple copies (e.g., about 5, 10, 20, 35, 50, 75, 100 or 150 copies), of a particular exogenous nucleic acid molecule. Again, the cells described herein can contain more than one particular exogenous nucleic acid molecule and/or copies thereof. For example, a particular cell can contain about 50 copies of exogenous nucleic acid molecule X as well as about 75 copies of exogenous nucleic acid molecule Y.

Any method can be used to introduce an exogenous nucleic acid molecule into a host cell. In fact, many methods for introducing nucleic acid into host cells such as bacteria and yeast are well known to those skilled in the art. For example, heat shock, lipofection, electroporation, nucleofection, conjugation, fusion of protoplasts, and biolistic delivery are common methods for introducing nucleic acid into bacteria and yeast cells. See, e.g., Ito et al., *J. Bacterol.* 153:163-168 (1983); Durrens et al., *Curr. Genet.* 18:7-12 (1990); and Becker and Guarente, *Methods in Enzymology* 194:182-187 (1991).

An exogenous nucleic acid molecule contained within a particular host cell can be maintained within that host cell in any form. For example, exogenous nucleic acid molecules can be integrated into the genome of the microorganism or maintained in an episomal state. In other words, a microorganism can be a stable or transient transformant. Again, a microorganism described herein can contain a single copy, or multiple copies (e.g., about 5, 10, 20, 35, 50, 75, 100 or 150 copies), of a particular exogenous nucleic acid molecule as described herein.

Suitable nucleic acid constructs for expressing the engineered enzymes and scaffolds include, for example, CRISPR plasmids, baculovirus vectors, bacteriophage vectors, plasmids, phagemids, cosmids, fosmids, bacterial artificial chromosomes, viral vectors (for example, viral vectors based on vaccinia virus, poliovirus, adenovirus, adeno-associated virus, SV40, herpes simplex virus, and the like), P1-based artificial chromosomes, yeast plasmids, yeast artificial chromosomes, and other vectors. Typically such constructs include a regulatory element that promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Any type of promoter can be used to express an amino acid sequence from an exogenous nucleic acid molecule. Examples of promoters include, without limitation, constitutive promoters, tissue-specific promoters, and inducible or repressible promoters that are responsive or unresponsive to a particular stimulus (e.g., light, oxygen, chemical concentration, sound, and the like).

In some embodiments, endogenous yeast promoters with varying constitutive activity levels can be used to express the engineered enzymes and/or scaffolds. To maintain an excess of enzymes relative to scaffold molecules, the scaffolds can be expressed under control of the weakest promoter. For example, one or more of the following yeast promoters can be used: the promoter from the gene encoding transcriptional elongation factor EF-1α (pTEF1), the promoter from the gene encoding phosphoglycerate kinase (PGK1), the promoter from the gene encoding triose phosphate isomerase (pTPI1), the promoter from the gene encoding a hexose transporter (pHXT7), HXT7, the promoter from the gene encoding pyruvate kinase 1 (pPYK1), the promoter from the gene encoding alcohol dehydrogenase 1 (pADH1), or the promoter from the gene encoding triphosphate dehydrogenase (pTDH3). For example, in the embodiment shown in FIG. 2A, the pTPI1 promoter can be used to express enzymes of the upper hexanoyl-CoA (HCA), enzymes of the lower HCA pathway, enzymes of the upper mevalonate (MVA) pathway, enzymes of the lower MVA pathway, and enzymes of the lower cannabinoid (CB) pathway, while the pTEF1 promoter can be used to express enzymes of the upper CB pathway, the atoB enzyme, and the enzymes of the malonyl-CoA pathway, and the pADH1 promoter can be used to express the scaffold. Of these promoters, the pADH1 promoter has the weakest activity (+ in FIG. 2A), the pTEF1 promoter has the strongest activity (+++ in FIG. 2A), and the activity of the pTPI1 promoter is between the other two (++ in FIG. 2A). In some embodiments, the Gal 1-10 promoter (e.g., from *S. cerevisiae*) can be used. See, e.g., FIG. 17.

A nucleic acid construct also can include a selectable marker, e.g., for an antibiotic such as neomycin resistance, ampicillin resistance, tetracycline resistance, chloramphenicol resistance, or kanamycin resistance). In some embodiments, a nutritional marker gene that confers prototrophy for an essential nutrient such as tryptophan (TRP1), uracil (URA3), histidine (HIS3), leucine (LEU2), lysine (LYS2), or methionine can be included on a nucleic acid construct. See, e.g., FIG. 17. As shown in Example 3, four different auxotrophic markers were used to sequentially select for transformed cells containing the desired combinations of nucleic acids encoding the enzymes and scaffold. For example, yeast cells transformed with a vector containing a TRP gene and the nucleic acids encoding enzymes of the hexanoyl-CoA pathway were grown in tryptophan deficient media. The transformed cells that grew in the tryptophan deficient media were selected and further transformed with a vector containing a LEU gene and nucleic acid encoding enzymes of the mevalonate pathway. The resulting transformed cells were grown on media lacking tryptophan and leucine, and the cells that grew in the media lacking tryptophan and leucine were transformed with a vector containing a HIS gene and nucleic acids encoding enzymes of the upper cannabinoid pathway. The resulting transformed cells were grown on media lacking tryptophan, leucine, and histidine, and the cells that grew in the media lacking tryptophan, leucine, and histidine were transformed with a vector containing a URA3 gene and a nucleic acid encoding a scaffold. The resulting transformed cells were grown on media lacking tryptophan, leucine, histidine, and uracil. Cells that grew in media lacking tryptophan, leucine, histidine, and uracil contained the desired combination of enzymes and scaffold as shown in FIG. 1B.

In some embodiments, the encoded enzymes (e.g., one or more enzymes from the cannabinoid biosynthesis pathway, mevalonate pathway, MEP pathway, hexanoyl-CoA pathway, or a hexanoyl-CoA synthetase) and/or the scaffold can include a targeting sequence that can be used to direct the enzymes or scaffold to one of several different intracellular compartments, including, for example, the endoplasmic reticulum (ER), mitochondria, plastids (such as chloroplasts), the vacuole, the Golgi apparatus, or protein storage vesicles (PSV). For example, a mitochondrial or plastidial targeting sequence can be used to facilitate mitochondrial or plastidial compartmentalization of cannabinoid/cannabinoid precursor biosynthesis such that the encoded enzymes and scaffold are expressed in the mitochondria or plastids of the host cell.

Figure 11:
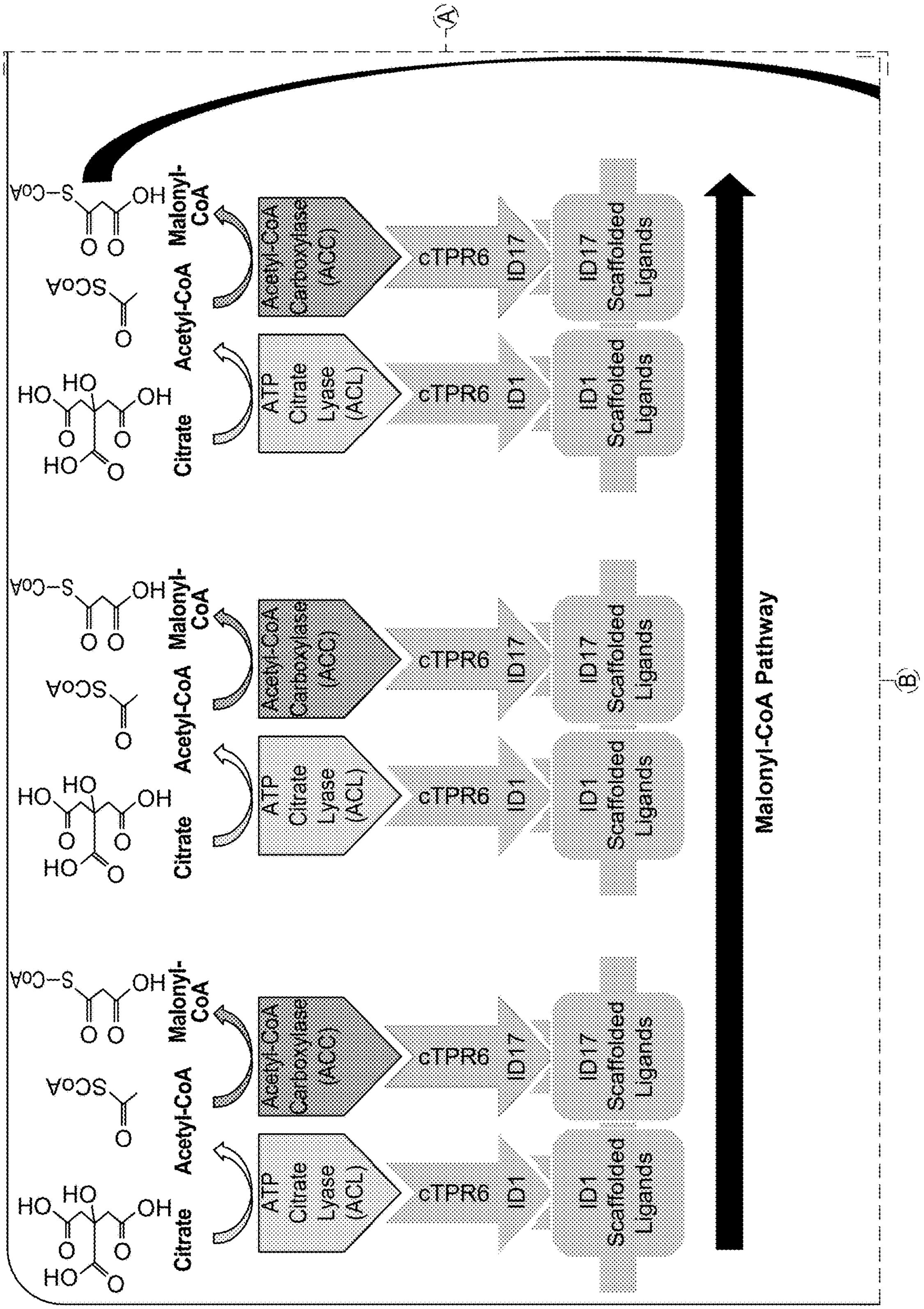
FIG. 11 is a schematic of one representative embodiment of a multi-enzymatic cannabinoidergic scaffold within dual compartments of a cell, the cytosol and mitochondria/plastid.
Figure 11:
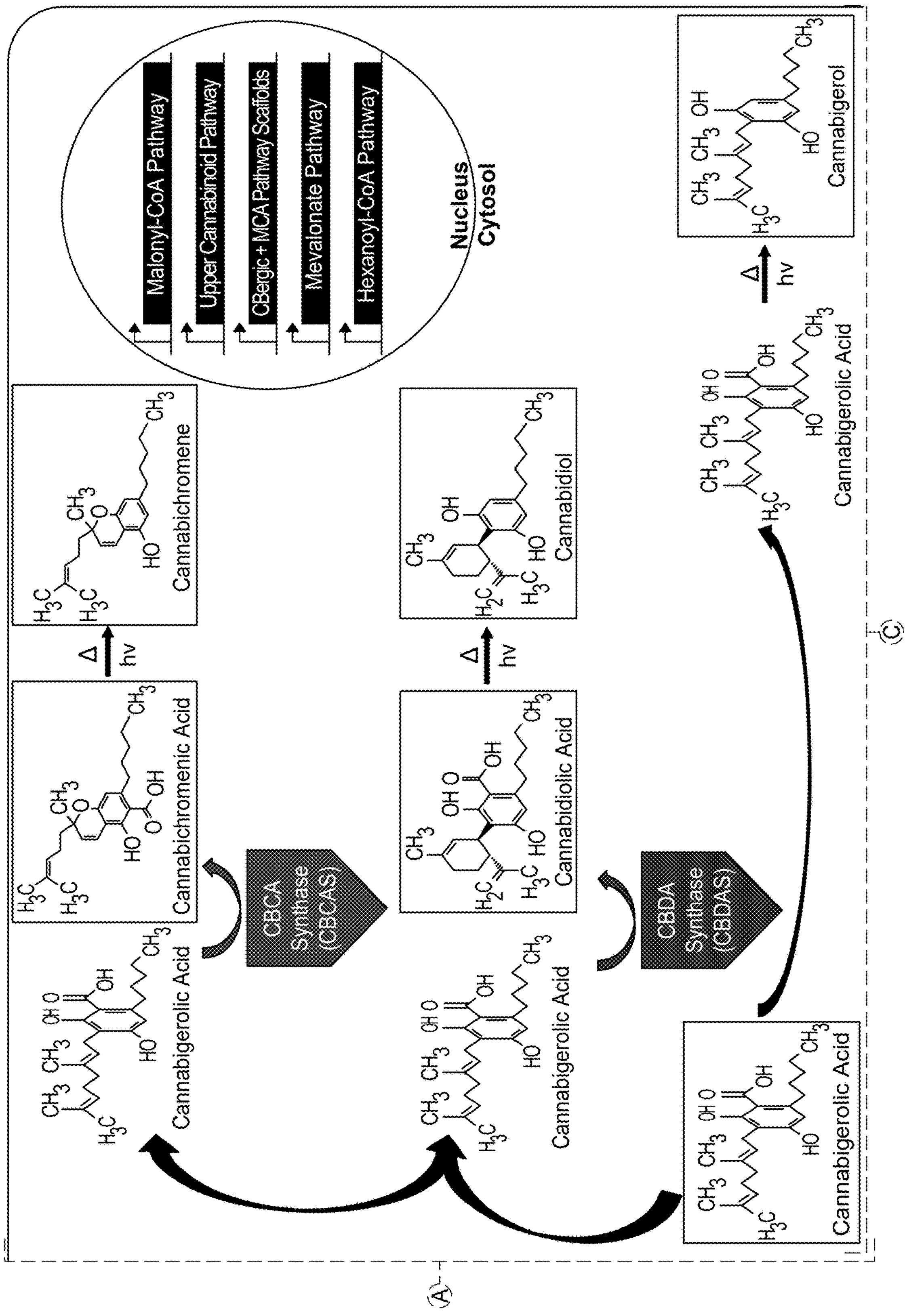
Figure 11:
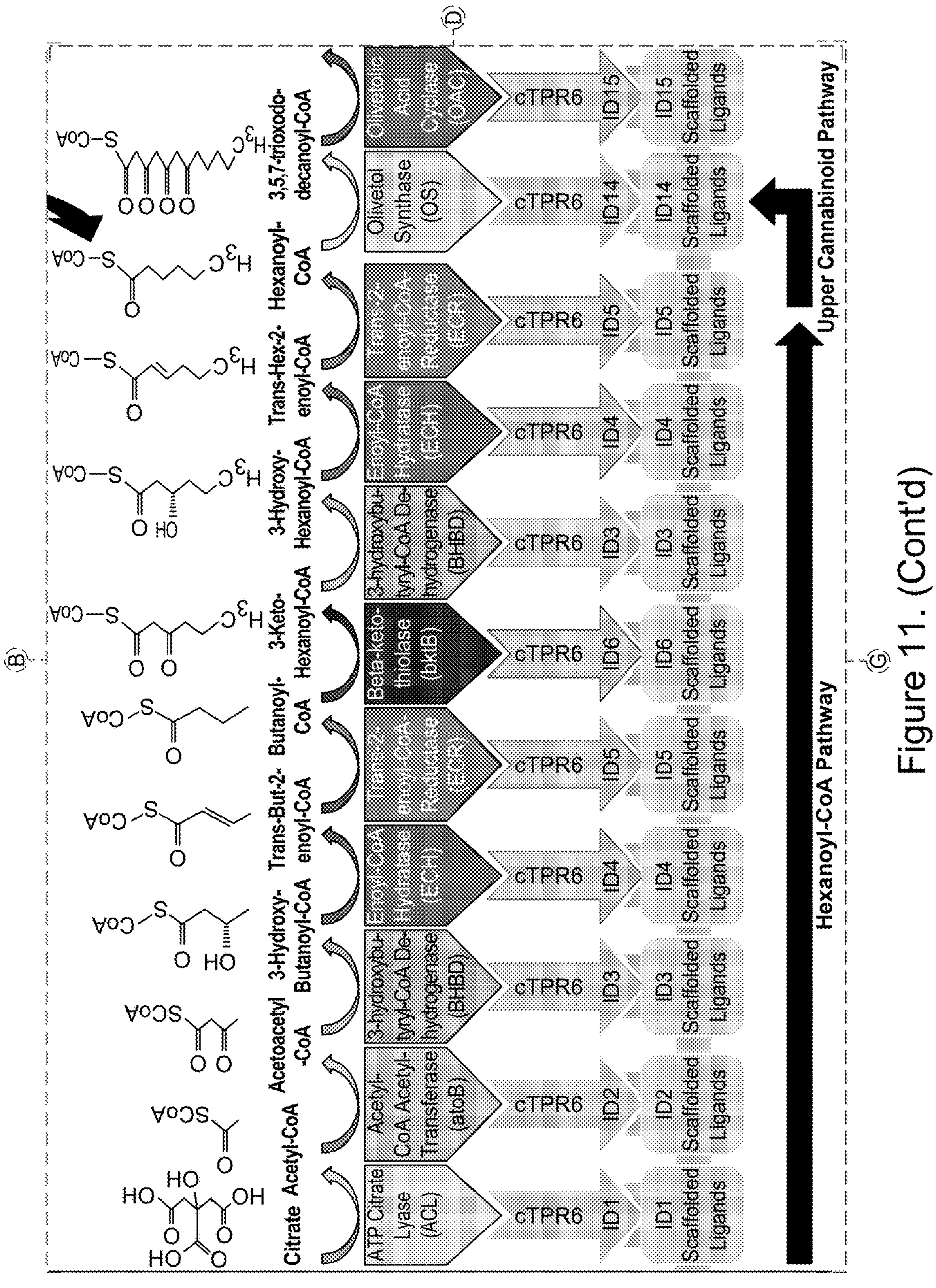
Figure 11:
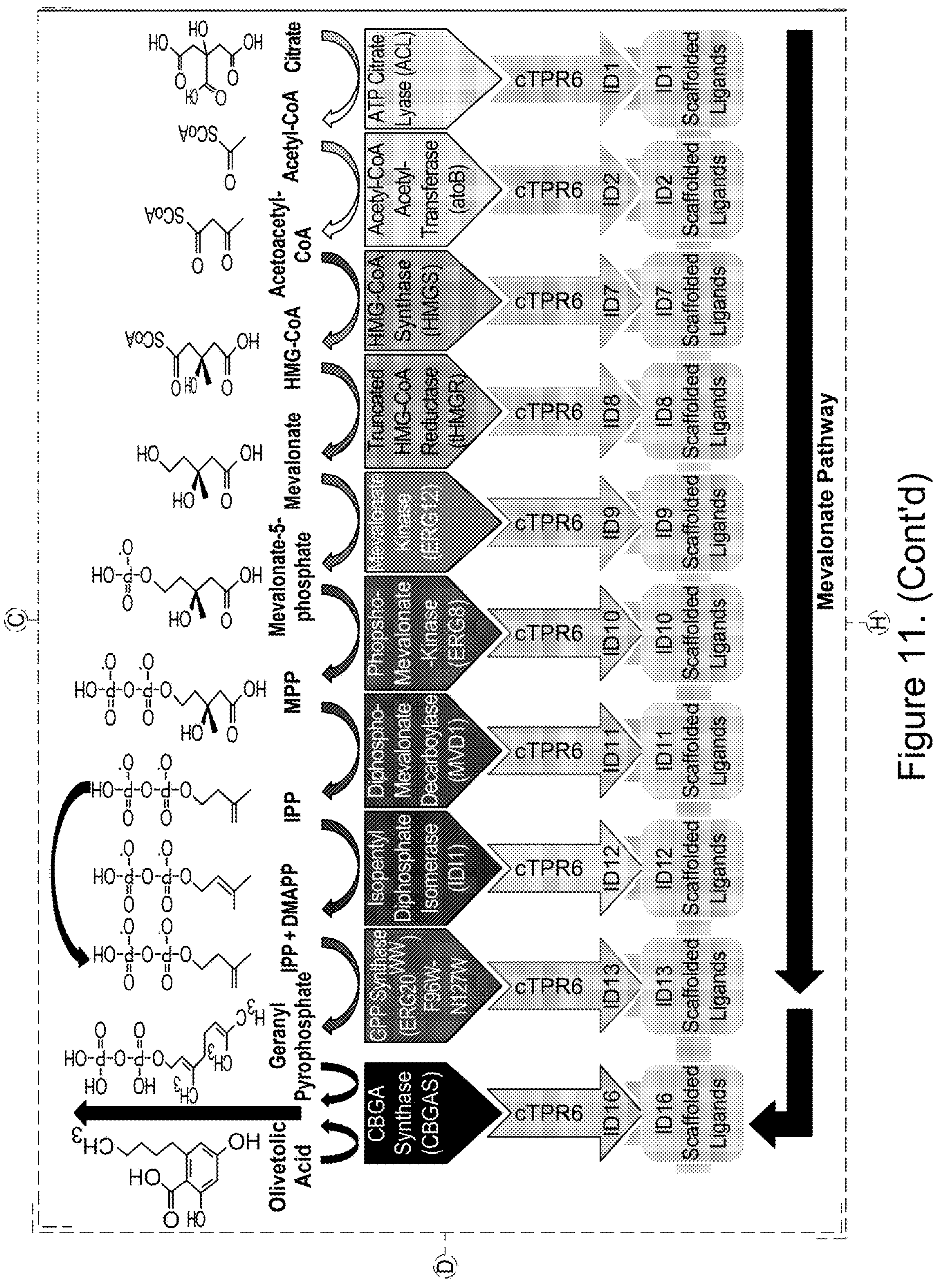
Figure 11:
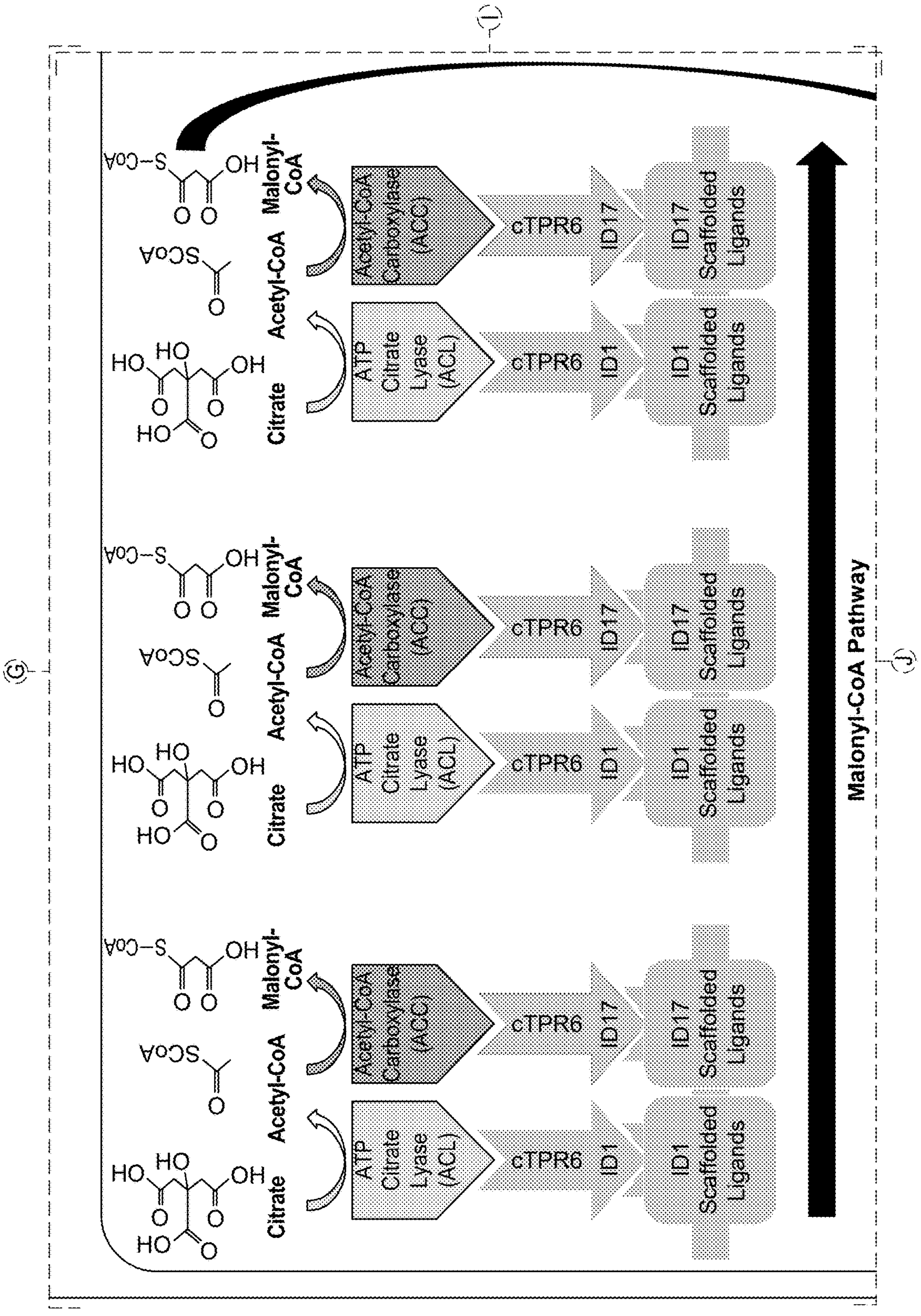
Figure 11:
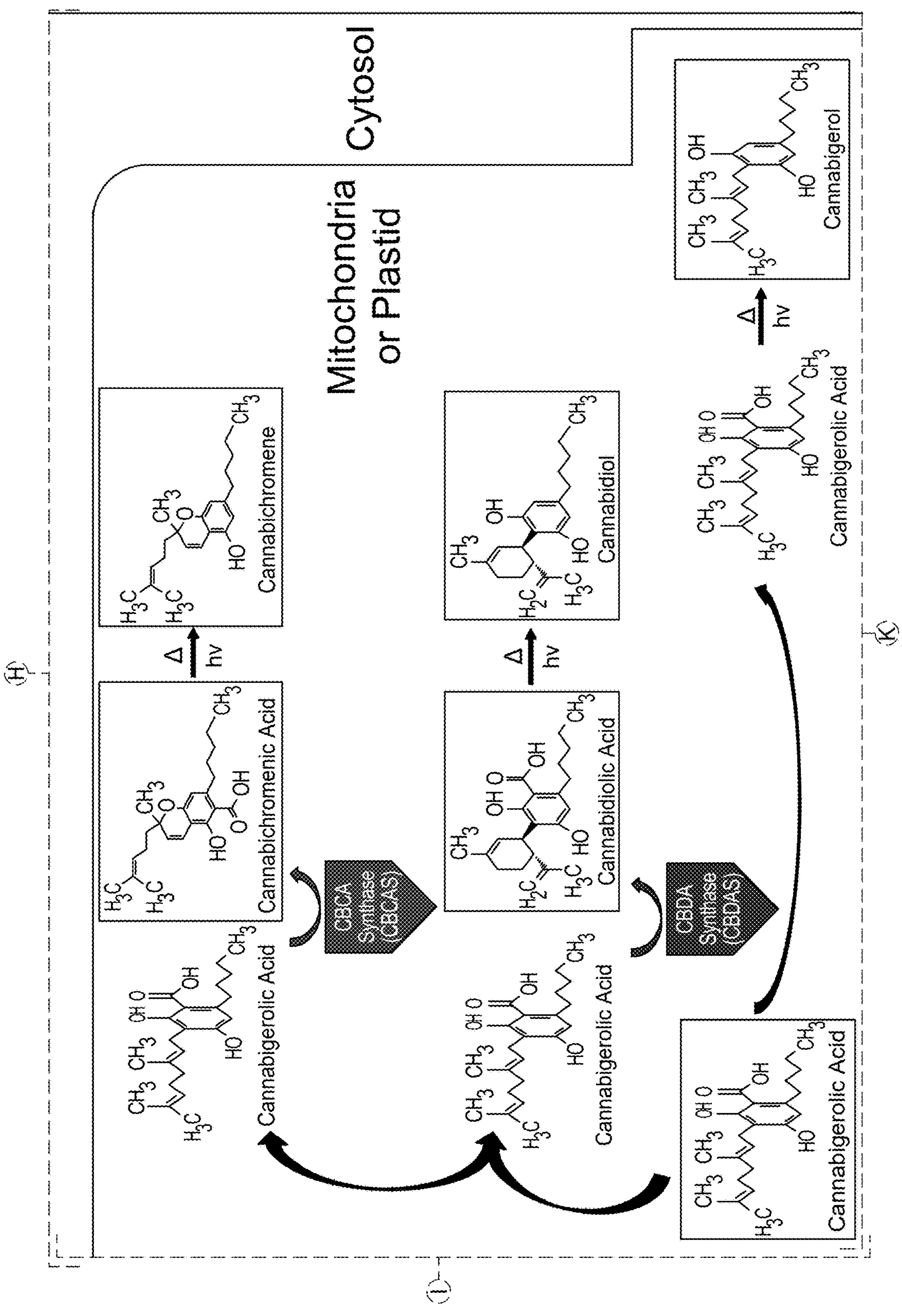
Figure 11:
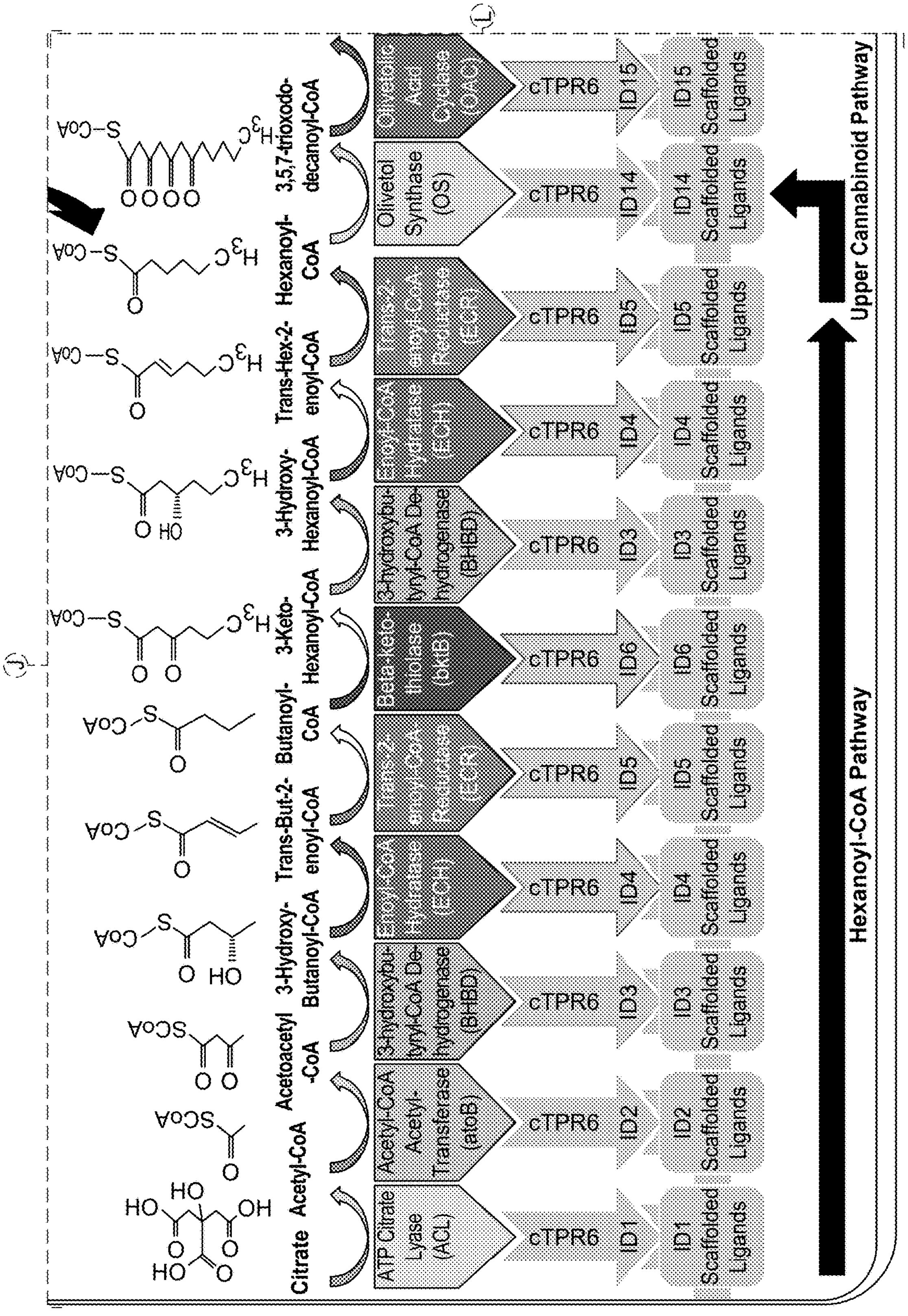
Figure 11:
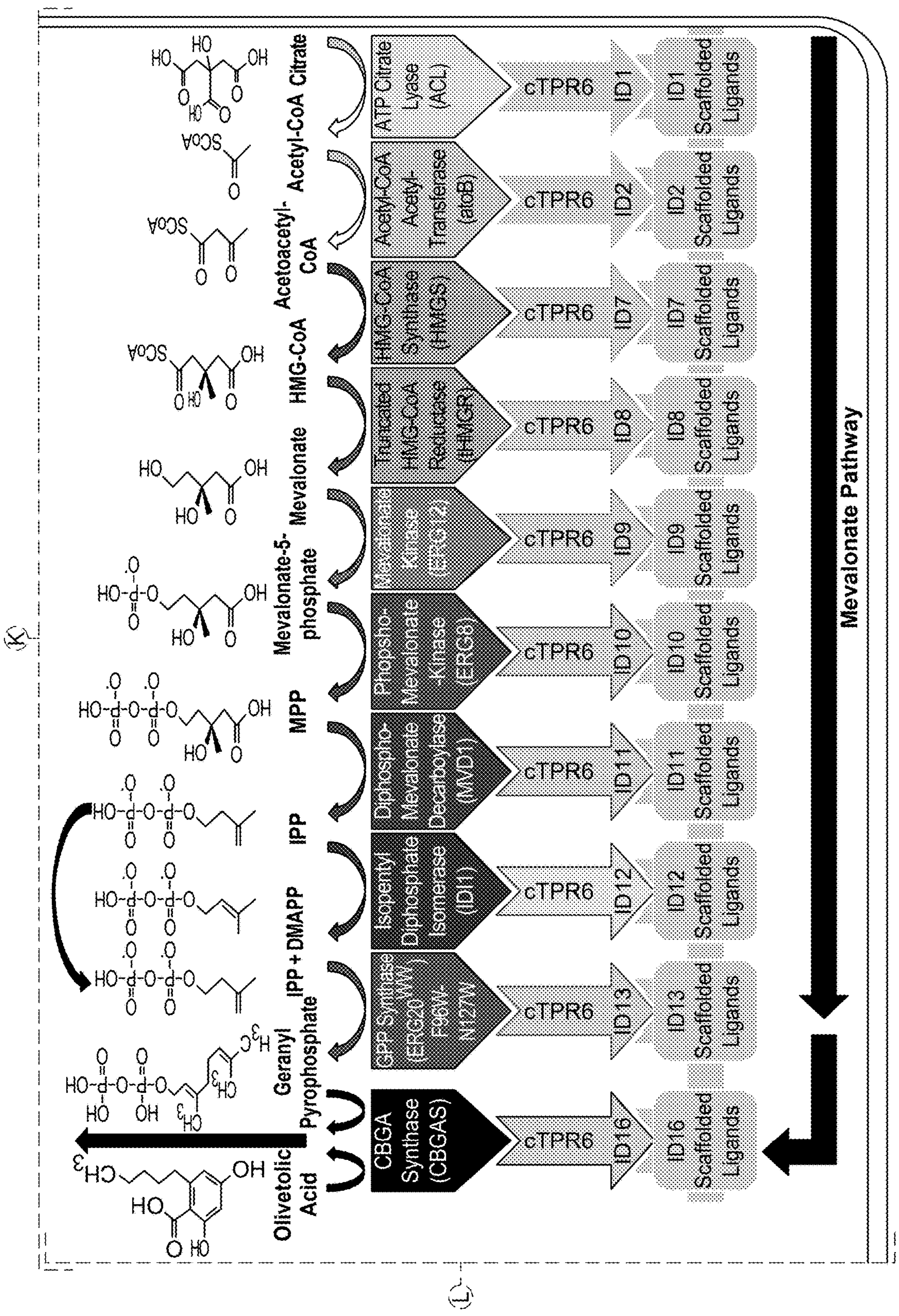

In some embodiments, cannabinoid/cannabinoid precursor biosynthesis can be performed in two compartments by co-expressing one or more engineered enzymes and a scaffold in both the cytosolic compartment and either the plastids or mitochondria of the host cell. See, for example, FIG. 11. It will be appreciated that while FIG. 11 depicts a scaffold containing enzymes of the hexanoyl-CoA pathway, enzymes of the upper cannabinoid pathway, and enzymes of the mevalonate pathway, dual-compartment engineering can be performed with any of the scaffolds and enzymes described herein. For example, dual-compartment engineering can be performed in two compartments by co-expressing a scaffold and enzymes of the hexanoyl-CoA pathway, enzymes of the upper cannabinoid pathway, and enzymes of the MEP pathway in both the cytosolic compartment and either the plastids of mitochondria of the host cell. Dual-compartment engineering also can be achieved by engineering separate haploid yeast strains for cytosolic and mitochondrial/plastidial cannabinoid biosynthesis, and then mating these two haploid strains to produce a diploid lineage that is heterozygous for cytosolic and mitochondrial/plastidial cannabinoid biosynthesis.

In some embodiments, the engineered enzymes and/or scaffolds also contain a tag that can be used for purification of the recombinant protein (e.g., c-myc, FLAG, polyhistidine (e.g., hexahistidine), hemagglutinin (HA), glutathione-S-transferase (GST), or maltose binding protein (MBP)) or as a detectable marker (e.g., luciferase, green fluorescent protein (GFP), or chloramphenicol acetyl transferase (CAT)). For example, in the embodiment shown in FIG. 6C and FIG. 6D, a scaffold can include a myc tag (e.g., $(Myc)_3$ tag) or a FLAG tag $(FLAG)_3$ tag at the C-terminus.

In some embodiments, a host cell can be engineered to increase acetyl-CoA availability for cannabinoid and cannabinoid precursor biosynthesis. For example, the mitochondrial enzyme isocitrate dehydrogenase-1 (IDH1) can be placed under transient micro-RNA-mediated inducible repression. Since mitochondrial IDH1 is primarily responsible for depletion of the cellular citrate pool, micro-RNA-mediated repression of IDH1 can increase the availability and cytosolic shuttling of citrate for production of acetyl-CoA by ATP citrate lyase. The resulting increase in acetyl-CoA bioavailability can further enhance downstream hexanoyl-CoA and geranyl pyrophosphate titers by improving initial substrate availability for the hexanoyl-CoA and mevalonate pathways. The combinatorial metabolic engineering of acetyl-CoA can mitigate issues related to the siphoning of acetyl-CoA away from the endogenous metabolism of the host cells.

In some embodiments, one or more conventional and/or contemporary gene editing techniques can be used to produce recombinant hosts. For example, clustered, regularly interspaced, short palindromic repeat (CRISPR) technology can be used to modify expression of an endogenous nucleic acid. The CRISPR/Cas system includes components of a prokaryotic adaptive immune system that is functionally analogous to eukaryotic RNA interference, using RNA base pairing to direct DNA or RNA cleavage. The Cas9 protein functions as an endonuclease, and CRISPR RNA (crRNA) and trans-activating RNA (tracrRNA) sequences complex with the Cas9 enzyme and direct it to a target DNA sequence (Makarova et al., *Nat Rev Microbiol* 9(6):467-477, 2011). The modification of a single targeting RNA can be sufficient to alter the nucleotide target of a Cas protein. In some cases, crRNA and tracrRNA can be engineered as a single cr/tracrRNA hybrid (also referred to as a "guide RNA" or "gRNA") to direct Cas9 cleavage activity (Jinek et al., *Science,* 337(6096):816-821, 2012). The CRISPR/Cas system can be used in a variety of prokaryotic and eukaryotic organisms (see, e.g., Jiang et al., *Nat Biotechnol,* 31(3):233-239, 2013; Dicarlo et al., *Nucleic Acids Res*, doi:10.1093/nar/gkt135, 2013; Cong et al., *Science,* 339(6121):819-823, 2013; Mali et al., *Science,* 339(6121):823-826, 2013; Cho et al., *Nat Biotechnol,* 31(3):230-232, 2013; and Hwang et al., *Nat Biotechnol,* 31(3):227-229, 2013).

Another gene-editing technique can include a sequence-specific nuclease created by fusing transcription activator-like effectors (TALEs) to, for example, the catalytic domain of the Fold endonuclease. Both native and custom TALE-nuclease ("TALEN") fusions direct DNA double-strand breaks to specific, targeted sites. See, for example, Christian, et al., *Genetics* 186: 757-761 (2010) and U.S. Patent Publication No. 20110145940.

Other suitable gene insertion techniques include the use of retroviral vectors and biolistic particle gene delivery systems (colloquially known as "gene guns").

Methods of identifying and/or selecting host cells that contain exogenous nucleic acid or a modified endogenous nucleic acid are well known to those skilled in the art. Such methods include, without limitation, the introduction and expression of a negative selection marker such as an antibiotic resistance gene, PCR, and nucleic acid hybridization techniques such as Northern and Southern analyses. In some cases, immunohistochemistry and biochemical techniques can be used to determine if a microorganism contains a particular nucleic acid by detecting the expression of the encoded enzymatic polypeptide encoded by that particular nucleic acid molecule. For example, an antibody having specificity for an encoded enzyme can be used to determine whether or not a particular cell contains that encoded enzyme. Further, biochemical techniques can be used to determine if a cell contains a particular nucleic acid molecule encoding an enzymatic polypeptide by detecting an organic product produced as a result of the expression of the enzymatic polypeptide.

This document also provides isolated nucleic acids molecules. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

In some embodiments, the production of one or more cannabinoids can be performed in vitro using the scaffold and immobilized enzymes described herein, using a lysate (e.g., a buffered cell lysate) from a recombinant host cell as a source of the scaffold and enzymes, using a plurality of lysates from different host cells as the source of the scaffold and enzymes, or using an acellular reaction buffer such as a synthetic reaction buffer. For example, following co-immunoprecipitation of C-terminal Myc/Flag-tagged enzyme-bound scaffolds, scaffold-enzyme complexes can be maintained in a citrate-supplemented and/or glucose-supplemented (or other carbon source-supplemented) reaction buffer which allows in-vitro scaffolded cannabinoid biosynthesis.

Producing Cannabinoids Using a Recombinant Host

Typically, one or more cannabinoids can be produced by providing a recombinant host such as a recombinant microorganism and culturing the microorganism with a culture medium. In general, the culture media and/or culture conditions can be such that the microorganisms grow to an adequate density and produce cannabinoids efficiently. For example, the microorganisms can be subjected to aerobic batch fermentation. In some embodiments, one or more precursors (e.g., citrate, glucose, hexanoic acid, and/or other carbon source and/or malonyl-CoA) are supplemented in the culture medium. In some embodiments, about 30 mg/L to about 10,000 mg/L (e.g., about 100 mg/L to about 5,000 mg/L, about 200 mg/L to about 4,000 mg/L, about 300 mg/L to about 3,000 mg/L, or about 350 mg/L to about 1,000 mg/L) of buffered citrate, pH 6.0 can be added to the culture medium.

For large-scale production processes, any method can be used such as those described elsewhere (Manual of Industrial Microbiology and Biotechnology, 2nd Edition, Editors: A. L. Demain and J. E. Davies, ASM Press; and Principles of Fermentation Technology, P. F. Stanbury and A. Whitaker, Pergamon). Briefly, a large vessel (e.g., a 100 gallon, 200 gallon, 500 gallon, or higher volume vessel) containing an appropriate culture medium is inoculated with a particular microorganism. After inoculation, the microorganism is incubated to allow biomass to be produced. Once a desired biomass or cellular confluency is attained, a portion or all of the broth containing the microorganisms can be transferred to a second vessel. This second vessel can be any size. For example, the second vessel can be larger, smaller, or the same size as the first vessel. Typically, the second vessel is larger than the first such that additional culture medium can be added to the broth from the first vessel. In addition, the culture medium within this second vessel can be the same as, or different from, that used in the first vessel. This system can expand to include an array consisting of any number of individual vessels.

Once transferred, the microorganisms can be incubated to allow for the production of one or more cannabinoids. Once produced, any method can be used to isolate cannabinoids. For example, common separation techniques can be used to remove the biomass from the broth, and common isolation procedures (e.g., extraction such as non-polar extraction with hexane followed by ethyl-acetate), high-performance liquid chromatography (e.g., HPLC with a diode array detector (HPLC-DAD)), gas chromatography-flame ionization detection (GC-FID), or ion-exchange procedures) can be used to obtain the cannabinoids from the biomass.

A host cell described herein can produce one or more cannabinoids at a concentration of at least about 10 mg per L (e.g., at least about 15 mg/L 25 mg/L, 50 mg/L, 75 mg/L, 100 mg/L, 150 mg/L, 200 mg/L, 250 mg/L or more). For example, in some embodiments, total cannabinoids (total of CBG, CBGA, CBD, CBDA, CBC, and CBCA) can be produced at a concentration of at least about 10 mg/L, 15 mg/L, 20 mg/L, 40 mg/L, 60 mg/L, 80 mg/L, or 100 mg/L or more. For example, in some embodiments, total cannabinoids (total of CBG, CBGA, CBD, CBDA, CBC, and CBCA) can be produced at a concentration from about 10 mg/L to about 500 mg/L (e.g., 20 mg/L to 450 mg/L, 40 mg/L to 380 mg/L, 60 mg/L to 280 mg/L, 60 mg/L to 250 mg/L, 60 mg/L to 150 mg/L, 80 mg/L to 400 mg/L, 80 mg/L to 300 mg/L, 80 mg/L to 250 mg/L, 80 mg/L to 200 mg/L, 80 mg/L to 175 mg/L, 90 mg/L to 400 mg/L, 90 mg/L to 300 mg/L, 90 mg/L to 250 mg/L, or 90 mg/L to 150 mg/L). In some embodiments, one or more individual cannabinoids (e.g., one or more of CBG, CBGA, CBD, CBDA, CBC, and CBCA) can be produced at concentrations of at least about 1 mg/L, 2 mg/L, 5 mg/L, 10 mg/L, 15 mg/L, 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 85 mg/L, 90 mg/L, 95 mg/L, 100 mg/L or more. For example, in some embodiments, one or more individual cannabinoids can be produced at a concentration from about 1 mg/L to about 100 mg/L (e.g., 2 to 90 mg/L, 2 to 80 mg/L, 2 to 70 mg/L, 2 to 60 mg/L, 2 to 50 mg/L, 2 to 40 mg/L, 2 to 30 mg/L, 2 to 20 mg/L, 2 to 15 mg/L, 3 to 90 mg/L, 3 to 80 mg/L, 3 to 70 mg/L, 3 to 60 mg/L, 3 to 50 mg/L, 3 to 40 mg/L, 3 to 30 mg/L, 3 to 20 mg/L, 3 to 15 mg/L, 4 to 90 mg/L, 4 to 80 mg/L, 4 to 70 mg/L, 4 to 60 mg/L, 4 to 50 mg/L, 4 to 40 mg/L, 4 to 30 mg/L, 4 to 20 mg/L, or 4 to 15 mg/L).

The invention will be further described in the following examples, which do not limit the scope of the invention described in the claims.

EXAMPLES

Example 1—General Methods

Enzymatic Constructs

Each enzyme construct is designed to include an interaction domain (ID) which is comprised of two tandem N-terminal or C-terminal ligand-binding motifs which are separated from the given enzyme and from one another by an amino acid sequence containing flexible GS-rich linkers flanking a rigid α-helical spacer sequence. The motifs comprising the ID of each enzyme specifically bind tandem peptide ligands which form ID-binding sites at discrete locations along a synthetic intracellular polypeptide scaffold. Expression of each enzyme is controlled by a constitutive or inducible promoter. The nucleic acid encoding the enzyme can be codon optimized, e.g., for expression in yeast.

Scaffolding Constructs

ID-binding sites containing tandem peptide ligands that are specific for the tandem scaffold-binding motifs, which comprise the ID of each enzyme, are inserted at discrete positions along an intracellular polypeptide scaffold.

The tandem ligands which comprise each scaffolded ID-binding site are separated from one another by a 36 amino acid residue sequence containing flexible GS-rich linkers flanking a rigid α-helical spacer sequence, while the scaffolded ID-binding sites themselves are separated from one another by a 50 amino acid residue sequence (or any other number of amino acid residues) containing flexible GS-rich linkers flanking a rigid α-helical spacer sequence. Specifically, the scaffold binding sites for each enzyme in the hexanoyl-CoA pathway are positioned (in order of catalysis) proximally to ATP citrate lyase and acetyl-CoA acetyltransferase at the N-terminus of the primary scaffold. Scaffold binding sites for each enzyme in the upper cannabinoid pathway are positioned proximally to (immediately downstream of) the binding sites for the hexanoyl-CoA pathway enzymes. The scaffold binding sites for each enzyme in the mevalonate (or MEP) pathway are positioned (in order of catalysis) proximally to ATP citrate lyase and acetyl-CoA acetyltransferase at the C-terminus of the primary scaffold. The enzyme catalyzing the rate-limiting/committed step in cannabinoid biosynthesis (CBGA synthase, the final enzymatic step in the upper cannabinoid pathway) is located at the intersection of the converging cannabinoid precursor pathways near the scaffold midpoint.

Assessment of Cannabinoidergic Potential by Transient Transfection

Competent yeast and/or green algae cells are transiently transfected with plasmids encoding various permutations of the scaffold and enzymes. To establish baseline cannabinoidergic capacity, cells first undergo transient transfection with the enzymes required for cannabinoid biosynthesis (but not the scaffolds), and biosynthesized cannabinoids are extracted, isolated, and quantified as described below (see "Cannabinoid Extraction, Isolation, and Analytical Characterization"). To measure the improvement in cannabinoidergic capacity conferred by multi-enzymatic scaffolding, a subset of the aforementioned cells is co-transfected with plasmids encoding one or more of the multi-enzymatic scaffolds described herein, and biosynthesized cannabinoids are extracted, isolated, and quantified. The presence of the plasmid DNA is confirmed by PCR, functional gene expression is confirmed by qRT-PCR, protein/polypeptide production is confirmed by Western blotting, and scaffolding of each enzyme is confirmed by co-immunoprecipitation of C-terminal myc/flag-tagged scaffolds followed by Western blot analysis of each co-immunoprecipitated enzyme.

Engineering of Stable Cannabinoidergic Cell Lines

The constructs can be integrated into the genome of host cells such yeast, green algae, or other suitable hosts via stable transfection. Gene integration is confirmed by PCR, functional gene expression is confirmed by qRT-PCR, and protein/polypeptide production is confirmed by Western blotting. Gene expression/protein synthesis is confirmed by comparing both qRT-PCR and Western blot results among samples with and without genetic engineering. To assess the improvement in cannabinoidergic capacity conferred by multi-enzymatic scaffolding for stably engineered cannabinoidergic cell lines, cannabinoid biosynthesis will be compared among cells that are stimulated for enzyme but not scaffold expression and cells that are stimulated for enzyme and scaffold expression.

Validation of Multi-enzymatic Scaffolding

To verify successful multi-enzymatic scaffolding in both transiently transfected and stably engineered cells, a myc-tag (or other immunoprecipitable tag) is inserted at the N-terminal or C-terminal of the polypeptide scaffold(s). Scaffolded enzymes are selectively co-immunoprecipitated by affinity chromatography using anti-myc affinity beads. Western blots are performed to detect and quantify each co-immunoprecipitated enzyme.

Aerobic Fed-batch Fermentation

Stably engineered cannabinoidergic yeast, green algae, or other host cells are grown in bioreactors (or any other vessel) via aerobic batch fermentation (or any other culture technique).

Cannabinoid Extraction, Isolation, and Analytical Characterization

Following sufficient elicitation of cannabinoid biosynthesis, engineered yeast/green algae cells are pelleted by centrifugation and washed with TBS. The supernatant (liquid culture media) is decanted and collected. Following washing with TBS, pelleted cells are resuspended in NaOH adjusted ethanol and lysed by iterative freeze-thawing and ultrasonication. Biosynthesized cannabinoid fermentates are then harvested from both lysates and supernatants via triplicate nonpolar extractions using hexane followed by ethyl-acetate. The resulting organic fractions are pooled and roto-evaporated. High-performance liquid chromatography with a diode array detector (HPLC-DAD) or gas chromatography-flame ionization detection (GC-FID) is then applied for quantitative and qualitative measurement of biosynthesized cannabinoids.

In the following examples, each 48-hour culture was lysed/homogenized by ultrasonication. Ultrasonicated samples were then subjected to triplicate liquid-liquid extractions with ethyl acetate (one volumetric equivalent of ethyl acetate per extraction). Following separation, the ethyl acetate fractions collected from each sample were pooled, and the pooled samples were centrifugally filtered. Ethyl acetate was then removed from each sample in a vacuum oven, and the residual samples were resuspended in 10 mL methanol for analytical characterization. Analytical characterization of all samples was conducted by a licensed, independent, third-party analytical testing facility (Precision Plant Molecules, Denver, CO). HPLC-DAD was utilized for quantitative and qualitative measurement of each parent and derivative cannabinoid as well as the cannabinoid precursor OVA.

Example 2—Synthetic Gene Cassette Assembly/Synthesis, Plasmid Preparation, and Polycistronic Vector Construction Five synthetic gene cassettes (entitled HCA, GPP, CAN, SCF, and SOL) were constructed for biosynthesizing cannabinoids in heterologous cells or acellular reaction buffers. See, FIG. 2B. The cassettes collectively encode all scaffold-binding engineered enzymes and the polypeptide scaffolds to which the engineered enzymes can bind.

The HCA gene cassette encoded scaffold-binding engineered enzymes for scaffolded hexanoyl-CoA biosynthesis, namely ACL, atoB, BHBD, ECH, ECR, and bktB, and encoded a soluble HCS for additional hexanoyl-CoA production from hexanoate-supplemented culture media or acellular reaction buffer. See, FIG. 13A. The GPP gene cassette encoded scaffold-binding engineered enzymes for scaffolded geranyl pyrophosphate (GPP) biosynthesis, namely HMGS, tHMGR, ERG12, ERGS, MVD1, IDI1, and ERG20$^{WW}$. See, FIG. 13B. The CAN gene cassette encoded scaffold-binding engineered enzymes for scaffolded OAC, malonyl-CoA, and CBGA biosynthesis, namely OS and OAC, ACC, and CBGAS, respectively, as well all enzymes for soluble (non-scaffolded) CBDA and CBCA biosynthesis, namely CBDAS and CBCAS, respectively. See, FIG. 13C. The SCF gene cassette encoded the polypeptide scaffolds for bidirectional scaffolded cannabinoid biosynthesis and scaffolded malonyl-CoA biosynthesis, namely the cannabinoidergic metabolon scaffold (CBSCF) and the malonyl-CoA metabolon scaffold (MCASCF), respectively, as well as additional copies of both ACL and atoB to enhance acetyl-CoA biosynthesis from supplemental and/or endogenous citrate and acetoacetyl-CoA biosynthesis from acetyl-CoA, respectively. See, FIG. 13D. The SOL gene cassette lacked the polypeptide scaffolds for bidirectional scaffolded cannabinoid biosynthesis and scaffolded malonyl-CoA biosynthesis (i.e., it was used for soluble cannabinoid biosynthesis) but, analogous to the SCF gene cassette, encoded additional copies of ACL and atoB to enhance acetyl-CoA biosynthesis from supplemental and/or endogenous citrate and acetoacetyl-CoA biosynthesis from acetyl-CoA. See FIG. 13A for the amino acids sequences of the ACL and atoB engineered enzymes.

Gene cassettes were assembled/synthesized using self-cleaving 2A peptides (P2As) to link multiple codon-optimized (for *S. cerevisiae*) gene sequences assigned to each cassette. To improve P2A cleavage, a GSG linker (comprised of a single serine residue flanked by single glycine residues) was inserted at the interface between each constituent gene sequence and the P2A linker sequence to which it was fused (of the format: gene cassette sequence 1—SG— P2A linker—gene cassette sequence 2— GSG—P2A linker—gene cassette sequence 3— GSG— P2A linker-) and so forth. See, FIGS. 14A-14D for codon-optimized nucleic acid sequences encoding the engineered enzymes and scaffolds. Following assembly, each synthetic gene cassette was inserted into a pCCI-Brick plasmid, resulting in plasmids entitled pHCA, pGPP, pCAN, pSCF, and pSOL as described in Table 3. See, FIGS. 15A-15E for the complete gene cassette inserted into the plasmids. Each of these plasmids then were used to amplify each synthetic gene cassette via standard plasmid prep. Plasmid DNA encoding each complete synthetic gene cassette was cloned into the SpeI/XhoI cloning site of polycistronic yeast auxotrophic selection vectors, resulting in vectors entitled vHCA, vGPP, vCAN, vSCF, and vSOL as described in Table 3, to allow iterative antibiotic/auxotrophic selection of only those cells that were transformants of one or more such polycistronic vector(s).

TABLE 3

| HCA Gene Cassette | | | | |
|---|---|---|---|---|
| Gene ID | Cassette Position | pCCI-Brick #1 ID | Yeast Vector | Yeast Vector ID |
| ACL | 1 | pHCA | pESC-TRP | vHCA |
| atoB | 2 | | | |
| BHBD | 3 | | | |
| ECH | 4 | | | |
| ECR | 5 | | | |

TABLE 3-continued

| | | | | |
|---|---|---|---|---|
| bktB | 6 | | | |
| HCS | 7 | | | |

MVA Gene Cassette

| Gene ID | Cassette Position | pCCI-Brick #2 ID | Yeast Vector | Yeast Vector ID |
|---|---|---|---|---|
| HMGS | 1 | pGPP | pESC-LEU | vGPP |
| tHMGR | 2 | | | |
| ERG12 | 3 | | | |
| ERG8 | 4 | | | |
| MVD1 | 5 | | | |
| IDI1 | 6 | | | |
| $ERG20^{WW}$ | 7 | | | |

CAN Gene Cassette

| Gene ID | Cassette Position | pCCI-Brick #3 ID | Yeast Vector | Yeast Vector ID |
|---|---|---|---|---|
| OS | 1 | pCAN | pESC-HIS | vCAN |
| OAC | 2 | | | |
| CBGAS | 3 | | | |
| CBDAS | 4 | | | |
| CBCAS | 5 | | | |
| ACC | 6 | | | |

SCFLD Gene Cassette

| Gene ID | Cassette Position | pCCI-Brick #4 ID | Yeast Vector | Yeast Vector ID |
|---|---|---|---|---|
| CBSCF | 1 | pSCF | pESC-URA #1 | vSCF |
| MCASCF | 2 | | | |
| ACL | 3 | | | |
| atoB | 4 | | | |

NSCFLD Gene Cassette

| Gene ID | Cassette Position | pCCI-Brick #5 ID | Yeast Vector | Yeast Vector ID |
|---|---|---|---|---|
| ACL | 1 | pSOL | pESC-URA #2 | vSOL |
| atoB | 2 | | | |

The genes assigned to each synthetic gene cassette as well as the plasmids and vectors into which each synthetic gene cassette was inserted are listed in Table 3, the amino acid sequences encoded by each synthetic gene cassette are provided in FIGS. 13A-13D, the codon-optimized nucleotide sequence fragments comprising each synthetic gene cassette are detailed in FIGS. 14A-14D, the complete nucleotide sequences of each fully-assembled synthetic gene cassette (the complete insert sequences for each plasmid and expression vector) are provided in FIGS. 15A-15E, a general map of pCCI-Brick plasmids is shown in FIG. 16, and a general map of a polycistronic yeast auxotrophic selection vector is shown in FIG. 17.

Example 3—Engineering of Cannabinoidergic Cells

To engineer a novel heterologous pathway for the biosynthesis of cannabinoids from citrate, and to evaluate the impacts of bidirectional multi-enzymatic scaffolding thereon, competent *S. cerevisiae* cells were sequentially/iteratively transformed with, and auxotrophically selected for, expression of vHCA, vGPP, vCAN, and either vSCF (for scaffolded cannabinoid biosynthesis) or vSOL (for non-scaffolded/soluble cannabinoid biosynthesis) constructs.

All vector transformation and auxotrophic selection procedures were conducted as follows. An aliquot of an overnight *S. cerevisiae* culture was inoculated into 100 mL YPD media (10 g/L yeast nitrogen base, 20 g/L peptone, and 20 g/L D-(+)-glucose) to $OD_{600mn}$=0.3 (stationary phase) and grown to $OD_{600mn}$=1.6 in an orbital shaker at 30° C. and 225 RPM. Cells then were harvested by centrifugation at 3000×g for 3 minutes followed by aspiration of media. The harvested cell pellet was next washed 2× with 50 mL chilled nuclease-free water and 1× with 50 mL chilled electroporation buffer (1M sorbitol/1 mM $CaCl_2$). Washed cells were conditioned by incubation for 30 minutes in 20 mL 0.1M LiAc/10 mM DTT in an orbital shaker at 30° C. and 225 RPM, harvested, washed 1× with 50 mL electroporation buffer, harvested, and resuspended in 100 μL electroporation buffer. The resuspended cells were transformed with a quantity of vector containing 3 μg of the target DNA insert (calculated using the vector-insert ratio for each vector) by electroporation at 2.5 kV and 25 g. To the electroporated cell suspension was then added 8 mL of YPD media containing 1M sorbitol, and the resulting suspension was incubated for one hour in an orbital shaker at 30° C. and 225 RPM. To isolate target transformants by auxotrophic selection, cells were harvested, resuspended in the appropriate yeast nitrogen base (YNB) dropout (selection) media as subsequently described for each iterative transformation step, transferred to a baffled culture flask, and incubated overnight in an orbital shaker at 30° C. and 225 RPM. The transformation and selection protocols were utilized sequentially for each assigned vector.

Applying the aforementioned approach, an initial culture of electrocompetent *S. cerevisiae* cells was first transformed with vHCA, which encodes scaffold-binding engineered enzymes required for biosynthesis of HCA from citrate. Cells transformed with vHCA (designated yHCA) were selected for by resuspension and incubation in tryptophan-deficient YNB media. Selected yHCA cells (i.e., cells that grew in tryptophan-deficient YNB media) were next transformed with vGPP, which encodes scaffold-binding engineered enzymes required for biosynthesis of GPP from citrate. Cells co-transformed with vHCA and vGPP (designated yHCAGPP) were selected for by resuspension and incubation in tryptophan- and leucine-deficient YNB media. Selected yHCAGPP cells (i.e., cells that grew in tryptophan- and leucine-deficient YNB media) were then transformed with vCAN, which encodes scaffold-binding engineered enzymes required for biosynthesis of malonyl-CoA from citrate, olivetol from HCA and malonyl-CoA, OVA (olivetoic acid) from olivetol, and CBGA from OVA and GPP as well as soluble enzymes required for biosynthesis of CBDA and CBCA from CBGA). Cells co-transformed with vHCA, vGPP, and vCAN (designated $yCB_{Parent}$) were selected for by resuspension and incubation in tryptophan-, leucine-, and histidine-deficient YNB media.

The $yCB_{Parent}$ culture containing cells that grew in tryptophan-, leucine-, and histidine-deficient YNB media then was split into two separate cultures. The first of the split $yCB_{Parent}$ cultures was transformed with vSCF, which encodes CBSCF (cannabinoidergic metabolon scaffold) and MCASCF (malonyl-CoA metabolon scaffold) as well as additional copies of ACL and atoB. Cells co-transformed with vHCA, vGPP, vCAN, and vSCF (designated $yCB_{SCF}$) were selected for by resuspension and incubation in tryptophan-, leucine-, histidine-, and uracil-deficient YNB media. The second of the split $yCB_{Parent}$ cultures was transformed with vSOL, which encodes additional copies of ACL and atoB but lacks both CB SCF and MCASCF. Cells co-transformed with vHCA, vGPP, vCAN, and vSOL (designated $yCB_{SOL}$) were also selected for by resuspension and incubation in tryptophan-, leucine-, histidine-, and uracil-deficient YNB media.

To quantify the improvement in cannabinoidergic capacity conferred by multi-enzymatic scaffolding, cannabinoid titers were compared between triplicate $yCB_{SOL}$ and $yCB_{SCF}$ cultures grown in 100 mL YPD media for 48 hours at 30° C. and 400 RPM in an incubator-shaker. To compare the proliferation rates of $yCB_{SOL}$ and $yCB_{SCF}$, each culture was initially diluted to $OD_{600mn}$=0.3, and $OD_{600}$ nm measurements were recorded in 12-hour intervals thereafter. Proliferation curves are depicted in FIG. 18. The extra sum-of-squares F-test indicated that the proliferation curves of $yCB_{SCF}$ and yCBSOL cultures did not significantly differ for any parameter over the 48-hour incubation period, indicating that scaffolding does not impact cellular proliferation.

Total cannabinoid titers, parent (carboxylated) cannabinoid (CBGA, CBDA, and CBCA) titers, derivative (decarboxylated) cannabinoid (CBG, CBD, and CBC) titers, and cannabinoid precursor (OVA) titers were measured. As shown in FIGS. 19A-19E, mixed ANOVA detected main effects of strain ($F_{1,4}$=943.8; p<0.0001) and analyte (cannabinoid and cannabinoid precursor) titers ($F_{10,40}$=216.4; p<0.0001) and a significant strain x analyte interaction ($F_{10,40}$=131.4; p<0.0001). Relative to yCBSOL cultures, yCBSCF cultures exhibited increased total cannabinoid (p<0.0001), OVA precursor (p<0.0001), CBG(A) (p<0.0001), CBD(A) (p<0.0001), CBC(A) (p<0.0001), CBGA (p<0.0001), CBDA (p<0.0001), CBCA (p<0.0001), CBG (p<0.0001), CBD (p<0.01), and CBC (p<0.001) titers.

Example 4—Impacts of Citrate and Hexanoate Supplementation on Scaffolded and Soluble Cannabinoid Biosynthesis To evaluate the impacts of culture media supplementation with citrate and hexanoate precursors, cannabinoid titers were compared between triplicate $yCB_{SOL}$ and $yCB_{SCF}$ cultures grown in 100 mL YPD media containing 300 mg/L of either buffered citrate (pH 6.0) or hexanoate for 48 hours at 30° C. and 400 RPM in an orbital shaker. All cultures were initially diluted to $OD_{600mn}$=0.3. Cannabinoid titers for cultures grown in YPD media, citrate-supplemented YPD media, and hexanoate-supplemented YPD media were assessed and analyzed by ANOVA. As shown in FIG. 20, mixed ANOVA detected main effects of strain ($F_{1,4}$=457.5; p<0.0001) and culture media supplementation ($F_{2,8}$=3 12.5; p<0.0001) and a significant strain x culture media supplementation interaction ($F_{2,8}$=289.6; p<0.0001). Compared to basal media cultures, yCBSCF but not yCBSOL cultures exhibited increased total cannabinoid titers when cultured in media supplemented with 300 mg/L citrate (p<0.0001). Neither yCBSCF nor yCBSOL cultures differed in total cannabinoid titers relative to basal media when cultured in media supplemented with 300 mg/L hexanoate. For all measures, n=3 biological replicates for yCBSCF and yCBSOL cultures. Moreover, relative to yCBSOL cultures, yCBSCF cultures exhibited increased total cannabinoid titers when cultured in basal media (p<0.0001, data also reported in FIG. 19) as well as media supplemented with 300 mg/L citrate (p<0.0001) and hexanoate (p<0.0001).

To delineate concentration-response relationships for the supplementation of culture media with citrate, cannabinoid titers were compared between triplicate $yCB_{SOL}$ and $yCB_{SCF}$ cultures grown in 100 mL YPD media containing 0, 10, 30, 100, 300, 1000, 3000, and 10000 mg/L buffered citrate (pH 6.0) for 48 hours at 30° C. and 400 RPM in an orbital shaker. All cultures were initially diluted to $OD_{600nm}$=0.3. Following quantification, asymmetric sigmoidal (five-parameter) logistic regressions were computed to fit concentration-response curves, from which were derived estimates of the maximal cannabinoid titer ($CB_{Max}$) and citrate $EC_{50}$ for cannabinoid biosynthesis in $yCB_{SOL}$ and $yCB_{SCF}$ cultures. Concentration-response curves, $CB_{Max}$ estimates, and citrate $EC_{50}$ estimates are depicted in FIGS. 21A and 21B. Mixed ANOVA detected main effects of strain ($F_{1,8}$=69.9; p<0.0001) and parameter ($F_{1,8}$=66.7; p<0.0001) and a significant strain x parameter interaction ($F_{1,8}$=5.3; p<0.05) for concentration-response parameter estimates ($CB_{Max}$ and citrate $EC_{50}$). Compared to $yCB_{SOL}$ cultures, $yCB_{SCF}$ cultures exhibited markedly increased $CB_{Max}$ (p<0.0001) and citrate $EC_{50}$ (p<0.001) estimates.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A host cell capable of producing one or more cannabinoids, said host cell comprising:

(a) a first exogenous nucleic acid encoding a first polypeptide having CBGA synthase activity and comprising a first heterologous interaction domain, (b) a second exogenous nucleic acid encoding a second polypeptide having olivetolic acid cyclase activity and comprising a second heterologous interaction domain, (c) a third exogenous nucleic acid encoding a third polypeptide having olivetol synthase activity and comprising a third heterologous interaction domain, (d) a fourth exogenous nucleic acid encoding a fourth polypeptide having trans-2-enoyl-CoA reductase activity and comprising a fourth heterologous interaction domain, (e) a fifth exogenous nucleic acid encoding a fifth polypeptide having enoyl-CoA hydratase activity and comprising a fifth heterologous interaction domain, (f) a sixth exogenous nucleic acid encoding a sixth polypeptide having 3-hydroxybutyryl-CoA dehydrogenase activity and comprising a sixth heterologous interaction domain, (g) a seventh exogenous nucleic acid encoding a seventh polypeptide having acetyl-CoA acetyltransferase activity and comprising a seventh heterologous interaction domain, (h) an eighth exogenous nucleic acid encoding an eighth polypeptide having ATP citrate lyase activity and comprising an eighth heterologous interaction domain, (i) a ninth exogenous nucleic acid encoding a ninth polypeptide having geranyl pyrophosphate synthase activity and comprising a ninth heterologous interaction domain, (j) a tenth exogenous nucleic acid encoding a tenth polypeptide having isopentyl-diphosphate isomerase activity and comprising a tenth heterologous interaction domain, (k) an eleventh exogenous nucleic acid encoding an eleventh polypeptide having diphospho-mevalonate decarboxylase activity and comprising an eleventh heterologous interaction domain, (l) a twelfth exogenous nucleic acid encoding a twelfth polypeptide having phosphomevalonate kinase activity and comprising a twelfth heterologous interaction domain, (m) a thirteenth exogenous nucleic acid encoding a thirteenth polypeptide having mevalonate kinase activity and comprising a thirteenth heterologous interaction domain, (n) a fourteenth exogenous nucleic acid encoding a fourteenth polypeptide having HMG-CoA reductase activity and comprising a fourteenth heterologous interaction domain, (o) a fifteenth exogenous nucleic acid encoding a fifteenth polypeptide having HMG-CoA synthase activity and comprising a fifteenth heterologous interaction domain, and (p) a sixteenth exogenous nucleic acid encoding a polypeptide scaffold comprising a peptide ligand for each of said first to fifteenth heterologous interaction domains, wherein each of said first to fifteenth heterologous interaction domains is different, wherein each peptide ligand for each of said first to fifteenth heterologous interaction domains is different, wherein said polypeptide scaffold comprises, in an order extending in a first direction away from said peptide ligand for said first heterologous interaction domain, (1) said peptide ligand for said second heterologous interaction domain, (2) said peptide ligand for said third heterologous interaction domain, (3) said peptide ligand for said fourth heterologous interaction domain, (4) said peptide ligand for said fifth heterologous interaction domain, (5) said peptide ligand for said sixth heterologous interaction domain, (6) said peptide ligand for said seventh heterologous interaction domain, and (7) said peptide ligand for said eighth heterologous interaction domain, and wherein said polypeptide scaffold comprises, in an order extending in the other direction away from said peptide ligand for said first heterologous interaction domain, (1) said peptide ligand for said ninth heterologous interaction domain, (2) said peptide ligand for said tenth heterologous interaction domain, (3) said peptide ligand for said eleventh heterologous interaction domain, (4) said peptide ligand for said twelfth heterologous interaction domain, (5) said peptide ligand for said thirteenth heterologous interaction domain, (6) said peptide ligand for said fourteenth heterologous interaction domain, (7) said peptide ligand for said fifteenth heterologous interaction domain, (8) said peptide ligand for said seventh heterologous interaction domain, and (9) said peptide ligand for said eighth heterologous interaction domain.

2. The host cell of claim 1, further comprising (q) a seventeenth exogenous nucleic acid encoding an acetyl-CoA carboxylase and comprising a seventeenth heterologous interaction domain, and (r) an eighteenth exogenous nucleic acid encoding a polypeptide scaffold comprising a peptide ligand for each of said eighth and seventeenth heterologous interaction domains.

3. The host cell of claim 1, wherein said host cell further comprises an exogenous nucleic acid encoding a cannabidiolic acid synthase and a cannabichromenic acid synthase.

4. The host cell of claim 1, wherein said host cell further comprises an exogenous cannabidiolic acid synthase.

5. The host cell of claim 1, wherein said host cell further comprises an exogenous cannabichromenic acid synthase.

6. The host cell of claim 1, wherein said host cell is a bacterial or a yeast host cell.

7. The host cell of claim 6, wherein said bacterial cell is selected from the group consisting of *Escherichia coli, Bacillus, Brevibacterium, Streptomyces*, and *Pseudomonas* cells.

8. The host cell of claim 6, wherein said yeast cell is selected from the group consisting of *Pichia pastoris, Saccharomyces cerevisiae, Yarrowia lipolytica, Kluyveromyces marxianus*, and Komagataella phaffii cells.

9. The host cell of claim 1, wherein said host cell is an algae or a plant cell.

10. The host cell of claim 9, wherein said algae is *Dunaliella* sp., *Chlorella variabilis, Euglena mutabilis*, or *Chlamydomonas reinhardtii* cells.

11. The host cell of claim 9, wherein said plant cell is a *Cannabis* or tobacco cell.

12. The host cell of claim 1, wherein each of said polypeptides is of the formula: enzyme-linker1-spacer-linker2-motifi-linker3-motif2, wherein linker1, linker2, and linker3 are the same or different, wherein motif1 and motif2 are the same or different, and wherein motif1 and motif2 form said heterologous interaction domain.

13. The host cell of claim 12, wherein said scaffold polypeptide comprises a linker between each adjacent peptide ligand.

14. The host cell of claim 13, wherein said scaffold polypeptide is tagged with a MYC tag, FLAG tag, or HA tag.

15. The host cell of claim 12, wherein said linker is a flexible GS-rich sequence flanking a rigid α-helical moiety.

16. The host cell of claim 12, wherein said spacer is the cTPR6 spacer.

17. The host cell of claim 1, wherein a constitutive promoter is operably linked to one or more of said exogenous nucleic acids encoding said polypeptides or to said sixteenth exogenous nucleic acid encoding said polypeptide scaffold.

18. The host cell of claim 1, wherein a first constitutive promoter is operably linked to one or more of said exogenous nucleic acids encoding said polypeptides and a second constitutive promoter is operably linked to said sixteenth exogenous nucleic acid encoding said polypeptide scaffold.

19. The host cell of claim 18, wherein said constitutive promoter used to express said polypeptide scaffold has weaker constitutive activity level than said constitutive promoter used to express said polypeptides.

20. The host cell of claim 1, wherein each said exogenous nucleic acid comprises an inducible promoter operably linked to the sequence encoding said polypeptide or said polypeptide scaffold.

21. The host cell of claim 20, wherein said promoter is the GAL1-10 promoter.

* * * * *

UNITED STATES PATENT AND TRADEMARK OFFICE

CERTIFICATE OF CORRECTION

PATENT NO. : 12,385,072 B2
APPLICATION NO. : 17/962229
DATED : August 12, 2025
INVENTOR(S) : Jordan Buck It is certified that error appears in the above-identified patent and that said Letters Patent is hereby corrected as shown below:

In the Specification

Column 1, Line 9 (approx.): after "2019," insert --now U.S. Pat. No. 11,525,148,--.

In the Claims

Column 217, Lines 21-22 (approx.), in Claim 12: delete "enzyme-linker1-spacer-linker2-motif1-linker3-motif2," and insert --enzyme-linker$_1$-spacer-linker$_2$-motif$_1$-linker$_3$-motif$_2$,--, therefor.

Column 217, Line 22, in Claim 12: delete "linker1, linker2," and insert --linker$_1$, linker$_2$,--, therefor.

Column 217, Line 23, in Claim 12: delete "linker3" and insert --linker$_3$--, therefor.

Column 217, Line 23, in Claim 12: delete "motif1" and insert --motif$_1$--, therefor.

Column 217, Line 23, in Claim 12: delete "motif2" and insert --motif$_2$--, therefor.

Column 217, Line 24, in Claim 12: delete "motif1" and insert --motif$_1$--, therefor.

Column 217, Line 24, in Claim 12: delete "motif2" and insert --motif$_2$--, therefor.

Signed and Sealed this
Fourteenth Day of October, 2025

John A. Squires
*Director of the United States Patent and Trademark Office*